(12) United States Patent
Wong et al.

(10) Patent No.: US 6,706,869 B1
(45) Date of Patent: Mar. 16, 2004

(54) MAP KINASE PHOSPHATASES AND POLYNUCLEOTIDES ENCODING THEM

(75) Inventors: Gordon G. Wong, Brookline, MA (US); Hilary F. Clark, Cambridge, MA (US); Kim Fechtel, Arlington, MA (US); Michael J. Agostino, Andover, MA (US)

(73) Assignee: Wyeth, MA (US)

( * ) Notice: Subject to any disclaimer, the term of this patent is extended or adjusted under 35 U.S.C. 154(b) by 57 days.

(21) Appl. No.: 09/311,021

(22) Filed: May 13, 1999

Related U.S. Application Data

(63) Continuation-in-part of application No. 09/287,150, filed on Apr. 6, 1999, now abandoned, and a continuation-in-part of application No. 09/248,059, filed on Feb. 10, 1999, now abandoned.

(60) Provisional application No. 60/114,415, filed on Dec. 31, 1998, provisional application No. 60/112,159, filed on Dec. 14, 1998, provisional application No. 60/111,799, filed on Dec. 11, 1998, provisional application No. 60/103,615, filed on Oct. 9, 1998, provisional application No. 60/102,329, filed on Sep. 29, 1998, provisional application No. 60/100,424, filed on Sep. 15, 1998, provisional application No. 60/099,843, filed on Sep. 11, 1998, provisional application No. 60/099,950, filed on Sep. 11, 1998, provisional application No. 60/096,824, filed on Aug. 17, 1998, provisional application No. 60/085,472, filed on May 14, 1998, provisional application No. 60/080,969, filed on Apr. 7, 1998, and provisional application No. 60/075,118, filed on Feb. 11, 1998.

(51) Int. Cl.[7] ............................................. C07H 21/04
(52) U.S. Cl. .................. 536/23.5; 530/350; 435/252.3; 435/69.1
(58) Field of Search ........................ 530/350; 536/23.5; 435/252.3, 69.1

(56) References Cited

U.S. PATENT DOCUMENTS

| | | | |
|---|---|---|---|
| 5,194,596 A | * 3/1993 | Tischer et al. ............... 530/350 |
| 5,631,407 A | 5/1997 | Racaniello et al. |
| 5,641,657 A | 6/1997 | Ruben et al. |
| 5,654,276 A | 8/1997 | Barrett et al. |
| 5,767,064 A | 6/1998 | Sims et al. |
| 5,786,323 A | 7/1998 | Nakahata |

FOREIGN PATENT DOCUMENTS

| WO | WO 94/01548 | * 1/1994 |
|---|---|---|
| WO | WO 99/15654 | * 4/1999 |

OTHER PUBLICATIONS

Skolnick, J., and J. S. Fetrow, "From genes to protein structure and function: novel applications of computational approaches in the genomic era", Trends in Bitechnology, 18(1) 34–39, 2000.*
Vukicevic, S. et al., Induction of nephrogenic mesenchyme by osteogenic protein 1 (bone morphogenic protein 7). PNAS, vol. 93, pp. 9021–9026, Aug. 1996.*
Hillier et al., Generation and analysis of 280,000 human expressed sequence tags, Accession No. AA126103, Database EST See Sequence alignment, NOv. 1996.*
Waterston, R. Accession No. Q19388, Database EMBL/Genbank/DDBJ, Nov. 1996.*
Bowie, J. et al., Deciphering the Message in Protein Sequences: Tolerance to Amino Acid Substitutions. Science, vol. 247, pp. 1306–1310, Mar. 1990.*
Pilbeam, C.C. et al., Comparison of the Effects of Various Lengths of Synthetic Human Parathyroid Hormone–Related Peptide (hPTHrP) of Malignancy on Bone Resorption and Formation in Organ Culture. Bone, vol. 14, pp. 717–720, Mar. 1990.*
Massague, Joan, The TGF–B Family of Growth and Differentiation Factors. Cell, vol. 49, pp. 437–438, May 1987.*
Benjamin, L.., et al., A Plasticity Window for Blood Vessel Remodeling is Defined by Pericyte Coverage of the Pre-formed Endothelial Network and is Regulated by PDGF–B and VEGF. Development, vol. 125, pp. 1591–1598, May 1998.*
Hillier et al, EST Database on STN, US Nat'l Library of Medicine Accession No. AA442366 Jun. 2, 1997.
Adams, M.D. et al, Database on (MPsrch), Accession No. AQ037466 (abstract) Jul. 10, 1998.

* cited by examiner

Primary Examiner—Yvonne Eyler
Assistant Examiner—Eileen B. O'Hara
(74) Attorney, Agent, or Firm—Fitzpatrick, Cella, Harper & Scinto

(57) ABSTRACT

Novel polynucleotides and the proteins encoded thereby are disclosed.

3 Claims, 2 Drawing Sheets

SEQUENCE LISTING

```
<160> NUMBER OF SEQ ID NOS: 268

<210> SEQ ID NO 1
<211> LENGTH: 1051
<212> TYPE: DNA
<213> ORGANISM: Homo sapiens

<400> SEQUENCE: 1
taggccatga aggccgcttg ctattattat gcaaataagt gttgtattac acatactaat      60
ttatgcatgg ttagattatg cagatgcatc acaaacatgg ttattgaata ataggatggg     120
gctcattctc tctaccatct ttataagcag ttttaagcaa attctcctgg taccaatgtg     180
gacatttaaa gaccctttac tcaatgaaat gtctctttcg tattcttttg ctttcatagt     240
taaagccatc agataagtgg aagagaaatc gtccaagttg ttaggttcaa gagtgttagt     300 ctcactttc aaattcgtag acttttttgt ttaaatgtaa tcttttcctt atagagaaaa      360
tctaaaatgc agttgcttgg catgaatgct ggcatttagt gagattttag tgtatatagc     420
cttgctgctt agctctaggt aacccatcaa attaaaatta catttcagg atttatagct      480 cattagaata tttatcttgg taagcttctt attctgtcag taatttctaa acaattcagc     540
```

```
ttggccaatt tgtgaaatcc cctaaaattt tgaaagtgaa ctcacaagcc ctatgcagta    600
tatttctcaa acaaatctta gtagaaaact tataagccat ccagtaaaaa ttccaaaggt    660
tgagaatgta gcaatattct tgagattcct aatgtctaga gtagttaatc agtgagattt    720
gatgggtgat gagtctaaga aatggatttt gccatggcca ggtgcagtgg cttacgcctg    780
taatcccagc actttgggag gccgaggtgg gcggatcacg aggtcaggag attgagacca    840
tcctggctaa catggtgaaa cccygtctct actaaaaata caaaaaaaaa aaattagccg    900
ggcgtggtgg cgggcacctg tagtccctgc tgaggcagga gaatggcttg aacccgggag    960
gtggagcttg cagtgagccg agatcacgcc actgcactcc agcctgggca acagagcaag   1020
attccgtctc aaaaacaaaa aaaaaaaaaa a                                  1051

<210> SEQ ID NO 2
<211> LENGTH: 75
<212> TYPE: PRT
<213> ORGANISM: Homo sapiens

<400> SEQUENCE: 2

Met Gln Ile Ser Val Val Leu His Ile Leu Ile Tyr Ala Trp Leu Asp
 1               5                  10                  15

Tyr Ala Asp Ala Ser Gln Thr Trp Leu Leu Asn Asn Arg Met Gly Leu
            20                  25                  30

Ile Leu Ser Thr Ile Phe Ile Ser Ser Phe Lys Gln Ile Leu Leu Val
        35                  40                  45

Pro Met Trp Thr Phe Lys Asp Pro Leu Leu Asn Glu Met Ser Leu Ser
    50                  55                  60

Tyr Ser Phe Ala Phe Ile Val Lys Ala Ile Arg
65                  70                  75

<210> SEQ ID NO 3
<211> LENGTH: 711
<212> TYPE: DNA
<213> ORGANISM: Homo sapiens

<400> SEQUENCE: 3
ttcaggttta gtgctattgt cattgaacac tggtattttc tgtatcatat aaaacattaa     60
aattcaaata attataagca tttggcaaaa acaagagaaa agaaacttgc catattttac    120
aagctgcaat tttagaaaag ctttaactta atgatagttt tatcattgtt tcttgtccc     180 aaacttatcc agggccatag aagtatgaat ctaattaaaa cagaaatggg aattattgca    240
cagaaatggg aaataactaa ttttaaatca gtcmaattgg cttcttatta aatacaataa    300
ttcttatgaa aatcatagta ccctattttc agacacagct gccagtttac acatttctca    360
gtatcctgaa aggaaaaaag tatagcccca cttatactat gtaaaattac caataaaata    420 ttttttatgac tacagatttt gcattttgt ttacaactat ttaaagagtt ttatgttgta    480
tttagaattt caacctagaa accacacagt acttaaattc tcctgggtc tcctgctttc    540 tcttaaccat ttgcttaata tatatctacc taaaggagac ttctgaattg taaatgaact    600
taaaaataga atgtggatgc aaaatatcac ataagcatc atgataacat ttgaagaaaa    660
aataaaactg tagaccctaa aaaaaaaaaa aaaaaaaaaa aaaaaaaaa a             711

<210> SEQ ID NO 4
<211> LENGTH: 46
<212> TYPE: PRT
<213> ORGANISM: Homo sapiens
```

```
<220> FEATURE:
<221> NAME/KEY: UNSURE
<222> LOCATION: (42)

<400> SEQUENCE: 4

Met Ile Val Leu Ser Leu Phe Ser Cys Pro Lys Leu Ile Gln Gly His
 1               5                  10                  15

Arg Ser Met Asn Leu Ile Lys Thr Glu Met Gly Ile Ile Ala Gln Lys
            20                  25                  30

Trp Glu Ile Thr Asn Phe Lys Ser Val Xaa Leu Ala Ser Tyr
        35                  40                  45

<210> SEQ ID NO 5
<211> LENGTH: 4529
<212> TYPE: DNA
<213> ORGANISM: Homo sapiens

<400> SEQUENCE: 5
cacctgggac ctctcacagg tggcatgccc ttccaagacc aggagagaac accacaactt      60
tgcaggacca gcatctctca gcctgcctcc tcccttttctc catatcaata tgatatggat    120
gagtactcat ccagcattgg atgatatgga tgaatggtca tccatcccag agcactgtcc    180
ctactccagt tccagggcac tcttagtctg ttcttggcac atacagcttt gcatctgtca    240
gtgtccatgc aaaagccaac acaagctgtg atggactgtg cattgggtag ccaccagagg    300
taactgccac ttatctatca gtcagccttt gacaggcctc acgtagatac gtacctccca    360
tcacctccaa gctggaatac actttactca tctgtaaaat gggtatgaac atgcctcctt    420
tgcagarctt ttttgaagat tctgcattta ctagtttaac aactgttcag tacctattat    480
gggcctagct accggcacat agtaaacact cagttacaat agctttaaga aaatctgtct    540
tagacaaagg agtttcaaaa ctatgtgaag agtatacaag aagtagtagt ccaaactgtt    600
ttttcagttg tttaatgatc tctatgataa agatgttcag ggagaggaat atcttgcgtg    660
ataactggag taaaacccac ttagatttct atgtccccaa acctctggtg tggtcagggt    720
tggcacctgc cctctcaacc atttgtctca ctgtacatgc atcttgtcta tgtcttccac    780
tagagaccat gagggcagag atcagaccta tgtacgttgc acattgctgt ccccagtacc    840
tagcacagca ccttgcccca gtacgcactt catatatatt tcctggacta cggcaggtga    900
gcccttttgtg agggttccac ctgcccactg gcctggcctt taatgtcagg ggagcatttc    960
tgatatatta atgcccctct aattgtgctg cattcgttta cataggcagt gcagcagcct   1020
ggctttggtg tttaaagacc ggattgcagt caaagctctg ctgtttgctg gctatgaact   1080
ccaggtaagt tgccaggttc ctctgagcac taatgataat attacctgcc tcacagggtt   1140
gttttgagag cagcttctgc tgctgcccca tgccccagaa ttatgaaaaa ccatttttgta   1200
aacttcaagt cacttcctct ccatagtaca gatcaatggt agaccagtga tcagggagga   1260
tacaaatcat aaccccaaaa aaggcttctt tgttgtattt tacctcaagt gttttcttag   1320
agaacctcaa caaaccacac tattttctag taatcagcca cttatcccac catttgcagt   1380
aaggaaaact gaggcacgcc ttgatggctt attcagcatc agcagcctca caaaagacag   1440
aagtctcctt tggattagct ttatcatctt tcccttaagc agagatgatg gtgccttttct   1500
cgctgctctg gctcagttaa gaagtcaagt ctgatttatt ggtcatccta actatcgttt   1560
cctgaaggcc cgaagccctg taatgctgtt gtctggcttc ccagatttat gaccatggtt   1620
tctggccccc aacaatatct ggagttcggt ttacatattc acttccacca tccaatccaa   1680
```

-continued

```
atcctcccag gcagcaatca agctggggct gattcctcat ccatttgtgg gctcactttt       1740
tctggcaagt cagccttcat tctccaggac gcttagaagc cgcatgttgg cggtggattg       1800
tgctacggga aagagtgaat gtgtagcctg cacatttgaa gccttgctgg ggtagagagc       1860
aacgctactg ctcctggaat gtccaggcca ctgttagaaa ggccatctta ttccttagaa       1920
gagtctagcc ctgctgcagg cttcagaaac gtgtgctcta agctcgttcc tgctcatttg       1980
aagcagtctt ctgaaaaggt ctgcagaaac ctgcctttac cctctccctc atcctgcgtg       2040
gcctttgtca catccttcct ccaaggttcc tctggtggtg gtagtaggga ggctgccacc       2100
tggctttgca tgtgggaaag cccagcctct ccctccacc  ctcacagcag gacagccaaa       2160
cttggatttt tcatgagga  agcaactctt atgagctctc tggttcagct ctctggttaa       2220
aagaccatac tgtgctgttt ctggggcagc acagacctgg ttgatcgtgt ccacaggaag       2280
aacagccttt gggattcatt agtctggtta agaccagccc tgcagcctcc tctgccagct       2340
atagaactat gtgttagagt tggtgctgaa gccagtcgca aacccatccc agatgcgtct       2400
ggtcttgttg atgttcaaat gccacctcct cctccaggaa gacttcacca cctccccaag       2460
gctgccttat gggctccttc tctgttccct ctcgactctc ccctctatc  actatggcca       2520 ttttatagaa ttttaattat tgtctcgggt gtctccacta gactgtaagt atcaagtgtg       2580
tagagacttt tgtttcaact ctgtatcccc aaaattcagc atagttcata gcacatacag       2640
tactctcaat gcctgttgaa tgaataaaga gtctgcttgc atgtaaaact acagtggttt       2700
ggtcttggag acacttgttt tggaattctt ctactgatat ggacagcatc aagatgatgg       2760
gaaatgtatt ggtctgggat ttgttttgcc tacaaagttt cttatgttgg ctcatctcca       2820
actagataaa accctgagtc taggcttccc cttctaacaa agctgctata cctttatgga       2880
cctccatttt cctgtctgta aaatgagagt gtgggctagc tagaaaaatt tctggtgtcc       2940
cccttgctgc tttgtaattc tggagtacgt tcggagaaca ccccaatgtg acaaaggatc       3000
tggaaattct tcataaaata ttcagggagg gagacaactc agggaacatg acaactgtct       3060
ggaattattt gaggggttgt catgtagaag atgaaaagga ttagattatc ttgaaaggcc       3120
ccacaggtta taaataagac caattattaa ttcattcaac aaatatttga gtacctgcca       3180
tgtgcaaggc actattctaa gcaataatga tgcagtaatg aatacaacag acaaaaatct       3240
tgttgccttt atggagttga cattctagtg aacagaaaca attcaaaaac aaacacaatg       3300
gagaggagct tcttggaccc tcaaaacgag ctgcctgtga actattgagc tctttgtgtt       3360
caggaatacg tttagtactt agaaatctgc ttccagtggc tgcttagact aaatgacctt       3420
gttaggtttt tttagcccag caatcccatg aatctaaggc tagcgaagat gtgtgatctc       3480
tctattctaa caccactaag ccaaatcatg acctcctctc aatggtaact gtcactctaa       3540
aaagagagat aaggtagatg cagtgggctg ttccttatgaa aaggcaccta aaaaatagta       3600
ctttagaaac atgcattgtg gtgggggtct gggtggaggg gttgcttttt cttgagatcc       3660
ctgtgatatt gaggatgaag aaagagaaac acaggggtg  ggcaacttcc ttgaaggacc       3720
agagagagtg agtcatgagg aagagaagga ggagacagag aacaggagag ttggggatga       3780
agcctttgat gagggagtg  aggaggggca gaagtaggag acagacatga ggaaaccacc       3840
aactgaagtc ccagaaaccc agcctccgtc ccctctaggt cctactgccg tcatcctctt       3900
tctgtaaagg tgagagtcta ggtgcagtgt cccaggttcc aaaacacaagt tcatactcat       3960 tgactagtgg gatgcccact gtgagagcag gaaggagggc tagagagatc taagagggca       4020
gaagccctgc cctgccagta ttttttgcct ccagccacct gctctgttct gagacatgcc       4080
```

-continued

| | |
|---|---|
| tgagaccagc tgcctacagg gggaccaggg tctgtttctg ctgttaacct tggttccctc | 4140 |
| ctgcattcct gcatgtgggg atgtagacag gaagcctgca ggtatggagc aattgaagca | 4200 |
| gagtctagat agagcccaga ctccttactt cccatagtac tattctgcat tttgtagtgc | 4260 |
| tgcttatgct tttcagtgtt tccacatcta tttactaata acatcatagt acaacagcaa | 4320 |
| gaacatggcc tcagaactca aagttctgga attctaatat tttatttgat tgtcagtatt | 4380 |
| tctgtgagat agataaaata ggaattattt cctctgatct gcaggtgagg aaactcagtc | 4440 |
| acaggagca catttatcca tacttgtgga gctatagtat aactagtatt aggacaagga | 4500 |
| tagccaacat agttaaaaaa aaaaaaaaa | 4529 |

<210> SEQ ID NO 6
<211> LENGTH: 98
<212> TYPE: PRT
<213> ORGANISM: Homo sapiens

<400> SEQUENCE: 6

```
Met Ile Ser Met Ile Lys Met Phe Arg Glu Arg Asn Ile Leu Arg Asp
 1               5                  10                  15

Asn Trp Ser Lys Thr His Leu Asp Phe Tyr Val Pro Lys Pro Leu Val
            20                  25                  30

Trp Ser Gly Leu Ala Pro Ala Leu Ser Thr Ile Cys Leu Thr Val His
        35                  40                  45

Ala Ser Cys Leu Cys Leu Pro Leu Glu Thr Met Arg Ala Glu Ile Arg
    50                  55                  60

Pro Met Tyr Val Ala His Cys Cys Pro Gln Tyr Leu Ala Gln His Leu
65                  70                  75                  80

Ala Pro Val Arg Thr Ser Tyr Ile Phe Pro Gly Leu Arg Gln Val Ser
                85                  90                  95

Pro Leu
```

<210> SEQ ID NO 7
<211> LENGTH: 3537
<212> TYPE: DNA
<213> ORGANISM: Homo sapiens

<400> SEQUENCE: 7

| | |
|---|---|
| aacttagatt tcttaaaact gtatacagat aactaatttt tattttgaaa tagcttttat | 60 |
| gttcttgtgt ttatgtaata gtcacattaa ttttgctctt ttggctttgt gttgtgttta | 120 |
| tttgatgact gttttattcg gtttaatttt ttcttgattt tgcaaattca tttttatcat | 180 |
| ctttaagtgg tggagtggcc atttcagctt gaaatatttc actgtcttta taatttcatt | 240 |
| ccatgcatgt gttttgtgtt tgtgacggtg tggtggtatt tagtctatag aagaacatgt | 300 |
| ggagcaggtc aaccaaaact gcatagcaga agattgccac atcaaggtag tattccaaga | 360 |
| tcttgtatt agctcattct ttaaagttca aggagctaac gcctcatctc tgatactaac | 420 |
| catgacctgc ccaactggct aactactcag agaactcata gtactcccat accacttcag | 480 |
| tggcacaggg gaggagatgc ttcactgtat ctggcttgct ctgtcttgcc cttggttctt | 540 |
| ctctttcttg ctccctgtcc catcttcact tgtcactttt tctgttttaa gcatggctgt | 600 |
| ttcatcttct tgattctgcc ttttctttcc ttcccatcac caaccctaag ccattgcatc | 660 |
| ttcctctcat cagtctcttt tattcctttc gaagtatccc tctttccaac ttttccttat | 720 |
| ttctgtctca ccacccttac ttcaaagggt ggtttctttg cggttttcta tggcttttta | 780 |

```
ctccactctg tgcctcttaa tgtatacaca ttcttattgc agaatattta tgcacttttg    840
gaagagctaa gagagacata ctactgtata aattactaat aaaaatatat tagccatgtt    900
ttataattaa tcagtatctt accatcacag tggaaattgg ggtgattaca ggacatcaga    960
gaatttaagc aaattttcca agctagtttt tcaacacatt aaagttactc ttacccttt    1020 ttcttgctgc tgctgctgct gctacatttt cttcttatcc tacatttaaa tcttatggga   1080
tgtgcataac tctaaataga gctgtgctgc agcaactaaa actgctgatg aatgttttct   1140
aggttgaagc tgatctgggc tatccaggtg gaaaggcgaa agtcatccat aaggaatctg   1200
atatgatcat ggcattttct gttaataagg caaattgtaa tgaaattgtt ttggcttcaa   1260
cacatgatgt tcaagaactt gatgttactt ctctactggc ctgtcagtca tacatatgga   1320
tcggagaaga atatgacaga gaatccaaaa gttcagatga tgttgattat cgtggttcca   1380
ctacaactct ttatcaaccc agtgcaacat cctattcagc aagtcaggtg catccacctt   1440
catctctgcc atggctgggc actggacaga ctagcactgg agctagtgtg cttatgaaaa   1500
ggaatctaca taatgttaag agaatgactt cacacccagt ccatcaatac tatcttacag   1560
gtgctcagga cggcagtgta cgaatgtttg aatggacgcg gcctcagcaa cttgtctgct   1620
ttcgtcaagc tggcaatgca agagttacta gattatattt taattcacaa ggcaacaagt   1680
gtggtgttgc ggatggagag ggttttctga gtatctggca agttaaccaa actgcatcaa   1740
atcctaaacc ttatatgagt tggcagtgcc acagtaaagc cacaagtgac tttgcattta   1800
ttacctcttc aagtctagtt gccacatctg gacactccaa tgacaataga aatgtttgcc   1860
tctgggacac attaatatca cccggaaaca gcctcattca tggtttcacg tgccacgatc   1920
atggtgccac ggtactgcag tatgcaccca acagcaact cctaatctcg gggggtagga   1980
aaggacacgt ctgcattttt gacatcaggc aaaggcagct cattcacacg ttccaggccc   2040
atgactcagc tattaaggct ctggccttgg atccctatga ggaatatttt accacaggtt   2100
cagcagaagg taacataaag gtttggagat tgacaggcca tggcctaatt cattcattta   2160
aaagtgaaca tgctaagcag tccatatttc gaaacattgg ggctggagtc atgcagattg   2220
acatcatcca gggcaatcgg ctcttctcct gtggtgcaga tggcacgctg aaaaccaggg   2280
ttttgcccaa tgcttttaac atccctaaca gaattcttga cattctataa agattggggt   2340
tttattttta tatacatttc agttaaaagg cacactacag tcatcactag gcaattctgc   2400
tttctaagca gttgtattga aaacagaaa tctctgtgta gaatttgaat atgacccaag   2460
ctgagtatta tctaaacagg ttggtggaat gaatgcgcat gtaccttatt atgctgacat   2520
actaaaaaaa ataaaaccta gtattgtatg aaggatagct attctttaca gcatttagca   2580
aacctgattc agaaaacatt tgagattagc aaattagtaa cttgaaataa tgaaaaggac   2640
gtttatacca aattaaggaa gaaaatgttg ctgatttggg tttttcttcc tgttcttacc   2700
actgactgaa gcatgcctgc agtctcctcc tctgttgaat gaaggataat cataaggtgt   2760
ttgttaggag cgctagacca cctggaaaac tttcttagct gtggagcagt gcgcagtgac   2820
cagttctctg ctgtgagagg ccgtttccat tctttcctgc tgaatatttt tcctgttagt   2880
gtttatactg agctagtact gtaacttgca aatgagtgca aatttaaatg caatgttta   2940 ctcacaattt gcacattcac attttttgga ctgctagttt ttctatttaa atatttgcct   3000
tcatgttagg aatgtactat gtgaacatga catatttgta gttaaccaaa cacaccttct   3060
tagtccagtt tagtactttt tctttttcgtg tattcaaggt taaacaccca aacatttaag   3120
gatatgttga aactacacca atagagcatt tcatatcata attaaaatga atgttaggct   3180
```

```
tcttgtggcc agttaatagt tgatgagatt ggtgacatta tttattgcca cagcctattg   3240
tataaactat gcagagttaa atatttgctt gtaaaatatt agccaatgtt gtcattattt   3300
tgatgtattt ccttggttat gaccaaaaat atgttgagat actgaaacta atgtctgtgt   3360
gtttaaatgt ttaccagcaa attgtcttat catgttaatg agaatgttca atgcctgtgt   3420
ggtaaatagt aaatacaatg gcataaaagt aactttctct gaagatgtga tgttcaggct   3480
gtgaaatata tatgtaaaag aaaaataaat gttatttgtt agaaaaaaaa aaaaaaa      3537
```

<210> SEQ ID NO 8
<211> LENGTH: 375
<212> TYPE: PRT
<213> ORGANISM: Homo sapiens

<400> SEQUENCE: 8

```
Met Ile Met Ala Phe Ser Val Asn Lys Ala Asn Cys Asn Glu Ile Val
 1               5                  10                  15

Leu Ala Ser Thr His Asp Val Gln Glu Leu Asp Val Thr Ser Leu Leu
            20                  25                  30

Ala Cys Gln Ser Tyr Ile Trp Ile Gly Glu Glu Tyr Asp Arg Glu Ser
        35                  40                  45

Lys Ser Ser Asp Asp Val Asp Tyr Arg Gly Ser Thr Thr Thr Leu Tyr
    50                  55                  60

Gln Pro Ser Ala Thr Ser Tyr Ser Ala Ser Gln Val His Pro Pro Ser
65                  70                  75                  80

Ser Leu Pro Trp Leu Gly Thr Gly Gln Thr Ser Thr Gly Ala Ser Val
                85                  90                  95

Leu Met Lys Arg Asn Leu His Asn Val Lys Arg Met Thr Ser His Pro
            100                 105                 110

Val His Gln Tyr Tyr Leu Thr Gly Ala Gln Asp Gly Ser Val Arg Met
        115                 120                 125

Phe Glu Trp Thr Arg Pro Gln Gln Leu Val Cys Phe Arg Gln Ala Gly
    130                 135                 140

Asn Ala Arg Val Thr Arg Leu Tyr Phe Asn Ser Gln Gly Asn Lys Cys
145                 150                 155                 160

Gly Val Ala Asp Gly Glu Gly Phe Leu Ser Ile Trp Gln Val Asn Gln
                165                 170                 175

Thr Ala Ser Asn Pro Lys Pro Tyr Met Ser Trp Gln Cys His Ser Lys
            180                 185                 190

Ala Thr Ser Asp Phe Ala Phe Ile Thr Ser Ser Leu Val Ala Thr
        195                 200                 205

Ser Gly His Ser Asn Asp Asn Arg Asn Val Cys Leu Trp Asp Thr Leu
    210                 215                 220

Ile Ser Pro Gly Asn Ser Leu Ile His Gly Phe Thr Cys His Asp His
225                 230                 235                 240

Gly Ala Thr Val Leu Gln Tyr Ala Pro Lys Gln Gln Leu Leu Ile Ser
                245                 250                 255

Gly Gly Arg Lys Gly His Val Cys Ile Phe Asp Ile Arg Gln Arg Gln
            260                 265                 270

Leu Ile His Thr Phe Gln Ala His Asp Ser Ala Ile Lys Ala Leu Ala
        275                 280                 285

Leu Asp Pro Tyr Glu Glu Tyr Phe Thr Thr Gly Ser Ala Glu Gly Asn
    290                 295                 300

Ile Lys Val Trp Arg Leu Thr Gly His Gly Leu Ile His Ser Phe Lys
```

|  |  | 305 |  |  |  | 310 |  |  |  | 315 |  |  |  | 320 |  |
|---|---|---|---|---|---|---|---|---|---|---|---|---|---|---|---|
| Ser | Glu | His | Ala | Lys | Gln | Ser | Ile | Phe | Arg | Asn | Ile | Gly | Ala | Gly | Val |
|  |  |  |  | 325 |  |  |  |  | 330 |  |  |  |  | 335 |  |
| Met | Gln | Ile | Asp | Ile | Ile | Gln | Gly | Asn | Arg | Leu | Phe | Ser | Cys | Gly | Ala |
|  |  |  | 340 |  |  |  |  | 345 |  |  |  |  | 350 |  |  |
| Asp | Gly | Thr | Leu | Lys | Thr | Arg | Val | Leu | Pro | Asn | Ala | Phe | Asn | Ile | Pro |
|  |  | 355 |  |  |  |  | 360 |  |  |  |  | 365 |  |  |  |
| Asn | Arg | Ile | Leu | Asp | Ile | Leu |
|  | 370 |  |  |  | 375 |  |

<210> SEQ ID NO 9
<211> LENGTH: 1466
<212> TYPE: DNA
<213> ORGANISM: Homo sapiens

<400> SEQUENCE: 9

| ccgcgcagga ggacggagcc ctaaccgcaa cccgcgccgc gccgcgccga tttgatttgt | 60 |
|---|---|
| atccactgtc accagcactg ctcacttagg actttctgga tccggaccca ggcagcgcac | 120 |
| actggactct tgaggaagaa ggagactcta attttggatt ccttggtgga ggaaaataaa | 180 |
| acactctggt cttgccgcca acgatgcaag tgtgactgct ggcgtcttca tgagctccag | 240 |
| aggtcacagc acgctaccaa ggactctcat ggcccctcgg atgatttccg agggagacat | 300 |
| argaggcatt gctcaaatca cctcctctct attcctgggc agaggcagtg tggcctccaa | 360 |
| tcggcacctc ctccaggctc gtggcatcac ctgcattgtt aatgctacca ttgagatccc | 420 |
| taatttcaac tggcccccaat ttgagtatgt taaagtgcct ctggctgaca tgccgcatgc | 480 |
| ccccattgga ctgtactttg acaccgtggc tgacaagatc cacagtgtga gcaggaagca | 540 |
| cggggccacc ttggtgcact gtgctgcagg ggtgagccgc tcagccacgc tgtgtatcgc | 600 |
| gtacctgatg aaattccaca acgtgtgcct gctggaggcg tacaactggg tgaaagcccg | 660 |
| gcgacctgtc atcaggccca acgtaggctt ctggaggcaa ctgatagact acgagcgcca | 720 |
| gctctttggg aagtcgacag ttaaaatggt acagacacct tatggcatag ttcccgacgt | 780 |
| ctatgagaag gagtcccgac acctgatgcc ttactggggg atttagtgcc actgaagcct | 840 |
| gcgtcagcag cccgagcggg gccggcatct gctccccgcc gtctgctccc tctccactct | 900 |
| cttctcaaat ggctgacttc tggttctccc tcaagtgttt tttacactgg gtgttcaaat | 960 |
| ttattttaag agatagggag ggaggggaca taaagggaat gcatacattg ctagtcacat | 1020 |
| ttttaaaatt aacattttgg aatagtgttt atggaaatct ttagctttta atcatttta | 1080 |
| ccaatttgaa cagtttaata aactggttct gctctcttct gaatctcakg ccttkggcac | 1140 |
| cttggtaggt gcaggaggag ctcagtgcaa aaatcacttt ggggcctcat taacccttta | 1200 |
| gagacaagyt ttgccccagg ytgcggacca gacagatgyt tagggaaggt tgataccagc | 1260 |
| ttcagtctct astggattag ccctactctt tcctttcccc tccattattt agtgactctg | 1320 |
| taagtaagtt aaatacaccc ttattattta gctgttaagt aactataatg aaatctgctg | 1380 |
| caaaatctct cttggaatcc atgtgcccag gattatatta gcattatttt taataaatct | 1440 |
| atatgcttaa caaaaaaaaa aaaaaa | 1466 |

<210> SEQ ID NO 10
<211> LENGTH: 198
<212> TYPE: PRT
<213> ORGANISM: Homo sapiens
<220> FEATURE:
<221> NAME/KEY: UNSURE -continued

<222> LOCATION: (25)

<400> SEQUENCE: 10

Met Ser Ser Arg Gly His Ser Thr Leu Pro Arg Thr Leu Met Ala Pro
 1               5                   10                  15

Arg Met Ile Ser Glu Gly Asp Ile Xaa Gly Ile Ala Gln Ile Thr Ser
            20                  25                  30

Ser Leu Phe Leu Gly Arg Gly Ser Val Ala Ser Asn Arg His Leu Leu
        35                  40                  45

Gln Ala Arg Gly Ile Thr Cys Ile Val Asn Ala Thr Ile Glu Ile Pro
    50                  55                  60

Asn Phe Asn Trp Pro Gln Phe Glu Tyr Val Lys Val Pro Leu Ala Asp
65                  70                  75                  80

Met Pro His Ala Pro Ile Gly Leu Tyr Phe Asp Thr Val Ala Asp Lys
                85                  90                  95

Ile His Ser Val Ser Arg Lys His Gly Ala Thr Leu Val His Cys Ala
            100                 105                 110

Ala Gly Val Ser Arg Ser Ala Thr Leu Cys Ile Ala Tyr Leu Met Lys
        115                 120                 125

Phe His Asn Val Cys Leu Leu Glu Ala Tyr Asn Trp Val Lys Ala Arg
    130                 135                 140

Arg Pro Val Ile Arg Pro Asn Val Gly Phe Trp Arg Gln Leu Ile Asp
145                 150                 155                 160

Tyr Glu Arg Gln Leu Phe Gly Lys Ser Thr Val Lys Met Val Gln Thr
                165                 170                 175

Pro Tyr Gly Ile Val Pro Asp Val Tyr Glu Lys Glu Ser Arg His Leu
            180                 185                 190

Met Pro Tyr Trp Gly Ile
        195

<210> SEQ ID NO 11
<211> LENGTH: 1521
<212> TYPE: DNA
<213> ORGANISM: Homo sapiens

<400> SEQUENCE: 11
aatttcttgg gcatttaccc atgccagaag gctaacctgg ggggaggggg gcgcttgtgc      60
tggtgaggca cttggataca tactgatgct gcaagttcag gggattttc ttactcttag     120 gtttaaccaa gaacactgag cagggaaaaa ccctgccttt cctaactgca tgtattttt     180 ccttttttgga aggtggtag agactcagaa gctttccttg ttttcttcag gcctgctccc    240
agttttctta acagtttctt tgttgctttt ctctctccct tgttgctttc catggcagta    300
atcctcctag agtccaagca gtctgttgta tggagcaggg tgtgtgggtt ttctgggccc    360
atcattatgg ctgcttcaga gtcagaagaa agccataggg cagtaggga gctcctattg     420 cctarccct ctccctttgt ggctcccact ctagctgcct attttttgctc atcagctggt     480 gagtcagtat gggccagcag ttctccctcc ctaagccctt gctactttat ggttagctt     540 tgcaggttttg gtggcttgag gggtggggggc aactcaccac tgccaggtaa ctccctgaag   600
ggtgggagtg gattatcttc taggctctta cccgcggtag ggaagggcat caacactgtc    660
ttccttccat tctcctttcc cccatcccat ttagtgctgc cacagggcag aagcacacaa    720
accaaccaca cagtctctga cttctcctaa gcactttgag ttgttgaatg gggctcaggg    780
gcaagagttt ttgctgccct ccccagcgtg gtcacagggt tattgaactg cctgcacttg    840

```
tttctcatgc aactccagca ttttccccag aagttgaact atggatagca gcttggtatg    900
gatttcctaa atcttaacat ttgaagcagc ttcttgaggc tggcaactat cctggtttct    960
gtcttggagg gggtggtttg tttgctgggg cccaacgtct gtcccaagtg gtggggtgag   1020
agtaagttaa ctttggtgcc aggtgagagg tgggggctct ttgcttagac tccctatcat   1080
ggaaagattg gagttttcta tgcagggcac tggggaaaag gattgctgat tctgactgac   1140
cctgatcaga gagattagga ttgtattttg acataggatt tggaacccat ctaaatgttg   1200
aagttccctg agacrgctct ccagctgctg agcctgcgcc aggggytaag cagcccctaa   1260
tgagaggctc tgctcccttt cccacctcgc caatgttgtt gttgctgcct ttttgatttg   1320
tatcctctgt tatagacatt ttttraaaac gatttcctct ttcattgtgc acaagtgctg   1380
agagtctgag gccccatttc tgctgtgtat atatatcctg actcggggct tttattcagc   1440
aaactgttca ttcttctgtc agacaatgtc atattcaact ctgttcatat taaaccactg   1500
tgaagcaaaa aaaaaaaaaa a                                              1521

<210> SEQ ID NO 12
<211> LENGTH: 81
<212> TYPE: PRT
<213> ORGANISM: Homo sapiens
<220> FEATURE:
<221> NAME/KEY: UNSURE
<222> LOCATION: (45)

<400> SEQUENCE: 12

Met Ala Val Ile Leu Leu Glu Ser Lys Gln Ser Val Val Trp Ser Arg
  1               5                  10                  15

Val Cys Gly Phe Ser Gly Pro Ile Ile Met Ala Ala Ser Glu Ser Glu
                 20                  25                  30

Glu Ser His Arg Ala Val Gly Glu Leu Leu Leu Pro Xaa Pro Ser Pro
             35                  40                  45

Phe Val Ala Pro Thr Leu Ala Ala Tyr Phe Cys Ser Ser Ala Gly Glu
         50                  55                  60

Ser Val Trp Ala Ser Ser Ser Pro Ser Leu Ser Pro Cys Tyr Phe Met
 65                  70                  75                  80

Gly

<210> SEQ ID NO 13
<211> LENGTH: 697
<212> TYPE: DNA
<213> ORGANISM: Homo sapiens

<400> SEQUENCE: 13
tgaagcttct gcacatgtag ttcctagagc tgctgcttat taaaatgtca acatcttcat     60
cttctagctg ggacaacctc ttagagtctc tctctctcag cacagtatgg aattggatac    120
aagcaagttt tttgggagag actagtgcac ctcagcaaac aagtttggga ctattatata    180
atcttgctcc agctgtgcaa atcatcttga ggatttcttt cttgatttta ttgggaatag    240
gaatatatgc cttatggaaa cgaagtattc agtcaattca gaaaacattg ttgtttgtaa    300
tcacactcta caaactttac aagaagggct cacatatttt tgaggctttg ctagccaacc    360
cagaaggaag tggtctccga attcaagaca ataataatct tttcctgtcc ttgggtctgc    420
aagagaaaat tttgaaaaaa cttaagacag tggaaaacaa aatgaagaac ctagaaggga    480
taatcgttgc tcaaaaacct gccacgaaga gggattgctc ctctgagccc tactgcagct    540
gctctgactg ccagagtccc ttgtccacat cagggtttac ttcccccatt tgaaatgtga    600
```

| | | |
|---|---|---|
| tggactccaa tctttccag gaaagcactg tttccctcat gtgtgcagtg gtgtatcaat | | 660 |
| aaagatagag aacgctattg aaaaaaaaaa aaaaaaa | | 697 |

```
<210> SEQ ID NO 14
<211> LENGTH: 182
<212> TYPE: PRT
<213> ORGANISM: Homo sapiens

<400> SEQUENCE: 14
```

Met Ser Thr Ser Ser Ser Ser Trp Asp Asn Leu Leu Glu Ser Leu
 1               5                  10                  15

Ser Leu Ser Thr Val Trp Asn Trp Ile Gln Ala Ser Phe Leu Gly Glu
                20                  25                  30

Thr Ser Ala Pro Gln Gln Thr Ser Leu Gly Leu Leu Tyr Asn Leu Ala
            35                  40                  45

Pro Ala Val Gln Ile Ile Leu Arg Ile Ser Phe Leu Ile Leu Leu Gly
        50                  55                  60

Ile Gly Ile Tyr Ala Leu Trp Lys Arg Ser Ile Gln Ser Ile Gln Lys
 65                 70                  75                  80

Thr Leu Leu Phe Val Ile Thr Leu Tyr Lys Leu Tyr Lys Lys Gly Ser
                85                  90                  95

His Ile Phe Glu Ala Leu Leu Ala Asn Pro Glu Gly Ser Gly Leu Arg
            100                 105                 110

Ile Gln Asp Asn Asn Asn Leu Phe Leu Ser Leu Gly Leu Gln Glu Lys
        115                 120                 125

Ile Leu Lys Lys Leu Lys Thr Val Glu Asn Lys Met Lys Asn Leu Glu
130                 135                 140

Gly Ile Ile Val Ala Gln Lys Pro Ala Thr Lys Arg Asp Cys Ser Ser
145                 150                 155                 160

Glu Pro Tyr Cys Ser Cys Ser Asp Cys Gln Ser Pro Leu Ser Thr Ser
                165                 170                 175

Gly Phe Thr Ser Pro Ile
            180

```
<210> SEQ ID NO 15
<211> LENGTH: 983
<212> TYPE: DNA
<213> ORGANISM: Homo sapiens

<400> SEQUENCE: 15
```

| | | |
|---|---|---|
| gggcgtggtg tcttgctgtc tcaggccctt cctctgtgca tccacgtaag tgtgggtaag | | 60 |
| ccaagaatag cctgggttca atccaccttt gccgttaat tggctgtgtg ctggtagaca | | 120 |
| agttacttag cttctctgtg cccccactcc ctcatctgca cgcgagaatt gtaacagagc | | 180 |
| cttcctcaga gcgatgatgg tgtttaggat gacatgcgct gcacagcaag tcctggccgt | | 240 |
| ggcggctgcc attgcagccc gtggggtcac cctggaggcc gtgattgctg atgttgtgct | | 300 |
| gttcttgtgc cttgctctct tcttctcggt gcccccagac tctctctgcc ttcggaggac | | 360 |
| ggcgtctctc tcgcctcaca ctgtgtgcac gggcagtgcg gacgggtgct ggcttggtct | | 420 |
| ttccagccct gcctcgctcg gggcctgctg catcgtagct caggcctagg acccatctct | | 480 |
| gtacctgcag gtcttgggtg ctgcccggca tgagtggagg agtttatcag aacaggacct | | 540 |
| tttataggag gttttaactt tagaagggaa tagaaaagtg tcatggcagc aatatttatt | | 600 |
| tctagatcac cctgagtttt ttttctttgt ttkgtttwat tgtcctcttt acaccatgag | | 660 |

```
tttttaatga tgaatgagtg aaggagtgac agtgcgggtt gagcatccct tatccagatg    720
ctccagaatc ggaaaccctc tgacaccgat gtggcacctc aggcatagct gagctagtga    780
cacctttgct ttctcatggg tcagtgtaca caaaccttgt ttcatgcaca aaattatcaa    840
aagtaccgca caaaattacc ctcaggctgt gtgtataagg tgtatatgaa acataaatga    900
atttcctgtt cagacctggg tcctatccaa acatatctca ttacgtatat acagatgttc    960
cgaatcagaa aaaaaaaaa aaa                                             983
```

<210> SEQ ID NO 16
<211> LENGTH: 91
<212> TYPE: PRT
<213> ORGANISM: Homo sapiens

<400> SEQUENCE: 16

Met Met Val Phe Arg Met Thr Cys Ala Ala Gln Gln Val Leu Ala Val
 1               5                  10                  15

Ala Ala Ala Ile Ala Ala Arg Gly Val Thr Leu Glu Ala Val Ile Ala
                20                  25                  30

Asp Val Val Leu Phe Leu Cys Leu Ala Leu Phe Phe Ser Val Pro Pro
            35                  40                  45

Asp Ser Leu Cys Leu Arg Arg Thr Ala Ser Leu Ser Pro His Thr Val
        50                  55                  60

Cys Thr Gly Ser Ala Asp Gly Cys Trp Leu Gly Leu Ser Ser Pro Ala
65                  70                  75                  80

Ser Leu Gly Ala Cys Cys Ile Val Ala Gln Ala
                85                  90

<210> SEQ ID NO 17
<211> LENGTH: 267
<212> TYPE: DNA
<213> ORGANISM: Homo sapiens

<400> SEQUENCE: 17

```
ggaaaacacc ctaaatgtgc atgcatctcc aagtcctcca ggagccacgc gtgctccaca    60
ttctttcttt tcctggcaca ttttggctg ccaggatgac tgagaaaata atcaaccttc    120
ccatcagtca cctgtttctc ttcctgagca gtttccttct gccactcagt caaaaggccc    180
acaaacatgt tcaccaagtc ctaacctcta aagggagag agacttcaga gactgatttt    240
tagctgcaac caaaaaaaaa aaaaaaa                                        267
```

<210> SEQ ID NO 18
<211> LENGTH: 73
<212> TYPE: PRT
<213> ORGANISM: Homo sapiens

<400> SEQUENCE: 18

Met Cys Met His Leu Gln Val Leu Gln Glu Pro Arg Val Leu His Ile
 1               5                  10                  15

Leu Ser Phe Pro Gly Thr Phe Leu Ala Ala Arg Met Thr Glu Lys Ile
                20                  25                  30

Ile Asn Leu Pro Ile Ser His Leu Phe Leu Phe Leu Ser Ser Phe Leu
            35                  40                  45

Leu Pro Leu Ser Gln Lys Ala His Lys His Val His Gln Val Leu Thr
        50                  55                  60

Ser Arg Arg Glu Arg Asp Phe Arg Asp
65                  70

-continued

<210> SEQ ID NO 19
<211> LENGTH: 679
<212> TYPE: DNA
<213> ORGANISM: Homo sapiens

<400> SEQUENCE: 19

```
aaacttctgg gatcacaggc atgagccacc gtgcctggcc ctgatctggg atttaaaggg      60
gcagttgctg agcaaataga agccagggca agaaaggatt tatgtgcttg ggattcttga     120
ggggttttcc agagtcagtc cccaattctg atgtttttat acgcaacact aggggtcctt     180
ctgaagttat cccggcccct gggaaactca cgtggcatgg ggccccttc tgccctggtc      240
tctttcatcc catctgtccc ggccccagag cctgtccagt ctggtcctct ctgtcctgct     300
tggtttgtca ccatgtgatg ttgggatggc ttgtctttgc cgcctcactt cctaagctga     360
cagacgtgtc tgctagggac caccagctcc caagccgcat gacggtgctt ccttcaagg      420
ttcagaggct tcccttcag tctggcccat ctcccacatc ctaatggctc tgctgtctca      480
ggggcagctc tcctttttaa cttattggca gagctgggat gacttatagg tccctggctc     540
agtgagtaag caagttcaga gacttggctt tggccatttt gttctcttag gctcatcctt     600
ggatgccaac agggaaataa cctgccagat ttcagtcact acttttagaa agttaaaaaa     660
aaaaaaaaaa aaaaaaaa                                                    679
```

<210> SEQ ID NO 20
<211> LENGTH: 120
<212> TYPE: PRT
<213> ORGANISM: Homo sapiens

<400> SEQUENCE: 20

```
Met Cys Leu Gly Phe Leu Arg Gly Phe Pro Glu Ser Val Pro Asn Ser
  1               5                  10                  15

Asp Val Phe Ile Arg Asn Thr Arg Gly Pro Ser Glu Val Ile Pro Ala
             20                  25                  30

Pro Gly Lys Leu Thr Trp His Gly Ala Pro Phe Cys Pro Gly Leu Phe
         35                  40                  45

His Pro Ile Cys Pro Gly Pro Arg Ala Cys Pro Val Trp Ser Ser Leu
     50                  55                  60

Ser Cys Leu Val Cys His His Val Met Leu Gly Trp Leu Val Phe Ala
 65                  70                  75                  80

Ala Ser Leu Pro Lys Leu Thr Asp Val Ser Ala Arg Asp His Gln Leu
                 85                  90                  95

Pro Ser Arg Met Thr Val Leu Ser Phe Lys Val Gln Arg Leu Pro Phe
            100                 105                 110

Gln Ser Gly Pro Ser Pro Thr Ser
        115                 120
```

<210> SEQ ID NO 21
<211> LENGTH: 3340
<212> TYPE: DNA
<213> ORGANISM: Homo sapiens

<400> SEQUENCE: 21

```
ggaggaacac ggcaacttcc ttattacagt tcctggaggg tcagatggtc caagtggagt      60
actgatctgc tctgaaaact atattactta caagaacttt ggtgaccagc cagatatccg     120
ctgtccaatt cccaggaggc ggaatgacct ggatgaccct gaaagaggaa tgattttgt      180
ctgctctgca acccataaaa ccaaatcgat gttcttcttt ttggctcaaa ctgagcaggg     240
```

-continued

```
agatatcttt aagatcactt tggagacaga tgaagatatg gttactgaga tccggctcaa    300
atattttgat actgtacccg ttgctgctgc catgtgtgtg cttaaaacag ggttcctttt    360
tgtagcatca gaatttggaa accattactt atatcaaatt gcacatcttg gagatgatga    420
tgaagaacct gagttttcat cagccatgcc tctggaagaa ggagacacat tcttttttca    480
gccmagacca cttaaaaacc ttgtgctggt tgatgagttg gacagcctct ctcccattct    540
gttttgccag atagctgatc tggccaatga agatactcca cagttgtatg tggcctgtgg    600
taggggaccc cgatcatctc tgagagtcct aagacatgga cttgaggtgt cagaaatggc    660
tgtttctgag ctacctggta accccaacgc tgtctggaca gtgcgtcgac acattgaaga    720
tgagtttgat gcctacatca ttgtgtcttt cgtgaatgcc accctagtgt tgtccattgg    780
agaaactgta gaagaagtga ctgactctgg gttcctgggg accaccccga ccttgtcctg    840
ctccttatta ggagatgatg ccttggtgca ggtctatcca gatggcattc ggcacatacg    900
agcagacaag agagtcaatg agtggaagac ccctggaaag aaaacaattg tgaagtgtgc    960
agtgaaccag cgacaagtgg tgattgccct gacaggagga gagctggtct atttcgagat   1020
ggatccttca ggacagctga atgagtacac agaacggaag gagatgtcag cagatgtggt   1080
gtgcatgagt ctggccaatg taccccctgg agagcagcgt tctcgcttcc tggctgtggg   1140
gcttgtggac aacactgtca gaatcatctc cctggatccc tcagactgtt gcaacctct   1200
aagcatgcag gctctcccag cccagcctga gtccttgtgt atcgtggaaa tgggtgggac   1260
tgagaagcag gatgagctgg gtgagagggg ctcgattggc ttcctatacc tgaatattgg   1320
gctacagaac ggtgtgctgc tgaggactgt cttggaccct gtcactgggg atttgtctga   1380
tactcgcact cggtacctgg ggtcccgtcc tgtgaagctc ttccgagtcc gaatgcaagg   1440
ccaggaggca gtattggcca tgtcaagccg ctcatggttg agctattctt accaatctcg   1500
cttccatctc accccactgt cttacgagac actggaattt gcatcgggtt ttgcctcgga   1560
acagtgtccc gagggcattg tggccatctc caccaacacc ctacggattt tggcattaga   1620
gaagctcggt gctgtcttca atcaagtagc cttcccactg cagtacacac caggaaatt   1680
tgtcatccac cctgagagta acaaccttat tatcattgaa acggaccaca atgcctacac   1740
tgaggccacg aaagctcaga gaaagcagca gatggcagag gaaatggtgg aagcagcagg   1800
ggaggatgag cgggagctgg ccgcagagat ggcagcagca ttcctcaatg aaaacctccc   1860
tgaatccatc tttggagctc ccaaggctgg caatgggcag tgggcctctg tgatccgagt   1920
gatgaatccc attcaaggga acacactgga ccttgtccag ctggaacaga atgaggcagc   1980
ttttagtgtg gctgtgtgca ggttttccaa cactggtgaa gactggtatg tgctggtggg   2040
tgtggccaag gacctgatac taaaccccg atctgtggca ggggcttcg tctatactta    2100
caagcttgtg aacaatgggg aaaaactgga gtttttgcac aagactcctg tggaagaggt   2160
ccctgctgct attgccccat tccaggggag ggtgttgatt ggtgtgggga agctgttgcg   2220
tgtctatgac ctgggaaaga agaagttact ccgaaaatgt gagaataagc atattgccaa   2280
ttatatctct gggatccaga ctattggaca tagggtaatt gtatctgatg tccaagaaag   2340
tttcatctgg gttcgctaca agcgtaatga aaaccagctt atcatctttg ctgatgatac   2400
ctaccccga tgggtcacta cagccagcct cttggactat gacactgtgg ctgggcaga   2460
caagtttggc aacatatgtg tggtgaggct cccacctaac accaatgatg aagtagatga   2520
ggatcctaca ggaaacaaag ccctgtggga ccgtggcttg ctcaatgggg cctcccagaa   2580
```

```
ggcagaggtg atcatgaatt accatgtcgg ggagacggtg ctgtccttgc agaagaccac    2640
gctgatccct ggaggctcag aatcacttgt ctataccacc ttgtctggag gaattggcat    2700
ccttgtgcca ttcacgtccc atgaggacca tgacttcttc cagcatgtgg aaatgcacct    2760
gcggtctgaa catcccctc tctgtgggcg ggaccacctc agctttcgct cctactactt     2820
ccctgtgaag aatgtgattg atggagacct ctgtgagcag ttcaattcca tggaacccaa    2880
caaacaaaag aacgtctctg aagaactgga ccgaacccca cccgaagtgt ccaagaaact    2940
cgaggatatc cggacccgct acgccttctg agccctcctt tcccggtggg gcttgccaga    3000
gactgtgtgt tttgtttccc ccaccaccat castgccacc tggcttctgc catgtggcag    3060
gagggtgact ggataattaa gastgcatta tgaaagtcaa cagctctttc ccctcagctc    3120
ttctcstgga atgactggct tccccctcaaa ttggcactga gatttgctac acttctcccc   3180
acctggtaca tgatacatga ccccaggttc cagtgtagaa cctgagtccc ccattcccca    3240
aagccatccc tgcattgata tgtcttgact ctcctgtcta cttttgcaca caccttaat    3300 ttttaattgg ttttcttgta aatacaaaaa aaaaaaaaaa                          3340
```

<210> SEQ ID NO 22
<211> LENGTH: 933
<212> TYPE: PRT
<213> ORGANISM: Homo sapiens

<400> SEQUENCE: 22

```
Met Ile Phe Val Cys Ser Ala Thr His Lys Thr Lys Ser Met Phe Phe
 1               5                  10                  15

Phe Leu Ala Gln Thr Glu Gln Gly Asp Ile Phe Lys Ile Thr Leu Glu
                20                  25                  30

Thr Asp Glu Asp Met Val Thr Glu Ile Arg Leu Lys Tyr Phe Asp Thr
            35                  40                  45

Val Pro Val Ala Ala Ala Met Cys Val Leu Lys Thr Gly Phe Leu Phe
        50                  55                  60

Val Ala Ser Glu Phe Gly Asn His Tyr Leu Tyr Gln Ile Ala His Leu
    65                  70                  75                  80

Gly Asp Asp Asp Glu Glu Pro Glu Phe Ser Ser Ala Met Pro Leu Glu
                85                  90                  95

Glu Gly Asp Thr Phe Phe Phe Gln Pro Arg Pro Leu Lys Asn Leu Val
                100                 105                 110

Leu Val Asp Glu Leu Asp Ser Leu Ser Pro Ile Leu Phe Cys Gln Ile
            115                 120                 125

Ala Asp Leu Ala Asn Glu Asp Thr Pro Gln Leu Tyr Val Ala Cys Gly
        130                 135                 140

Arg Gly Pro Arg Ser Ser Leu Arg Val Leu Arg His Gly Leu Glu Val
    145                 150                 155                 160

Ser Glu Met Ala Val Ser Glu Leu Pro Gly Asn Pro Asn Ala Val Trp
                165                 170                 175

Thr Val Arg Arg His Ile Glu Asp Glu Phe Asp Ala Tyr Ile Ile Val
            180                 185                 190

Ser Phe Val Asn Ala Thr Leu Val Leu Ser Ile Gly Glu Thr Val Glu
        195                 200                 205

Glu Val Thr Asp Ser Gly Phe Leu Gly Thr Thr Pro Thr Leu Ser Cys
    210                 215                 220

Ser Leu Leu Gly Asp Asp Ala Leu Val Gln Val Tyr Pro Asp Gly Ile
225                 230                 235                 240
```

-continued

```
Arg His Ile Arg Ala Asp Lys Arg Val Asn Glu Trp Lys Thr Pro Gly
                245                 250                 255

Lys Lys Thr Ile Val Lys Cys Ala Val Asn Gln Arg Gln Val Val Ile
            260                 265                 270

Ala Leu Thr Gly Gly Glu Leu Tyr Phe Glu Met Asp Pro Ser Gly
        275                 280                 285

Gln Leu Asn Glu Tyr Thr Glu Arg Lys Glu Met Ser Ala Asp Val Val
    290                 295                 300

Cys Met Ser Leu Ala Asn Val Pro Pro Gly Glu Gln Arg Ser Arg Phe
305                 310                 315                 320

Leu Ala Val Gly Leu Val Asp Asn Thr Val Arg Ile Ile Ser Leu Asp
                325                 330                 335

Pro Ser Asp Cys Leu Gln Pro Leu Ser Met Gln Ala Leu Pro Ala Gln
            340                 345                 350

Pro Glu Ser Leu Cys Ile Val Glu Met Gly Gly Thr Glu Lys Gln Asp
        355                 360                 365

Glu Leu Gly Glu Arg Gly Ser Ile Gly Phe Leu Tyr Leu Asn Ile Gly
    370                 375                 380

Leu Gln Asn Gly Val Leu Leu Arg Thr Val Leu Asp Pro Val Thr Gly
385                 390                 395                 400

Asp Leu Ser Asp Thr Arg Thr Arg Tyr Leu Gly Ser Arg Pro Val Lys
                405                 410                 415

Leu Phe Arg Val Arg Met Gln Gly Gln Glu Ala Val Leu Ala Met Ser
            420                 425                 430

Ser Arg Ser Trp Leu Ser Tyr Ser Tyr Gln Ser Arg Phe His Leu Thr
        435                 440                 445

Pro Leu Ser Tyr Glu Thr Leu Glu Phe Ala Ser Gly Phe Ala Ser Glu
    450                 455                 460

Gln Cys Pro Glu Gly Ile Val Ala Ile Ser Thr Asn Thr Leu Arg Ile
465                 470                 475                 480

Leu Ala Leu Glu Lys Leu Gly Ala Val Phe Asn Gln Val Ala Phe Pro
                485                 490                 495

Leu Gln Tyr Thr Pro Arg Lys Phe Val Ile His Pro Glu Ser Asn Asn
            500                 505                 510

Leu Ile Ile Ile Glu Thr Asp His Asn Ala Tyr Thr Glu Ala Thr Lys
        515                 520                 525

Ala Gln Arg Lys Gln Gln Met Ala Glu Glu Met Val Glu Ala Ala Gly
    530                 535                 540

Glu Asp Glu Arg Glu Leu Ala Ala Glu Met Ala Ala Phe Leu Asn
545                 550                 555                 560

Glu Asn Leu Pro Glu Ser Ile Phe Gly Ala Pro Lys Ala Gly Asn Gly
                565                 570                 575

Gln Trp Ala Ser Val Ile Arg Val Met Asn Pro Ile Gln Gly Asn Thr
            580                 585                 590

Leu Asp Leu Val Gln Leu Glu Gln Asn Glu Ala Ala Phe Ser Val Ala
        595                 600                 605

Val Cys Arg Phe Ser Asn Thr Gly Glu Asp Trp Tyr Val Leu Val Gly
610                 615                 620

Val Ala Lys Asp Leu Ile Leu Asn Pro Arg Ser Val Ala Gly Gly Phe
                625                 630                 635                 640

Val Tyr Thr Tyr Lys Leu Val Asn Asn Gly Glu Lys Leu Glu Phe Leu
            645                 650                 655

His Lys Thr Pro Val Glu Glu Val Pro Ala Ala Ile Ala Pro Phe Gln
```

```
                660                 665                 670
    Gly Arg Val Leu Ile Gly Val Gly Lys Leu Leu Arg Val Tyr Asp Leu
                675                 680                 685
    Gly Lys Lys Lys Leu Leu Arg Lys Cys Glu Asn Lys His Ile Ala Asn
                690                 695                 700
    Tyr Ile Ser Gly Ile Gln Thr Ile Gly His Arg Val Ile Val Ser Asp
    705                 710                 715                 720
    Val Gln Glu Ser Phe Ile Trp Val Arg Tyr Lys Arg Asn Glu Asn Gln
                        725                 730                 735
    Leu Ile Ile Phe Ala Asp Asp Thr Tyr Pro Arg Trp Val Thr Thr Ala
                    740                 745                 750
    Ser Leu Leu Asp Tyr Asp Thr Val Ala Gly Ala Asp Lys Phe Gly Asn
                755                 760                 765
    Ile Cys Val Val Arg Leu Pro Pro Asn Thr Asn Asp Glu Val Asp Glu
    770                 775                 780
    Asp Pro Thr Gly Asn Lys Ala Leu Trp Asp Arg Gly Leu Leu Asn Gly
    785                 790                 795                 800
    Ala Ser Gln Lys Ala Glu Val Ile Met Asn Tyr His Val Gly Glu Thr
                    805                 810                 815
    Val Leu Ser Leu Gln Lys Thr Thr Leu Ile Pro Gly Gly Ser Glu Ser
                820                 825                 830
    Leu Val Tyr Thr Thr Leu Ser Gly Gly Ile Gly Ile Leu Val Pro Phe
                835                 840                 845
    Thr Ser His Glu Asp His Asp Phe Phe Gln His Val Glu Met His Leu
                850                 855                 860
    Arg Ser Glu His Pro Pro Leu Cys Gly Arg Asp His Leu Ser Phe Arg
    865                 870                 875                 880
    Ser Tyr Tyr Phe Pro Val Lys Asn Val Ile Asp Gly Asp Leu Cys Glu
                        885                 890                 895
    Gln Phe Asn Ser Met Glu Pro Asn Lys Gln Lys Asn Val Ser Glu Glu
                    900                 905                 910
    Leu Asp Arg Thr Pro Pro Glu Val Ser Lys Lys Leu Glu Asp Ile Arg
                915                 920                 925
    Thr Arg Tyr Ala Phe
            930

<210> SEQ ID NO 23
<211> LENGTH: 1496
<212> TYPE: DNA
<213> ORGANISM: Homo sapiens

<400> SEQUENCE: 23
gccagcccca ccgctgaccc agagcttgga actgaggagc cccaggcagg gagttgatgg      60
gaccccgaaa gaaagtgtgg gatggagggt ctagccccgg gcagctgcgg ctcartgggc     120
agcsggaccc cgggaggagg aggcggcacc tccgccccac agcctcaccc ggcccttccc     180
tcccgctcac ttggctgcaa gccagtgtcc tccgtggtga gccggccctt gctgctctgc     240
atgatcaggc tcgggaacct gaggtcagcc atgctgtgct ccggcagccc ctgcctgcct     300
cctcgcggag cccttctgcc ccttgggctg cstgtgccgg ggcgaggcct gtgtggggcc     360
tgtgatggca gctcctggaa aacgctgtgg ggcagggtg aggcccacga ggccatgggg      420
acagctcacc atgggagca cacctgcagg tggggagggc tgcctttccc cacagcactc      480
agaagatgca cgtggccggg gctgatgagc tgccccgagc caccctgggg ggtcactgag     540
```

-continued

```
ggcagggctg gcagcacaga tgcccctgct cggggcctga gtggggccag cgctgacagg    600
ctgtcctctc gtcctctttt tcatggcggc ggtccttctt cagatgacga cgccggctct    660
gcacccctga agagcagcgg gcagcaccag aatgacaaag caagaacgt ccgccagagg     720 aactcttcct gaggcaggtg gcccgaggac gctccctgct ccgcgtctgc gccgccgccg    780
gagtccactc ccagtgcttg caagattcca agttctcacc tcttaaagaa acccaccccc    840
gtagattccc atcatacact tccttctttt ttaaaaaagt tgggttttct ccattcagga    900
ttctgttcct taggattttt tccttctgaa gtgtttcacg agagcccggg agctgctgcc    960
ctgcggcccc gtctgtggct ttcagcctct gggtctgagt catggccggg tgggcggcac   1020
agccttctcc actggccgga gtcagtgcca ggtccttgcc ctttgtggaa agtcacaggt   1080
cacacgaggg gccccgtgtc ctgcctgtct gaagccaatg ctgtctggtt gcgccatttt   1140
tgtgctttta tgtttaattt tatgagggcc acgggtctgt gttcgactca gcctcaggga   1200
cgactctgac ctcttggcca cagaggactc acttgcccac accgagggcg accccgtcac   1260
agcctcaagt cactcccaag cccctcctt gtctgtgcat ccgggggcag ctctggaggg    1320
ggtttgctgg ggaactggcg ccatcgccgg gactccagaa ccgcagaagc ctccccagct   1380
caccctggga ggacggccgg ctctctatag caccagggct cacgtgggaa ccccctccc    1440 acccaccgcc acaataaaga tcgcccccac ctccacctc aaaaaaaaaa aaaaaa        1496
```

<210> SEQ ID NO 24
<211> LENGTH: 216
<212> TYPE: PRT
<213> ORGANISM: Homo sapiens
<220> FEATURE:
<221> NAME/KEY: UNSURE
<222> LOCATION: (12)
<220> FEATURE:
<221> NAME/KEY: UNSURE
<222> LOCATION: (15)
<220> FEATURE:
<221> NAME/KEY: UNSURE
<222> LOCATION: (84)

<400> SEQUENCE: 24

```
Met Glu Gly Leu Ala Pro Gly Ser Cys Gly Ser Xaa Gly Ser Xaa Thr
 1               5                  10                  15

Pro Gly Gly Gly Gly Thr Ser Ala Pro Gln Pro His Pro Ala Leu
                20                  25                  30

Pro Ser Arg Ser Leu Gly Cys Lys Pro Val Ser Val Val Ser Arg
        35                  40                  45

Pro Leu Leu Leu Cys Met Ile Arg Leu Gly Asn Leu Arg Ser Ala Met
    50                  55                  60

Leu Cys Ser Gly Ser Pro Cys Leu Pro Pro Arg Gly Ala Leu Leu Pro
65                  70                  75                  80

Leu Gly Leu Xaa Val Pro Gly Arg Gly Leu Cys Gly Ala Cys Asp Gly
                85                  90                  95

Ser Ser Trp Lys Thr Leu Trp Gly Arg Gly Glu Ala His Glu Ala Met
                100                 105                 110

Gly Thr Ala His His Gly Glu His Thr Cys Arg Trp Gly Gly Leu Pro
            115                 120                 125

Phe Pro Thr Ala Leu Arg Arg Cys Thr Trp Pro Gly Leu Met Ser Cys
    130                 135                 140

Pro Glu Pro Pro Leu Gly Val Thr Glu Gly Arg Ala Gly Ser Thr Asp
145                 150                 155                 160
```

```
Ala Pro Ala Arg Gly Leu Ser Gly Ala Ser Ala Asp Arg Leu Ser Ser
            165                 170                 175

Arg Pro Leu Phe His Gly Gly Pro Ser Ser Asp Asp Asp Ala Gly
        180                 185                 190

Ser Ala Pro Leu Lys Ser Ser Gly Gln His Gln Asn Asp Lys Gly Lys
        195                 200                 205

Asn Val Arg Gln Arg Asn Ser Ser
    210                 215

<210> SEQ ID NO 25
<211> LENGTH: 2113
<212> TYPE: DNA
<213> ORGANISM: Homo sapiens

<400> SEQUENCE: 25
gcagctatgg ctgctggcgt accctgtgcg ttagtcacca gctgctcctc cgtcttctca      60
ggagaccagc tggtccaaca tatccttgga acagaagatc ttattgtgga agtgacttcc    120
aatgatgctg tgagatttta tccctggacc attgataata aatactattc agcagacatc    180
aatctatgtg tggtgccaaa caaatttctt gttactgcag agattgcaga atctgtccaa    240
gcatttgtgg tttactttga cagcacacaa aaatcgggcc ttgatagtgt ctcctcrtgg    300
cttccactgg caaaagcatg gttacctgag gtgatgatct tggtctgcga tagagtgtct    360
gaagatggta taaccgaca aaaagctcaa gaatggtgcc tcaaacatgg ctttgaattg    420
gtagaactta gtccagagga gttgcctgag gaggatgatg acttcccaga atctacagga    480
gtaaagcgaa ttgtccaagc cctgaatgcc aatgtgtggt ccaatgtagt gatgaagaat    540
gataggaacc aaggctttag ccttctcaac tcattgactg gaacaaacca tagcattggg    600
tcagcagatc cctgtcaccc agagcaaccc catttgccag cagcagatag tactgaatcc    660
ctctctgatc atcggggtgg tgcatctaac acaacagatg cccaggttga tagcattgtg    720
gatcccatgt tagatctgga tattcaagaa ttagccagtc ttaccactgg aggaggagat    780
gtggagaatt tgaaagact cttttcaaag ttaaaggaaa tgaaagacaa ggctgcgacg    840
cttcctcatg agcaaagaaa agtgcatgca gaaaaggtgg ccaaagcatt ctggatggca    900
atcgggggag acagagatga aattgaaggc ctttcatctg atgaagagca ctgaattatt    960
catactaggg tttgaccaac aaagatgcta gctgtctctg agatacctct ctactcagcc   1020
cagtcatatt ttgccaaaat tgcccttatc atgttggctg cctgacttgt ttataggggtc   1080 cccttaattt tagttttttag taggaggtta aggagaaatc ttttttttcc tcagtatatt   1140
gtaagagagt gaggaataca gtgatagtaa tgagtgagga tttcttaaat gtactttttt   1200
tttgttctag gaatgagggt aggataaatc tcagaggtct gtgtgattta ctcaagttga   1260
agacaacctc caggccattc ctggtcaacg ttttaagtag catttccagc attcacactt   1320
gatactgcac atcaggagtt gtgtcacctt tcctgggtga tttgggtttt ctccattcaa   1380
ggagcttgta gctctgagct atgatgcttt tattgggagg aaaggaggca gctgcagaat   1440
tgatgtgagc tatgtggggc cgaagtctca gcccgcagct aagtctctac ctaagaaaat   1500
gcctctgggc attcttttga agtatagtgt ctgagctcat gctagaaaga atcaaaaagc   1560
cagtgtggat ttttagactg taataaatga ggcaaaggat ttctattcca gtgggaagaa   1620
aacctctcta ctgagttgtg ggggatatgt tgtatgttag agagaacctt aaggagtcct   1680
tgtatgggcc atggagacag tatgtgataa cataccgtga ttttcatgaa gaaattcttc   1740
tgtcttagag ttctcccctg ctgcttgaga tgccagagct gtgttgttgc acacctgcaa   1800
```

-continued

```
aacaaggcac atttccccct ttctctttaa agccaaagag agatcactgc caaagtggga      1860
gcactaaggg gtgggtgggg aagtgaaatg ttaggcgatg aattcctgag caccttgttt      1920
ttcttccaag gttcgtagct tctctctgcc cttccaagcc tgtaacctcg gaggactatc      1980
ttttgttctt tatcctttgt cttgttwgag tgggtcagcc ccagaggaac tgataagcaa      2040
atggcaagtt tttaaaggaa gagtggaaag tactgcaaat aaaaatcctt atttgttaaa      2100
aaaaaaaaaa aaa                                                        2113
```

<210> SEQ ID NO 26
<211> LENGTH: 315
<212> TYPE: PRT
<213> ORGANISM: Homo sapiens

<400> SEQUENCE: 26

```
Met Ala Ala Gly Val Pro Cys Ala Leu Val Thr Ser Cys Ser Ser Val
 1               5                  10                  15

Phe Ser Gly Asp Gln Leu Val Gln His Ile Leu Gly Thr Glu Asp Leu
            20                  25                  30

Ile Val Glu Val Thr Ser Asn Asp Ala Val Arg Phe Tyr Pro Trp Thr
        35                  40                  45

Ile Asp Asn Lys Tyr Tyr Ser Ala Asp Ile Asn Leu Cys Val Val Pro
    50                  55                  60

Asn Lys Phe Leu Val Thr Ala Glu Ile Ala Glu Ser Val Gln Ala Phe
65                  70                  75                  80

Val Val Tyr Phe Asp Ser Thr Gln Lys Ser Gly Leu Asp Ser Val Ser
                85                  90                  95

Ser Trp Leu Pro Leu Ala Lys Ala Trp Leu Pro Glu Val Met Ile Leu
            100                 105                 110

Val Cys Asp Arg Val Ser Glu Asp Gly Ile Asn Arg Gln Lys Ala Gln
        115                 120                 125

Glu Trp Cys Leu Lys His Gly Phe Glu Leu Val Glu Leu Ser Pro Glu
    130                 135                 140

Glu Leu Pro Glu Glu Asp Asp Asp Phe Pro Glu Ser Thr Gly Val Lys
145                 150                 155                 160

Arg Ile Val Gln Ala Leu Asn Ala Asn Val Trp Ser Asn Val Val Met
                165                 170                 175

Lys Asn Asp Arg Asn Gln Gly Phe Ser Leu Leu Asn Ser Leu Thr Gly
            180                 185                 190

Thr Asn His Ser Ile Gly Ser Ala Asp Pro Cys His Pro Glu Gln Pro
        195                 200                 205

His Leu Pro Ala Ala Asp Ser Thr Glu Ser Leu Ser Asp His Arg Gly
    210                 215                 220

Gly Ala Ser Asn Thr Thr Asp Ala Gln Val Asp Ser Ile Val Asp Pro
225                 230                 235                 240

Met Leu Asp Leu Asp Ile Gln Glu Leu Ala Ser Leu Thr Thr Gly Gly
                245                 250                 255

Gly Asp Val Glu Asn Phe Glu Arg Leu Phe Ser Lys Leu Lys Glu Met
            260                 265                 270

Lys Asp Lys Ala Ala Thr Leu Pro His Glu Gln Arg Lys Val His Ala
        275                 280                 285

Glu Lys Val Ala Lys Ala Phe Trp Met Ala Ile Gly Gly Asp Arg Asp
    290                 295                 300

Glu Ile Glu Gly Leu Ser Ser Asp Glu Glu His
```

<210> SEQ ID NO 27
<211> LENGTH: 1541
<212> TYPE: DNA
<213> ORGANISM: Homo sapiens

<400> SEQUENCE: 27

```
ttaaaagaca aaattttaaa atctgacccc agcccttgtg attgttcagt atataatcaa      60
tggtatctta caaggactat tttatttgga atcaatcaaa tttgtttcct gccaacaata     120
agttaggttg ttttttgcag ttctcaagta acaaatatga ggaccgaact ctcattcaac     180
atccaagccc ttgcagtttg tgcaaatata tgtttagcaa caaggacag acagaatcca      240
tcattagtat ggcttttac tggaatgttt tgcatttatt cattgttctt tgcttggaga      300
gcaaatttag atatttcaaa accacttttc atgggtgtgg tggaacgatt ctggatgcag     360
agcaatgcag tagtggccgt cctcgctggc attggtttgg ctgcagttgt gtctgagact     420
aaccgagtgc tgaatagcaa tgggcttcag tgtctggaat ggctttctgc mactcttttt     480
gtagtttacc aaatatattc taattacaga aagaaacat ttgtttgcat aggaattcat      540
gaaggcgacc caacctggaa aaagaactat tcactttggc catggggtc ttgtgacaaa      600
ttagttcctt tggagattgt attcaaccct gaggaatgga ttaaacttac aaaaaatatc     660
tataactgga ccgaagaata tggaaggttt gatccatctt cttgggaatc tgtggccaat     720
gaagaaatgt ggcaagcgag gatgaaaaca ccgttcttca tctttaacct ggcagaaact     780
gctcacatgc cttcaaaagt gaaagctcaa ctctacgctc aagcatatga cctttataag     840
gagattgtct atttacaaaa ggagcaccca gtgaattggc acaagaacta tgccatcgcc     900
tgtgagcgga tgctgcgtct tcaggcaaga gatgcagatc ctgaagtgct gttatcggaa     960
accatcagac atttccgtct gtactctcag aaagcaccga atgacccaca gcaagctgat    1020
attttaggtg ctctaaagca cctaagaaaa gaactgcaaa gtctgagaaa taggaaaaat    1080
gtctgagaca gcaaaatatg aaaaacctgc tcatcgttca gcttccaaaa ttctgaagtc    1140
tggaagtttt tccttcaaag aaaagaaact gcataaaaaa tttaaaacta agtcatctcc    1200
cagatataag tatcatggtc cagcagtact gtttaatggg gtattcagtg actaaggtct    1260
gctatttatg caaaattctg tttatcccgt gttaccaaat taccatttca gtgagaagct    1320
tttgaaaagt cttctgactt ccagtctttc accagatgac tgcactggat tagattctag    1380
aagagaatga accattttca tataactaaa tattggtcat gaactgtgta agggccatgc    1440
ttattgggat cagttttaaa gttaaattct tttgatatta ataccagacc aaagacattt    1500
tctgtttcct gaaaaaaaaa aaaaaaaaa aaaaaaaaa a                           1541
```

<210> SEQ ID NO 28
<211> LENGTH: 309
<212> TYPE: PRT
<213> ORGANISM: Homo sapiens

<400> SEQUENCE: 28

```
Met Arg Thr Glu Leu Ser Phe Asn Ile Gln Ala Leu Ala Val Cys Ala
 1               5                  10                  15

Asn Ile Cys Leu Ala Thr Lys Asp Arg Gln Asn Pro Ser Leu Val Trp
            20                  25                  30

Leu Phe Thr Gly Met Phe Cys Ile Tyr Ser Leu Phe Phe Ala Trp Arg
        35                  40                  45
```

```
Ala Asn Leu Asp Ile Ser Lys Pro Leu Phe Met Gly Val Val Glu Arg
 50                  55                  60
Phe Trp Met Gln Ser Asn Ala Val Val Ala Val Leu Ala Gly Ile Gly
 65                  70                  75                  80
Leu Ala Ala Val Val Ser Glu Thr Asn Arg Val Leu Asn Ser Asn Gly
                 85                  90                  95
Leu Gln Cys Leu Glu Trp Leu Ser Ala Thr Leu Phe Val Val Tyr Gln
            100                 105                 110
Ile Tyr Ser Asn Tyr Arg Lys Glu Thr Phe Val Cys Ile Gly Ile His
        115                 120                 125
Glu Gly Asp Pro Thr Trp Lys Lys Asn Tyr Ser Leu Trp Pro Trp Gly
130                 135                 140
Ser Cys Asp Lys Leu Val Pro Leu Glu Ile Val Phe Asn Pro Glu Glu
145                 150                 155                 160
Trp Ile Lys Leu Thr Lys Asn Ile Tyr Asn Trp Thr Glu Glu Tyr Gly
                165                 170                 175
Arg Phe Asp Pro Ser Ser Trp Glu Ser Val Ala Asn Glu Glu Met Trp
            180                 185                 190
Gln Ala Arg Met Lys Thr Pro Phe Phe Ile Phe Asn Leu Ala Glu Thr
        195                 200                 205
Ala His Met Pro Ser Lys Val Lys Ala Gln Leu Tyr Ala Gln Ala Tyr
210                 215                 220
Asp Leu Tyr Lys Glu Ile Val Tyr Leu Gln Lys Glu His Pro Val Asn
225                 230                 235                 240
Trp His Lys Asn Tyr Ala Ile Ala Cys Glu Arg Met Leu Arg Leu Gln
                245                 250                 255
Ala Arg Asp Ala Asp Pro Glu Val Leu Leu Ser Glu Thr Ile Arg His
            260                 265                 270
Phe Arg Leu Tyr Ser Gln Lys Ala Pro Asn Asp Pro Gln Gln Ala Asp
        275                 280                 285
Ile Leu Gly Ala Leu Lys His Leu Arg Lys Glu Leu Gln Ser Leu Arg
290                 295                 300
Asn Arg Lys Asn Val
305

<210> SEQ ID NO 29
<211> LENGTH: 539
<212> TYPE: DNA
<213> ORGANISM: Homo sapiens
<220> FEATURE:
<221> NAME/KEY: unsure
<222> LOCATION: (495)

<400> SEQUENCE: 29
gcgggccgga gggtgatggg accatctagc ccctaaccat gggcccagaa gagaagacca     60
tcatgacaga taggtctgca gctgtttcca tccaggcctg gtggcggggc atgctggtgc    120
gacgacactg ctgcatgcag ccctcagggc ttggttcatt cagtgctggt ggaggcaggt    180
gctggagaag ctgctggcaa agaggcggag gatggtgttg gagttctatg tgcagcagga    240
atgggcagca gtcaggctgc agtcctgggt ccgcatgtgg tgtgtccgcc agcgtaactg    300
ttgtttgctc aacgctgtcc gcatcatcca ggtctattgg cgctggcaca gctgccattc    360
ccgtggcaaa attgagggcc actatgaact caaaaaaaac caacaaaaaa acaacatga    420 aaacaccttg ggctaacagg cttgtaaggt gcaacaatgc ataccccttc cattaaaaaa    480
atgaccaggt ctgcnaaaaa aaaaaaaaaa aaaaaaaaaa aaaaaaaa                 539
```

<210> SEQ ID NO 30
<211> LENGTH: 145
<212> TYPE: PRT
<213> ORGANISM: Homo sapiens

<400> SEQUENCE: 30

Met Gly Pro Glu Glu Lys Thr Ile Met Thr Asp Arg Ser Ala Ala Val
 1               5                  10                  15

Phe Ile Gln Ala Trp Arg Gly Met Leu Val Arg Arg His Cys Cys
             20                  25                  30

Met Gln Pro Ser Gly Leu Gly Ser Phe Ser Ala Gly Gly Arg Cys
         35                  40                  45

Trp Arg Ser Cys Trp Gln Arg Gly Gly Gly Trp Cys Trp Ser Ser Met
     50                  55                  60

Cys Ser Arg Asn Gly Gln Gln Ser Gly Cys Ser Pro Gly Ser Ala Cys
 65                  70                  75                  80

Gly Val Ser Ala Ser Val Thr Val Val Cys Ser Thr Leu Ser Ala Ser
                 85                  90                  95

Ser Arg Ser Ile Gly Ala Gly Thr Ala Ala Ile Pro Val Ala Lys Leu
                100                 105                 110

Arg Ala Thr Met Asn Ser Lys Lys Thr Asn Lys Lys Asn Asn Met Lys
            115                 120                 125

Thr Pro Trp Ala Asn Arg Leu Val Arg Cys Asn Asn Ala Tyr Pro Phe
        130                 135                 140

His
145

<210> SEQ ID NO 31
<211> LENGTH: 2408
<212> TYPE: DNA
<213> ORGANISM: Homo sapiens

<400> SEQUENCE: 31
cacatctcag agcctaagaa ataggactaa gcccagaact cctagaatca cctataaatg      60
ctaggcatag atggaaatta ttgtgttcca ccagaagcac agctccaaac tatacctaaa     120
aaatatttct gcacttccca gagacctgga cttcaaactt tcccagtgga gcctgattat     180
agaacttgag gtcctatctc aggatgaagg ggagaggcc ctggcttcac gggaaggtat      240
tccagcattg ttctgcttca cccttgactg cgttgtctgg cagtttctgt gtgctgccag     300
gatattatat ggaactggag aagttggagt caggtctctg aagctagagt ttcactaatt     360
agatgcctct gtacatgaga actattactg tctgcaggtc catatagcta agctgccagg     420
aaaaacacat tatcttccaa aactttcaga gcatgtgcag aaccctttct tagcgttttc     480
ttctcagcat tttctctgcc tcccagaggc tggcagccat gacactgca gagttcagca     540 tgttctaacc atgcacgcag ggcaggggct gccttggccc tcctcaggct tcgttggga     600 gagcaggcag tggtggagcc cttctgggtg cagtcctctg gggttgctct ttggaactca     660
tgtatgagtt tgactccaca aggcttggca tggataccaa acagttgca acaaattagt      720 tctgaacctg gaacagagaa ttcagtgctt ctgttactca ggaaggaggt gttcagaatg     780 cccccgtgcag agcagccagt cattactctt gtttgttctc acctgggtgc gcaccctcat    840
gatgcagtgg ctgtagcacc ttcatgccag gtgctgagag aatgggaaat tcttcctccc    900
cattgacctg agtcccagag acttagggac acagacttca ggtgaggctg cggacctcag    960

-continued

```
aagcagtgga taatagattg gggcattaaa agcttttgag gcaggggggct catgttttga    1020 ctgcagggag ttatgctgag caaagagatg tgttttttcaa aaccagggtt caaaaccagt    1080
gtccacgctg gagtaagtgg agcatgcttc tctgtgttct ctgaatgatc ttgcactcct    1140
cttaagcaaa ggagtaccat gaccatagtc agtgggatcc cacaaatgtt cttaaatggg    1200
taaggcttta agtagccaga gagtatccag cctaccattg gcttctccac atcctaaaac    1260
ctgagacagc cttggtatat gctttataaa tgtttctttt cttgttgttt aagtaattaa    1320
agtgtttaaa atgtcttcat tagatgtgac gattgtttaa tgagtttgcc tctgacgtgt    1380
ggctccatgg gagataggca agtaattaa gaagttacca gaaattggtc ggctggggaa    1440
atgcaaaagt tagcatttca gtagtgaatt tctcctggaa caaatgagca attttttcctc    1500 tttctcttaa gtagtatacc ctttttctcac ttagtaattt aatggtatat aaagacatgt    1560
gtataagtga gtgcatacat atgaggtatg actataggggt tgtttgtggg aatttctttt    1620
cctaacatac agaagatcaa agtgttcatc tcaccccgcc ctccttaaaa ggtgtctttt    1680
gggagactat gtgctcattg actatagtgc tgccaagtaa aatatcttgg gaactcttct    1740
actagaatgg ccttcagggc ttggcatgtt cctttggttt acccttagag atgagaaatc    1800
ctcctccttt gaggatggat ttaagttctg gaaataatct caagtgcttg atagcacagt    1860
tggatgaaaa aagatggcaa ttaaggtaag ttacaccatt tttgtttcta aaaaaatccc    1920
taagaaattt cttggaatga gtctttggcc tcagagcctc tcaaagtgtc cacttcaagg    1980
ggggatcatc ctcattagca cacagatttt taaaaatcaa ttctcttgcc atgcctccta    2040
tgtgttcaca tctctgcata cactacagat ataagtgcat aatcattcat ataaacatct    2100
ggtaggtatt ctgtaaaact gtgtttactt tagtgcatgt tattgtcatg ttatgatgtg    2160
actggggtgt ttctttgtca tgaaactttg cttcttcaca gaattagaat actgctctct    2220
ctatattgaa ctacatatac agcgttttct tgtatcagcc cccaaagtct ggatgcccgg    2280
tgttgtgttt acatgtgatt gtgcctagga gtctgttcac atagagacac ctgtaagtat    2340
ttattacaaa acggaatgta agcaaatata tccacattgg ttttatttga aaaaaaaaa    2400 aaaaaaaa                                                              2408
```

<210> SEQ ID NO 32
<211> LENGTH: 80
<212> TYPE: PRT
<213> ORGANISM: Homo sapiens

<400> SEQUENCE: 32

```
Met Ser Leu Thr Pro Gln Gly Leu Ala Trp Ile Pro Lys Gln Leu Gln
  1               5                  10                  15

Gln Ile Ser Ser Glu Pro Gly Thr Glu Asn Ser Val Leu Leu Leu Leu
             20                  25                  30

Arg Lys Glu Val Phe Arg Met Pro Arg Ala Glu Gln Pro Val Ile Thr
         35                  40                  45

Leu Val Cys Ser His Leu Gly Ala His Pro His Asp Ala Val Ala Val
     50                  55                  60

Ala Pro Ser Cys Gln Val Leu Arg Glu Trp Glu Ile Leu Pro Pro His
 65                  70                  75                  80
```

<210> SEQ ID NO 33
<211> LENGTH: 970
<212> TYPE: DNA
<213> ORGANISM: Homo sapiens -continued

```
<400> SEQUENCE: 33
gtgcgagatt gaggaagggt cggggcttaa cgggggaggt gggggtggcg ggggggggaac      60 agcacggcgc ggcgcctagc ctgcgagatg gagtcggagt ggggggtgcga gcggtcctcc     120 accgcctctg cccgatccgt acctcacaat ggactgctcg agtttgtatc taggcctgtc     180
caggattgtt tactccttca attaatcagc tttatctctt ttccccctcc ccccacctcc     240
accaaatctg gagaggagtg ggaaagaact ggaaaactca cagggcaaag agagaaagcc     300
aacagtcata gtgcgggagg aggcacgcct gggatgcaat acccaacagt ctcctccctg     360 cttcctgca atttgcaggt cattgtcttt cttatttgta gcttttttt ttttcttca       420 gtagccggta acaatcgaa cgacgggtag ggaggtcaga ggggatgggg ctgtgggaga      480
gattctactc aggctaggtg ctttagattt ggacctggct gtgtccctac tttattaaaa     540
ttctcatgtg gcgcgcgctg tcttctctct tctctctctc tctctctcac acacacacgc     600
acatacacac acagcccgag agaaatttcc aatcctttga gcaaatctct tccatctagt     660
ccttgaaaca gaggaaagga catgggacct gaaggagagt tatgattgaa ttttctaaaa    720
tttagttttg acattgcaaa gtaaaagtga ggaccgtatt cccaatacag acccagaggg     780
tggttatttc aggtgagggg acctcagcct gtgacgtcta tgatcaacca gacaaagacc     840
ccttcctaaa tctgaagtcc cacccccacc cgtggcaaac atggaataca agggagggga     900
aggatggcac aatagtgggt tctgtttttcc aagaactgcc cccacctcc attgcaaaaa     960 aaaaaaaaaa                                                            970

<210> SEQ ID NO 34
<211> LENGTH: 120
<212> TYPE: PRT
<213> ORGANISM: Homo sapiens

<400> SEQUENCE: 34

Met Glu Ser Glu Trp Gly Cys Glu Arg Ser Ser Thr Ala Ser Ala Arg
  1               5                  10                  15

Ser Val Pro His Asn Gly Leu Leu Glu Phe Val Ser Arg Pro Val Gln
             20                  25                  30

Asp Cys Leu Leu Leu Gln Leu Ile Ser Phe Ile Ser Phe Pro Pro Pro
         35                  40                  45

Pro Thr Ser Thr Lys Ser Gly Glu Glu Trp Glu Arg Thr Gly Lys Leu
     50                  55                  60

Thr Gly Gln Arg Glu Lys Ala Asn Ser His Ser Ala Gly Gly Gly Thr
 65                  70                  75                  80

Pro Gly Met Gln Tyr Pro Thr Val Ser Ser Leu Leu Ser Cys Asn Leu
                 85                  90                  95

Gln Val Ile Val Phe Leu Ile Cys Ser Phe Phe Phe Ser Ser Val
            100                 105                 110

Ala Gly Lys Gln Ser Asn Asp Gly
        115                 120

<210> SEQ ID NO 35
<211> LENGTH: 2084
<212> TYPE: DNA
<213> ORGANISM: Homo sapiens

<400> SEQUENCE: 35
ggtagccgtt gggttgggaa agtgagggat ttttggcctc gttctcctg cttctttttct      60 cctcccttt actttgccgg tagaacacag ttatgggtcg caagaagaag aagcagctga    120
```

```
agccgtggtg ctggtattgt catagagatt ttgatgatga aagatcctt  attcagcacc    180 aaaaagcaaa gcattttaaa tgccatatat gtcacaagaa attgtataca ggacctggct    240
tagctattca ttgcatgcag gtacataaag aaacaataga tgccgtacca aatgcaatac    300
ctggaagaac agacatagag ttggaaatat atggtatgga aggtattcca gaaaaagaca    360
tggatgaaag acgacgactt cttgaacaga aaacacaaga agtctaaaa  aagaagcaac    420 aagatgattc tgatgaatat gatgatgacg actctgcagc ctcaacttca tttcagccac    480
agcctgttca acctcagcaa ggttatattc tccaatggc  acagccagga ctgccaccag    540
taccaggagc accaggaatg cctccaggca tacctccatt aatgccacgt gttcctcctc    600
tgatgccagg aatgccacca gttatgccag gcatgccacc tggattgcat catcagagaa    660
aatacaccca gtcatttgc  ggtgaaaaca taatgatgcc aatgggtgga atgatgccac    720
ctggaccagg aataccacct ctgatgcctg gaatgccacc aggtatgccc ccacctgttc    780
cacgtcctgg aattcctcca atgactcaag cacaggctgt ttcagcgcca ggtattctta    840
atagaccacc tgcaccaaca gcaactgtac ctgccccaca gcctccagtt actaagcctc    900
ttttccctag tgctggacag gctcaggcag ctgtccaagg acctgttggt acagatttca    960
aacccttaaa tagtacccct gcaacaacta cagaacccccc aaagcctaca ttccctgctt   1020
atacacagtc tacagcttca acaactagta caacaaatag tactgcagct aaaccagcgg   1080
cttcaataac aagtaagcct gctacactta caacaactag tgcaaccagt aagttgatcc   1140
atccagatga ggatatatcc ctggaagaga aagggcaca  gttacctaag tatcaacgta   1200
atcttcctcg gccaggacag gcccccatcg gtaatccacc agttggacca attggaggta   1260
tgatgccacc acagccaggc atcccacagc aacaaggaat gagacccccca atgccacctc   1320 atggtcagta tggtggtcat catcaaggca tgccaggata ccttcctggt gctatgcccc   1380
cgtatgggca gggaccgcca atggtgcccc cttaccaggg tgggcctcct cgacctccga   1440
tgggaatgag acctcctgta atgtcgcaag gtggccgtta ctgatcttac ttcatccagt   1500
ctaataggtt tggagattaa accttttctc aacttgtgct gtttatatag ccaagcttcc   1560
gtcaataagg cttcattgtg actttaacaa acattctctt cccacatacc aggaactatt   1620
ggacatttat tttacatggg aaaaattatt tggaataata aagcaggaac ttttcctgaa   1680
gttgcaattt atactgtatg gcttcttttt catgtttcat ctaggttttt agaagtgaag   1740
tatagtaaat ttggttcgtt aaattgtgaa ggcgctggaa ttcatgaac  ataccaccct   1800 agtaaaggca gttctgtaa  gcttacattg ctatttgtaa agtttgcctt cacagcattt   1860
cagatgctgt tggacttcat gtccccaacc tagcttggtg agggctgtaa ctgtttccaa   1920
gtacttgtac attggaagtc tgaatgtgta acaatattta atgtatttag agttcctcat   1980
gttgcagggt ttaagaaatc tgacccacca aggtcatgtg acttttctgt actgttaaac   2040
ttcattgtaa taaatgaga  gaaaaaaaaa aaaaaaaaa  aaaa               2084
```

<210> SEQ ID NO 36
<211> LENGTH: 463
<212> TYPE: PRT
<213> ORGANISM: Homo sapiens

<400> SEQUENCE: 36

Met Gly Arg Lys Lys Lys Lys Gln Leu Lys Pro Trp Cys Trp Tyr Cys
 1               5                  10                  15

His Arg Asp Phe Asp Asp Glu Lys Ile Leu Ile Gln His Gln Lys Ala

-continued

```
                20                  25                  30
Lys His Phe Lys Cys His Ile Cys His Lys Lys Leu Tyr Thr Gly Pro
                35                  40                  45
Gly Leu Ala Ile His Cys Met Gln Val His Lys Glu Thr Ile Asp Ala
            50                  55                  60
Val Pro Asn Ala Ile Pro Gly Arg Thr Asp Ile Glu Leu Glu Ile Tyr
 65                  70                  75                  80
Gly Met Glu Gly Ile Pro Glu Lys Asp Met Asp Glu Arg Arg Arg Leu
                85                  90                  95
Leu Glu Gln Lys Thr Gln Glu Ser Leu Lys Lys Lys Gln Gln Asp Asp
                100                 105                 110
Ser Asp Glu Tyr Asp Asp Asp Ser Ala Ala Ser Thr Ser Phe Gln
            115                 120                 125
Pro Gln Pro Val Gln Pro Gln Gly Tyr Ile Pro Pro Met Ala Gln
            130                 135                 140
Pro Gly Leu Pro Pro Val Pro Gly Ala Pro Gly Met Pro Gly Ile
145                 150                 155                 160
Pro Pro Leu Met Pro Arg Val Pro Pro Leu Met Pro Gly Met Pro Pro
                165                 170                 175
Val Met Pro Gly Met Pro Pro Gly Leu His His Gln Arg Lys Tyr Thr
            180                 185                 190
Gln Ser Phe Cys Gly Glu Asn Ile Met Met Pro Met Gly Gly Met Met
            195                 200                 205
Pro Pro Gly Pro Gly Ile Pro Pro Leu Met Pro Gly Met Pro Pro Gly
            210                 215                 220
Met Pro Pro Val Pro Arg Pro Gly Ile Pro Pro Met Thr Gln Ala
225                 230                 235                 240
Gln Ala Val Ser Ala Pro Gly Ile Leu Asn Arg Pro Pro Ala Pro Thr
            245                 250                 255
Ala Thr Val Pro Ala Pro Gln Pro Pro Val Thr Lys Pro Leu Phe Pro
            260                 265                 270
Ser Ala Gly Gln Ala Gln Ala Ala Val Gln Gly Pro Val Gly Thr Asp
            275                 280                 285
Phe Lys Pro Leu Asn Ser Thr Pro Ala Thr Thr Thr Glu Pro Pro Lys
            290                 295                 300
Pro Thr Phe Pro Ala Tyr Thr Gln Ser Thr Ala Ser Thr Thr Ser Thr
305                 310                 315                 320
Thr Asn Ser Thr Ala Ala Lys Pro Ala Ala Ser Ile Thr Ser Lys Pro
                325                 330                 335
Ala Thr Leu Thr Thr Thr Ser Ala Thr Ser Lys Leu Ile His Pro Asp
            340                 345                 350
Glu Asp Ile Ser Leu Glu Glu Arg Ala Gln Leu Pro Lys Tyr Gln
            355                 360                 365
Arg Asn Leu Pro Arg Pro Gly Gln Ala Pro Ile Gly Asn Pro Pro Val
            370                 375                 380
Gly Pro Ile Gly Gly Met Met Pro Pro Gln Gly Ile Pro Gln Gln
385                 390                 395                 400
Gln Gly Met Arg Pro Pro Met Pro Pro His Gly Gln Tyr Gly Gly His
                405                 410                 415
His Gln Gly Met Pro Gly Tyr Leu Pro Gly Ala Met Pro Pro Tyr Gly
                420                 425                 430
Gln Gly Pro Pro Met Val Pro Pro Tyr Gln Gly Gly Pro Pro Arg Pro
            435                 440                 445
```

```
Pro Met Gly Met Arg Pro Pro Val Met Ser Gln Gly Gly Arg Tyr
    450                 455                 460
```

<210> SEQ ID NO 37
<211> LENGTH: 1250
<212> TYPE: DNA
<213> ORGANISM: Homo sapiens

<400> SEQUENCE: 37

| | | | | | |
|---|---|---|---|---|---|
| gtatgttgtc | agaccagggt | tttcagagtt | gatggaaaag | agtcttgtga | gaaaacttat | 60 |
| tttgataaat | tattacacac | gcagaaaaac | tgatcacact | gactggatct | gtccacgaca | 120 |
| tggaaaataa | actggatttt | cagaatattg | ttgttttctg | tagtgttcaa | ggtattgttt | 180 |
| ctaaacataa | acatactcta | aacatgcttt | attcacttgt | taaagtcata | cttttaaaag | 240 |
| taataccctta | ctaaagatgg | tgattacttt | tccgaggtca | gaaaaggaaa | gctaagcgtt | 300 |
| ttcattatca | aatacacaag | cttattaaat | gaatgactgt | taactacttt | atttttcattt | 360 |
| gcacattaat | tttggaattg | tttctgtttt | gctgctgacg | gaaatactat | tttggctctg | 420 |
| tgtatatttg | tattttgatt | tttctggttt | gtttaccccc | atttgctttt | agctccgcct | 480 |
| tatgtttaaa | tatattctaa | cttatgtaaa | gagcataatc | ttagagcaaa | atacttgag | 540 |
| gttttatgtc | agatctaatc | ttaagtgttt | gttgtttttt | aaaggtgtt | ttctcagatg | 600 |
| gctgcagtgt | ttttgctatt | tctgcataaa | taccctacct | ggactcccca | gttttcacca | 660 |
| gaaactgtta | tttttttttg | ttgttgttcc | cactgagact | gatggtgatg | gggaaattaa | 720 |
| aaacaacaca | ctagcacact | cccacaaaac | ttgaggaaga | gttagaatgg | caataaaata | 780 |
| ttaaatagac | cttatactta | aaataaggtt | tcactatata | atttgtcaca | attcaatcta | 840 |
| atcagctaaa | gttaaatgta | gttagaatta | gccacaggag | aatgtaaagc | atgctttgac | 900 |
| gaagctatcg | gtaacacata | ttgaatgtct | ttgagactct | tagattgtac | tatttgctta | 960 |
| atagattaat | gaaatttatc | agatacaacc | tgtatttcca | aaaacaagct | agaaggaacc | 1020 |
| tgaggaatgt | ggtttacatt | tgagatccac | cttactgtgt | tttctacttt | cagaaaagat | 1080 |
| tctgtagttt | tggtttttgg | catctttctt | atactcagtt | ttttctgcct | taattcccat | 1140 |
| ttaccagcag | ttaactcatg | tttattgtgc | tttcatgcat | tgtgatatgg | aatgtgttta | 1200 |
| gtaatttact | ccttataaat | atggtaaagt | acaaaaaaaa | aaaaaaaaa | | 1250 |

<210> SEQ ID NO 38
<211> LENGTH: 90
<212> TYPE: PRT
<213> ORGANISM: Homo sapiens

<400> SEQUENCE: 38

```
Met Phe Lys Tyr Ile Leu Thr Tyr Val Lys Ser Ile Ile Leu Glu Gln
  1               5                  10                  15

Lys Tyr Leu Arg Phe Tyr Val Arg Ser Asn Leu Lys Cys Leu Leu Phe
                 20                  25                  30

Phe Lys Arg Cys Phe Leu Arg Trp Leu Gln Cys Phe Cys Tyr Phe Cys
             35                  40                  45

Ile Asn Thr Leu Pro Gly Leu Pro Ser Phe His Gln Lys Leu Leu Phe
         50                  55                  60

Phe Phe Val Val Val Pro Thr Glu Thr Asp Gly Asp Gly Glu Ile Lys
 65                  70                  75                  80

Asn Asn Thr Leu Ala His Ser His Lys Thr
                 85                  90
```

<210> SEQ ID NO 39
<211> LENGTH: 793
<212> TYPE: DNA
<213> ORGANISM: Homo sapiens

<400> SEQUENCE: 39

```
ggcgccttgg aggcgatggc ccacggggct gctagccgtg ctgcggcccc tgctcacctg     60
ccggcccctg caaggcacga cgctgcaacg ggatgtgctg ctctttgagc atgatcgggg    120
ccgcttcttc accatcctcg ggctgttctg cgcgggccag ggcgtcttct ggcttccat    180
ggctgtggca gccgtgtccc ggcccccggt tccggtgcag cctctggatg cggaggtccc    240
aaatcgtggc cccttcgacc tgcgctccgc gctctggcgc tacggtctgg ccgtcggctg    300
cggcgccatc ggagccctcg tactcggtgc tggtcttctc ttctctctcc ggtctgtgcg    360
ctcagtggtg cttcgagctg gagggcagca ggtgaccctc accactcatg cccccttgg    420
cttgggggcc catttcacag ttcctttgaa gcaggtatct tgcatggccc accggggtga    480
agtccctgcc atgctacctc tgaaagtcaa aggccgacgc ttctatttcc tcttggacaa    540
aactggacac ttccctaaca caaaactctt tgacaatact gtgggtgcct accggagctt    600
gtgaagaaat gacctcaagt cactcacctc tccaagagga ggataaaaac tgaaccttgg    660
ggagccaggt gtgttggttc acgcctgttg taatcccagc actttgggag ggtgaggcag    720
gagcactgct cgagcccagg ctgggcaaca tagcgagacc ttgtctctat ttacaaaaaa    780
aaaaaaaaaa aaa                                                       793
```

<210> SEQ ID NO 40
<211> LENGTH: 141
<212> TYPE: PRT
<213> ORGANISM: Homo sapiens

<400> SEQUENCE: 40

```
Met Ala Val Ala Ala Val Ser Arg Pro Pro Val Pro Val Gln Pro Leu
 1               5                  10                  15

Asp Ala Glu Val Pro Asn Arg Gly Pro Phe Asp Leu Arg Ser Ala Leu
                20                  25                  30

Trp Arg Tyr Gly Leu Ala Val Gly Cys Gly Ala Ile Gly Ala Leu Val
            35                  40                  45

Leu Gly Ala Gly Leu Leu Phe Ser Leu Arg Ser Val Arg Ser Val Val
        50                  55                  60

Leu Arg Ala Gly Gly Gln Gln Val Thr Leu Thr Thr His Ala Pro Phe
 65                  70                  75                  80

Gly Leu Gly Ala His Phe Thr Val Pro Leu Lys Gln Val Ser Cys Met
                85                  90                  95

Ala His Arg Gly Glu Val Pro Met Leu Pro Leu Lys Val Lys Gly
            100                 105                 110

Arg Arg Phe Tyr Phe Leu Leu Asp Lys Thr Gly His Phe Pro Asn Thr
        115                 120                 125

Lys Leu Phe Asp Asn Thr Val Gly Ala Tyr Arg Ser Leu
    130                 135                 140
```

<210> SEQ ID NO 41
<211> LENGTH: 1970
<212> TYPE: DNA
<213> ORGANISM: Homo sapiens

<400> SEQUENCE: 41

```
atggcctgtc cgcgttaaac catcacaagc catggttgcg aagggccac gcgtccccag    60
taggagaatg actccgattc gtgaccctca gcgccggtgc atgtcgatat atttattgag   120
tgtctactgt gtgccaggca ctatatctat gtgcatagaa aaaccctgga aggccgtaca   180
acaatatata tagagtgatc gtctctgctt gctgagctaa cagcaagttt atttctgatc   240
gtgaaagtag aagaagtctc acaaacagcc atttggaaaa aagaagtgt gatgagtata   300
ttccaggtac aacctcctta ggcatgtctg tttttaacct aagcaacgcc attatgggca   360
gtgggatttt gggactcgcc tttgccctgg caaacactgg aatcctactt tttctggtac   420
ttttgacttc agtgacattg ctgtctatat attcaataaa cctcctattg atctgttcaa   480
aagaaacagg ctgcatggtg tatgaaaagc tgggggaaca agtctttggc accacaggga   540
agttcgtaat ctttggagcc acctctctac agaacactgg agcaatgctg agctacctct   600
tcatcgtaaa aaatgaacta ccctctgcca taaagtttct aatgggaaag gaagagacat   660
tttcagcctg gtacgtggat ggccgcgttc tggtggtgat agttaccttt ggcataattc   720
tccctctgtg tctcttgaag aacttagggt atcttggcta tactagtgga ttttccttga   780
gctgtatggt ttttttccta attgtggtta tttacaagaa atttcaaatt ccctgcattg   840
ttccagagct aaattcaaca ataagtgcta attcaacaaa tgctgacacg tgtacgccaa   900
aatatgttac cttcaattca aagaccgtgt atgctttacc caccattgca tttgcatttg   960
tttgccaccc gtcagtcctg ccaatttaca gtgagcttaa agaccgatca cagaaaaaaa  1020
tgcagatggt ttcaaacatc tccttttttcg ccatgtttgt tatgtacttc ttgactgcca  1080
tttttggcta cttgacattc tatgacaacg tgcagtccga cctccttcac aaatatcaga  1140
gtaaagatga cattctcatc ctgacagtgc ggctggctgt cattgttgct gtgatcctca  1200
cagtgccggt gttatttttc acggttcgtt catctttatt tgaactggct aagaaaacaa  1260
agtttaattt atgtcgtcat accgtggtta cctgcatact cttggttgtt atcaacttgt  1320
tggtgatctt cataccctcc atgaaggata ttttggagt cgtaggagtt acatctgcta  1380
acatgcttat tttcattctt ccttcatctc tttatttaaa aatcacagac caggatggag  1440
ataaaggaac tcaaagaatt tgggctgccc ttttcttggg cctgggggtg ttgtctcctt  1500
gtcagcattc ccttgtcatc tatgactggg cctgctcatc gagtagtgac gaaggccact  1560
gaacccgccg agaaaaagaa acatccctgt tgtctgctca gtcaagtccc cacacatcag  1620
caatctctca ccacttcttt tgcaagttta cagaagcaaa cagaaatgta caggatactt  1680
aaaatggaat aacttttttgg ttgcaaaaca gagacatggt tctataatgc ttcatgtccc  1740
tccaagattt gagatcaatt tagggattgt gaattttttt tttcaaattt catacaatca  1800
tatttcccag tacttttcac aatcattttt tacccatcta actctatgtt ttgtggcttc  1860
ccggtctctt agaactttga aaacatgata tacaataatg tttatttatt atacatccag  1920
attctgaaat aattttccta ctgatggtca actctaaaaa aaaaaaaaaa              1970
```

<210> SEQ ID NO 42
<211> LENGTH: 412
<212> TYPE: PRT
<213> ORGANISM: Homo sapiens

<400> SEQUENCE: 42

Met Ser Val Phe Asn Leu Ser Asn Ala Ile Met Gly Ser Gly Ile Leu
 1               5                  10                  15

Gly Leu Ala Phe Ala Leu Ala Asn Thr Gly Ile Leu Leu Phe Leu Val

```
                    20                  25                  30
Leu Leu Thr Ser Val Thr Leu Ser Ile Tyr Ser Ile Asn Leu Leu
            35                  40                  45

Leu Ile Cys Ser Lys Glu Thr Gly Cys Met Val Tyr Glu Lys Leu Gly
50                  55                  60

Glu Gln Val Phe Gly Thr Thr Gly Lys Phe Val Ile Phe Gly Ala Thr
65                  70                  75                  80

Ser Leu Gln Asn Thr Gly Ala Met Leu Ser Tyr Leu Phe Ile Val Lys
                85                  90                  95

Asn Glu Leu Pro Ser Ala Ile Lys Phe Leu Met Gly Lys Glu Glu Thr
            100                 105                 110

Phe Ser Ala Trp Tyr Val Asp Gly Arg Val Leu Val Ile Val Thr
        115                 120                 125

Phe Gly Ile Ile Leu Pro Leu Cys Leu Leu Lys Asn Leu Gly Tyr Leu
    130                 135                 140

Gly Tyr Thr Ser Gly Phe Ser Leu Ser Cys Met Val Phe Phe Leu Ile
145                 150                 155                 160

Val Val Ile Tyr Lys Lys Phe Gln Ile Pro Cys Ile Val Pro Glu Leu
                165                 170                 175

Asn Ser Thr Ile Ser Ala Asn Ser Thr Asn Ala Asp Thr Cys Thr Pro
            180                 185                 190

Lys Tyr Val Thr Phe Asn Ser Lys Thr Val Tyr Ala Leu Pro Thr Ile
        195                 200                 205

Ala Phe Ala Phe Val Cys His Pro Ser Val Leu Pro Ile Tyr Ser Glu
    210                 215                 220

Leu Lys Asp Arg Ser Gln Lys Met Gln Met Val Ser Asn Ile Ser
225                 230                 235                 240

Phe Phe Ala Met Phe Val Met Tyr Phe Leu Thr Ala Ile Phe Gly Tyr
                245                 250                 255

Leu Thr Phe Tyr Asp Asn Val Gln Ser Asp Leu Leu His Lys Tyr Gln
            260                 265                 270

Ser Lys Asp Asp Ile Leu Ile Leu Thr Val Arg Leu Ala Val Ile Val
        275                 280                 285

Ala Val Ile Leu Thr Val Pro Val Leu Phe Phe Thr Val Arg Ser Ser
    290                 295                 300

Leu Phe Glu Leu Ala Lys Lys Thr Lys Phe Asn Leu Cys Arg His Thr
305                 310                 315                 320

Val Val Thr Cys Ile Leu Leu Val Val Ile Asn Leu Leu Val Ile Phe
                325                 330                 335

Ile Pro Ser Met Lys Asp Ile Phe Gly Val Val Gly Val Thr Ser Ala
            340                 345                 350

Asn Met Leu Ile Phe Ile Leu Pro Ser Ser Leu Tyr Leu Lys Ile Thr
        355                 360                 365

Asp Gln Asp Gly Asp Lys Gly Thr Gln Arg Ile Trp Ala Ala Leu Phe
    370                 375                 380

Leu Gly Leu Gly Val Leu Ser Pro Cys Gln His Ser Leu Val Ile Tyr
385                 390                 395                 400

Asp Trp Ala Cys Ser Ser Ser Asp Glu Gly His
                405                 410

<210> SEQ ID NO 43
<211> LENGTH: 812
<212> TYPE: DNA
<213> ORGANISM: Homo sapiens
```

<400> SEQUENCE: 43

```
gaacatggcg cgcggaaccg gcgcgcgcgc ctagctggcg ggaccgttag atcgaggcgg      60
atgcggcccg gaccccgtgg atatggagca gtcgccgccg ctggcgccgg agcccaccca     120
agggccaacc accgcaagga gctgaaggcg gcgggagccc gagtcgccgc cggcgtcggt     180
gccgtcaaag aagatggcca gggagacagc agcgtggtca gagtggtagg agctggccat     240
cggtgagagc tgctccatgc ctggctgctg ggttctagag cttgtggacc actggcttgc     300
ctcactgtgg ttggtggtgg cggtgacaga gtgtgcagca cgaccagagt ggcttttctg     360
gctttgccgc ccagctgctc catgccagga ggaggaggag acacctagag cctgcgacac     420
catggctcgc ctcgctgcag gttctaccca tgtaacagat gaggaaacca aggagcacag     480
ttatttacta actcgcacaa ggttcgaggc cgagctcaga cctgtggagc agaagctgag     540
tgcgctgcag tccccgctgg cccagaggcc cttcttcgag gtgccctcac ccctgggcgc     600
cgtggacctg tacgagtatg catgcgggga tgaggacctg gagccactgt gacgccaccc     660
atgagaacgc cgctgcgggg ccgctccaca cgtgccacgg ccaccactgg gacaccgccg     720
cttgtgtaaa aactgttgtc ttttgtggaa aatgagtgtg tttgcatgga atgataaatt     780
tttatttatt cacaaaaaaa aaaaaaaaaa aa                                   812
```

<210> SEQ ID NO 44
<211> LENGTH: 131
<212> TYPE: PRT
<213> ORGANISM: Homo sapiens

<400> SEQUENCE: 44

```
Met Pro Gly Cys Trp Val Leu Glu Leu Val Asp His Trp Leu Ala Ser
  1               5                  10                  15

Leu Trp Leu Val Val Ala Val Thr Glu Cys Ala Ala Arg Pro Glu Trp
             20                  25                  30

Leu Phe Trp Leu Cys Arg Pro Ala Ala Pro Cys Gln Glu Glu Glu Glu
         35                  40                  45

Thr Pro Arg Ala Cys Asp Thr Met Ala Arg Leu Ala Ala Gly Ser Thr
     50                  55                  60

His Val Thr Asp Glu Glu Thr Lys Glu His Ser Tyr Leu Leu Thr Arg
 65                  70                  75                  80

Thr Arg Phe Glu Ala Glu Leu Arg Pro Val Glu Gln Lys Leu Ser Ala
                 85                  90                  95

Leu Gln Ser Pro Leu Ala Gln Arg Pro Phe Phe Glu Val Pro Ser Pro
            100                 105                 110

Leu Gly Ala Val Asp Leu Tyr Glu Tyr Ala Cys Gly Asp Glu Asp Leu
        115                 120                 125

Glu Pro Leu
    130
```

<210> SEQ ID NO 45
<211> LENGTH: 1533
<212> TYPE: DNA
<213> ORGANISM: Homo sapiens
<220> FEATURE:
<221> NAME/KEY: unsure
<222> LOCATION: (360)

<400> SEQUENCE: 45

```
ggattgaatt ctagaccagc ggccgcaggt ccgaagctca acggctctga aagttgagc      60
```

-continued

```
tcccactggc tctaactgac ccaaagggat gtcagtggtg ttctggcttt ctggaaggcc    120
atcaaagtca ggcttcttcg ggcccccgag gcaggaaatg gggtctctcc atgggagaca    180
ggatgctgag gccgcggaaa gtcagcctcc tcacccccca ggtacgaggc caggaagggg    240
acgtcctcac caatgctggg tcccagctcc agcagcacgt cttctcggcc agcttggtt     300 agcagctcga gcagtctgcc tacagaagcg ccaggggcct ccctgccagg cgtccagcan    360
cctgccagtt gggtccgctt gtgtctccag ttgccggatc tccaagttac tcaaagtcca    420
tctcctccgc cagcgcggtc aagtcggccc ccacctgtgt ccgctcgttc aagaacagag    480
acaggcggcg ccgcactcgc atgttgagag cagccagggg aagggaggat gtggaggaga    540
ccggggccgc agacccgcg ccgggacctc ctgcagccat gcgggcggt cctggagcct      600 cagcgcggtc gggtcgcatt gtctgccagc gcttcctctt tctcctgcgg cacccgcccc    660
gcccccgccg ctttcgcttt ccgagaagcg ccgccctgcc ctacaatctg agccccgag     720 caaaagtgcg gaggcggggg tgcccacctc tacccttgag gtctcgaggc gggtgatgtg    780
gggggcgtaa gaagtaggaa tctgcctttt gagatctgga gaggtccacg gcaccgccct    840
cgaaggtctg gtgatggtgc tagtaggttg gcggcggagt gaggacaccc tccttcgggg    900
gttgtaggaa acgggccttg cttttgggga tctggtggag ccacagttct tccaccgaag    960
aatctgaggg gttcatacgg tcctgccctc caggatggcg aggagggac aagtgggaag     1020 gcaccactct gccctccacc gtctcttggg aacacacaa tcctgccagt agggtatggg      1080
aagaccctgc tgtgctcccc aagtgggagt ggaaacgaac actgccttct gagcgtgagc    1140
atgccgtggc cctgccctcg aaatggttgg ggatgtcatg acactaggtt ggggagcaca    1200
aggcaccctg tcctttggtg tctgtggaaa gcccagcact actctccagg gtctcaggtg    1260
aagacatggc cctgctattg ggagtccaag ggggcacgtg gccttgccct ttaggtttag    1320
ggacacagtc ctgacctggg gagccctggt tcattcattt actcattcga caagtactta    1380
ttgattatct actaagtgtc aagggtgtcg caggctcccc ggaaaaatgg aaccttttttg   1440 ccttggtgga gacccccagcc tagcacggga atgggcact aataaaatca tttccaattg     1500
ggtgtaaaac tggtaaaaaa aaaaaaaaaa aaa                                 1533
```

<210> SEQ ID NO 46
<211> LENGTH: 233
<212> TYPE: PRT
<213> ORGANISM: Homo sapiens
<220> FEATURE:
<221> NAME/KEY: UNSURE
<222> LOCATION: (91)

<400> SEQUENCE: 46

```
Met Ser Val Val Phe Trp Leu Ser Gly Arg Pro Ser Lys Ser Gly Phe
 1               5                  10                  15

Phe Gly Pro Pro Arg Gln Glu Met Gly Ser Leu His Gly Arg Gln Asp
            20                  25                  30

Ala Glu Ala Glu Ser Gln Pro Pro His Pro Gly Thr Arg Pro
        35                  40                  45

Gly Arg Gly Arg Pro His Gln Cys Trp Val Pro Ala Pro Ala Ala Arg
     50                  55                  60

Leu Leu Gly Pro Ala Trp Leu Ala Ala Arg Ala Val Cys Leu Gln Lys
 65                  70                  75                  80

Arg Gln Gly Pro Pro Cys Gln Ala Ser Ser Xaa Leu Pro Val Gly Ser
            85                  90                  95
```

```
Ala Cys Val Ser Ser Cys Arg Ile Ser Lys Leu Leu Lys Val His Leu
            100                 105                 110

Leu Arg Gln Arg Gly Gln Val Gly Arg His Leu Cys Pro Leu Val Gln
        115                 120                 125

Glu Gln Arg Gln Ala Ala Pro His Ser His Val Glu Ser Ser Gln Gly
    130                 135                 140

Lys Gly Gly Cys Gly Gly Asp Arg Gly Arg Pro Arg Ala Gly Thr
145                 150                 155                 160

Ser Cys Ser His Gly Gly Arg Ser Trp Ser Leu Ser Ala Val Gly Ser
                165                 170                 175

His Cys Leu Pro Ala Leu Pro Leu Ser Pro Ala Ala Pro Ala Pro Pro
            180                 185                 190

Arg Arg Leu Ser Leu Ser Glu Lys Arg Arg Pro Ala Leu Gln Ser Gly
        195                 200                 205

Ala Pro Ser Lys Ser Ala Glu Ala Gly Val Pro Thr Ser Thr Leu Glu
    210                 215                 220

Val Ser Arg Arg Val Met Trp Gly Ala
225                 230
```

<210> SEQ ID NO 47
<211> LENGTH: 3023
<212> TYPE: DNA
<213> ORGANISM: Homo sapiens

<400> SEQUENCE: 47

```
tcacattgcc aaaagacggc aatatggtgg aaaataacat atagacaaac gcacaccggc      60
cttattccaa gcggcttcgg ccagtaacgt tagaattgcc gagaagtcat gataatttcg     120
tttgttcttc cagatttagg catatactta tttaatcaat aatgtgttaa cagctgacac     180
ctgtggttgc tgtgacaggc actatttgaa gtgctttatc atggattaac tcttaatcct     240
cagctaccgt ataaagtagg acataacccc atttcacatg cactacactg agacttgcct     300
cctctccccc cacattgaag atgttctttt tcataacta tatactattc cattgcatga     360
atattctgta atttatttaa tccctatgg attgataatt aggttcatta tagatagaag     420
tgtaattaac attcctgtac atgtattttg ctacttgtgt gggtatttct gtaggatgaa     480
taactagaaa tttattggat caggtttcac atttgcagtt ttgaaaacta ctaccaaaaa     540
gatttcacca atttacaact ccatcattag taagaatgcc tgtttgccta tagtctgcca     600
accctgaatc cttaaaaatt tttgccaatc tggtaggcaa aatttctttc ttttctttga     660
atattaatga ggaggaacat cttttcatgt tccttggcca tttgcatttc ctattatgaa     720
ttgcttttgc ccattttcct ttttttaatt atgaaagtct aatgactacc ttctcattgt     780
ataaaaaaca cagttctttg aatagagaga cccttttctc caatgctacc aatcacattc     840
cacttaccac agtttaacat acatcctcta gtcacctttc cgtacgaata tacatacaca     900
taaaaacact ttttacataa ataggatctc atattctgta gcttttttaaa attttggtct     960
caaaaaaga taacaggtct ttaaatttct ttaatggttg actatgatta aatactatga    1020
aaatgccatt atttattccc ttaatttttt tccctctcgc tattacattg ccaaagttaa    1080
catcctattc agatgtcttt gtgcatgtgt gtgaatattt ctttagtctg gagtccagta    1140
aggtggattt ttggatcaaa gggtttgttc tctgtccacc ttcagtcttc ccaaaggcct    1200
tcataactgt attttcacca agtgtatgga gaatgttcat ttcccccatat aaccatacct    1260
acacttgata gttttttatct gttgggcgaa aaagaacctt ttcttatttt gcatttccct    1320
```

-continued

```
gattataaaa aaaaatggtg agattggggt tattttcatg tttattggcc atttatagtt    1380
tactgtggat tgtttgtatc ccttacctgc tttctattgg gttatgtgtg gatatattgt    1440
ttttatttgt tcagcatctc cttccccatc ttctggtaac acaacctta tttatttgtg     1500 gggaacctat tccctgtggc ttaggtgagc atgtgaccag gcctggcctc ctgagtccca    1560
cagcttccta gccacagtga taaaagaatg ggtatataac ttaagccagg ctaaggaaag    1620
cccttaacag aacttctgct ggaactactg gaaagaaggc tttatggaga tcccaggaac    1680
caaggaccat gtaagcctga atttgtgcca tgtggagaga gtctgtctga ggagaaactc    1740
ggatgctagc agaaatggaa agagaactaa gttctgatgt catttttctg gaggccctag    1800
atccagctgt gcctaaagcc tgccctacct ccggacttta agttttgtg agccaataaa     1860 gtcccttct tgtttaagat aattgaattg agtttctgtt ctgattaata taggttatgt     1920
gtattttctt attgatttgt agaaaaccttt gtaattttaa attctagact ttatgcccta   1980
tataagttac taaactctgt ctcaataaaa aaaaggaaa acccacagcc aacattatca     2040
ctagtggtaa cagggaaaat gtccccttg accccaccc caagtacaga acatgcaagg      2100
acgcctgttc tcactgcatg tcttctgtgt tgtactgaag ctcctagctg gtgcagtgag    2160
gcaagacaaa gaaaggaaat ataggtgcac tgggaaggaa gaagaaacac tgcctttatt    2220
ctttaggtga catgattgtg tgcttttaaa ataataaagg aatcaacaga aaagttgctt    2280
aacctaatga atgagtttat caaagtcaca agatacaagg tcagtataca aaaatcagtt    2340
ggatttctac atggtagaaa caactgtaca tggaaaaatg tttaatagtg taagatatgt    2400
acattggaaa ctatgaaaga gtgtaaaaaa taaagaagtg aaataaatgg agaagatacc    2460
accttgatgg atggaagcct taaggtaaag atgctcattc tccccacact gacctgtaca    2520
ttccccacag gcctaatcaa aacccccaca ggcttctgtg tagaaattga catgctgatc    2580
ctgaaattta tatgaaaatg caaagagtct ggaataacca aaataatttt gtaaaagaac    2640
aaagaagact tctactacct ggttataaga cttctctgaa gcacagaagt caaggcagtg    2700
tggtggtggc ataagtaatg taaatcatcc aggtgtggtg gctcaggcca gtcatccagc    2760
actttgggag gctgaggcag gagaatcgct agagcccagg agttggaaac cagcctgggc    2820
agcatagcaa gactcatctc tacaaaaaat acgaaacaat tagctgggtg tctgtagcac    2880
atgcctgtag tcccagctgc gcgggaggct gagctgggaa gatcacttta gcctgggaag    2940 tcagggagc tgtgatcaca ccactgcact ccagcctggg caacagagca gacccccatc     3000
tcaaaaacaa aaaaaaaaaa aaa                                            3023
```

<210> SEQ ID NO 48
<211> LENGTH: 83
<212> TYPE: PRT
<213> ORGANISM: Homo sapiens

<400> SEQUENCE: 48

```
Met Lys Met Pro Leu Phe Ile Pro Leu Ile Phe Phe Pro Leu Ala Ile
 1               5                  10                  15

Thr Leu Pro Lys Leu Thr Ser Tyr Ser Asp Val Phe Val His Val Cys
             20                  25                  30

Glu Tyr Phe Phe Ser Leu Glu Ser Ser Lys Val Asp Phe Trp Ile Lys
         35                  40                  45

Gly Phe Val Leu Cys Pro Pro Ser Val Phe Pro Lys Ala Phe Ile Thr
     50                  55                  60

Val Phe Ser Pro Ser Val Trp Arg Met Phe Ile Ser Pro Tyr Asn His
```

```
                    65                  70                  75                  80
Thr Tyr Thr

<210> SEQ ID NO 49
<211> LENGTH: 1049
<212> TYPE: DNA
<213> ORGANISM: Homo sapiens

<400> SEQUENCE: 49
gtaactatct ccatgtttgt ccttttctac ctcgtttttt caccactccc aaacataacc     60
tcccaatctt ttttgttagt ccggccgtca atttgtatag taccaatttc tgtaaattct    120
ctcaattcat tgaagatcgt agggttaaac tttttgtgt gtgatttaaa cttacaaaca    180
agtgaagaag ctatcgttta tttcagacga ggctgtagtt taaataccaa agagggaaa    240 ataaaaaaga acctttgtaa aatatatctg aacctaatgg tttgtacact ggagaatcgt    300
tctagatagt taccaattaa atataactcc gccagtgtaa gggtgtgagg tgcagttgtc    360
caggagacga ttttgtatag tattttcttt gtacattact tccagtaaat atttgaaaat    420
atattgaagt aaacttgatt ttttttttgt cacaagaaaa tattaagagt tattgttgca    480
gttctgatga gctgcaggtt ttttgaactc acttctggag gtgcagagcc acaaacgcac    540
tttcggggcc tagttttgct cgaatatgaa tttagatagg tatcaagctg taactaagac    600
aatatttgat aaatgttgga tgacatttaa tttaatggag catgtactta tttgcatttg    660
ctggcagttc aggcatagtt aaagtgagag ttctccgata tttcataata agtgggtctg    720
ccaaaaccca tgtattaaat aaattgtcca agtgaaactc gactaacttt ggcctttgtg    780
tatttcctga aggtaatatt gttaactgtt aataaatact tctgcacta catttaaatg    840 tttgcagatt ctgcaaacta attgctcatt gtaatgttga ataaatttgg atatttcaca    900
ttgaaatgaa aagcctttct ctggagcatt ttagatttgc attttaaatg catgaaatgt    960
aattgattta tttgtaaaat tttaaatggg gttaataaac tcagaaaaaa aaaaaaaaa   1020 aaaaaaaaaa aaaaaaaaaa aaaaaaaaa                                     1049

<210> SEQ ID NO 50
<211> LENGTH: 98
<212> TYPE: PRT
<213> ORGANISM: Homo sapiens

<400> SEQUENCE: 50

Met Phe Val Leu Phe Tyr Leu Val Phe Ser Pro Leu Pro Asn Ile Thr
  1               5                  10                  15

Ser Gln Ser Phe Leu Leu Val Arg Pro Ser Ile Cys Ile Val Pro Ile
                 20                  25                  30

Ser Val Asn Ser Leu Asn Ser Leu Lys Ile Val Gly Leu Asn Phe Phe
             35                  40                  45

Val Cys Asp Leu Asn Leu Gln Thr Ser Glu Glu Ala Ile Val Tyr Phe
         50                  55                  60

Arg Arg Gly Cys Ser Leu Asn Thr Lys Arg Gly Lys Ile Lys Lys Asn
 65                  70                  75                  80

Leu Cys Lys Ile Tyr Leu Asn Leu Met Val Cys Thr Leu Glu Asn Arg
                 85                  90                  95

Ser Arg

<210> SEQ ID NO 51
<211> LENGTH: 1707
```

<212> TYPE: DNA
<213> ORGANISM: Homo sapiens

<400> SEQUENCE: 51

```
cacacagctc ccggatgaag ataacagttg gtagaccaaa aggtgacctc gcttagtata      60
ttgaaaacac acaccacaca tcacacacag aactgaatca taccacgtgc tgcctatggg     120
acttcagtta ctgtttcctg agttactgtt tatccgctgg caatggtgtg atttgtctgg     180
atcagatccg tgctattccc caacccacct ccagataatg tgagaaaata gccatgtcag     240
tatgtaggaa ctctgatggt gctcagattt gtgtgttcaa tcaatgggct taaatcagca     300
aaatattatg cctaaagtaa atctgttctt aacaagggct ctaccactgc attttcacat     360
gtaccttcag ggggttatct ttttttttt cccctcctat tttaatcagc aaaatccata     420
ccaaaacaac gacaacaacg ccctcttaag ggaccaccct ttggtcaatc ataacatgct     480
gtttaaagca gctgtttaca ggatgtgtag tggtatgccc ttgtcatata ctcttagcat     540
atcttttttt cctttggctt tgcatggctt tcttcaggta ctgtctcggt atcattctgc     600
taatcattgt tacagaatgg tgacttcatt tgtgctaaca gtacaacagc agatttgggt     660
caggcttaat ctagtgttaa cttttttttc tggtgctttt ttggattgat gactgtctca     720
ctttgactat acccatgttt tgcatgcaat gactcatgca tggttttctt aactagctaa     780
tattaacaat ttattccata taaaaatgga attttgcaac atcctttaat aaggtgaggg     840
aagcatgaac ctcagacttc tggcactatt acatagtaag cacatgaagt agtttgataa     900
taaatagcag ttctagtact tcacatttca cccgtgtgtg caatgccttt ttctgggggg     960
tgggggggtga gggaaaacct ggtagtgaat gtgtagttgg ggaataaaga aaagcactaa    1020
atcctgccct ttttgtgtgg tttccttttg atacaactag gttattcata atgtatacct    1080
agaaaagtga aattgaaaat accaaaagat gtatcattt tatttgaatc catcatgcag    1140
tgtacatttc agataatttc cttcagtctc cagataggag tgtatccaaa catctaattt    1200
tatgtgcact gtgtatctta tatgaatgtt ttattttata taccacatgc aaaaatgtcc    1260
atatgcacta tttaaatgtt ttaaataata tattccttct ttataatgct aaatctatat    1320
gagtaccata tttttataag tcagtggtct gactggtttc attttagaat taacagctgc    1380
ttcaatatgt tattcaatgt taatgtttgg ctgtgagtag aatatgtaaa agtggcatgg    1440
cagcacttat gctctgtgac agtattgtgt gtcatagttg agcagtagct ggtagaatta    1500
ggcagttggt gatagttta ctttggtaca aataaaaact gtatatcat atacaaataa    1560
tatatagata tatatgtcca ccagtataat ggcattgctg tgtctggcac ttcattgtac    1620
ggactttat aataaaagaa cttgaaagtt tttaaaaaa aaaaaaaaa aaaaaaaaa    1680
aaaaaaaaa aaaaaaaaa aaaaaaa                                        1707
```

<210> SEQ ID NO 52
<211> LENGTH: 141
<212> TYPE: PRT
<213> ORGANISM: Homo sapiens

<400> SEQUENCE: 52

```
Met Gly Leu Asn Gln Gln Asn Ile Met Pro Lys Val Asn Leu Phe Leu
  1               5                  10                  15

Thr Arg Ala Leu Pro Leu His Phe His Met Tyr Leu Gln Gly Val Ile
             20                  25                  30

Phe Phe Phe Phe Pro Ser Tyr Phe Asn Gln Gln Asn Pro Tyr Gln Asn
         35                  40                  45
```

```
Asn Asp Asn Asn Ala Leu Leu Arg Asp His Pro Leu Val Asn His Asn
 50                  55                  60
Met Leu Phe Lys Ala Ala Val Tyr Arg Met Cys Ser Gly Met Pro Leu
 65                  70                  75                  80
Ser Tyr Thr Leu Ser Ile Ser Phe Phe Pro Leu Ala Leu His Gly Phe
                 85                  90                  95
Leu Gln Val Leu Ser Arg Tyr His Ser Ala Asn His Cys Tyr Arg Met
            100                 105                 110
Val Thr Ser Phe Val Leu Thr Val Gln Gln Gln Ile Trp Val Arg Leu
        115                 120                 125
Asn Leu Val Leu Thr Phe Phe Ser Gly Ala Phe Leu Asp
130                 135                 140

<210> SEQ ID NO 53
<211> LENGTH: 1922
<212> TYPE: DNA
<213> ORGANISM: Homo sapiens

<400> SEQUENCE: 53
aaagcaccag gaactggttg accacctttc ccagcatgtc tcttaggggc ctgacctcag      60
gatttcagac tggattcact gtgacagaac taagggaata atacattttt atgtccacgt     120
tcccactctg gtgtaccatc tgtccacaga ggggagagaa caagcaagag gttggggtgt     180
gccatccagt gtccctgga gcagaccttg gcctctggtc ttcagtgccc ggtcctcctg      240
tctgttgtct ggcctggtga ggaagccctg acttgtaact ctcaaagcct aacttcaggg     300
gttgccctgc cagtgccctc tccgggagct ttgggtccct ggttataagc tttcagttct     360
cagtgtctgc tgtcaccagt aaccaagtgc tgaaaatgat ctgtaccact ttgctgacaa     420
gggcggctgg gccagggtgc cccgcccag cttcctctac tctccctgtg gcctggggct     480
acacttgggt taaaactccc cattatggag ccaactgatt ctcccacttg gccccagggc     540
atgatttaag caaacttaaa actcaatgct ttattgatag tttaaataat taacattacg     600
taaagaaaaa tctaaatgta aacagttttt gcaaacgagt atccattaag ggacttccaa     660
gtacctaacc cctattaaac aatttatgta aaccactctt ccttaaagaa atcgaatgc      720
ccagctcctt cccaatcctc caagctctga agtagggaag aggtgcagct aggagcagat     780
ggggcagtgt gtgtgttgga ggtggaggag tgggggaaat caaatcagct cacctgtgtg     840
gttatttatc agtgaaactt aataaactgg tactgggaaa gaaaaggagg ctagtgattg     900
acagcatccc gggctgctga gaggaccagc atgatgagct gtcttggagt tggcaattag     960
gagctcgtga gcgacctttg ccagaacagt tccatggac gacctggctg gaggcctaat    1020
tgcaacagat ttatgatctt gcttggccag atatcctggg aggcagaaac gaggactgtt    1080
ctgaacatat gcatcaggac gcataatggg gctttgttcg ggcctgggca gacatggagg    1140
gcaatgcctg agctctcttc cagtttatct ccacgtcctc caagctcaaa tctggcagcc    1200
ctggagtggt ttgaagttga aactccacag agcagtggac ttaatgctcc aaagatgcgt    1260
tgacattcag ccattgtccc tggcccccaa gtgtccgtgg gagttgctga gttttcatgg    1320
agatgatcca cgtccctggg tgtcgcctgc ttcctctcac agtgtgaaaa ccacacagct    1380
actgttacta gagatcatcc tggaatttct gggacagccc ttgtttaaag cactctgtgt    1440
tccagattga tcagacacgt ctctctccac cccttcacaa aactccacta aaagagtga     1500
gaaattttaa agggtgcaca ttcacaacta cagagagaat gaaaaagatg tcagtgaaga    1560
```

```
agagattatg cattctgggg caatggaaag cggatagagg ctgggcacag tggctcactc    1620
ctgtattccc agcactttgg gagcccaagg caggcggatc acctgaggtc agaagttcaa    1680
gaccagcctg gccaacgtgg tgaaacccca tctctacaaa aatacaaaaa ttagctgggc    1740
atggtggtgg gtacctgtag tcccagctac tcaggaggct gaggctactc gggaatcaca    1800
tgaacccaag aggcggaggt tgcagtgagc aggtatcacg ccaatgcacc ccagcctggg    1860
caacaaagcg agaatctgtc aaaaaaaaaa aaaaaaaaa aaaaaaaaa aaaaaaaaa      1920 aa                                                                    1922
```

<210> SEQ ID NO 54
<211> LENGTH: 114
<212> TYPE: PRT
<213> ORGANISM: Homo sapiens

<400> SEQUENCE: 54

```
Met Gly Leu Cys Ser Gly Leu Gly Arg His Gly Gly Gln Cys Leu Ser
  1               5                  10                  15

Ser Leu Pro Val Tyr Leu His Val Leu Gln Ala Gln Ile Trp Gln Pro
                 20                  25                  30

Trp Ser Gly Leu Lys Leu Lys Leu His Arg Ala Val Asp Leu Met Leu
             35                  40                  45

Gln Arg Cys Val Asp Ile Gln Pro Leu Ser Leu Ala Pro Lys Cys Pro
         50                  55                  60

Trp Glu Leu Leu Ser Phe His Gly Asp Asp Pro Arg Pro Trp Val Ser
 65                  70                  75                  80

Pro Ala Ser Ser His Ser Val Lys Thr Thr Gln Leu Leu Leu Leu Glu
                 85                  90                  95

Ile Ile Leu Glu Phe Leu Gly Gln Pro Leu Phe Lys Ala Leu Cys Val
            100                 105                 110

Pro Asp
```

<210> SEQ ID NO 55
<211> LENGTH: 589
<212> TYPE: DNA
<213> ORGANISM: Homo sapiens

<400> SEQUENCE: 55

```
tttttccaca ctcagctttc ccctagcatg gacaagattt tcagccattt ttgccacata     60 tacatttta aggaaaaaag atttttctct gtaagaaagt tctggttatg ctgttttaaa    120
ggtgacttgt caggagttga gacttccctg ccggattcta ttttgaaagt aaatggtctt    180
ccctccttgt tccgattctg cgttcccatc gtcagacaac tttggagtat tagaaaccac    240
tgtatatatg tggaaagcca ggtcagccag actgttagat tggtgtgcac tcacctgaga    300
gatctggcag gttggatata tttatgtgta tttctccaca gtgcttgctt tgccctgttg    360
gtaaggattt taaataacca tgctcaaaag agctgttcta atctgcgttt tgcatgttaa    420
gtgttaatat caaacattct taacgtgctc gaggaattgc ttttaacatt ctactttgcc    480
agtttcttca ttagattaat tgacatgtat tatttaaatg accagtgatg ctttgtgcaa    540
ttatgaatgt tgaagattaa agtacatagt tactaaaaaa aaaaaaaaa                589
```

<210> SEQ ID NO 56
<211> LENGTH: 130
<212> TYPE: PRT
<213> ORGANISM: Homo sapiens

<400> SEQUENCE: 56

```
Met Asp Lys Ile Phe Ser His Phe Cys His Ile Tyr Ile Phe Lys Glu
  1               5                  10                  15

Lys Arg Phe Phe Ser Val Arg Lys Phe Trp Leu Cys Cys Phe Lys Gly
             20                  25                  30

Asp Leu Ser Gly Val Glu Thr Ser Leu Pro Asp Ser Ile Leu Lys Val
         35                  40                  45

Asn Gly Leu Pro Ser Leu Phe Arg Phe Cys Val Pro Ile Val Arg Gln
     50                  55                  60

Leu Trp Ser Ile Arg Asn His Cys Ile Tyr Val Glu Ser Gln Val Ser
 65                  70                  75                  80

Gln Thr Val Arg Leu Val Cys Thr His Leu Arg Asp Leu Ala Gly Trp
             85                  90                  95

Ile Tyr Leu Cys Val Phe Leu His Ser Ala Cys Phe Ala Leu Leu Val
            100                 105                 110

Arg Ile Leu Asn Asn His Ala Gln Lys Ser Cys Ser Asn Leu Arg Phe
        115                 120                 125

Ala Cys
    130
```

```
<210> SEQ ID NO 57
<211> LENGTH: 1363
<212> TYPE: DNA
<213> ORGANISM: Homo sapiens
```

<400> SEQUENCE: 57

```
gtagtggact tgatcttcct taacacagaa gtgtcactgt cacaagcctt ggaggatgtt      60
agcaggggag gttctccttt tgctattgtc atcacccagc aacaccagat tcaccgctcc     120
tgcacagtca acatcatgtt tggaaccccg caagagcatc gcaacatgcc ccaagcagat     180
gccatggtgc tggtggccag aaattatgag cgttacaaga atgagtgccg ggagaaggaa     240
cgtgaggaga ttgccagaca ggcagccaag atggccgatg aagccatcct gcaggaaaga     300
gagagaggag gccctgagga gggagtgcgt gggggccacc ctccagccat ccagagcctc     360
atcaacctgc tggcagacaa caggtacctc actgctgaag agactgacaa gatcatcaac     420
tacctgcgag agggaaggag cggctgatga ggagcagcac cgactctctg cctggggagc     480
tacgtggcag ggccgaggcc cgatttcccg ccaaccactc ggggcgacct cgggtgcctc     540
gctgaagaca cagccaagct cccaaccgct ccagagcggc caagtgctcc cctctgctac     600
acccactcca tctgcacccc ccacctccca gcaagagctt caggccaaaa tcctcagcct     660
cttcaatagt ggcaccgtga cggccaatag cagctctgca tcccctcgg ttgctgccgg      720 aaacacccca aaccagaatt tttccacagc agcaaacagc cagcctcaac aaagatcaca     780
ggcttctggc aatcagcctc caagcatttt gggacaggga ggatctgctc agaacatggg     840
ccccagacct ggggctcctt cccaagggct ttttggccag ccttccagtc gcctggcacc     900
tgctagcaac atgactagcc agaggcctgt gtcttccaca ggtatcaact ttgacaatcc     960
aagtgtacag aaggctctgg ataccctgat ccagagtggc cctgctctct cccacctggt    1020
tagccagacc acagcacaga tggggcagcc acaggccccc atgggatctt accagaggca    1080
ttactgagag ctaaatcttt caactctccc cagtcccctc atccctggc ctcctcccac     1140 ttacttgttc taaatagagc tgtttggagg atgttctctg cgctcccagg ccggcatcga    1200
gtgtcatcaa tttctaccac ctgctctctc ttctgcccaa ggctgtgttg cttattcctt    1260
```

-continued

```
acaaagttta tactgcattt ggggctgtat cttttttttgt tttttgtttt gtagaaaata   1320
aaaatctccg gggcaaaaa aaaaaaaaaa aaaaaaaaaa aaa                      1363
```

<210> SEQ ID NO 58
<211> LENGTH: 343
<212> TYPE: PRT
<213> ORGANISM: Homo sapiens

<400> SEQUENCE: 58

```
Met Leu Ala Gly Glu Val Leu Leu Leu Leu Ser Ser Pro Ser Asn
 1               5                  10                  15

Thr Arg Phe Thr Ala Pro Ala Gln Ser Thr Ser Cys Leu Glu Pro Arg
                20                  25                  30

Lys Ser Ile Ala Thr Cys Pro Lys Gln Met Pro Trp Cys Trp Trp Pro
            35                  40                  45

Glu Ile Met Ser Val Thr Arg Met Ser Ala Gly Arg Arg Asn Val Arg
        50                  55                  60

Arg Leu Pro Asp Arg Gln Pro Arg Trp Pro Met Lys Pro Ser Cys Arg
65                  70                  75                  80

Lys Glu Arg Glu Glu Ala Leu Arg Arg Glu Cys Val Gly Ala Thr Leu
                85                  90                  95

Gln Pro Ser Arg Ala Ser Ser Thr Cys Trp Gln Thr Thr Gly Thr Ser
            100                 105                 110

Leu Leu Lys Arg Leu Thr Arg Ser Ser Thr Cys Glu Arg Glu Gly
        115                 120                 125

Ala Ala Asp Glu Glu Gln His Arg Leu Ser Ala Trp Gly Ala Thr Trp
    130                 135                 140

Gln Gly Arg Gly Pro Ile Ser Arg Gln Pro Leu Gly Ala Thr Ser Gly
145                 150                 155                 160

Ala Ser Leu Lys Thr Gln Pro Ser Ser Gln Pro Leu Gln Ser Gly Gln
                165                 170                 175

Val Leu Pro Ser Ala Thr Pro Thr Pro Ser Ala Pro Pro Thr Ser Gln
            180                 185                 190

Gln Glu Leu Gln Ala Lys Ile Leu Ser Leu Phe Asn Ser Gly Thr Val
        195                 200                 205

Thr Ala Asn Ser Ser Ser Ala Ser Pro Ser Val Ala Ala Gly Asn Thr
    210                 215                 220

Pro Asn Gln Asn Phe Ser Thr Ala Ala Asn Ser Gln Pro Gln Gln Arg
225                 230                 235                 240

Ser Gln Ala Ser Gly Asn Gln Pro Pro Ser Ile Leu Gly Gln Gly Gly
                245                 250                 255

Ser Ala Gln Asn Met Gly Pro Arg Pro Gly Ala Pro Ser Gln Gly Leu
            260                 265                 270

Phe Gly Gln Pro Ser Ser Arg Leu Ala Pro Ala Ser Asn Met Thr Ser
        275                 280                 285

Gln Arg Pro Val Ser Ser Thr Gly Ile Asn Phe Asp Asn Pro Ser Val
    290                 295                 300

Gln Lys Ala Leu Asp Thr Leu Ile Gln Ser Gly Pro Ala Leu Ser His
305                 310                 315                 320

Leu Val Ser Gln Thr Thr Ala Gln Met Gly Gln Pro Ala Pro Met
                325                 330                 335

Gly Ser Tyr Gln Arg His Tyr
            340
```

<210> SEQ ID NO 59
<211> LENGTH: 1613
<212> TYPE: DNA
<213> ORGANISM: Homo sapiens

<400> SEQUENCE: 59

```
cctcgctaca caagaaaagt tgtgtcctgg tttaagcttt gactgaaact cattcacatc      60
cgtgtgttaa tttgcatttt caggcctctt ctctctgaat ctctcctaga gaagaaaatt     120
atggaatagt tggttgcttt ctgtttgggg tcaggagaat tagggagaga tttctctttg     180
tttccaatgg atcctgaagg tgagctgcca tcacctcatc tctaggaggt gctgtaggga     240
gaaaaactgg aggtagcagg gtatttctct ctcttttctc ccctccgtct agccttaatt     300
aatagtttca tcttttgggt catcgaaaaa gtcagctctg attcatccat atccaataaa     360
ttgcagggtc acatggatcg ggtcttccga gccacctgcc ttctttttct caagttccct     420
ggtggcgcct cttcaggtcc tcacatctct tctgtcccgt cacagaggaa cacctcagac     480
ccatcctctc taccttggca tatcaccccc tggtcccttg atgcttcttc cttctggtcc     540
tcggagtctt ttctgagctc cagcgtcacc ggcgttggtg gcctttccac cctcccctct     600
cgcatgtgcc ttttccagtc cattgggact actccctgct cccccgtcac acacgttccc     660
taggccagtt cctttttcacc tggctgtagt cctcatgacc agctaaaagt gcgcctgccc     720
cagatatttg tgatttccct ctcttcagag aaagcaggga gcccctggca tccctatctg     780
tgacaggtgc cacacccgcc ttacaatgca ggtctgtgtg cccttgttgt atccctaact     840
gctctcaaat cccttagtga cggcctcatt tctctgcctt tgtgtagcat ttaaacagtt     900
taaatggctg ggcacgtggc tcacatctct aatcccagca ctttggaagg ccaaggcggg     960
acgatcactg gagtctcggg gagttcgaga ccagcctggc caacatggtg aaaccccttt    1020
ctactaaaaa tacagaaatc ggcgggctgg ttggtgcgtt cctgtaatcc cggctactgg    1080
gggggctaag gagggagaat tgtttggacc cgggaggttg cagtgagcag agtatgcgtc    1140
attgcactcc agattgggga acaagagcga gactctgtct caaaataagt aagttgataa    1200
aagtgaacag tttaaatgga tgaacctttg accctgcagt aaattccaga catgtaggag    1260
aaacagccag gtgtagaggg aaggcagtgg ggttctgagt caggcagacc taagtttggc    1320
atctggctcc tgtgctggtg gctgagttcc ttaacctttg tgtgttctta cagctctgtg    1380
ggtctcaatt gttccaccta taaacaggg atgacactgt gacctttcag ggttgtggag    1440
tagttgtgtg atgttccttg tttaggccag gcccagtggc tcacgcctgt aatcccaata    1500
ctttgggaag ccaaggtgag tggattgctt gagcccgta gtttgagacc agcctacaca    1560
acatggcaag accccatctc cgcaaaaaaa aaaaaaaaa aaaaaaaaaa aaa            1613
```

<210> SEQ ID NO 60
<211> LENGTH: 96
<212> TYPE: PRT
<213> ORGANISM: Homo sapiens

<400> SEQUENCE: 60

```
Met Asp Arg Val Phe Arg Ala Thr Cys Leu Leu Phe Leu Lys Phe Pro
  1               5                  10                  15

Gly Gly Ala Ser Ser Gly Pro His Ile Ser Ser Val Pro Ser Gln Arg
                 20                  25                  30

Asn Thr Ser Asp Pro Ser Ser Leu Pro Trp His Ile Thr Pro Trp Ser
             35                  40                  45

Leu Asp Ala Ser Ser Phe Trp Ser Ser Glu Ser Phe Leu Ser Ser Ser
```

|  |  | 50 |  |  | 55 |  |  | 60 |  |
|---|---|---|---|---|---|---|---|---|---|

Val Thr Gly Val Gly Gly Leu Ser Thr Leu Pro Ser Arg Met Cys Leu
 65                  70                  75                  80

Phe Gln Ser Ile Gly Thr Thr Pro Cys Ser Pro Val Thr His Val Pro
                 85                  90                  95

<210> SEQ ID NO 61
<211> LENGTH: 1700
<212> TYPE: DNA
<213> ORGANISM: Homo sapiens

<400> SEQUENCE: 61

| aagctgtgcg | aggagttcct | ggcgcacgcc | cgcggccggc | tggagaagga | gctgagaaac |   60 |
|---|---|---|---|---|---|---|
| ctggaggccg | agctggggcc | ctcacctccg | gctcccgacg | tgttagagtt | caccgaccat |  120 |
| ggaggcagtg | gcttcgtggg | cggcctctgc | caggtggcgg | cggcctacca | ggagctgttt |  180 |
| gcggcccagg | gcccagcagg | tgccgagaag | ctggcggcct | tcgcccggca | gctgggcagc |  240 |
| cgctattttg | cgctggtgga | gcggcggctg | gcgcaggagc | aggtggtgg | tgacaactca |  300 |
| ctgctggtgc | gggcgctgga | ccgcttccac | cggcgcttgc | gggctcccgg | ggccctgctg |  360 |
| gccgctgccg | ggctcgcaga | cgctgccacg | gagatcgtgg | aacgagtggc | ccgcgagcgc |  420 |
| ctgggccacc | acctgcaggg | tctccgggcg | gccttcctgg | gctgcctgac | agacgtccgc |  480 |
| caggcgctgg | cagcacctcg | cgtgctgggg | aaggagggcc | ctggcctggc | cgagttgctg |  540 |
| gccaatgtgg | ccagctccat | cctgagccac | attaaggcct | ctctggcagc | agtgcacctt |  600 |
| tcaccgcca | aagaggtgtc | cttctccaac | aagccctact | tccggggtga | gttctgcagt |  660 |
| cagggtgtcc | gtgagggcct | catcgtgggc | ttcgtccact | ctatgttcca | gacggctcag |  720 |
| agcttctgcg | acagccctgg | ggagaaaggg | ggtgccacac | cacctgccct | gctcctgctg |  780 |
| ctctcccgcc | tctgcctgga | ctacgagacg | gccaccatct | cctacatcct | cactctcact |  840 |
| gatgaacagt | ttctggtgca | ggatcagttc | ccagtgacgc | ccgtgagcac | gctgtgtgca |  900 |
| gaggccaggg | aaacggcgcg | gcggctgctg | acccatacgg | gaagtgcagg | gcctggtcat |  960 |
| atcacagatg | ctgcgcaaga | gcgtggagac | tcgcgactgg | ctcagcactc | tggagccccg | 1020 |
| gaatgtgcgg | gctgtcatga | agcgggtggt | ggaggatacc | accgccatcg | acgtgcaggt | 1080 |
| ggggctcctg | tacgaagagg | gtgttcgcaa | ggcccagagc | agcgactcca | gcaagaggac | 1140 |
| tttctccgtg | tacagcagct | ctcggcagca | gggccgctac | gccccagct | ataccccag | 1200 |
| tgccccgatg | gacaccaacc | tcttgagcaa | tatccagaag | ctattctctg | aacgtattga | 1260 |
| tgtgttcagc | cctgtggagt | tcaacaaggt | gtcggtgctg | accggcatca | tcaagatcag | 1320 |
| cctgaagacg | ctgctggagt | gtgtgcggct | gcgcacccttt | gggcgcttcg | ggctgcagca | 1380 |
| ggtgcaagtg | gactgccact | ttctgcagct | ctacctgtgg | cggttttgtg | gccgacgaag | 1440 |
| aactcgtgca | cttgctgctg | gacgaagtgg | tggcctctgc | tgccctgcgc | tgcccagacc | 1500 |
| ctgtgcccat | ggagcccagt | gtggttgagg | tcatctgcga | gcgcggctag | gcgcagccgc | 1560 |
| tgccatgcac | cggtctgtcc | ctgcacccca | tggcacccag | gatctggtct | cggtggtcct | 1620 |
| tccccgcagg | caggtgtcag | gaccggccta | ataaacatgt | gtggcctccc | caaaaaaaa | 1680 |
| aaaaaaaaa | aaaaaaaaa |  |  |  |  | 1700 |

<210> SEQ ID NO 62
<211> LENGTH: 116
<212> TYPE: PRT
<213> ORGANISM: Homo sapiens

<400> SEQUENCE: 62

| Met | Glu | Ala | Val | Ala | Ser | Trp | Ala | Ala | Ser | Ala | Arg | Trp | Arg | Arg | Pro |
|---|---|---|---|---|---|---|---|---|---|---|---|---|---|---|---|
| 1 | | | | 5 | | | | | 10 | | | | | 15 | |

| Thr | Arg | Ser | Cys | Leu | Arg | Pro | Arg | Ala | Gln | Gln | Val | Pro | Arg | Ser | Trp |
|---|---|---|---|---|---|---|---|---|---|---|---|---|---|---|---|
| | | | 20 | | | | | 25 | | | | | 30 | | |

| Arg | Pro | Ser | Pro | Gly | Ser | Trp | Ala | Ala | Ile | Leu | Arg | Trp | Trp | Ser |
|---|---|---|---|---|---|---|---|---|---|---|---|---|---|---|
| | | 35 | | | | | 40 | | | | | 45 | | |

| Gly | Gly | Trp | Arg | Arg | Ser | Arg | Val | Val | Val | Thr | Thr | His | Cys | Trp | Cys |
|---|---|---|---|---|---|---|---|---|---|---|---|---|---|---|---|
| | 50 | | | | | 55 | | | | | 60 | | | | |

| Gly | Arg | Trp | Thr | Ala | Ser | Thr | Gly | Ala | Cys | Gly | Leu | Pro | Gly | Pro | Cys |
|---|---|---|---|---|---|---|---|---|---|---|---|---|---|---|---|
| 65 | | | | | 70 | | | | | 75 | | | | | 80 |

| Trp | Pro | Leu | Pro | Gly | Ser | Gln | Thr | Leu | Pro | Arg | Arg | Ser | Trp | Asn | Glu |
|---|---|---|---|---|---|---|---|---|---|---|---|---|---|---|---|
| | | | | 85 | | | | | 90 | | | | | 95 | |

| Trp | Pro | Ala | Ser | Ala | Trp | Ala | Thr | Thr | Cys | Arg | Val | Ser | Gly | Arg | Pro |
|---|---|---|---|---|---|---|---|---|---|---|---|---|---|---|---|
| | | | 100 | | | | | 105 | | | | | 110 | | |

| Ser | Trp | Ala | Ala |
|---|---|---|---|
| | | 115 | |

<210> SEQ ID NO 63
<211> LENGTH: 1616
<212> TYPE: DNA
<213> ORGANISM: Homo sapiens
<220> FEATURE:
<221> NAME/KEY: unsure
<222> LOCATION: (869)

<400> SEQUENCE: 63

| tcttaatata | tgcacatatg | tatatgtaac | acataaataa | ttacatacat | aatacaggaa | 60 |
|---|---|---|---|---|---|---|
| gacacagaaa | taattacata | catgatacag | gaagacacag | aaaaagagaa | actggtctga | 120 |
| taccagaagt | atcaactcag | gaacaatttt | ctactagctg | agcctcagaa | gcagcaactt | 180 |
| ttccaaagtg | aagtgatgaa | tggaggcgcc | agccctcctc | ctcaggttaa | gaaaggcaaa | 240 |
| gagccctgct | tttggctgta | aaaagccagg | ttccctaatc | aggtgaaggc | ctgaggcagg | 300 |
| gactccttag | ggcagtgtaa | ctagtagcca | aggcacaggc | tccaaaggga | ggttgcctgg | 360 |
| gctcaagccc | ggctctgcca | cttcacagct | gggtgtcccg | gggtgagcct | ctcagccccct | 420 |
| cgttcagcct | cagttccaca | tgtgtaaatg | gaggtctagt | agctacctca | cagggcagtt | 480 |
| gttgaaaata | agctaatgct | cctaaaaccc | tgagaacagt | gctctgtgta | tgataagtgt | 540 |
| tcatagacgt | cacattattt | atttattttg | aaaattcttc | ttttagtcaa | acttataagt | 600 |
| tttctgtggc | tcaaaatatt | ctcaaccagg | gtttctttag | tggccatcag | ctcccagggg | 660 |
| gtgatatcat | ggaagctgtt | atgcttagga | atttgtttaa | aaagacgtcc | tgccctgtgc | 720 |
| cccagtacat | ttcaacacca | cccagccaca | cagccgcctt | ctggcccaac | actcttaaag | 780 |
| acacagtgct | tgggaaatgt | cctcatgccc | cctttcctga | ggcaggtttg | ccactgtttc | 840 |
| cccaggcctg | gcagtcacag | atggcagtna | ctgacctgct | gtggatttga | gagatggaga | 900 |
| gaaaacctcc | actcttctta | ttctcccaat | agctcagtct | ctgcctcagt | tccaatttcc | 960 |
| ctttggcgta | actatgattg | tcgtccaagg | cccccctaga | taggcaagac | tcatgatacc | 1020 |
| caagggtga | tcagggaata | gagatgagat | gtctggtgg | atggcggaat | gggtatttt | 1080 |
| ctaactaatg | gggtgcaggg | gtacctgagc | ctgctctcaa | atgtgttata | cccctaaaaa | 1140 |
| atgttttta | ggtagtgggt | tgatataaca | gttgttaaga | ccatgatgct | agaggcaaga | 1200 |
| tcgtgagatc | catggagaag | gtagtggaag | gggtagggcc | tttattcaca | tatatgctgc | 1260 |

```
cttctccccc aactgatgtg atatccttta tattcgtgac tccagtgaac ccacgcctcg    1320
gaggatttac accctgtatt ggtactcctc ttgagtctgg gctggcctgt gactttaatc    1380
agtgcaaggc ggaagtgggt tcagtgccag ttctaagact acaaagagaa agaaaagttc    1440
aaccttccaa tatcccagca gacatcaggc cccagctgtg tcaccagctt cacgcccacg    1500
agtgaccaca acaaacccag cagaaccaac cagcgcatcc cagccctggt tgcagaatca    1560
tgagtaaata aatggttgc tgttccaaaa aaaaaaaaaa aaaaaaaaaa aaaaaa        1616
```

<210> SEQ ID NO 64
<211> LENGTH: 97
<212> TYPE: PRT
<213> ORGANISM: Homo sapiens

<400> SEQUENCE: 64

```
Met Glu Lys Val Val Glu Gly Val Gly Pro Leu Phe Thr Tyr Met Leu
  1               5                  10                  15

Pro Ser Pro Pro Thr Asp Val Ile Ser Phe Ile Phe Val Thr Pro Val
                 20                  25                  30

Asn Pro Arg Leu Gly Gly Phe Thr Pro Cys Ile Gly Thr Pro Leu Glu
             35                  40                  45

Ser Gly Leu Ala Cys Asp Phe Asn Gln Cys Lys Ala Glu Val Gly Ser
         50                  55                  60

Val Pro Val Leu Arg Leu Gln Arg Glu Arg Lys Val Gln Pro Ser Asn
     65                  70                  75                  80

Ile Pro Ala Asp Ile Arg Pro Gln Leu Cys His Gln Leu His Ala His
                 85                  90                  95

Glu
```

<210> SEQ ID NO 65
<211> LENGTH: 937
<212> TYPE: DNA
<213> ORGANISM: Homo sapiens

<400> SEQUENCE: 65

```
gattgccgga agctgaaggg atgctttgaa cgtggggggg ctgcgtcaca gttggactcc     60
cacttgcaga ggacctgatt atgtccagtg accacctgaa caacagcaca ctgaaggagg    120
ctcagttcaa agacctgttc ttaaaaaaag cggagctgga gttcgcccaa atcatcatca    180
tcgtcgtggt ggtcacggtg atggtggtgg tcatcgtctg cctgctgaac cactacaaag    240
tctccacgcg gtccttcatc aaccgcccga accagagccg gaggcgggag gacgggctgc    300
cgcaggaagg gtgcctgtgg ccttcagaca gcgccgcacc gcgctgggc gcctcggaga    360 tcatgcatgc cccgcggtcc agggacaggt tcacagcgcc gtccttcatc cagagggatc    420
gcttcagccg cttccagccc cctaccccct atgtgcagca cgagattgat cttcctccca    480
ccatctccct gtccgacggt gaagagccac ctccttacca ggggccctgc accctgcagc    540
tccgggaccc tgaacagcag atggaactca accgagagtc cgtgagggcc ccacccaacc    600
gaaccatatt tgacagtgat ttaatagaca ttgctatgta tagcgggggt ccatgcccac    660
ccagcagcaa ctcgggcatc agtgcaagca cctgcagcag taacgggagg atggaggggc    720 cacccccac atacagcgag gtgatgggcc accaccagg cgcctctttc ctccatcacc    780
agcgcagcaa cgcacacagg ggcagcagac tgcagtttca gcagaacaat gcagagagca    840
caatagtacc catcaaaggc aaagatagga agcctgggaa cctggtctga ttccttccaa    900
```

```
cgtgcacttc agctggagaa agaaaccaag aagggaa                              937
```

<210> SEQ ID NO 66
<211> LENGTH: 269
<212> TYPE: PRT
<213> ORGANISM: Homo sapiens

<400> SEQUENCE: 66

```
Met Ser Ser Asp His Leu Asn Asn Ser Thr Leu Lys Glu Ala Gln Phe
 1               5                  10                  15
Lys Asp Leu Phe Leu Lys Lys Ala Glu Leu Glu Phe Ala Gln Ile Ile
             20                  25                  30
Ile Ile Val Val Val Thr Val Met Val Val Ile Val Cys Leu
         35                  40                  45
Leu Asn His Tyr Lys Val Ser Thr Arg Ser Phe Ile Asn Arg Pro Asn
 50                  55                  60
Gln Ser Arg Arg Arg Glu Asp Gly Leu Pro Gln Glu Gly Cys Leu Trp
 65                  70                  75                  80
Pro Ser Asp Ser Ala Ala Pro Arg Trp Gly Ala Ser Glu Ile Met His
             85                  90                  95
Ala Pro Arg Ser Arg Asp Arg Phe Thr Ala Pro Ser Phe Ile Gln Arg
            100                 105                 110
Asp Arg Phe Ser Arg Phe Gln Pro Thr Tyr Pro Tyr Val Gln His Glu
            115                 120                 125
Ile Asp Leu Pro Pro Thr Ile Ser Leu Ser Asp Gly Glu Glu Pro Pro
130                 135                 140
Pro Tyr Gln Gly Pro Cys Thr Leu Gln Leu Arg Asp Pro Glu Gln Gln
145                 150                 155                 160
Met Glu Leu Asn Arg Glu Ser Val Arg Ala Pro Pro Asn Arg Thr Ile
            165                 170                 175
Phe Asp Ser Asp Leu Ile Asp Ile Ala Met Tyr Ser Gly Gly Pro Cys
            180                 185                 190
Pro Pro Ser Ser Asn Ser Gly Ile Ser Ala Ser Thr Cys Ser Ser Asn
            195                 200                 205
Gly Arg Met Glu Gly Pro Pro Pro Thr Tyr Ser Glu Val Met Gly His
210                 215                 220
His Pro Gly Ala Ser Phe Leu His His Gln Arg Ser Asn Ala His Arg
225                 230                 235                 240
Gly Ser Arg Leu Gln Phe Gln Gln Asn Asn Ala Glu Ser Thr Ile Val
            245                 250                 255
Pro Ile Lys Gly Lys Asp Arg Lys Pro Gly Asn Leu Val
            260                 265
```

<210> SEQ ID NO 67
<211> LENGTH: 1467
<212> TYPE: DNA
<213> ORGANISM: Homo sapiens

<400> SEQUENCE: 67

```
ttttacaggt agaataaaca tagcatttcc ttctgtagac agaaggtgat atagttaacc       60
tcatgcactt tcatccacta agactccaag tcaaatgcca ccacactgca gcacacccaa      120
gagagcctgg tctacctgct tccaggagtt cacacgatgt acaggaaaag gcactaagta      180
aatttaactt tccattattt tttttttctgg agttatttct tattgtacaa agatttccag      240
acaactcctt ttccatttca ttcattgcca tttctgcttt atccagcagc acggagcctc      300
```

```
agctttgaga aatctcttga ccagagtgat ttttattttc ctcacacata aaatgtatgg    360
aaatggagat atcttttgg gcatatcagg gctatcatga aagataaag ccatcaagct    420 gtaataatgg ttatgaaagc acttccaaca attctaaaga tgataaaaca gtggatgatc    480
cactgttgca caaaattcta gcaacaaatt ctaattcagc cacacttgtt cttaataaca    540
gattgctctg ttttcataa ttattctaca tattaatatc actgtgaagt cattacaaca    600
gctgtgtttt tttggtcaca gatgttttat tttcaaagaa aacaaaattg tgtacgttt    660 tttccttgga gttctgattg aaccagtttt atatctaaag aaatacagaa atatctattc    720
ttgcctatcc atgatgtaca gccattatca aagtcttata agttaatctt ttttcaatca    780
tagtttattc cttttggtat taaaaaaatc ctatttacag acagtgcaaa actgatagaa    840
aagtaggaag agagaaaatt aaatagccaa ttagaaaaat actgtagaat tgcagttcca    900
gagtatggat aggatatcat agcaagctgt tgagtaaggc gaggaaggct tctctgagga    960
ggtgaccatc aactgagaga gggtttatag aatgagaaat gtaaggaata taaggaagct   1020
gtggtgcggg aaagaatatg tgcggcaaca agaggacaat actgtagggt tcgtagacca   1080
tcaatctggt accatttctg gagccattaa ttctttatat gagggtaagt ttaagacagg   1140
cttgtggctg ggcacagtgg ctcatgcctg taatcccagc actttggaag gccgaagcgg   1200
gctgatcacc tgaggtcagg aatttgagaa cagcctggcc aacatggtga cacccatctc   1260
tactaaatat acaaaattag ccgggtgtgg tggtgggagc ctgtaatccc agctactcgt   1320
aaggctgagg caggagaatt gcatgaaccc aggaggtgga ggttgcagtg agccgagatt   1380
gtgccactgt cccactgtcc tccagcctgg gccacagagt gatactctgc ctcaccaaaa   1440
aaaaaaaaaa aaaaaaaaa aaaaaaa                                        1467
```

<210> SEQ ID NO 68
<211> LENGTH: 81
<212> TYPE: PRT
<213> ORGANISM: Homo sapiens

<400> SEQUENCE: 68

```
Met His Phe His Pro Leu Arg Leu Gln Val Lys Cys His His Thr Ala
  1               5                  10                  15

Ala His Pro Arg Glu Pro Gly Leu Pro Ala Ser Arg Ser Ser His Asp
             20                  25                  30

Val Gln Glu Lys Ala Leu Ser Lys Phe Asn Phe Pro Leu Phe Phe Phe
         35                  40                  45

Leu Glu Leu Phe Leu Ile Val Gln Arg Phe Pro Asp Asn Ser Phe Ser
     50                  55                  60

Ile Ser Phe Ile Ala Ile Ser Ala Leu Ser Ser Ser Thr Glu Pro Gln
 65                  70                  75                  80

Leu
```

<210> SEQ ID NO 69
<211> LENGTH: 1235
<212> TYPE: DNA
<213> ORGANISM: Homo sapiens

<400> SEQUENCE: 69

```
tttctccttt cctctccctg tgcctcatct tcctctcctc tctctctccc ttctctcttc     60
tccgtttctc ttttcaccc cactccttca tcttgtctcg ctgtctatat tgttttcctt    120
ctctgtatct tcattgcctt tgctttcttt caaactttct ccttcacaga ttttttcttta   180
```

-continued

```
ttaatcagaa tcatactgac caacatgtgc tgaggacttt ctgtgtgctc tgtgcttcac      240
atacagtcat gtgcatcttt ccagttccac aagtgagtta tcctcatttc tcgggccat       300 agagctagtg agtgacagag ctaggttttg tatgtcaaag cctctgtcct acatgacatg      360
gcttttcctg ctgccttctc ccctggtatt cgtctccctc ttttctcctc tggctctgct      420
ggctctcctc tggctctgcg aggggtggt tttcagcctg ggcccttgca gatgtgtctg      480
tggcagcagg ccacacagac cgcagcgggc tgggcagcgt cctgagagac ctagtgaagc      540
caggcgacga gaaccttcgg gagatgaaca agaagctgca gaacatgctg gaggagcagc      600
tcaccaagaa tatgcacttg cacaaggata tggaagttct gtcccaggaa attgtgcggc      660
tcagcaagga gtgcgtgggg cctcctgacc cagacctaga gccaggagaa accagctaaa      720
gacctgcagg ctgcacccac ctcctcccct cctacccc taggatgcta tttcccttgg       780
gctgtggtgg aaaaatgagg gctggagcca aaatcaaata gcttgggaga ctggacatta      840 aagggctag aggcctgatg gttagtgtta atgatcctgt cttagggcag aggccaccag       900
ggagtgggga tcctgaggga agggcaggg atttctcctt cttcttggtc ctggctccca       960
agggcttctg tcttcatctc tgcatgagct ctccttccca gagaccaact ctttttttatt   1020 ttatttttatt ttatttttta atttatgtct ggagcctggc tactctgcat ttgggattgg   1080
ggatgctggg tgggtgtgtg gtccatgttc agcgttctag caacacgtgt gtgtgtgtgt   1140
gtgtaaaggc tatgcagcca aaataccatc tggccagacg ggcccacccc aaaaaaaaaa   1200 aaagaaaaa aaaaaaaaaa aaaaaaaaaa aaaaa                                1235
```

<210> SEQ ID NO 70
<211> LENGTH: 118
<212> TYPE: PRT
<213> ORGANISM: Homo sapiens

<400> SEQUENCE: 70

```
Met Ser Lys Pro Leu Ser Tyr Met Thr Trp Leu Phe Leu Leu Pro Ser
 1               5                  10                  15

Pro Leu Val Phe Val Ser Leu Phe Ser Pro Leu Ala Leu Leu Ala Leu
            20                  25                  30

Leu Trp Leu Cys Glu Gly Val Val Phe Ser Leu Gly Pro Cys Arg Cys
        35                  40                  45

Val Cys Gly Ser Arg Pro His Arg Pro Gln Arg Ala Gly Gln Arg Pro
    50                  55                  60

Glu Arg Pro Ser Glu Ala Arg Arg Glu Pro Ser Gly Asp Glu Gln
 65                  70                  75                  80

Glu Ala Ala Glu His Ala Gly Gly Ala Ala His Gln Glu Tyr Ala Leu
                85                  90                  95

Ala Gln Gly Tyr Gly Ser Ser Val Pro Gly Asn Cys Ala Ala Gln Gln
            100                 105                 110

Gly Val Arg Gly Ala Ser
        115
```

<210> SEQ ID NO 71
<211> LENGTH: 835
<212> TYPE: DNA
<213> ORGANISM: Homo sapiens

<400> SEQUENCE: 71

```
gggggaaaag ggcggaaaag gacaaggatc caaactggcg aatttgctga tcttcgcgtc       60
cctctccgct ttccggccgg cagcgctgcc agggtatatt tccttttttc cgatcctgca     120
```

```
acagcctctt taaactgttt aaatgagaat gtccttggct cagagagtac tactcacctg    180
gcttttcaca ctactcttct tgatcatgtt ggtgttgaaa ctggatgaga aagcaccttg    240
gaactggttc ctcatattta ttccagtctg gatatttgat actatccttc ttgtcctgct    300
gattgtgaaa atggctgggc ggtgtaagtc tggctttgac cctcgacatg gatcacacaa    360
tattaaaaaa aaagcctggt acctcattgc aatgttactt aaattagcct tctgcctcgc    420
actctgtgct aaactggaac agtttactac catgaatcta tcctatgtct tcattccttt    480
atgggccttg ctggctgggg cttaaacaga actcggatat aatgtctttt gtgagagaga    540
ctgacttcta agtacatcat ctcctttcta ttgcggttca acaagttacc attaaagtgt    600
tctgaatctg tcaagcttca agaataccag agaactgagg ggaaatacca aaggtagttt    660
tatactactt ccataaaaca agattggtga atcacggact tctagtcaac ctacagctta    720
attattcagc atttgagtta ttgagatccc tattatctct agggaaataa agtttgtttt    780
ggacctcaaa aaaaaaaaaa aaaaaaaaaa aaaaaaaaaa aaaaaaaaaa aaaaa         835

<210> SEQ ID NO 72
<211> LENGTH: 120
<212> TYPE: PRT
<213> ORGANISM: Homo sapiens

<400> SEQUENCE: 72

Met Arg Met Ser Leu Ala Gln Arg Val Leu Leu Thr Trp Leu Phe Thr
  1               5                  10                  15
Leu Leu Phe Leu Ile Met Leu Val Leu Lys Leu Asp Glu Lys Ala Pro
                 20                  25                  30
Trp Asn Trp Phe Leu Ile Phe Ile Pro Val Trp Ile Phe Asp Thr Ile
             35                  40                  45
Leu Leu Val Leu Leu Ile Val Lys Met Ala Gly Arg Cys Lys Ser Gly
         50                  55                  60
Phe Asp Pro Arg His Gly Ser His Asn Ile Lys Lys Ala Trp Tyr
 65                  70                  75                  80
Leu Ile Ala Met Leu Leu Lys Leu Ala Phe Cys Leu Ala Leu Cys Ala
                 85                  90                  95
Lys Leu Glu Gln Phe Thr Thr Met Asn Leu Ser Tyr Val Phe Ile Pro
                100                 105                 110
Leu Trp Ala Leu Leu Ala Gly Ala
            115                 120

<210> SEQ ID NO 73
<211> LENGTH: 1287
<212> TYPE: DNA
<213> ORGANISM: Homo sapiens

<400> SEQUENCE: 73
ccgaggcggg aggatgaagt tgattgacta tggtctctcc ggctaccagg aagagtctgc     60
cgaaggtgaa ggccatggac ttcatcacct ccacagccat cctgccctg ctgttcggct    120 gcctgggcgt cttcggcctc ttccggctgc tgcagtgggt gcgcgggaag gcctacctgc    180
ggaatgctgt ggtggtgatc acaggcgcca cctcagggct gggcaaagaa tgtgcaaaag    240
tcttctatgc tgcgggtgct aaactggtgc tctgtggccg gaatggtggg gccctagaag    300
agctcatcag agaactcacc gcttctcatg ccaccaaggt gcagacacac aagcttact    360 tggtgacctt cgacctcaca gactctgggg ccatagttgc agcagcagct gagatcctgc    420
```

-continued

```
agtgctttgg ctatgtcgac atacttgtca acaatgctgg gatcagctac cgtggtacca    480
tcatggacac cacagtggat gtggacaaga gggtcatgga gacaaactac tttggcccag    540
ttgctctaac gaaagcactc ctgccctcca tgatcaagag gaggcaaggc cacattgtcg    600
ccatcagcag catccagggc aagatgagca ttccttttcg atcagcatat gcagcctcca    660
agcacgcaac ccaggctttc tttgactgtc tgcgtgccga gatggaacag tatgaaattg    720
aggtgaccgt catcagcccc ggctacatcc acaccaacct ctctgtaaat gccatcaccg    780
cggatggatc taggtatgga gttatggaca ccaccacagc ccagggccga agccctgtgg    840
aggtggccca ggatgttctt gctgctgtgg ggaagaagaa gaaagatgtg atcctggctg    900
acttactgcc ttccttggct gtttatcttc gaactctggc tcctgggctc ttcttcagcc    960
tcatggcctc cagggccaga aaagagcgga atccaagaa ctcctagtac tctgaccagc   1020
cagggccagg gcagagaagc agcactctta ggcttgctta ctctacaagg gacagttgca   1080
tttgttgaga ctttaatgga gattttctc acaagtggga aagactgaag aaacacatct   1140
cgtgcagatc tgctggcaga ggacaatcaa aaacgacaac aagcttcttc ccagggtgag   1200
gggaaacact taaggaataa atatggagct ggggtttaac actaaaacta gaaataaaca   1260
tctcaaacag taaaaaaaaa aaaaaaa                                       1287
```

<210> SEQ ID NO 74
<211> LENGTH: 325
<212> TYPE: PRT
<213> ORGANISM: Homo sapiens

<400> SEQUENCE: 74

```
Met Val Ser Pro Ala Thr Arg Lys Ser Leu Pro Lys Val Lys Ala Met
 1               5                  10                  15

Asp Phe Ile Thr Ser Thr Ala Ile Leu Pro Leu Leu Phe Gly Cys Leu
                20                  25                  30

Gly Val Phe Gly Leu Phe Arg Leu Leu Gln Trp Val Arg Gly Lys Ala
            35                  40                  45

Tyr Leu Arg Asn Ala Val Val Val Ile Thr Gly Ala Thr Ser Gly Leu
        50                  55                  60

Gly Lys Glu Cys Ala Lys Val Phe Tyr Ala Ala Gly Ala Lys Leu Val
 65                  70                  75                  80

Leu Cys Gly Arg Asn Gly Gly Ala Leu Glu Glu Leu Ile Arg Glu Leu
                85                  90                  95

Thr Ala Ser His Ala Thr Lys Val Gln Thr His Lys Pro Tyr Leu Val
            100                 105                 110

Thr Phe Asp Leu Thr Asp Ser Gly Ala Ile Val Ala Ala Ala Glu
        115                 120                 125

Ile Leu Gln Cys Phe Gly Tyr Val Asp Ile Leu Val Asn Asn Ala Gly
    130                 135                 140

Ile Ser Tyr Arg Gly Thr Ile Met Asp Thr Thr Val Asp Val Asp Lys
145                 150                 155                 160

Arg Val Met Glu Thr Asn Tyr Phe Gly Pro Val Ala Leu Thr Lys Ala
                165                 170                 175

Leu Leu Pro Ser Met Ile Lys Arg Arg Gln Gly His Ile Val Ala Ile
            180                 185                 190

Ser Ser Ile Gln Gly Lys Met Ser Ile Pro Phe Arg Ser Ala Tyr Ala
        195                 200                 205

Ala Ser Lys His Ala Thr Gln Ala Phe Phe Asp Cys Leu Arg Ala Glu
    210                 215                 220
```

```
Met Glu Gln Tyr Glu Ile Glu Val Thr Val Ile Ser Pro Gly Tyr Ile
225                 230                 235                 240

His Thr Asn Leu Ser Val Asn Ala Ile Thr Ala Asp Gly Ser Arg Tyr
                245                 250                 255

Gly Val Met Asp Thr Thr Thr Ala Gln Gly Arg Ser Pro Val Glu Val
            260                 265                 270

Ala Gln Asp Val Leu Ala Ala Val Gly Lys Lys Lys Asp Val Ile
        275                 280                 285

Leu Ala Asp Leu Leu Pro Ser Leu Ala Val Tyr Leu Arg Thr Leu Ala
        290                 295                 300

Pro Gly Leu Phe Phe Ser Leu Met Ala Ser Arg Ala Arg Lys Glu Arg
305                 310                 315                 320

Lys Ser Lys Asn Ser
            325

<210> SEQ ID NO 75
<211> LENGTH: 1396
<212> TYPE: DNA
<213> ORGANISM: Homo sapiens

<400> SEQUENCE: 75
cggaggaggt ggcggcgctg gagctcctcc cggggaccag cgacccgggg agcgagcacg     60
tcgctccgca ccgctcttcc tccagccgct gagccgtccc ttctcgccat gtcccagagc    120
aggcaccgcg ccgaggcccc gccgctggag cgcgaggaca gtgggacctt cagtttgggg    180
aagatgataa cagctaagcc agggaaaaca ccgattcagg tattacacga atacggcatg    240
aagaccaaga acatcccagt ttatgaatgt gaaagatctg atgtgcaaat acacgtgccc    300
actttcacct tcagagtaac cgttggtgac ataacctgca caggtgaagg tacaagtaag    360
aagctggcga acatagagc tgcagaggct gccataaaca ttttgaaagc caatgcaagt    420
atttgctttg cagttcctga ccccttaatg cctgaccctt ccaagcaacc aaagaaccag    480
cttaatccta ttggttcatt acaggaattg gctattcatc atggctggag acttcctgaa    540
tatacccttt cccaggaggg aggacctgct cataagagag aatatactac aatttgcagg    600
ctagagtcat ttatggaaac tggaaagggg gcatcaaaaa agcaagccaa aggaatgct    660 gctgagaaat tcttgccaa atttagtaat atttctccag agaaccacat ttctttaaca    720
aatgtagtag gacattcttt aggatgtact tggcattcct tgaggaattc tcctggtgaa    780
aagatcaact tactgaaaag aagcctcctt agtattccaa atacagatta catccagctg    840
cttagtgaaa ttgccaagga acaaggtttt aaatataaca tttggatat agatgaactg    900 agcgccaatg gacaatatca atgtcttgct gaactgtcca ccagccccat cacagtctgt    960
catggctccg gtatctcctg tggcaatgca caagtgatg cagctcacaa tgctttgcag   1020
tatttaaaga taatagcaga agaaagtaa atctggagca acttaaaaaa tctttcagta   1080
gcacataaaa agttccctc tggccccttc ccaagtaaaa cttttaccgt agtgtttatg   1140
tcttgtttct aaatctcttc atagattcca tcaacactcc agatttaatt atctcctcat   1200
agttgttatt aagctctttt taatggcttc aactttgtat cagtatactg tatttataaa   1260
ctttgtacca caagagagag tgtagcaccc attttacagt gccatgcaca tcagagaaag   1320
aaactgcatg tttgttgttg atgatgaaat aaaaatgcta gcgacagtca aaaaaaaaa   1380 aaaaaaaaaa aaaaaa                                                   1396
```

<210> SEQ ID NO 76
<211> LENGTH: 313
<212> TYPE: PRT
<213> ORGANISM: Homo sapiens

<400> SEQUENCE: 76

Met Ser Gln Ser Arg His Arg Ala Glu Ala Pro Leu Glu Arg Glu
1               5                   10                  15

Asp Ser Gly Thr Phe Ser Leu Gly Lys Met Ile Thr Ala Lys Pro Gly
            20                  25                  30

Lys Thr Pro Ile Gln Val Leu His Glu Tyr Gly Met Lys Thr Lys Asn
        35                  40                  45

Ile Pro Val Tyr Glu Cys Glu Arg Ser Asp Val Gln Ile His Val Pro
    50                  55                  60

Thr Phe Thr Phe Arg Val Thr Val Gly Asp Ile Thr Cys Thr Gly Glu
65                  70                  75                  80

Gly Thr Ser Lys Lys Leu Ala Lys His Arg Ala Ala Glu Ala Ala Ile
                85                  90                  95

Asn Ile Leu Lys Ala Asn Ala Ser Ile Cys Phe Ala Val Pro Asp Pro
            100                 105                 110

Leu Met Pro Asp Pro Ser Lys Gln Pro Lys Asn Gln Leu Asn Pro Ile
        115                 120                 125

Gly Ser Leu Gln Glu Leu Ala Ile His His Gly Trp Arg Leu Pro Glu
    130                 135                 140

Tyr Thr Leu Ser Gln Glu Gly Pro Ala His Lys Arg Glu Tyr Thr
145                 150                 155                 160

Thr Ile Cys Arg Leu Glu Ser Phe Met Glu Thr Gly Lys Gly Ala Ser
                165                 170                 175

Lys Lys Gln Ala Lys Arg Asn Ala Ala Glu Lys Phe Leu Ala Lys Phe
            180                 185                 190

Ser Asn Ile Ser Pro Glu Asn His Ile Ser Leu Thr Asn Val Val Gly
        195                 200                 205

His Ser Leu Gly Cys Thr Trp His Ser Leu Arg Asn Ser Pro Gly Glu
    210                 215                 220

Lys Ile Asn Leu Leu Lys Arg Ser Leu Leu Ser Ile Pro Asn Thr Asp
225                 230                 235                 240

Tyr Ile Gln Leu Leu Ser Glu Ile Ala Lys Glu Gln Gly Phe Asn Ile
                245                 250                 255

Thr Tyr Leu Asp Ile Asp Glu Leu Ser Ala Asn Gly Gln Tyr Gln Cys
            260                 265                 270

Leu Ala Glu Leu Ser Thr Ser Pro Ile Thr Val Cys His Gly Ser Gly
        275                 280                 285

Ile Ser Cys Gly Asn Ala Gln Ser Asp Ala Ala His Asn Ala Leu Gln
    290                 295                 300

Tyr Leu Lys Ile Ile Ala Glu Arg Lys
305                 310

<210> SEQ ID NO 77
<211> LENGTH: 1238
<212> TYPE: DNA
<213> ORGANISM: Homo sapiens

<400> SEQUENCE: 77
tccgcggatt cccagcttga gaaacacctc tttgccccgt catgccaaag aggaaagtga      60
ccttccaagg cgtgggagat gaggaggatg aggatgaaat cattgtcccc aagaagaagc    120

```
tggtggaccc tgtggctggg tcaggggtc ctgggagccg ctttaaaggc aaacactctt      180
tggatagcga tgaggaggag gatgatgatg atggggggtc cagcaaatat gacatcttgg      240
cctcagagga tgtagaaggt caggaggcag ccacactccc cagcgagggg ggtgttcgga      300 tcacacccctt taacctgcag gaggagatgg aggaaggcca ctttgatgcc gatggcaact      360
acttcctgaa ccgggatgct cagatccgag acagctggct ggacaacatt gactgggtga      420
agatccggga gcggccacct ggccagcgcc aggcctcaga ctcggaggag gaggacagct      480
tgggccagac ctcaatgagt gcccaagccc tcttggaggg acttttggag ctcctattgc      540
ctagagagac agtggctggg gcactgaggc gtctggggc ccgaggagga ggcaaaggga      600
gaaaggggcc tggcaaccc agttcccctc agcgcctgga ccggctctcc gggttggccg      660
accagatggt ggcccgggc aaccttggtg tgtaccagga aacaagggaa cggttggcta      720
tgcgtctgaa gggtttgggg tgtcagaccc taggacccca caatcccaca cccccaccct      780
ccctggacat gttcgctgag gagttggcgg aggaggaact ggagacccca acccctaccc      840
agagaggaga agcagagtcg cggggagatg gtctggtgga tgtgatgtgg gaatataagt      900
gggagaacac gggggatgcc gagctgtatg ggcccttcac cagcgcccag atgcagaccg      960
gggtgagtga aggctacttc ccggacggtg tttattgccg gaagctgggc cccctgggg      1020 gtcagttcta caactccaaa cgcattgacg ttgacctcta caccggagcc ggctgggggc      1080
ccagtttggt gggcccttct ttcctggact tgtggagga ggcgccaagt gtctcaggca      1140
gcgcaggaaa ttggaggcca tttttcagtc aatttccctt tcccaataaa agcctttagt      1200
tgtgtaaaaa aaaaaaaaaa aaaaaaaaaa aaaaaaaa                             1238

<210> SEQ ID NO 78
<211> LENGTH: 385
<212> TYPE: PRT
<213> ORGANISM: Homo sapiens

<400> SEQUENCE: 78

Met Pro Lys Arg Lys Val Thr Phe Gln Gly Val Gly Asp Glu Glu Asp
  1               5                  10                  15

Glu Asp Glu Ile Ile Val Pro Lys Lys Leu Val Asp Pro Val Ala
             20                  25                  30

Gly Ser Gly Gly Pro Gly Ser Arg Phe Lys Gly Lys His Ser Leu Asp
         35                  40                  45

Ser Asp Glu Glu Asp Asp Asp Gly Gly Ser Ser Lys Tyr Asp
     50                  55                  60

Ile Leu Ala Ser Glu Asp Val Glu Gly Gln Glu Ala Ala Thr Leu Pro
 65                  70                  75                  80

Ser Glu Gly Gly Val Arg Ile Thr Pro Phe Asn Leu Gln Glu Glu Met
                 85                  90                  95

Glu Glu Gly His Phe Asp Ala Asp Gly Asn Tyr Phe Leu Asn Arg Asp
            100                 105                 110

Ala Gln Ile Arg Asp Ser Trp Leu Asp Asn Ile Asp Trp Val Lys Ile
        115                 120                 125

Arg Glu Arg Pro Pro Gly Gln Arg Gln Ala Ser Asp Ser Glu Glu Glu
    130                 135                 140

Asp Ser Leu Gly Gln Thr Ser Met Ser Ala Gln Ala Leu Leu Glu Gly
145                 150                 155                 160

Leu Leu Glu Leu Leu Pro Arg Glu Thr Val Ala Gly Ala Leu Arg
                165                 170                 175
```

-continued

```
Arg Leu Gly Ala Arg Gly Gly Lys Gly Arg Lys Gly Pro Gly Gln
            180                 185                 190
Pro Ser Ser Pro Gln Arg Leu Asp Arg Leu Ser Gly Leu Ala Asp Gln
        195                 200                 205
Met Val Ala Arg Gly Asn Leu Gly Val Tyr Gln Glu Thr Arg Glu Arg
    210                 215                 220
Leu Ala Met Arg Leu Lys Gly Leu Gly Cys Gln Thr Leu Gly Pro His
225                 230                 235                 240
Asn Pro Thr Pro Pro Ser Leu Asp Met Phe Ala Glu Glu Leu Ala
                245                 250                 255
Glu Glu Glu Leu Glu Thr Pro Thr Pro Thr Gln Arg Gly Glu Ala Glu
            260                 265                 270
Ser Arg Gly Asp Gly Leu Val Asp Val Met Trp Glu Tyr Lys Trp Glu
        275                 280                 285
Asn Thr Gly Asp Ala Glu Leu Tyr Gly Pro Phe Thr Ser Ala Gln Met
    290                 295                 300
Gln Thr Gly Val Ser Glu Gly Tyr Phe Pro Asp Gly Val Tyr Cys Arg
305                 310                 315                 320
Lys Leu Gly Pro Pro Gly Gly Gln Phe Tyr Asn Ser Lys Arg Ile Asp
                325                 330                 335
Val Asp Leu Tyr Thr Gly Ala Gly Trp Gly Pro Ser Leu Val Gly Pro
            340                 345                 350
Ser Phe Leu Asp Phe Val Glu Glu Ala Pro Ser Val Ser Gly Ser Ala
        355                 360                 365
Gly Asn Trp Arg Pro Phe Phe Ser Gln Phe Pro Phe Pro Asn Lys Ser
    370                 375                 380
Leu
385

<210> SEQ ID NO 79
<211> LENGTH: 1558
<212> TYPE: DNA
<213> ORGANISM: Homo sapiens
<220> FEATURE:
<221> NAME/KEY: unsure
<222> LOCATION: (1488..1489)

<400> SEQUENCE: 79
cttctgtgcc gggggtcttc ctgctgtcat gaaggacgta ccgggcttcc tacagcagag      60
ccagaactcc gggcccgggc agcccgctgt gtggcaccgt ctggaggagc tctacacgaa     120
gaagttgtgg catcagctga cacttcaggt gcttgatttt gtgcaggatc cgtgctttgc     180
ccaaggagat ggtctcatta agctttatga aactttatc agtgaatttg aacacagggt     240
gaaccctttg tccctcgtgg aaatcattct tcatgtagtt agacagatga ctgatcctaa     300
tgtggctctt acttttctgg aaaagactcg tgagaaggtg aaaagtagtg atgaggcagt     360
gatcctgtgt aaaacagcaa ttggagctct aaaattaaac atcggggacc tacaggttac     420
aaaggaaaca attgaagatg ttgaagaaat gctcaacaac cttcctggtg tgacatcggt     480
tcacagtcgt ttctatgatc tctccagtaa atactatcaa caatcggaa accacgcgtc     540 ctactacaaa gatgctctgc ggttttgggg ctgtgttgac atcaaggatc taccagtgtc     600
tgagcagcag gagagagcct tcacgctggg gctagcagga cttctcggcg agggagtttt     660
taactttgga gaactcctca tgcacccgtg gctggagtcc ctgaggaata ctgaccggca     720
gtggctgatt gacaccctct atgccttcaa cagtggcaac gtagagcggt tccagactct     780
```

-continued

```
gaagactgcc tggggccagc agcctgattt agcagctaat gaagcccagc ttctgaggaa    840
aattcagttg ttgtgcctca tggagatgac tttcacacga cctgccaatc acagacaact    900 cactttttgaa gaaattgcca aaagtgctaa aatcacagtg aatgaggtgg agcttctggt    960
gatgaaggcc ctttcggtgg ggctggtgaa aggcagtata gacgaggtgg acaaacgagt   1020
ccacatgacc tggtgcagc cccgagtgtt ggatttgcaa cagatcaagg gaatgaagga    1080
ccgcctggag ttctggtgca cggatgtgaa gagcatggag atgctggtgg agcaccaggc   1140
ccatgacatc ctcacctagg gcccctggt tccccgtcgt gtctcctttg actcacctga    1200
gagaggcgtt tgcagccaat gaagctggct gctcagacgg tcgacattga atttgggtgg   1260
gggttgggat cctgtctgaa gtacagactg ttcttgctct aaaaacagga ctgtccctga   1320
tgggagccag gccacaggga ggaggcttct tgtgggtct ctcctgcaga gggtgggggt    1380
ctcagggtct taggtgatac gggagagaaa gaacgtgcca ggcaggaggc cccctgaagt   1440
ctgtgtactc cgaggtggat ctccatcccc atccacctgt acggacannt tttccgttgc   1500
ggtttgagaa tgttcctata ataaaccct ctgctttgtt cttaaaaaaa aaaaaaaa     1558
```

<210> SEQ ID NO 80
<211> LENGTH: 376
<212> TYPE: PRT
<213> ORGANISM: Homo sapiens

<400> SEQUENCE: 80

```
Met Lys Asp Val Pro Gly Phe Leu Gln Gln Ser Gln Asn Ser Gly Pro
 1               5                  10                  15

Gly Gln Pro Ala Val Trp His Arg Leu Glu Glu Leu Tyr Thr Lys Lys
            20                  25                  30

Leu Trp His Gln Leu Thr Leu Gln Val Leu Asp Phe Val Gln Asp Pro
        35                  40                  45

Cys Phe Ala Gln Gly Asp Gly Leu Ile Lys Leu Tyr Glu Asn Phe Ile
    50                  55                  60

Ser Glu Phe Glu His Arg Val Asn Pro Leu Ser Leu Val Glu Ile Ile
65                  70                  75                  80

Leu His Val Val Arg Gln Met Thr Asp Pro Asn Val Ala Leu Thr Phe
                85                  90                  95

Leu Glu Lys Thr Arg Glu Lys Val Lys Ser Ser Asp Glu Ala Val Ile
            100                 105                 110

Leu Cys Lys Thr Ala Ile Gly Ala Leu Lys Leu Asn Ile Gly Asp Leu
        115                 120                 125

Gln Val Thr Lys Glu Thr Ile Glu Asp Val Glu Glu Met Leu Asn Asn
    130                 135                 140

Leu Pro Gly Val Thr Ser Val His Ser Arg Phe Tyr Asp Leu Ser Ser
145                 150                 155                 160

Lys Tyr Tyr Gln Thr Ile Gly Asn His Ala Ser Tyr Tyr Lys Asp Ala
                165                 170                 175

Leu Arg Phe Leu Gly Cys Val Asp Ile Lys Asp Leu Pro Val Ser Glu
            180                 185                 190

Gln Gln Glu Arg Ala Phe Thr Leu Gly Leu Ala Gly Leu Leu Gly Glu
        195                 200                 205

Gly Val Phe Asn Phe Gly Glu Leu Leu Met His Pro Val Leu Glu Ser
    210                 215                 220

Leu Arg Asn Thr Asp Arg Gln Trp Leu Ile Asp Thr Leu Tyr Ala Phe
225                 230                 235                 240
```

| | | | | | | | | | | |
|---|---|---|---|---|---|---|---|---|---|---|
|Asn|Ser|Gly|Asn|Val|Glu|Arg|Phe|Gln|Thr|Leu|Lys|Thr|Ala|Trp|Gly|
| | | |245| | | | |250| | | | |255| | |
|Gln|Gln|Pro|Asp|Leu|Ala|Ala|Asn|Glu|Ala|Gln|Leu|Leu|Arg|Lys|Ile|
| | |260| | | | |265| | | | |270| | | |
|Gln|Leu|Leu|Cys|Leu|Met|Glu|Met|Thr|Phe|Thr|Arg|Pro|Ala|Asn|His|
| | |275| | | | |280| | | | |285| | | |
|Arg|Gln|Leu|Thr|Phe|Glu|Glu|Ile|Ala|Lys|Ser|Ala|Lys|Ile|Thr|Val|
| |290| | | | |295| | | | |300| | | | |
|Asn|Glu|Val|Glu|Leu|Leu|Val|Met|Lys|Ala|Leu|Ser|Val|Gly|Leu|Val|
|305| | | | |310| | | | |315| | | | |320|
|Lys|Gly|Ser|Ile|Asp|Glu|Val|Asp|Lys|Arg|Val|His|Met|Thr|Trp|Val|
| | | |325| | | | |330| | | | |335| | |
|Gln|Pro|Arg|Val|Leu|Asp|Leu|Gln|Gln|Ile|Lys|Gly|Met|Lys|Asp|Arg|
| | |340| | | | |345| | | | |350| | | |
|Leu|Glu|Phe|Trp|Cys|Thr|Asp|Val|Lys|Ser|Met|Glu|Met|Leu|Val|Glu|
| | |355| | | | |360| | | | |365| | | |
|His|Gln|Ala|His|Asp|Ile|Leu|Thr|
| |370| | | |375| | |

<210> SEQ ID NO 81
<211> LENGTH: 1257
<212> TYPE: DNA
<213> ORGANISM: Homo sapiens
<220> FEATURE:
<221> NAME/KEY: unsure
<222> LOCATION: (1201)
<220> FEATURE:
<221> NAME/KEY: unsure
<222> LOCATION: (1204)
<220> FEATURE:
<221> NAME/KEY: unsure
<222> LOCATION: (1206)
<220> FEATURE:
<221> NAME/KEY: unsure
<222> LOCATION: (1215)
<220> FEATURE:
<221> NAME/KEY: unsure
<222> LOCATION: (1217)

<400> SEQUENCE: 81

```
ccagctctgg tatcgtaaat gtttgtagcc aatacaacat ccctggttat gatagaagga      60
tgcccttgac tggcccagct ctggtatcct aaatgttcgg agccgatata acatccctgg     120
ttatgataga aggatgcctt ttcttagacg tgaggatgcg tcccacgggc ttcagcactg     180
ggtctgctct gtggaacttc caggccgaag ctggggaggg taatgggca gcatggctgc     240 aggagtcgag ctcagtgcct gagccgggag ctcgatgcgg gagctgtggg ctgctcctcc     300
tccctgctag gagcaggtgc aagaggcctg cagagtgctg gggctgggca cggacctcac     360
agtgccatga agcctcgtgc agctttgaat ttcacttgtg atttcttcat ggaacttcaa     420
agccctagca atgtaggcgc gtagtcaatt attatttgag taagtgactg cgtgcaatgg     480
cccaggataa gggggttctg gagagggcag tccgtgctcc tattctttct ctgtctactt     540
tattatgatt tttgcttttt actatgaaaa attttaagcc ttcagaaaag tagagtgata     600
tgccacccat atacctatta tctagattta agaagaagaa tgattttcca tctgttattt     660
gctgtgtttg ggaaggattt taaagtacag acgtcatgac attttacctc taaatgcttc     720
ggatgcaact ctaaaaaata aggatgtttt catacttaac cacattttta tgaatacgct     780
gaacaaagca aatcagttta tttgtccccc aaatattttg atttgttcaa acaagaattc     840
agtcagagtc cccatgatgc gtgtggtggt gcttggtggt gccttagttc ctttgacatg     900
```

```
ggacagcccc tcccagctct tcatttctca tgagttgaaa aggctgggcc gggcccgatg      960
ctcacgcctg taatcccagc actttgggag gcgtgaggca ggtggatcac gaggtcagga     1020
gatcgagacc atcctggcta acatggtgaa accctgtctg tactaaaaga atacaaaaaa     1080
ttagccgggt gtggtggcgc gcgcccgtag tccctgctac ctgggaggct gaggcaggag     1140
agtggtgtga acccggcagg cggaaattaa agtgagccga gatcgctctt tgtactcgta     1200
ngtngnggtc agatngngga ctctcgtctc aaaaaaaaaa aaaaaaaaaa aaaaaaa        1257
```

<210> SEQ ID NO 82
<211> LENGTH: 102
<212> TYPE: PRT
<213> ORGANISM: Homo sapiens

<400> SEQUENCE: 82

```
Met Phe Gly Ala Asp Ile Thr Ser Leu Val Met Ile Glu Gly Cys Leu
 1               5                  10                  15

Phe Leu Asp Val Arg Met Arg Pro Thr Gly Phe Ser Thr Gly Ser Ala
            20                  25                  30

Leu Trp Asn Phe Gln Ala Glu Ala Gly Glu Gly Asn Gly Ala Ala Trp
        35                  40                  45

Leu Gln Glu Ser Ser Val Pro Glu Pro Gly Ala Arg Cys Gly Ser
    50                  55                  60

Cys Gly Leu Leu Leu Pro Ala Arg Ser Arg Cys Lys Arg Pro Ala
65                  70                  75                  80

Glu Cys Trp Gly Trp Ala Arg Thr Ser Gln Cys His Glu Ala Ser Cys
                85                  90                  95

Ser Phe Glu Phe His Leu
            100
```

<210> SEQ ID NO 83
<211> LENGTH: 2520
<212> TYPE: DNA
<213> ORGANISM: Homo sapiens

<400> SEQUENCE: 83

```
ccacctgccg ggtaagggcc cctcgggccg tggtcgggca tcgattggcc ccgcctggcg       60
cagcccccgc ccctgcagcg gactgcggtg ctcatcagac ctgagcagtt gctccggcgg      120
cgctcgggga gggagccagc agcctagggc ctaggcccgg ccaccatggc cgctgcctcc      180
aggcccagcc gccctccggc acacactgct gctcctgcca gcccttctga gctcaggttg      240
gggggagttg gagccacaaa tagatggtca gacctgggct gagcgggcac ttcgggagaa      300
tgaacgccac gccttcacct gccgggtggc aggggggcct ggcaccccca gattggcctg      360
gtatctggat ggacagctgc aggaggccag caccctcaaga ctgctgagcg tgggagggga    420
ggccttctct ggaggcacca gcaccttcac tgtcactgcc catcgggccc agcatgagct      480
caactgctct ctgcaggacc ccagaagtgg ccgatcagcc aacgcctctg tcatccttaa      540
tgtgcaattc aagccagaga ttgcccaagt cggcgccaag taccaggaag ctcagggccc      600
aggcctcctg gttgtcctgt ttgccctggt gcgtgccaac ccgccggcca atgtcacctg      660
gatcgaccag gatgggccag tgactgtcaa cacctctgac ttcctggtgc tggatgcgca      720
gaactacccc tggctcacca accacacggt gcagctgcag ctccgcagcc tggcacacaa      780
cctctcggtg gtgccaccac atgacgtggg tgtcaccagt gcgtcgcttc cagccccagg      840
gcttctggct acccgggtgg aagtgccact gctgggcatt gttgtggctg ctgggcttgc      900
```

```
actgggcacc ctcgtgggt tcagcacctt ggtggcctgc ctggtctgca gaaaagagaa      960
gaaaaccaaa ggcccctccc ggcacccatc tctgatatca agtgactcca acaacctaaa   1020
actcaacaac gtgcgcctgc cacgggagaa catgtccctc ccgtccaacc ttcagctcaa   1080
tgacctcact ccagattcca gagcagtgaa accagcagac cggcagatgg ctcagaacaa   1140
cagccggcca gagcttctgg acccggagcc cggcggcctc ctcaccagcc aaggtttcat   1200
ccgcctccca gtgctgggct atatctatcg agtgtccagc gtgagcagtg atgagatctg   1260
gctctgagcc gagggcgaga caggagtatt ctcttggcct ctggacaccc tcccattcct   1320
ccaaggcatc ctctacctag ctaggtcacc aacgtgaaga agttatgcca ctgccacttt   1380
tgcttgccct cctggctggg gtgccctcca tgtcatgcac gtgatgcatt tcactgggct   1440
gtaacccgca ggggcacagg tatctttggc aaggctacca gttggacgta agcccctcat   1500
gctgactcag ggtgggccct gcatgtgatg actgggcct tccagaggga gctctttggc   1560
cagggtgtt cagatgtcat ccagcatcca agtgtggcat ggcctgctgt ataccccacc   1620
ccagtactcc acagcacctt gtacagtagg catgggggcg tgcctgtgtg ggggacaggg   1680
agggccctgc atggattttc ctccttccta tgctatgtag ccttgttccc tcaggtaaaa   1740
tttaggaccc tgctagctgt gcagaaccca attgcccttt gcacagaaac caaccccctga   1800
cccagcggta ccggccaagc acaaacgtcc tttttgctgc acacgtctct gcccttcact   1860
tcttctcttc tgtcccacct cctcttggga attctaggtt acacgttgga ccttctctac   1920
tacttcactg ggcactagac ttttctattg gcctgtgcca tcgcccagta ttagcacaag   1980
ttagggagga agaggcaggc gatgagtcta gtagcaccca ggacggcttg tagctatgca   2040
tcatttctcct acggcgttag cactttaagc acatccctag ggagggtga gtgagggccc   2100
agagccctct ttgtggcttc cccacgtttg gccttctggg attcactgtg agtgtcctga   2160
gctctcgggg ttgatggttt ttctctcagc atgtctcctc caccacggga ccccagccct   2220
gaccaaccca tggttgcctc atcagcagga aggtgccctt cctggaggat ggtcgccaca   2280
ggcacataat tcaacagtgt ggaagcttta ggggaacatg gagaaagaag gagaccacat   2340
accccaaagt gacctaagaa cactttaaaa agcaacatgt aaatgattgg aaattaatat   2400
agtacagaat atattttcc cttgttgaga tcttcttttg taatgttttt catgttactg   2460
cctagggcgg tgctgagcac acagcaagtt taataaactt gactgaattc aaaaaaaaaa   2520
```

<210> SEQ ID NO 84
<211> LENGTH: 366
<212> TYPE: PRT
<213> ORGANISM: Homo sapiens

<400> SEQUENCE: 84

```
Met Ala Leu Pro Pro Gly Pro Ala Ala Leu Arg His Thr Leu Leu Leu
  1               5                  10                  15

Leu Pro Ala Leu Leu Ser Ser Gly Trp Gly Glu Leu Glu Pro Gln Ile
             20                  25                  30

Asp Gly Gln Thr Trp Ala Glu Arg Ala Leu Arg Glu Asn Glu Arg His
         35                  40                  45

Ala Phe Thr Cys Arg Val Ala Gly Gly Pro Gly Thr Pro Arg Leu Ala
     50                  55                  60

Trp Tyr Leu Asp Gly Gln Leu Gln Glu Ala Ser Thr Ser Arg Leu Leu
 65                  70                  75                  80

Ser Val Gly Gly Glu Ala Phe Ser Gly Gly Thr Ser Thr Phe Thr Val
```

```
            85                  90                  95
Thr Ala His Arg Ala Gln His Glu Leu Asn Cys Ser Leu Gln Asp Pro
               100                 105                 110
Arg Ser Gly Arg Ser Ala Asn Ala Ser Val Ile Leu Asn Val Gln Phe
           115                 120                 125
Lys Pro Glu Ile Ala Gln Val Gly Ala Lys Tyr Gln Glu Ala Gln Gly
       130                 135                 140
Pro Gly Leu Leu Val Val Leu Phe Ala Leu Val Arg Ala Asn Pro Pro
145                 150                 155                 160
Ala Asn Val Thr Trp Ile Asp Gln Asp Gly Pro Val Thr Val Asn Thr
               165                 170                 175
Ser Asp Phe Leu Val Leu Asp Ala Gln Asn Tyr Pro Trp Leu Thr Asn
           180                 185                 190
His Thr Val Gln Leu Gln Leu Arg Ser Leu Ala His Asn Leu Ser Val
       195                 200                 205
Val Ala Thr Asn Asp Val Gly Val Thr Ser Ala Ser Leu Pro Ala Pro
210                 215                 220
Gly Leu Leu Ala Thr Arg Val Glu Val Pro Leu Leu Gly Ile Val Val
225                 230                 235                 240
Ala Ala Gly Leu Ala Leu Gly Thr Leu Val Gly Phe Ser Thr Leu Val
               245                 250                 255
Ala Cys Leu Val Cys Arg Lys Glu Lys Lys Thr Lys Gly Pro Ser Arg
           260                 265                 270
His Pro Ser Leu Ile Ser Ser Asp Ser Asn Asn Leu Lys Leu Asn Asn
       275                 280                 285
Val Arg Leu Pro Arg Glu Asn Met Ser Leu Pro Ser Asn Leu Gln Leu
   290                 295                 300
Asn Asp Leu Thr Pro Asp Ser Arg Ala Val Lys Pro Ala Asp Arg Gln
305                 310                 315                 320
Met Ala Gln Asn Asn Ser Arg Pro Glu Leu Leu Asp Pro Glu Pro Gly
               325                 330                 335
Gly Leu Leu Thr Ser Gln Gly Phe Ile Arg Leu Pro Val Leu Gly Tyr
           340                 345                 350
Ile Tyr Arg Val Ser Ser Val Ser Ser Asp Glu Ile Trp Leu
       355                 360                 365

<210> SEQ ID NO 85
<211> LENGTH: 1692
<212> TYPE: DNA
<213> ORGANISM: Homo sapiens
<220> FEATURE:
<221> NAME/KEY: unsure
<222> LOCATION: (1317)
<220> FEATURE:
<221> NAME/KEY: unsure
<222> LOCATION: (1394)
<220> FEATURE:
<221> NAME/KEY: unsure
<222> LOCATION: (1424)

<400> SEQUENCE: 85
ctatgtatca tactgagtgt tctgagctgt tagtttcttt ggtgttcatc tagatggaag      60
ctggggcttc cttcctttca gatattggtg ctaacatgaa gctgaccaaa gaattgatgg     120
gatctgcaca ctgtaaagcc ggtttcagga tggctgagct gacggtcaag aaagaagaga     180
agatatgagc cgcctgcatt ttggggtggt ggcagtgaaa tttagacttg tgatttggta     240
tgacaatata tggcttttty tgattgttaa cattaatgaa acaagaaaa attagttgct      300
```

```
caaaagttga aaatggatt cataaacttt ttattagaat aaggcaaaag aacatattaa    360
aatagaggta aattagaaat gtcaataaga acccatggac attttttata aggagacttt    420
atctgttctg tccctacagt gatttatgct cttggatatt tttgctgtca tcctgacaaa    480
ttctagttgg aatatggaac aagcttattt gtagacctag tgcctgtggc ttctaaagca    540
attttctgaa aagagaaacc actgcctgtt ggaagaatag ttgattccat acctcaagct    600
agggaaaaaa aaaatcagaa ttagtctgtg aattctagat gttgagagaa agcagggttt    660
cattagggca tcggagagtc acaagtccat aggatgcaaa aaggaagatg aaataaaatt    720
gcctgaaaaa cgcacctgaa tttctggcat tgtttactga aaaggctgtg tattgatgaa    780
ccccaattat gtgaggtcta catttaagag tttataatca acagtttgaa aatgcagggt    840
gttgtttctt tctataagga gacaaaacag tcagaaggga gtgtcacagg acattatcac    900
aaaatcaaag ttcttcatga aatgtgttca tttgctagaa ataatgcagc ctattggaga    960
gaatcagggc ttctagtgat gctagggatg accttaagca ttgtttgtaa atcacacttt   1020
ttcctagtct ttcagcagca gctgcacaga gtaggcctgc ttcttcccat gaaagccaca   1080
ctgagtttat caactagtag tgtgtggcac tattgcaagt tatgttgtgt tgttatggcc   1140
atttatccaa cagtgctttc ctctgtgtgg ggctctgcag cctcgttcta tgttattttt   1200
attaccacgt gtctgtgcgc ctcaggtggc aaagcagaat cagcttctct accctcagca   1260
gggctcacta tgactcacta taagggaaga aaatcttaca gatgtcagaa atgttnggt    1320 aagtggacag tgataaacac aaaacagcaa gtggtcagta tcaaagagaa aaacagtatg   1380
ttggtgaggg agangtgtca aagctggtta aaaaggtgac gggngaaatg taaggggaca   1440
atactccaca aaaatttaga ttgtaactga gcttcttctc ctaaagagat ttaaaaataa   1500
agtataggaa atacatgaag aaacaaagta aaatgccaag gtgtaagttt gaccatgaat   1560
gtctagggaa aaacatactt gcactaaaac aaccaaatat gcaaaaatca gtggaaaaa    1620 caggtcaaaa taatgccagt tgatgtctgt aagaactaaa tgtataataa aatgagcaaa   1680
aaaaaaaaaa aa                                                       1692
```

<210> SEQ ID NO 86
<211> LENGTH: 195
<212> TYPE: PRT
<213> ORGANISM: Homo sapiens
<220> FEATURE:
<221> NAME/KEY: UNSURE
<222> LOCATION: (162)
<220> FEATURE:
<221> NAME/KEY: UNSURE
<222> LOCATION: (188)

<400> SEQUENCE: 86

Met Gln Gly Val Val Ser Phe Tyr Lys Glu Thr Lys Gln Ser Glu Gly
 1               5                  10                  15

Ser Val Thr Gly His Tyr His Lys Ile Lys Val Leu His Glu Met Cys
            20                  25                  30

Ser Phe Ala Arg Asn Asn Ala Ala Tyr Trp Arg Glu Ser Gly Leu Leu
        35                  40                  45

Val Met Leu Gly Met Thr Leu Ser Ile Val Cys Lys Ser His Phe Phe
    50                  55                  60

Leu Val Phe Gln Gln Gln Leu His Arg Val Gly Leu Leu Pro Met
65                  70                  75                  80

Lys Ala Thr Leu Ser Leu Ser Thr Ser Ser Val Trp His Tyr Cys Lys

```
                    85                  90                  95
Leu Cys Cys Val Val Met Ala Ile Tyr Pro Thr Val Leu Ser Ser Val
                100                 105                 110

Trp Gly Ser Ala Ala Ser Phe Tyr Val Ile Phe Ile Thr Thr Cys Leu
        115                 120                 125

Cys Ala Ser Gly Gly Lys Ala Glu Ser Ala Ser Leu Pro Ser Ala Gly
    130                 135                 140

Leu Thr Met Thr His Tyr Lys Gly Arg Lys Ser Tyr Arg Cys Gln Lys
145                 150                 155                 160

Met Xaa Gly Lys Trp Thr Val Ile Asn Thr Lys Gln Gln Val Val Ser
            165                 170                 175

Ile Lys Glu Lys Asn Ser Met Leu Val Arg Glu Xaa Cys Gln Ser Trp
        180                 185                 190

Leu Lys Arg
        195

<210> SEQ ID NO 87
<211> LENGTH: 802
<212> TYPE: DNA
<213> ORGANISM: Homo sapiens

<400> SEQUENCE: 87
ggcattcttg ccgctggccc agtcactatg tagtggaggg gcagacaccc tcccgcaaat     60
tctggaaggt tcttagtctc gactagggca gtagccccag gactcctagt cgccggcttc    120
aggtcactgc cggctgaacg gagctgccgt cgccatgttt ggctgcttgg tggcggggag    180
gctggtgcaa acagctgcac agcaagtggc agaggataaa tttgtttttg acttacctga    240
ttatgaaagt atcaaccatg ttgtggtttt tatgctggga acaatcccat tcctgagggg    300
aatgggagga tctgtctact tttcttatcc tgattcaaat ggaatgccag tatggcaact    360
cctaggattt gtcacgaatg ggaagccaag tgccatcttc aaaatttcag gtcttaaatc    420
tggagaagga agccaacatc cttttggagc catgaatatt gtccgaactc catctgttgc    480
tcagattgga atttcagtgg aattattaga cagtatggct cagcagactc ctgtaggtaa    540
tgctgctgta tcctcagttg actcattcac tcagttcaca caaaaggtgt tggacaattt    600
ctacaatttt gcttcatcat tgctgtctc tcaggccccg atgacaccca gcccctctga    660
aatgttcatt ccggccaatg tggttctgaa atggtatgaa aactttcaag ggcgactggc    720
accgaacccct ctcttttggg aaacataatt tgaataaaat aatttttttt ggaaaaaaaa    780
aaaaaaaaa aaaaaaaaa aa                                               802

<210> SEQ ID NO 88
<211> LENGTH: 197
<212> TYPE: PRT
<213> ORGANISM: Homo sapiens

<400> SEQUENCE: 88

Met Phe Gly Cys Leu Val Ala Gly Arg Leu Val Gln Thr Ala Ala Gln
1               5                   10                  15

Gln Val Ala Glu Asp Lys Phe Val Phe Asp Leu Pro Asp Tyr Glu Ser
            20                  25                  30

Ile Asn His Val Val Val Phe Met Leu Gly Thr Ile Pro Phe Pro Glu
        35                  40                  45

Gly Met Gly Gly Ser Val Tyr Phe Ser Tyr Pro Asp Ser Asn Gly Met
    50                  55                  60
```

```
Pro Val Trp Gln Leu Leu Gly Phe Val Thr Asn Gly Lys Pro Ser Ala
 65                  70                  75                  80

Ile Phe Lys Ile Ser Gly Leu Lys Ser Gly Glu Gly Ser Gln His Pro
                 85                  90                  95

Phe Gly Ala Met Asn Ile Val Arg Thr Pro Ser Val Ala Gln Ile Gly
            100                 105                 110

Ile Ser Val Glu Leu Leu Asp Ser Met Ala Gln Gln Thr Pro Val Gly
        115                 120                 125

Asn Ala Ala Val Ser Ser Val Asp Ser Phe Thr Gln Phe Thr Gln Lys
    130                 135                 140

Val Leu Asp Asn Phe Tyr Asn Phe Ala Ser Ser Phe Ala Val Ser Gln
145                 150                 155                 160

Ala Pro Met Thr Pro Ser Pro Ser Glu Met Phe Ile Pro Ala Asn Val
                165                 170                 175

Val Leu Lys Trp Tyr Glu Asn Phe Gln Gly Arg Leu Ala Pro Asn Pro
            180                 185                 190

Leu Phe Trp Glu Thr
        195
```

<210> SEQ ID NO 89
<211> LENGTH: 732
<212> TYPE: DNA
<213> ORGANISM: Homo sapiens

<400> SEQUENCE: 89

```
ctggttttct ccgcgggcgc ctcgggcgga acctggagat aatgggcagc acctggggga    60
gccctggctg ggtgcgactc gctctttgcc tgacgggctt agtgctctcg ctctacgcgc   120
tgcacgtgaa ggcggcgcgc gcccgggacc gggattaccg cgcgctctgc gacgtgggca   180
ccgccatcag ctgttcgcgc gtcttctcct ccaggttgcc tgcggacacg ctgggcctct   240
gtcctgatgc tgctgagctc cctggtgtct ctcgctggtt ctgtctacct ggcctggatc   300
ctgttcttcg tgctctatga tttctgcatt gtttgtatca ccacctatgc tatcaacgtg   360
agcctgatgt ggctcagttt ccggaaggtc caagaacccc agggcaaggc taagaggcac   420
tgagccctca acccaagcca ggctgacctc atctgctttg cttggcatg tgagccttgc    480
ctaaggggc atatctgggt ccctagaagg ccctagatgt ggggcttcta gattacccc    540
tcctcctgcc ataccacac atgacaatgg accaaatgtg ccacgctc gctcttttt      600
acacccagtg cctctgactc tgtccccatg ggctggtctc aaagctctt tccattgccc    660
agggagggaa ggttctgagc aataaagttt cttagatcaa ccaaaaaaaa aaaaaaaaa   720
aaaaaaaaaa aa                                                       732
```

<210> SEQ ID NO 90
<211> LENGTH: 92
<212> TYPE: PRT
<213> ORGANISM: Homo sapiens

<400> SEQUENCE: 90

```
Met Gly Ser Thr Trp Gly Ser Pro Gly Trp Val Arg Leu Ala Leu Cys
  1               5                  10                  15

Leu Thr Gly Leu Val Leu Ser Leu Tyr Ala Leu His Val Lys Ala Ala
             20                  25                  30

Arg Ala Arg Asp Arg Asp Tyr Arg Ala Leu Cys Asp Val Gly Thr Ala
         35                  40                  45

Ile Ser Cys Ser Arg Val Phe Ser Ser Arg Leu Pro Ala Asp Thr Leu
```

Gly Leu Cys Pro Asp Ala Ala Glu Leu Pro Gly Val Ser Arg Trp Phe
65                  70                  75                  80

Cys Leu Pro Gly Leu Asp Pro Val Leu Arg Ala Leu
            85                  90

<210> SEQ ID NO 91
<211> LENGTH: 901
<212> TYPE: DNA
<213> ORGANISM: Homo sapiens

<400> SEQUENCE: 91

| | | | | | |
|---|---|---|---|---|---|
| ggcgcgatga | ggttccggtt | ctgtggtgat | ctggactgtc | ccgactgggt | cctggcagaa | 60 |
| atcagcacgc | tggccaagat | gtcctctgtg | aagttgcggc | tgctctgcag | ccaggtacta | 120 |
| aaggagctgc | tgggacaggg | gattgattat | gagaagatcc | tgaagctcac | ggctgacgcc | 180 |
| aagtttgagt | caggcgatgt | gaaggccaca | gtggcagtgc | tgagtttcat | cctctccagt | 240 |
| gcggccaagc | acagtgtcga | tggcgaatcc | ttgtccagtg | aactgcagca | gctggggctg | 300 |
| cccaaagagc | acgcggccag | cctgtgccgc | tgttatgagg | agaagcaaag | ccccttgcag | 360 |
| aagcacttgc | gggtctgcag | cctacgcatg | aataggttgg | caggtgtggg | ctggcgggtg | 420 |
| gactacaccc | tgagctccag | cctgctgcaa | tccgtggaag | agcccatggt | gcacctgcgg | 480 |
| ctggaggtgg | cagctgcccc | agggacccca | gcccagcctg | ttgccatgtc | cctctcagca | 540 |
| gacaagttcc | aggtcctcct | ggcagaactg | aagcaggccc | agaccctgat | gagctccctg | 600 |
| ggctgaggag | aagggtgttc | caggcctgtg | tggagccgcc | ctgcccgtat | ggagtcacgc | 660 |
| cctctgaact | gctcttcggg | aggcagccct | ggttctagga | tgctgaggcc | ctggcccgga | 720 |
| ctctggcctc | ccagatcccc | agctgcctca | cttctctctt | gagaacttgg | ctcagggctc | 780 |
| ctgaggacct | ttcccagcat | taccttccct | tcccttgaaa | ggcaattgtt | ggctgttttc | 840 |
| ataagcagga | aaaataaaca | gaagtataaa | ggaaaaaaaa | aaaaaaaaaa | aaaaaaaaa | 900 |
| a | | | | | | 901 |

<210> SEQ ID NO 92
<211> LENGTH: 199
<212> TYPE: PRT
<213> ORGANISM: Homo sapiens

<400> SEQUENCE: 92

Met Arg Phe Arg Phe Cys Gly Asp Leu Asp Cys Pro Asp Trp Val Leu
1               5                   10                  15

Ala Glu Ile Ser Thr Leu Ala Lys Met Ser Ser Val Lys Leu Arg Leu
            20                  25                  30

Leu Cys Ser Gln Val Leu Lys Glu Leu Leu Gly Gln Gly Ile Asp Tyr
        35                  40                  45

Glu Lys Ile Leu Lys Leu Thr Ala Asp Ala Lys Phe Glu Ser Gly Asp
    50                  55                  60

Val Lys Ala Thr Val Ala Val Leu Ser Phe Ile Leu Ser Ser Ala Ala
65                  70                  75                  80

Lys His Ser Val Asp Gly Glu Ser Leu Ser Ser Glu Leu Gln Gln Leu
                85                  90                  95

Gly Leu Pro Lys Glu His Ala Ala Ser Leu Cys Arg Cys Tyr Glu Glu
            100                 105                 110

Lys Gln Ser Pro Leu Gln Lys His Leu Arg Val Cys Ser Leu Arg Met
        115                 120                 125

```
Asn Arg Leu Ala Gly Val Gly Trp Arg Val Asp Tyr Thr Leu Ser Ser
    130                 135                 140

Ser Leu Leu Gln Ser Val Glu Glu Pro Met Val His Leu Arg Leu Glu
145                 150                 155                 160

Val Ala Ala Ala Pro Gly Thr Pro Ala Gln Pro Val Ala Met Ser Leu
                165                 170                 175

Ser Ala Asp Lys Phe Gln Val Leu Leu Ala Glu Leu Lys Gln Ala Gln
                180                 185                 190

Thr Leu Met Ser Ser Leu Gly
            195

<210> SEQ ID NO 93
<211> LENGTH: 1579
<212> TYPE: DNA
<213> ORGANISM: Homo sapiens

<400> SEQUENCE: 93
```

| | | | | |  |
|---|---|---|---|---|---|
| gattaaaata | ttattttaaa | gaaaccactg | tttcccccta | aaatgtcata | agagcactga | 60 |
| agaacttgaa | atatttttt | cagagtttct | cacacacttt | aaaagtctaa | cttttttgtg | 120 |
| tgtaagcatt | tagcttgcca | gcatatttct | ttttggctcc | ttaaattgcg | gttgtgtttg | 180 |
| cagtattgtc | acttttgctc | tcactgttat | gttgaataat | aattagcata | taattgtcta | 240 |
| cagaagcaag | agcaatctgg | aaggaacaaa | aatgttttct | gtgattaaca | gtgaagacct | 300 |
| tgtaaatgca | gatgtgtgat | aaagcattta | gtcagtcccc | caaacagtca | tgccaactgt | 360 |
| gaaggaatgt | cccacaaaac | atttccattc | cctgaggaaa | aacatttttct | ttcctacatg | 420 |
| tatctctggt | atttagaatt | gtcactaata | accttttcaa | gtgattttgg | ctattctcta | 480 |
| atgaagatat | ggtcatttgt | ttttcttcct | gcaatgtggt | gtgcagagat | gctgcatatc | 540 |
| cttttttatgg | gattgcgtgt | gaatttgaac | catgagacat | tcctaataat | ttgttgtgag | 600 |
| atataccaag | catggatgat | aagtgtgttt | ttagtggtgt | gttgtttttt | taaagaggtg | 660 |
| attcaagtac | cgttgctaag | ctgtcaacat | accaagctgt | tgaaaaaatt | gaccatttct | 720 |
| ttcagaagta | attctcagcc | tgtggaataa | tagcaggtga | agacttcata | gaaggcgaca | 780 |
| gattgatagg | gaggctattg | aagcagtttt | tctgaagcct | gcattttgag | ttagtttata | 840 |
| gtgctaatag | attctatata | actgtgagag | tttggtagta | aaccagtagg | gattgttttc | 900 |
| tctcctaaaa | atttgcacac | tacttcattg | tctacaactt | tttacatatt | ggaaaataga | 960 |
| aattgcaaat | acatacatgt | atggaaacat | attcagattg | ggaaaaacat | ggacattagt | 1020 |
| tttttaaaag | ttacgtggag | caagatttct | atattttgtt | ttttaaagga | cgcagtcatt | 1080 |
| ctttctacta | aatccatttc | aggctagttc | tctgaaaatt | ttgccattta | tctacagaaa | 1140 |
| tttgattata | aatatgttcc | ttttcaaaga | aactttattc | tagaacaaaa | tagtctatat | 1200 |
| ggtacttgat | ctacatataa | gtggaaaaat | tagcagtatt | tgaaagctca | gtttatgtca | 1260 |
| ttgtcttaac | ttcagataca | aataactgaa | cagaaagtta | taacctttaa | tatctcatgt | 1320 |
| tctgtttttt | attcagtatt | ttcctatatg | ttaattcaat | tatatacttc | tgaatggcac | 1380 |
| cttacttttt | ggaaacaaat | cttctgttat | ttacaaaata | tataattttt | aaaaaacatt | 1440 |
| taaaaaaatc | caaagctgct | ctcgataata | gtcaacattt | gcatatatat | ggaatttctt | 1500 |
| acttttttc | tcccaaactc | tatttaataa | acttatttta | atgtttgtat | aaaaaaaaa | 1560 |
| aaaaaaaaa | aaaaaaaa |  |  |  |  | 1579 |

<210> SEQ ID NO 94
<211> LENGTH: 127
<212> TYPE: PRT
<213> ORGANISM: Homo sapiens

<400> SEQUENCE: 94

```
Met Ser His Lys Thr Phe Pro Phe Pro Glu Glu Lys His Phe Leu Ser
 1               5                  10                  15

Tyr Met Tyr Leu Trp Tyr Leu Glu Leu Ser Leu Ile Thr Phe Ser Ser
             20                  25                  30

Asp Phe Gly Tyr Ser Leu Met Lys Ile Trp Ser Phe Val Phe Leu Pro
         35                  40                  45

Ala Met Trp Cys Ala Glu Met Leu His Ile Leu Phe Met Gly Leu Arg
     50                  55                  60

Val Asn Leu Asn His Glu Thr Phe Leu Ile Ile Cys Cys Glu Ile Tyr
 65                  70                  75                  80

Gln Ala Trp Met Ile Ser Val Phe Leu Val Val Cys Cys Phe Lys
                 85                  90                  95

Glu Val Ile Gln Val Pro Leu Leu Ser Cys Gln His Thr Lys Leu Leu
            100                 105                 110

Lys Lys Leu Thr Ile Ser Phe Arg Ser Asn Ser Gln Pro Val Glu
        115                 120                 125
```

<210> SEQ ID NO 95
<211> LENGTH: 1891
<212> TYPE: DNA
<213> ORGANISM: Homo sapiens

<400> SEQUENCE: 95

```
agctggaggg agtcatggtg tcactggggt acaggagggt gaatgaaggg catgcaggcc      60
ctcagcccgg gctgtgccag ccctcccagc cccaggccca tctgagggac caagacgctg     120
ttacgcaggc ccttcttttcc agctatcagc actttcagca tcggctcttc agcagatcca    180
aaccccctca gcaacttgca gaggacctgt cccctctcaa aagtcccctg cctagggtg     240
gggaccccca aacctacggc aaagccagca acagtagcag cctgctccca tttgctgggg    300
aggagatcat cttgttcccc tggccccca ctctccctcc atgtccatcc aaaaaccata     360
aaatcactgg gttccacatc agcctccatg aggccaagcc ttgtacctgc aaggctcttg    420
gcctaaccat tcctctgtcc tcttctctgg cctgcctggg gagcccgtga aggccgcacg    480
ggtgcctcca gcctgagaca tcaggggaga gcctgcagct gagttcagca gaaaggagga   540
atcctggccc tcaggaagaa gatagtcaca tgttttttctt ccttgtcccc acagccccca  600
gaacaacatt ctccctgctg gcagcccttc catgtctcca aacctgggtc agagtgaaag   660
gacctttggg ggtgggtggg agcaaagggc ccacctgctg gttggtgaaa gcagtggtgc   720
cggagtgcta ggtaccgcac gagagggtgc ggggcttgg gaagcagacc agggttggac    780
aaaaccccat gagggcgggg agctggaaga aaagtctctt ggggacctct ggggcaagga   840
gctgagaagt cctgcagcac caggtgaaac ttgcttacag tggatgccac ttttaggcct   900
ctggaccgca gatgccttct tccttctgga cacctggctt ctgggcctcc aggtaaagag   960
agagagccag ccaagcctgt tccctcagt cctcctttgc tcctgctgct tcttccaaca   1020
gccactgtta ggaggtagta gaccccagcc tcaaggctct gaccttcttc atgtgggcac   1080
agaggtcctg acactctggc agggcctgag ctggggcagg cctccctcag ggccaggggc   1140
gatggcaccc cggggacagg cagacctcct tcctgccgtc agcacccct tccttatcac    1200
```

-continued

```
tgtctggtct ccgagcttcg gctgcagcct gaggtgtgtc ctgggctcct cagagcctga    1260
agcaagcttt tggaagcctg cagtcctccc agctccagtg cagaagcctc tctctccagc    1320
ctttccccag gcaggagttg gggttggggg cctctgtccc tcatcgctta ccttggaaag    1380
gtgggaagct ggcaatctgc accttgggc ctgggctccc cctctctgtg ccagcggctt     1440
cccagcacct gggaggggct gcagccccag ctggactcca gcctgtccct cttagcactc    1500
tagctgccca ctccagggca gggactcgaa accccctccg tcctgagcag ccacctccag    1560
ggccctgttt gggaccactc tctcagtccc caggtcctca gggccccaga gcggagggt     1620 ctcctacctg gaagtccccc tgagctccag ggcccagccc tacctgccag tgctggtgtc    1680
agggcactca acccccgagtg tggggccacg ccccttgcca tgcccacggc ctcctcctgt    1740 agccctgcc tgccccccg atgctgcacg ggcccgccct ggtgggctc ggcgagtaat        1800 gtgttttgtc cccagttaac caccattctg cggcctggtt ctgcaaggaa ccagggctgc    1860
cccaccacca cgaaacacaa aaaaaaaaa a                                    1891
```

<210> SEQ ID NO 96
<211> LENGTH: 287
<212> TYPE: PRT
<213> ORGANISM: Homo sapiens

<400> SEQUENCE: 96

```
Met Ser Pro Asn Leu Gly Gln Ser Glu Arg Thr Phe Gly Gly Gly Trp
 1               5                   10                  15

Glu Gln Arg Ala His Leu Leu Val Gly Glu Ser Ser Gly Ala Gly Val
            20                  25                  30

Leu Gly Thr Ala Arg Glu Gly Ala Gly Ala Trp Glu Ala Asp Gln Gly
        35                  40                  45

Trp Thr Lys Pro His Glu Gly Glu Leu Glu Lys Ser Leu Gly
    50                  55                  60

Asp Leu Trp Gly Lys Glu Leu Arg Ser Pro Ala Ala Pro Gly Glu Thr
65                  70                  75                  80

Cys Leu Gln Trp Met Pro Leu Leu Gly Leu Trp Thr Ala Asp Ala Phe
                85                  90                  95

Phe Leu Leu Asp Thr Trp Leu Leu Gly Leu Gln Val Lys Arg Glu Ser
            100                 105                 110

Gln Pro Ser Leu Phe Pro Ser Val Leu Leu Cys Ser Cys Cys Phe Phe
        115                 120                 125

Gln Gln Pro Leu Leu Gly Gly Ser Arg Pro Gln Pro Gln Gly Ser Asp
130                 135                 140

Leu Leu His Val Gly Thr Glu Val Leu Thr Leu Trp Gln Gly Leu Ser
145                 150                 155                 160

Trp Gly Arg Pro Pro Ser Gly Pro Gly Ala Met Ala Pro Arg Gly Gln
                165                 170                 175

Ala Asp Leu Leu Pro Ala Val Ser Thr Pro Phe Leu Ile Thr Val Trp
            180                 185                 190

Ser Pro Ser Phe Gly Cys Ser Leu Arg Cys Val Leu Gly Ser Ser Glu
        195                 200                 205

Pro Glu Ala Ser Phe Trp Lys Pro Ala Val Leu Pro Ala Pro Val Gln
    210                 215                 220

Lys Pro Leu Ser Pro Ala Phe Pro Gln Ala Gly Val Gly Val Gly Gly
225                 230                 235                 240

Leu Cys Pro Ser Ser Leu Thr Leu Glu Arg Trp Glu Ala Gly Asn Leu
                245                 250                 255
```

His Leu Gly Ala Trp Ala Pro Pro Leu Cys Ala Ser Gly Phe Pro Ala
          260                 265                 270

Pro Gly Arg Gly Cys Ser Pro Ser Trp Thr Pro Ala Cys Pro Ser
        275                 280                 285

<210> SEQ ID NO 97
<211> LENGTH: 2192
<212> TYPE: DNA
<213> ORGANISM: Homo sapiens
<220> FEATURE:
<221> NAME/KEY: unsure
<222> LOCATION: (891)

<400> SEQUENCE: 97

| | | | | | |
|---|---|---|---|---|---|
| ctgttaacag | tactttaatt | gagccgtctg | tgttctagtt | ctgtccagag | ccccgccgt | 60 |
| tttcccctcc | agcacaggat | tcatttcagg | atcatcactt | gcgttatatg | cccaaggggt | 120 |
| ccctctcttg | gtgtgtgggc | agagccagag | ctgggaacaa | tgggggtggt | gtgtgggttc | 180 |
| tgggctcagg | cttcctggat | ttggcattgg | cctcctgatg | tcatgtatcg | gctggaagac | 240 |
| tcaggacaac | cttctgcctt | tctgagcctc | cgtttcctca | aacctgaagt | gaggatgaag | 300 |
| gcagcgtgca | tggcttaggg | gcgttgggtg | ctcagcatcg | tgcgtgagat | gctgagtgtt | 360 |
| caccactcag | tattagccat | ggatgtcttt | ttggaaattc | cccacagccc | tctccacaca | 420 |
| gagtcaaatg | tcaaaaacct | gctgccaact | ggcacctggt | tctcacagct | gctctctggg | 480 |
| gctctggggc | ctgtcagagc | cacctgtcca | agattcagga | ttcagcacat | cacctctgcc | 540 |
| ccaccctac | cggcagcatt | cctttcctac | ctgtccagcc | tcttctctgt | ccccagccac | 600 |
| attccccact | cctgccccca | aactcttggc | ctagaaggcc | ctggcctgct | ccccaggcct | 660 |
| cctctgctaa | gccttgccta | cctgtcccca | ctgtgccccc | cactgcctgc | gcatctctgg | 720 |
| ccagcacagg | cgtgggagga | actatggctc | ttcttcctta | ggaagagtct | ctgacaagta | 780 |
| ggactttgtt | ttcttcccag | catgcactgc | agtgcaggtg | tcttaaccct | tggcgcacac | 840 |
| acaggatgaa | ggcagagagc | caactattga | gggtgggaat | tgggaagcct | nctgcctgga | 900 |
| tcatcttaga | aactggaggc | cccttttcac | tcgggtctcc | cctgtgccgt | gcacgccacc | 960 |
| tctttcaggg | cccactcacc | ctgggtggaa | ttggatggcc | actttgccag | aacttcttcg | 1020 |
| tcttttgttg | acctgttctg | gccattaaga | ccaccttctc | ttttctgggg | ggtttccgcc | 1080 |
| tgtccttttgc | tacggtactt | ggagacaggt | gagctcactt | tgttctttgc | tttaagtctg | 1140 |
| ttacctcttg | agccaaggtg | aggcacctcc | aggggcagcc | aggcccctgc | ttctggcccc | 1200 |
| gcacaccctc | tacactttga | cctttccggc | tgtttacctg | cctggagtgt | gcctcactcc | 1260 |
| cctcccctca | gttgatcttt | tactgtgctc | tctctatgta | gcgccctctt | gctcccttct | 1320 |
| aaaactccat | tctggaaaaa | ctcagccatt | gtctttttt | gtttgttttt | ttcctgttt | 1380 |
| aatctttagt | gagcctgtgt | atccataggg | cttgtgagga | aaaacagcgg | cccttttgccc | 1440 |
| caaccagcat | ccaccctagg | gacaatcact | ttcaactcag | tggactcttg | gaatttgcgc | 1500 |
| ccgtagctct | aaaaactgtg | ctggctgctt | ctcagtcttt | cagctcaggg | cagaatccat | 1560 |
| tgccttccac | caggagagct | gaacatcagt | gctctcgtgg | ctccatgagt | cctcttagcc | 1620 |
| cctttctctc | ctctcatctt | ccctggtagt | tccccataat | tgtgatgaga | ataccctgtgt | 1680 |
| aggtcagtca | tcggagtggt | gtgaagggat | gtgtggccca | gtgacatctc | agctgccatt | 1740 |
| tctgcttgct | ttgccgtgag | tgttctttgc | tttgtttctt | ggctctaacc | caattccagg | 1800 |
| cttcctcctg | attgtttcac | tcttctctct | ggccacttat | ttatttattt | ttcgagatgg | 1860 |

```
agtctccctc tgtcacccag gctggagtgc attggtgtgt tctctgctca ctgcaacctc   1920
tgcctcctgg gttcaagcaa ttctcctacc tcagcctcct gagtagctgg gactacaggc   1980
gtgtgccact atgcctggct aatttattta tttttatttt tttatttttt tgagatggag   2040
tctcactctg tcacccaggc tggagtgcag tggcgcgttc tcggctcact gcaactccgc   2100
ctcccaggtt cacgccattc tcctacctca gcctcccagg tagctgggac tacaggtgct   2160
cgccaccacc acgaaacaaa aaaaaaaaaa aa                                 2192
```

<210> SEQ ID NO 98
<211> LENGTH: 141
<212> TYPE: PRT
<213> ORGANISM: Homo sapiens

<400> SEQUENCE: 98

```
Met Leu Ser Val His His Ser Val Leu Ala Met Asp Val Phe Leu Glu
  1               5                  10                  15

Ile Pro His Ser Pro Leu His Thr Glu Ser Asn Val Lys Asn Leu Leu
             20                  25                  30

Pro Thr Gly Thr Trp Phe Ser Gln Leu Leu Ser Gly Ala Leu Gly Pro
         35                  40                  45

Val Arg Ala Thr Cys Pro Arg Phe Arg Ile Gln His Ile Thr Ser Ala
     50                  55                  60

Pro Pro Leu Pro Ala Ala Phe Leu Ser Tyr Leu Ser Ser Leu Phe Ser
 65                  70                  75                  80

Val Pro Ser His Ile Pro His Ser Cys Pro Gln Thr Leu Gly Leu Glu
                 85                  90                  95

Gly Pro Gly Leu Leu Pro Arg Pro Pro Leu Leu Ser Leu Ala Tyr Leu
            100                 105                 110

Ser Pro Leu Cys Pro Pro Leu Pro Ala His Leu Trp Pro Ala Gln Ala
        115                 120                 125

Trp Glu Glu Leu Trp Leu Phe Phe Leu Arg Lys Ser Leu
    130                 135                 140
```

<210> SEQ ID NO 99
<211> LENGTH: 1774
<212> TYPE: DNA
<213> ORGANISM: Homo sapiens

<400> SEQUENCE: 99

```
cagaggagga ataatgagga actggtagtg tcagcctcct gtaaggaacc agagcaggag     60
ccagtgccag cacagttcca gaaagtaaag cccccaaaga ctaatcataa acgaggaagg    120
aaataggcag tcagtgtaaa agtgctccta ggaaagcaga tgtgatgctg ttgtcacggg    180
gacctgtgct gggaggactg agtgaagatt ctttcagctg tttgtgtaag gctgtgactt    240
tctcagctcc ttcctcctgt gtaaatttca ctgtcttccc ttcttacatt ttgattcccc    300 cctcccttt tagtaggttt tcctgctatt cctcgtcaag tcctcttgtt tttttatctt    360
gcccaaagag ctccctctca aggccaacta taggctccgc ttgccctgta caaaactaag    420
aaacctcttt ggttgtcctt tccttcctgg ggtatagaat gttcttggaa gctccattga    480
tttagtagct gctccatcat ctagcttgtg aaaccattcc aaactaattt tttaaaacca    540
taactgattt gtcattttgt atttgtgata taacaagtct agaagttaga actgttgtca    600
ttcacataat aagattactc tgtctccttg ggaaaaaaac tttatggagg ctgtttgtcc    660
tctcaatatg gttttaagat tgaaagtaag aaaacggatt taggatgaaa actctagaac    720
```

```
tacccatgc tgtttatact gggaaatgct ttgtaccaag tagcagtgac tagacccaca    780
gacatgaaaa gcaaccttag gagtaaagtg acccaaacat taaaatgaca ggaaagagaa    840
agtagaagca gcaataaata ctgccccaac ttccttggag cccgaggcct catccatagc    900
tatgatcact tgccctctga agcttatttt tgcttctttg gttttaagaa ttgagaaata    960
tcacattgcc cctgatgttt tgaacagtct ccaagtgctc ctggtagtgc cactaaggga   1020
aaaccaaggt gcgcattcct tctccctgga ctttacctta cttgttagtc tacgccccac   1080
tgtttccacc catcccctta gccaacctct gtcttttga attttctgag aatattgtcc    1140
tatcctcttt tatatatgga gttctctcct ctttatatcc tgagactttg acaccagatg   1200
tagatattta tctggagctg gaagaaaaa ttcttttct gtacctcatg cctatctggt    1260
aatgtttaat gggttatttc tctttgaggg tggctttctc tggaacattg gttagagcag   1320
ctttgttgtc gtgtttctgg attctcttcc ccattttgcg taaatattgg tcttatatat   1380
tcttgcctat tttgtggcat atgccacata aaaatgaac ctgatataga caagtactac     1440
cttttcaaat tctgaaaggc tattaccact ttaactcttt gtgctcctcc aaatagcttt   1500
aaaatgtggg cttttgtgaa gaccactttc aaacaaggga gcactgaaac ctgaattgga   1560
tactgccaga ataggtagtt ttgaaacaag ttaaggacat ggtatatgca ctctgcattt    1620
tcattggcag tgtgcccttta agcccttc agtagatgag ggttgtcagg gaggagaaat    1680
gaagaagcta tgttaatttc tggtgagtaa gacctgggga atgtttggca atgacaaaag   1740
aaataaatga ctctcaggaa aaaaaaaaa aaaa                                 1774
```

<210> SEQ ID NO 100
<211> LENGTH: 84
<212> TYPE: PRT
<213> ORGANISM: Homo sapiens

<400> SEQUENCE: 100

Met Leu Leu Ser Arg Gly Pro Val Gly Gly Leu Ser Glu Asp Ser
1               5                   10                  15

Phe Ser Cys Leu Cys Lys Ala Val Thr Phe Ser Ala Pro Ser Ser Cys
                20                  25                  30

Val Asn Phe Thr Val Phe Pro Ser Tyr Ile Leu Ile Pro Pro Ser Pro
            35                  40                  45

Phe Ser Arg Phe Ser Cys Tyr Ser Ser Ser Ser Pro Leu Val Phe Leu
        50                  55                  60

Ser Cys Pro Lys Ser Ser Leu Ser Arg Pro Thr Ile Gly Ser Ala Cys
65                  70                  75                  80

Pro Val Gln Asn

<210> SEQ ID NO 101
<211> LENGTH: 1324
<212> TYPE: DNA
<213> ORGANISM: Homo sapiens

<400> SEQUENCE: 101

```
ggtgtcgagc cctctggcag agggttaacc tgggtcaaat gcacggattc tcacctcgta     60
cagttacgct ctcccgcggc acgtccgcga ggacttgaag tcctgagcgc tcaagtttgt    120
ccgtaggtcg agagaaggcc atggaggtgc cgccaccggc accgcggagc tttctctgta    180
gagcattgtg cctatttccc cgagtctttg ctgccgaagc tgtgactgcc gattcggaag    240
tccttgagga gcgtcagaag cggcttccct acgtcccaga gccctattac ccggaatctg    300
```

-continued

```
gatgggaccg cctccgggag ctgtttggca aagatgaaca gcagagaatt tcaaaggacc      360
ttgctaatat ctgtaagacg gcagctacag caggcatcat tggctgggtg tatgggggaa      420
taccagcttt tattcatgct aaacaacaat acattgagca gagccaggca gaaatttatc      480
ataaccggtt tgatgctgtg caatctgcac atcgtgctgc cacacgaggc ttcattcgtt      540
atggctggcg ctggggttgg agaactgcag tgtttgtgac tatattcaac acagtgaaca      600
ctagtctgaa tgtataccga aataaagatg ccttaagcca ttttgtaatt gcaggagctg      660
tcacgggaag tcttttttagg ataaacgtag gcctgcgtgg cctggtggct ggtggcataa      720
ttggagcctt gctgggcact cctgtaggag gcctgctgat ggcatttcag aagtactctg      780
gtgagactgt tcaggaaaga aaacagaagg atcgaaaggc actccatgag ctaaaactgg      840
aagagtggaa aggcagacta caagttactg agcacctccc tgagaaaatt gaaagtagtt      900
tacaggaaga tgaacctgag aatgatgcta agaaaattga agcactgcta aaccttccta      960
gaaaccettc agtaatagat aaacaagaca aggactgaaa gtgctctgaa cttgaaactc     1020
actggagagc tgaagggagc tgccatgtcc gatgaatgcc aacagacagg ccactctttg     1080
gtcagcctgc tgacaaattt aagtgctggt acctgtggtg gcagtggctt gctcttgtct     1140
ttttcttttc ttttttaacta agaatggggc tgttgtactc tcactttact tatccttcaa     1200
tttaaataca tacttatgtt tgtattaatc tatcaatata tgcatacatg aatatatcca     1260
cccacctaga ttttaagcag taaataaaac atttcgcaaa agaaaaaaaa aaaaaaaaaa     1320
aaaa                                                                    1324
```

<210> SEQ ID NO 102
<211> LENGTH: 285
<212> TYPE: PRT
<213> ORGANISM: Homo sapiens

<400> SEQUENCE: 102

```
Met Glu Val Pro Pro Ala Pro Arg Ser Phe Leu Cys Arg Ala Leu
 1               5                  10                  15

Cys Leu Phe Pro Arg Val Phe Ala Ala Glu Ala Val Thr Ala Asp Ser
                20                  25                  30

Glu Val Leu Glu Glu Arg Gln Lys Arg Leu Pro Tyr Val Pro Glu Pro
            35                  40                  45

Tyr Tyr Pro Glu Ser Gly Trp Asp Arg Leu Arg Glu Leu Phe Gly Lys
        50                  55                  60

Asp Glu Gln Gln Arg Ile Ser Lys Asp Leu Ala Asn Ile Cys Lys Thr
 65                  70                  75                  80

Ala Ala Thr Ala Gly Ile Ile Gly Trp Val Tyr Gly Gly Ile Pro Ala
                85                  90                  95

Phe Ile His Ala Lys Gln Gln Tyr Ile Glu Gln Ser Gln Ala Glu Ile
                100                 105                 110

Tyr His Asn Arg Phe Asp Ala Val Gln Ser Ala His Arg Ala Ala Thr
            115                 120                 125

Arg Gly Phe Ile Arg Tyr Gly Trp Arg Gly Trp Arg Thr Ala Val
        130                 135                 140

Phe Val Thr Ile Phe Asn Thr Val Asn Thr Ser Leu Asn Val Tyr Arg
145                 150                 155                 160

Asn Lys Asp Ala Leu Ser His Phe Val Ile Ala Gly Ala Val Thr Gly
                165                 170                 175

Ser Leu Phe Arg Ile Asn Val Gly Leu Arg Gly Leu Val Ala Gly Gly
```

```
                    180                 185                 190
Ile Ile Gly Ala Leu Leu Gly Thr Pro Val Gly Gly Leu Leu Met Ala
            195                 200                 205

Phe Gln Lys Tyr Ser Gly Glu Thr Val Gln Glu Arg Lys Gln Lys Asp
        210                 215                 220

Arg Lys Ala Leu His Glu Leu Lys Leu Glu Glu Trp Lys Gly Arg Leu
225                 230                 235                 240

Gln Val Thr Glu His Leu Pro Glu Lys Ile Glu Ser Ser Leu Gln Glu
                245                 250                 255

Asp Glu Pro Glu Asn Asp Ala Lys Lys Ile Glu Ala Leu Leu Asn Leu
            260                 265                 270

Pro Arg Asn Pro Ser Val Ile Asp Lys Gln Asp Lys Asp
        275                 280                 285

<210> SEQ ID NO 103
<211> LENGTH: 977
<212> TYPE: DNA
<213> ORGANISM: Homo sapiens

<400> SEQUENCE: 103
ggcagaggca tcatggaggg tccccgggga tggctggtgc tctgtgtgct ggccatatcg      60
ctggcctcta tggtgaccga ggacttgtgc cgagcaccag acgggaagaa aggggaggca     120
ggaagacctg gcagacgggg gcggccaggc ctcaagggg agcaagggga gccggggggcc     180
cctggcatcc ggacaggcat ccaaggcctt aaggagacc aggggggaacc tgggccctct     240
ggaaaccccg gcaaggtggg ctacccaggg cccagcggcc ccctcggagc ccgtggcatc     300
ccgggaatta aggcaccaa gggcagccca ggaaacatca aggaccagcc gaggccagcc     360
ttcaccgcca ttcggcggaa ccccccaatg gggggcaacg tggtcatctt cgacacggtc     420
atcaccaacc aggaagaacc gtaccagaac cactccggcc gattcgtctg cactgtaccc     480
ggctactact acttcacctt ccaggtgctg tcccagtggg aaatctgcct gtccatcgtc     540
tcctcctcaa ggggccaggt ccgacgctcc ctgggcttct gtgacaccac caacaagggg     600
ctcttccagg tggtgtcagg gggcatggtg cttcagctgc agcagggtga ccaggtctgg     660
gttgaaaaag accccaaaaa gggtcacatt taccagggct ctgaggccga cagcgtcttc     720
agcggcttcc tcatcttccc atctgcctga gccaggaag gacccccctcc cccacccacc     780
tctctggctt ccatgtccgc ctgtaaaatg ggggcgctat tgcttcagct gctgaaggga     840
gggggctggc tctgagagcc ccaggactgg ctgccccgtg acacatgctc taagaagctc     900
gtttcttaga cctcttcctg gaataaacat ctgtgtctgt gtctgccaaa aaaaaaaaa     960
aaaaaaaaaa aaaaaaa                                                     977

<210> SEQ ID NO 104
<211> LENGTH: 245
<212> TYPE: PRT
<213> ORGANISM: Homo sapiens

<400> SEQUENCE: 104

Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45
```

```
Gly Glu Gln Gly Glu Pro Gly Ala Pro Gly Ile Arg Thr Gly Ile Gln
 50                  55                  60
Gly Leu Lys Gly Asp Gln Gly Glu Pro Gly Pro Ser Gly Asn Pro Gly
 65                  70                  75                  80
Lys Val Gly Tyr Pro Gly Pro Ser Gly Pro Leu Gly Ala Arg Gly Ile
                 85                  90                  95
Pro Gly Ile Lys Gly Thr Lys Gly Ser Pro Gly Asn Ile Lys Asp Gln
            100                 105                 110
Pro Arg Pro Ala Phe Thr Ala Ile Arg Arg Asn Pro Pro Met Gly Gly
            115                 120                 125
Asn Val Ile Phe Asp Thr Val Ile Thr Asn Gln Glu Glu Pro Tyr
130                 135                 140
Gln Asn His Ser Gly Arg Phe Val Cys Thr Val Pro Gly Tyr Tyr Tyr
145                 150                 155                 160
Phe Thr Phe Gln Val Leu Ser Gln Trp Glu Ile Cys Leu Ser Ile Val
                165                 170                 175
Ser Ser Ser Arg Gly Gln Val Arg Arg Ser Leu Gly Phe Cys Asp Thr
            180                 185                 190
Thr Asn Lys Gly Leu Phe Gln Val Val Ser Gly Gly Met Val Leu Gln
        195                 200                 205
Leu Gln Gln Gly Asp Gln Val Trp Val Glu Lys Asp Pro Lys Lys Gly
    210                 215                 220
His Ile Tyr Gln Gly Ser Glu Ala Asp Ser Val Phe Ser Gly Phe Leu
225                 230                 235                 240
Ile Phe Pro Ser Ala
                245

<210> SEQ ID NO 105
<211> LENGTH: 1034
<212> TYPE: DNA
<213> ORGANISM: Homo sapiens
<220> FEATURE:
<221> NAME/KEY: unsure
<222> LOCATION: (618)
<220> FEATURE:
<221> NAME/KEY: unsure
<222> LOCATION: (905..906)

<400> SEQUENCE: 105
ctcaggcctt gagggacact tccttcctcc ccactcgcct cctctccact agactttggt      60
tcctagaggg cgtggggccg ggtctgaggt tcttgcctgc cttccctccc attggtcttt    120
ggttgctcat ccctctaact gcacccttc ttggtccttc ctccacagac ttcagataat    180
agataagtca ttagcaaacc agaccgaatc tttagggtga agagctcccc aaagccatct    240
ggtgaggtca ttttggggac cagggactga ttatttgtca cctggatcac aaagatggga    300
ctgtctgctc aggctggtgg tgacaggatc ctgacccgtg gtcctctccc gctccctctg    360
ctccaccagg acacatgtat aggacactgt gctgtgtgca gtggagaaat ctccctgggc    420
caggggaaag ttcagacagt gcctctagat tgtgttttgc ctcctccaat gttgagttga    480
catctggacc ccagagccca gcaggcttt ctgtcagaca tgctagggtg gtagaaatgg    540
gccctccagg tccccttgca gtgcactggg cagagacctc cggaaagccg gcagcgggag    600
cgctttctgg gccgcttnct cccgcacagt gttcccaacc cagtccatcc ggaaaacagt    660
ctgtacagca aatgctgtgt gagatcttag gcttttcact ttttttgttt tgttttgttt    720
ttgaaagata gaaaaaaata caattaacaa gcctcttttg taaatgggtt tccttctat     780
```

-continued

```
gtataaaatc gtggtggtcc cttgttttta catgttcatg ctgtgtaatt ttgagatgtt      840
actgagatat gttctgaaca taatgtgcat ttttttctgt acagatgaaa taggcgaatt      900
taatnnagtg attgatggtt ttttaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaaaaaaaa     1020
aaaaaaaaaa aaaa                                                       1034
```

<210> SEQ ID NO 106
<211> LENGTH: 118
<212> TYPE: PRT
<213> ORGANISM: Homo sapiens
<220> FEATURE:
<221> NAME/KEY: UNSURE
<222> LOCATION: (82)

<400> SEQUENCE: 106

```
Met Tyr Arg Thr Leu Cys Cys Val Gln Trp Arg Asn Leu Pro Gly Pro
 1               5                  10                  15

Gly Glu Ser Ser Asp Ser Ala Ser Arg Leu Cys Phe Ala Ser Ser Asn
             20                  25                  30

Val Glu Leu Thr Ser Gly Pro Gln Ser Pro Ala Gly Leu Ser Val Arg
         35                  40                  45

His Ala Arg Val Val Glu Met Gly Pro Gly Pro Leu Ala Val His
     50                  55                  60

Trp Ala Glu Thr Ser Gly Lys Pro Ala Ala Gly Ala Leu Ser Gly Pro
 65                  70                  75                  80

Leu Xaa Pro Ala Gln Cys Ser Gln Pro Ser Pro Ser Gly Lys Gln Ser
                 85                  90                  95

Val Gln Gln Met Leu Cys Glu Ile Leu Gly Phe Ser Leu Phe Leu Phe
            100                 105                 110

Cys Phe Val Phe Glu Arg
        115
```

<210> SEQ ID NO 107
<211> LENGTH: 882
<212> TYPE: DNA
<213> ORGANISM: Homo sapiens

<400> SEQUENCE: 107

```
cccatctgcc cctcacctcg tcatccaggg acccaaaccc tgcaccttcc atgtgggccc       60
acagatcctt ggcaggtacc tgaggtgcac cattgagtgt cggatttggg gttagcatcc      120
agaaagaaga atgcgcatga cgctctgtga aggctggaac tcaggtcttc agggagagaa      180
aggaagactg gattgcacct tgatgcctcc tgaggaggcg acccctct tgaggtgggc        240 gtgggcccgg cccagcctta tccaagtcgc tctgtccacc tccccttcc tggcccccac      300 cccactcctg tgcctcccag gagccctccc tgtgctccac ctgcctccgc agaaggaagc      360
ctctttctct gtttccctgg gtgaggggc tggcaggtgg ctaaccccat ttagcatctc      420
caggccctgc catggtgtct catcttgctg ttatctctag atctttccct cctcccattt      480
cctttagtag ttgaattttg caaagcttgt agcagtagct cagttgcctg cagcatcctt      540
gtgtgtagat aaattagtcg acagaaactc agcactgggg acaggattgc aaagtcgggg      600
acatagatgc agacagttgt tgagatttgg ggatagccgg gcttgtgagc ggtgcccatt      660
tccagatgaa gcctttcagc ccttctgagt ccccggccct tggtgcgatg tctgtgagtt      720
tgacctgccc agcgtgtggg ctggctcaat gctgaataaa gtgggtttgt gtcaaaaaaa      780
```
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaaaaaaaa aa                        882

<210> SEQ ID NO 108
<211> LENGTH: 109
<212> TYPE: PRT
<213> ORGANISM: Homo sapiens

<400> SEQUENCE: 108

Met Arg Met Thr Leu Cys Glu Gly Trp Asn Ser Gly Leu Gln Gly Glu
 1               5                  10                  15

Lys Gly Arg Leu Asp Cys Thr Leu Met Pro Pro Glu Glu Ala Asp Pro
            20                  25                  30

Leu Leu Arg Trp Ala Trp Ala Arg Pro Ser Leu Ile Gln Val Ala Leu
        35                  40                  45

Ser Thr Ser Pro Phe Leu Ala Pro Thr Pro Leu Leu Cys Leu Pro Gly
    50                  55                  60

Ala Leu Pro Val Leu His Leu Pro Pro Gln Lys Glu Ala Ser Phe Ser
65                  70                  75                  80

Val Ser Leu Gly Glu Gly Ala Gly Arg Trp Leu Thr Pro Phe Ser Ile
                85                  90                  95

Ser Arg Pro Cys His Gly Val Ser Cys Cys Tyr Leu
            100                 105

<210> SEQ ID NO 109
<211> LENGTH: 1547
<212> TYPE: DNA
<213> ORGANISM: Homo sapiens

<400> SEQUENCE: 109
cctaaaagtc ctgcccttta gttcagtgga ttctggattc tgaggatact cttggtcctt      60
tccagagatg aaggcaggca ggggtcaggg cccacagaag ggaatcccta tattcttggg     120
gttgtctgag ccagggctca tgcctgtctg gtgctttcaa ccaaacctct ctcatgggct    180
ctgtaaaagg aacaatcagg ccattctgaa tcccccagat cttgtaccta ccttttagaa     240
ttgtcttgag agtgtgtgtg ctgattctcc taaagtactt cgtgtggttc ctgacctata     300
ataagtgctt cataaatctt agtcattatt gttaaaatcc caaagagtgg ttttgctcga    360
gtctgaatcc aaaaggaag ctccaggtaa gaggagaaac tagagaacag gacacagaaa     420
ccatcctgtg ttttttctat cctgtgaaac catcaccatg acactggcct tccctctcag     480
tgtggcctca tcctccatgt ccctcccctgt agtcccctta actgtgaagt gtccagcctc    540
tccagcactt actcccaggc ccagctccac ttcaggcagg cctgctgggg ctcagaatag    600
cccagctgct gtctcagcag atggccaggc taattttagc catgtggtac tcacccaggg    660
accaggctgg gcttttttaga tttgaataag ccagtgtgca actttggttt agagccaata    720
acaaagtttg gagctgttgt gatctctgtg tctgcctagc actttataag attccagaaa    780
tataatttta aaggattttg tttctgtgaa ccaacaagaa cccaagctat ggagccagca    840
ggcagtcaag ccagcagggt attgatggag ggtggtgaga agcagatggt ggcaccagct    900
cctgcctctt ctccctgatg acaaagcggg tggcagggcc tcagtatccc gggtgcactg    960
tgctctcact gctctcctgg ccaaagtgaa agaaggccgc cgccaactca gcctcctgga   1020
tcatcctctg aaccagtcgt gggtggcagg ctgcatctta atgatgtgga acaaatgtgg   1080
tccgggagaa gtcagcccga tgccagcaag aacctactct ggcactttca tgtgcagtaa   1140

```
atagagacaa cataatgtga agtaggcaga tgtggaaaaa ggctcagaga ggtaagaggt   1200
cccaagagag gctgagattg agccaggttg agaacgtgtc ttttaaattg tgatgtttct   1260
gccttgttgt tcttcatatg tgaagactgc ctttcatccc agttcttcca gagagttcag   1320
ggacaacaca cagtgactcg gaaagccaca ttccagcctg ccttcacctt tccatgatta   1380
atttctagtt gcagaagcaa gttgcccaga gaagacagta gaatgaggag accggactgg   1440
tcatgcttcc taaactgggt ccatggactc ttaaaagttg gtttgggtgg tctttgggga   1500
atctgtttgt ccgttgcgct gtttccgctt aaaaaaaaaa aaaaaaa                 1547
```

<210> SEQ ID NO 110
<211> LENGTH: 73
<212> TYPE: PRT
<213> ORGANISM: Homo sapiens

<400> SEQUENCE: 110

```
Met Thr Leu Ala Phe Pro Leu Ser Val Ala Ser Ser Met Ser Leu
 1               5                  10                  15

Pro Val Val Pro Leu Thr Val Lys Cys Pro Ala Ser Pro Ala Leu Thr
                20                  25                  30

Pro Arg Pro Ser Ser Thr Ser Gly Arg Pro Ala Gly Ala Gln Asn Ser
        35                  40                  45

Pro Ala Ala Val Ser Ala Asp Gly Gln Ala Asn Phe Ser His Val Val
    50                  55                  60

Leu Thr Gln Gly Pro Gly Trp Ala Phe
65                  70
```

<210> SEQ ID NO 111
<211> LENGTH: 650
<212> TYPE: DNA
<213> ORGANISM: Homo sapiens

<400> SEQUENCE: 111

```
cagaagtagt ctgtctatcc cttttatgaa taaaaaagat attactgaag agaaatacag     60
tatttgtgtc atataatact taagctgaaa aagctaagtc tgaataaatc agtcattggc    120 atttaccta catatggcaa tgaatagtga ctttatagtt agaaatgtat gggtgaaaca    180
gtatcagaat gataatgtag aaacatatat aagccccaga ctgcccccta cagcaaaatg    240
cgattattaa taactattct gcttgaaata tttggtgaga ttctttcacc catcaagtgc    300
ttgtttgtta atattttaat cgggtcggtg tttctttggt tttgtaaatt gtgcacgttt    360
acaaagcact ggctgttctc aggcagtttt caagtttaaa tattcttgcc tttagggtca    420
ttatttgttc ctggttcccc cactctgcca ttactttttc atacttttc cacaaagatt    480 tcagccatac tccctgactt tggtttatct tctactctga catatctgca tgaagtagtt    540
tctgtctgaa atgtcttgaa accagggatg ttcttataat aatacttact gtgcagtgag    600
tggatagcca caagtaatcc ataattttac tttttaaaaa aaaaaaaaa               650
```

<210> SEQ ID NO 112
<211> LENGTH: 53
<212> TYPE: PRT

<400> SEQUENCE: 112

```
Met Arg Leu Leu Ile Thr Ile Leu Leu Glu Ile Phe Gly Glu Ile Leu
 1               5                  10                  15

Ser Pro Ile Lys Cys Leu Phe Val Asn Ile Leu Ile Gly Ser Val Phe
                20                  25                  30
```

Leu Trp Phe Cys Lys Leu Cys Thr Phe Thr Lys His Trp Leu Phe Ser
        35                  40                  45

Gly Ser Phe Gln Val
     50

<210> SEQ ID NO 113
<211> LENGTH: 1136
<212> TYPE: DNA
<213> ORGANISM: Homo sapiens

<400> SEQUENCE: 113

| | | | | | | |
|---|---|---|---|---|---|---|
| ggaagatggc | gtaccagagc | ttgcggctgg | agtacctgca | gatcccaccg | gtcagccgcg | 60 |
| cctacaccac | tgcctgcgtc | ctcaccaccg | ccgccgtgca | gttggaattg | atcacacctt | 120 |
| ttcagttgta | cttcaatcct | gaattaatct | taaacactt  | tcaaatatgg | agattaatca | 180 |
| ccaacttctt | attttttggg | ccagttggat | tcaattttt  | atttaacatg | attttctat  | 240 |
| atcgttactg | tcgaatgcta | aagaaggct  | ctttccgagg | tcggacagca | gactttgtat | 300 |
| ttatgttcct | ttttggtgga | ttcttaatga | ccctttttgg | tctgtttgtg | agcttagttt | 360 |
| tcttgggcca | ggcctttaca | ataatgctcg | tctatgtgtg | gagccgaagg | aacccctatg | 420 |
| tccgcatgaa | cttcttcggc | cttctcaact | tccaggcccc | ctttctgccc | tgggtgctca | 480 |
| tgggattttc | cttgttgttg | gggaactcaa | tcattgtgga | ccttttgggt | attgcagttg | 540 |
| gacacatata | tttttcttg  | gaagatgtat | ttcccaatca | acctggtgga | ataagaattc | 600 |
| tgaaaacacc | atctattttg | aaagctattt | ttgatacacc | agatgaggat | ccaaattaca | 660 |
| atccactacc | tgaggaacgg | ccaggaggct | tcgcctgggg | tgagggccag | cggcttggag | 720 |
| gttaaagcag | cagtgccaat | aatgagaccc | agctgggaag | gactcggtga | tacccactgg | 780 |
| gatcttttat | cctttgttgc | aaaagtgtgg | acacttttga | cagcttggca | gattttaact | 840 |
| ccagaagcac | tttatgaaat | ggtacactga | ctaatccaga | agacatttcc | aacagtttgc | 900 |
| cagtggttcc | tcactacact | ggtactgaaa | gtgtaatttc | ttagagccaa | aaaactggag | 960 |
| aaacaaatat | cctgccacct | ctaacaagta | catgagtact | tgatttttat | gggtataagg | 1020 |
| cagagccttt | tcttcctctt | cttgatagat | gaggccatgg | gtgtaaatgg | aagtttcaga | 1080 |
| gaggacaaaa | taaaacggaa | ttccattttt | ctctcactgt | aaaaaaaaaa | aaaaaa | 1136 |

<210> SEQ ID NO 114
<211> LENGTH: 239
<212> TYPE: PRT
<213> ORGANISM: Homo sapiens

<400> SEQUENCE: 114

Met Ala Tyr Gln Ser Leu Arg Leu Glu Tyr Leu Gln Ile Pro Pro Val
 1               5                  10                  15

Ser Arg Ala Tyr Thr Thr Ala Cys Val Leu Thr Thr Ala Ala Val Gln
            20                  25                  30

Leu Glu Leu Ile Thr Pro Phe Gln Leu Tyr Phe Asn Pro Glu Leu Ile
        35                  40                  45

Phe Lys His Phe Gln Ile Trp Arg Leu Ile Thr Asn Phe Leu Phe Phe
    50                  55                  60

Gly Pro Val Gly Phe Asn Phe Leu Phe Asn Met Ile Phe Leu Tyr Arg
65                  70                  75                  80

Tyr Cys Arg Met Leu Glu Glu Gly Ser Phe Arg Gly Arg Thr Ala Asp
                85                  90                  95

```
Phe Val Phe Met Phe Leu Phe Gly Gly Phe Leu Met Thr Leu Phe Gly
                100                 105                 110

Leu Phe Val Ser Leu Val Phe Leu Gly Gln Ala Phe Thr Ile Met Leu
            115                 120                 125

Val Tyr Val Trp Ser Arg Arg Asn Pro Tyr Val Arg Met Asn Phe Phe
        130                 135                 140

Gly Leu Leu Asn Phe Gln Ala Pro Phe Leu Pro Trp Val Leu Met Gly
145                 150                 155                 160

Phe Ser Leu Leu Leu Gly Asn Ser Ile Ile Val Asp Leu Leu Gly Ile
                165                 170                 175

Ala Val Gly His Ile Tyr Phe Leu Glu Asp Val Phe Pro Asn Gln
            180                 185                 190

Pro Gly Gly Ile Arg Ile Leu Lys Thr Pro Ser Ile Leu Lys Ala Ile
        195                 200                 205

Phe Asp Thr Pro Asp Glu Asp Pro Asn Tyr Asn Pro Leu Pro Glu Glu
    210                 215                 220

Arg Pro Gly Gly Phe Ala Trp Gly Glu Gly Gln Arg Leu Gly Gly
225                 230                 235

<210> SEQ ID NO 115
<211> LENGTH: 1617
<212> TYPE: DNA
<213> ORGANISM: Homo sapiens
<220> FEATURE:
<221> NAME/KEY: unsure
<222> LOCATION: (1164)

<400> SEQUENCE: 115
tgttgtgtgg gtggcatttt tcttaacgag atttgcttct gtcttagcct cacacaggga      60
aaatatccat ttatcttctc tctcgtgctt aattaatagc tttatctttt tttataccat     120
tttatccttt tctctttaac agaaagtaaa tatgtataaa atttgaagga atcgaactaa     180
caatacattc tgtgtatatt attttaatga agaaaataaa ttgattactg gcattggaac     240
agtataaaat accagtttgt acagtatgac ctatatgtga ccatgttact ccttccatt     300
tcacacaaag aaatagacac aactgcagtt cacaagtagt actggctcca ccccttggtg     360
ctggcagtgt ttggggacat tatgctgaaa gagctcccta gcatcagagg attaacacta     420
gcagattctg ttccatcttt gcactgttgc ttacctgctg attttcttaa ctgttcttgt     480
gcaatcgaca atgtgctaac ctgcttttct cttttttgtaa acgttttttgc attacaggct     540
gcattcttgc cttactgtat agaaaaagaa aaaaggctgg gtttactatt gcacattta     600
agcttttata ccttatcttt cttggaatgg tcagattctg aactggacag tcagaaccac     660
aggtctgctg ttaagggatt ttaaattgtg cattttttaac cctacagtga aataacttaa     720
gatatccctg tgttcacagt gtgaggggct gttttatgtc atgttggcat aaattgttt      780
gtaaaaggga aagtgtttct aaaggtgttt cagcgcttgt gctgatacaa agtaagttat     840
tactttgcac caggtggttt ggccactgaa ttaatactgt atagcaagag aaacaatctt     900
atttttttgg acaacatgtt ttattaagtt cttcatttct gttgattttt ttattgcatt     960
tatgattcag tggctgggaa ttgagaattt atttgaaata gaataggtaa cacctcagcg    1020
tactatagaa aatgcactca gctcaactgc tgtgtttaaa atacacattt taaatccctc    1080
tttacagaca ctaacataaa agtacatctt tctgggttgt aaacatgtgg tagtaccaga    1140
gtattgtata gtcaatgtta aatnaaagcc aaaactgaa tgtgcagaaa gtaggctttg    1200
gttaatttgt ggattcattt ttattttttgt ctttgtttaa cttttttaaaa aataagattt    1260
```

```
ctggagtaga ttggtatatt ctgttaaaga cttacagtga tccattttgc ttacactgtt    1320
gcatcacaag ggactcaccc agggaccatg acctgctggt gtgtgtgtat atttacaaaa    1380
acaaaacaaa caaaccaccc attgggatat aaggtagcaa tcacaaacta aagactgcgg    1440
cttgttgagg tgcaataccc tgactcccaa agttagttac agtgggtttt attgttttg     1500 tgactgaagg atttattcag actgctgtac tcttcatttg atgtaacaaa atgctattaa    1560
tctaaatatt tgtaaataaa gtacctgtat ctagattaaa ttaaaaaaaa aaaaaaa       1617
```

<210> SEQ ID NO 116
<211> LENGTH: 100
<212> TYPE: PRT
<213> ORGANISM: Homo sapiens

<400> SEQUENCE: 116

```
Met Leu Glu Arg Ala Pro Ser Ile Arg Gly Leu Thr Leu Ala Asp Ser
  1               5                  10                  15

Val Pro Ser Leu His Cys Cys Leu Pro Ala Asp Phe Leu Asn Cys Ser
                 20                  25                  30

Cys Ala Ile Asp Asn Val Leu Thr Cys Phe Ser Leu Phe Val Asn Val
             35                  40                  45

Phe Ala Leu Gln Ala Ala Phe Leu Pro Tyr Cys Ile Glu Lys Glu Lys
         50                  55                  60

Arg Leu Gly Leu Leu Leu His Ile Leu Ser Phe Tyr Thr Phe Ile Phe
 65                  70                  75                  80

Leu Glu Trp Ser Asp Ser Glu Leu Asp Ser Gln Asn His Arg Ser Ala
                 85                  90                  95

Val Lys Gly Phe
            100
```

<210> SEQ ID NO 117
<211> LENGTH: 849
<212> TYPE: DNA
<213> ORGANISM: Homo sapiens

<400> SEQUENCE: 117

```
gaataattgt tatctttaac acttggatgt tttgttttaa tcagacatcc agacctgcca      60
agatacttag atgactctgt ccctgggctc taaagatggg atgagtgggc ttcccacctc     120
actaacctgc accccacatt ttctgactag accaggcatt ctggggcagc tgcctgaggc     180
tgtgtgcttg ttaaggctcc aaacccacct ctctttccca ggctgggtcc ctcacacccc     240
tcctcttctt atgtatcacc acctgctccc ttcaaccagc ccagtttgtt cacctcttcc     300
tagatccacc ctccttgctc tgtttcctac atgtctgccc atccccacct ccttcaagtc     360
cctataaagc tcatggccat gtccattctc ctccagactt ctcccctagt aatcttaaac     420
acaacaataa ctaacactta ttaagcacat attacatccc aagtcctgtt actcgtttca     480
tttaatcctt ataactaccc gtgagggtag acttattatt aacccatttt gagagaggaa     540
aaaaattaag gatcgaaaag gtgaagaaac ctactcaagg tcaaacaatt tctaagtggc     600
aaagccaggc ttcgcattca agtctgtcat atgtatttca tgcccttat ccctatctga      660 tattatacta catatttatt catgtattca tttggttgtt attatctaga atgtaggctt     720
cctaagggca gaggttatct tatttagcat ttcctatatc agtacctgct acataattga     780
tgctcaataa atatttaagt gaataaatga attgatggca aaaaaaaaaa aaaaaaaaa     840 aaaaaaaaa                                                             849
```

<210> SEQ ID NO 118
<211> LENGTH: 98
<212> TYPE: PRT
<213> ORGANISM: Homo sapiens

<400> SEQUENCE: 118

Met Thr Leu Ser Leu Gly Ser Lys Asp Gly Met Ser Gly Leu Pro Thr
 1               5                  10                  15

Ser Leu Thr Cys Thr Pro His Phe Leu Thr Arg Pro Gly Ile Leu Gly
            20                  25                  30

Gln Leu Pro Glu Ala Val Cys Leu Leu Arg Leu Gln Thr His Leu Ser
        35                  40                  45

Phe Pro Gly Trp Val Pro His Thr Pro Pro Leu Leu Met Tyr His His
    50                  55                  60

Leu Leu Pro Ser Thr Ser Pro Val Cys Ser Pro Leu Pro Arg Ser Thr
65                  70                  75                  80

Leu Leu Ala Leu Phe Pro Thr Cys Leu Pro Ile Pro Thr Ser Phe Lys
                85                  90                  95

Ser Leu

<210> SEQ ID NO 119
<211> LENGTH: 925
<212> TYPE: DNA
<213> ORGANISM: Homo sapiens
<220> FEATURE:
<221> NAME/KEY: unsure
<222> LOCATION: (883)

<400> SEQUENCE: 119
cgcatcgtcg tcctccccga ccgcgtcctg cagcagctgc cagtggagcc gcctgacaag      60
gactgccatc caccatggtg aagctgggct gcagcttctc tgggaagcca ggtaaagacc     120
ctggggacca ggatggggct gccatggaca gtgtgcctct gatcagcccc ttggacatca     180
gccagctcca gccgccactc cctgaccagg tggtcatcaa gacacagaca gaataccagc     240
tgtcctcccc agaccagcag aatttccctg acctggaggg ccagaggctg aactgcagcc     300
acccagagga agggcgcagg ctgcccaccg cacggatgat cgccttcgcc atggcgctac     360
tgggctgcgt gctgatcatg tacaaggcca tctggtacga ccagttcacc tgccccgacg     420
gcttcctgct gcggcacaag atctgcacgc gctgaccct ggagatgtac tacacgagga     480
tggaccccga gcgccaccgc agcatcctgg cggccatcgg ggcctacccg ctgagccgca     540
agcacggcac ggagacgccg gcggcctggg gggacggcta ccgcgcagcc aaggaggagc     600
gcaaggggcc cacccaggct ggggcggcgg cggcggccac cgaacccccc gggaagccgt     660
cggccaaggc ggagaaggag gcggcgcgga aggcggccgg gagcgcggcg ccccgcccg      720 cgcagtgacg tctccagccc cgcagcccgg cccgggcgtc ctccgccagc tcctgtgacc     780
agcgcgtctc ccgatgctct ccgccgtgtt cgtgtcccca ggcgcccgcg ctgcagcccc     840
gcgccccgtg ggtctctgac tctgtcgctt ttctctaagt aangatttca cgtccaaaaa     900 aaaaaaaaa aaaaaaaaaa aaaaa                                           925

<210> SEQ ID NO 120
<211> LENGTH: 217
<212> TYPE: PRT
<213> ORGANISM: Homo sapiens

<400> SEQUENCE: 120

-continued

```
Met Val Lys Leu Gly Cys Ser Phe Ser Gly Lys Pro Gly Lys Asp Pro
 1               5                  10                  15

Gly Asp Gln Asp Gly Ala Ala Met Asp Ser Val Pro Leu Ile Ser Pro
            20                  25                  30

Leu Asp Ile Ser Gln Leu Gln Pro Pro Leu Pro Asp Gln Val Val Ile
        35                  40                  45

Lys Thr Gln Thr Glu Tyr Gln Leu Ser Ser Pro Asp Gln Gln Asn Phe
    50                  55                  60

Pro Asp Leu Glu Gly Gln Arg Leu Asn Cys Ser His Pro Glu Glu Gly
65                  70                  75                  80

Arg Arg Leu Pro Thr Ala Arg Met Ile Ala Phe Ala Met Ala Leu Leu
                85                  90                  95

Gly Cys Val Leu Ile Met Tyr Lys Ala Ile Trp Tyr Asp Gln Phe Thr
            100                 105                 110

Cys Pro Asp Gly Phe Leu Leu Arg His Lys Ile Cys Thr Pro Leu Thr
            115                 120                 125

Leu Glu Met Tyr Tyr Thr Glu Met Asp Pro Glu Arg His Arg Ser Ile
        130                 135                 140

Leu Ala Ala Ile Gly Ala Tyr Pro Leu Ser Arg Lys His Gly Thr Glu
145                 150                 155                 160

Thr Pro Ala Ala Trp Gly Asp Gly Tyr Arg Ala Ala Lys Glu Glu Arg
                165                 170                 175

Lys Gly Pro Thr Gln Ala Gly Ala Ala Ala Ala Thr Glu Pro Pro
            180                 185                 190

Gly Lys Pro Ser Ala Lys Ala Glu Lys Glu Ala Ala Arg Lys Ala Ala
            195                 200                 205

Gly Ser Ala Ala Pro Pro Pro Ala Gln
        210                 215
```

<210> SEQ ID NO 121
<211> LENGTH: 1645
<212> TYPE: DNA
<213> ORGANISM: Homo sapiens

<400> SEQUENCE: 121

```
caaaaacctg tgactatact ttctattggg caaggctctc tactcctgtg acttctgtct    60
gccctgatag ctggtagcat tttcctgggt acctgccata tgccaggcac aatagaacct   120
tatcttcttc ccatttcaca gagaagaaag gtgaggctcg agagggaaa gtgacttgcc    180
caagcttgag ctgctgggaa aaatgccagg gaccaggata cagaccttgg tcatctgact   240
ccaaagtccc ccgtgatgtt ttctgtgttt ggtggcctgt tggtgagggg ccctgccctc   300
agaacacccc tctgccagag caagatgtgt gagcacatcc ctgaagccag caagcctgca   360
gctagcggta tcattaccat catggtagcc ggagccaggg gtgccatctg ccagcaggga   420
gagaagtatg cacatctcag gtaggggtg ttagagaaac atcgccatgg ggctgacagc    480
caggtaggat ggcaggagtc acctggggtg aggaggggca ggtgctctag cagaaaaaa    540
ccgcagcagc aaaggtgtgg aggtggaagg atcagggctc tgctgagaga atgtatagtt   600
ggggcttcag tgcaggagag agcactgaga gatgaggtca gaggcccgag agggagtcag   660
cctgggcat gcaaagctgc gaggcactgg ggagccatgg aaggttcaag caggagagag    720
gcctgctctg gttggtgctt caggaaactc ccccagctga caggtttgga gggcagtgtg   780
taagcagaga gtgaggcaag gtggcagctg caggcaggag atggttggta tgtgggccag   840
```

```
ggtgggggtag tggggcagga gaaaagtggg cagactttgg aggcagcctc ttccctcctt      900
ggtgcctggg ctgactgtgg gggatgggga ggagggaaga gtgacctgga atgcccgggg      960
ctggcttgga tgcaatggcc ctgcccttct aaggaggtga ggaacagaaa agctaccaag     1020
gtctgggggt cacagataag tgtgtgggggg gcctaagaga ctcccaggct gtagcacgaa     1080
ggctccaaga agtggtggct cagccctgtg gcccaccaga cctgattcag cttccaggcc     1140
cagtcgccca gccccccagt tgagtggcag ctgtcacaga acccaatgtc tccccgcacc     1200
atgtccaaat aaaggaaaaa ccaaaatacg tttccctttg tccgaatcca gcagggtga      1260 gttgggcgag agtcatccgc tattgtgtgc tgaggcccac actgcttctt acataagccc     1320
cgagttaaaa atatgcccgg aattctcatt ctcaagctct gcctgggatt gcaccctgac     1380
ccccagcctc ggcagcttct agcacccaca gggatgaaga aactgcccca tggcacaacg     1440
ctggcacgtg gcacttctag ctctgtctgc ctccagtgcc acgaacagta agagtgcgcc     1500
gggtgcggtg ctcacgcctg taatcccagc actttgggag gccaaggtgg gcagatcact     1560
tgagcccagg agtttgagac cagcctgggc aacatagca agaccccatc tctacaaaaa      1620
aaaaaaaaaa aaaaaaaaaa aaaaa                                            1645
```

<210> SEQ ID NO 122
<211> LENGTH: 175
<212> TYPE: PRT
<213> ORGANISM: Homo sapiens

<400> SEQUENCE: 122

```
Met Phe Ser Val Phe Gly Gly Leu Leu Val Arg Gly Pro Ala Leu Arg
  1               5                  10                  15

Thr Pro Leu Cys Gln Ser Lys Met Cys Glu His Ile Pro Glu Ala Ser
             20                  25                  30

Lys Pro Ala Ala Ser Gly Ile Ile Thr Ile Met Val Ala Gly Ala Arg
         35                  40                  45

Gly Ala Ile Cys Gln Gln Gly Glu Lys Tyr Ala His Leu Arg Val Gly
     50                  55                  60

Val Leu Glu Lys His Arg His Gly Ala Asp Ser Gln Val Gly Trp Gln
 65                  70                  75                  80

Glu Ser Pro Gly Val Arg Arg Gly Arg Cys Ser Arg Gln Lys Lys Pro
                 85                  90                  95

Gln Gln Gln Arg Cys Gly Gly Gly Arg Ile Arg Ala Leu Leu Arg Glu
            100                 105                 110

Cys Ile Val Gly Ala Ser Val Gln Glu Arg Ala Leu Arg Asp Glu Val
        115                 120                 125

Arg Gly Pro Arg Gly Ser Gln Pro Gly Ala Cys Lys Ala Ala Arg His
    130                 135                 140

Trp Gly Ala Met Glu Gly Ser Ser Arg Arg Glu Ala Cys Ser Gly Trp
145                 150                 155                 160

Cys Phe Arg Lys Leu Pro Gln Leu Thr Gly Leu Glu Gly Ser Val
                165                 170                 175
```

<210> SEQ ID NO 123
<211> LENGTH: 2515
<212> TYPE: DNA
<213> ORGANISM: Homo sapiens

<400> SEQUENCE: 123

```
ctttgggtaa tggaggaggt tgcagttccc gtgctgtaat tagacatctt ttaattagac       60
```

-continued

| | |
|---|---|
| atcttttcca gcagagccat ttaaaatatt ttcctagagg acctgccccc taacctcagc | 120 |
| cagtcaatgg ggaggagttt tgaatgccac actccccagt ttgccaccaa accacaggca | 180 |
| gagagttgtg ttcatcacac tagacagaaa tctgtgtcag tcagggtcct tgcccatatg | 240 |
| tctccccttt gtcccctct gtacgggatt caatcaatgt ttgtcaaagc atatcattac | 300 |
| gtaaactgtc agaatatggt gctgagtagg aatggcaccg cgttattcat tcagtccctt | 360 |
| tatcgaggat ctaccatgca cctacattta tctaaatcta attattagta cacattttca | 420 |
| aatttgaact tctatgtgga gaggtacata aaaatataaa ttattggctg ggtgtggtgg | 480 |
| ctcacattta taatccttat aagcccagca ctttgggagg ccaaggtgcc tggattgctt | 540 |
| gagcctagga attcgaggcc agcctgggca acatggtgaa accctgtctc tacaaaaaat | 600 |
| ttaaaaatta gctgggcatg gtggcatgca cctgtagtcc cagctactag ggaggctgag | 660 |
| gtgggaagat cgcttgagcc ctggaggcag aggttgcagt gagctatgat tgtaccactg | 720 |
| cactctagtc tgggcaagag aagagaacct gtctcaaaaa atgtgtatat taaaaacata | 780 |
| taaatccttg ctcataacag aaaacagtag catatatgga aattaatcaa acctcttcca | 840 |
| actcttccct ctttgacaca tggaatttcc aagcaagttg tatcactggt ctactttaag | 900 |
| ggccatctca gtgggagac ataaaggtgt tttcccatct atgggaatat tgacaagagc | 960 |
| taacagaagg aatttcaaaa ggttccacag tcacagagca accaacagga agtgaaggca | 1020 |
| ggaagattcc tcatcaactc tattagtaca gcagaacagc aagatgaatg ttatgaagaa | 1080 |
| gttgagtcat tttctactgg tacttaggtc cacccggacc ttatcccttc actccccatt | 1140 |
| catcagccac atcctttgtg tcttgcctgc cctgctgtgg aatatgccat gagaatcatg | 1200 |
| tatatccagc ttcatcagct actgtcagct tgggaagacc cagtttcctt gaggttgacg | 1260 |
| tcctgtttca gaacaaatca ctggacttct tcagcataac atggcttttg ataagaagaa | 1320 |
| attctccatt tctttaagta tcctctgtag aaacagttta tataaagtcc ttggggtgac | 1380 |
| ctcaatccca tccacagctt caatttatga gatgatgact cagaccacat ttctggctca | 1440 |
| gaactttata tcaggctcca gatccatgtt ttcaaatgcc ttgaacatcc caagggtggc | 1500 |
| ttgaacttga actcacctca ctgccccgc tttctgtcct aaatctaaat tttagtaaat | 1560 |
| tatagcatta catatctaat gataggttca caaaccagca attggaagca tccacagtag | 1620 |
| gtgaggcacg agcaggctgg ctttggtctg ctggaatctg gtttatttga aactaatgcc | 1680 |
| aagacacagc ttcctcttac tctcccaccc caggcaattg ctcttgcctt ggctgtgtcc | 1740 |
| tacaggctgc ctcattctcc tctcctgccc ctgcttccac ccacctggaa tcacttctcc | 1800 |
| aggtcataca aagcaccttt gccccacaca aggattcaag caggctgacc aacagaagtc | 1860 |
| atcttgagga tcttgtgaaa actatagatt cccatgctct tccccacgac cctctgattc | 1920 |
| tgggagtcta ggttgagacc taatccaccg tggggaccat cagagaattc agtctgtgcc | 1980 |
| ctagtgcaca acatgaaaaa aactatgatg ttctgtgtct ccccacaagt ttggagtact | 2040 |
| gttctcacaa gcattgatgg cactacacac acacatcaca cacatgcaca aatgcatcca | 2100 |
| cacacatgca caaatacaaa tgcatacatg tgtgacacaa atgcatttta gtcatactgt | 2160 |
| cactgtgccc aggtctcctt ccgttgtttc tacaaataat cattgagtaa caatcatct | 2220 |
| actaagccat tcggagctcc cagctctgct cgcgcattgc cagacttgcc ccttccccct | 2280 |
| gatgaccacg gcaccctcct gactggtctc cctccctctg ggctgccctc tacacttctg | 2340 |
| acttagtggt ctttggaaat gcagattgag gtcaccgaag tgccttgacc ctacatgaag | 2400 |
| gtcaaacttc tcagctctga aaacagtgct tgcccagtgt ctggggcttc atttggtctg | 2460 | cctccgaca gccgctcctc aatgcgccac caccacgaaa caaaaaaaaa aaaaa 2515

<210> SEQ ID NO 124
<211> LENGTH: 93
<212> TYPE: PRT
<213> ORGANISM: Homo sapiens

<400> SEQUENCE: 124

```
Met Gly Arg Ser Phe Glu Cys His Thr Pro Gln Phe Ala Thr Lys Pro
  1               5                  10                  15
Gln Ala Glu Ser Cys Val His Thr Arg Gln Lys Ser Val Ser Val
                 20                  25                  30
Arg Val Leu Ala His Met Ser Pro Leu Cys Pro Leu Tyr Gly Ile
             35                  40                  45
Gln Ser Met Phe Val Lys Ala Tyr His Tyr Val Asn Cys Gln Asn Met
         50                  55                  60
Val Leu Ser Arg Asn Gly Thr Ala Leu Phe Ile Gln Ser Leu Tyr Arg
 65                  70                  75                  80
Gly Ser Thr Met His Leu His Leu Ser Lys Ser Asn Tyr
                 85                  90
```

<210> SEQ ID NO 125
<211> LENGTH: 1763
<212> TYPE: DNA
<213> ORGANISM: Homo sapiens

<400> SEQUENCE: 125
gcctcagcaa caaagaaaaa gtgaattttt aatgctgaag ataaagtaag ctaaagtacc     60
agcagaagcc ttggctattt atagcagttc tgacaatagt tttataagaa catgaagaga    120
acagaatcac ttgaaaatgg atgccagtca tctcttgttc ccactactga attcttataa    180
agtggtggca agatagggaa gggataatct gagaattttt aaaagatgat ttaatgagaa    240
gaagcacaat tttgattgtg atgagtcact ttctgtaaac aatcttggtc tatctttacc    300 cttataccctt atctgtaatt taccatttat tgtatttgca aagcgagtag gggttgaatc    360
acaggaaatc ctttgtattc cagactttag ggcagagcct gagggagtat tattttacat    420
aacccgtcct agagtaacat tttaggcaac attcttcatt gcaagtaaaa gatccataag    480 tggcattttta cacggctgcg agtattgtta tatctaatcc tatttttaaaa gattttttggt    540 aatatgaagc ttgaatactg gtaacagtga tgcaatatac gcaagctgca caacctgtat    600
attgtatgca ttgctgcgtg gaggctgttt atttcaacct ttttaaaaat tgtgtttttt    660
agtaaaatgg cttattttttt cccaaaggtg gaatttagca ttttgtaatg atgaatataa    720
aaatacctgt catccccaga tcatttaaaa gttaactaaa gtgagaatga aaaacaaaa    780 ttccaagaca ctttttaaaa gaatgtctgc cctcacacac ttttatggat ttgttttttct    840 tacataccca tcttttaact tagagatagc attttttgcc ctctttattt tgttgtttgt    900
ttctccagag agtaaacgct ttgtagttct ttcttttaaaa aacatttttt ttaaagaaga    960
agaagccact tgaaccctca ataaaggctg ttgcctaagc atggcatact tcatctgttc   1020
tcatttgtgc catctgccgt gatgtcgtca cttttatggc gttaattttcc tgccactaca   1080 gatctttttga agattgctgg aatactggtg tctgttagaa tgcttcagac tacagatgta   1140
attaaaggct tttcttaata tgttttaacc aaagatgtgg agcaatccaa gccacatatc   1200
ttctacatca aatttttcca ttttggttat tttcataatc tggtattgca ttttgccttc   1260

```
cctgttcata cctcaaattg attcatacct cagtttaatt cagagaggtc agttaagtga    1320
cggattctgt tgtggtttga atgcagtacc agtgttctct tcgagcaaag tagacctggg    1380
tcactgtagg cataggactt ggattgcttc agatggtttg ctgtatcatt tttcttcttt    1440
ttcttttcct ggggacttgt ttccattaaa tgagagtaat taaaatcgct tgtaaatgag    1500
ggcatacatg catttgcaac aaatattcaa atagaggctc acagcggcat aagctggact    1560
ttgtcgccac tagatgacag gatgttataa ctaagttaaa ccacatctgt gtatctcagg    1620
ggacttaatt cagctgtctg tagtgaataa agtgggaaa ttttcaaaag tttctcctgc    1680
tggaaataag gtataatttg tttttgcag acaattcggt aaagttactg gctttcttgg    1740
tgaaaaagaa aaaaaaaaa aaa                                             1763

<210> SEQ ID NO 126
<211> LENGTH: 102
<212> TYPE: PRT
<213> ORGANISM: Homo sapiens

<400> SEQUENCE: 126

Met Trp Ser Asn Pro Ser His Ile Ser Ser Thr Ser Asn Phe Ser Ile
 1               5                  10                  15

Leu Val Ile Phe Ile Ile Trp Tyr Cys Ile Leu Pro Ser Leu Phe Ile
                20                  25                  30

Pro Gln Ile Asp Ser Tyr Leu Ser Leu Ile Gln Arg Gly Gln Leu Ser
            35                  40                  45

Asp Gly Phe Cys Cys Gly Leu Asn Ala Val Pro Val Phe Ser Ser Ser
        50                  55                  60

Lys Val Asp Leu Gly His Cys Arg His Arg Thr Trp Ile Ala Ser Asp
 65                 70                  75                  80

Gly Leu Leu Tyr His Phe Ser Ser Phe Ser Phe Pro Gly Asp Leu Phe
                85                  90                  95

Pro Leu Asn Glu Ser Asn
            100

<210> SEQ ID NO 127
<211> LENGTH: 1698
<212> TYPE: DNA
<213> ORGANISM: Homo sapiens

<400> SEQUENCE: 127
caaagaaaag gttggttaga ataagtaaaa tttcagttag aaagatatag cttaccagtt      60
ttccatgtgc ttaaggaagt caagaatatt tcaggttgtt gagaactgtt gtaaatgga     120 attgaagcta gtgtctctca ccttcttagg tgtatcagag agaggaagtg gaaggccagt    180
agtagcatct tcatacttac ttttgccagc ccagcctcca tttcaaagac tttgtcttcc    240
atcctatcca atgacatggt cagggatggg ctctgaggag gcagtgaggc cccaccttgg    300
tttgctccac tgtggtgtgt agtctccaaa cagcttaagg gttttttaagt tttctcacga    360 ttacctccac tccactcatc tactatcagc atcagaaagg ttaacatccc tgggaccatt    420
ctacttataa aagagatgaa ctagtgtgct ttctccccttt ttccaggtgt gccatccata    480
tacaatctcc tcttggccaa gttcaacaaa tgtttccagg gaacccgtg ggttgaggca    540 agtagccaa gatgtattga gttaagtttt tctagaggac aaaagtatttt cttgtccctt    600 ttccctcatg ctcatatgtt ttagctgagg cgtaaatggc caagttgagt aatatctgtg    660
gaactgagac agagagccag ggacccatgt acccagggac cagtcccctg gggaatcaca    720
```

-continued

```
cagtggctca gactagactg ctctatccca ccagaactct gctgctgttc atttccatca        780
ggaccaccca ggaaagcaaa taagttagcc ttctcatcat taggtcacct aatctcttgg        840
ggtgcaggat gagagcatat atagatctcc tgtttagaga gtgtgttcat aattgtagaa        900
agggatagaa aatggaataa ccaagaggct gtgtcatttt ttaagaggat ggcaaggatg        960
acctcaaatg agctcaacaa aactgggaat ccaaggaatg gtgcttgtag ggaagagag        1020 gtcagttgtg gtccttaaac ctcttggcac cttgtgcggg ttataaaaca aggagctgga       1080
gtaaaattgc ccttaccccc aatccaaatg ctgtccagga tttaggagct acccaacctg       1140
tggttatatg gtgttggttt ccattttttg tttgtttgct tgtttccaaa atagccttgc       1200
ttggtactgc atggaaagtt caagcttttc ttcttgcccg ctcagggctg gcctcttccc       1260
cgtgtcttca cagcgtccct aaggaagatt tttgcagcac tctctggagc tgagggagt       1320 gaaatttggt ccagagaagg cggaaggaaa tagttttcct gtttcctttt ctcgaggtgg       1380
atgtcctcag gcttccttca cacctccttc tcatgggtgc ggctggcagt acagtcaggc       1440
tgtggaggag ggctgagaag aaaggggcac tggtccagcc ccaggtttgg tctgagacag       1500
gtacacagca gataccatcc caccttcctc tctaaagaac aggccagcca cacatataac       1560
ccttccccta ctttactaat gtatccctta tgtggtacca gcaatggagg acaggcagac       1620
ttaccccctg ccatctagag agaatgttgt tattacccgt aaaacttgac caccccacga       1680
aacaaaaaaa aaaaaaaa                                                      1698

<210> SEQ ID NO 128
<211> LENGTH: 85
<212> TYPE: PRT
<213> ORGANISM: Homo sapiens

<400> SEQUENCE: 128

Met Cys Leu Arg Lys Ser Arg Ile Phe Gln Val Val Glu Asn Cys Cys
  1               5                  10                  15

Lys Met Glu Leu Lys Leu Val Ser Leu Thr Phe Leu Gly Val Ser Glu
             20                  25                  30

Arg Gly Ser Gly Arg Pro Val Val Ala Ser Ser Tyr Leu Leu Leu Pro
         35                  40                  45

Ala Gln Pro Pro Phe Gln Arg Leu Cys Leu Pro Ser Tyr Pro Met Thr
     50                  55                  60

Trp Ser Gly Met Gly Ser Glu Glu Ala Val Arg Pro His Leu Gly Leu
 65                  70                  75                  80

Leu His Cys Gly Val
             85

<210> SEQ ID NO 129
<211> LENGTH: 2110
<212> TYPE: DNA
<213> ORGANISM: Homo sapiens

<400> SEQUENCE: 129
agcagagaag attgaagatg tggaaatcac actggtgtga tgatgggctt gcccatccat         60
tactgctaca atcaaggcca ggcttggagt ttggccagtc ttgttttta ggcacctttg        120 catgatgatg actcttgaac agagcaaaaa acaaggagga ttatgtgtga ctgggtggcc       180
tggtagactc ctcccacgtt ttgaatattt cgtgcctttt ttttttgttg tcattttcta       240
tgtcatttct cctaccatag cacaaatcct agcggaccct atgatcaaag agggggcag        300 cctcatgcct aacagtggtc tgttttatat gaagactcaa gaacaagcct cattccaggg       360
```

-continued

```
cacagtccct aaattactga tcatgtgcac tcgtacagta tattactgtg accacaaggg    420
atgtggcaaa gattctcatc tttcttcaag tggcttttgc tcatctgatt gagaattaat    480
cagatcatgt tggctacata aggaaacaga aggagggatt tcaggagagg ctggctcctc    540
cccaaggtta gtccccagac tgagaaagtg aaaccttatt gggaaaaatt ggactgccct    600
gaatttagca ccaattgcat taacgcacat ctcttccaca actaacagac ttaaaataac    660
agtgtccttc gtattaatat ctgtgccatt catttagaat tagcagagct aatatggagg    720
ggctgaacta gtagccacat cttgttcatc acatagacta atagaaagga gctgtggcta    780
aagcagaaat ggaacttccg gatctgaaat tagcccatat aatgttcttt tgtatttggg    840
tattttcat cttaattttt acagcatata ctcttcttac cagtatcctt agaatccaaa    900
tgtctagata agttgaggac atacctgc attgttgagc ttctctactg ggacgcccc    960
ggcattattt tattcccaag ccagcagacc ggcccagaca gccaggctgt ggctggtcca   1020
gaccaactgc tatggtggaa atgcagcttc ccaggtccca ctaccctgac atttccgtgg   1080
aaggaagaac ctggtggctc gtggaggaaa ccagctttct atgagaaagg actgaaggat   1140
tgcgcaccct gcacaagtac agattgacca ggaaaagaca agtgtcttct gtgtgtcaca   1200
gggaaagcca ggagtggcct tctctgcaac cagcaagcct gcagcaacag gtgccccac   1260
gtcaggtgct gactgttcgc tgtccgctcc tgtagaaagt tgggagcaca atacctatgg   1320
acttaaggat gttcgccggt tgtgggttgg gttttttttt tttcctgggg taagaaatcg   1380
aatttgcgga atttaaatct tccaggttgt ataatgcttt gaaaactcca tccctcctaa   1440
agaatcataa aaaacttga aatgctcgcc aaatgtcccc catggggatt tttgaccaaa   1500
aggtaaggtg ataacaggag aaattttgg ttctttgatc acttcagtga caatacccctt   1560
taatgcatct tctccatgat ttgggggttt ttttcgttgt tgtttttac acttcttaac   1620
ctgttgatct atttgaggtc tttggtgttt atcaaactaa ttcttaagtt taaaaagaa   1680
attaaaaggg tggtttttttt aagatttta agtttgctaa catattaaaa atcttcaat   1740
gcttattaaa tagagcagtt cttgccaccc agtctggtat tctgtcttta gctagccaaa   1800
ttgtccttga atttgggttt tccacaacct caaagggtta tttgaaatct tttgtagtat   1860
tttaaaatat tttttggaag agctgctaat tttatttaa aaaacagagt tgtgaaaaca   1920
tgcctccttt ttaaaaaata acccctccat ccaggatatg gaatccagca ccacagtgca   1980
caggtcaggg ctcggaggga gcctctgtgc agatgtgctt tctttacagt ggctgtaaaa   2040
agtttgtatt tactatgtat aaaatgttga ataataaaa aaatggaatt aaaaaaaaaa   2100
aaaaaaaaa                                                           2110
```

<210> SEQ ID NO 130
<211> LENGTH: 116
<212> TYPE: PRT
<213> ORGANISM: Homo sapiens

<400> SEQUENCE: 130

```
Met Met Met Thr Leu Glu Gln Ser Lys Lys Gln Gly Gly Leu Cys Val
  1               5                  10                  15

Thr Gly Trp Pro Gly Arg Leu Leu Pro Arg Phe Glu Tyr Phe Val Pro
             20                  25                  30

Phe Phe Phe Val Val Ile Phe Tyr Val Ile Ser Pro Thr Ile Ala Gln
         35                  40                  45

Ile Leu Ala Asp Pro Met Ile Lys Glu Gly Gly Ser Leu Met Pro Asn
```

```
                         50                  55                  60
Ser Gly Leu Phe Tyr Met Lys Thr Gln Glu Gln Ala Ser Phe Gln Gly
 65                  70                  75                  80

Thr Val Pro Lys Leu Leu Ile Met Cys Thr Arg Thr Val Tyr Tyr Cys
                 85                  90                  95

Asp His Lys Gly Cys Gly Lys Asp Ser His Leu Ser Ser Ser Gly Phe
            100                 105                 110

Cys Ser Ser Asp
        115

<210> SEQ ID NO 131
<211> LENGTH: 752
<212> TYPE: DNA
<213> ORGANISM: Homo sapiens

<400> SEQUENCE: 131
cccgtgtttc cgggctggg tatttgcctc gcaccatggc gcccaagggc aaagtgggca      60
cgagagggaa gaagcagata tttgaagaga acagagagac tctgaagttc tacctgcgga    120
tcatactggg ggccaatgcc atttactgcc ttgtgacgtt ggtcttcttt tactcatctg    180
cctcattttg ggcctggttg gccctgggct ttagtctggc agtgtatggg gccagctacc    240
actctatgag ctcgatggca cgagcagcgt tctctgagga tggggccctg atggatggtg    300
gcatggacct caacatggag cagggcatgg cagagcacct taaggatgtg atcctactga    360
cagccatcgt gcaggtgctc agctgcttct ctctctatgt ctggtccttc tggcttctgg    420
ctccaggccg ggccctttac ctcctgtggg tgaatgtgct gggcccctgg ttcactgcag    480
acagtggcac cccagcacca gagcacaatg agaaacggac gcgccgacag gagcggcggc    540
agatgaagcg gttatagcca ttgacattat tgccacaggc cactggccct gggtggctct    600
gtcagggtgc acagcccctc atgcctggag caatgagggt ttagtccagg ggccaaaagc    660
agtctgaggt attgggtata cttatactct atagggtcgt tgaataaatg cttagaatg     720 tgaaaaaaaa aaaaaaaaa aaaaaaaaa aa                                    752

<210> SEQ ID NO 132
<211> LENGTH: 173
<212> TYPE: PRT
<213> ORGANISM: Homo sapiens

<400> SEQUENCE: 132

Met Ala Pro Lys Gly Lys Val Gly Thr Arg Gly Lys Lys Gln Ile Phe
  1               5                  10                  15

Glu Glu Asn Arg Glu Thr Leu Lys Phe Tyr Leu Arg Ile Ile Leu Gly
                 20                  25                  30

Ala Asn Ala Ile Tyr Cys Leu Val Thr Leu Val Phe Phe Tyr Ser Ser
             35                  40                  45

Ala Ser Phe Trp Ala Trp Leu Ala Leu Gly Phe Ser Leu Ala Val Tyr
 50                  55                  60

Gly Ala Ser Tyr His Ser Met Ser Ser Met Ala Arg Ala Ala Phe Ser
 65                  70                  75                  80

Glu Asp Gly Ala Leu Met Asp Gly Gly Met Asp Leu Asn Met Glu Gln
                 85                  90                  95

Gly Met Ala Glu His Leu Lys Asp Val Ile Leu Leu Thr Ala Ile Val
            100                 105                 110

Gln Val Leu Ser Cys Phe Ser Leu Tyr Val Trp Ser Phe Trp Leu Leu
        115                 120                 125
```

```
Ala Pro Gly Arg Ala Leu Tyr Leu Leu Trp Val Asn Val Leu Gly Pro
        130                 135                 140
Trp Phe Thr Ala Asp Ser Gly Thr Pro Ala Pro Glu His Asn Glu Lys
145                 150                 155                 160
Arg Gln Arg Arg Gln Glu Arg Arg Gln Met Lys Arg Leu
                165                 170

<210> SEQ ID NO 133
<211> LENGTH: 698
<212> TYPE: DNA
<213> ORGANISM: Homo sapiens

<400> SEQUENCE: 133
ggcagccatg gtcggggcgc tgtgcggctg ctggttccgc ctgggcgggg cccgcccgct    60
catcccgttg ggcccgactg tggtacagac ctccatgagc cggtcccagg tagccctgct   120
gggcctgagt ctgctgctca tgctcctact gtatgtgggg ctgccaggcc cccctgagca   180
gacttcctgc ctctggggag accccaatgt cacagtcctg gctggtctca cccctggcaa   240
ctcgcccatc ttttaccgcg aggtgctccc acccacccag aactacaccc aggagcaatt   300
ctgggctgtg aagactccaa cccttatcct gtatggagag ctggaccaca tcctggctcg   360
agagtcactg cggcagctcc gccacctgcc caaccactct gtggtgaagc tacgcaatgc   420
aggccatgcc tgttacctcc acaagccgca agacttccac cttgtcctgc ttgccttcct   480
tgaccatcta ccttgaacta acccactccc agctcccagc ctggcatgag cttggacagt   540
ctggaccgcc accctccctg aaccaggag acagcctctg ggattggagg ccagaggcca   600
gggtcagacc cagccaggac tcctcatttc atctcacaga cacaataaaa aagcatattt   660
gtcctgccaa aaaaaaaaaa aaaaaaaaaa aaaaaaaa                            698

<210> SEQ ID NO 134
<211> LENGTH: 162
<212> TYPE: PRT
<213> ORGANISM: Homo sapiens

<400> SEQUENCE: 134

Met Val Gly Ala Leu Cys Gly Cys Trp Phe Arg Leu Gly Gly Ala Arg
  1               5                  10                  15
Pro Leu Ile Pro Leu Gly Pro Thr Val Val Gln Thr Ser Met Ser Arg
                 20                  25                  30
Ser Gln Val Ala Leu Leu Gly Leu Ser Leu Leu Met Leu Leu Leu
             35                  40                  45
Tyr Val Gly Leu Pro Gly Pro Pro Glu Gln Thr Ser Cys Leu Trp Gly
         50                  55                  60
Asp Pro Asn Val Thr Val Leu Ala Gly Leu Thr Pro Gly Asn Ser Pro
 65                  70                  75                  80
Ile Phe Tyr Arg Glu Val Leu Pro Pro Thr Gln Asn Tyr Thr Gln Glu
                 85                  90                  95
Gln Phe Trp Ala Val Lys Thr Pro Thr Leu Ile Leu Tyr Gly Glu Leu
            100                 105                 110
Asp His Ile Leu Ala Arg Glu Ser Leu Arg Gln Leu Arg His Leu Pro
        115                 120                 125
Asn His Ser Val Val Lys Leu Arg Asn Ala Gly His Ala Cys Tyr Leu
    130                 135                 140
His Lys Pro Gln Asp Phe His Leu Val Leu Leu Ala Phe Leu Asp His
145                 150                 155                 160
```

Leu Pro

<210> SEQ ID NO 135
<211> LENGTH: 1825
<212> TYPE: DNA
<213> ORGANISM: Homo sapiens

<400> SEQUENCE: 135

```
tgtgcgttat gtaggttgta atgaagctaa cagtttcagt tatgtactac tattttgtc      60
catacttagt tcattgtaaa ctctatatta atttctttga taacatgtat ttgatttttt    120
tgcaatacgg cttccaggtt cttgccattc ttcagattct catgcttatt cagatttctc    180
atttggctgg cattttgtta tcagtgaacc aaaattatct cattttaaat tcacataaga    240
caaaagcacc agtagtcagt attctagttc tccttactaa tttacggagg tgtgatctgg    300
gtgattttta aattaattta attatcattt catattcata gtgatgattt ttaaaatttt    360
acaaactttt cacctatata aacatcttta ttgtcaggtg tctgacaagc taatttcttt    420
gctaactatt ttagttatta atatattatg taggttgtat cagaattttg tttttcaccc    480
aatgctttt cacaattccc aagtcaagaa ggatgcatta caatgtttac attagcatct    540
aaaggcaatg taaagtcggg aaacattttt agtatataat ttcataattc aaagacattt    600
ttaaaaatg aatggttaaa ccagtatctc actgcattaa atgtaattca atacattaaa    660
tttagttatt agaagatgtt attacaagcc tcaacatgta acatgcttac ttacaaatca    720
aaaatctcag atcaagtggc tggaactgca ggggcctgcc aggcatctgg gtatttacat    780
gattcctttc catgtggtta tggcagagca tggccatttc aaggtagtca aacttcttac    840
acaaaagctg gcttaccaca gagtgggtat ttcaagggag ggaaacagaa gaagcaacat    900
atgtataatt ggaaacccgg aggaggaaaa agagggcagt gacaccaaac agtatttaaa    960
tatcaaaacc tataatctga aaacatactt acaggctttt gtgttctcca tttttccctt   1020
agcataatac ttttaaaatt tatagatatt gttccatata tcagtagttt gttttttttt   1080
ttggttttgc tccgttgtgt gatgtatagt catatgttta tatagttgcc cctggataga   1140
cgtttgggtt tttacatttt tgggcctatt agaataaaag ctcgtgaata ttccagtaaa   1200
aatttgtgtg tgaatatata tttttaatct tcttgggtaa atacatagaa atgcaatttc   1260
tgtgtcattt gttatgatca acttcattaa aaactgcaga ctctttttcaa aatcagccat   1320
atcattttgc attctcagga tgttacttga caacatcacc acatttggta tggtagtttt   1380
tttaaatttt agtgattctg gtggatgtat agtggtattt tttagtttga atttgaattt   1440
ctgaaataag taatgatatt gaacttgttt tgttattgtg atttgccatt tatacattat   1500
ctttttttgaa gtatcttaaa atcttttgtc tgttttaaaa attaggttgt tgtcttaata   1560
ttgagttgtg agatttattt atttcatgta agggctttat catatatata ttttataaat   1620
attctctccc attttatagt ttgtcttttc atttcataat gggaaattgt ccccaaatac   1680
acttttgttg taatctattg taatcagcat tttaatgcat agttagcatt cagtaaaatt   1740
aatcaatttt gactgtacaa tctagtgagt tttgacagct gtataaagca gtttcccacc   1800
accacgaaaa aaaaaaaaaa aaaaa                                          1825
```

<210> SEQ ID NO 136
<211> LENGTH: 96
<212> TYPE: PRT
<213> ORGANISM: Homo sapiens

```
<400> SEQUENCE: 136

Met Lys Leu Thr Val Ser Val Met Tyr Tyr Phe Cys Pro Tyr Leu
 1               5                  10                  15

Val His Cys Lys Leu Tyr Ile Asn Phe Phe Asp Asn Met Tyr Leu Ile
                20                  25                  30

Phe Leu Gln Tyr Gly Phe Gln Val Leu Ala Ile Leu Gln Ile Leu Met
            35                  40                  45

Leu Ile Gln Ile Ser His Leu Ala Gly Ile Leu Leu Ser Val Asn Gln
        50                  55                  60

Asn Tyr Leu Ile Leu Asn Ser His Lys Thr Lys Ala Pro Val Val Ser
 65                 70                  75                  80

Ile Leu Val Leu Leu Thr Asn Leu Arg Arg Cys Asp Leu Gly Asp Phe
                85                  90                  95

<210> SEQ ID NO 137
<211> LENGTH: 1503
<212> TYPE: DNA
<213> ORGANISM: Homo sapiens
<220> FEATURE:
<221> NAME/KEY: unsure
<222> LOCATION: (1193)

<400> SEQUENCE: 137
ccagagtcca gactgacatt acagcgcaag agtttgcaag tgtgtccagc atgcaccaac      60
tgtgcagaac ttggctcggt aactttgcgt ggaaaaataa agtacatttt gaagtatctt    120
gagggttggg tcaattgaga catttctagc attacttaat gacttgcatt gtggtttttc    180
tgcaagcaac tttaatgact tttttttatac cacatggtct cccagtttct agatgaatgc    240
aacatgatga tggtgatgat gacgatgagt ttaatcattg ttcatttatt gcctttaggg    300
ctgagggaaa gggaaggttt gtttttttttt ctccccattt tccccattc tgtctttctt    360
ttggtgactt acaccacatg taatgacgct atgactaatt ctgctcccaa gcccttgtat    420
cttgggcttc attttaggct catgtgtcca gatctgcatg cattgcttgc atttttctgg    480
tatctgaatg ttggttcctt gttccaggaa ttcaacatta atttccaaaa gtatcatggg    540
acttgtgaca atacaagaca tgaatctatg tataaaattt atcggccttt ctcatttacc    600
tgctctagta ttattgtatt gtgtgtgcgt gcgtgtgtga tgtcaggctg ccacgtaaaa    660
cttcagagaa aaatcttaaa agcagaccat ccttttgcat gctctattct aagtagaatg    720
ttcaatgtaa ctgactaaaa ttgcatgtta aagatattta ggtttttttg ttttctttat    780
ttttatttgt tttcagtttc ctgtatattt gcttactgtg ccgttttagt ggttttagga    840
taaaaatgca ctggtgaagc aaatgtagtg ccaacagaag gtgattttcc agttgtaaat    900
gtcatgcagc atttgaaggg actgtgtttt cttaaaaaaa aaatcacagt tacttctaaa    960
ccagatttca tttcttttat tgttttatgt gccaaaccac gaagtgcatt gggcttcaat   1020
ctctgaacac tgtagaccca ttagaagact gttccgattg ttacaaattg tagtgcctga   1080
aaacactctt aagctgatgg tcttaacaaa atgaaagttc tccaaagaca aaacagaaca   1140
attattataa caaataatt atggttgaaa tgtctgtggt tccttggaat atntgcgctc    1200
tttgtgtttt tccatcatta gtgcagttgg aatgaatgtg tataggtcag aggtcttcgt   1260
gttcacattt taaaattagg taaatgacct catctttcaa gcttgaattc atttttaatt   1320
ttaattttat tttatacaat gtgtagacag ttccctgttc tctgcattta gaagtataca   1380
caatataaat ctgttaattc tgtaagtaat ttttataatt atgatgtaac tctatcttat   1440
```

```
ccttaaaaca tttaaaataa acccttttatg tgcaaaaaaa aaaaaaaaaa aaaaaaaaaa    1500
aaa                                                                  1503
```

<210> SEQ ID NO 138
<211> LENGTH: 174
<212> TYPE: PRT
<213> ORGANISM: Homo sapiens

<400> SEQUENCE: 138

```
Met Val Ser Gln Phe Leu Asp Glu Cys Asn Met Met Val Met Met
 1               5                  10                  15

Thr Met Ser Leu Ile Ile Val His Leu Leu Pro Leu Gly Leu Arg Glu
             20                  25                  30

Arg Glu Gly Leu Phe Phe Phe Leu Pro Ile Phe Pro His Ser Val Phe
         35                  40                  45

Leu Leu Val Thr Tyr Thr Thr Cys Asn Asp Ala Met Thr Asn Ser Ala
     50                  55                  60

Pro Lys Pro Leu Tyr Leu Gly Leu His Phe Arg Leu Met Cys Pro Asp
 65                  70                  75                  80

Leu His Ala Leu Leu Ala Phe Phe Trp Tyr Leu Asn Val Gly Ser Leu
                 85                  90                  95

Phe Gln Glu Phe Asn Ile Asn Phe Gln Lys Tyr His Gly Thr Cys Asp
            100                 105                 110

Asn Thr Arg His Glu Ser Met Tyr Lys Ile Tyr Arg Pro Phe Ser Phe
        115                 120                 125

Thr Cys Ser Ser Ile Ile Val Leu Cys Val Arg Ala Cys Val Met Ser
    130                 135                 140

Gly Cys His Val Lys Leu Gln Arg Lys Ile Leu Lys Ala Asp His Pro
145                 150                 155                 160

Phe Ala Cys Ser Ile Leu Ser Arg Met Phe Asn Val Thr Asp
                165                 170
```

<210> SEQ ID NO 139
<211> LENGTH: 1772
<212> TYPE: DNA
<213> ORGANISM: Homo sapiens

<400> SEQUENCE: 139

```
ggttagaatc tattgctagg gagctggtgt gatcctgtgg aggagttaaa acacggtctt      60
tttgtattgc tggaattctt gcactgattc tttctcatct gaaggaggtg ttgctgctta    120
ttttttaatt ttccatcatt tggatgggac ttttttgattt tttcgtcttg tttcacttga    180
gggtatgact gtggtgtatg ttgcgtatga tcatttggct tcatttccag gtgttttcag    240
ggggccaagg ctctgtatga gttccttggt tgtggatagc ttttgtgtgg tggctttctc    300
aaatgctgct tgttgtaaca atgtattggg tgtatgagtc aacacactgt ctcctgcagg    360
gctgagagtg ctgaggtctc aggaagctta tcttgtacac tagtgctatg accttttgac    420
agcaggattt ttatttggtg gtgctatttg gttgccattc cagtaggtgg cacttaagaa    480
taaaaaccag ctcacccttg agtagtctga taatgaatag aggcaacttt cctgactggg    540
gagatccttt tggactgcac tgaggtctct tggggaaggg gtggtgaggg ggaagttgca    600
ctaacttctc aacctgggcc agcaaacatg taatccactt ccctatcaca cctagttgc     660 attgctcatg accttcagtt cttataaaca ttgccctttg actccctgct gcagtgtggg    720
tgtggactgc aggaatgccc ctttgacagc taacaccaaa gtgggctcag tgcagagcct    780
```

-continued

```
cttataccag tccaaagcag ataatattgc acatacgtgc cttgtattgc tgggatgctg      840
ccatactgtg cagaaatggg ccctatacct tgtggaagcc ttgctatggg gatcacttaa      900
tcaggatgca gctaccatga aagcactgaa agtaacctaa aagagagtgg cagtcagcaa      960
gtacacacac atcagccccc agctggagag cctctcctgt gtctgcaaga gtagatgggg     1020
agcaggagat gaccccctgt ccatgtccat ttctgacaca tgtaccttcc cctttagcag     1080
ttggtgccat gcccatgttt ttctttgtcc taagtgggct ttggtgggct gaattcttcc     1140
ctttccctag gggcagccca tactgagtgc tggatctcca gagatgctgc agttccctag     1200
agacctgctg gcccctgtgg ttgtgaaagt caaagctggt tgtggggtac gtttgcaggg     1260
ggtctggtga tgtggcaatt caaaggctga ggttccctgg ggagggcagt gggccacaat     1320
cggtgaacaa ccaatatggc acctgctgtc tcagttcagg cctaagggt  atgcaggcac     1380 ttctgtgtga gttggtacct ggttctctat ccctggaagt tcccagattg ccaccaacag     1440
catttcctgg ggtcatgaga gcacagggac tcctcaaaaa tttggtggtc agcaaattgt     1500
gacaggggta agaggagcag agaagcccta ccctttccgt agggctatgg gtttctcagg     1560
ggttgatctc tgctgcactc ctgctgcttt ccttttctgc actacagctt cattctctgg     1620
actctctgac agatcctggt tgtcttcctt cattttttca ttcagatttt gaccattcac     1680
ctataatttt gatcttattt ctgaggagaa ctggcatctg acatccctag ttagccatct     1740
tgaaaaaaaa aaaaaaaaaa aaaaaaaaaa aa                                   1772
```

<210> SEQ ID NO 140
<211> LENGTH: 90
<212> TYPE: PRT
<213> ORGANISM: Homo sapiens

<400> SEQUENCE: 140

```
Met Thr Phe Ser Ser Tyr Lys His Cys Pro Leu Thr Pro Cys Cys Ser
  1               5                  10                  15

Val Gly Val Asp Cys Arg Asn Ala Pro Leu Thr Ala Asn Thr Lys Val
             20                  25                  30

Gly Ser Val Gln Ser Leu Leu Tyr Gln Ser Lys Ala Asp Asn Ile Ala
         35                  40                  45

His Thr Cys Leu Val Leu Leu Gly Cys Cys His Thr Val Gln Lys Trp
     50                  55                  60

Ala Leu Tyr Leu Val Glu Ala Leu Leu Trp Gly Ser Leu Asn Gln Asp
 65                  70                  75                  80

Ala Ala Thr Met Lys Ala Leu Lys Val Thr
                 85                  90
```

<210> SEQ ID NO 141
<211> LENGTH: 1067
<212> TYPE: DNA
<213> ORGANISM: Homo sapiens

<400> SEQUENCE: 141

```
gaaacatgtt agttgattat acctgaaatg gattatttat ctcatcagca agtattattt       60
gaataaaatg agaaatgctt aagaaaaatt gttgctctat agtaatttgg tttcgaagaa      120
tggaatggta actattttt  cccatcgttc ttttgagaga aggaagtgtg atgactgatg      180
atcttgaaaa gcccatttct gattgcacgt tgactggaat tctttctttg tgtctgtgga     240
ctagcgatgc tgtttgtaaa atgaagattc gggactggtg catatctttt tatctaacta      300
gatgtcagat cttgaaatct gtattctcga agcaattctg ccacttgatc gtattcacag      360
```

```
gggccctggt aggctccttt agaaggacca tttctgttcc tagagcttaa ctagaattca    420
ttcttcactg aaaaaaaaaa aagttactta agaaagcatt tctttcctaa tctcactcaa    480
atctgcagaa ttatttgtaa ttagtaatac aaaatctggc caaaaggaga cttgtaaata    540
gcgtaaagtg gtgtcttatg ctaaacggtg gaatgtatag gcagagaagc tctttgaagt    600
tgtcagatga gctgggctca caagcctgat tcaaacaggc tgtcggtctc ctctcacccc    660
ttaatactgt gcagcccaaa ctcctaggac tcttgaacat ctgagcagtt ttgtgctttg    720
agccactttt tgacaaaaat ggctccattt tccacagcg tggttttctt aaaatagttt    780
aatgttttat agtctcatag tagtagtgtt gctttctaag ctataaccgt cgactttatt    840
cttctactct gaaaaatctt tacttgtttg agtgttttta attttataa agggagcctt     900 aatggattgg ttttcataat ttaatatttt ttgtatttgc tcttgtataa ttgttttaa     960 cggaaagtat taaagaattg agggtggaat tcttagaacc aaagttattc ttaataaaaa   1020
tcaccacatg cttggaccaa aaaaaaaaaa aaaaaaaaa aaaaaa                    1067
```

<210> SEQ ID NO 142
<211> LENGTH: 79
<212> TYPE: PRT
<213> ORGANISM: Homo sapiens

<400> SEQUENCE: 142

```
Met Thr Asp Asp Leu Glu Lys Pro Ile Ser Asp Cys Thr Leu Thr Gly
 1               5                  10                  15

Ile Leu Ser Leu Cys Leu Trp Thr Ser Asp Ala Val Cys Lys Met Lys
            20                  25                  30

Ile Arg Asp Trp Leu Ile Ser Phe Tyr Leu Thr Arg Cys Gln Ile Leu
        35                  40                  45

Lys Ser Val Phe Ser Lys Gln Phe Cys His Leu Ile Val Phe Thr Gly
    50                  55                  60

Ala Leu Val Gly Ser Phe Arg Arg Thr Ile Ser Val Pro Arg Ala
65                  70                  75
```

<210> SEQ ID NO 143
<211> LENGTH: 1415
<212> TYPE: DNA
<213> ORGANISM: Homo sapiens
<220> FEATURE:
<221> NAME/KEY: unsure
<222> LOCATION: (1208)

<400> SEQUENCE: 143

```
gtcaggttca ggcttttaga tgcaaataga tcttttccca tatgttttga attgctaaaa     60
cagaaagagt ggaaagaatt ttgaaacaaa caagacccct gacctactgg atcttcagtc    120
tggcctctac ctgcctcaca ggcactgctc atcccaccta ggcatggctg gatacttgag    180
ccatgctcca gccatgttgg cttctttcag ttcctccagt gccccttgct tcttcctgcc    240
acagggtctt tgcataactt ttccacttg caagtctatt ctcttttcct tcaacctctt     300
ccccatttgc ctaattaact tctctagatc ctctacatct cagttcaaac ttttctttgc    360
accagtcaca ttcgctgacc tctgtgacca ggccaacccc gtaccaaaaa tattcttccg    420
ccaagcattt ccagttatca ccttgcattt cttcctttga tgttttttgat ttatgtctac   480 atccccacc taaccgtaag ctcctagatg aaaaagactt gttctctta acctgctcat      540 tattccccta gcacctccaa gtatagttgg cccatcacac agcaggtgct taataaatat    600
```

```
ttgatgattt ctttaatgag tgagtgaatg aacctgttga tttcattcac cttagtctcc      660
ctcaaatttt ttccaaaaga gttactaata gtgtgaaagc tcttctgatg aagaatgcca      720
ctctgtagtt ttaactcagt aagtaagaaa gaatcataaa actcaactag ggcattgaca      780
aaatgaaagt acagtcaatg accaaaatcg tccctttta attttcttc taggaattta       840 agaaaagaag gcaaatttag caccagtggt ccctgtaagt gagccctagg ccatatctgg      900
atgcttttta ttttaggatc atttccaaac tagttacaat gattttatt tgataaagtg       960 aaattcatcc caatctctag agggatactc agtctctaaa tgtttcaatg gtgccatcat     1020 cttatttta aaagagtca cacttggacc tagatggtat gttaatgaat atataatata        1080
aggtttgaat ttttgtgtaa tttttatatt tagtttaact ttctgtttta aaaggaagt      1140 ctggcatctt gagaattcta agaccgttta ccaaacttat tctgcattga agattggagt     1200
atgagggngt gtgggagctt ggtatcattt agtgttttat gagcaataac atgaatggta     1260
agataatttt aggaagtggt agacagattg gattcacttg gaacacagcc agaaaaatca     1320
ataaatgatt atttactaat tcagaaaaga tgatgattct aagtctttta aaatgcattt     1380
ttaaaaactg ttttccagtt cggcaaaaaa aaaaa                                1415
```

<210> SEQ ID NO 144
<211> LENGTH: 98
<212> TYPE: PRT
<213> ORGANISM: Homo sapiens
<400> SEQUENCE: 144

```
Met Ala Gly Tyr Leu Ser His Ala Pro Ala Met Leu Ala Ser Phe Ser
 1               5                  10                  15

Ser Ser Ser Ala Pro Cys Phe Phe Leu Pro Gln Gly Leu Cys Ile Thr
             20                  25                  30

Phe Ser Thr Cys Lys Ser Ile Leu Phe Ser Phe Asn Leu Phe Pro Ile
         35                  40                  45

Cys Leu Ile Asn Phe Ser Arg Ser Ser Thr Ser Gln Phe Lys Leu Phe
     50                  55                  60

Phe Ala Pro Val Thr Phe Ala Asp Leu Cys Asp Gln Ala Asn Pro Val
 65                  70                  75                  80

Pro Lys Ile Phe Phe Arg Gln Ala Phe Pro Val Ile Thr Leu His Phe
                 85                  90                  95

Phe Leu
```

<210> SEQ ID NO 145
<211> LENGTH: 1118
<212> TYPE: DNA
<213> ORGANISM: Homo sapiens
<400> SEQUENCE: 145

```
ggctctcctc tgggggctag aagatacttg aggcccagct tcatggggag ctccccttg       60 ccccagacgc catgttgcaa acccttgaga aggatcctgg acagaggccc ttgcttttca      120
tctggaattc tgagtgctgc aaccttgcaa ctttggtcca gttagaattg gatcggaagc      180
tagtcaggca gcaggcgagc cccagttact cccagataac ctcctgcatt gctgtggttt      240
ctggagcttt ctgtagggtg ggcagtggga gccagggtag gtggggtagg cccgcccctg      300
cgagtgtctt cggcaccctc ccttccaccc cgccctgcgc gcggtgctct gcgccgacag      360
cccgccaacc tctagccccc aggcccaggc cctggtggag gggagagctg ggagggctga     420
gctggtccag gtggcagagc cactcttgga gccccagctg ggtgggtcc agggcctgtg      480
```

```
ctcctgattc ccatctggag tagcctccca gagctgcttc tgggctggtg gtgtggcagt    540
gccatccttc atgtatttgg gttctctcca cagagggacc atctgtgttc tctccacccc    600
tgtctttgaa aacaaagatg ataccacgct gtacatctta gtctgcaatc tgccatcttc    660
acgtgacagt ctctcaagat ctttatatat gagagacata ttttccttt taatatcttc     720 actgtatctc ttaggagatc tgtgattttt tttttcccaa tccgccatca tttactcaga    780
gtcagcatta aaaaaattta aaatttgtga gaggacaact atgtctgata agcatgtca     840 tggaaggctg ggcacagcag ctcacacctg taatcccagc acttgggag accgaggcag     900 gcagatcatg aggtcaagag atcgagacca tcctggccaa catggtgaaa ccctgtctct    960
actaaaaata caaaaattat ggtggcgggt gcctgtagtt ccagctactc tggaggctga    1020
ggcaggagaa tcgcttaaac ctgggagcca ctgcactcca gcctggcagc aaagcgagac    1080
tctgtctcca aaaaaaaaaa aaaaaaaaa aaaaaaa                              1118
```

<210> SEQ ID NO 146
<211> LENGTH: 143
<212> TYPE: PRT
<213> ORGANISM: Homo sapiens

<400> SEQUENCE: 146

Met Leu Gln Thr Leu Glu Lys Asp Pro Gly Gln Arg Pro Leu Leu Phe
1               5                   10                  15

Ile Trp Asn Ser Glu Cys Cys Asn Leu Ala Thr Leu Val Gln Leu Glu
            20                  25                  30

Leu Asp Arg Lys Leu Val Arg Gln Gln Ala Ser Pro Ser Tyr Ser Gln
        35                  40                  45

Ile Thr Ser Cys Ile Ala Val Val Ser Gly Ala Phe Cys Arg Val Gly
    50                  55                  60

Ser Gly Ser Gln Gly Arg Trp Gly Arg Pro Ala Pro Ser Val Phe
65                  70                  75                  80

Gly Thr Leu Pro Ser Thr Pro Pro Cys Ala Arg Cys Ser Ala Pro Thr
                85                  90                  95

Ala Arg Gln Pro Leu Ser Pro Arg Pro Arg Pro Trp Trp Arg Gly Glu
            100                 105                 110

Leu Gly Gly Leu Ser Trp Ser Arg Trp Gln Ser His Ser Trp Ser Pro
        115                 120                 125

Ser Trp Gly Gly Ser Arg Ala Cys Ala Pro Asp Ser His Leu Glu
    130                 135                 140

<210> SEQ ID NO 147
<211> LENGTH: 1582
<212> TYPE: DNA
<213> ORGANISM: Homo sapiens

<400> SEQUENCE: 147

```
ccagctcctc cgggtgcagg gtccctcctg ctgaccagcc tccagctctt cccagttctg    60
ggctccgcag cgagcggctt gggggcacta cctgacacag gagaccatgt ctgggcagag    120
ggtggctgca ggtggagtct gtggcgtgtg gcgcacaccc aggggctccc ccgatgctgg    180
ttactatctg ggctatggtg gccacagctg tcttgcccct cctcacggcc gtgctgggtg    240
ttaccgtggt cacccgcagg gacacggagg ggccaggcag agcagcccta gttcacctca    300
ccgggagccc ccgccagaag gtgggcacct ctggagggga gggactgcca ggccttgggg    360
cttcctgtgc tgagtcagag ctggaacggg agacgcagga gccccgcagc tgcgggaggt    420
```

-continued

```
gcagatttgg ggctgccagg tggcgccagg tccccttggc cagccccag cgccctttc    480 ttctgtcccc agggcctcgg cttcacagga tggggctgcc agtgtcctgg gcccctcctg    540
ccctctgggt tctagggtgc tgcgcccctgc tcctctcgct gtgggcgctg tgcacagcct    600
gccgcagccg gaggacgctg tagccccag aagagggcg cggaggcagc gggcgaggct    660
gcagggcagt gcgacggcgg cggaagcgca agtcggacac cagactgcac gagctgcacc    720
ggggcccgcg cagcagcaag ggccctgcgg cctgccagca tggatctcct gcgcccacac    780
tggctggagg tgtccaggga catcacggga ccgcaggcag cccccctctg ccttcccaca    840
ccaggagctg ccccgggctc tgccggcagc tgcagccacc gcaggtgcgc tggcctcgag    900
gccacctatt ccaacgtggg gctggcggcc cttcccgggg tcacctggcg ccagccctg    960 tggtggccga gtatgcccgc gtccagaagc gcaagggac ccatcgcatt ccccaagagc    1020
cacagcaggg gaagactgag gtgaccccgg ccgctcaggt ggacgtcctg tactccaggg    1080
tctgcaagcc taaaggagg gacccaggac ccaccacaga cccgctggac cccaagggcc    1140
agggagcgat tctggcctgg cgggtgacct ggcctaccag accctcccgc tcagggccct    1200
ggatgtggac agcggccccc tggaaaacgt gtatgagagc atccgggagc tgggggaccc    1260
tgctggcagg agcagcacgt gcggggctgg gacgccccct gcttccagct gccccagcct    1320 agggagggc tggagacccc tccctgcctc cctgccctga acactcaagg acctgtgctc    1380
cttcctccag agtgaggccc gtccccgcc ccgccccgcc tcacagctga cagcgccagt    1440
cccaggtccc cggctgccag cccgtgaggt ccgtgaggtc ctggccgctc tgacagccgc    1500
ggcctccccg ggctccagag aaggcccgcg tctaaataaa gcgccagcgc aggatgaaaa    1560
aaaaaaaaaa aaaaaaaaaa aa    1582
```

<210> SEQ ID NO 148
<211> LENGTH: 149
<212> TYPE: PRT
<213> ORGANISM: Homo sapiens

<400> SEQUENCE: 148

```
Met Leu Val Thr Ile Trp Ala Met Val Ala Thr Ala Val Leu Pro Leu
 1               5                   10                  15

Leu Thr Ala Val Leu Gly Val Thr Val Thr Arg Arg Asp Thr Glu
            20                  25                  30

Gly Pro Gly Arg Ala Ala Leu Val His Leu Thr Gly Ser Pro Arg Gln
        35                  40                  45

Lys Val Gly Thr Ser Gly Arg Glu Gly Leu Pro Gly Leu Gly Ala Ser
    50                  55                  60

Cys Ala Glu Ser Glu Leu Glu Arg Glu Thr Gln Glu Pro Arg Ser Cys
65                  70                  75                  80

Gly Arg Cys Arg Phe Gly Ala Ala Arg Trp Arg Gln Val Pro Leu Ala
                85                  90                  95

Ser Pro Gln Arg Pro Phe Leu Ser Pro Gly Pro Arg Leu His Arg
            100                 105                 110

Met Gly Leu Pro Val Ser Trp Ala Pro Pro Ala Leu Trp Val Leu Gly
        115                 120                 125

Cys Cys Ala Leu Leu Leu Ser Leu Trp Ala Leu Cys Thr Ala Cys Arg
    130                 135                 140

Ser Arg Arg Thr Leu
145
```

<210> SEQ ID NO 149
<211> LENGTH: 1172
<212> TYPE: DNA
<213> ORGANISM: Homo sapiens

<400> SEQUENCE: 149

```
tttcctgggg agagctaccc gccagcttgg gctgccgtgg gccccctggct gaacaacgtc    60
ctgtgtctgg caggtggctg aggtcctgtg ctctggtgtg tgggtgattg ggcagggcct   120
gagctggaca ggggagctcc tagtagggga ggggagggga tgctgggatc taggtgacat   180
gcctgtccct gtctgctccc gtctgggctg ccagacgtcc ttctcttccc ggataagaag   240
cagaggacct tccagccacc cgcgacaggc acaagcgtt ccacgagcga aggcgcctgg    300
ccacagctgc cctctggcct ctccatgatg aggtgcctcc acaacttcct gacagatggg   360
gtcctgcgga gggggcgttc actgaagact tccaggcct acgggcagag gtggagacca    420
tctccaagga actggagctt ttggacagag agctgtgcca gctgctgctg gagggcctgg   480
agggggtgct gcgggaccag ctggccctgc gagcccttgg acgacgcgct ggagcagggc   540
cagagccttg ggccggtgga gcccctggac ggtccagcag gtgctgtcct ggagtgcctg   600
gtgttgtcct ccggaatgct ggtgccgaaa ctcgctatcc ctgttgtcta cctgctgggg   660
gcactgacca tgctgagtga aacgcagcac aagctgctgg cggaggcgct ggagtcgcag   720
accctgttgg ggccgctcga gctggtgggc agcctcttgg agcagagtgc cccgtggcag   780
gagcgcagca ccatgtccct gccccccggg ctcctgggga cagctgggg cgaaggagca    840
ccggcctggg tcttgctgga cgagtgtggc ctagagctgg gggaggacac tccccacgtg   900
tgctgggagc cgcaggccca gggccgcatg tgtgcactct acgcctccct ggcactgcta   960
tcaggactga gccaggagcc ccactagcct gtgcccgggc atggcctggc agctctccag  1020
cagggcagag tgtttgccca ccagctgcta gccctaggaa ggccaggagc ccagtagcca  1080
tgtggccagt ctaccatggg gcccaggagt tggggaaaca caataaaggt ggcatacgaa  1140
ggaaaaaaaa aaaaaaaaa aaaaaaaaaa aa                                 1172
```

<210> SEQ ID NO 150
<211> LENGTH: 220
<212> TYPE: PRT
<213> ORGANISM: Homo sapiens

<400> SEQUENCE: 150

```
Met Met Arg Cys Leu His Asn Phe Leu Thr Asp Gly Val Leu Arg Arg
  1               5                  10                  15

Gly Arg Ser Leu Lys Thr Ser Arg Ala Tyr Gly Gln Arg Trp Arg Pro
             20                  25                  30

Ser Pro Arg Asn Trp Ser Phe Trp Thr Glu Ser Cys Ala Ser Cys Cys
         35                  40                  45

Trp Arg Ala Trp Arg Gly Cys Cys Gly Thr Ser Trp Pro Cys Glu Pro
     50                  55                  60

Leu Asp Asp Ala Leu Glu Gln Gly Gln Ser Leu Gly Pro Val Glu Pro
 65                  70                  75                  80

Leu Asp Gly Pro Ala Gly Ala Val Leu Glu Cys Leu Val Leu Ser Ser
                 85                  90                  95

Gly Met Leu Val Pro Glu Leu Ala Ile Pro Val Val Tyr Leu Leu Gly
            100                 105                 110

Ala Leu Thr Met Leu Ser Glu Thr Gln His Lys Leu Leu Ala Glu Ala
        115                 120                 125
```

Leu Glu Ser Gln Thr Leu Leu Gly Pro Leu Glu Val Gly Ser Leu
            130                 135                 140

Leu Glu Gln Ser Ala Pro Trp Gln Glu Arg Ser Thr Met Ser Leu Pro
145                 150                 155                 160

Pro Gly Leu Leu Gly Asn Ser Trp Gly Glu Gly Ala Pro Ala Trp Val
                165                 170                 175

Leu Leu Asp Glu Cys Gly Leu Glu Leu Gly Glu Asp Thr Pro His Val
            180                 185                 190

Cys Trp Glu Pro Gln Ala Gln Gly Arg Met Cys Ala Leu Tyr Ala Ser
            195                 200                 205

Leu Ala Leu Leu Ser Gly Leu Ser Gln Glu Pro His
            210                 215                 220

<210> SEQ ID NO 151
<211> LENGTH: 1111
<212> TYPE: DNA
<213> ORGANISM: Homo sapiens

<400> SEQUENCE: 151
attgaattct gccccacatg ttgacagtag agttggaact ggattcttgg gattacttat      60
ctaaaaaact ggagcatcag gtccatttct gttctgctgg tttggaatct tttccgtaat     120
gctatttatt gccaacaatg gcctctcttt gtgtccatat atgccttaca ccgtgctgac     180
ctgggtatca tccatgtgct ctgaagcatc caacttract ttgcaggtgc atcaatgtag     240
tcctgtccct gaactgagta accgtgttcc tgaaaagtac actagggaaa ttcacctgct     300
tgcttgtctt tgtattggca tggcacttgt gattgcacca tggagcatgc tcagagctat     360
taaattggtc tcccatctcc caccaggata tgaaaggtcc atatgggagg ccacgtaatc     420
acttattaca gtggttacat aatacactgg ctcactgcag actctcttgt tttttgatac     480
agtttcgtgc tggcttcatt tgccaattgt gttgtttagt tcggaagtaa gagggtcttg     540
agattgaggg gtagggaggg ctacactgac tgatccgtgg cttaagacag agattatct     600
ctgtactcca gtggcatctc cttagccaag atgtgaaata aaaatcatag ttcgcctcat     660
ttaaaaattc taataaagca ctcaaacttt gaaaagcttt tacttttccc tcctactaaa     720
aaaaatgtat gtacctcata gccctgtgtc atttagtgtt cagcactttt gggaacatca     780
gttggtgaac tttaaaattt gctgtctact cactgggcac ggtggctcac acctgtaatc     840
ccagcacttt gggaggctga ggcaggtgga tcacctgagg tcaggagttt gagaccagcc     900
tgaccaacat ggtgaaaccc cgtctctact aaaaatgcag aaattaggtg gcgcctgta     960
atcccagcta cttgggaggc tgaggcgaga taatcgcttg aacctgggag gcagaggttg    1020
cagtgagccg agattgcacc actgtcgccc accctgggtg ataagagtga aactccttct    1080
caaaaaaaaa aaaaaaaaa aaaaaaaaa a                                    1111

<210> SEQ ID NO 152
<211> LENGTH: 99
<212> TYPE: PRT
<213> ORGANISM: Homo sapiens

<400> SEQUENCE: 152

Met Leu Phe Ile Ala Asn Asn Gly Leu Ser Leu Cys Pro Tyr Met Pro
  1               5                  10                  15

Tyr Thr Val Leu Thr Trp Val Ser Ser Met Cys Ser Glu Ala Ser Asn
                20                  25                  30

```
Phe Thr Leu Gln Val His Gln Cys Ser Pro Val Pro Glu Leu Ser Asn
            35                  40                  45

Arg Val Pro Glu Lys Tyr Thr Arg Glu Ile His Leu Leu Ala Cys Leu
 50                  55                  60

Cys Ile Gly Met Ala Leu Val Ile Ala Pro Trp Ser Met Leu Arg Ala
 65                  70                  75                  80

Ile Lys Leu Val Ser His Leu Pro Pro Gly Tyr Glu Arg Ser Ile Trp
                 85                  90                  95

Glu Ala Thr
```

<210> SEQ ID NO 153
<211> LENGTH: 551
<212> TYPE: DNA
<213> ORGANISM: Homo sapiens

<400> SEQUENCE: 153

```
ggctggcgtt tcccacattt ctctgtggga gggtccttga gaggacacag ggatgaaatg      60
gtgactctgt ccagcaccct tggacagaga agcctatgcc ggagccacct ctcactacag     120
gtcctgagct tggtgctgag gacgcctgga ggaatcacag agcccatctg aacagccca     180
tctcctggct gggttggatc agcctctggt ttcttctcag agcactgaga aggtctggct     240
caaccacctc caagattcat cttgttctgt ggacacagca tctagtgaca caagacaaga     300
gagcaccaaa actctctagg agcacaggaa gtccttcagc tttcaggaat cagaagaggt     360
gtcacagctc tgaagaataa ggacttccac aagcccagga gatgagaagg ggtggaagtt     420
ggagggggcgg gactgggtgg agtggacatt ccaggagctg ggtgaggtaa aaacacggag     480
gcaggaaaat gcggagtgct ttggaaacca taaaaaaaaa aaaaaaaaaa aaaaaaaaa     540
aaaaaaaaaa a                                                          551
```

<210> SEQ ID NO 154
<211> LENGTH: 94
<212> TYPE: PRT
<213> ORGANISM: Homo sapiens

<400> SEQUENCE: 154

```
Met Pro Glu Pro Pro Leu Thr Thr Gly Pro Glu Leu Gly Ala Glu Asp
  1               5                  10                  15

Ala Trp Arg Asn His Arg Ala His Leu Glu Gln Pro Ile Ser Trp Leu
                 20                  25                  30

Gly Trp Ile Ser Leu Trp Phe Leu Leu Arg Ala Leu Arg Arg Ser Gly
             35                  40                  45

Ser Thr Thr Ser Lys Ile His Leu Val Leu Trp Thr Gln His Leu Val
 50                  55                  60

Thr Gln Asp Lys Arg Ala Pro Lys Leu Ser Arg Ser Thr Gly Ser Pro
 65                  70                  75                  80

Ser Ala Phe Arg Asn Gln Lys Arg Cys His Ser Ser Glu Glu
                 85                  90
```

<210> SEQ ID NO 155
<211> LENGTH: 888
<212> TYPE: DNA
<213> ORGANISM: Homo sapiens

<400> SEQUENCE: 155

```
gccgccgccc aggaagggga tgcggaaacc cctggctcgg tggagcggag aggcaggcgg      60
ggtgagggc gttgccaggc aaagggcgag cgccgtggct ggggagccga ggacggcatg     120
```

-continued

```
tcccaggccc cgggagcaca gccgagccca cccaccgtgt accacgaacg gcagcgcctg      180
gagctgtgtg ctgtccacgc cctcaacaac gttctgcagc agcagctctt tagccaggag      240
gctgccgatg agatctgcaa gaggttggcc ccagactccc ggctgaaccc tcatcgcagc      300
ctcctgggca ccggcaacta tgatgtcaat gtgatcatgg ccgctctgca ggggctgggc      360
ctggccgccg tgtggtggga caggaggagg ccctgtccc agctggccct gccccaggta      420
ctggggctga tcctgaacct gccctcgccc gtgtcgctgg gctgctgtc actgccgctg      480 cgccggcgga ctgggtggc cctgcgccag gtggacggtg tctactacaa cctggactcc      540
aagctgcggg cgcccgaggc cctgggggat gaggacggag tcagggcctt cctggcggct      600
gcgctggccc agggcctgtg cgaggtgctg ctggtagtga ccaaggaggt ggaggagaag      660
ggcagctggc tgcggacaga ctgaccatgg ctgaccatcg gcgcccacag cgcagtccct      720 gcgcatccc ctccggtgcg cacactgcat gcctgggaaa ggccagcact tcatggaccc      780
tggggaggcc ccgccccctc cccacacccc tgctccccac tgccgctgct gcctcaataa      840
atctgctgat ttgctgccaa aaaaaaaaaa aaaaaaaaa aaaaaaaa                    888
```

<210> SEQ ID NO 156
<211> LENGTH: 188
<212> TYPE: PRT
<213> ORGANISM: Homo sapiens

<400> SEQUENCE: 156

```
Met Ser Gln Ala Pro Gly Ala Gln Pro Ser Pro Thr Val Tyr His
  1               5                  10                  15

Glu Arg Gln Arg Leu Glu Leu Cys Ala Val His Ala Leu Asn Asn Val
             20                  25                  30

Leu Gln Gln Gln Leu Phe Ser Gln Glu Ala Ala Asp Glu Ile Cys Lys
         35                  40                  45

Arg Leu Ala Pro Asp Ser Arg Leu Asn Pro His Arg Ser Leu Leu Gly
     50                  55                  60

Thr Gly Asn Tyr Asp Val Asn Val Ile Met Ala Ala Leu Gln Gly Leu
 65                  70                  75                  80

Gly Leu Ala Ala Val Trp Trp Asp Arg Arg Arg Pro Leu Ser Gln Leu
                 85                  90                  95

Ala Leu Pro Gln Val Leu Gly Leu Ile Leu Asn Leu Pro Ser Pro Val
            100                 105                 110

Ser Leu Gly Leu Leu Ser Leu Pro Leu Arg Arg Arg His Trp Val Ala
        115                 120                 125

Leu Arg Gln Val Asp Gly Val Tyr Tyr Asn Leu Asp Ser Lys Leu Arg
    130                 135                 140

Ala Pro Glu Ala Leu Gly Asp Glu Asp Gly Val Arg Ala Phe Leu Ala
145                 150                 155                 160

Ala Ala Leu Ala Gln Gly Leu Cys Glu Val Leu Leu Val Val Thr Lys
                165                 170                 175

Glu Val Glu Glu Lys Gly Ser Trp Leu Arg Thr Asp
            180                 185
```

<210> SEQ ID NO 157
<211> LENGTH: 659
<212> TYPE: DNA
<213> ORGANISM: Homo sapiens

<400> SEQUENCE: 157

-continued

```
gaaacactga atatttcaac agcagaaatt gaatgggggg attgatagcg ctggcgaggg      60
aagcagctgg aaagagacag atggcaccct gagacagccc agaggtgaat aggaccccca     120
ggctgcaggg ataaagctca gtggtggtgt tacctcaccg gggaccaggg tcacacagca     180
aagctggaac aacagaggcg tgttgtgggg gagcctcaga ggggacaaaa cctctgcctg     240
agatcccacc ccaggtgggc atgggggcca ctgaggttgg ggatgaaaat gccggtaccg     300
tcagtgcaca gccctgttcc agacagtgct gcctggaaga tttctgggct ctcctgaggc     360
gccaccccgc acctgagcca cctccttgga ctcctgtcct ctacccttg aggacctccc      420 tcccttctac cctagctgtc ttcttgaact tgggactctc ctttcccaag acttccatca     480
ctagctcctg gagggactgg actttgcatc ttcccttcgc gtggagcctc agtgtgagag     540
gccctgccaa tgcgtgcatg tcagaggtgg tggggaccac atcagaagaa gagggggtg      600 atgaaattaa caaataaaaa gtatgggaa acaaaaaaaa aaaaaaaaa aaaaaaaa         659
```

<210> SEQ ID NO 158
<211> LENGTH: 118
<212> TYPE: PRT
<213> ORGANISM: Homo sapiens

<400> SEQUENCE: 158

```
Met Gly Ala Thr Glu Val Gly Asp Glu Asn Ala Gly Thr Val Ser Ala
  1               5                  10                  15

Gln Pro Cys Ser Arg Gln Cys Cys Leu Glu Asp Phe Trp Ala Leu Leu
                 20                  25                  30

Arg Arg His Pro Ala Pro Glu Pro Pro Trp Thr Pro Val Leu Tyr
             35                  40                  45

Pro Leu Arg Thr Ser Leu Pro Ser Thr Leu Ala Val Phe Leu Asn Leu
 50                  55                  60

Gly Leu Ser Phe Pro Lys Thr Ser Ile Thr Ser Ser Trp Arg Asp Trp
 65                  70                  75                  80

Thr Leu His Leu Pro Phe Ala Trp Ser Leu Ser Val Arg Gly Pro Ala
                 85                  90                  95

Asn Ala Cys Met Ser Glu Val Val Gly Thr Thr Ser Glu Glu Glu Gly
            100                 105                 110

Gly Asp Glu Ile Asn Lys
        115
```

<210> SEQ ID NO 159
<211> LENGTH: 550
<212> TYPE: DNA
<213> ORGANISM: Homo sapiens

<400> SEQUENCE: 159

```
ccttgagtct ccgggccgcc ttgccatggc tgcccgtggt gtcatcgctc cagttggcga      60
gagtttgcgc tacgctgagt acttgcagcc ctcggccaaa cggccagacg ccgacgtcga     120
ccagcagaga ctggtaagaa gtttgatagc tgtaggcctg ggtgttgcag ctcttgcatt     180
tgcaggtcgc tacgcatttc ggatctggaa acctctagaa caagttatca cagaaactgc     240
aaagaagatt tcaactccta gcttttcatc ctactataaa ggaggatttg aacagaaaat     300
gagtaggcga gaagctggtc ttatttttagg tgtaagccca tctgctggca aggctaagat     360
tagaacagct cataggagag tcatgatttt gaatcaccca gataaaggtg gatctcctta     420
cgtagcagcc aaaataaatg aagcaaaaga cttgctagaa caaccacca aacattgatg      480 cttaaggacc acactgaagg aaaaaaaaag agggactcc aaaaaaaaaa aaaaaaaaa      540
```
aaaaaaaaaa                                                                                             550

<210> SEQ ID NO 160
<211> LENGTH: 150
<212> TYPE: PRT
<213> ORGANISM: Homo sapiens

<400> SEQUENCE: 160

Met Ala Ala Arg Gly Val Ile Ala Pro Val Gly Glu Ser Leu Arg Tyr
 1               5                  10                  15

Ala Glu Tyr Leu Gln Pro Ser Ala Lys Arg Pro Asp Ala Asp Val Asp
            20                  25                  30

Gln Gln Arg Leu Val Arg Ser Leu Ile Ala Val Gly Leu Gly Val Ala
        35                  40                  45

Ala Leu Ala Phe Ala Gly Arg Tyr Ala Phe Arg Ile Trp Lys Pro Leu
    50                  55                  60

Glu Gln Val Ile Thr Glu Thr Ala Lys Lys Ile Ser Thr Pro Ser Phe
65                  70                  75                  80

Ser Ser Tyr Tyr Lys Gly Gly Phe Glu Gln Lys Met Ser Arg Arg Glu
                85                  90                  95

Ala Gly Leu Ile Leu Gly Val Ser Pro Ser Ala Gly Lys Ala Lys Ile
            100                 105                 110

Arg Thr Ala His Arg Arg Val Met Ile Leu Asn His Pro Asp Lys Gly
        115                 120                 125

Gly Ser Pro Tyr Val Ala Ala Lys Ile Asn Glu Ala Lys Asp Leu Leu
    130                 135                 140

Glu Thr Thr Thr Lys His
145                 150

<210> SEQ ID NO 161
<211> LENGTH: 622
<212> TYPE: DNA
<213> ORGANISM: Homo sapiens

<400> SEQUENCE: 161
ctcacctgtg ctgccacttc ctagtgcaca cctcacggct catcctcaag ctggaagata      60
cctctctggc cccggcacat gtcaccctg cactcctgcc ttcccgtggg cacttccaca     120
tcctctgggc ctctggcagt tcccagggac tgttttcacc tctgctgtct ctggggtcag     180
ctgctgctca tcagctgccc gctagcatgt ggccaggggc gcagggtggc gggggtcag     240
cagcatgtcc ctgggcaggc cctgggcacc ctgtctcccc tggtctcact gctgacctgg     300
gctggtccca gcctggattg gcctcatcca ggatctttgg tcaccccacg ctgccccatc     360
ttgcctgctg ttccagttct ggtcaagggc cttgggggct ggccccccac caggccttct     420
agagcagcac cagtctcagg gccctgggac cagctgccct acttcccagg tttgtagcca     480
ggagaagggg gcatcacaga gctgatggtc aataagggg ggtgtgagcc ccgcagggac     540
tggcccgcac ctgccttgga tgttttcagc aattaaactt ttttaagctg acaaaaaaaa     600
aaaaaaaaa aaaaaaaaaa aa                                              622

<210> SEQ ID NO 162
<211> LENGTH: 132
<212> TYPE: PRT
<213> ORGANISM: Homo sapiens

<400> SEQUENCE: 162

```
Met Ser Pro Leu His Ser Cys Leu Pro Val Gly Thr Thr Ser Ser
1               5                   10                  15

Gly Pro Leu Ala Val Pro Arg Asp Cys Phe His Leu Cys Cys Leu Trp
            20                  25                  30

Gly Gln Leu Leu Leu Ile Ser Cys Pro Leu Ala Cys Gly Gln Gly Cys
            35                  40                  45

Arg Val Ala Gly Gly Gln Gln His Val Pro Gly Gln Ala Leu Gly Thr
        50                  55                  60

Leu Ser Pro Leu Val Ser Leu Leu Thr Trp Ala Gly Pro Ser Leu Asp
65                  70                  75                  80

Trp Pro His Pro Gly Ser Leu Val Thr Pro Arg Cys Pro Ile Leu Pro
                85                  90                  95

Ala Val Pro Val Leu Val Lys Gly Leu Gly Gly Trp Pro Pro Thr Arg
            100                 105                 110

Pro Ser Arg Ala Ala Pro Val Ser Gly Pro Trp Asp Gln Leu Pro Tyr
        115                 120                 125

Phe Pro Gly Leu
        130
```

<210> SEQ ID NO 163
<211> LENGTH: 596
<212> TYPE: DNA
<213> ORGANISM: Homo sapiens

<400> SEQUENCE: 163

```
ctcgcttctc tgcattacac gccggtcagg attcgcgacc cgacatggag cgtccccgca      60
gtccccaatg ctcggccccg gcctctgcct cagcttcggt taccctggcg cagtcctgc     120
agctggtcca gcagggccag gaactcccgg gcctggagaa cgccacatc gcggcgatcc     180
acggcgaacc cacagcgtcc cggctgccgc ggaggcccaa gccctgggag ccgcggcgtt     240
tggctgagtc ccttccccct ccgaccctca ggataggaac ggccccggcg agcctggct     300
tggttgaggc agcgactgcg ccttcttcat ggcatacagt gggcccctga ggttccaggt     360
cctttgcggc ggcgatctgg agggcgtggc tacaggaccc gggatgccat tcagttactc     420
atctttatg ctttcgtcct gacctgtctc aactagactt gctcctgcaa ccaccatggg     480
ggttttgcat ttacatttgt ggaccatgtt acagttaaga aaatcctgt ttcagtcctt     540
atatgtaata aatgtttta tgatggaaaa aaaaaaaaa aaaaaaaaa aaaaaa          596
```

<210> SEQ ID NO 164
<211> LENGTH: 101
<212> TYPE: PRT
<213> ORGANISM: Homo sapiens

<400> SEQUENCE: 164

```
Met Glu Arg Pro Arg Ser Pro Gln Cys Ser Ala Pro Ala Ser Ala Ser
1               5                   10                  15

Ala Ser Val Thr Leu Ala Gln Leu Leu Gln Leu Val Gln Gln Gly Gln
            20                  25                  30

Glu Leu Pro Gly Leu Glu Lys Arg His Ile Ala Ala Ile His Gly Glu
        35                  40                  45

Pro Thr Ala Ser Arg Leu Pro Arg Arg Pro Lys Pro Trp Glu Ala Ala
    50                  55                  60

Ala Leu Ala Glu Ser Leu Pro Pro Thr Leu Arg Ile Gly Thr Ala
65                  70                  75                  80
```

```
Pro Ala Glu Pro Gly Leu Val Glu Ala Ala Thr Ala Pro Ser Ser Trp
             85                  90                  95

His Thr Val Gly Pro
            100

<210> SEQ ID NO 165
<211> LENGTH: 670
<212> TYPE: DNA
<213> ORGANISM: Homo sapiens

<400> SEQUENCE: 165
cttagaaagc ggcggtgagg tcagcttcac attctcagga actctccttc tttgggtctg      60
gctgaagttg aggatctctt actctctagg ccacggaatt aacccgagca ggcatggagg     120
cctctgctct cacctcatca gcagtgacca gtgtggccaa agtggtcagg gtggcctctg     180
gctctgccgt agttttgccc ctggccagga ttgctacagt tgtgattgga ggagttgtgg     240
ctgtgcccat ggtgctcagt gccatgggct tcactgcggg gggaatcgcc tcgtcctcca     300
tagcagccaa gatgatgtcc gcggcggcca ttgccaatgg gggtggagtt gcctcgggca     360
gccttgtggc tactctgcag tcactgggag caactggact ctccggattg accaagttca     420
tcctgggctc cattgggtct gccattgcgg ctgtcattgc gaggttctac tagctccctg     480
cccctcgccc tgcagagaag agaaccatgc caggggagaa ggcacccagc catcctgacc     540
cagcgaggag ccaactatcc caaatatacc tggggtgaaa tataccaaat tctgcatctc     600
cagaggaaaa taagaaataa agatgaattg ttgcaactat aaaaaaaaaa aaaaaaaaa      660 aaaaaaaaaa                                                           670

<210> SEQ ID NO 166
<211> LENGTH: 119
<212> TYPE: PRT
<213> ORGANISM: Homo sapiens

<400> SEQUENCE: 166

Met Glu Ala Ser Ala Leu Thr Ser Ser Ala Val Thr Ser Val Ala Lys
  1               5                  10                  15

Val Val Arg Val Ala Ser Gly Ser Ala Val Val Leu Pro Leu Ala Arg
             20                  25                  30

Ile Ala Thr Val Val Ile Gly Gly Val Val Ala Val Pro Met Val Leu
         35                  40                  45

Ser Ala Met Gly Phe Thr Ala Gly Gly Ile Ala Ser Ser Ser Ile Ala
     50                  55                  60

Ala Lys Met Met Ser Ala Ala Ala Ile Ala Asn Gly Gly Gly Val Ala
 65                  70                  75                  80

Ser Gly Ser Leu Val Ala Thr Leu Gln Ser Leu Gly Ala Thr Gly Leu
                 85                  90                  95

Ser Gly Leu Thr Lys Phe Ile Leu Gly Ser Ile Gly Ser Ala Ile Ala
            100                 105                 110

Ala Val Ile Ala Arg Phe Tyr
        115

<210> SEQ ID NO 167
<211> LENGTH: 850
<212> TYPE: DNA
<213> ORGANISM: Homo sapiens

<400> SEQUENCE: 167
caaacttaca cagtgctttg ggaattccaa agtactcagt ggagagaggt gtttcaggag      60
```

-continued

```
ccgtagagcc agatcgtcat catgtctgca ttgtggctgc tgctgggcct ccttgccctg    120
atggacttgt ctgaaagcag caactgggga tgctatggaa acatccaaag cctggacacc    180
cctggagcat cttgtgggat tggaagacgt cacggcctga actactgtgg agttcgtgct    240
tctgaaaggc tggctgaaat agacatgcca tacctcctga atatcaacc catgatgcaa    300 accattggcc aaaagtactg catggatcct gccgtgatcg ctggtgtctt gtccaggaag    360
tctcccggtg acaaaattct ggtcaacatg ggcgatagga ctagcatggt gcaggaccct    420
ggctctcaag ctcccacatc ctggattagt gagtctcagg tttcccagac aactgaagtt    480
ctgactacta gaatcaaaga aatccagagg aggtttccaa cctggacccc tgaccagtac    540
ctgagaggtg gactctgtgc ctacagtggg ggtgctggct atgtccgaag cagccaggac    600
ctgagctgtg acttctgcaa tgatgtcctt gcacgagcca agtacctcaa gagacatggc    660
ttctaacatc tcagatgaaa cccaagacca tgatcacata tgcagcctca atgttacac    720 agataaaact agccaagggc acctgtaact gggaatctga gtttgaccta aaagtcatta    780
aaataacatg aatcacatta aaggaagaat tttgacctgc aaaaaaaaaa aaaaaaaaaa    840
aaaaaaaaaa                                                          850
```

<210> SEQ ID NO 168
<211> LENGTH: 194
<212> TYPE: PRT
<213> ORGANISM: Homo sapiens

<400> SEQUENCE: 168

```
Met Ser Ala Leu Trp Leu Leu Gly Leu Leu Ala Leu Met Asp Leu
  1               5                  10                  15

Ser Glu Ser Ser Asn Trp Gly Cys Tyr Gly Asn Ile Gln Ser Leu Asp
                 20                  25                  30

Thr Pro Gly Ala Ser Cys Gly Ile Gly Arg Arg His Gly Leu Asn Tyr
             35                  40                  45

Cys Gly Val Arg Ala Ser Glu Arg Leu Ala Glu Ile Asp Met Pro Tyr
         50                  55                  60

Leu Leu Lys Tyr Gln Pro Met Met Gln Thr Ile Gly Gln Lys Tyr Cys
 65                  70                  75                  80

Met Asp Pro Ala Val Ile Ala Gly Val Leu Ser Arg Lys Ser Pro Gly
                 85                  90                  95

Asp Lys Ile Leu Val Asn Met Gly Asp Arg Thr Ser Met Val Gln Asp
            100                 105                 110

Pro Gly Ser Gln Ala Pro Thr Ser Trp Ile Ser Glu Ser Gln Val Ser
        115                 120                 125

Gln Thr Thr Glu Val Leu Thr Thr Arg Ile Lys Glu Ile Gln Arg Arg
    130                 135                 140

Phe Pro Thr Trp Thr Pro Asp Gln Tyr Leu Arg Gly Gly Leu Cys Ala
145                 150                 155                 160

Tyr Ser Gly Gly Ala Gly Tyr Val Arg Ser Ser Gln Asp Leu Ser Cys
                165                 170                 175

Asp Phe Cys Asn Asp Val Leu Ala Arg Ala Lys Tyr Leu Lys Arg His
            180                 185                 190

Gly Phe
```

<210> SEQ ID NO 169
<211> LENGTH: 494
<212> TYPE: DNA

<213> ORGANISM: Homo sapiens

<400> SEQUENCE: 169

```
gccagtgctt ctaattttga cttagtttca tacagtaaag cctaaatgtg aaacgcacac    60
gctggaagat attgttccta tcaatatttt gctttttata acaagggttt gttcatattg   120
atgccatttt tgcaggattt cttcgtgatt tctgtccata tgaaaatgct gacattaaac   180
attaacacat ggagaccgtg ccctgtggcc ctgccgtggc tgccagcatg gtctgtgttt   240
ccttgtggat tcacctgtgg ccctgctgtg gccaccagca tggtctgtgt cctcgtggat   300
tcactgcagc tgtcggatgc gagtttctgt cataatcatt tgtttcctga tacaattgtt   360
cttattcttt tccaaaactg taaaataatc tcctccctca aatgcaaagg ttgttttttgt   420
tctgtttctg ttttctttga aataaaatta taacgttaaa agacaaaaaa aaaaaaaaaa   480
aaaaaaaaaa aaaa                                                     494
```

<210> SEQ ID NO 170
<211> LENGTH: 110
<212> TYPE: PRT
<213> ORGANISM: Homo sapiens

<400> SEQUENCE: 170

```
Met Pro Phe Leu Gln Asp Phe Phe Val Ile Ser Val His Met Lys Met
  1               5                  10                  15
Leu Thr Leu Asn Ile Asn Thr Trp Arg Pro Cys Pro Val Ala Leu Pro
                 20                  25                  30
Trp Leu Pro Ala Trp Ser Val Phe Pro Cys Gly Phe Thr Cys Gly Pro
             35                  40                  45
Ala Val Ala Thr Ser Met Val Cys Val Leu Val Asp Ser Leu Gln Leu
         50                  55                  60
Ser Asp Ala Ser Phe Cys His Asn His Leu Phe Pro Asp Thr Ile Val
 65                  70                  75                  80
Leu Ile Leu Phe Gln Asn Cys Lys Ile Ile Ser Ser Leu Lys Cys Lys
                 85                  90                  95
Gly Cys Phe Cys Ser Val Ser Val Phe Phe Glu Ile Lys Leu
            100                 105                 110
```

<210> SEQ ID NO 171
<211> LENGTH: 2262
<212> TYPE: DNA
<213> ORGANISM: Homo sapiens

<400> SEQUENCE: 171

```
gtgctcagtg ttcacgctat atcccttggg caatgtgggg ttggatgggg cccccacttc    60
cattcccatg gaaggaggcc aggtccccag ccacctccca ctcagccatg cacgcacttg   120
ctgggctggc ctcctgggaa acacaggtga ctcgaatgaa ctctgcattt tcaacgtgcc   180
ttctactgct tcaggacctg ggggtccccc tgaccctcac tggcttgccc ccagccctgg   240
gcctggcccc acctgtcctg gagcccagag cccctggcct ggagctgcct ctctggggtg   300
ggtctcaggc ccacccctc cctcttttga gttcagtgcc ttgctcagcc cctcccatgt   360
atctcagcgt cttcagacct ctgacagagc gacgatgtag ggtctcccgg ggcccaaggt   420
ggtctcaggg tcaggggtgg gatttgcagg gaactcgggg agcccacggg ttgcgccacc   480
tctgccctgg cagctgaagc ctgggagagt ccctgcgtgg tgtaattggc ctcagcccgc   540
tttctctgtg ccgtcgcacc tcagtgtttc tcatagcttg tccccacgtg tcactttcca   600
```

-continued

```
tccacgggaa aaacaaatgc cccttctcca tctatcattg cgacttcctc ccaggaggcc      660
tctcaggttg ggtagagcag gggcctgcag tggtcaggcc aagagcaagg aagacctggc      720
tgccccactg tggctgaaaa ctcaaaacat ctggaactac ccttctccaa ttacgttccc      780
tcttgcttaa agacaaagct aattaaatca tcctgccacc cgaggctcca aaccaaatct      840
tggacgcaaa ttaatgagtt tgataagccc aggttgattg atgagacagt ctggaaccgc      900
caagccatgg agtcggtggc cgtgttcccg gccctggagg aactggccag cagtgaccca      960
catcgatgat gccgagtggg gaccctcacc actgcggtgg tcaagctgct ggctcctca     1020
gtgtcctcgt gctgtaagtc agatgaggtc accttcctct ccatcgatgc caggcttctg     1080
ccgctgacgg ccaatggggc ttggggccag gggcagagaa ccccaacagc aagagagccc     1140
caggtgatgc tggctctcca cgtgcatccg gcacgtttca ctgcagccat catcaacttg     1200
gcaaagtagg caagctcagc ttgtggtttc cattttgcag atgggccccc ggggtcagtg     1260
atgggaagag cagaagagga tgccagccca gcctggccca ggagcaggtg tcgttgtgga     1320
ggaaagctta aactcaacag cctctaccca acatctgcca cctgcatggc cccagatgcc     1380
cccggtgcag gccaggtcaa ggtgggagta aactttcttt gcctccctcc ccacagaagc     1440
accagaccca cttgagcccc agagcctcat gccagcagct cctggctgtt cctcacctga     1500
ggctagagca gcagctgcca gcttatagat ggggcggctg gcaggtgata gaatgggaag     1560
cattggtggg tggtggaggt gggcagtggc accatgacgg gcccctagcc aaacagctgt     1620
cctcaatacg gggcagggag cagccttggc aacaggcaaa ggccagagtc agagtggtgg     1680
ggaggacagg ggctgctgcc ccgctcctgg aaagccactg cagaggggca gtggctggca     1740
gtgccaggcc tgggggaagt ggaagcgtcc tgtctggggg cagattccca agcaaggtga     1800
cccatggtta agggccactg gaaagctgga gagagcttgg gatcccttcc acctggggcc     1860
aatggtgttg attgcagact ggagggtaa cctccgctga gggtcattat gtgccaggca     1920
tggcattggg tactttctgc attgggacca ggcagccggg cctgccattt gaggcagcga     1980
gcctccgtga cctgtcctcc ctcatttgta agtgggggta acagctatgt cactggccag     2040
ttgtggggat taaagtgctg agctatagtg cccagcccaa aatgctcaat aaagctattc     2100
agtgatgaaa aaaaaaaaaa aaaaaaaaaa aaaaaaaaaa aaaaaaaaaa aaaaaaaaaa     2160
aaaaaaaaaa aaaaaaaaaa aaaaaaaaaa aaaaaaaaaa aaaaaaaaaa aaaaaaaaaa     2220
aaaaaaaaaa aaaaaaaaaa aaaaaaaaaa aaaaaaaaaa aa                        2262
```

<210> SEQ ID NO 172
<211> LENGTH: 154
<212> TYPE: PRT
<213> ORGANISM: Homo sapiens

<400> SEQUENCE: 172

```
Met Trp Gly Trp Met Gly Pro Pro Leu Pro Phe Pro Trp Lys Glu Ala
  1               5                  10                  15

Arg Ser Pro Ala Thr Ser His Ser Ala Met His Ala Leu Ala Gly Leu
             20                  25                  30

Ala Ser Trp Glu Thr Gln Val Thr Arg Met Asn Ser Ala Phe Ser Thr
         35                  40                  45

Cys Leu Leu Leu Leu Gln Asp Leu Gly Val Pro Leu Thr Leu Thr Gly
     50                  55                  60

Leu Pro Pro Ala Leu Gly Leu Ala Pro Pro Val Leu Glu Pro Arg Ala
 65                  70                  75                  80
```

```
Pro Gly Leu Glu Leu Pro Leu Trp Gly Ser Gln Ala Pro Pro Leu
            85                  90                  95

Pro Leu Leu Ser Ser Val Pro Cys Ser Ala Pro Pro Met Tyr Leu Ser
            100                 105                 110

Val Phe Arg Pro Leu Thr Glu Arg Arg Cys Arg Val Ser Arg Gly Pro
            115                 120                 125

Arg Trp Ser Gln Gly Gln Gly Trp Asp Leu Gln Gly Thr Arg Gly Ala
        130                 135                 140

His Gly Leu Arg His Leu Cys Pro Gly Ser
145                 150

<210> SEQ ID NO 173
<211> LENGTH: 2538
<212> TYPE: DNA
<213> ORGANISM: Homo sapiens

<400> SEQUENCE: 173
```

| | | | | | |
|---|---|---|---|---|---|
| gaaaagtgga | gatagttcct | gtctcatgga | ttgctagggg | gattaagagg | agtgcctgta | 60 |
| gaacacatag | ctcaggtgct | agtgcacagc | aggtgtgtcc | cagaggtgag | ctgtggttgt | 120 |
| tagtctttgt | gagtggagag | ctgggctagg | tcccaggcct | gactctgtct | gatgttgttt | 180 |
| ctcctctgca | ctgtagtact | ttattcccag | attctgcttt | ttaattcttt | tttggtgtaa | 240 |
| ttacaagaat | aaggactttg | gggtcaaact | gaggcttgag | ctgcagagat | ggaggatgca | 300 |
| ggtctggctg | gtgggcatag | tggtttcccc | tagggctggg | ggaggttggg | gagggaggag | 360 |
| ggtgtgggct | gcctcggtgc | atctctctga | caggtcctgg | ccctgggtca | gtccaagatg | 420 |
| cttgttcagc | ctgtggagtc | cagtaggatg | agggttgtct | gtcgagtggg | tctggaggca | 480 |
| cacccccacc | tcttccctag | ttattgggct | gggagttgct | gtcagactcc | aatatccaga | 540 |
| ggaattacct | tgattcttcc | tcttaaaacc | taagatgcca | ggactaccct | gttccccacg | 600 |
| tccccatgcc | tgcctggccc | tgcagtaatg | tagtggcttc | catctgttga | gtcctgctgt | 660 |
| gagtagacgt | cccatgaggc | catttaattc | tttctacatt | cactccttgc | gcagtgggtg | 720 |
| ttagcatcct | tattttgcag | atgagaaagc | tgaggcctgg | agaagctaaa | tgatgtgccc | 780 |
| ggagttctag | agctggtagg | tgttagctgc | cgacctaccc | gccccttcta | cacaccttgc | 840 |
| cacctgttgg | accttccatc | aaggccttgg | gtccaatgtt | acccactcat | cacagtcaaa | 900 |
| aaacttcctc | ctccagccag | aattaacccg | tccttccttc | attgtctgac | tgctgtttgt | 960 |
| catttatctc | tcatgaaaga | gtcaggtgtt | ccagatgctt | gcgttcattt | ttcccttccc | 1020 |
| catgaaactg | tgggcttctt | ggaagcagga | tatgtcatga | acgcatctct | gacttgctga | 1080 |
| tagaggatag | agcaaaggat | agaaagaaca | cagcaccctg | gcaggatgaa | tctgcccctc | 1140 |
| tccagtcaag | gtgggcttc | ttgggaaagt | tcttgaagca | gatttcagt | acagcaactc | 1200 |
| agagtggctc | tcaattttg | agactcagtt | cccccttta | aaatggggga | atgacccctg | 1260 |
| tctggccaat | tgttaggggc | agatgggatg | aagtatgtag | aattagcctg | aaaactggaa | 1320 |
| tggctgtacc | tgtgtttggc | tggtggttgg | ttggtttatc | catatttatc | ggatgcccgc | 1380 |
| tgtgctccca | gtgttgggtt | ctgccctggg | acaccatgga | gaaccaacag | atggagccct | 1440 |
| tgcctcctcg | gagctcgcag | cctggagggt | cggtgtttgc | aggttccccc | ttcaggctgg | 1500 |
| ccgggtttcc | aggcctctgt | gcggcatcag | caccttatca | tttgctgtct | gtcctaggca | 1560 |
| gactccagtt | ctccagccag | tctcagcctc | atgacctcag | acaatctcac | ccagccttgg | 1620 |
| tctgctgagt | cacagaatgg | aaactggtgc | tcactcccct | ggccagggta | gcatgagaat | 1680 |

```
cagtgaggta gggtggaaaa gggctctcta ggtggctaac aattgggaac tctaggacag    1740
gtcagaactt gagtttgcag accagccctc tacaggacac tggtggacac agagtgttaa    1800
atcctgggct tgaggactgc tttgggcagc ccttttcttg tacctgttgc cgattctggt    1860
ggcttaagct ttcttcttgg agtgaatacc tactcattgt ctcaggcaat acaggccaac    1920
aactttcctc tttcagcaag tctgcagggt gtctcctgtc ccagcttcat acctctccct    1980
ccccactctt cccattccca ctctctccat ggctctggct gctatgcact cagaatacgg    2040
aagagctatt tgctggggtg gggtagagaa aactaaattc ccattgcttg atgttggctg    2100
agcaggtggc actgttggag actcgcctcc tattcctctt tctcctcctc attttttttc    2160
attatcctac agtgatcaat tgagcattgt taggtactgg accaatcatc tttttaaaaa    2220
tgaatcatct taacagccat gcacctgtag tcccagctag tggtgaggct gagacaggag    2280
gattgcttga agccaggagg attgcttgaa gccaggagtt caagaccagc ctgggtaaca    2340
tagtgatact ctgtctttac ttttaaaatt taaaaattag ctaggttgat ggtgtgcacc    2400
tgtagtctca gctactaggg aggctgaggg ggaggatcgc ttgggcccgg gagttcaagg    2460
atgcagtgaa ctgtagtcaa gccactgtac tccagcctgg gtgacagagc aagattccgt    2520
ctcaaaaaaa aaaaaaaa                                                  2538

<210> SEQ ID NO 174
<211> LENGTH: 125
<212> TYPE: PRT
<213> ORGANISM: Homo sapiens

<400> SEQUENCE: 174

Met Thr Pro Val Trp Pro Ile Val Arg Gly Arg Trp Asp Glu Val Cys
 1               5                  10                  15

Arg Ile Ser Leu Lys Thr Gly Met Ala Val Pro Val Phe Gly Trp Trp
            20                  25                  30

Leu Val Gly Leu Ser Ile Phe Ile Gly Cys Pro Leu Cys Ser Gln Cys
        35                  40                  45

Trp Val Leu Pro Trp Asp Thr Met Glu Asn Gln Gln Met Glu Pro Leu
    50                  55                  60

Pro Pro Arg Ser Ser Gln Pro Gly Gly Ser Val Phe Ala Gly Ser Pro
65                  70                  75                  80

Phe Arg Leu Ala Gly Phe Pro Gly Leu Cys Ala Ala Ser Ala Pro Tyr
                85                  90                  95

His Leu Leu Ser Val Leu Gly Arg Leu Gln Phe Ser Ser Gln Ser Gln
            100                 105                 110

Pro His Asp Leu Arg Gln Ser His Pro Ala Leu Val Cys
        115                 120                 125

<210> SEQ ID NO 175
<211> LENGTH: 2371
<212> TYPE: DNA
<213> ORGANISM: Homo sapiens
<220> FEATURE:
<221> NAME/KEY: unsure
<222> LOCATION: (285)

<400> SEQUENCE: 175
tgacttccag gtgaagggat gggaaaagtg gactctcatt gtagtgactc ccaacctacc      60
taataatttg ttaacttagg aatatgctat cattgttgac ttgttcttcc ttaggagaag     120
gacgattttc acccacccctt tctgttctat ggtggactct taacaggtgc tatgtgacca    180
```

-continued

```
ggaatctagc cgggagtagc agaggccctg tcttctgaag tctcaggctt agaagttacc      240
aaagtgggct cagaaactgt catctcctgg ttccaagttc gggcnctggc agcccagccg      300
ctatcttagc tgtctttccc agcggtgcta agagtggtct cagtgagaag gtagatgcca      360
actggagggc cagacctgtg tcctgtccca tgtcctcctt ggtggacgtt tctgtttact      420
cagagctgct agagaccatc ctgcccatcc gagttctgag attgggactg tgatgttggg      480
acctgaggac tggatggtag aatactgggg tcccccagct cttagcagga tgcaggctat      540
tgcttccaca cccctggccg tgagaacgtg gtatgtagga gagttggctg tagctttagg      600
atttctggaa gccaatttgg catggcctat ttgatctctg gcttgtgctc ctgctacact      660
gacagactga ttgcgtggct ctttcagaag acccaggaag ggcagctcca gccagaggac      720
cttcctggct atgcaggtgc acagctctta ggcatcaagc aaagggtcag ccagtcagta      780
gtagtgggag gaagcccttc ctcctcttat gcaagcagct cgcagccagc ccagaatctc      840
ttatgcagcc caagggctt cttgaggtag agagccctcc ccagtgtctt cccaggataa       900
gtagaaatat gatcacagag caacggagca aaagctttcg ggagtgtgag gctgcatctg      960
ctggagcaaa aggaaaccgt gggcttttcc ggccagatac tcttgagctc tgtgaccctg     1020
ctcctgtcac cccaatttct ccaagccaga ggtagctttc tcagagcccc ttggtggttc     1080
tgtcctccaa atgctgctgt gggagcgggc cttccagctc tcagtggcag tgcacctcct     1140
cctaaatgca ggcacttgct aggaagagtg tgagctggcg tcttctgttc accctgccta     1200
gcagttgtca ccattcacaa gtggcattat ttatgttgtg ctgctgtcca gctgctaaga     1260
tcccttcatc tgcacaagcc ctggctagat atgtgtgaat gtgtggcatc atttcacttc     1320
agccgcccaa ttccatctct cctctgcagc cagattcact ggctgatgct cactgctcac     1380
tgtctatccc cacgaaattt agttttatca gtagtcttaa agtgttgatc tcaaacaagt     1440
acattagaaa aatcatgttt cttctctctc atcttacttt ttcttctcag atttctccct     1500
tcctagaaca ttctctctgt ttagcactaa tgttcacctc gtattttttg gaagtgcaaa     1560
aatctcaatt tgtgtctgtt tacagctctc tctcctcact gctcacagca aggggttctg     1620
tatcagtgga tttcattttg tagctgttga gatgttaagg caagcctcag catctgcccc     1680
tgctgggtgc acaatgctgc ttcctcgaag agaagacaca gagtccaagt ggcaggactt     1740
gaggttggct tcccactctg ccttagaagt taattttcca aagtacatta caaatctctg     1800
aggccattag gggaaaagga aggggtgtgg tttgtctttg aaattacagt taatactttt     1860
agacagtaag tccggctggt tgcagggcta tttgccccga cagcatcagc ctgtaacatt     1920
tcttctcttt cctttgtgcc actgagtcgt tccctggcca gaggacataa atggtgctgg     1980
taggaggtta tcagagtaag gaaggtagca gatataggtg cagggtgcct gtcattcact     2040
gtgttatttg gtttaaatca aagtgattct gggggaagct atgctctttc agtggataat     2100
aaaattggta actctattgt aaaacatgtc aatggtgtgt gaagaaaaat caaccaatct     2160
gtaggtgttg ataactagac agtactgtgt atgttacgtg cctgtgtgga tgtgcacttc     2220
cagcatggta tgtgtagcga tgtggatcat gccagagttc gtagatcctg ttttgggtt      2280 tgcacatgga tcgtatgtta agcttttttct tttcaataaa tgaattttat ttttattttc    2340
gaaaaaaaaa aaaaaaaaa aaaaaaaaaa a                                     2371
```

<210> SEQ ID NO 176
<211> LENGTH: 114
<212> TYPE: PRT
<213> ORGANISM: Homo sapiens

<400> SEQUENCE: 176

```
Met Cys Gly Ile Ile Ser Leu Gln Pro Pro Asn Ser Ile Ser Pro Leu
  1               5                  10                  15

Gln Pro Asp Ser Leu Ala Asp Ala His Cys Ser Leu Ser Ile Pro Thr
             20                  25                  30

Lys Phe Ser Phe Ile Ser Ser Leu Lys Val Leu Ile Ser Asn Lys Tyr
         35                  40                  45

Ile Arg Lys Ile Met Phe Leu Leu Ser His Leu Thr Phe Ser Ser Gln
     50                  55                  60

Ile Ser Pro Phe Leu Glu His Ser Leu Cys Leu Ala Leu Met Phe Thr
 65                  70                  75                  80

Ser Tyr Phe Leu Glu Val Gln Lys Ser Gln Phe Val Ser Val Tyr Ser
                 85                  90                  95

Ser Leu Ser Ser Leu Leu Thr Ala Arg Gly Ser Val Ser Val Asp Phe
                100                 105                 110

Ile Leu
```

<210> SEQ ID NO 177
<211> LENGTH: 1665
<212> TYPE: DNA
<213> ORGANISM: Homo sapiens
<220> FEATURE:
<221> NAME/KEY: unsure
<222> LOCATION: (1633)

<400> SEQUENCE: 177

| | |
|---|---:|
| atggcagcgc ccagcaacaa gacagagctg gcctggagtc gcggctggc cgcgtgagta | 60 |
| ggtgattgtc tgacaagcag aggcatgagc tgggtccagg ccaccctact ggcccgaggc | 120 |
| ctctgtaggg cctggggagg cacctgcggg ccgcccctca caggaacctc catctctcag | 180 |
| gtccctcgcc ggctccctcg gggcctccac tgcagcgcag ctgcccatag ctctgaacag | 240 |
| tccctggttc ccagcccacc ggaacccccgg cagaggccca ccaaggctct ggtgcccttt | 300 |
| gaggacctgt ttgggcaggc gcctggtggg gaacgggaca aggcgagctt cctgcagacg | 360 |
| gtgcagaaat ttgcggagca cagcgtgcgt aagcggggcc acattgactt catctacctg | 420 |
| gccctgcgca agatgcggga gtatggtgtc gagcgggacc tggctgtgta caaccagctg | 480 |
| ctcaacatct ccccaagga ggtcttccgg cctcgcaaca tcatccagcg catcttcgtc | 540 |
| cactaccctc ggcagcagga gtgtgggatt gctgtcctgg agcagatgga gaaccacggt | 600 |
| gtgatgccca acaaggagac ggagttcctg ctgattcaga tctttggacg caaaagctac | 660 |
| cccatgctca agttggtgcg cctgaagctg tggttccctc gattcatgaa cgtcaacccc | 720 |
| ttcccagtgc cccgggacct gccccaggac cctgtggagc tggccatgtt tggcctgcgg | 780 |
| cacatggagc tgaccttag tgccagggtc accatctacc aggttccttt gcccaaagac | 840 |
| tcaacaggtg cagcagatcc cccccagccc cacatcgtag gaatccagag tcccgatcag | 900 |
| caggccgccc tggcccggca caatccagcc cggcctgtct tgttgaggg ccccttctcc | 960 |
| ctgtggctcc gcaacaagtg tgtgtattac cacatcctca gagctgactt gctgccccccg | 1020 |
| gaggagaggg aagtggaaga gacgccggag gagtggaacc tctactaccc gatgcagctg | 1080 |
| gacctggagt atgtgaggag tggctgggac aactacgagt ttgacatcaa tgaagtggag | 1140 |
| gaaggccctg tcttcgccat gtgcatggcg ggtgctcatg accaggcgac gatggctaag | 1200 |
| tggatccagg gcctgcagga gaccaaccca accctggccc agatccccgt ggtcttccgc | 1260 |

-continued

```
ctcgccgggt ccacccggga gctccagaca tcctcctgcag ggctggagga gccgcccctg      1320
cccgaggacc accaggaaga agacgacaac ctgcagcgac agcagcaggg ccagagctag      1380
tctgagccgg cgcgagggca cgggctgtgg cccgaggagg cggtggactg aaggcatgag      1440
atgccctttg agtgtacagc aaatcaatgt tttcctgctt ggggctctct tccctcatct      1500
ctagcagtat ggcatcccct ccccaggatc tcgggctgcc agcgatgggc aggcgagacc      1560
cctccagaat ctgcaggcgc ctctggttct ccgaattcaa ataaataggt gcgggagcgc      1620
tgttggttgt gcncgaaaaa aaaaaaaaaa aaaaaaaaaa aaaaa                      1665
```

<210> SEQ ID NO 178
<211> LENGTH: 431
<212> TYPE: PRT
<213> ORGANISM: Homo sapiens

<400> SEQUENCE: 178

```
Met Ser Trp Val Gln Ala Thr Leu Leu Ala Arg Gly Leu Cys Arg Ala
 1               5                  10                  15

Trp Gly Gly Thr Cys Gly Ala Ala Leu Thr Gly Thr Ser Ile Ser Gln
            20                  25                  30

Val Pro Arg Arg Leu Pro Arg Gly Leu His Cys Ser Ala Ala His
        35                  40                  45

Ser Ser Glu Gln Ser Leu Val Pro Ser Pro Glu Pro Arg Gln Arg
    50                  55                  60

Pro Thr Lys Ala Leu Val Pro Phe Glu Asp Leu Phe Gly Gln Ala Pro
65                  70                  75                  80

Gly Gly Glu Arg Asp Lys Ala Ser Phe Leu Gln Thr Val Gln Lys Phe
                85                  90                  95

Ala Glu His Ser Val Arg Lys Arg Gly His Ile Asp Phe Ile Tyr Leu
            100                 105                 110

Ala Leu Arg Lys Met Arg Glu Tyr Gly Val Glu Arg Asp Leu Ala Val
        115                 120                 125

Tyr Asn Gln Leu Leu Asn Ile Phe Pro Lys Glu Val Phe Arg Pro Arg
    130                 135                 140

Asn Ile Ile Gln Arg Ile Phe Val His Tyr Pro Arg Gln Gln Glu Cys
145                 150                 155                 160

Gly Ile Ala Val Leu Glu Gln Met Glu Asn His Gly Val Met Pro Asn
                165                 170                 175

Lys Glu Thr Glu Phe Leu Leu Ile Gln Ile Phe Gly Arg Lys Ser Tyr
            180                 185                 190

Pro Met Leu Lys Leu Val Arg Leu Lys Leu Trp Phe Pro Arg Phe Met
        195                 200                 205

Asn Val Asn Pro Phe Pro Val Pro Arg Asp Leu Pro Gln Asp Pro Val
    210                 215                 220

Glu Leu Ala Met Phe Gly Leu Arg His Met Glu Pro Asp Leu Ser Ala
225                 230                 235                 240

Arg Val Thr Ile Tyr Gln Val Pro Leu Pro Lys Asp Ser Thr Gly Ala
                245                 250                 255

Ala Asp Pro Pro Gln Pro His Ile Val Gly Ile Gln Ser Pro Asp Gln
            260                 265                 270

Gln Ala Ala Leu Ala Arg His Asn Pro Ala Arg Pro Val Phe Val Glu
        275                 280                 285

Gly Pro Phe Ser Leu Trp Leu Arg Asn Lys Cys Val Tyr Tyr His Ile
    290                 295                 300
```

```
Leu Arg Ala Asp Leu Leu Pro Pro Glu Arg Glu Val Glu Glu Thr
305                 310                 315                 320

Pro Glu Glu Trp Asn Leu Tyr Tyr Pro Met Gln Leu Asp Leu Glu Tyr
                325                 330                 335

Val Arg Ser Gly Trp Asp Asn Tyr Glu Phe Asp Ile Asn Glu Val Glu
            340                 345                 350

Glu Gly Pro Val Phe Ala Met Cys Met Ala Gly Ala His Asp Gln Ala
        355                 360                 365

Thr Met Ala Lys Trp Ile Gln Gly Leu Gln Glu Thr Asn Pro Thr Leu
    370                 375                 380

Ala Gln Ile Pro Val Val Phe Arg Leu Ala Gly Ser Thr Arg Glu Leu
385                 390                 395                 400

Gln Thr Ser Ser Ala Gly Leu Glu Glu Pro Pro Leu Pro Glu Asp His
                405                 410                 415

Gln Glu Glu Asp Asp Asn Leu Gln Arg Gln Gln Gly Gln Ser
            420                 425                 430

<210> SEQ ID NO 179
<211> LENGTH: 2080
<212> TYPE: DNA
<213> ORGANISM: Homo sapiens

<400> SEQUENCE: 179
ctccggccgg cgtccagttt gagtctaggt tggagttgga accgtggaga tgcggaagga      60
aaccccaccc ccctagtgc ccccggcggc ccgggagtgg aatcttcccc caaatgcgcc     120
cgcctgcatg gaacggcagt tggaggctgc gcggtaccgg tccgatgggg cgcttctcct     180
cggggcctcc agcctgagtg ggcgctgctg ggccggctcc ctctggcttt ttaaggaccc     240
ctgtgccgcc cccaacgaag gcttctgctc cgccggagtc caaacggagg ctggagtggc     300
tgacctcact tgggttgggg agagaggtat tctagtggcc tccgattcag gtgctgttga     360
attgtgggaa ctagatgaga atgagacact tattgtcagc aagttctgca agtatgagca     420
tgatgacatt gtgtctacag tcagtgtctt gagctctggc acacaagctg tcagtggtag     480
caaagacatc tgcatcaagg tttgggacct tgctcagcag gtggtactga gttcataccg     540
agctcatgct gctcaggtca cttgtgttgc tgcctctcct cacaaggact ctgtgttctc     600
ttcatgcagc gaggacaata gaatttttact ctgggatacc cgctgtccca gccagcatc     660 acagattggc tgcagtgcgc ctggctacct tcctacctcg ctggcttggc atcctcagca     720
aagtgaagtc tttgtctttg gtgatgagaa tgggacagtc tcccttgtgg acaccaagag     780
tacaagctgt gtcctgagct cagctgtaca ctcccagtgt gtcactgggc tggtgttctc     840
cccacacagt gttcccttcc tggcctctct cagtgaagac tgctcacttg ctgtgctgga     900
ctcaagcctt tctgagttgt ttagaagcca agcccacaga cttttgtga gagatgcgac     960 ttggtccccg ctcaatcact ccctgcttac cacagtgggc tgggaccatc aggtcgtcca    1020
ccacgttgtg cccacagaac ctctcccagc ccctggacct gcaagtgtta ctgagtagat    1080
tggatttaag acaaaaagca agtccccat gagtgtccac ttctttgccc tgccctctca    1140
gcttgtgaga caacacagga gccttctata gtatgttgat atgctagatc tgtgccgtta    1200
ataggcatcg tctctcagcc tgagggaggc tggattctgg gttcctgtag tcacagggag    1260
gaaaagcttt cttaaaaatg gacatgtatg tgcgtgtgag tgtgtgtgta gatttatagt    1320
ttttggtagt ggcaggaata aaaaaaatcc atcctacatc ttccctaagc actgcctctc    1380
tctcaccccc caaaacaagt tgacgaaagg gtttttatgta gctgtctatg aggaattggc    1440
```

-continued

```
cgtgtctggg tgggttatgg gatgtgggca tccctgggtt cttggaagca gctcttatgc      1500
tactcataga gatgggattg actttatttt tttatagtgc ttaattcacc attatgagaa      1560
atgcttccag tcacaaaaat gcagcccagc tcactctgag aagaagcag  gacttggtac      1620 ggttttacac aactccttac cattaaactg aatcagaaat ccattttctg gctgaataaa      1680
aagtttggct tgcctgtgta atgcccactc ccttccccct ggctccctag tgatgggaca      1740
tatatgagac agaagtgttt ttctatcata gacaccatag gggaaagttt ggggatgaag      1800
gagagcttaa aggtgtttca attaagttag aaaactgaca caggctgttg agaattcttt      1860 gccactttc ccaccccaaa acagcatggg gcctgacatc ttctgccctg gtccccttc        1920 tcttgatgtg gaaagtctga atgcagtatt tatagacttc taaggtttta aaatccagta      1980
ttcaagaaga aaatcagaaa tactggttgg tgaaataaag agtttaggca ttgttggcct      2040
gtcttttttg aaaaaaaaaa aaaaaaaaaa aaaaaaaaa                              2080
```

<210> SEQ ID NO 180
<211> LENGTH: 342
<212> TYPE: PRT
<213> ORGANISM: Homo sapiens

<400> SEQUENCE: 180

```
Met Arg Lys Glu Thr Pro Pro Leu Val Pro Ala Ala Arg Glu
  1               5                  10                  15

Trp Asn Leu Pro Pro Asn Ala Pro Ala Cys Met Glu Arg Gln Leu Glu
                 20                  25                  30

Ala Ala Arg Tyr Arg Ser Asp Gly Ala Leu Leu Leu Gly Ala Ser Ser
             35                  40                  45

Leu Ser Gly Arg Cys Trp Ala Gly Ser Leu Trp Leu Phe Lys Asp Pro
 50                  55                  60

Cys Ala Ala Pro Asn Glu Gly Phe Cys Ser Ala Gly Val Gln Thr Glu
 65                  70                  75                  80

Ala Gly Val Ala Asp Leu Thr Trp Val Gly Glu Arg Gly Ile Leu Val
                 85                  90                  95

Ala Ser Asp Ser Gly Ala Val Glu Leu Trp Glu Leu Asp Glu Asn Glu
            100                 105                 110

Thr Leu Ile Val Ser Lys Phe Cys Lys Tyr Glu His Asp Asp Ile Val
        115                 120                 125

Ser Thr Val Ser Val Leu Ser Ser Gly Thr Gln Ala Val Ser Gly Ser
    130                 135                 140

Lys Asp Ile Cys Ile Lys Val Trp Asp Leu Ala Gln Gln Val Val Leu
145                 150                 155                 160

Ser Ser Tyr Arg Ala His Ala Ala Gln Val Thr Cys Val Ala Ala Ser
                165                 170                 175

Pro His Lys Asp Ser Val Phe Leu Ser Cys Ser Glu Asp Asn Arg Ile
            180                 185                 190

Leu Leu Trp Asp Thr Arg Cys Pro Lys Pro Ala Ser Gln Ile Gly Cys
        195                 200                 205

Ser Ala Pro Gly Tyr Leu Pro Thr Ser Leu Ala Trp His Pro Gln Gln
    210                 215                 220

Ser Glu Val Phe Val Phe Gly Asp Glu Asn Gly Thr Val Ser Leu Val
225                 230                 235                 240

Asp Thr Lys Ser Thr Ser Cys Val Leu Ser Ser Ala Val His Ser Gln
                245                 250                 255
```

```
Cys Val Thr Gly Leu Val Phe Ser Pro His Ser Val Pro Phe Leu Ala
            260                 265                 270

Ser Leu Ser Glu Asp Cys Ser Leu Ala Val Leu Asp Ser Ser Leu Ser
            275                 280                 285

Glu Leu Phe Arg Ser Gln Ala His Arg Asp Phe Val Arg Asp Ala Thr
            290                 295                 300

Trp Ser Pro Leu Asn His Ser Leu Leu Thr Thr Val Gly Trp Asp His
305                 310                 315                 320

Gln Val Val His His Val Val Pro Thr Glu Pro Leu Pro Ala Pro Gly
                325                 330                 335

Pro Ala Ser Val Thr Glu
            340
```

```
<210> SEQ ID NO 181
<211> LENGTH: 1313
<212> TYPE: DNA
<213> ORGANISM: Homo sapiens
<220> FEATURE:
<221> NAME/KEY: unsure
<222> LOCATION: (1165)

<400> SEQUENCE: 181
tgcttaagca cgaagcttct tttcctgttt agtcctagtg gttagtgtcg aaagaggaat      60
catcgaggtt tcttgatgaa acctagtgcg gtccaacctc tgcctttttt tctgttgtct    120
tttttcctac tccgggctgt tggcggtgtc agcaccgctg ctgggggcgg gggtggaggg    180
gagaaagagt cgggttaccg aagtgcgtca ttcctggctc tagcagggcc tgctcgggag    240
ctgctggtgt ttgttactgt cctcgcagca ctttttctgcc aaccttctct ctctgcgtat    300
tggttaggag caaaagcagg aggcggtctc ctaattctgt ctgtagccta gcgcgttgcg    360
tttaagggta tatctgaact tattttgtta aaaaaaaggc tctgggaagt ggatgcattt    420
gtttaatgac atataattca ggtagtttag gcttgctctc atatactttc cgatgaacag    480
tggggttaat tttcaacatt ttcaaccact taacgttaaa atgcctggtt ttctttctac    540
attgatatca atctataatt agggatcaga aggaccagtt taaggtatat aagtgttcag    600 cagttttttca agtggttgaa ttgcagttttt atgacacatt atgttaaata gtcgattttt    660
tttttttcat tttgaactaa ggtgccacgt taagtaagtt aattgcagat gtttaagttc    720
gttttcatca catttcccta tttgtctttt taggtataat tttaaatatg ccctttgggt    780
ttatggactt cattaaaatt cttaaagatg gttatatctt tgtgtttaac tgaattctta    840
aatttatcac ctaccaaaga attgtgtaag gcgtaaggcg gctgtatagt tacattgttg    900
gattttgact taacatgcta gttttttgata cttttgctat ctttgggtag aagtgtactt    960
agagaacata gtatcttcct cttaattctt tttgaagata ataatgagag gagggagtgg   1020
gtaggaggta ggtgtgaagc agaagtggcc ttgagttgat tattgtagct ggatgaatac   1080
agaagcgctc attgttacta ttattctctc tacttttgtg cgtgctgtta aacatttcca   1140
tagtttaaga taaactttt ttgcnagtag aatttccaga ttgtcttaca gtcttggggg   1200
taatgactta agtttatatt tacatgtcaa aattacttgc ataggaaatt tagccttgtg   1260
taagtgatta cacaatgctt ggcaaaaaaa aaaaaaaaa aaaaaaaaaa aaa            1313
```

```
<210> SEQ ID NO 182
<211> LENGTH: 91
<212> TYPE: PRT
<213> ORGANISM: Homo sapiens
```

<400> SEQUENCE: 182

```
Met Lys Pro Ser Ala Val Gln Pro Leu Pro Phe Phe Leu Leu Ser Phe
1               5                   10                  15
Phe Leu Leu Arg Ala Val Gly Gly Val Ser Thr Ala Ala Gly Gly Gly
            20                  25                  30
Gly Gly Gly Glu Lys Glu Ser Gly Tyr Arg Ser Ala Ser Phe Leu Ala
        35                  40                  45
Leu Ala Gly Pro Ala Arg Glu Leu Leu Val Phe Val Thr Val Leu Ala
    50                  55                  60
Ala Leu Phe Cys Gln Pro Ser Leu Ser Ala Tyr Trp Leu Gly Ala Lys
65                  70                  75                  80
Ala Gly Gly Gly Leu Leu Ile Leu Ser Val Ala
                85                  90
```

<210> SEQ ID NO 183
<211> LENGTH: 1484
<212> TYPE: DNA
<213> ORGANISM: Homo sapiens

<400> SEQUENCE: 183

| | | | | | |
|---|---|---|---|---|---|
| gttttcatct | ctaaaagttg | gatttgggtg | tgtgtttcat | gtcttccatt | tatatatgtt | 60 |
| tttaatgaac | atgcgtaata | taataactac | attcatgtct | tgctaattc | taacatatgt | 120 |
| gccaattctg | gttggttgat | taataaatct | cttcattatg | ggtatttcct | aatatattac | 180 |
| ctgtgttata | attttacatt | ttatgtcaga | cattgtgaat | ttttaccttg | ttgggtgctg | 240 |
| tatattttg | tattcctgta | agtgttacac | tttgttctgt | cacacaatta | agctagtcgg | 300 |
| aaacaatttt | atctttttaa | gatatggtag | atggtttgg | agcagtgctc | agcctagaac | 360 |
| tgatttactt | ttgacttcta | aggcaaggcc | cttttatgca | gtgtatccac | tgctctatgt | 420 |
| atcatgcagc | ttttcagtc | tggctgaggg | aacaggcgtg | ggtgctggcc | cttttgtgca | 480 |
| tcaggccttt | gttatcacag | aactttcatt | tggttctttt | cctggcttcc | tgtcatttct | 540 |
| tcacgtgt | gggttgatca | gtattcacca | gaatacctga | ggagaccagc | ccaggcaaca | 600 |
| tagtgagacc | ccctttctcc | ccattaaaac | agacacaccc | acacacccac | ccacccacac | 660 |
| cccttgccca | aagtcatagt | ttttaggtgg | tatagatgtg | atttgaactt | agatcccggc | 720 |
| tttgataaac | cagtgttttt | taaagcactt | tatgttgcct | gccctgtaca | gcgtctttcc | 780 |
| tcttccttt | gatgagataa | aatactgaaa | gcataactct | gaattacagt | ataaaaatac | 840 |
| acattttggc | ttattagggc | agtgggatgt | ctctgccctc | ttcccccaca | tttcttttat | 900 |
| gttcatgcag | aaaataaaat | ggaaatcctt | tttcttttg | caagaacatg | aattataagc | 960 |
| ttataggaat | catttatcat | ccatgtttaa | aaaattccca | tctctcagct | aaaagactac | 1020 |
| atcatatgac | ttaattctaa | taggtcaact | ctactgaagt | taagagcatt | cccaaagaat | 1080 |
| gctctatata | aaacttgtgt | gtatgtttgc | aggaatctta | atggatatgt | ttctagagga | 1140 |
| aatgctccca | tgagcattct | ctccatcatt | tagcagctgt | taaaatgatg | ctcttcccaa | 1200 |
| tgcccttgtt | ccctcattgt | aaacgtgctc | tgagttaacc | tggtagccag | tacacagtac | 1260 |
| acagtaaatg | acatttctta | tctgtatgtt | agaactacta | ttcaataagc | taaaatattc | 1320 |
| tgagcttcct | cagattttct | ccttttttt | tttttgggac | ggagtcttgc | cctgttgccc | 1380 |
| aggctggagt | gcagtgagct | gagatcacgc | cactacactc | catcctgggt | ggtggagtga | 1440 |
| gaccctgtct | aagcaaaaaa | aaaaaaaaa | aaaaaaaaa | aaaa | | 1484 |

<210> SEQ ID NO 184
<211> LENGTH: 125
<212> TYPE: PRT
<213> ORGANISM: Homo sapiens

<400> SEQUENCE: 184

```
Met Ser Asp Ile Val Asn Phe Tyr Leu Val Gly Cys Cys Ile Phe Leu
  1               5                  10                  15

Tyr Ser Cys Lys Cys Tyr Thr Leu Phe Cys His Thr Ile Lys Leu Val
             20                  25                  30

Gly Asn Asn Phe Ile Phe Leu Arg Tyr Gly Arg Trp Val Trp Ser Ser
         35                  40                  45

Ala Gln Pro Arg Thr Asp Leu Leu Leu Thr Ser Lys Ala Arg Pro Phe
     50                  55                  60

Tyr Ala Val Tyr Pro Leu Leu Tyr Val Ser Cys Ser Phe Phe Ser Leu
 65                  70                  75                  80

Ala Glu Gly Thr Gly Val Gly Ala Gly Pro Phe Val His Gln Ala Phe
                 85                  90                  95

Val Ile Thr Glu Leu Ser Phe Gly Ser Phe Pro Gly Phe Leu Ser Phe
            100                 105                 110

Leu His Thr Cys Gly Leu Ile Ser Ile His Gln Asn Thr
            115                 120                 125
```

<210> SEQ ID NO 185
<211> LENGTH: 2520
<212> TYPE: DNA
<213> ORGANISM: Homo sapiens

<400> SEQUENCE: 185

```
cccgagtgca tctggaatac gcagagtcag taagaccatg gctacgtcct cgatgtctaa    60
gggttgcttt gttttttaagc caaactccaa aaagagaaag atctctctgc caatagagga   120
ctattttaac aaagggaaaa atgagcctga ggacagtaag cttcgattcg aaacttatca   180
gttgatatgg cagcagatga aatctgaaaa tgagcgacta caagaggaat aaataaaaa    240 cttgtttgac aatctgattg aatttctgca aaatcacat tctggattcc agaagaattc    300
aagagacttg ggcggtcaaa taaaactcag agaaattcca actgctgctc ttgttcttgg   360
tgtgaatgtc acagatcatg atttgacatt cggaagtcta acagaggccc ttcagaataa   420
tgtcacacca tatgtagtct cattgcaagc taaagattgt ccagatatga acatttttt    480 gcaaaagttg atctcacagt tgatggactg ctgtgtagat ataaaatcca agagggagga   540
aagtgttcac gtcacccaaa gaaagacaca ttattcaatg gattcacttt ccagttggta   600
tatgactgtc acacagaaga cggacccaaa aatgctaagc aaaaaaagga ctacttctag   660
ccaatggcag tctcctcctg ttgtcgttat cttgaaggat atggaaagct tgccacaaa    720 agtactacaa gacttcataa ttatcagcag tcaacatctc catgaatttc cactaatact   780 cattttttgga atagccacat ctcctattat catccaccga ttgcttcctc atgcagtatc   840
atctctattg tgcatagaac tgttccaatc tttgtcttgt aaggagcacc tgactacggt   900
actcgataag ctacttctta caactcagtt tccctttaaa ataaatgaaa agtattaca    960 ggttctgacc aacatctttt tgtatcatga tttctcagtt caaaacttta taaaggact   1020 tcagctttct ctattagagc atttctattc ccagccctta agtgtcctgt gctgtaatct   1080
tccagaagcc aaaagaagaa taatttttt atcaaataat caatgtgaaa acatccgacg   1140
tctaccatct tttaggaggt acgtggaaaa gcaagcttca gaaaagcaag ttgcgctctt   1200
```

-continued

```
gaccaatgag agatatttga aggaggaaac acaattatta ctagaaaacc tgcatgttta    1260
tcatatgaat tacttcctgg ttttgagatg tcttcataag ttcacctctt ctcttcccaa    1320
gtatccacta ggtcgacaga tcagagagtt gtactgtaca tgtttagaaa agaacatatg    1380
ggattcagag gagtatgcat cagtcttgca gctgctgagg atgttggcaa aggatgaact    1440
gatgaccata cttgagaaat gtttcaaggt ttttaagtct tattgtgaaa accaccttgg    1500
cagcacagct aagagaatag aggagttcct ggcccagttt cagagcctcg atgaaaccaa    1560
agaggaagaa gatgcttctg ggtcacagcc aaagggcttt cagaagacag acctctatca    1620
tcttcagaag tccttattgg aaatgaagga gttaagaaga agtaagaagc aaaccaaatt    1680
tgaagtactc agagaaaatg ttgtgaactt cattgactgt ctagtgagag aatacctcct    1740
gcctcctgag acacagcctc tccatgaggt ggtgtacttc agtgctgccc atgcccttcg    1800
tgagcattta aatgctgctc cgcgaattgc cctccatact gcactcaaca atccttacta    1860
ttatctcaag aatgaagcac tgaaaagcga agaaggctgc attccgaata tcgccccaga    1920
catctgcata gcatacaaac tgcacctaga gtgtagcagg ctcatcaacc tcgtggactg    1980
gtcagaggct tttgcaacag ttgtgacagc tgctgaaaaa atggatgcaa attctgcaac    2040
ctcagaagaa atgaatgaaa ttatccatgc tcggtttatt agagctgttt ctgaactaga    2100
acttttagga tttataaaac ctaccaaaca gaagactgac catgtggcaa gactaacatg    2160
gggaggctgc tagaaagcaa ataagcaaag ccagaactat cacatttagc ttaagagaaa    2220
aaggtgacca gtcatatttta catatattag aggagcctgt tttgttgaga agataaatgt    2280
gtaaccccca ttgatgttta accagaaaag tacattgcta accccaaaca ggcatgtatc    2340
aaaacacctg tggagtactt tagactccaa caaataataa tgtaactaaa actgctcaca    2400
cattttactg tactttccaa agtcattact aaattgtgag taaatcattc ttgaacttag    2460
agtatgtaaa tgtaataaat tccgttatcc aaaaaaaaaa aaaaaaaaaa aaaaaaaaaa    2520
```

<210> SEQ ID NO 186
<211> LENGTH: 711
<212> TYPE: PRT
<213> ORGANISM: Homo sapiens

<400> SEQUENCE: 186

```
Met Ala Thr Ser Ser Met Ser Lys Gly Cys Phe Val Phe Lys Pro Asn
 1               5                  10                  15

Ser Lys Lys Arg Lys Ile Ser Leu Pro Ile Glu Asp Tyr Phe Asn Lys
            20                  25                  30

Gly Lys Asn Glu Pro Glu Asp Ser Lys Leu Arg Phe Glu Thr Tyr Gln
        35                  40                  45

Leu Ile Trp Gln Gln Met Lys Ser Glu Asn Glu Arg Leu Gln Glu Glu
    50                  55                  60

Leu Asn Lys Asn Leu Phe Asp Asn Leu Ile Glu Phe Leu Gln Lys Ser
65                  70                  75                  80

His Ser Gly Phe Gln Lys Asn Ser Arg Asp Leu Gly Gly Gln Ile Lys
                85                  90                  95

Leu Arg Glu Ile Pro Thr Ala Ala Leu Val Leu Gly Val Asn Val Thr
            100                 105                 110

Asp His Asp Leu Thr Phe Gly Ser Leu Thr Glu Ala Leu Gln Asn Asn
        115                 120                 125

Val Thr Pro Tyr Val Val Ser Leu Gln Ala Lys Asp Cys Pro Asp Met
    130                 135                 140
```

-continued

```
Lys His Phe Leu Gln Lys Leu Ile Ser Gln Leu Met Asp Cys Cys Val
145                 150                 155                 160

Asp Ile Lys Ser Lys Glu Glu Ser Val His Val Thr Gln Arg Lys
            165                 170                 175

Thr His Tyr Ser Met Asp Ser Leu Ser Ser Trp Tyr Met Thr Val Thr
                180                 185                 190

Gln Lys Thr Asp Pro Lys Met Leu Ser Lys Arg Thr Thr Ser Ser
            195                 200                 205

Gln Trp Gln Ser Pro Pro Val Val Ile Leu Lys Asp Met Glu Ser
    210                 215                 220

Phe Ala Thr Lys Val Leu Gln Asp Phe Ile Ile Ile Ser Ser Gln His
225                 230                 235                 240

Leu His Glu Phe Pro Leu Ile Leu Ile Phe Gly Ile Ala Thr Ser Pro
                245                 250                 255

Ile Ile Ile His Arg Leu Leu Pro His Ala Val Ser Ser Leu Leu Cys
                260                 265                 270

Ile Glu Leu Phe Gln Ser Leu Ser Cys Lys Glu His Leu Thr Thr Val
                275                 280                 285

Leu Asp Lys Leu Leu Leu Thr Thr Gln Phe Pro Phe Lys Ile Asn Glu
    290                 295                 300

Lys Val Leu Gln Val Leu Thr Asn Ile Phe Leu Tyr His Asp Phe Ser
305                 310                 315                 320

Val Gln Asn Phe Ile Lys Gly Leu Gln Leu Ser Leu Leu Glu His Phe
                325                 330                 335

Tyr Ser Gln Pro Leu Ser Val Leu Cys Cys Asn Leu Pro Glu Ala Lys
                340                 345                 350

Arg Arg Ile Asn Phe Leu Ser Asn Asn Gln Cys Glu Asn Ile Arg Arg
                355                 360                 365

Leu Pro Ser Phe Arg Arg Tyr Val Glu Lys Gln Ala Ser Glu Lys Gln
    370                 375                 380

Val Ala Leu Leu Thr Asn Glu Arg Tyr Leu Lys Glu Thr Gln Leu
385                 390                 395                 400

Leu Leu Glu Asn Leu His Val Tyr His Met Asn Tyr Phe Leu Val Leu
                405                 410                 415

Arg Cys Leu His Lys Phe Thr Ser Ser Leu Pro Lys Tyr Pro Leu Gly
                420                 425                 430

Arg Gln Ile Arg Glu Leu Tyr Cys Thr Cys Leu Glu Lys Asn Ile Trp
    435                 440                 445

Asp Ser Glu Glu Tyr Ala Ser Val Leu Gln Leu Leu Arg Met Leu Ala
450                 455                 460

Lys Asp Glu Leu Met Thr Ile Leu Glu Lys Cys Phe Lys Val Phe Lys
465                 470                 475                 480

Ser Tyr Cys Glu Asn His Leu Gly Ser Thr Ala Lys Arg Ile Glu Glu
                485                 490                 495

Phe Leu Ala Gln Phe Gln Ser Leu Asp Glu Thr Lys Glu Glu Asp
                500                 505                 510

Ala Ser Gly Ser Gln Pro Lys Gly Leu Gln Lys Thr Asp Leu Tyr His
    515                 520                 525

Leu Gln Lys Ser Leu Leu Glu Met Lys Glu Leu Arg Arg Ser Lys Lys
    530                 535                 540

Gln Thr Lys Phe Glu Val Leu Arg Glu Asn Val Val Asn Phe Ile Asp
545                 550                 555                 560

Cys Leu Val Arg Glu Tyr Leu Leu Pro Pro Glu Thr Gln Pro Leu His
```

```
                565                570                575
Glu Val Val Tyr Phe Ser Ala Ala His Ala Leu Arg Glu His Leu Asn
                    580                585                590
Ala Ala Pro Arg Ile Ala Leu His Thr Ala Leu Asn Asn Pro Tyr Tyr
                595                600                605
Tyr Leu Lys Asn Glu Ala Leu Lys Ser Glu Glu Gly Cys Ile Pro Asn
            610                615                620
Ile Ala Pro Asp Ile Cys Ile Ala Tyr Lys Leu His Leu Glu Cys Ser
625                630                635                640
Arg Leu Ile Asn Leu Val Asp Trp Ser Glu Ala Phe Ala Thr Val Val
                    645                650                655
Thr Ala Ala Glu Lys Met Asp Ala Asn Ser Ala Thr Ser Glu Glu Met
                660                665                670
Asn Glu Ile Ile His Ala Arg Phe Ile Arg Ala Val Ser Glu Leu Glu
            675                680                685
Leu Leu Gly Phe Ile Lys Pro Thr Lys Gln Lys Thr Asp His Val Ala
        690                695                700
Arg Leu Thr Trp Gly Gly Cys
705                710

<210> SEQ ID NO 187
<211> LENGTH: 3116
<212> TYPE: DNA
<213> ORGANISM: Homo sapiens

<400> SEQUENCE: 187
gggttctctt gcaatggtta tagaaggctt gaagtacatc tggattcctt atgtgtgcat     60
gttagcagca tttggtgtat gttctcccga actttggatg cacttttca agtggcttcg    120 attaagaact gtacacccaa tattgttggc tcttattctg agcatggccg tgcctactat    180
aataggtctc agcttatgga agagttttt tcccagatta atgacagaat taatggaact    240
acaggaattc tatgacccag atacagtgga acttatgacc tggataaaaa ggcaagctcc    300
agttgcagct gtgttttgcag ggagtccaca gttaatgggt gcgattaaat tatgcactgg    360
atggatggtg acaagtttgc ctctttacaa tgatgatgat cttctcaaga gaaatgaaaa    420
tatctaccaa atctattcaa agcgatctgc tgaggatatt tataaaatac tgacatctta    480
caaagctaat tacctaattg tagaggatgc tatctgcaat gaggtgggac ccatgagagg    540
ctgtagggtt aaagatttat tagacattgc aaatggccac atggtttgtg aagaaggtga    600
caagctaacc tactcaaaat atgggcgatt ttgtcatgag gtcaaaatta actattctcc    660
atatgtgaat tatttcacta gagtatactg aacagatcc tactttgtat ataaaatcaa    720
cactgtgata tccttccagt cttgaaaaat aacagagcct tcatttcaaa gactacctga    780
agtaaaatgc agttttcttc tacctactcg gtgtcttttg cagatcagag tatggacatt    840
cgaaatattg ctgcttcttt cccccttctg ctgttaactg gatccagagt tctgtgggaa    900
atagaagatc aagcattact gtcctttgat taaatgtgat atctaccact ctgcaatatt    960
ccagacaggt gtcttcctta ccgttacatg gtctttaaca cttttactga ttgcaatatt   1020
ttccccataa atcttcatt ctattataat attgatcttg aatttgaata tgtgcaaggt   1080
cagatacatt tctcaaacat aacatttaat aaataatgtg atataattat ttaatagaaa   1140
gaataattcc gaccttcaag caagtttctg aaggtatttt atgatgtata acaactgaag   1200
ttttacaata aaaactaatt taaatgttag ctgaagatat gtggcattta aattaaaatg   1260
```

-continued

```
gaaattatat aaaggaaagt gattttaag gatatacata aagatatatt tagaattttc    1320
atgatactgt tctcctcatc tactgcttat gttaagtgag aactttctta gtaatacata    1380
atgcatgatg ttactgcatt ttctaaatga ctagtaagtg attagttttt tcacttatgc    1440
ctattaattt gataccaatt taatcatgat aaaacaataa ccgttaacat atattttgtt    1500
aaatggacat ttaaaagaat gttgttcagg ttttttttt aaatactgat atggggcata     1560
caatctattc acatgttttc tactgaagta ctaagtaaaa aaattaaatc attatcagaa    1620
taaaaatatg tgttctaaaa ttagcaacaa tttctgggga tacatgcaga tgttgttaaa    1680
cgtacctctg catacagata tattataaaa cacaagcaat gttatttatg aaactgtgat    1740
gcagtcttca acatcaagaa aaatgacaa ctataataaa atttacaaca cagtttcaca    1800
gtctaaatgc tatgttcctt taagtatttt catatttta atcatttatt aagagaaaat    1860
tgtgaaaagt taatttggcc ttatagagag attcaggata gatgtagcct atagatgtgt    1920
cattttaata agttgggata catgtttagt ttttccttat attcctgttc agtgaacaga    1980
ttttcataat tctcacttgt taagtgctg caaaaattgc attttcagta ctctaaatta     2040
ctacattaga agagagcatt tctccattgt ctttattttc tgttatatat gtgttgtaaa    2100
agtacactac attagaaggg agcttttccg ttgtctttat tttctgttat acatgtgttg    2160
ttaaagtaca tgcattctta gactaactct cagatgcttt gctcttttgg agctgaagaa    2220
ttgtttgatg gtgatgtcat atatctgata gattagtttc agtggttctc atttcactt     2280 tatacgtaat ttcttaacta tattaagata gttgcaggca gtgtacctca ggttgactct    2340
gtacatctga atagtgagtc actagtattt tgcttcaagc cttctgaaaa tataaccata    2400
gttacctaag cacacagtga aagtcacat ggtagtactt gtgattagag catgtaaaac     2460
aatgtaattg aaaagtcagc ttccatattt tgtagggga atagaacacc ctacttttta    2520
tctagtgtga aatatttaat cgaattttg ttgatttata ttatgttacc tgtgctgaat     2580
taggtttggt acttgtgttt tgtttgacat attagtaagt tgcttttgct tctttctgtc    2640
aacttatttt ttaaataaaa ttgatctgga aaaattgtta atgggatgtt ttaaataatg    2700 aattttcat ccagcatcag ttgaaaagga aagaaagct tcattatgga aatgacaata     2760
ttgaatatga cagataagtt tatttgcttc tgttttaact gcagttaata gtactagaca    2820
actttaagtg gaaagcattt agttatttc ttcacttatt tgtagagtga acaaatgatt     2880
cacaattcta caagtaattc cacttaggta acttacagtt gttaggtttg acaataaaga    2940
tctactatga gaggagaaga atttatgggt tttgggtgga aggaatttct caagaaata     3000 aaaaatgttc tttgcccttg atactgcaaa aaaaaaaaa aaaaaaaaa aaaaaaaaa      3060 aaaaaaaaa aaaaaaaaa aaaaaaaaa aaaaaaaaa aaaaaaaaa aaaaaa           3116
```

<210> SEQ ID NO 188
<211> LENGTH: 243
<212> TYPE: PRT
<213> ORGANISM: Homo sapiens

<400> SEQUENCE: 188

```
Met Val Ile Glu Gly Leu Lys Tyr Ile Trp Ile Pro Tyr Val Cys Met
  1               5                  10                  15

Leu Ala Ala Phe Gly Val Cys Ser Pro Glu Leu Trp Met Thr Leu Phe
              20                  25                  30

Lys Trp Leu Arg Leu Arg Thr Val His Pro Ile Leu Leu Ala Leu Ile
          35                  40                  45
```

```
Leu Ser Met Ala Val Pro Thr Ile Ile Gly Leu Ser Leu Trp Lys Glu
 50                  55                  60

Phe Phe Pro Arg Leu Met Thr Glu Leu Met Glu Leu Gln Glu Phe Tyr
 65                  70                  75                  80

Asp Pro Asp Thr Val Glu Leu Met Thr Trp Ile Lys Arg Gln Ala Pro
                 85                  90                  95

Val Ala Ala Val Phe Ala Gly Ser Pro Gln Leu Met Gly Ala Ile Lys
                100                 105                 110

Leu Cys Thr Gly Trp Met Val Thr Ser Leu Pro Leu Tyr Asn Asp Asp
                115                 120                 125

Asp Leu Leu Lys Arg Asn Glu Asn Ile Tyr Gln Ile Tyr Ser Lys Arg
130                 135                 140

Ser Ala Glu Asp Ile Tyr Lys Ile Leu Thr Ser Tyr Lys Ala Asn Tyr
145                 150                 155                 160

Leu Ile Val Glu Asp Ala Ile Cys Asn Glu Val Gly Pro Met Arg Gly
                165                 170                 175

Cys Arg Val Lys Asp Leu Leu Asp Ile Ala Asn Gly His Met Val Cys
                180                 185                 190

Glu Glu Gly Asp Lys Leu Thr Tyr Ser Lys Tyr Gly Arg Phe Cys His
                195                 200                 205

Glu Val Lys Ile Asn Tyr Ser Pro Tyr Val Asn Tyr Phe Thr Arg Val
210                 215                 220

Tyr Trp Asn Arg Ser Tyr Phe Val Tyr Lys Ile Asn Thr Val Ile Ser
225                 230                 235                 240

Phe Gln Ser

<210> SEQ ID NO 189
<211> LENGTH: 839
<212> TYPE: DNA
<213> ORGANISM: Homo sapiens

<400> SEQUENCE: 189
ggtatcaggg ccgggagccc tttgggagga agggaggcgt tagaggagct gccttcggag      60
gctcagggag tccctttgga gctggttgtt tccttggccc tgcagcgcac tgctcggggc    120
tcccaaggag gttgtgtgta tggttcttaa ttcatcagga caaagacccc cagcatgtgt    180
gtaccctggg acccgatttc tctgggccca catctatctc aatacctca gcctcagatc     240 agacccttc ttttttgtct ttcttctctt aattttaaa tgcctctttt cttgagcatt      300
ccatctctct ttttgaccct ctcaggactg ggcttagctg tccagagccc tgccggaggg    360
tgctgggggc tgtccctctg caggcactgt gttttcctca ggggctgtcc tcagaacacc    420
cctcctgctc cctgggcgtc tcagggagc catttcagct ggagtctcag gtctcaaaaa     480
caacttctcc aggaggccaa aaaagactg ggttggcttc tggtcctcat gacggctttt     540
atcctcctgg gacactttgg gtatattcat gggcattgtt tccatctgtc ttttctacct    600
gtgccacccc tgccctgatt ccacggctgc ctcaggcagg caggcaagga gctaggccgg    660
tgcccggccc tggcagcaag gggtctttgt gcagttggag atgctgccgt tgtggcagag    720
cgtcctgcag ccccgcttcc atcagcaggc tctggggtgg gggctttgca ggggatgctc    780
tctgatgttt gttccgttgt ttaaataaaa tgcacttatt tttgtttttt tttttgcta    839

<210> SEQ ID NO 190
<211> LENGTH: 112
<212> TYPE: PRT
<213> ORGANISM: Homo sapiens
```

<400> SEQUENCE: 190

Met Pro Leu Phe Leu Ser Ile Pro Ser Leu Phe Leu Thr Leu Ser Gly
1               5                   10                  15

Leu Gly Leu Ala Val Gln Ser Pro Ala Gly Gly Cys Trp Gly Leu Ser
            20                  25                  30

Leu Cys Arg His Cys Val Phe Leu Arg Gly Cys Pro Gln Asn Thr Pro
        35                  40                  45

Pro Ala Pro Trp Gly Ser Ser Gly Ser His Phe Ser Trp Ser Leu Arg
    50                  55                  60

Ser Gln Lys Gln Leu Gln Glu Ala Lys Lys Arg Leu Gly Trp Leu
65                  70                  75                  80

Leu Val Leu Met Thr Ala Phe Ile Leu Leu Gly His Phe Gly Tyr Ile
                85                  90                  95

His Gly His Cys Phe His Leu Ser Phe Leu Pro Val Pro Pro Leu Pro
            100                 105                 110

<210> SEQ ID NO 191
<211> LENGTH: 491
<212> TYPE: DNA
<213> ORGANISM: Homo sapiens

<400> SEQUENCE: 191
gtcagggcca gggccagaga gccggagaga ggagcccccg accgagagcc caggtagagc      60
gcacagaggt gcttcgctcc tgttccagcc ctgtcttctc ccgggtgctg gcccttgagt     120
atttttttga ggagaagcag cccctgcagt tccacgtgtt cgatgccgag gacggagcca     180
ccagccctag cccgtgactg cctccctccg gaccgacact ccctcagcct ctcagtgcct     240
gtcctgaccc tcgtgactcc agtgaccaat gcctccacct cttggaccag gtgtgccccc     300
tgggttctgg acgtgagtgg tgggtcctgc tcctatctct ccaaaccca taccctcaa       360 tgctgtggcc cctcagtgac ttccttgggt gatcctgact ttctagccat taataaagag     420
aactgctcct agcaaaaaaa aaaaaaaaa aaaaaaaaa aaaaaaaaa                    480 aaaaaaaaaa a                                                          491

<210> SEQ ID NO 192
<211> LENGTH: 89
<212> TYPE: PRT
<213> ORGANISM: Homo sapiens
<400> SEQUENCE: 192

Met Pro Arg Thr Glu Pro Pro Ala Leu Ala Arg Asp Cys Leu Pro Pro
1               5                   10                  15

Asp Arg His Ser Leu Ser Leu Ser Val Pro Val Leu Thr Leu Val Thr
            20                  25                  30

Pro Val Thr Asn Ala Ser Thr Ser Trp Thr Arg Cys Ala Pro Trp Val
        35                  40                  45

Leu Asp Val Ser Gly Gly Ser Cys Ser Tyr Leu Ser Lys Pro His Thr
    50                  55                  60

Leu Gln Cys Cys Gly Pro Ser Val Thr Ser Leu Gly Asp Pro Asp Phe
65                  70                  75                  80

Leu Ala Ile Asn Lys Glu Asn Cys Ser
                85

<210> SEQ ID NO 193
<211> LENGTH: 2619
<212> TYPE: DNA

<213> ORGANISM: Homo sapiens

<400> SEQUENCE: 193

```
atcgtgagtg ctcggtaaat atctgtggct ttaatggatg aatgaatgaa tgactacatg    60
gctaaactcc attctagggc aacatctgtg gctgcagtgg atgggccta gtgaatggat   120
atttaacgga tatcgtacta ttcctcatct ccacagggtc aggctgtgcc acatccaccc   180
agccttgcct ggggtcattt atcctacatg tactcagatc acgtgaactg gtgatgggcc   240
acccatgtgc ctgcctggag actcctattc acccttcaga tcaatatccc ccaaataaac   300
tcccagtcac tctggcatcc catgttgctt tgtgatctct gcctctctct agaccatttg   360
gctcctatgc acaggcagct atgtctttt catatttggg tccccaaaat gcacagtgcg   420
gtgcctgcct caaaacaaat gcttttcaat ccgtcaatca atcagttgac atggatcatc   480
ttttctcagc actgatgtat ggactacaac ttgaattcc attaaagctc ctggggtcaa   540
gaaaaaagt gattcaagtt tatttattta ttttttttg agacagagtc tcattctgtc   600
gcccaggctg gagtgcagtg gcacgatctt ggctcactgc aacctctgcc tctgggttc   660
aagtgattct cactcatgcc tcagcctccc aagtagctgg gcaagagcca gcacacccgg   720
gctaatttt gtattttag tagggacggg cttttcgccat gttggccaga ctggtctcga   780
gctcctggct tcaagtgatc tgcccacttc agcctcccaa agtgctggga ttacaggcat   840
ttaatcactg cacccgggtg agccactgca cccggccaag ttcatattct aaaagtgaaa   900
cattaatgct gcattgtgta ttttttggtc aagtgcttca gatgtgtgga aggaatttct   960
ttgtataaat gcaattattc gtcaccatga tgataattat aacgagggtg actgcacaga  1020
actgtgcctc cccagcaagc atgggctggg cagggccggg tattcccttc gctgacttgc  1080
ttcactagtt gactaacaga ccttattccc gggcctgagc tgatgatatc ctgccaatgc  1140
cagcttccca acatggaggg gacgcaagag cgagcgccat gggatcctgg gggaaaagca  1200
gcctgtgttt gctgctgctt tgacagttga ggctctgaga gggactggca acaatggga  1260
aatgaaacat ttgagtggtt gcaaaaaatt ccatgggaaa tcccccctgg tggtatttat  1320
gtgcgacggc tgtgacaagg agagcgcagg gcttcgatt tcaagggttc ctgagcagac  1380
cacaatggcc ttccaagatg gcaatccccg ggaacagctc tctcggccac aaaaggccag  1440
tttgtctgtc cagggaagat ctggcccat gcatcaagtt ggccatgagc tgcagtgtct  1500
tctttggggc atgacccaca tttataggt ctgggcctct gaaccttctg ctcctaagac  1560
agatctatct cagttgtccc tctggttttc ccaggcctca aggacctggg ggctgatggg  1620
ggctgagggg tttccctcgg gctcagcctc catctgcaga actgtgggaa cctcagcctc  1680
catcagaccc ctccccattt tctggtcagc acgtggcctc ctcctgtttc ctccattccc  1740
gttggtaatg gacatttatt taacttttac tccccctcca ttctcattta gaaaagaaag  1800
tgaactgata ttaaccaatc tttgttttgc cttctttaac actaatgcat atgcaaaata  1860
gttaccacta ttgataatat cttattgctg ctgtgatata tgtgtgtata tgtacagatc  1920
tgcttgaagg taagctttat atagattttt agagatactt ggtaaatgag aaaatggaaa  1980
ctgaaagagg ttaaataaac tgcccatgtg tattggtcat gaggtttcag ttgcaaagtg  2040
acaaaatcct gacttagatg aacttaaacc ggatggaaaa tgtacattgt attatttgag  2100
aagcaaggtc tggataagct tcaggcatgg ctggatccag gccctcagtt aagtcttttag  2160
gaatttccct ctctctagct ttttggcttt gcttttccct gtattggttt catgtttaga  2220
ttggctcact tcacctgttt tacatctttc cagagtcaaa tccagccttt ttcctggttg  2280
```

-continued

```
cctccataaa agtcccaggg ttaggtttag tgtgctctga tagattcagc tgcccattgc      2340
tgaagcagtg actctggcaa cagggatgga ctgatctaag tgcccaggtt ccagtcactg      2400
ctgaagccca gccagaccac ctggacacag taagagtgag tggttccccc aaagaaaact      2460
ggggtgctct taccagaaga aggaggaatc gacaaaaaga cctgatgtcc taaactcccg      2520
tgtcacactg tcactaatgg gcaggcagac ccatacagca gctcctctgc atcttcatgc      2580
tgctagagac caccaccacg aaacaaaaaa aaaaaaaa                              2619
```

<210> SEQ ID NO 194
<211> LENGTH: 199
<212> TYPE: PRT
<213> ORGANISM: Homo sapiens

<400> SEQUENCE: 194

```
Met Lys His Leu Ser Gly Cys Lys Lys Phe His Gly Lys Ser Pro Leu
 1               5                  10                  15

Val Val Phe Met Cys Asp Gly Cys Asp Lys Glu Ser Ala Gly Leu Ser
                20                  25                  30

Ile Ser Arg Val Pro Glu Gln Thr Thr Met Ala Phe Gln Asp Gly Asn
            35                  40                  45

Pro Arg Glu Gln Leu Ser Arg Pro Gln Lys Ala Ser Leu Ser Val Gln
        50                  55                  60

Gly Arg Ser Gly Pro Met His Gln Val Gly His Glu Leu Gln Cys Leu
    65                  70                  75                  80

Leu Trp Gly Met Thr His Ile Tyr Arg Val Trp Ala Ser Glu Pro Ser
                85                  90                  95

Ala Pro Lys Thr Asp Leu Ser Gln Leu Ser Leu Trp Phe Ser Gln Ala
               100                 105                 110

Ser Arg Thr Trp Gly Leu Met Gly Ala Glu Gly Phe Pro Ser Gly Ser
           115                 120                 125

Ala Ser Ile Cys Arg Thr Val Gly Thr Ser Ala Ser Ile Arg Pro Leu
       130                 135                 140

Pro Ile Phe Trp Ser Ala Arg Gly Leu Leu Leu Phe Pro Pro Phe Pro
145                 150                 155                 160

Leu Val Met Asp Ile Tyr Leu Thr Phe Thr Pro Pro Pro Phe Ser Phe
                165                 170                 175

Arg Lys Glu Ser Glu Leu Ile Leu Thr Asn Leu Cys Phe Ala Phe Phe
            180                 185                 190

Asn Thr Asn Ala Tyr Ala Lys
        195
```

<210> SEQ ID NO 195
<211> LENGTH: 2874
<212> TYPE: DNA
<213> ORGANISM: Homo sapiens

<400> SEQUENCE: 195

```
gaagaaagca aaagttcaga agagatgtca gtagaaaaca aaataggac cagagatcaa       60 gaagccccag aggatgtaca agtcaggcca gaggatactc cttcagatct cagtgttagt      120
aattccagtg tcatactgga aaacacgatg gaagaccatg ctgctgaggc atccgggaag     180
cctctaggtg aaattagtgt tccactggac agctctttac tttgtacttt gtcctcagaa     240
tctcaccagg aagcagctag taatgagaat gataaaaaac ctggtaacta caaatctatg     300
ttacgaccag aggttggcac cacttcacaa gattcagctc tcttagatca ggaattgtat     360
```

```
aactccttcc atttctggag gactcctctt cctgaaatag atctagacat agagcttgaa    420
cagaactctg ggggaaaacc cagcccagag ggaccagagg aagaatctga gggccctgtg    480
cccagttctc caaacatcac catggccacc agaaaggaac tggaagaaat gatagaaaat    540
ctagagcccc acattgatga tccagatgtt aaagcacaag tggaagtgct gtccgctgca    600
ctacgtgctt ccagcctgga tgcacatgaa gagaccatca gtatagaaaa gagaagtgat    660
ttgcaagatg aactggatat aaatgagcta ccaaattgta aaataaatca agaagattct    720
gtgcctttaa tcagcgatgc tgttgagaat atggactcca ctcttcacta tattcacagc    780
gattcagact tgagcaacaa tagcagtttt agccctgatg aggaaaggag aactaaagta    840
caagatgttg tacctcaggc gttgttagat cagtatttat ctatgactga cccttctcgt    900
gcacagacgg ttgacactga aattgctaag cactgtgcat atagcctccc tggtgtggcc    960
ttgacactcg aagacagaa ttggcactgc ctgagagaga cgtatgagac tctggcctca   1020
gacatgcagt ggaaagttcg acgaactcta gcattctcca ttcacgagct tgcagttatt   1080
cttggagatc aattgacagc tgcagatctg gttccaattt ttaatggatt tttaaaagac   1140
ctcgatgaag tcaggatagg tgttcttaaa cacttgcatg atttttctgaa gcttcttcat   1200 attgacaaaa gaagagaata tctttatcaa cttcaggagt ttttggtgac agataatagt   1260
agaaattggc ggtttcgagc tgaactggct gaacagctga ttttacttct agagttatat   1320
agtcccagag atgtttatga ctatttacgt cccattgctc tgaatctgtg tgcagacaaa   1380
gtttcttctg ttcgttggat ttcctacaag ttggtcagcg agatggtgaa gaagctgcac   1440
gcggcaacac caccaacgtt cggagtggac ctcatcaatg agcttgtgga aactttggc    1500 agatgtccca gtggtctgg tcggcaagcc tttgtctttg tctgccagac tgtcattgag   1560
gatgactgcc ttcccatgga ccagtttgct gtgcatctca tgccgcatct gctaacctta   1620
gcaaatgaca gggttcctaa cgtgcgagtg ctgcttgcaa agacattaag acaaactcta   1680
ctagaaaaag actatttctt ggcctttgcc agctgccacc aggaggctgt ggagcagacc   1740
atcatggctc ttcagatgga ccgtgacagc gatgtcaagt attttgcaag catccaccct   1800
gccagtacca aaatctccga agatgccatg agcacagcgt cctcaaccta ctagaaggct   1860
tgaatctcgg tgtctttcct gcttccatga gagccgaggt tcagtgggca ttcgccacgc   1920
atgtgacctg ggatagcttt cggggagga gagaccttcc tctcctgcgg acttcattgc   1980
aggtgcaagt tgcctacacc caataccagg gatttcaaga gtcaagagaa agtacagtaa   2040
acactattat cttatcttga ctttaagggg aaataatttc tcagaggatt ataattgtca   2100
ccgaagcctt aaatccttct gtcttcctga ctgaatgaaa cttgaattgg cagagcattt   2160
tccttatgga agggatgaga ttcccagaga cctgcattgc tttctcctgg ttttatttaa   2220
caatcgacaa atgaaattct tacagcctga aggcagacgt gtgcccagat gtgaaagaga   2280
ccttcagtat cagccctaac tcttctctcc caggaaggac ttgctgggct ctgtggccag   2340
ctgtccagcc cagccctgtg tgtgaatcgt ttgtgacgtg tgcaaatggg aaaggagggg   2400 ttttttacatc tcctaaagga cctgatgcca acacaagtag gattgactta aactcttaag   2460
cgcagcatat tgctgtacac atttacagaa tggttgctga gtgtctgtgt ctgatttttt   2520
catgctggtc atgacctgaa ggaaatttat tagacgtata atgtatgtct ggtgttttta   2580
acttgatcat gatcagctct gaggtgcaac ttcttcacat actgtacata cctgtgacca   2640
ctcttgggag tgctgcagtc tttaatcatg ctgtttaaac tgttgtggca caagttctct   2700
```

-continued

```
tgtccaaata aaatttatta ataagatcta tagagagaga tatatacact tttgattgtt    2760
ttctagatgt ctaccaataa atgcaatttg tgacctgtat taatgattta aagtggggaa    2820
actagattaa aatatttgtc ttttaaaaaa aaaaaaaaaa aaaaaaaaaa aaaa          2874
```

<210> SEQ ID NO 196
<211> LENGTH: 609
<212> TYPE: PRT
<213> ORGANISM: Homo sapiens

<400> SEQUENCE: 196

```
Met Ser Val Glu Asn Lys Asn Arg Thr Arg Asp Gln Glu Ala Pro Glu
  1               5                  10                  15

Asp Val Gln Val Arg Pro Glu Asp Thr Pro Ser Asp Leu Ser Val Ser
             20                  25                  30

Asn Ser Ser Val Ile Leu Glu Asn Thr Met Glu Asp His Ala Ala Glu
         35                  40                  45

Ala Ser Gly Lys Pro Leu Gly Glu Ile Ser Val Pro Leu Asp Ser Ser
     50                  55                  60

Leu Leu Cys Thr Leu Ser Ser Glu Ser His Gln Glu Ala Ala Ser Asn
 65                  70                  75                  80

Glu Asn Asp Lys Lys Pro Gly Asn Tyr Lys Ser Met Leu Arg Pro Glu
                 85                  90                  95

Val Gly Thr Thr Ser Gln Asp Ser Ala Leu Leu Asp Gln Glu Leu Tyr
            100                 105                 110

Asn Ser Phe His Phe Trp Arg Thr Pro Leu Pro Glu Ile Asp Leu Asp
        115                 120                 125

Ile Glu Leu Glu Gln Asn Ser Gly Gly Lys Pro Ser Pro Glu Gly Pro
    130                 135                 140

Glu Glu Glu Ser Glu Gly Pro Val Pro Ser Ser Pro Asn Ile Thr Met
145                 150                 155                 160

Ala Thr Arg Lys Glu Leu Glu Glu Met Ile Glu Asn Leu Glu Pro His
                165                 170                 175

Ile Asp Asp Pro Asp Val Lys Ala Gln Val Glu Val Leu Ser Ala Ala
            180                 185                 190

Leu Arg Ala Ser Ser Leu Asp Ala His Glu Glu Thr Ile Ser Ile Glu
        195                 200                 205

Lys Arg Ser Asp Leu Gln Asp Glu Leu Asp Ile Asn Glu Leu Pro Asn
    210                 215                 220

Cys Lys Ile Asn Gln Glu Asp Ser Val Pro Leu Ile Ser Asp Ala Val
225                 230                 235                 240

Glu Asn Met Asp Ser Thr Leu His Tyr Ile His Ser Asp Ser Asp Leu
                245                 250                 255

Ser Asn Asn Ser Ser Phe Ser Pro Asp Glu Glu Arg Arg Thr Lys Val
            260                 265                 270

Gln Asp Val Val Pro Gln Ala Leu Leu Asp Gln Tyr Leu Ser Met Thr
        275                 280                 285

Asp Pro Ser Arg Ala Gln Thr Val Asp Thr Glu Ile Ala Lys His Cys
    290                 295                 300

Ala Tyr Ser Leu Pro Gly Val Ala Leu Thr Leu Gly Arg Gln Asn Trp
305                 310                 315                 320

His Cys Leu Arg Glu Thr Tyr Glu Thr Leu Ala Ser Asp Met Gln Trp
                325                 330                 335

Lys Val Arg Arg Thr Leu Ala Phe Ser Ile His Glu Leu Ala Val Ile
            340                 345                 350
```

-continued

```
Leu Gly Asp Gln Leu Thr Ala Ala Asp Leu Val Pro Ile Phe Asn Gly
            355                 360                 365
Phe Leu Lys Asp Leu Asp Glu Val Arg Ile Gly Val Leu Lys His Leu
        370                 375                 380
His Asp Phe Leu Lys Leu Leu His Ile Asp Lys Arg Arg Glu Tyr Leu
385                 390                 395                 400
Tyr Gln Leu Gln Glu Phe Leu Val Thr Asp Asn Ser Arg Asn Trp Arg
                405                 410                 415
Phe Arg Ala Glu Leu Ala Glu Gln Leu Ile Leu Leu Glu Leu Tyr
            420                 425                 430
Ser Pro Arg Asp Val Tyr Asp Tyr Leu Arg Pro Ile Ala Leu Asn Leu
        435                 440                 445
Cys Ala Asp Lys Val Ser Ser Val Arg Trp Ile Ser Tyr Lys Leu Val
    450                 455                 460
Ser Glu Met Val Lys Lys Leu His Ala Ala Thr Pro Pro Thr Phe Gly
465                 470                 475                 480
Val Asp Leu Ile Asn Glu Leu Val Glu Asn Phe Gly Arg Cys Pro Lys
                485                 490                 495
Trp Ser Gly Arg Gln Ala Phe Val Phe Val Cys Gln Thr Val Ile Glu
            500                 505                 510
Asp Asp Cys Leu Pro Met Asp Gln Phe Ala Val His Leu Met Pro His
        515                 520                 525
Leu Leu Thr Leu Ala Asn Asp Arg Val Pro Asn Val Arg Val Leu Leu
    530                 535                 540
Ala Lys Thr Leu Arg Gln Thr Leu Leu Glu Lys Asp Tyr Phe Leu Ala
545                 550                 555                 560
Phe Ala Ser Cys His Gln Glu Ala Val Glu Gln Thr Ile Met Ala Leu
                565                 570                 575
Gln Met Asp Arg Asp Ser Asp Val Lys Tyr Phe Ala Ser Ile His Pro
            580                 585                 590
Ala Ser Thr Lys Ile Ser Glu Asp Ala Met Ser Thr Ala Ser Ser Thr
        595                 600                 605
Tyr
```

<210> SEQ ID NO 197
<211> LENGTH: 2029
<212> TYPE: DNA
<213> ORGANISM: Homo sapiens

<400> SEQUENCE: 197

```
agcagccgaa tcttgagact gtcaatgaca gaaagctgaa gagaggcctc tatttcttcc      60
ttttcctttt cttctgtcta aaaactctct cttgttcccc ttttccagct tcccttggac     120
tactgcccca atggcccctt ggactcgcgt ttcatgtatg cgagcacaca cacacacaaa     180
cttgcaaaat accgttttc ttaaggattg tgggaccgaa taatatcacg tgccttcatc      240
ttttcctttt atagttagat gaacctcttc ctctttacaa ttttttttaaa aagtgatagg    300
ggaggttgat gtgttagtgg aagatttggg catcgtttga gaagtaactt tgtttaaca     360
cattccccct aaacattgaa cacaaacatt tcaaccccctt catgcactc tttggacatt    420
taaagcattg agtaaccatg tacatgacag cctaaatccg tttgatttca gagcatttcc    480
tgaacattgt atttcataga cttctctgat tttttcaaaa atgaggtgag caatggcaag    540
cagccttgtt ctcccaattt ggtgcttttg cttttggtgt ggggtgggca tgggggttg    600
```

-continued

| | |
|---|---|
| ggggtggtgt gggtgtgttt agaaaaaaga tgcattcctg aagatctctg gtgctgaagg | 660 |
| gcctcgagtt cctttcagag actgtatttg acacacttta ggtacacaca aacgaatggt | 720 |
| atcacatgca atattttaat ggagcaatgg gagaggctct ttgaaatggg gtttgcatct | 780 |
| ttttgtaaca ttatgatttc tctggtgcct tattcctact tgatgctggc actcacatac | 840 |
| ccacaagaag ctgacacaga agtcagcctt aggcgtgggg acatatgggt gatgtttgag | 900 |
| catgcagggg ccatggggag tttggtgtca gatggtggag aagggactag atggcatctc | 960 |
| ttagccgagg ccaacaggaa ctgcacaagt ccattatagt caaagttagc aattttgata | 1020 |
| cgtaaacaca atacttcatt cttcctcatc tgagctttcc ttccttcttc cttttctatc | 1080 |
| tctaccttct cataaaggtg ctgctgctgc tgctaaggtg cccggagtcc agaatgtcca | 1140 |
| ttaatcactc aggcacgagc ctggcactgc cacgtcagcc cccagcatga ccaaacccag | 1200 |
| gtttctcttg cttggggctg agaactgtca gattttttctc atcaaaaatg ttttccaagg | 1260 |
| aatcagtgga ttacagtttt tctgcattga aaatgcactt taaaaaataa attaaagctc | 1320 |
| cagactgttt aaaatataca gagggagcag gggaaagtta agcatgtgct agtgtctgaa | 1380 |
| cccagttcag tttatctcca gttgaaacga tatacactat attatgtata aatgtataca | 1440 |
| cacttcctat atgtatccac atatatatag tgtatatatt atacatgtat aggtgtgtat | 1500 |
| atgtgcatat atacacacat gcacataaca aaatcagatg ctcattacaa atccagatgc | 1560 |
| tcattacaaa accagatgct acacaaacag cagcagagga acaaggttg gactcttgca | 1620 |
| acagatcaca aaaataaaa acagctactt gcagtgactt tggtcatttc tgtatgttca | 1680 |
| taaagaatgg attgtaacaa ggaaaaaaag gaacagtgtt agtgaaaaag gaaaaatggg | 1740 |
| cgaaaccatc ttgatccgat gcgaatgcag taatgttcta tataccatt catcagttat | 1800 |
| ttcttttagt catgttgatt tgatttcagt ttctggctat gaaaaacatt tttaaactcg | 1860 |
| tcacccacaa caaactgaac aaaactacta cagtgaaagc ccttttcagt gaagatgtc | 1920 |
| agaaacctca aaacctttgg cctgactcag aactaccatg tgaaaatcag tactctctta | 1980 |
| atgtttgaaa taaaaactga aaaaaaaaaa aaaaaaaaa aaaaaaaaa | 2029 |

<210> SEQ ID NO 198
<211> LENGTH: 86
<212> TYPE: PRT
<213> ORGANISM: Homo sapiens

<400> SEQUENCE: 198

Met Glu Gln Trp Glu Arg Leu Phe Glu Met Gly Phe Ala Ser Phe Cys
1               5                   10                  15

Asn Ile Met Ile Ser Leu Val Pro Tyr Ser Tyr Leu Met Leu Ala Leu
            20                  25                  30

Thr Tyr Pro Gln Glu Ala Asp Thr Glu Val Ser Leu Arg Arg Gly Asp
        35                  40                  45

Ile Trp Val Met Phe Glu His Ala Gly Ala Met Gly Ser Leu Val Ser
    50                  55                  60

Asp Gly Gly Glu Gly Thr Arg Trp His Leu Leu Ala Glu Ala Asn Arg
65                  70                  75                  80

Asn Cys Thr Ser Pro Leu
                85

<210> SEQ ID NO 199
<211> LENGTH: 2304
<212> TYPE: DNA
<213> ORGANISM: Homo sapiens

```
<400> SEQUENCE: 199
cagggtctgg ccactgcaca gccaggcacg ctggctgctg tggcagggtg ggaagctcca      60
tatgccagct ccctttgagg ctgcggctgg accagatgtg ccacaagtgg cttccactgt     120
gggcaccagc gtctggataa agggaatgtg gtggtgcccg aaagctcaga gacaccagga     180
actgcagagt ccccaaatag gtgttacagc atgtcacagc catggctcag ggagcaccaa     240
ggtctgggct tccagaaggg ctgcagtctc tctctacttc ttgttatcta cagtgtggtg     300
agtgggggga catgtttcag cccatttgtg ttacagctct ttcagtccca ccaccttgct     360
ctggcccgtg gctcatgggc tggaccagcc ccactgctgc ttcccatcat gtggggtggc     420
cactcagcac cagcagaggg tgggagggct atagtgttaa cagcagctcc agctctgagg     480
tctgggcccc cagaagggtt gccatccttt actcccatag cccaggagca tgtcaccacc     540
cacagctcag cgagctggtc aagaacatgt tacagctcct ttcacttccg ccgttcagca     600
ggtcctgagt tcttgtcccg tgtctaggaa gaatgaggtt atgcagacaa ctgggtgaac     660
aaggcaggca ggagctttat tgagtgacag aacagctgtc aggagaccca aagtgggtag     720
ctccttttcta caggtggtcc agacaagtgt cttaggctgg ctgagtctgg ggttttttaag    780
ggctcagaag ggaggaaggg catgctgatt ggtccatagg tggtcatagg caggcctgga     840
aaaagcacca tctgattggc aaaaggcatc agtgaagttc tcactccagg ttgcggactc     900
cacctggaac ggacagctga gcccccaggc ttcaggccat ccctggctta aggtagggt      960
ttcactagag acccacccct tcctgcctag gaacctgtct gcctcccact gccatcaaca    1020
tgccatccat ggcacccagg ctatctgcac tgaggggcac ccacatgccc acgctcagct    1080
gccctcaatg cccccagcct ccctcccaca ctcatcactg cccgaagtcc agaaagggct    1140
gaggcagcag ggtgctgggt ctgccacaac tttgcttcgc actggagcgg gcacttggag    1200
agaggagagg ccagagagtg ggaacaggca cctctgcctg aaggaatagg gggcttccca    1260
ggccctggag agtgcaggga tgcccaggtc cacagctggg cagctgcaac tgcctgggag    1320
aacaggctcc catcctgcca gcttggtagg gcgcagggct cctgctggga tcacctattc    1380
ctggcccctg ccagctccac agagtgcaca atcccagcca tggcttcccc cactgcagct    1440
ggcgtcctca cagcagccac cccagatggg ccactgctgc tgtcaacagt tggcaggaag    1500
gcaggctaag cctggtgtct caaccagagg actttgcagc agaggtaatt gccaacccca    1560
cttccactgc cttgacgtcc ctcttgcagc agagaagcta atcctgccca gcctggccat    1620
gagtgagggc acctgaaggg gtgaggaggc ggggtaatg ttgtgtaggt gggaggggc      1680
agtagagagt cccatactca aagtgactgc caaatccagg gctgtgcata gagtgactgc    1740
tgacagcctt tgataagctt tgctgtgagt ccaaaagaat gatcggatag atgcctgtct    1800
tgcagcgcat ctacattaat tcatagcaa attattcgtc tcatattaga gaaagtttag     1860
ctttcttaga agcttgatgg gaaagagcct cccagctctt agagtttgat tttcgcaact    1920
cagttcacat cttcttctta ctccaggttc ccagctcctt gagccttgcc cgtgaagggg    1980
ttggagtcag gatgggaagc cttgagctgc cttgacctgc tccatctctg actcagggat    2040
gtgccctgct tgtcacagca tgggtgtgct gggccttggg gcatcttttc aggcagagag    2100
caagacgttg gcattgtgga aagctgtccc tccaaacagc agcccattca cagactacag    2160
aggaagaaaa gaccacactt gctacagtaa caatgcaatt cagtaccagg gaataactta    2220
acatgaaaca tgtcaaatct atgtaaacaa ctggaaggca ctcctaaaaa atacaaaaaa    2280
```
aaaaaaaaaa aaaaaaaaaa aaaa                                                    2304

<210> SEQ ID NO 200
<211> LENGTH: 128
<212> TYPE: PRT
<213> ORGANISM: Homo sapiens

<400> SEQUENCE: 200

Met Ala Gln Gly Ala Pro Arg Ser Gly Leu Pro Glu Gly Leu Gln Leu
1               5                   10                  15

Phe Ser Thr Ser Cys Tyr Leu Gln Cys Gly Glu Trp Gly Asp Met Phe
            20                  25                  30

Gln Pro Ile Cys Val Thr Ala Leu Ser Val Pro Pro Cys Ser Gly
        35                  40                  45

Pro Trp Leu Met Gly Trp Thr Ser Pro Thr Ala Ala Ser His His Val
    50                  55                  60

Gly Trp Pro Leu Ser Thr Ser Arg Gly Trp Glu Gly Tyr Ser Val Asn
65                  70                  75                  80

Ser Ser Ser Ser Glu Val Trp Ala Pro Arg Arg Val Ala Ile Leu
                85                  90                  95

Tyr Ser His Ser Pro Gly Ala Cys His His Pro Gln Leu Ser Glu Leu
            100                 105                 110

Val Lys Asn Met Leu Gln Leu Leu Ser Leu Pro Pro Phe Ser Arg Ser
        115                 120                 125

<210> SEQ ID NO 201
<211> LENGTH: 1458
<212> TYPE: DNA
<213> ORGANISM: Homo sapiens
<220> FEATURE:
<221> NAME/KEY: unsure
<222> LOCATION: (493)

<400> SEQUENCE: 201
gggccatggt tccctgcggg cggcggggag ggatttcctg gggcgccccc tggaatccaa      60
gcccgaccgc agtgtctgac catggtccgc ggcgcggccg ggtggtcctg caggggccgc     120
gcatagctcc gactacagca tgtggaggaa gaaccagtac gtcagtaacg gctgcgcga     180 cttttgcggag cgcggcgagg cctgggcgct gatgaaggag atcgaggcgg cggggaggc     240 gctgcagagc gtgcacgcgg tgttttcggc gcccgccgtc cccagcggca ccgggcagac     300
gtcggcggag ctggaggtgc agcgcaggca ctcgctggtc tcgtttgtgg tgcgcatcgt     360
gcccagcccc gactggttcg tgggcgtgaa cagcctggac ctgtgcgacg gggaccgttg     420
gcgggaacag gcggcgctgg acctgtaccc ctacgacgcc gggacggaca gcggcttcac     480
cttctcctcc ccnaacttcg ccaccatccc gcaggacacg gtgaccgaga taacgtcctc     540
ctctcccagc caccgggcca actccttcta ctacccgcgg ctgaaggccc tgcctcccat     600
cgccagggtg acactggtgc ggctgcgaca gagcccagg gccttcatcc ctcccgcccc     660
agtcctgccc agcagggaca atgagattgt agacagcgcc tcagttccag aaacgccgct     720
ggactgcgag gtctccctgt ggtcgtcctg gggactgtgc ggaggcccac tgtgggaggc     780
tcgggaccaa gagcaggact cgctacgtcc gggtccagcc cgccaacaaa cgggagcccc     840
tgccccgagc tcgaagaaga ggctgagtgc gtccctgata actgcgtcta agaccagagc     900
cccgcagccc ctggggcccc ccggagccat ggggtgtcgg gggctcctgt gcaggctcat     960
gctgcaggcg gccgagggca caggggggttt cgcgctgctc ctgaccgcgg tgaggccgcg    1020

-continued

```
ccgaccatct ctgcactgaa gggccctctg gtggccggca cgggcattgg gaaacagcct    1080
cctcctttcc caaccttgct tcttaggggc ccccgtgtcc cgtctgctct cagcctcctc    1140
ctcctgcagg ataaagtcat ccccaaggct ccagctactc taaattatgt ctccttataa    1200
gttattgctg ctccaggaga ttgtccttca tcgtccaggg gcctggctcc cacgtggttg    1260
cagatacctc agacctggtg ctctaggctg tgctgagccc actctcccga gggcgcatcc    1320 aagcggggc cacttgagaa gtgaataaat ggggcggttt cggaagcgtc agtgtttcca    1380
tgttatggat ctctctgcgt ttgaataaag actatctctg ttgctcacaa aaaaaaaaa    1440 aaaaaaaaaa aaaaaaaa                                                  1458
```

<210> SEQ ID NO 202
<211> LENGTH: 299
<212> TYPE: PRT
<213> ORGANISM: Homo sapiens

<400> SEQUENCE: 202

```
Met Trp Arg Lys Asn Gln Tyr Val Ser Asn Gly Leu Arg Asp Phe Ala
 1               5                  10                  15

Glu Arg Gly Glu Ala Trp Ala Leu Met Lys Glu Ile Glu Ala Ala Gly
            20                  25                  30

Glu Ala Leu Gln Ser Val His Ala Val Phe Ser Ala Pro Ala Val Pro
        35                  40                  45

Ser Gly Thr Gly Gln Thr Ser Ala Glu Leu Glu Val Gln Arg Arg His
    50                  55                  60

Ser Leu Val Ser Phe Val Val Arg Ile Val Pro Ser Pro Asp Trp Phe
65                  70                  75                  80

Val Gly Val Asn Ser Leu Asp Leu Cys Asp Gly Asp Arg Trp Arg Glu
                85                  90                  95

Gln Ala Ala Leu Asp Leu Tyr Pro Tyr Asp Ala Gly Thr Asp Ser Gly
            100                 105                 110

Phe Thr Phe Ser Ser Pro Asn Phe Ala Thr Ile Pro Gln Asp Thr Val
        115                 120                 125

Thr Glu Ile Thr Ser Ser Ser Pro Ser His Pro Ala Asn Ser Phe Tyr
    130                 135                 140

Tyr Pro Arg Leu Lys Ala Leu Pro Pro Ile Ala Arg Val Thr Leu Val
145                 150                 155                 160

Arg Leu Arg Gln Ser Pro Arg Ala Phe Ile Pro Pro Ala Pro Val Leu
                165                 170                 175

Pro Ser Arg Asp Asn Glu Ile Val Asp Ser Ala Ser Val Pro Glu Thr
            180                 185                 190

Pro Leu Asp Cys Glu Val Ser Leu Trp Ser Ser Trp Gly Leu Cys Gly
        195                 200                 205

Gly Pro Leu Trp Glu Ala Arg Asp Gln Glu Gln Asp Ser Leu Arg Pro
    210                 215                 220

Gly Pro Ala Arg Gln Gln Thr Gly Ala Pro Ala Pro Ser Ser Lys Lys
225                 230                 235                 240

Arg Leu Ser Ala Ser Leu Ile Thr Ala Ser Lys Thr Arg Ala Pro Gln
                245                 250                 255

Pro Leu Gly Pro Pro Gly Ala Met Gly Cys Arg Gly Leu Leu Cys Arg
            260                 265                 270

Leu Met Leu Gln Ala Ala Glu Gly Thr Gly Gly Phe Ala Leu Leu Leu
        275                 280                 285

Thr Ala Val Arg Pro Arg Arg Pro Ser Leu His
    290                 295
```

<210> SEQ ID NO 203
<211> LENGTH: 1100
<212> TYPE: DNA
<213> ORGANISM: Homo sapiens

<400> SEQUENCE: 203

```
attacaggcg tgagccatgc gtccagcagg aaaaggtttt ttaatgaacc atagagacct      60
ctcagagctc cagatttggg ggatggggtc agataatcag gagagttccc gaagaaagtg     120
ccatttgagc tgtgatctga aggaacacta gtaagtagtc agctaggcac agatggggag     180
aggagaggga attctgggcc gaggacacag cgtgggtgaa atcctggagg tgggaagcgg     240
cactgtgctc cagagggact ggaggagagc cagagtgact ggcacatcag gagggcacag     300
gggatgcccg agctgctggt gagacagaca ggactgagag aaacagcaag ctggtctctg     360
acagcttccc gtcaagtggt gatctgtctc ccttcgtcct ccctgccct cccactatct      420
ctgttttccc cagtgccctt tctttccttt ccctgttctt ccttttggaa gaacatacga     480
gctcacctgt gttctggttc cttttctaaa gggctttatg attacttaac caacctcata     540
accatggacc agccaacatt tcacaaatac tcactcaaaa caagcctgtt attatcaccc     600
tcgtttcaca gaagtggaaa ctggggtgca gaaagatgaa gggtcagcag ctggtcagtg     660
acgagccagg gtccaaggcc aggatgtctg cccagccgcc atgctcactg cctttcatct     720
tggttctcct aggaagagtt agttacttct agggtattat tagattggtg caaaagtaat     780
tgtgggtttt gccattgaaa ataattactt ctacaccaac ctaatacttt tttcccaagg     840
ggtttagtag aaggattcct gcagaccaga aacccagagg gatattgctg atgtggtagg     900
tgttgggcca gcagggagag aggtctgagc ccctgccagg tgctacctgg gagccacttt     960
gtcagcattt gtttgttcta cttgggaggt agccctgcca gggacacctg ggacaccctt    1020
ttcccactgg aagcgccatc tgaatccaga accgttttct ttgtcttaag aaaaaaaaa     1080
aaaaaaaaaa aaaaaaaaa                                                1100
```

<210> SEQ ID NO 204
<211> LENGTH: 111
<212> TYPE: PRT
<213> ORGANISM: Homo sapiens

<400> SEQUENCE: 204

```
Met Pro Glu Leu Leu Val Arg Gln Thr Gly Leu Arg Glu Thr Ala Ser
  1               5                  10                  15

Trp Ser Leu Thr Ala Ser Arg Gln Val Val Ile Cys Leu Pro Ser Ser
             20                  25                  30

Ser Pro Ala Leu Pro Leu Ser Leu Phe Ser Pro Val Pro Phe Leu Ser
         35                  40                  45

Phe Pro Cys Ser Ser Phe Trp Lys Asn Ile Arg Ala His Leu Cys Ser
     50                  55                  60

Gly Ser Phe Ser Lys Gly Leu Tyr Asp Tyr Leu Thr Asn Leu Ile Thr
 65                  70                  75                  80

Met Asp Gln Pro Thr Phe His Lys Tyr Ser Leu Lys Thr Ser Leu Leu
                 85                  90                  95

Leu Ser Pro Ser Phe His Arg Ser Gly Asn Trp Gly Ala Glu Arg
            100                 105                 110
```

<210> SEQ ID NO 205

<211> LENGTH: 1395
<212> TYPE: DNA
<213> ORGANISM: Homo sapiens

<400> SEQUENCE: 205

```
ttcaagacca gcctgaccaa catggagaaa ccctgtctct actaaaaata caaaattagc      60
cgggcatggt ggcaatgcct gcctgtaatc ccagctactc gggaggctga ggcaaaagaa     120
tcgcttgaac ccaggaggca gaggttgcag tgagctgaga ttgtgctatt gcactccagc     180
ctggataaca gagcgagac tccgtctcaa aaaaaaaaa aaatttgtag agatagtgtt       240
ttgctacgtt actcaggtg gtctcaaact cctggcctca ggcagttctg cctaggcttc     300
ccaaagtact gggattacag gcagaagcca ctgcgcctac catagaatat tagttatctt     360
ttgaagtgat taaaaaggga aaagattttc ttccaagttt aatgatgaga aaagtgaaag     420
aacagttatt ttaaagcccc tgatatttcc aacatctagg tcataaatga gtctcgttct     480
gttgatagct ttatctcttg gtaatgtgca tgcctgtgtg tgtgtgtgtg tgtgtgttct     540
attctgtgat gtcttataat ttttagttta atggcaaaca tcatgtatac aagaccagta     600
gagactgagg tagatggtat tctgtgtctg gatataggca cgcctctccc atcaggccaa     660
ttgcctgtga cattgagtca acctagtctg gagttgaggt ggatttggat tttgatgttg     720
gtatcattat gttcagtgta cttgggctgc tgttacctgg tacctggagc ctggggtacc     780
agatggtttt tcttcagtgt ttctgttcca ctgttggctt tcctcagtcc catcatgcct     840
ccatcacaga gggggagtct ctattcatat ccttgcccct tcactagtgg ttgactgatg     900
ctgcttgtta ctcagtgcta ggcttatggt ggtgtcatag gtggttttct attgtcctgg     960
ttcagcctta gctttaggca gtccctgttc atttgaaccc caggggtggt acttaatctg    1020
cccttcctg agcagtagca aacctctgct tggcatcaga ttcttgggcc aatgaggatt     1080
ctctcctgct ctcccagaaa caagatgttt gcttctacct ctcccccagc agcaataggg    1140
tatgtgagag gtgggaggtt tacttgaacc caggaggtcg aggctgcagt gagccatgat    1200
agtggcacca cactccagcc tgggtgacag agcaagacc tgtctcaaaa caacaacaac     1260
aacccaaaaa actgtcaagg tcatcaggaa caaaacatag ccaatagcca agaaactgtc    1320
acataccaga ggagactaag gaaacatgat gactaaatgc aatacaaaaa aaaaaaaaa    1380
aaaaaaaaaa aaaaa                                                    1395
```

<210> SEQ ID NO 206
<211> LENGTH: 107
<212> TYPE: PRT
<213> ORGANISM: Homo sapiens

<400> SEQUENCE: 206

```
Met Ala Asn Ile Met Tyr Thr Arg Pro Val Glu Thr Glu Val Asp Gly
  1               5                  10                  15
Ile Leu Cys Leu Asp Ile Gly Thr Pro Leu Pro Ser Gly Gln Leu Pro
                 20                  25                  30
Val Thr Leu Ser Gln Pro Ser Leu Glu Leu Arg Trp Ile Trp Ile Leu
             35                  40                  45
Met Leu Val Ser Leu Cys Ser Val Tyr Leu Gly Cys Cys Tyr Leu Val
         50                  55                  60
Pro Gly Ala Trp Gly Thr Arg Trp Phe Phe Phe Ser Val Ser Val Pro
 65                  70                  75                  80
Leu Leu Ala Phe Leu Ser Pro Ile Met Pro Pro Ser Gln Arg Gly Ser
                 85                  90                  95
```

Leu Tyr Ser Tyr Pro Cys Pro Phe Thr Ser Gly
        100                 105

<210> SEQ ID NO 207
<211> LENGTH: 1617
<212> TYPE: DNA
<213> ORGANISM: Homo sapiens

<400> SEQUENCE: 207

| | | | | | |
|---|---|---|---|---|---|
| tccacttatt | ctggatattc | ttactattca | agtcattcga | aaaaatctca | cagacaaggg | 60 |
| gaaagaacta | gagagagaca | caagtcaccc | cggaataaag | acggcagagg | gtcagaaaag | 120 |
| tctgtcacca | ttcaacctcc | cactggagag | cccctgttgg | gaaatgattc | tactcggaca | 180 |
| gaggaagttc | aggatgacaa | ctggggagag | accaccacgg | ccatcacagg | cacctcggag | 240 |
| cacagcatat | cccaagagga | cattgccagg | atcagcaagg | acatggagga | cagcgtgggg | 300 |
| ctggattgca | aacgctacct | gggcctcacc | gtcgcctctt | tcttggact | tctagttttc | 360 |
| ctcaccccta | ttgccttcat | ccttttacct | ccgatcctgt | ggagggatga | gctggagcct | 420 |
| tgtggcacaa | tttgtgaggg | gctctttatc | tccatggcat | tcaaactcct | cattctgctc | 480 |
| atagggacct | gggcactttt | tttccgcaag | cggagagctg | acatgccacg | ggtgtttgtg | 540 |
| tttcgtgccc | ttttgttggt | cctcattttt | ctctttgtgg | tttcctattg | gcttttttac | 600 |
| ggggtccgca | ttttggactc | tcgggaccgg | aattaccagg | gcattgtgca | atatgcagtc | 660 |
| tcccttgtgg | atgccctcct | cttcatccat | tacctggcca | tcgtcctgct | ggagctcagg | 720 |
| cagctgcagc | ccatgttcac | gctgcaggtg | gtccgctcca | ccgatggcga | gtcccgcttc | 780 |
| tacagcctgg | gacacctgag | tatccagcga | gcagcattgg | tggtcctaga | aaattactac | 840 |
| aaagatttca | ccatctataa | cccaaacctc | ctaacagcct | ccaaattccg | agcagccaag | 900 |
| catatggccg | ggctgaaagt | ctacaatgta | gatggcccca | gtaacaatgc | cactggccag | 960 |
| tcccgggcca | tgattgctgc | agctgctcgg | cgcagggact | caagccacaa | cgagttgtat | 1020 |
| tatgaagagg | ccgaacatga | acggcgagta | agaagcggga | aagcaaggct | ggtggttgca | 1080 |
| gtggaagagg | ccttcatcca | cattcagcgt | ctccaggctg | aggagcagca | gaaagcccca | 1140 |
| ggggaggtga | tggaccctag | ggaggccgcc | caggccattt | tccctccat | ggccagggct | 1200 |
| ctccagaagt | acctgcgcat | cacccggcag | cagaactacc | acagcatgga | gagcatcctg | 1260 |
| cagcacctgg | cctctgcat | caccaacggc | atgaccccca | aggccttcct | agaacggtac | 1320 |
| ctcagtgcgg | gccccaccct | gcaatatgac | aaggaccgct | ggctctctac | acagtggagg | 1380 |
| cttgtcagtg | atgaggctgt | gactaatgga | ttacgggatg | gaattgtgtt | cgtccttaag | 1440 |
| tgcttggact | tcagcctcgt | agtcaatgtg | aagaaaattc | cattcatcat | actctctgaa | 1500 |
| gagttcatag | accccaaatc | tcacaaattt | gtccttcgct | acagtctga | gacatccgtt | 1560 |
| taaaagttct | atatttgtgg | ctttattaaa | aaaaaaaaa | aaaaaaaaa | aaaaaaa | 1617 |

<210> SEQ ID NO 208
<211> LENGTH: 426
<212> TYPE: PRT
<213> ORGANISM: Homo sapiens

<400> SEQUENCE: 208

Met Glu Asp Ser Val Gly Leu Asp Cys Lys Arg Tyr Leu Gly Leu Thr
1               5                   10                  15

Val Ala Ser Phe Leu Gly Leu Leu Val Phe Leu Thr Pro Ile Ala Phe
            20                  25                  30

```
Ile Leu Leu Pro Pro Ile Leu Trp Arg Asp Glu Leu Glu Pro Cys Gly
         35                  40                  45

Thr Ile Cys Glu Gly Leu Phe Ile Ser Met Ala Phe Lys Leu Leu Ile
     50                  55                  60

Leu Leu Ile Gly Thr Trp Ala Leu Phe Phe Arg Lys Arg Arg Ala Asp
 65                  70                  75                  80

Met Pro Arg Val Phe Val Arg Ala Leu Leu Leu Val Leu Ile Phe
                 85                  90                  95

Leu Phe Val Val Ser Tyr Trp Leu Phe Tyr Gly Val Arg Ile Leu Asp
                100                 105                 110

Ser Arg Asp Arg Asn Tyr Gln Gly Ile Val Gln Tyr Ala Val Ser Leu
            115                 120                 125

Val Asp Ala Leu Leu Phe Ile His Tyr Leu Ala Ile Val Leu Leu Glu
 130                 135                 140

Leu Arg Gln Leu Gln Pro Met Phe Thr Leu Gln Val Val Arg Ser Thr
145                 150                 155                 160

Asp Gly Glu Ser Arg Phe Tyr Ser Leu Gly His Leu Ser Ile Gln Arg
                165                 170                 175

Ala Ala Leu Val Val Leu Glu Asn Tyr Tyr Lys Asp Phe Thr Ile Tyr
            180                 185                 190

Asn Pro Asn Leu Leu Thr Ala Ser Lys Phe Arg Ala Ala Lys His Met
        195                 200                 205

Ala Gly Leu Lys Val Tyr Asn Val Asp Gly Pro Ser Asn Asn Ala Thr
        210                 215                 220

Gly Gln Ser Arg Ala Met Ile Ala Ala Ala Arg Arg Arg Asp Ser
225                 230                 235                 240

Ser His Asn Glu Leu Tyr Tyr Glu Glu Ala Glu His Glu Arg Arg Val
                245                 250                 255

Lys Lys Arg Lys Ala Arg Leu Val Ala Val Glu Glu Ala Phe Ile
            260                 265                 270

His Ile Gln Arg Leu Gln Ala Glu Glu Gln Lys Ala Pro Gly Glu
            275                 280                 285

Val Met Asp Pro Arg Glu Ala Ala Gln Ala Ile Phe Pro Ser Met Ala
290                 295                 300

Arg Ala Leu Gln Lys Tyr Leu Arg Ile Thr Arg Gln Gln Asn Tyr His
305                 310                 315                 320

Ser Met Glu Ser Ile Leu Gln His Leu Ala Phe Cys Ile Thr Asn Gly
                325                 330                 335

Met Thr Pro Lys Ala Phe Leu Glu Arg Tyr Leu Ser Ala Gly Pro Thr
            340                 345                 350

Leu Gln Tyr Asp Lys Asp Arg Trp Leu Ser Thr Gln Trp Arg Leu Val
            355                 360                 365

Ser Asp Glu Ala Val Thr Asn Gly Leu Arg Asp Gly Ile Val Phe Val
        370                 375                 380

Leu Lys Cys Leu Asp Phe Ser Leu Val Val Asn Val Lys Lys Ile Pro
385                 390                 395                 400

Phe Ile Ile Leu Ser Glu Glu Phe Ile Asp Pro Lys Ser His Lys Phe
                405                 410                 415

Val Leu Arg Leu Gln Ser Glu Thr Ser Val
            420                 425

<210> SEQ ID NO 209
<211> LENGTH: 2259
```

```
<212> TYPE: DNA
<213> ORGANISM: Homo sapiens
<220> FEATURE:
<221> NAME/KEY: unsure
<222> LOCATION: (2194)

<400> SEQUENCE: 209
ccaaagaggc ctagacactt tgggggtgca ctggcacttt gcagggttca ctggcacttt      60
ctggggctca ttgacactt tgggtacact ggcattcttt ggtgttcact ggcattttgg     120
gggtgcactg gcactttgga acaacggcac gcctcttggc ccttgcccag ctggtgctcc    180
tggctgggaa gctgaacaca ctggctgctg tggtcactgt cttctacctg gtggcctatg    240
ctgccgtgga cctgtcctgc ctgagcctgg agtgggcctc ggccccaact tccggtgaga    300
gactcagatc tgtgtcccca gagagaagaa gggaggactc gggctcaggc gtggggctgg    360
ggactgcagc ctcgtgtgcg gcctgccctg agtttctgtc cctcctcccc tccatgcccg    420
tagccccacc ttcagcctgt tctcctggca cacctgcctg ctgggggtgg cctcctgcct    480
gctcatgatg ttcctcatca gtcctggcgc ggctggtggc tccctgctcc tcatgggtct    540
gctggctgcc ctgctcaccg cgcgaggagg ccccagtagc tggggctatg tcagccaggc    600
cttgcttttc caccaggtgc gtaagtatct gcttcggctg gacgtccgga aggatcacgt    660
gaagttctgg cggcccagc tgctgctcct ggtgggaaac cccgggggcg ccctgcctct    720
gctgcggttg gccaaccagc ttaagaaggg gggctgtat gtgctgggcc acgtcaccct    780
gggagacctc gactccctgc cctcggaccc tgtacagccg cagtatgggg catggctcag    840
cctggtggac cgtgcccagg tgaaggcttt tgtggatcta accctctcac cctccgtgcg    900
ccaggggct cagcatctgc tgcgaatctc cggcctcggt ggcatgaagc ccaacacgtt    960
ggtcctaggt ttctacgatg acgctccacc gcaggaccat ttcctgacgg acccggcttt   1020
ctctgagcct gcagacagca ccaggggagg cagttcccca gctctgagca ccctgttccc   1080
tcctccccgg gctcctggga gccccgggc cctcaatccc caggactatg tggccacggt   1140
ggccgacgcc ctcaagatga acaagaatgt ggtgctggcc cgggcagcg gggccttgcc   1200
ccctgagcgg ctgagccggg ggtctggggg cacctctcag ctgcaccatg tggacgtgtg   1260
gccctcaacc tgctgcggcc ccggggtggg cccggctatg tggatgtctg cggcctcttc   1320
ctgctgcaga tggcaaccat cttgggcatg gtgcccgctt ggcatagcgc ccggctccgg   1380
atcttcctgt gcctggggcc tcgggaggcg cctggggcgg ccgagggcgg ctgcgggcac   1440
tgctgagcca actgaggatc cgggctgagg tgcagaaggt ggtgtgggc gaggggcccg   1500
gggctgggga acccgaggcg gaggaggaag gggactttgt gaacagtggg cggggagacg   1560
cagaggcaga ggccctggca cgcagcgcca acgcctggt tcgggcccag caggggcgcg   1620
gcacaggagg agggccgggt gggccggagg gtggggatgc tgagggcccc atcacagccc   1680
tcaccttcct gtacttgcct cggccgccag ccgatcccgc ccgataccc cgctacctgg    1740
cgctactgga gactctaacc cgagacctgg gccccacgct gctggttcat ggggtcactc   1800
cagtcacctg cactgatctg tgatgcccct gcctccaggg ctaggtagag agggcccagg   1860
caggcggcct atcctgatcc ttggaggagg tggaagagga ggccactgtg gcccgtggcc   1920
ctgcccttgg gacgtggagc ccaggggagg tttgaagggg atcctgggct tgggcatcac   1980
gcccacctcc tttggcagag ggaccccagc acactaactc tgggtggctg tcccaccgt    2040
gcgggggggg gagtccgcag cctcccttca ctggtgcctt gatgctgggg gccaggcctc   2100
ctctgtgact ctgggctccc tcagtttccc cattttggcc agactcaccg gcccactggg   2160
```

-continued

```
gtggtgatgt tttcgttctg ttttattttt ctanctctgc tgaccatgaa taaaagacca    2220
aaacactatt aaaaaaaaaa aaaaaaaaaa aaaaaaaaa                           2259
```

<210> SEQ ID NO 210
<211> LENGTH: 327
<212> TYPE: PRT
<213> ORGANISM: Homo sapiens

<400> SEQUENCE: 210

```
Met Met Phe Leu Ile Ser Pro Gly Ala Ala Gly Gly Ser Leu Leu Leu
 1               5                  10                  15

Met Gly Leu Leu Ala Ala Leu Leu Thr Ala Arg Gly Gly Pro Ser Ser
            20                  25                  30

Trp Gly Tyr Val Ser Gln Ala Leu Leu Phe His Gln Val Arg Lys Tyr
        35                  40                  45

Leu Leu Arg Leu Asp Val Arg Lys Asp His Val Lys Phe Trp Arg Pro
    50                  55                  60

Gln Leu Leu Leu Val Gly Asn Pro Arg Gly Ala Leu Pro Leu Leu
65                  70                  75                  80

Arg Leu Ala Asn Gln Leu Lys Lys Gly Gly Leu Tyr Val Leu Gly His
                85                  90                  95

Val Thr Leu Gly Asp Leu Asp Ser Leu Pro Ser Asp Pro Val Gln Pro
            100                 105                 110

Gln Tyr Gly Ala Trp Leu Ser Leu Val Asp Arg Ala Gln Val Lys Ala
        115                 120                 125

Phe Val Asp Leu Thr Leu Ser Pro Ser Val Arg Gln Gly Ala Gln His
    130                 135                 140

Leu Leu Arg Ile Ser Gly Leu Gly Met Lys Pro Asn Thr Leu Val
145                 150                 155                 160

Leu Gly Phe Tyr Asp Asp Ala Pro Pro Gln Asp His Phe Leu Thr Asp
                165                 170                 175

Pro Ala Phe Ser Glu Pro Ala Asp Ser Thr Arg Glu Gly Ser Ser Pro
            180                 185                 190

Ala Leu Ser Thr Leu Phe Pro Pro Arg Ala Pro Gly Ser Pro Arg
        195                 200                 205

Ala Leu Asn Pro Gln Asp Tyr Val Ala Thr Val Ala Asp Ala Leu Lys
    210                 215                 220

Met Asn Lys Asn Val Val Leu Ala Arg Ala Ser Gly Ala Leu Pro Pro
225                 230                 235                 240

Glu Arg Leu Ser Arg Gly Ser Gly Gly Thr Ser Gln Leu His His Val
                245                 250                 255

Asp Val Trp Pro Ser Thr Cys Cys Gly Pro Val Gly Pro Ala Met
            260                 265                 270

Trp Met Ser Ala Ala Ser Ser Cys Cys Arg Trp Gln Pro Ser Trp Ala
        275                 280                 285

Trp Cys Pro Leu Gly Ile Ala Pro Gly Ser Gly Ser Cys Ala Trp
    290                 295                 300

Gly Leu Gly Arg Arg Leu Gly Arg Pro Arg Ala Ala Gly Thr Ala
305                 310                 315                 320

Glu Pro Thr Glu Asp Pro Gly
                325
```

<210> SEQ ID NO 211
<211> LENGTH: 1001

```
<212> TYPE: DNA
<213> ORGANISM: Homo sapiens
<220> FEATURE:
<221> NAME/KEY: unsure
<222> LOCATION: (812)

<400> SEQUENCE: 211
gaaaccgttg atgggactga gaaaccagag ttaaaacctc tttggagctt ctgaggactc    60
agctggaacc aacgggcaca gttggcaaca ccatcatgac atcacaacct gttcccaatg   120
agaccatcat agtgctccca tcaaatgtca tcaacttctc ccaagcagag aaacccgaac   180
ccaccaacca ggggcaggat agcctgaaga acatctaca cgcagaaatc aaagttattg   240
ggactatcca gatcttgtgt ggcatgatgg tattgagctt ggggatcatt ttggcatctg   300
cttccttctc tccaaatttt acccaagtga cttctacact gttgaactct gcttacccat   360
tcataggacc ctttttttttt atcatctctg gctctctatc aatcgccaca gagaaaaggt   420
taaccaagct tttggtgcat agcagcctgg ttggaagcat tctgagtgct ctgtctgccc   480
tggtgggttt cattatcctg tctgtcaaac aggccacctt aaatcctgcc tcactgcagt   540
gtgagttgga caaaaataat ataccaacaa gaagttatgt ttcttacttt tatcatgatt   600
cactttatac cacggactgc tatacagcca aagccagtct ggctggaact ctctctctga   660
tgctgatttg cactctgctg gaattctgcc ttgctgtgct cactgctgtg ctgcggtgga   720
aacaggctta ctctgacttc cctgggagtg tacttttcct gcctcacagt tacattggta   780
attctggcat gtcctcaaaa atgactcatg anctgtggat atgaagaact attgacttct   840
taagaaaaaa gggagaaata ttaatcagaa agttgattct tatgataata tggaaaagtt   900
aaccattata gaaaagcaaa gcttgagttt cctaaatgta agcttttaaa gtaatgaaca   960
ttaaaaaaaa ccattatttc actgtcaaaa aaaaaaaaaa a                     1001

<210> SEQ ID NO 212
<211> LENGTH: 242
<212> TYPE: PRT
<213> ORGANISM: Homo sapiens
<220> FEATURE:
<221> NAME/KEY: UNSURE
<222> LOCATION: (239)

<400> SEQUENCE: 212

Met Thr Ser Gln Pro Val Pro Asn Glu Thr Ile Ile Val Leu Pro Ser
  1               5                  10                  15

Asn Val Ile Asn Phe Ser Gln Ala Glu Lys Pro Glu Pro Thr Asn Gln
                 20                  25                  30

Gly Gln Asp Ser Leu Lys Lys His Leu His Ala Glu Ile Lys Val Ile
             35                  40                  45

Gly Thr Ile Gln Ile Leu Cys Gly Met Met Val Leu Ser Leu Gly Ile
         50                  55                  60

Ile Leu Ala Ser Ala Ser Phe Ser Pro Asn Phe Thr Gln Val Thr Ser
 65                  70                  75                  80

Thr Leu Leu Asn Ser Ala Tyr Pro Phe Ile Gly Pro Phe Phe Phe Ile
                 85                  90                  95

Ile Ser Gly Ser Leu Ser Ile Ala Thr Glu Lys Arg Leu Thr Lys Leu
                100                 105                 110

Leu Val His Ser Ser Leu Val Gly Ser Ile Leu Ser Ala Leu Ser Ala
            115                 120                 125

Leu Val Gly Phe Ile Ile Leu Ser Val Lys Gln Ala Thr Leu Asn Pro
        130                 135                 140
```

Ala Ser Leu Gln Cys Glu Leu Asp Lys Asn Asn Ile Pro Thr Arg Ser
145                 150                 155                 160

Tyr Val Ser Tyr Phe Tyr His Asp Ser Leu Tyr Thr Thr Asp Cys Tyr
                165                 170                 175

Thr Ala Lys Ala Ser Leu Ala Gly Thr Leu Ser Leu Met Leu Ile Cys
            180                 185                 190

Thr Leu Leu Glu Phe Cys Leu Ala Val Leu Thr Ala Val Leu Arg Trp
        195                 200                 205

Lys Gln Ala Tyr Ser Asp Phe Pro Gly Ser Val Leu Phe Leu Pro His
    210                 215                 220

Ser Tyr Ile Gly Asn Ser Gly Met Ser Ser Lys Met Thr His Xaa Leu
225                 230                 235                 240

Trp Ile

<210> SEQ ID NO 213
<211> LENGTH: 1079
<212> TYPE: DNA
<213> ORGANISM: Homo sapiens

<400> SEQUENCE: 213
gcatcctcct ctatcctgtt tcgaggtaga gagcttggca cttctgttac aagctgagag      60
tctggaggtg ctgagtttaa cgtggctgtg caggtgattt caaggcatga gctgaacagc     120
gttgacacag ccgtgactta caattaaacc ctttcaatta cagtacagat tctgtgtgct     180
acttgatgag atgttaccca aggccagttt ggacttactg cttttgtccc tcatattaaa     240
ttatcaaatg atgccgatga atgcttgaa aatgattctg ctctcaaagt tatgcttccc     300
tagaaaggtg tcatgtcggg cacttgtgtt gggtgactat gacatcccag cagtgctggt     360
caggtctcag agttgctttc acctagagct gatgcttcca caaggggaca tttgtgttac     420
tttgctccag gggtctgtca taaaaacaat ggtaactact tcatccctag gaagcccaag     480
acttcagggc actgttagct gattggtaaa taagggacac gatattcacg ggaattgttt     540
actgctcccc actagtaatt ctcatggggc actttttta actctttcta attaacacct     600
cttctcagca tagagcagag gatgcagtca tttctctgtt gaaatctatg tagtattat      660
gtagaatgtc attatatgaa agcgaattca gaatcctaac tctgggaaag cgctctctgg     720
aaatgtagtt tgataatagt gtcttatagg ggccacggga atttgttct ctataaagcg      780
atgggctcca gtgtcatgtt accagagtta tcgctcagtt ttgtttgtta aggcttttgc     840
tagaacctat tatgtatcca gttttaaaa catacttcat tcccttgata gcagagatcc      900
agagcacaga tggcaagttg tgtggatgat actgaatatg tttattttcc taagataaa      960
tgtcacgaca cgacatttct cagtttttat ttagatgttt attaccatgt gttaacagaa    1020
tcttaaaacc caagggattt cttcagtaaa ctagactttg attcaaaaaa aaaaaaaaa     1079

<210> SEQ ID NO 214
<211> LENGTH: 103
<212> TYPE: PRT
<213> ORGANISM: Homo sapiens

<400> SEQUENCE: 214

Met Leu Pro Lys Ala Ser Leu Asp Leu Leu Leu Ser Leu Ile Leu
1               5                   10                  15

Asn Tyr Gln Met Met Pro Met Lys Cys Leu Lys Met Ile Leu Leu Ser
                20                  25                  30

```
Lys Leu Cys Phe Pro Arg Lys Val Ser Cys Arg Ala Leu Val Leu Gly
        35                  40                  45

Asp Tyr Asp Ile Pro Ala Val Leu Val Arg Ser Gln Ser Cys Phe His
    50                  55                  60

Leu Glu Leu Met Leu Pro Gln Gly Asp Ile Cys Val Thr Leu Leu Gln
65                  70                  75                  80

Gly Ser Val Ile Lys Thr Met Val Thr Thr Ser Ser Leu Gly Ser Pro
                85                  90                  95

Arg Leu Gln Gly Thr Val Ser
            100

<210> SEQ ID NO 215
<211> LENGTH: 19
<212> TYPE: DNA
<213> ORGANISM: Artificial Sequence
<220> FEATURE:
<223> OTHER INFORMATION: oligonucleotide

<400> SEQUENCE: 215
ggatggggct cattctctc                                              19

<210> SEQ ID NO 216
<211> LENGTH: 20
<212> TYPE: DNA
<213> ORGANISM: Artificial Sequence
<220> FEATURE:
<223> OTHER INFORMATION: oligonucleotide

<400> SEQUENCE: 216
gaaatgtgta aactggcagc                                             20

<210> SEQ ID NO 217
<211> LENGTH: 21
<212> TYPE: DNA
<213> ORGANISM: Artificial Sequence
<220> FEATURE:
<223> OTHER INFORMATION: oligonucleotide

<400> SEQUENCE: 217
gaatgcagca caattagagg g                                           21

<210> SEQ ID NO 218
<211> LENGTH: 21
<212> TYPE: DNA
<213> ORGANISM: Artificial Sequence
<220> FEATURE:
<223> OTHER INFORMATION: oligonucleotide

<400> SEQUENCE: 218
ctgcttagaa agcagaattg c                                           21

<210> SEQ ID NO 219
<211> LENGTH: 19
<212> TYPE: DNA
<213> ORGANISM: Artificial Sequence
<220> FEATURE:
<223> OTHER INFORMATION: oligonucleotide

<400> SEQUENCE: 219
tgtgactagc aatgtatgc                                              19

<210> SEQ ID NO 220
<211> LENGTH: 20
<212> TYPE: DNA
```

<213> ORGANISM: Artificial Sequence
<220> FEATURE:
<223> OTHER INFORMATION: oligonucleotide

<400> SEQUENCE: 220
tcagaagaaa gccatagggc                    20

<210> SEQ ID NO 221
<211> LENGTH: 21
<212> TYPE: DNA
<213> ORGANISM: Artificial Sequence
<220> FEATURE:
<223> OTHER INFORMATION: oligonucleotide

<400> SEQUENCE: 221
cctcaagatg atttgcacag c                   21

<210> SEQ ID NO 222
<211> LENGTH: 19
<212> TYPE: DNA
<213> ORGANISM: Artificial Sequence
<220> FEATURE:
<223> OTHER INFORMATION: oligonucleotide

<400> SEQUENCE: 222
ggagagcacg ttcagaggg                     19

<210> SEQ ID NO 223
<211> LENGTH: 20
<212> TYPE: DNA
<213> ORGANISM: Artificial Sequence
<220> FEATURE:
<223> OTHER INFORMATION: oligonucleotide

<400> SEQUENCE: 223
gactgactct gggttcctgg                    20

<210> SEQ ID NO 224
<211> LENGTH: 20
<212> TYPE: DNA
<213> ORGANISM: Artificial Sequence
<220> FEATURE:
<223> OTHER INFORMATION: oligonucleotide

<400> SEQUENCE: 224
ggtagtgaag actgtgccgg                    20

<210> SEQ ID NO 225
<211> LENGTH: 21
<212> TYPE: DNA
<213> ORGANISM: Artificial Sequence
<220> FEATURE:
<223> OTHER INFORMATION: oligonucleotide

<400> SEQUENCE: 225
ggaagtgact tccaatgatg c                   21

<210> SEQ ID NO 226
<211> LENGTH: 18
<212> TYPE: DNA
<213> ORGANISM: Artificial Sequence
<220> FEATURE:
<223> OTHER INFORMATION: oligonucleotide

<400> SEQUENCE: 226
ctcgctggca ttggtttg                      18

<210> SEQ ID NO 227
<211> LENGTH: 20
<212> TYPE: DNA
<213> ORGANISM: Artificial Sequence
<220> FEATURE:
<223> OTHER INFORMATION: oligonucleotide

<400> SEQUENCE: 227
ccatgaccat agtcagtggg                                                  20

<210> SEQ ID NO 228
<211> LENGTH: 20
<212> TYPE: DNA
<213> ORGANISM: Artificial Sequence
<220> FEATURE:
<223> OTHER INFORMATION: oligonucleotide

<400> SEQUENCE: 228
aaatgtccaa tagttcctgg                                                  20

<210> SEQ ID NO 229
<211> LENGTH: 19
<212> TYPE: DNA
<213> ORGANISM: Artificial Sequence
<220> FEATURE:
<223> OTHER INFORMATION: oligonucleotide

<400> SEQUENCE: 229
ggagcaatgc tgagctacc                                                   19

<210> SEQ ID NO 230
<211> LENGTH: 18
<212> TYPE: DNA
<213> ORGANISM: Artificial Sequence
<220> FEATURE:
<223> OTHER INFORMATION: oligonucleotide

<400> SEQUENCE: 230
ctgcgacacc cttgacac                                                    18

<210> SEQ ID NO 231
<211> LENGTH: 21
<212> TYPE: DNA
<213> ORGANISM: Artificial Sequence
<220> FEATURE:
<223> OTHER INFORMATION: oligonucleotide

<400> SEQUENCE: 231
tcaccaagtg tatggagaat g                                                21

<210> SEQ ID NO 232
<211> LENGTH: 20
<212> TYPE: DNA
<213> ORGANISM: Artificial Sequence
<220> FEATURE:
<223> OTHER INFORMATION: oligonucleotide

<400> SEQUENCE: 232
tatctgaacc taatggtttg                                                  20

<210> SEQ ID NO 233
<211> LENGTH: 20
<212> TYPE: DNA
<213> ORGANISM: Artificial Sequence
<220> FEATURE:

```
<223> OTHER INFORMATION: oligonucleotide

<400> SEQUENCE: 233
cagtcagatt tgggtcaggc                                                    20

<210> SEQ ID NO 234
<211> LENGTH: 20
<212> TYPE: DNA
<213> ORGANISM: Artificial Sequence
<220> FEATURE:
<223> OTHER INFORMATION: oligonucleotide

<400> SEQUENCE: 234
tcttacctca ggtgatccgc                                                    20

<210> SEQ ID NO 235
<211> LENGTH: 18
<212> TYPE: DNA
<213> ORGANISM: Artificial Sequence
<220> FEATURE:
<223> OTHER INFORMATION: oligonucleotide

<400> SEQUENCE: 235
gaaagccagg tcagccag                                                      18

<210> SEQ ID NO 236
<211> LENGTH: 20
<212> TYPE: DNA
<213> ORGANISM: Artificial Sequence
<220> FEATURE:
<223> OTHER INFORMATION: oligonucleotide

<400> SEQUENCE: 236
cagaggaaca cctcagaccc                                                    20

<210> SEQ ID NO 237
<211> LENGTH: 18
<212> TYPE: DNA
<213> ORGANISM: Artificial Sequence
<220> FEATURE:
<223> OTHER INFORMATION: oligonucleotide

<400> SEQUENCE: 237
ttcgtccagc agcaagtg                                                      18

<210> SEQ ID NO 238
<211> LENGTH: 18
<212> TYPE: DNA
<213> ORGANISM: Artificial Sequence
<220> FEATURE:
<223> OTHER INFORMATION: oligonucleotide

<400> SEQUENCE: 238
tatggttcgg ttgggtgg                                                      18

<210> SEQ ID NO 239
<211> LENGTH: 18
<212> TYPE: DNA
<213> ORGANISM: Artificial Sequence
<220> FEATURE:
<223> OTHER INFORMATION: oligonucleotide

<400> SEQUENCE: 239
ctacaggagg aggccgtg                                                      18
```

```
<210> SEQ ID NO 240
<211> LENGTH: 21
<212> TYPE: DNA
<213> ORGANISM: Artificial Sequence
<220> FEATURE:
<223> OTHER INFORMATION: oligonucleotide

<400> SEQUENCE: 240
ccagggaaga tgagaggaga g                                              21

<210> SEQ ID NO 241
<211> LENGTH: 21
<212> TYPE: DNA
<213> ORGANISM: Artificial Sequence
<220> FEATURE:
<223> OTHER INFORMATION: oligonucleotide

<400> SEQUENCE: 241
gcgaaatggt ttatttactg c                                              21

<210> SEQ ID NO 242
<211> LENGTH: 18
<212> TYPE: DNA
<213> ORGANISM: Artificial Sequence
<220> FEATURE:
<223> OTHER INFORMATION: oligonucleotide

<400> SEQUENCE: 242
cagcccttct gagtcccc                                                  18

<210> SEQ ID NO 243
<211> LENGTH: 21
<212> TYPE: DNA
<213> ORGANISM: Artificial Sequence
<220> FEATURE:
<223> OTHER INFORMATION: oligonucleotide

<400> SEQUENCE: 243
tgagagtgtg tgtgctgatt c                                              21

<210> SEQ ID NO 244
<211> LENGTH: 18
<212> TYPE: DNA
<213> ORGANISM: Artificial Sequence
<220> FEATURE:
<223> OTHER INFORMATION: oligonucleotide

<400> SEQUENCE: 244
tccaccctcc ttgctctg                                                  18

<210> SEQ ID NO 245
<211> LENGTH: 21
<212> TYPE: DNA
<213> ORGANISM: Artificial Sequence
<220> FEATURE:
<223> OTHER INFORMATION: oligonucleotide

<400> SEQUENCE: 245
ttctcattct caagctctgc c                                              21

<210> SEQ ID NO 246
<211> LENGTH: 19
<212> TYPE: DNA
<213> ORGANISM: Artificial Sequence
<220> FEATURE:
<223> OTHER INFORMATION: oligonucleotide
```

<400> SEQUENCE: 246
agaatcagag ggtcgtggg                                              19

<210> SEQ ID NO 247
<211> LENGTH: 21
<212> TYPE: DNA
<213> ORGANISM: Artificial Sequence
<220> FEATURE:
<223> OTHER INFORMATION: oligonucleotide

<400> SEQUENCE: 247
ttgaggtatg aacagggaag g                                           21

<210> SEQ ID NO 248
<211> LENGTH: 20
<212> TYPE: DNA
<213> ORGANISM: Artificial Sequence
<220> FEATURE:
<223> OTHER INFORMATION: oligonucleotide

<400> SEQUENCE: 248
ccaaatcatg gagaagatgc                                             20

<210> SEQ ID NO 249
<211> LENGTH: 20
<212> TYPE: DNA
<213> ORGANISM: Artificial Sequence
<220> FEATURE:
<223> OTHER INFORMATION: oligonucleotide

<400> SEQUENCE: 249
gcccttgtat cttgggcttc                                             20

<210> SEQ ID NO 250
<211> LENGTH: 18
<212> TYPE: DNA
<213> ORGANISM: Artificial Sequence
<220> FEATURE:
<223> OTHER INFORMATION: oligonucleotide

<400> SEQUENCE: 250
ctccacctct gcccgtag                                               18

<210> SEQ ID NO 251
<211> LENGTH: 20
<212> TYPE: DNA
<213> ORGANISM: Artificial Sequence
<220> FEATURE:
<223> OTHER INFORMATION: oligonucleotide

<400> SEQUENCE: 251
tgggtacttt ctgcattggg                                             20

<210> SEQ ID NO 252
<211> LENGTH: 19
<212> TYPE: DNA
<213> ORGANISM: Artificial Sequence
<220> FEATURE:
<223> OTHER INFORMATION: oligonucleotide

<400> SEQUENCE: 252
ggactaccct gttccccac                                              19

<210> SEQ ID NO 253
<211> LENGTH: 21

```
<212> TYPE: DNA
<213> ORGANISM: Artificial Sequence
<220> FEATURE:
<223> OTHER INFORMATION: oligonucleotide

<400> SEQUENCE: 253
tgagcagtga ggagagagag c                                              21

<210> SEQ ID NO 254
<211> LENGTH: 21
<212> TYPE: DNA
<213> ORGANISM: Artificial Sequence
<220> FEATURE:
<223> OTHER INFORMATION: oligonucleotide

<400> SEQUENCE: 254
gcacaaccaa cagcgctccc g                                              21

<210> SEQ ID NO 255
<211> LENGTH: 18
<212> TYPE: DNA
<213> ORGANISM: Artificial Sequence
<220> FEATURE:
<223> OTHER INFORMATION: oligonucleotide

<400> SEQUENCE: 255
taacccaccc agacacgg                                                  18

<210> SEQ ID NO 256
<211> LENGTH: 19
<212> TYPE: DNA
<213> ORGANISM: Artificial Sequence
<220> FEATURE:
<223> OTHER INFORMATION: oligonucleotide

<400> SEQUENCE: 256
tgtctcagga ggcagaagg                                                 19

<210> SEQ ID NO 257
<211> LENGTH: 21
<212> TYPE: DNA
<213> ORGANISM: Artificial Sequence
<220> FEATURE:
<223> OTHER INFORMATION: oligonucleotide

<400> SEQUENCE: 257
aacaacatct gcatgtatcc c                                              21

<210> SEQ ID NO 258
<211> LENGTH: 21
<212> TYPE: DNA
<213> ORGANISM: Artificial Sequence
<220> FEATURE:
<223> OTHER INFORMATION: oligonucleotide

<400> SEQUENCE: 258
agcttatcca gaccttgctt c                                              21

<210> SEQ ID NO 259
<211> LENGTH: 21
<212> TYPE: DNA
<213> ORGANISM: Artificial Sequence
<220> FEATURE:
<223> OTHER INFORMATION: oligonucleotide

<400> SEQUENCE: 259
```

-continued

```
gtgttcttaa acacttgcat g                                              21
```

<210> SEQ ID NO 260
<211> LENGTH: 21
<212> TYPE: DNA
<213> ORGANISM: Artificial Sequence
<220> FEATURE:
<223> OTHER INFORMATION: oligonucleotide

<400> SEQUENCE: 260

```
tgtggataca tataggaagt g                                              21
```

<210> SEQ ID NO 261
<211> LENGTH: 19
<212> TYPE: DNA
<213> ORGANISM: Artificial Sequence
<220> FEATURE:
<223> OTHER INFORMATION: oligonucleotide

<400> SEQUENCE: 261

```
gttctcactc caggttgcg                                                 19
```

<210> SEQ ID NO 262
<211> LENGTH: 21
<212> TYPE: DNA
<213> ORGANISM: Artificial Sequence
<220> FEATURE:
<223> OTHER INFORMATION: oligonucleotide

<400> SEQUENCE: 262

```
tgatgagaaa agtgaaagaa c                                              21
```

<210> SEQ ID NO 263
<211> LENGTH: 19
<212> TYPE: DNA
<213> ORGANISM: Artificial Sequence
<220> FEATURE:
<223> OTHER INFORMATION: oligonucleotide

<400> SEQUENCE: 263

```
ctgtgtagag agccagcgg                                                 19
```

<210> SEQ ID NO 264
<211> LENGTH: 18
<212> TYPE: DNA
<213> ORGANISM: Artificial Sequence
<220> FEATURE:
<223> OTHER INFORMATION: oligonucleotide

<400> SEQUENCE: 264

```
gcctcctctt ccacctcc                                                  18
```

<210> SEQ ID NO 265
<211> LENGTH: 113
<212> TYPE: PRT
<213> ORGANISM: Homo sapiens

<400> SEQUENCE: 265

Met Ser Arg Pro Leu Leu Glu Arg Pro Ser Tyr Ser Leu Glu Glu Ser
 1               5                  10                  15

Ser Pro Ala Ala Gly Phe Arg Asn Val Cys Ser Lys Leu Val Pro Ala
            20                  25                  30

His Leu Lys Gln Ser Ser Glu Lys Val Cys Arg Asn Leu Pro Leu Pro
        35                  40                  45

Ser Pro Ser Ser Cys Val Ala Phe Val Thr Ser Phe Leu Gln Gly Ser
    50                  55                  60

Ser Gly Gly Gly Ser Arg Glu Ala Ala Thr Trp Leu Cys Met Trp Glu
65                  70                  75                  80

Ser Pro Ala Ser Ser Leu His Pro His Ser Arg Thr Ala Lys Leu Gly
                85                  90                  95

Phe Phe His Glu Glu Ala Thr Leu Met Ser Ser Leu Val Gln Leu Ser
            100                 105                 110

Gly

<210> SEQ ID NO 266
<211> LENGTH: 85
<212> TYPE: PRT
<213> ORGANISM: Homo sapiens

<400> SEQUENCE: 266

Met Ser Ser Gly Phe Leu His Thr Ser Phe Ser Trp Val Arg Leu Ala
1               5                   10                  15

Val Gln Ser Gly Cys Gly Gly Leu Arg Arg Lys Gly His Trp Ser
                20                  25                  30

Ser Pro Arg Phe Gly Leu Arg Gln Val His Ser Arg Tyr His Pro Thr
            35                  40                  45

Phe Leu Ser Lys Glu Gln Ala Ser His Thr Tyr Asn Pro Phe Pro Thr
    50                  55                  60

Leu Leu Met Tyr Pro Leu Cys Gly Thr Ser Asn Gly Gly Gln Ala Asp
65                  70                  75                  80

Leu Pro Pro Ala Ile
                85

<210> SEQ ID NO 267
<211> LENGTH: 88
<212> TYPE: PRT
<213> ORGANISM: Homo sapiens

<400> SEQUENCE: 267

Met Leu Leu Gln Ala Ser Thr Cys Asn Met Leu Thr Tyr Lys Ser Lys
1               5                   10                  15

Ile Ser Asp Gln Val Ala Gly Thr Ala Gly Ala Cys Gln Ala Ser Gly
                20                  25                  30

Tyr Leu His Asp Ser Phe Pro Cys Gly Tyr Gly Arg Ala Trp Pro Phe
            35                  40                  45

Gln Gly Ser Gln Thr Ser Tyr Thr Lys Ala Gly Leu Pro Gln Ser Gly
    50                  55                  60

Tyr Phe Lys Gly Gly Lys Gln Lys Lys Gln His Met Tyr Asn Trp Lys
65                  70                  75                  80

Pro Gly Gly Gly Lys Arg Gly Gln
                85

<210> SEQ ID NO 268
<211> LENGTH: 59
<212> TYPE: PRT
<213> ORGANISM: Homo sapiens

<400> SEQUENCE: 268

Met Leu Gly Pro Gly Leu Cys Leu Ser Phe Gly Tyr Pro Gly Ala Ala
1               5                   10                  15

Pro Ala Ala Gly Pro Ala Gly Pro Gly Thr Pro Gly Pro Gly Glu Thr
                20                  25                  30

-continued

```
Pro His Arg Gly Asp Pro Arg Arg Thr His Ser Val Pro Ala Ala Ala
        35                  40                  45
Glu Ala Gln Ala Leu Gly Gly Arg Gly Phe Gly
    50                  55
```

US 6,706,869 B1

MAP KINASE PHOSPHATASES AND POLYNUCLEOTIDES ENCODING THEM

This application is a continuation-in-part of the following applications:
(1) provisional application Ser. No. 60/075,118, filed Feb. 11, 1998, now abandoned;
(2) application Ser. No. 09/248,059, filed Feb. 10, 1999 (now abandoned); which is a continuation-in-part of provisional application Ser. No. 60/075,118, filed Feb. 11, 1998, now abandoned;
(3) provisional application Ser. No. 60/080,969, filed Apr. 7, 1998, now abandoned;
(4) application Ser. No. 09/287,150, filed Apr. 6, 1999 (now abandoned); which is a continuation-in-part of provisional application Ser. No. 60/080,969, filed Apr. 7, 1998, now abandoned;
(5) provisional application Ser. No. 60/085,472, filed May 14, 1998;
(6) provisional application Ser. No. 60/096,824, filed Aug. 17, 1998;
(7) provisional application Ser. No. 60/099,950, filed Sep. 11, 1998;
(8) provisional application Ser. No. 60/099,843, filed Sep. 11, 1998;
(9) provisional application Ser. No. 60/100,424, filed Sep. 15, 1998;
(10) provisional application Ser. No. 60/102,329, filed Sep. 29, 1998;
(11) provisional application Ser. No. 60/103,615, filed Oct. 9, 1998;
(12) provisional application Ser. No. 60/111,799, filed Dec. 11, 1998;
(13) provisional application Ser. No. 60/112,159, filed Dec. 14, 1998;
(14) provisional application Ser. No. 60/114,415, filed Dec. 31, 1998;
all of which are incorporated by reference herein.

FIELD OF THE INVENTION

The present invention provides novel polynucleotides and proteins encoded by such polynucleotides, along with therapeutic, diagnostic and research utilities for these polynucleotides and proteins.

BACKGROUND OF THE INVENTION

Technology aimed at the discovery of protein factors (including e.g., cytokines, such as lymphokines, interferons, CSFs and interleukins) has matured rapidly over the past decade. The now routine hybridization cloning and expression cloning techniques clone novel polynucleotides "directly" in the sense that they rely on information directly related to the discovered protein (i.e., partial DNA/amino acid sequence of the protein in the case of hybridization cloning; activity of the protein in the case of expression cloning). More recent "indirect" cloning techniques such as signal sequence cloning, which isolates DNA sequences based on the presence of a now well-recognized secretory leader sequence motif, as well as various PCR-based or low stringency hybridization cloning techniques, have advanced the state of the art by making available large numbers of DNA/amino acid sequences for proteins that are known to have biological activity by virtue of their secreted nature in the case of leader sequence cloning, or by virtue of the cell or tissue source in the case of PCR-based techniques. It is to these proteins and the polynucleotides encoding them that the present invention is directed.

SUMMARY OF THE INVENTION

In one embodiment, the present invention provides a composition comprising an isolated polynucleotide selected from the group consisting of:

(a) a polynucleotide comprising the nucleotide sequence of SEQ ID NO:1;
(b) a polynucleotide comprising the nucleotide sequence of SEQ ID NO:1 from nucleotide 29 to nucleotide 253;
(c) a polynucleotide comprising the nucleotide sequence of the full-length protein coding sequence of clone ya15_1 deposited under accession number ATCC 98650;
(d) a polynucleotide encoding the full-length protein encoded by the cDNA insert of clone ya15_1 deposited under accession number ATCC 98650;
(e) a polynucleotide comprising the nucleotide sequence of a mature protein coding sequence of clone ya15_1 deposited under accession number ATCC 98650;
(f) a polynucleotide encoding a mature protein encoded by the cDNA insert of clone ya15_1 deposited under accession number ATCC 98650;
(g) a polynucleotide encoding a protein comprising the amino acid sequence of SEQ ID NO:2;
(h) a polynucleotide encoding a protein comprising a fragment of the amino acid sequence of SEQ ID NO:2 having biological activity, the fragment comprising eight contiguous amino acids of SEQ ID NO:2;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:1.

Preferably, such polynucleotide comprises the nucleotide sequence of SEQ ID NO:1 from nucleotide 29 to nucleotide 253; the nucleotide sequence of the full-length protein coding sequence of clone ya15_1 deposited under accession number ATCC 98650; or the nucleotide sequence of a mature protein coding sequence of clone ya15_1 deposited under accession number ATCC 98650. In other preferred embodiments, the polynucleotide encodes the full-length or a mature protein encoded by the cDNA insert of clone ya15_1 deposited under accession number ATCC 98650. In further preferred embodiments, the present invention provides a polynucleotide encoding a protein comprising a fragment of the amino acid sequence of SEQ ID NO:2 having biological activity, the fragment preferably comprising eight (more preferably twenty, most preferably thirty) contiguous amino acids of SEQ ID NO:2, or a polynucleotide encoding a protein comprising a fragment of the amino acid sequence of SEQ ID NO:2 having biological activity, the fragment comprising the amino acid sequence from amino acid 32 to amino acid 41 of SEQ ID NO:2.

Other embodiments provide the gene corresponding to the cDNA sequence of SEQ ID NO:1.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:1, but excluding the poly(A) tail at the 3' end of SEQ ID NO:1; and
    (ab) the nucleotide sequence of the cDNA insert of clone ya15_1 deposited under accession number ATCC 98650;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:1, but excluding the poly(A) tail at the 3' end of SEQ ID NO:1; and
    (bb) the nucleotide sequence of the cDNA insert of clone ya15_1 deposited under accession number ATCC 98650;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:1, and extending contiguously from a nucleotide sequence corresponding to the 5' end of SEQ ID NO:1 to a nucleotide sequence corresponding to the 3' end of SEQ ID NO:1, but excluding the poly(A) tail at the 3' end of SEQ ID NO:1. Also preferably the polynucleotide isolated according to the above process comprises a nucleotide sequence corresponding to the cDNA sequence of SEQ ID NO:1 from nucleotide 29 to nucleotide 253, and extending contiguously from a nucleotide sequence corresponding to the 5' end of said sequence of SEQ ID NO:1 from nucleotide 29 to nucleotide 253, to a nucleotide sequence corresponding to the 3' end of said sequence of SEQ ID NO:1 from nucleotide 29 to nucleotide 253.

In other embodiments, the present invention provides a composition comprising a protein, wherein said protein comprises an amino acid sequence selected from the group consisting of:
  (a) the amino acid sequence of SEQ ID NO:2;
  (b) a fragment of the amino acid sequence of SEQ ID NO:2, the fragment comprising eight contiguous amino acids of SEQ ID NO:2; and
  (c) the amino acid sequence encoded by the cDNA insert of clone ya15_1 deposited under accession number ATCC 98650;
the protein being substantially free from other mammalian proteins. Preferably such protein comprises the amino acid sequence of SEQ ID NO:2. In further preferred embodiments, the present invention provides a protein comprising a fragment of the amino acid sequence of SEQ ID NO:2 having biological activity, the fragment preferably comprising eight (more preferably twenty, most preferably thirty) contiguous amino acids of SEQ ID NO:2, or a protein comprising a fragment of the amino acid sequence of SEQ ID NO:2 having biological activity, the fragment comprising the amino acid sequence from amino acid 32 to amino acid 41 of SEQ ID NO:2.

In one embodiment, the present invention provides a composition comprising an isolated polynucleotide selected from the group consisting of:
  (a) a polynucleotide comprising the nucleotide sequence of SEQ ID NO:3;
  (b) a polynucleotide comprising the nucleotide sequence of SEQ ID NO:3 from nucleotide 151 to nucleotide 288;
  (c) a polynucleotide comprising the nucleotide sequence of SEQ ID NO:3 from nucleotide 196 to nucleotide 288;
  (d) a polynucleotide comprising the nucleotide sequence of the full-length protein coding sequence of clone ya24_1 deposited under accession number ATCC 98650;
  (e) a polynucleotide encoding the full-length protein encoded by the cDNA insert of clone ya24_1 deposited under accession number ATCC 98650;
  (f) a polynucleotide comprising the nucleotide sequence of a mature protein coding sequence of clone ya24_1 deposited under accession number ATCC 98650;
  (g) a polynucleotide encoding a mature protein encoded by the cDNA insert of clone ya24_1 deposited under accession number ATCC 98650;
  (h) a polynucleotide encoding a protein comprising the amino acid sequence of SEQ ID NO:4;
  (i) a polynucleotide encoding a protein comprising a fragment of the amino acid sequence of SEQ ID NO:4 having biological activity, the fragment comprising eight contiguous amino acids of SEQ ID NO:4;
  (j) a polynucleotide which is an allelic variant of a polynucleotide of (a)–(g) above;
  (k) a polynucleotide which encodes a species homologue of the protein of (h) or (i) above;
  (l) a polynucleotide that hybridizes under stringent conditions to any one of the polynucleotides specified in (a)–(i); and
  (m) a polynucleotide that hybridizes under stringent conditions to any one of the polynucleotides specified in (a)–(i) and that has a length that is at least 25% of the length of SEQ ID NO:3.

Preferably, such polynucleotide comprises the nucleotide sequence of SEQ ID NO:3 from nucleotide 151 to nucleotide 288; the nucleotide sequence of SEQ ID NO:3 from nucleotide 196 to nucleotide 288; the nucleotide sequence of the full-length protein coding sequence of clone ya24_1 deposited under accession number ATCC 98650; or the nucleotide sequence of a mature protein coding sequence of clone ya24_1 deposited under accession number ATCC 98650. In other preferred embodiments, the polynucleotide encodes the full-length or a mature protein encoded by the cDNA insert of clone ya24_1 deposited under accession number ATCC 98650. In further preferred embodiments, the present invention provides a polynucleotide encoding a protein comprising a fragment of the amino acid sequence of SEQ ID NO:4 having biological activity, the fragment preferably comprising eight (more preferably twenty, most preferably thirty) contiguous amino acids of SEQ ID NO:4, or a polynucleotide encoding a protein comprising a fragment of the amino acid sequence of SEQ ID NO:4 having biological activity, the fragment comprising the amino acid sequence from amino acid 18 to amino acid 27 of SEQ ID NO:4.

Other embodiments provide the gene corresponding to the cDNA sequence of SEQ ID NO:3.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:3, but excluding the poly(A) tail at the 3' end of SEQ ID NO:3; and
    (ab) the nucleotide sequence of the cDNA insert of clone ya24_1 deposited under accession number ATCC 98650;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:3, but excluding the poly(A) tail at the 3' end of SEQ ID NO:3; and
    (bb) the nucleotide sequence of the cDNA insert of clone ya24_1 deposited under accession number ATCC 98650;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:3, and extending contiguously from a nucleotide sequence corresponding to the 5' end of SEQ ID NO:3 to a nucleotide sequence corresponding to the 3' end of SEQ ID NO:3, but excluding the poly(A) tail at the 3' end of SEQ ID NO:3. Also preferably the polynucleotide isolated according to the above process comprises a nucleotide sequence corresponding to the cDNA sequence of SEQ ID NO:3 from nucleotide 151 to nucleotide 288, and extending contiguously from a nucleotide sequence corresponding to the 5' end of said sequence of SEQ ID NO:3 from nucleotide 151 to nucleotide 288, to a nucleotide sequence corresponding to the 3' end of said sequence of SEQ ID NO:3 from nucleotide 151 to nucleotide 288. Also preferably the polynucleotide isolated according to the above process comprises a nucleotide sequence corresponding to the cDNA sequence of SEQ ID NO:3 from nucleotide 196 to nucleotide 288, and extending contiguously from a nucleotide sequence corresponding to the 5' end of said sequence of SEQ ID NO:3 from nucleotide 196 to nucleotide 288, to a nucleotide sequence corresponding to the 3' end of said sequence of SEQ ID NO:3 from nucleotide 196 to nucleotide 288.

In other embodiments, the present invention provides a composition comprising a protein, wherein said protein comprises an amino acid sequence selected from the group consisting of:
(a) the amino acid sequence of SEQ ID NO:4;
(b) a fragment of the amino acid sequence of SEQ ID NO:4, the fragment comprising eight contiguous amino acids of SEQ ID NO:4; and
(c) the amino acid sequence encoded by the cDNA insert of clone ya24_1 deposited under accession number ATCC 98650;

the protein being substantially free from other mammalian proteins. Preferably such protein comprises the amino acid sequence of SEQ ID NO:4. In further preferred embodiments, the present invention provides a protein comprising a fragment of the amino acid sequence of SEQ ID NO:4 having biological activity, the fragment preferably comprising eight (more preferably twenty, most preferably thirty) contiguous amino acids of SEQ ID NO:4, or a protein comprising a fragment of the amino acid sequence of SEQ ID NO:4 having biological activity, the fragment comprising the amino acid sequence from amino acid 18 to amino acid 27 of SEQ ID NO:4.

In one embodiment, the present invention provides a composition comprising an isolated polynucleotide selected from the group consisting of:
(a) a polynucleotide comprising the nucleotide sequence of SEQ ID NO:5;
(b) a polynucleotide comprising the nucleotide sequence of SEQ ID NO:5 from nucleotide 615 to nucleotide 908;
(c) a polynucleotide comprising the nucleotide sequence of SEQ ID NO:5 from nucleotide 774 to nucleotide 908;
(d) a polynucleotide comprising the nucleotide sequence of the full-length protein coding sequence of clone yb42_1 deposited under accession number ATCC 98650;
(e) a polynucleotide encoding the full-length protein encoded by the cDNA insert of clone yb42_1 deposited under accession number ATCC 98650;
(f) a polynucleotide comprising the nucleotide sequence of a mature protein coding sequence of clone yb42_1 deposited under accession number ATCC 98650;
(g) a polynucleotide encoding a mature protein encoded by the cDNA insert of clone yb42_1 deposited under accession number ATCC 98650;
(h) a polynucleotide encoding a protein comprising the amino acid sequence of SEQ ID NO:6;
(i) a polynucleotide encoding a protein comprising a fragment of the amino acid sequence of SEQ ID NO:6 having biological activity, the fragment comprising eight contiguous amino acids of SEQ ID NO:6;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:5.

Preferably, such polynucleotide comprises the nucleotide sequence of SEQ ID NO:5 from nucleotide 615 to nucleotide 908; the nucleotide sequence of SEQ ID NO:5 from nucleotide 774 to nucleotide 908; the nucleotide sequence of the full-length protein coding sequence of clone yb42_1 deposited under accession number ATCC 98650; or the nucleotide sequence of a mature protein coding sequence of clone yb42_1 deposited under accession number ATCC 98650. In other preferred embodiments, the polynucleotide encodes the full-length or a mature protein encoded by the cDNA insert of clone yb42_1 deposited under accession number ATCC 98650. In further preferred embodiments, the present invention provides a polynucleotide encoding a protein comprising a fragment of the amino acid sequence of SEQ ID NO:6 having biological activity, the fragment preferably comprising eight (more preferably twenty, most preferably thirty) contiguous amino acids of SEQ ID NO:6, or a polynucleotide encoding a protein comprising a fragment of the amino acid sequence of SEQ ID NO:6 having biological activity, the fragment comprising the amino acid sequence from amino acid 44 to amino acid 53 of SEQ ID NO:6.

Other embodiments provide the gene corresponding to the cDNA sequence of SEQ ID NO:5.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:5, but excluding the poly(A) tail at the 3' end of SEQ ID NO:5; and
    (ab) the nucleotide sequence of the cDNA insert of clone yb42_1 deposited under accession number ATCC 98650;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:5, but excluding the poly(A) tail at the 3' end of SEQ ID NO:5; and
    (bb) the nucleotide sequence of the cDNA insert of clone yb42_1 deposited under accession number ATCC 98650;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:5, and extending contiguously from a nucleotide sequence corresponding to the 5' end of SEQ ID NO:5 to a nucleotide sequence corresponding to the 3' end of SEQ ID NO:5, but excluding the poly(A) tail at the 3' end of SEQ ID NO:5. Also preferably the polynucleotide isolated according to the above process comprises a nucleotide sequence corresponding to the cDNA sequence of SEQ ID NO:5 from nucleotide 615 to nucleotide 908, and extending contiguously from a nucleotide sequence corresponding to the 5' end of said sequence of SEQ ID NO:5 from nucleotide 615 to nucleotide 908, to a nucleotide sequence corresponding to the 3' end of said sequence of SEQ ID NO:5 from nucleotide 615 to nucleotide 908. Also preferably the polynucleotide isolated according to the above process comprises a nucleotide sequence corresponding to the cDNA sequence of SEQ ID NO:5 from nucleotide 774 to nucleotide 908, and extending contiguously from a nucleotide sequence corresponding to the 5' end of said sequence of SEQ ID NO:5 from nucleotide 774 to nucleotide 908, to a nucleotide sequence corresponding to the 3' end of said sequence of SEQ ID NO:5 from nucleotide 774 to nucleotide 908.

In other embodiments, the present invention provides a composition comprising a protein, wherein said protein comprises an amino acid sequence selected from the group consisting of:

(a) the amino acid sequence of SEQ ID NO:6;
(b) a fragment of the amino acid sequence of SEQ ID NO:6, the fragment comprising eight contiguous amino acids of SEQ ID NO:6; and
(c) the amino acid sequence encoded by the cDNA insert of clone yb42_1 deposited under accession number ATCC 98650;

the protein being substantially free from other mammalian proteins. Preferably such protein comprises the amino acid sequence of SEQ ID NO:6. In further preferred embodiments, the present invention provides a protein comprising a fragment of the amino acid sequence of SEQ ID NO:6 having biological activity, the fragment preferably comprising eight (more preferably twenty, most preferably thirty) contiguous amino acids of SEQ ID NO:6, or a protein comprising a fragment of the amino acid sequence of SEQ ID NO:6 having biological activity, the fragment comprising the amino acid sequence from amino acid 44 to amino acid 53 of SEQ ID NO:6.

In one embodiment, the present invention provides a composition comprising an isolated polynucleotide selected from the group consisting of:

(a) a polynucleotide comprising the nucleotide sequence of SEQ ID NO:7;
(b) a polynucleotide comprising the nucleotide sequence of SEQ ID NO:7 from nucleotide 1203 to nucleotide 2327;
(c) a polynucleotide comprising the nucleotide sequence of the full-length protein coding sequence of clone yc9_1 deposited under accession number ATCC 98650;
(d) a polynucleotide encoding the full-length protein encoded by the cDNA insert of clone yc9_1 deposited under accession number ATCC 98650;
(e) a polynucleotide comprising the nucleotide sequence of a mature protein coding sequence of clone yc9_1 deposited under accession number ATCC 98650;
(f) a polynucleotide encoding a mature protein encoded by the cDNA insert of clone yc9_1 deposited under accession number ATCC 98650;
(g) a polynucleotide encoding a protein comprising the amino acid sequence of SEQ ID NO:8;
(h) a polynucleotide encoding a protein comprising a fragment of the amino acid sequence of SEQ ID NO:8 having biological activity, the fragment comprising eight contiguous amino acids of SEQ ID NO:8;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:7.

Preferably, such polynucleotide comprises the nucleotide sequence of SEQ ID NO:7 from nucleotide 1203 to nucleotide 2327; the nucleotide sequence of the full-length protein coding sequence of clone yc9_1 deposited under accession number ATCC 98650; or the nucleotide sequence of a mature protein coding sequence of clone yc9_1 deposited under accession number ATCC 98650. In other preferred embodiments, the polynucleotide encodes the full-length or a mature protein encoded by the cDNA insert of clone yc9_1 deposited under accession number ATCC 98650. In further preferred embodiments, the present invention provides a polynucleotide encoding a protein comprising a fragment of the amino acid sequence of SEQ ID NO:8 having biological activity, the fragment preferably comprising eight (more preferably twenty, most preferably thirty) contiguous amino acids of SEQ ID NO:8, or a polynucleotide encoding a protein comprising a fragment of the amino acid sequence of SEQ ID NO:8 having biological activity, the fragment comprising the amino acid sequence from amino acid 182 to amino acid 191 of SEQ ID NO:8.

Other embodiments provide the gene corresponding to the cDNA sequence of SEQ ID NO:7.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:7, but excluding the poly(A) tail at the 3' end of SEQ ID NO:7; and
    (ab) the nucleotide sequence of the cDNA insert of clone yc9_1 deposited under accession number ATCC 98650;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:7, but excluding the poly(A) tail at the 3' end of SEQ ID NO:7; and
    (bb) the nucleotide sequence of the cDNA insert of clone yc9_1 deposited under accession number ATCC 98650;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:7, and extending contiguously from a nucleotide sequence corresponding to the 5' end of SEQ ID NO:7 to a nucleotide sequence corresponding to the 3' end of SEQ ID NO:7, but excluding the poly(A) tail at the 3' end of SEQ ID NO:7. Also preferably the polynucleotide isolated according to the above process comprises a nucleotide sequence corresponding to the cDNA sequence of SEQ ID NO:7 from nucleotide 1203 to nucleotide 2327, and extending contiguously from a nucleotide sequence corresponding to the 5' end of said sequence of SEQ ID NO:7 from nucleotide 1203 to nucleotide 2327, to a nucleotide sequence corresponding to the 3' end of said sequence of SEQ ID NO:7 from nucleotide 1203 to nucleotide 2327.

In other embodiments, the present invention provides a composition comprising a protein, wherein said protein comprises an amino acid sequence selected from the group consisting of:

(a) the amino acid sequence of SEQ ID NO:8;
(b) a fragment of the amino acid sequence of SEQ ID NO:8, the fragment comprising eight contiguous amino acids of SEQ ID NO:8; and
(c) the amino acid sequence encoded by the cDNA insert of clone yc9_1 deposited under accession number ATCC 98650;

the protein being substantially free from other mammalian proteins. Preferably such protein comprises the amino acid sequence of SEQ ID NO:8. In further preferred embodiments, the present invention provides a protein comprising a fragment of the amino acid sequence of SEQ ID NO:8 having biological activity, the fragment preferably comprising eight (more preferably twenty, most preferably thirty) contiguous amino acids of SEQ ID NO:8, or a protein comprising a fragment of the amino acid sequence of SEQ ID NO:8 having biological activity, the fragment comprising the amino acid sequence from amino acid 182 to amino acid 191 of SEQ ID NO:8.

In one embodiment, the present invention provides a composition comprising an isolated polynucleotide selected from the group consisting of:

(a) a polynucleotide comprising the nucleotide sequence of SEQ ID NO:9;
(b) a polynucleotide comprising the nucleotide sequence of SEQ ID NO:9 from nucleotide 230 to nucleotide 823;
(c) a polynucleotide comprising the nucleotide sequence of SEQ ID NO:9 from nucleotide 584 to nucleotide 823;
(d) a polynucleotide comprising the nucleotide sequence of the full-length protein coding sequence of clone yc19_1 deposited under accession number ATCC 98650;
(e) a polynucleotide encoding the full-length protein encoded by the cDNA insert of clone yc19_1 deposited under accession number ATCC 98650;
(f) a polynucleotide comprising the nucleotide sequence of a mature protein coding sequence of clone yc19_1 deposited under accession number ATCC 98650;
(g) a polynucleotide encoding a mature protein encoded by the cDNA insert of clone yc19_1 deposited under accession number ATCC 98650;
(h) a polynucleotide encoding a protein comprising the amino acid sequence of SEQ ID NO:10;
(i) a polynucleotide encoding a protein comprising a fragment of the amino acid sequence of SEQ ID NO:10 having biological activity, the fragment comprising eight contiguous amino acids of SEQ ID NO:10;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:9.

Preferably, such polynucleotide comprises the nucleotide sequence of SEQ ID NO:9 from nucleotide 230 to nucleotide 823; the nucleotide sequence of SEQ ID NO:9 from nucleotide 584 to nucleotide 823; the nucleotide sequence of the full-length protein coding sequence of clone yc19_1 deposited under accession number ATCC 98650; or the nucleotide sequence of a mature protein coding sequence of clone yc19_1 deposited under accession number ATCC 98650. In other preferred embodiments, the polynucleotide encodes the full-length or a mature protein encoded by the cDNA insert of clone yc19_1 deposited under accession number ATCC 98650. In further preferred embodiments, the present invention provides a polynucleotide encoding a protein comprising a fragment of the amino acid sequence of SEQ ID NO:10 having biological activity, the fragment preferably comprising eight (more preferably twenty, most preferably thirty) contiguous amino acids of SEQ ID NO:10, or a polynucleotide encoding a protein comprising a fragment of the amino acid sequence of SEQ ID NO:10 having biological activity, the fragment comprising the amino acid sequence from amino acid 94 to amino acid 103 of SEQ ID NO:10.

Other embodiments provide the gene corresponding to the cDNA sequence of SEQ ID NO:9.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:9, but excluding the poly(A) tail at the 3' end of SEQ ID NO:9; and
    (ab) the nucleotide sequence of the cDNA insert of clone yc19_1 deposited under accession number ATCC 98650;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:9, but excluding the poly(A) tail at the 3' end of SEQ ID NO:9; and
    (bb) the nucleotide sequence of the cDNA insert of clone yc19_1 deposited under accession number ATCC 98650;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:9, and extending contiguously from a nucleotide sequence corresponding to the 5' end of SEQ ID NO:9 to a nucleotide sequence corresponding to the 3' end of SEQ ID NO:9, but excluding the poly(A) tail at the 3' end of SEQ ID NO:9. Also preferably the polynucleotide isolated according to the above process comprises a nucleotide sequence corresponding to the cDNA sequence of SEQ ID NO:9 from nucleotide 230 to nucleotide 823, and extending contiguously from a nucleotide sequence corresponding to the 5' end of said sequence of SEQ ID NO:9 from nucleotide 230 to nucleotide 823, to a nucleotide sequence corresponding to the 3' end of said sequence of SEQ ID NO:9 from nucleotide 230 to nucleotide 823. Also preferably the polynucleotide isolated according to the above process comprises a nucleotide sequence corresponding to the cDNA sequence of SEQ ID NO:9 from nucleotide 584 to nucleotide 823, and extending contiguously from a nucleotide sequence corresponding to the 5' end of said sequence of SEQ ID NO:9 from nucleotide 584 to nucleotide 823, to a nucleotide sequence corresponding to the 3' end of said sequence of SEQ ID NO:9 from nucleotide 584 to nucleotide 823.

In other embodiments, the present invention provides a composition comprising a protein, wherein said protein comprises an amino acid sequence selected from the group consisting of:

(a) the amino acid sequence of SEQ ID NO:10;
(b) a fragment of the amino acid sequence of SEQ ID NO:10, the fragment comprising eight contiguous amino acids of SEQ ID NO:10; and
(c) the amino acid sequence encoded by the cDNA insert of clone yc19_1 deposited under accession number ATCC 98650;

the protein being substantially free from other mammalian proteins. Preferably such protein comprises the amino acid sequence of SEQ ID NO:10. In further preferred embodiments, the present invention provides a protein comprising a fragment of the amino acid sequence of SEQ ID NO:10 having biological activity, the fragment preferably comprising eight (more preferably twenty, most preferably thirty) contiguous amino acids of SEQ ID NO:10, or a protein comprising a fragment of the amino acid sequence of SEQ ID NO:10 having biological activity, the fragment comprising the amino acid sequence from amino acid 94 to amino acid 103 of SEQ ID NO:10.

In one embodiment, the present invention provides a composition comprising an isolated polynucleotide selected from the group consisting of:

(a) a polynucleotide comprising the nucleotide sequence of SEQ ID NO:11;
(b) a polynucleotide comprising the nucleotide sequence of SEQ ID NO:11 from nucleotide 292 to nucleotide 534;
(c) a polynucleotide comprising the nucleotide sequence of the full-length protein coding sequence of clone yc20_1 deposited under accession number ATCC 98650;
(d) a polynucleotide encoding the full-length protein encoded by the cDNA insert of clone yc20_1 deposited under accession number ATCC 98650;
(e) a polynucleotide comprising the nucleotide sequence of a mature protein coding sequence of clone yc20_1 deposited under accession number ATCC 98650;
(f) a polynucleotide encoding a mature protein encoded by the cDNA insert of clone yc20_1 deposited under accession number ATCC 98650;
(g) a polynucleotide encoding a protein comprising the amino acid sequence of SEQ ID NO:12;
(h) a polynucleotide encoding a protein comprising a fragment of the amino acid sequence of SEQ ID NO:12 having biological activity, the fragment comprising eight contiguous amino acids of SEQ ID NO:12;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:11.

Preferably, such polynucleotide comprises the nucleotide sequence of SEQ ID NO:11 from nucleotide 292 to nucleotide 534; the nucleotide sequence of the full-length protein coding sequence of clone yc20__1 deposited under accession number ATCC 98650; or the nucleotide sequence of a mature protein coding sequence of clone yc20__1 deposited under accession number ATCC 98650. In other preferred embodiments, the polynucleotide encodes the full-length or a mature protein encoded by the cDNA insert of clone yc20__1 deposited under accession number ATCC 98650. In further preferred embodiments, the present invention provides a polynucleotide encoding a protein comprising a fragment of the amino acid sequence of SEQ ID NO:12 having biological activity, the fragment preferably comprising eight (more preferably twenty, most preferably thirty) contiguous amino acids of SEQ ID NO:12, or a polynucleotide encoding a protein comprising a fragment of the amino acid sequence of SEQ ID NO:12 having biological activity, the fragment comprising the amino acid sequence from amino acid 35 to amino acid 44 of SEQ ID NO:12.

Other embodiments provide the gene corresponding to the cDNA sequence of SEQ ID NO:11.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:11, but excluding the poly(A) tail at the 3' end of SEQ ID NO:11; and
(ab) the nucleotide sequence of the cDNA insert of clone yc20__1 deposited under accession number ATCC 98650;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:11, but excluding the poly(A) tail at the 3' end of SEQ ID NO:11; and
(bb) the nucleotide sequence of the cDNA insert of clone yc20__1 deposited under accession number ATCC 98650;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:11, and extending contiguously from a nucleotide sequence corresponding to the 5' end of SEQ ID NO:11 to a nucleotide sequence corresponding to the 3' end of SEQ ID NO:11, but excluding the poly(A) tail at the 3' end of SEQ ID NO:11. Also preferably the polynucleotide isolated according to the above process comprises a nucleotide sequence corresponding to the cDNA sequence of SEQ ID NO:11 from nucleotide 292 to nucleotide 534, and extending contiguously from a nucleotide sequence corresponding to the 5' end of said sequence of SEQ ID NO:11 from nucleotide 292 to nucleotide 534, to a nucleotide sequence corresponding to the 3' end of said sequence of SEQ ID NO:11 from nucleotide 292 to nucleotide 534.

In other embodiments, the present invention provides a composition comprising a protein, wherein said protein comprises an amino acid sequence selected from the group consisting of:

(a) the amino acid sequence of SEQ ID NO:12;
(b) a fragment of the amino acid sequence of SEQ ID NO:12, the fragment comprising eight contiguous amino acids of SEQ ID NO:12; and
(c) the amino acid sequence encoded by the cDNA insert of clone yc20__1 deposited under accession number ATCC 98650;

the protein being substantially free from other mammalian proteins. Preferably such protein comprises the amino acid sequence of SEQ ID NO:12. In further preferred embodiments, the present invention provides a protein comprising a fragment of the amino acid sequence of SEQ ID NO:12 having biological activity, the fragment preferably comprising eight (more preferably twenty, most preferably thirty) contiguous amino acids of SEQ ID NO:12, or a protein comprising a fragment of the amino acid sequence of SEQ ID NO:12 having biological activity, the fragment comprising the amino acid sequence from amino acid 35 to amino acid 44 of SEQ ID NO:12.

In one embodiment, the present invention provides a composition comprising an isolated polynucleotide selected from the group consisting of:

(a) a polynucleotide comprising the nucleotide sequence of SEQ ID NO:13;
(b) a polynucleotide comprising the nucleotide sequence of SEQ ID NO:13 from nucleotide 45 to nucleotide 590;
(c) a polynucleotide comprising the nucleotide sequence of SEQ ID NO:13 from nucleotide 126 to nucleotide 590;
(d) a polynucleotide comprising the nucleotide sequence of the full-length protein coding sequence of clone ya9__1 deposited under accession number ATCC 98724;
(e) a polynucleotide encoding the full-length protein encoded by the cDNA insert of clone ya9__1 deposited under accession number ATCC 98724;
(f) a polynucleotide comprising the nucleotide sequence of a mature protein coding sequence of clone ya9__1 deposited under accession number ATCC 98724;
(g) a polynucleotide encoding a mature protein encoded by the cDNA insert of clone ya9__1 deposited under accession number ATCC 98724;
(h) a polynucleotide encoding a protein comprising the amino acid sequence of SEQ ID NO:14;

(i) a polynucleotide encoding a protein comprising a fragment of the amino acid sequence of SEQ ID NO:14 having biological activity, the fragment comprising eight contiguous amino acids of SEQ ID NO:14;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:13.

Preferably, such polynucleotide comprises the nucleotide sequence of SEQ ID NO:13 from nucleotide 45 to nucleotide 590; the nucleotide sequence of SEQ ID NO:13 from nucleotide 126 to nucleotide 590; the nucleotide sequence of the full-length protein coding sequence of clone ya9_1 deposited under accession number ATCC 98724; or the nucleotide sequence of a mature protein coding sequence of clone ya9_1 deposited under accession number ATCC 98724. In other preferred embodiments, the polynucleotide encodes the full-length or a mature protein encoded by the cDNA insert of clone ya9_1 deposited under accession number ATCC 98724. In further preferred embodiments, the present invention provides a polynucleotide encoding a protein comprising a fragment of the amino acid sequence of SEQ ID NO:14 having biological activity, the fragment preferably comprising eight (more preferably twenty, most preferably thirty) contiguous amino acids of SEQ ID NO:14, or a polynucleotide encoding a protein comprising a fragment of the amino acid sequence of SEQ ID NO:14 having biological activity, the fragment comprising the amino acid sequence from amino acid 86 to amino acid 95 of SEQ ID NO:14.

Other embodiments provide the gene corresponding to the cDNA sequence of SEQ ID NO:13.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:13, but excluding the poly(A) tail at the 3' end of SEQ ID NO:13; and
    (ab) the nucleotide sequence of the cDNA insert of clone ya9_1 deposited under accession number ATCC 98724;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:13, but excluding the poly(A) tail at the 3' end of SEQ ID NO:13; and
    (bb) the nucleotide sequence of the cDNA insert of clone ya9_1 deposited under accession number ATCC 98724;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:13, and extending contiguously from a nucleotide sequence corresponding to the 5' end of SEQ ID NO:13 to a nucleotide sequence corresponding to the 3' end of SEQ ID NO:13, but excluding the poly(A) tail at the 3' end of SEQ ID NO:13. Also preferably the polynucleotide isolated according to the above process comprises a nucleotide sequence corresponding to the cDNA sequence of SEQ ID NO:13 from nucleotide 45 to nucleotide 590, and extending contiguously from a nucleotide sequence corresponding to the 5' end of said sequence of SEQ ID NO:13 from nucleotide 45 to nucleotide 590, to a nucleotide sequence corresponding to the 3' end of said sequence of SEQ ID NO:13 from nucleotide 45 to nucleotide 590. Also preferably the polynucleotide isolated according to the above process comprises a nucleotide sequence corresponding to the cDNA sequence of SEQ ID NO:13 from nucleotide 126 to nucleotide 590, and extending contiguously from a nucleotide sequence corresponding to the 5' end of said sequence of SEQ ID NO:13 from nucleotide 126 to nucleotide 590, to a nucleotide sequence corresponding to the 3' end of said sequence of SEQ ID NO:13 from nucleotide 126 to nucleotide 590.

In other embodiments, the present invention provides a composition comprising a protein, wherein said protein comprises an amino add sequence selected from the group consisting of:

(a) the amino acid sequence of SEQ ID NO:14;

(b) a fragment of the amino acid sequence of SEQ ID NO:14, the fragment comprising eight contiguous amino acids of SEQ ID NO:14; and (c) the amino acid sequence encoded by the cDNA insert of clone ya9_1 deposited under accession number ATCC 98724;

the protein being substantially free from other mammalian proteins. Preferably such protein comprises the amino acid sequence of SEQ ID NO:14. In further preferred embodiments, the present invention provides a protein comprising a fragment of the amino acid sequence of SEQ ID NO:14 having biological activity, the fragment preferably comprising eight (more preferably twenty, most preferably thirty) contiguous amino acids of SEQ ID NO:14, or a protein comprising a fragment of the amino acid sequence of SEQ ID NO:14 having biological activity, the fragment comprising the amino acid sequence from amino acid 86 to amino acid 95 of SEQ ID NO:14.

In one embodiment, the present invention provides a composition comprising an isolated polynucleotide selected from the group consisting of:

(a) a polynucleotide comprising the nucleotide sequence of SEQ ID NO:15;

(b) a polynucleotide comprising the nucleotide sequence of SEQ ID NO:15 from nucleotide 194 to nucleotide 466;

(c) a polynucleotide comprising the nucleotide sequence of SEQ ID NO:15 from nucleotide 338 to nucleotide 466;

(d) a polynucleotide comprising the nucleotide sequence of the full-length protein coding sequence of clone ya11_1 deposited under accession number ATCC 98724;

(e) a polynucleotide encoding the full-length protein encoded by the cDNA insert of clone ya11_1 deposited under accession number ATCC 98724;
(f) a polynucleotide comprising the nucleotide sequence of a mature protein coding sequence of clone ya11_1 deposited under accession number ATCC 98724;
(g) a polynucleotide encoding a mature protein encoded by the cDNA insert of clone ya11_1 deposited under accession number ATCC 98724;
(h) a polynucleotide encoding a protein comprising the amino acid sequence of SEQ ID NO:16;
(i) a polynucleotide encoding a protein comprising a fragment of the amino acid sequence of SEQ ID NO:16 having biological activity, the fragment comprising eight contiguous amino acids of SEQ ID NO:16;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:15.

Preferably, such polynucleotide comprises the nucleotide sequence of SEQ ID NO:15 from nucleotide 194 to nucleotide 466; the nucleotide sequence of SEQ ID NO:15 from nucleotide 338 to nucleotide 466; the nucleotide sequence of the full-length protein coding sequence of clone ya11_1 deposited under accession number ATCC 98724; or the nucleotide sequence of a mature protein coding sequence of clone ya11_1 deposited under accession number ATCC 98724. In other preferred embodiments, the polynucleotide encodes the full-length or a mature protein encoded by the cDNA insert of clone ya11_1 deposited under accession number ATCC 98724. In further preferred embodiments, the present invention provides a polynucleotide encoding a protein comprising a fragment of the amino acid sequence of SEQ ID NO:16 having biological activity, the fragment preferably comprising eight (more preferably twenty, most preferably thirty) contiguous amino acids of SEQ ID NO:16, or a polynucleotide encoding a protein comprising a fragment of the amino acid sequence of SEQ ID NO:16 having biological activity, the fragment comprising the amino acid sequence from amino acid 40 to amino acid 49 of SEQ ID NO:16.

Other embodiments provide the gene corresponding to the cDNA sequence of SEQ ID NO:15.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:15, but excluding the poly(A) tail at the 3' end of SEQ ID NO:15; and
(ab) the nucleotide sequence of the cDNA insert of clone ya11_1 deposited under accession number ATCC 98724;
(ii) hybridizing said probe(s) to human genomic DNA in conditions at least as stringent as 4×SSC at 50 degrees C.; and
(iii) isolating the DNA polynucleotides detected with the probe(s);

and
(b) a process comprising the steps of:
(i) preparing one or more polynucleotide primers that hybridize in 6×SSC at 65 degrees C. to a nucleotide sequence selected from the group consisting of:
(ba) SEQ ID NO:15, but excluding the poly(A) tail at the 3' end of SEQ ID NO:15; and
(bb) the nucleotide sequence of the cDNA insert of clone ya11_1 deposited under accession number ATCC 98724;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:15, and extending contiguously from a nucleotide sequence corresponding to the 5' end of SEQ ID NO:15 to a nucleotide sequence corresponding to the 3' end of SEQ ID NO:15, but excluding the poly(A) tail at the 3' end of SEQ ID NO:15. Also preferably the polynucleotide isolated according to the above process comprises a nucleotide sequence corresponding to the cDNA sequence of SEQ ID NO:15 from nucleotide 194 to nucleotide 466, and extending contiguously from a nucleotide sequence corresponding to the 5' end of said sequence of SEQ ID NO:15 from nucleotide 194 to nucleotide 466, to a nucleotide sequence corresponding to the 3' end of said sequence of SEQ ID NO:15 from nucleotide 194 to nucleotide 466. Also preferably the polynucleotide isolated according to the above process comprises a nucleotide sequence corresponding to the cDNA sequence of SEQ ID NO:15 from nucleotide 338 to nucleotide 466, and extending contiguously from a nucleotide sequence corresponding to the 5' end of said sequence of SEQ ID NO:15 from nucleotide 338 to nucleotide 466, to a nucleotide sequence corresponding to the 3' end of said sequence of SEQ ID NO:15 from nucleotide 338 to nucleotide 466.

In other embodiments, the present invention provides a composition comprising a protein, wherein said protein comprises an amino acid sequence selected from the group consisting of:
(a) the amino acid sequence of SEQ ID NO:16;
(b) a fragment of the amino acid sequence of SEQ ID NO:16, the fragment comprising eight contiguous amino acids of SEQ ID NO:16; and
(c) the amino acid sequence encoded by the cDNA insert of clone ya11_1 deposited under accession number ATCC 98724;

the protein being substantially free from other mammalian proteins. Preferably such protein comprises the amino acid sequence of SEQ ID NO:16. In further preferred embodiments, the present invention provides a protein comprising a fragment of the amino acid sequence of SEQ ID NO:16 having biological activity, the fragment preferably comprising eight (more preferably twenty, most preferably thirty) contiguous amino acids of SEQ ID NO:16, or a protein comprising a fragment of the amino acid sequence of SEQ ID NO:16 having biological activity, the fragment comprising the amino acid sequence from amino acid 40 to amino acid 49 of SEQ ID NO:16.

In one embodiment, the present invention provides a composition comprising an isolated polynucleotide selected from the group consisting of:
(a) a polynucleotide comprising the nucleotide sequence of SEQ ID NO:17;

(b) a polynucleotide comprising the nucleotide sequence of SEQ ID NO:17 from nucleotide 15 to nucleotide 233;
(c) a polynucleotide comprising the nucleotide sequence of SEQ ID NO:17 from nucleotide 174 to nucleotide 233;
(d) a polynucleotide comprising the nucleotide sequence of the full-length protein coding sequence of clone ya28_1 deposited under accession number ATCC 98724;
(e) a polynucleotide encoding the full-length protein encoded by the cDNA insert of clone ya28_1 deposited under accession number ATCC 98724;
(f) a polynucleotide comprising the nucleotide sequence of a mature protein coding sequence of clone ya28_1 deposited under accession number ATCC 98724;
(g) a polynucleotide encoding a mature protein encoded by the cDNA insert of clone ya28_1 deposited under accession number ATCC 98724;
(h) a polynucleotide encoding a protein comprising the amino acid sequence of SEQ ID NO:18;
(i) a polynucleotide encoding a protein comprising a fragment of the amino acid sequence of SEQ ID NO:18 having biological activity, the fragment comprising eight contiguous amino acids of SEQ ID NO:18;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:17.

Preferably, such polynucleotide comprises the nucleotide sequence of SEQ ID NO:17 from nucleotide 15 to nucleotide 233; the nucleotide sequence of SEQ ID NO:17 from nucleotide 174 to nucleotide 233; the nucleotide sequence of the full-length protein coding sequence of clone ya28_1 deposited under accession number ATCC 98724; or the nucleotide sequence of a mature protein coding sequence of clone ya28_1 deposited under accession number ATCC 98724. In other preferred embodiments, the polynucleotide encodes the full-length or a mature protein encoded by the cDNA insert of clone ya28_1 deposited under accession number ATCC 98724. In further preferred embodiments, the present invention provides a polynucleotide encoding a protein comprising a fragment of the amino acid sequence of SEQ ID NO:18 having biological activity, the fragment preferably comprising eight (more preferably twenty, most preferably thirty) contiguous amino acids of SEQ ID NO:18, or a polynucleotide encoding a protein comprising a fragment of the amino acid sequence of SEQ ID NO:18 having biological activity, the fragment comprising the amino acid sequence from amino acid 31 to amino acid 40 of SEQ ID NO:18.

Other embodiments provide the gene corresponding to the cDNA sequence of SEQ ID NO:17.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:17, but excluding the poly(A) tail at the 3' end of SEQ ID NO:17; and
(ab) the nucleotide sequence of the cDNA insert of clone ya28_1 deposited under accession number ATCC 98724;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:17, but excluding the poly(A) tail at the 3' end of SEQ ID NO:17; and
(bb) the nucleotide sequence of the cDNA insert of clone ya28_1 deposited under accession number ATCC 98724;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:17, and extending contiguously from a nucleotide sequence corresponding to the 5' end of SEQ ID NO:17 to a nucleotide sequence corresponding to the 3' end of SEQ ID NO:17, but excluding the poly(A) tail at the 3' end of SEQ ID NO:17. Also preferably the polynucleotide isolated according to the above process comprises a nucleotide sequence corresponding to the cDNA sequence of SEQ ID NO:17 from nucleotide 15 to nucleotide 233, and extending contiguously from a nucleotide sequence corresponding to the 5' end of said sequence of SEQ ID NO:17 from nucleotide 15 to nucleotide 233, to a nucleotide sequence corresponding to the 3' end of said sequence of SEQ ID NO:17 from nucleotide 15 to nucleotide 233. Also preferably the polynucleotide isolated according to the above process comprises a nucleotide sequence corresponding to the cDNA sequence of SEQ ID NO:17 from nucleotide 174 to nucleotide 233, and extending contiguously from a nucleotide sequence corresponding to the 5' end of said sequence of SEQ ID NO:17 from nucleotide 174 to nucleotide 233, to a nucleotide sequence corresponding to the 3' end of said sequence of SEQ ID NO:17 from nucleotide 174 to nucleotide 233.

In other embodiments, the present invention provides a composition comprising a protein, wherein said protein comprises an amino acid sequence selected from the group consisting of:
(a) the amino acid sequence of SEQ ID NO:18;
(b) a fragment of the amino acid sequence of SEQ ID NO:18, the fragment comprising eight contiguous amino acids of SEQ ID NO:18; and
(c) the amino acid sequence encoded by the cDNA insert of clone ya28_1 deposited under accession number ATCC 98724;
the protein being substantially free from other mammalian proteins. Preferably such protein comprises the amino acid sequence of SEQ ID NO:18. In further preferred embodiments, the present invention provides a protein comprising a fragment of the amino acid sequence of SEQ ID NO:18 having biological activity, the fragment preferably comprising eight (more preferably twenty, most preferably thirty) contiguous amino acids of SEQ ID NO:18, or a protein comprising a fragment of the amino acid sequence of SEQ ID NO:18 having biological activity, the fragment comprising the amino acid sequence from amino acid 31 to amino acid 40 of SEQ ID NO:18.

In one embodiment, the present invention provides a composition comprising an isolated polynucleotide selected from the group consisting of:
 (a) a polynucleotide comprising the nucleotide sequence of SEQ ID NO:19;
 (b) a polynucleotide comprising the nucleotide sequence of SEQ ID NO:19 from nucleotide 102 to nucleotide 461;
 (c) a polynucleotide comprising the nucleotide sequence of the full-length protein coding sequence of clone yb81_1 deposited under accession number ATCC 98724;
 (d) a polynucleotide encoding the full-length protein encoded by the cDNA insert of clone yb81_1 deposited under accession number ATCC 98724;
 (e) a polynucleotide comprising the nucleotide sequence of a mature protein coding sequence of clone yb81_1 deposited under accession number ATCC 98724;
 (f) a polynucleotide encoding a mature protein encoded by the cDNA insert of clone yb81_1 deposited under accession number ATCC 98724;
 (g) a polynucleotide encoding a protein comprising the amino acid sequence of SEQ ID NO:20;
 (h) a polynucleotide encoding a protein comprising a fragment of the amino acid sequence of SEQ ID NO:20 having biological activity, the fragment comprising eight contiguous amino acids of SEQ ID NO:20;
 (i) a polynucleotide which is an allelic variant of a polynucleotide of (a)–(f) above;
 (j) a polynucleotide which encodes a species homologue of the protein of (g) or (h) above;
 (k) a polynucleotide that hybridizes under stringent conditions to any one of the polynucleotides specified in (a)–(h); and
 (l) a polynucleotide that hybridizes under stringent conditions to any one of the polynucleotides specified in (a)–(h) and that has a length that is at least 25% of the length of SEQ ID NO:19.

Preferably, such polynucleotide comprises the nucleotide sequence of SEQ ID NO:19 from nucleotide 102 to nucleotide 461; the nucleotide sequence of the full-length protein coding sequence of clone yb81l1 deposited under accession number ATCC 98724; or the nucleotide sequence of a mature protein coding sequence of clone yb81l1 deposited under accession number ATCC 98724. In other preferred embodiments, the polynucleotide encodes the full-length or a mature protein encoded by the cDNA insert of clone yb81_1 deposited under accession number ATCC 98724. In further preferred embodiments, the present invention provides a polynucleotide encoding a protein comprising a fragment of the amino acid sequence of SEQ ID NO:20 having biological activity, the fragment preferably comprising eight (more preferably twenty, most preferably thirty) contiguous amino acids of SEQ ID NO:20, or a polynucleotide encoding a protein comprising a fragment of the amino acid sequence of SEQ ID NO:20 having biological activity, the fragment comprising the amino acid sequence from amino acid 55 to amino acid 64 of SEQ ID NO:20.

Other embodiments provide the gene corresponding to the cDNA sequence of SEQ ID NO:19.

Further embodiments of the invention provide isolated polynucleotides produced according to a process selected from the group consisting of:
 (a) a process comprising the steps of:
  (i) preparing one or more polynucleotide probes that hybridize in 6×SSC at 65 degrees C. to a nucleotide sequence selected from the group consisting of:
   (aa) SEQ ID NO:19, but excluding the poly(A) tail at the 3' end of SEQ ID NO:19; and
   (ab) the nucleotide sequence of the cDNA insert of clone yb81_1 deposited under accession number ATCC 98724;
  (ii) hybridizing said probe(s) to human genomic DNA in conditions at least as stringent as 4×SSC at 50 degrees C.; and
  (iii) isolating the DNA polynucleotides detected with the probe(s);
 and
 (b) a process comprising the steps of:
  (i) preparing one or more polynucleotide primers that hybridize in 6×SSC at 65 degrees C. to a nucleotide sequence selected from the group consisting of:
   (ba) SEQ ID NO:19, but excluding the poly(A) tail at the 3' end of SEQ ID NO:19; and
   (bb) the nucleotide sequence of the cDNA insert of clone yb811 deposited under accession number ATCC 98724;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:19, and extending contiguously from a nucleotide sequence corresponding to the 5' end of SEQ ID NO:19 to a nucleotide sequence corresponding to the 3' end of SEQ ID NO:19, but excluding the poly(A) tail at the 3' end of SEQ ID NO:19. Also preferably the polynucleotide isolated according to the above process comprises a nucleotide sequence corresponding to the cDNA sequence of SEQ ID NO:19 from nucleotide 102 to nucleotide 461, and extending contiguously from a nucleotide sequence corresponding to the 5' end of said sequence of SEQ ID NO:19 from nucleotide 102 to nucleotide 461, to a nucleotide sequence corresponding to the 3' end of said sequence of SEQ ID NO:19 from nucleotide 102 to nucleotide 461.

In other embodiments, the present invention provides a composition comprising a protein, wherein said protein comprises an amino acid sequence selected from the group consisting of:
 (a) the amino acid sequence of SEQ ID NO:20;
 (b) a fragment of the amino acid sequence of SEQ ID NO:20, the fragment comprising eight contiguous amino acids of SEQ ID NO:20; and
 (c) the amino acid sequence encoded by the cDNA insert of clone yb81_1 deposited under accession number ATCC 98724;
the protein being substantially free from other mammalian proteins. Preferably such protein comprises the amino acid sequence of SEQ ID NO:20. In further preferred embodiments, the present invention provides a protein comprising a fragment of the amino acid sequence of SEQ ID NO:20 having biological activity, the fragment preferably comprising eight (more preferably twenty, most preferably thirty) contiguous amino acids of SEQ ID NO:20, or a protein comprising a fragment of the amino acid sequence of SEQ ID NO:20 having biological activity, the fragment comprising the amino acid sequence from amino acid 55 to amino acid 64 of SEQ ID NO:20.

In one embodiment, the present invention provides a composition comprising an isolated polynucleotide selected from the group consisting of:
(a) a polynucleotide comprising the nucleotide sequence of SEQ ID NO:21;
(b) a polynucleotide comprising the nucleotide sequence of SEQ ID NO:21 from nucleotide 170 to nucleotide 2968;
(c) a polynucleotide comprising the nucleotide sequence of the full-length protein coding sequence of clone yc14_1 deposited under accession number ATCC 98724;
(d) a polynucleotide encoding the full-length protein encoded by the cDNA insert of clone yc14_1 deposited under accession number ATCC 98724;
(e) a polynucleotide comprising the nucleotide sequence of a mature protein coding sequence of clone yc14_1 deposited under accession number ATCC 98724;
(f) a polynucleotide encoding a mature protein encoded by the cDNA insert of clone yc14_1 deposited under accession number ATCC 98724;
(g) a polynucleotide encoding a protein comprising the amino acid sequence of SEQ ID NO:22;
(h) a polynucleotide encoding a protein comprising a fragment of the amino acid sequence of SEQ ID NO:22 having biological activity, the fragment comprising eight contiguous amino acids of SEQ ID NO:22;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:21.

Preferably, such polynucleotide comprises the nucleotide sequence of SEQ ID NO:21 from nucleotide 170 to nucleotide 2968; the nucleotide sequence of the full-length protein coding sequence of clone yc14_1 deposited under accession number ATCC 98724; or the nucleotide sequence of a mature protein coding sequence of clone yc14_1 deposited under accession number ATCC 98724. In other preferred embodiments, the polynucleotide encodes the full-length or a mature protein encoded by the cDNA insert of clone yc14_1 deposited under accession number ATCC 98724. In further preferred embodiments, the present invention provides a polynucleotide encoding a protein comprising a fragment of the amino acid sequence of SEQ ID NO:22 having biological activity, the fragment preferably comprising eight (more preferably twenty, most preferably thirty) contiguous amino acids of SEQ ID NO:22, or a polynucleotide encoding a protein comprising a fragment of the amino acid sequence of SEQ ID NO:22 having biological activity, the fragment comprising the amino acid sequence from amino acid 461 to amino acid 470 of SEQ ID NO:22.

Other embodiments provide the gene corresponding to the cDNA sequence of SEQ ID NO:21.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:21, but excluding the poly(A) tail at the 3' end of SEQ ID NO:21; and
(ab) the nucleotide sequence of the cDNA insert of clone yc14_1 deposited under accession number ATCC 98724;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:21, but excluding the poly(A) tail at the 3' end of SEQ ID NO:21; and
(bb) the nucleotide sequence of the cDNA insert of done yc14_1 deposited under accession number ATCC 98724;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:21, and extending contiguously from a nucleotide sequence corresponding to the 5' end of SEQ ID NO:21 to a nucleotide sequence corresponding to the 3' end of SEQ ID NO:21, but excluding the poly(A) tail at the 3' end of SEQ ID NO:21. Also preferably the polynucleotide isolated according to the above process comprises a nucleotide sequence corresponding to the cDNA sequence of SEQ ID NO:21 from nucleotide 170 to nucleotide 2968, and extending contiguously from a nucleotide sequence corresponding to the 5' end of said sequence of SEQ ID NO:21 from nucleotide 170 to nucleotide 2968, to a nucleotide sequence corresponding to the 3' end of said sequence of SEQ ID NO:21 from nucleotide 170 to nucleotide 2968.

In other embodiments, the present invention provides a composition comprising a protein, wherein said protein comprises an amino acid sequence selected from the group consisting of:
(a) the amino acid sequence of SEQ ID NO:22;
(b) a fragment of the amino acid sequence of SEQ ID NO:22, the fragment comprising eight contiguous amino acids of SEQ ID NO:22; and
(c) the amino acid sequence encoded by the cDNA insert of clone yc14_1 deposited under accession number ATCC 98724;
the protein being substantially free from other mammalian proteins. Preferably such protein comprises the amino acid sequence of SEQ ID NO:22. In further preferred embodiments, the present invention provides a protein comprising a fragment of the amino acid sequence of SEQ ID NO:22 having biological activity, the fragment preferably comprising eight (more preferably twenty, most preferably thirty) contiguous amino acids of SEQ ID NO:22, or a protein comprising a fragment of the amino acid sequence of SEQ ID NO:22 having biological activity, the fragment comprising the amino acid sequence from amino acid 461 to amino acid 470 of SEQ ID NO:22.

In one embodiment, the present invention provides a composition comprising an isolated polynucleotide selected from the group consisting of:
- (a) a polynucleotide comprising the nucleotide sequence of SEQ ID NO:23;
- (b) a polynucleotide comprising the nucleotide sequence of SEQ ID NO:23 from nucleotide 82 to nucleotide 729;
- (c) a polynucleotide comprising the nucleotide sequence of the full-length protein coding sequence of clone yc24_1 deposited under accession number ATCC 98755;
- (d) a polynucleotide encoding the full-length protein encoded by the cDNA insert of clone yc24_1 deposited under accession number ATCC 98755;
- (e) a polynucleotide comprising the nucleotide sequence of a mature protein coding sequence of clone yc24_1 deposited under accession number ATCC 98755;
- (f) a polynucleotide encoding a mature protein encoded by the cDNA insert of clone yc24_1 deposited under accession number ATCC 98755;
- (g) a polynucleotide encoding a protein comprising the amino acid sequence of SEQ ID NO:24;
- (h) a polynucleotide encoding a protein comprising a fragment of the amino acid sequence of SEQ ID NO:24 having biological activity, the fragment comprising eight contiguous amino acids of SEQ ID NO:24;
- (i) a polynucleotide which is an allelic variant of a polynucleotide of (a)–(f) above;
- (j) a polynucleotide which encodes a species homologue of the protein of (g) or (h) above;
- (k) a polynucleotide that hybridizes under stringent conditions to any one of the polynucleotides specified in (a)–(h); and
- (l) a polynucleotide that hybridizes under stringent conditions to any one of the polynucleotides specified in (a)–(h) and that has a length that is at least 25% of the length of SEQ ID NO:23.

Preferably, such polynucleotide comprises the nucleotide sequence of SEQ ID NO:23 from nucleotide 82 to nucleotide 729; the nucleotide sequence of the full-length protein coding sequence of clone yc24_1 deposited under accession number ATCC 98755; or the nucleotide sequence of a mature protein coding sequence of clone yc24_1 deposited under accession number ATCC 98755. In other preferred embodiments, the polynucleotide encodes the full-length or a mature protein encoded by the cDNA insert of clone yc24_1 deposited under accession number ATCC 98755. In further preferred embodiments, the present invention provides a polynucleotide encoding a protein comprising a fragment of the amino acid sequence of SEQ ID NO:24 having biological activity, the fragment preferably comprising eight (more preferably twenty, most preferably thirty) contiguous amino acids of SEQ ID NO:24, or a polynucleotide encoding a protein comprising a fragment of the amino acid sequence of SEQ ID NO:24 having biological activity, the fragment comprising the amino acid sequence from amino acid 103 to amino acid 112 of SEQ ID NO:24.

Other embodiments provide the gene corresponding to the cDNA sequence of SEQ ID NO:23.

Further embodiments of the invention provide isolated polynucleotides produced according to a process selected from the group consisting of:
- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:23, but excluding the poly(A) tail at the 3' end of SEQ ID NO:23; and
    - (ab) the nucleotide sequence of the cDNA insert of clone yc24_1 deposited under accession number ATCC 98755;
  - (ii) hybridizing said probe(s) to human genomic DNA in conditions at least as stringent as 4×SSC at 50 degrees C.; and
  - (iii) isolating the DNA polynucleotides detected with the probe(s);

and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:23, but excluding the poly(A) tail at the 3' end of SEQ ID NO:23; and
    - (bb) the nucleotide sequence of the cDNA insert of clone yc24_1 deposited under accession number ATCC 98755;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b) (iii).

Preferably the polynucleotide isolated according to the above process comprises a nucleotide sequence corresponding to the cDNA sequence of SEQ ID NO:23, and extending contiguously from a nucleotide sequence corresponding to the 5' end of SEQ ID NO:23 to a nucleotide sequence corresponding to the 3' end of SEQ ID NO:23, but excluding the poly(A) tail at the 3' end of SEQ ID NO:23. Also preferably the polynucleotide isolated according to the above process comprises a nucleotide sequence corresponding to the cDNA sequence of SEQ ID NO:23 from nucleotide 82 to nucleotide 729, and extending contiguously from a nucleotide sequence corresponding to the 5' end of said sequence of SEQ ID NO:23 from nucleotide 82 to nucleotide 729, to a nucleotide sequence corresponding to the 3' end of said sequence of SEQ ID NO:23 from nucleotide 82 to nucleotide 729.

In other embodiments, the present invention provides a composition comprising a protein, wherein said protein comprises an amino acid sequence selected from the group consisting of:
- (a) the amino acid sequence of SEQ ID NO:24;
- (b) a fragment of the amino acid sequence of SEQ ID NO:24, the fragment comprising eight contiguous amino acids of SEQ ID NO:24; and
- (c) the amino acid sequence encoded by the cDNA insert of clone yc24_1 deposited under accession number ATCC 98755;

the protein being substantially free from other mammalian proteins. Preferably such protein comprises the amino acid sequence of SEQ ID NO:24. In further preferred embodiments, the present invention provides a protein comprising a fragment of the amino acid sequence of SEQ ID NO:24 having biological activity, the fragment preferably comprising eight (more preferably twenty, most preferably thirty) contiguous amino acids of SEQ ID NO:24, or a protein comprising a fragment of the amino acid sequence of SEQ ID NO:24 having biological activity, the fragment comprising the amino acid sequence from amino acid 103 to amino acid 112 of SEQ ID NO:24.

In one embodiment, the present invention provides a composition comprising an isolated polynucleotide selected from the group consisting of:

(a) a polynucleotide comprising the nucleotide sequence of SEQ ID NO:25;

(b) a polynucleotide comprising the nucleotide sequence of SEQ ID NO:25 from nucleotide 7 to nucleotide 951;

(c) a polynucleotide comprising the nucleotide sequence of SEQ ID NO:25 from nucleotide 61 to nucleotide 951;

(d) a polynucleotide comprising the nucleotide sequence of the full-length protein coding sequence of clone yc25_1 deposited under accession number ATCC 98755;

(e) a polynucleotide encoding the full-length protein encoded by the cDNA insert of clone yc25_1 deposited under accession number ATCC 98755;

(f) a polynucleotide comprising the nucleotide sequence of a mature protein coding sequence of clone yc25_1 deposited under accession number ATCC 98755;

(g) a polynucleotide encoding a mature protein encoded by the cDNA insert of clone yc25_1 deposited under accession number ATCC 98755;

(h) a polynucleotide encoding a protein comprising the amino acid sequence of SEQ ID NO:26;

(i) a polynucleotide encoding a protein comprising a fragment of the amino acid sequence of SEQ ID NO:26 having biological activity, the fragment comprising eight contiguous amino acids of SEQ ID NO:26;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:25.

Preferably, such polynucleotide comprises the nucleotide sequence of SEQ ID NO:25 from nucleotide 7 to nucleotide 951; the nucleotide sequence of SEQ ID NO:25 from nucleotide 61 to nucleotide 951; the nucleotide sequence of the full-length protein coding sequence of clone yc25_1 deposited under accession number ATCC 98755; or the nucleotide sequence of a mature protein coding sequence of clone yc25_1 deposited under accession number ATCC 98755. In other preferred embodiments, the polynucleotide encodes the full-length or a mature protein encoded by the cDNA insert of clone yc25_1 deposited under accession number ATCC 98755. In further preferred embodiments, the present invention provides a polynucleotide encoding a protein comprising a fragment of the amino acid sequence of SEQ ID NO:26 having biological activity, the fragment preferably comprising eight (more preferably twenty, most preferably thirty) contiguous amino acids of SEQ ID NO:26, or a polynucleotide encoding a protein comprising a fragment of the amino acid sequence of SEQ ID NO:26 having biological activity, the fragment comprising the amino acid sequence from amino acid 152 to amino acid 161 of SEQ ID NO:26.

Other embodiments provide the gene corresponding to the cDNA sequence of SEQ ID NO:25.

Further embodiments of the invention provide isolated polynucleotides produced according to a process selected from the group consisting of:

(a) a process comprising the steps of:
    (i) preparing one or more polynucleotide probes that hybridize in 6×SSC at 65 degrees C. to a nucleotide sequence selected from the group consisting of:
        (aa) SEQ ID NO:25, but excluding the poly(A) tail at the 3' end of SEQ ID NO:25; and
        (ab) the nucleotide sequence of the cDNA insert of clone yc25_1 deposited under accession number ATCC 98755;
    (ii) hybridizing said probe(s) to human genomic DNA in conditions at least as stringent as 4×SSC at 50 degrees C.; and
    (iii) isolating the DNA polynucleotides detected with the probe(s);

and (b) a process comprising the steps of:
    (i) preparing one or more polynucleotide primers that hybridize in 6×SSC at 65 degrees C. to a nucleotide sequence selected from the group consisting of:
        (ba) SEQ ID NO:25, but excluding the poly(A) tail at the 3' end of SEQ ID NO:25; and
        (bb) the nucleotide sequence of the cDNA insert of clone yc25_1 deposited under accession number ATCC 98755;
    (ii) hybridizing said primer(s) to human genomic DNA in conditions at least as stringent as 4×SSC at 50 degrees C.;
    (iii) amplifying human DNA sequences; and
    (iv) isolating the polynucleotide products of step (b) (iii).

Preferably the polynucleotide isolated according to the above process comprises a nucleotide sequence corresponding to the cDNA sequence of SEQ ID NO:25, and extending contiguously from a nucleotide sequence corresponding to the 5' end of SEQ ID NO:25 to a nucleotide sequence corresponding to the 3' end of SEQ ID NO:25, but excluding the poly(A) tail at the 3' end of SEQ ID NO:25. Also preferably the polynucleotide isolated according to the above process comprises a nucleotide sequence corresponding to the cDNA sequence of SEQ ID NO:25 from nucleotide 7 to nucleotide 951, and extending contiguously from a nucleotide sequence corresponding to the 5' end of said sequence of SEQ ID NO:25 from nucleotide 7 to nucleotide 951, to a nucleotide sequence corresponding to the 3' end of said sequence of SEQ ID NO:25 from nucleotide 7 to nucleotide 951. Also preferably the polynucleotide isolated according to the above process comprises a nucleotide sequence corresponding to the cDNA sequence of SEQ ID NO:25 from nucleotide 61 to nucleotide 951, and extending contiguously from a nucleotide sequence corresponding to the 5' end of said sequence of SEQ ID NO:25 from nucleotide 61 to nucleotide 951, to a nucleotide sequence corresponding to the 3' end of said sequence of SEQ ID NO:25 from nucleotide 61 to nucleotide 951.

In other embodiments, the present invention provides a composition comprising a protein, wherein said protein comprises an amino acid sequence selected from the group consisting of:

(a) the amino acid sequence of SEQ ID NO:26;
(b) a fragment of the amino acid sequence of SEQ ID NO:26, the fragment comprising eight contiguous amino acids of SEQ ID NO:26; and
(c) the amino acid sequence encoded by the cDNA insert of clone yc25_1 deposited under accession number ATCC 98755;
the protein being substantially free from other mammalian proteins. Preferably such protein comprises the amino acid sequence of SEQ ID NO:26. In further preferred embodiments, the present invention provides a protein comprising a fragment of the amino acid sequence of SEQ ID NO:26 having biological activity, the fragment preferably comprising eight (more preferably twenty, most preferably thirty) contiguous amino acids of SEQ ID NO:26, or a protein comprising a fragment of the amino acid sequence of SEQ ID NO:26 having biological activity, the fragment comprising the amino acid sequence from amino acid 152 to amino acid 161 of SEQ ID NO:26.

In one embodiment, the present invention provides a composition comprising an isolated polynucleotide selected from the group consisting of:
(a) a polynucleotide comprising the nucleotide sequence of SEQ ID NO:27;
(b) a polynucleotide comprising the nucleotide sequence of SEQ ID NO:27 from nucleotide 157 to nucleotide 1083;
(c) a polynucleotide comprising the nucleotide sequence of the full-length protein coding sequence of clone ye2_1 deposited under accession number ATCC 98755;
(d) a polynucleotide encoding the full-length protein encoded by the cDNA insert of clone ye2_1 deposited under accession number ATCC 98755;
(e) a polynucleotide comprising the nucleotide sequence of a mature protein coding sequence of clone ye2_1 deposited under accession number ATCC 98755;
(f) a polynucleotide encoding a mature protein encoded by the cDNA insert of clone ye2_1 deposited under accession number ATCC 98755;
(g) a polynucleotide encoding a protein comprising the amino acid sequence of SEQ ID NO:28;
(h) a polynucleotide encoding a protein comprising a fragment of the amino acid sequence of SEQ ID NO:28 having biological activity, the fragment comprising eight contiguous amino acids of SEQ ID NO:28;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:27.

Preferably, such polynucleotide comprises the nucleotide sequence of SEQ ID NO:27 from nucleotide 157 to nucleotide 1083; the nucleotide sequence of the full-length protein coding sequence of clone ye2_1 deposited under accession number ATCC 98755; or the nucleotide sequence of a mature protein coding sequence of clone ye2_1 deposited under accession number ATCC 98755. In other preferred embodiments, the polynucleotide encodes the full-length or a mature protein encoded by the cDNA insert of clone ye2_1 deposited under accession number ATCC 98755. In further preferred embodiments, the present invention provides a polynucleotide encoding a protein comprising a fragment of the amino acid sequence of SEQ ID NO:28 having biological activity, the fragment preferably comprising eight (more preferably twenty, most preferably thirty) contiguous amino acids of SEQ ID NO:28, or a polynucleotide encoding a protein comprising a fragment of the amino acid sequence of SEQ ID NO:28 having biological activity, the fragment comprising the amino acid sequence from amino acid 149 to amino acid 158 of SEQ ID NO:28.

Other embodiments provide the gene corresponding to the cDNA sequence of SEQ ID NO:27.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:27, but excluding the poly(A) tail at the 3' end of SEQ ID NO:27; and
(ab) the nucleotide sequence of the cDNA insert of clone ye2_1 deposited under accession number ATCC 98755;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:27, but excluding the poly(A) tail at the 3' end of SEQ ID NO:27; and
(bb) the nucleotide sequence of the cDNA insert of clone ye2_1 deposited under accession number ATCC 98755;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:27, and extending contiguously from a nucleotide sequence corresponding to the 5' end of SEQ ID NO:27 to a nucleotide sequence corresponding to the 3' end of SEQ ID NO:27, but excluding the poly(A) tail at the 3' end of SEQ ID NO:27. Also preferably the polynucleotide isolated according to the above process comprises a nucleotide sequence corresponding to the cDNA sequence of SEQ ID NO:27 from nucleotide 157 to nucleotide 1083, and extending contiguously from a nucleotide sequence corresponding to the 5' end of said sequence of SEQ ID NO:27 from nucleotide 157 to nucleotide 1083, to a nucleotide sequence corresponding to the 3' end of said sequence of SEQ ID NO:27 from nucleotide 157 to nucleotide 1083.

In other embodiments, the present invention provides a composition comprising a protein, wherein said protein comprises an amino acid sequence selected from the group consisting of:

(a) the amino acid sequence of SEQ ID NO:28;

(b) a fragment of the amino acid sequence of SEQ ID NO:28, the fragment comprising eight contiguous amino acids of SEQ ID NO:28; and (c) the amino acid sequence encoded by the cDNA insert of clone ye2__1 deposited under accession number ATCC 98755;

the protein being substantially free from other mammalian proteins. Preferably such protein comprises the amino acid sequence of SEQ ID NO:28. In further preferred embodiments, the present invention provides a protein comprising a fragment of the amino acid sequence of SEQ ID NO:28 having biological activity, the fragment preferably comprising eight (more preferably twenty, most preferably thirty) contiguous amino acids of SEQ ID NO:28, or a protein comprising a fragment of the amino acid sequence of SEQ ID NO:28 having biological activity, the fragment comprising the amino acid sequence from amino acid 149 to amino acid 158 of SEQ ID NO:28.

In one embodiment, the present invention provides a composition comprising an isolated polynucleotide selected from the group consisting of:

(a) a polynucleotide comprising the nucleotide sequence of SEQ ID NO:29;

(b) a polynucleotide comprising the nucleotide sequence of SEQ ID NO:29 from nucleotide 39 to nucleotide 473;

(c) a polynucleotide comprising the nucleotide sequence of the full-length protein coding sequence of clone ya65__1 deposited under accession number ATCC 98834;

(d) a polynucleotide encoding the full-length protein encoded by the cDNA insert of clone ya65__1 deposited under accession number ATCC 98834;

(e) a polynucleotide comprising the nucleotide sequence of a mature protein coding sequence of clone ya65__1 deposited under accession number ATCC 98834;

(f) a polynucleotide encoding a mature protein encoded by the cDNA insert of clone ya65__1 deposited under accession number ATCC 98834;

(g) a polynucleotide encoding a protein comprising the amino acid sequence of SEQ ID NO:30;

(h) a polynucleotide encoding a protein comprising a fragment of the amino acid sequence of SEQ ID NO:30 having biological activity, the fragment comprising eight contiguous amino acids of SEQ ID NO:30;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:29.

Preferably, such polynucleotide comprises the nucleotide sequence of SEQ ID NO:29 from nucleotide 39 to nucleotide 473; the nucleotide sequence of the full-length protein coding sequence of clone ya65__1 deposited under accession number ATCC 98834; or the nucleotide sequence of a mature protein coding sequence of clone ya65__1 deposited under accession number ATCC 98834. In other preferred embodiments, the polynucleotide encodes the full-length or a mature protein encoded by the cDNA insert of clone ya65__1 deposited under accession number ATCC 98834. In further preferred embodiments, the present invention provides a polynucleotide encoding a protein comprising a fragment of the amino acid sequence of SEQ ID NO:30 having biological activity, the fragment preferably comprising eight (more preferably twenty, most preferably thirty) contiguous amino acids of SEQ ID NO:30, or a polynucleotide encoding a protein comprising a fragment of the amino acid sequence of SEQ ID NO:30 having biological activity, the fragment comprising the amino acid sequence from amino acid 67 to amino acid 76 of SEQ ID NO:30.

Other embodiments provide the gene corresponding to the cDNA sequence of SEQ ID NO:29.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:29, but excluding the poly(A) tail at the 3' end of SEQ ID NO:29; and
    (ab) the nucleotide sequence of the cDNA insert of clone ya65__1 deposited under accession number ATCC 98834;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:29, but excluding the poly(A) tail at the 3' end of SEQ ID NO:29; and
    (bb) the nucleotide sequence of the cDNA insert of clone ya65__1 deposited under accession number ATCC 98834;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:29, and extending contiguously from a nucleotide sequence corresponding to the 5' end of SEQ ID NO:29 to a nucleotide sequence corresponding to the 3' end of SEQ ID NO:29, but excluding the poly(A) tail at the 3' end of SEQ ID NO:29. Also preferably the polynucleotide isolated according to the above process comprises a nucleotide sequence corresponding to the cDNA sequence of SEQ ID NO:29 from nucleotide 39 to nucleotide 473, and extending contiguously from a nucleotide sequence corresponding to the 5' end of said sequence of SEQ ID NO:29 from nucleotide 39 to nucleotide 473, to a nucleotide sequence corresponding to the 3' end of said sequence of SEQ ID NO:29 from nucleotide 39 to nucleotide 473.

In other embodiments, the present invention provides a composition comprising a protein, wherein said protein comprises an amino acid sequence selected from the group consisting of:

(a) the amino acid sequence of SEQ ID NO:30;
(b) a fragment of the amino acid sequence of SEQ ID NO:30, the fragment comprising eight contiguous amino acids of SEQ ID NO:30; and
(c) the amino acid sequence encoded by the cDNA insert of clone ya65_1 deposited under accession number ATCC 98834;

the protein being substantially free from other mammalian proteins. Preferably such protein comprises the amino acid sequence of SEQ ID NO:30. In further preferred embodiments, the present invention provides a protein comprising a fragment of the amino acid sequence of SEQ ID NO:30 having biological activity, the fragment preferably comprising eight (more preferably twenty, most preferably thirty) contiguous amino acids of SEQ ID NO:30, or a protein comprising a fragment of the amino acid sequence of SEQ ID NO:30 having biological activity, the fragment comprising the amino acid sequence from amino acid 67 to amino acid 76 of SEQ ID NO:30.

In one embodiment, the present invention provides a composition comprising an isolated polynucleotide selected from the group consisting of:
(a) a polynucleotide comprising the nucleotide sequence of SEQ ID NO:31;
(b) a polynucleotide comprising the nucleotide sequence of SEQ ID NO:31 from nucleotide 664 to nucleotide 903;
(c) a polynucleotide comprising the nucleotide sequence of the full-length protein coding sequence of clone yb60_1 deposited under accession number ATCC 98834;
(d) a polynucleotide encoding the full-length protein encoded by the cDNA insert of clone yb60_1 deposited under accession number ATCC 98834;
(e) a polynucleotide comprising the nucleotide sequence of a mature protein coding sequence of clone yb60_1 deposited under accession number ATCC 98834;
(f) a polynucleotide encoding a mature protein encoded by the cDNA insert of clone yb60_1 deposited under accession number ATCC 98834;
(g) a polynucleotide encoding a protein comprising the amino acid sequence of SEQ ID NO:32;
(h) a polynucleotide encoding a protein comprising a fragment of the amino acid sequence of SEQ ID NO:32 having biological activity, the fragment comprising eight contiguous amino acids of SEQ ID NO:32;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:31.

Preferably, such polynucleotide comprises the nucleotide sequence of SEQ ID NO:31 from nucleotide 664 to nucleotide 903; the nucleotide sequence of the full-length protein coding sequence of clone yb60_1 deposited under accession number ATCC 98834; or the nucleotide sequence of a mature protein coding sequence of clone yb60_1 deposited under accession number ATCC 98834. In other preferred embodiments, the polynucleotide encodes the full-length or a mature protein encoded by the cDNA insert of clone yb60_1 deposited under accession number ATCC 98834. In further preferred embodiments, the present invention provides a polynucleotide encoding a protein comprising a fragment of the amino acid sequence of SEQ ID NO:32 having biological activity, the fragment preferably comprising eight (more preferably twenty, most preferably thirty) contiguous amino acids of SEQ ID NO:32, or a polynucleotide encoding a protein comprising a fragment of the amino acid sequence of SEQ ID NO:32 having biological activity, the fragment comprising the amino acid sequence from amino acid 35 to amino acid 44 of SEQ ID NO:32.

Other embodiments provide the gene corresponding to the cDNA sequence of SEQ ID NO:31.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:31, but excluding the poly(A) tail at the 3' end of SEQ ID NO:31; and
    (ab) the nucleotide sequence of the cDNA insert of clone yb60_1 deposited under accession number ATCC 98834;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:31, but excluding the poly(A) tail at the 3' end of SEQ ID NO:31; and
    (bb) the nucleotide sequence of the cDNA insert of clone yb60_1 deposited under accession number ATCC 98834;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:31, and extending contiguously from a nucleotide sequence corresponding to the 5' end of SEQ ID NO:31 to a nucleotide sequence corresponding to the 3' end of SEQ ID NO:31, but excluding the poly(A) tail at the 3' end of SEQ ID NO:31. Also preferably the polynucleotide isolated according to the above process comprises a nucleotide sequence corresponding to the cDNA sequence of SEQ ID NO:31 from nucleotide 664 to nucleotide 903, and extending contiguously from a nucleotide sequence corresponding to the 5' end of said sequence of SEQ ID NO:31 from nucleotide 664 to nucleotide 903, to a nucleotide sequence corresponding to the 3' end of said sequence of SEQ ID NO:31 from nucleotide 664 to nucleotide 903.

In other embodiments, the present invention provides a composition comprising a protein, wherein said protein comprises an amino acid sequence selected from the group consisting of:

(a) the amino acid sequence of SEQ ID NO:32;
(b) a fragment of the amino acid sequence of SEQ ID NO:32, the fragment comprising eight contiguous amino acids of SEQ ID NO:32; and
(c) the amino acid sequence encoded by the cDNA insert of clone yb60_1 deposited under accession number ATCC 98834;

the protein being substantially free from other mammalian proteins. Preferably such protein comprises the amino acid sequence of SEQ ID NO:32. In further preferred embodiments, the present invention provides a protein comprising a fragment of the amino acid sequence of SEQ ID NO:32 having biological activity, the fragment preferably comprising eight (more preferably twenty, most preferably thirty) contiguous amino acids of SEQ ID NO:32, or a protein comprising a fragment of the amino acid sequence of SEQ ID NO:32 having biological activity, the fragment comprising the amino acid sequence from amino acid 35 to amino acid 44 of SEQ ID NO:32.

In one embodiment, the present invention provides a composition comprising an isolated polynucleotide selected from the group consisting of:
(a) a polynucleotide comprising the nucleotide sequence of SEQ ID NO:33;
(b) a polynucleotide comprising the nucleotide sequence of SEQ ID NO:33 from nucleotide 88 to nucleotide 447;
(c) a polynucleotide comprising the nucleotide sequence of SEQ ID NO:33 from nucleotide 427 to nucleotide 447;
(d) a polynucleotide comprising the nucleotide sequence of the full-length protein coding sequence of clone yb139_1 deposited under accession number ATCC 98834;
(e) a polynucleotide encoding the full-length protein encoded by the cDNA insert of clone yb139_1 deposited under accession number ATCC 98834;
(f) a polynucleotide comprising the nucleotide sequence of a mature protein coding sequence of clone yb139_1 deposited under accession number ATCC 98834;
(g) a polynucleotide encoding a mature protein encoded by the cDNA insert of clone yb139_1 deposited under accession number ATCC 98834;
(h) a polynucleotide encoding a protein comprising the amino acid sequence of SEQ ID NO:34;
(i) a polynucleotide encoding a protein comprising a fragment of the amino acid sequence of SEQ ID NO:34 having biological activity, the fragment comprising eight contiguous amino acids of SEQ ID NO:34;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:33.

Preferably, such polynucleotide comprises the nucleotide sequence of SEQ ID NO:33 from nucleotide 88 to nucleotide 447; the nucleotide sequence of SEQ ID NO:33 from nucleotide 427 to nucleotide 447; the nucleotide sequence of the full-length protein coding sequence of clone yb139_1 deposited under accession number ATCC 98834; or the nucleotide sequence of a mature protein coding sequence of clone yb139_1 deposited under accession number ATCC 98834. In other preferred embodiments, the polynucleotide encodes the full-length or a mature protein encoded by the cDNA insert of clone yb139_1 deposited under accession number ATCC 98834. In further preferred embodiments, the present invention provides a polynucleotide encoding a protein comprising a fragment of the amino acid sequence of SEQ ID NO:34 having biological activity, the fragment preferably comprising eight (more preferably twenty, most preferably thirty) contiguous amino acids of SEQ ID NO:34, or a polynucleotide encoding a protein comprising a fragment of the amino acid sequence of SEQ ID NO:34 having biological activity, the fragment comprising the amino acid sequence from amino acid 55 to amino acid 64 of SEQ ID NO:34.

Other embodiments provide the gene corresponding to the cDNA sequence of SEQ ID NO:33.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:33, but excluding the poly(A) tail at the 3' end of SEQ ID NO:33; and
    (ab) the nucleotide sequence of the cDNA insert of clone yb139_1 deposited under accession number ATCC 98834;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:33, but excluding the poly(A) tail at the 3' end of SEQ ID NO:33; and
    (bb) the nucleotide sequence of the cDNA insert of clone yb139_1 deposited under accession number ATCC 98834;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:33, and extending contiguously from a nucleotide sequence corresponding to the 5' end of SEQ ID NO:33 to a nucleotide sequence corresponding to the 3' end of SEQ ID NO:33, but excluding the poly(A) tail at the 3' end of SEQ ID NO:33. Also preferably the polynucleotide isolated according to the above process comprises a nucleotide sequence corresponding to the cDNA sequence of SEQ ID NO:33 from nucleotide 88 to nucleotide 447, and extending contiguously from a nucleotide sequence corresponding to the 5' end of said sequence of SEQ ID NO:33 from nucleotide 88 to nucleotide 447, to a nucleotide sequence corresponding to the 3' end of said sequence of SEQ ID NO:33 from nucleotide 88 to nucleotide 447. Also preferably the polynucleotide isolated according to the above process comprises a nucleotide sequence corresponding to the cDNA sequence of SEQ ID NO:33 from nucleotide 427 to nucleotide 447, and extending contiguously from a nucleotide sequence corresponding to the 5' end of said sequence of SEQ ID NO:33 from nucleotide 427 to nucleotide 447, to a nucleotide sequence corresponding to the 3' end of said sequence of SEQ ID NO:33 from nucleotide 427 to nucleotide 447.

In other embodiments, the present invention provides a composition comprising a protein, wherein said protein comprises an amino acid sequence selected from the group consisting of:
- (a) the amino acid sequence of SEQ ID NO:34;
- (b) a fragment of the amino acid sequence of SEQ ID NO:34, the fragment comprising eight contiguous amino acids of SEQ ID NO:34; and
- (c) the amino acid sequence encoded by the cDNA insert of clone yb139_1 deposited under accession number ATCC 98834;

the protein being substantially free from other mammalian proteins. Preferably such protein comprises the amino acid sequence of SEQ ID NO:34. In further preferred embodiments, the present invention provides a protein comprising a fragment of the amino acid sequence of SEQ ID NO:34 having biological activity, the fragment preferably comprising eight (more preferably twenty, most preferably thirty) contiguous amino acids of SEQ ID NO:34, or a protein comprising a fragment of the amino acid sequence of SEQ ID NO:34 having biological activity, the fragment comprising the amino acid sequence from amino acid 55 to amino acid 64 of SEQ ID NO:34.

In one embodiment, the present invention provides a composition comprising an isolated polynucleotide selected from the group consisting of:
- (a) a polynucleotide comprising the nucleotide sequence of SEQ ID NO:35;
- (b) a polynucleotide comprising the nucleotide sequence of SEQ ID NO:35 from nucleotide 93 to nucleotide 1481;
- (c) a polynucleotide comprising the nucleotide sequence of the full-length protein coding sequence of clone yc29_1 deposited under accession number ATCC 98834;
- (d) a polynucleotide encoding the full-length protein encoded by the cDNA insert of clone yc29_1 deposited under accession number ATCC 98834;
- (e) a polynucleotide comprising the nucleotide sequence of a mature protein coding sequence of clone yc29_1 deposited under accession number ATCC 98834;
- (f) a polynucleotide encoding a mature protein encoded by the cDNA insert of clone yc29_1 deposited under accession number ATCC 98834;
- (g) a polynucleotide encoding a protein comprising the amino acid sequence of SEQ ID NO:36;
- (h) a polynucleotide encoding a protein comprising a fragment of the amino acid sequence of SEQ ID NO:36 having biological activity, the fragment comprising eight contiguous amino acids of SEQ ID NO:36;
- (i) a polynucleotide which is an allelic variant of a polynucleotide of (a)–(f) above;
- (j) a polynucleotide which encodes a species homologue of the protein of (g) or (h) above;
- (k) a polynucleotide that hybridizes under stringent conditions to any one of the polynucleotides specified in (a)–(h); and
- (l) a polynucleotide that hybridizes under stringent conditions to any one of the polynucleotides specified in (a)–(h) and that has a length that is at least 25% of the length of SEQ ID NO:35.

Preferably, such polynucleotide comprises the nucleotide sequence of SEQ ID NO:35 from nucleotide 93 to nucleotide 1481; the nucleotide sequence of the full-length protein coding sequence of done yc29_1 deposited under accession number ATCC 98834; or the nucleotide sequence of a mature protein coding sequence of clone yc29_1 deposited under accession number ATCC 98834. In other preferred embodiments, the polynucleotide encodes the full-length or a mature protein encoded by the cDNA insert of clone yc29_1 deposited under accession number ATCC 98834. In further preferred embodiments, the present invention provides a polynucleotide encoding a protein comprising a fragment of the amino acid sequence of SEQ ID NO:36 having biological activity, the fragment preferably comprising eight (more preferably twenty, most preferably thirty) contiguous amino acids of SEQ ID NO:36, or a polynucleotide encoding a protein comprising a fragment of the amino acid sequence of SEQ ID NO:36 having biological activity, the fragment comprising the amino acid sequence from amino acid 226 to amino acid 235 of SEQ ID NO:36.

Other embodiments provide the gene corresponding to the cDNA sequence of SEQ ID NO:35.

Further embodiments of the invention provide isolated polynucleotides produced according to a process selected from the group consisting of:
- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:35, but excluding the poly(A) tail at the 3' end of SEQ ID NO:35; and
    - (ab) the nucleotide sequence of the cDNA insert of clone yc29_1 deposited under accession number ATCC 98834;
  - (ii) hybridizing said probe(s) to human genomic DNA in conditions at least as stringent as 4×SSC at 50 degrees C.; and
  - (iii) isolating the DNA polynucleotides detected with the probe(s);

and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:35, but excluding the poly(A) tail at the 3' end of SEQ ID NO:35; and
    - (bb) the nucleotide sequence of the cDNA insert of clone yc29_1 deposited under accession number ATCC 98834;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b)(iii).

Preferably the polynucleotide isolated according to the above process comprises a nucleotide sequence corresponding to the cDNA sequence of SEQ ID NO:35, and extending contiguously from a nucleotide sequence corresponding to the 5' end of SEQ ID NO:35 to a nucleotide sequence corresponding to the 3' end of SEQ ID NO:35, but excluding the poly(A) tail at the 3' end of SEQ ID NO:35. Also preferably the polynucleotide isolated according to the above process comprises a nucleotide sequence corresponding to the cDNA sequence of SEQ ID NO:35 from nucleotide 93 to nucleotide 1481, and extending contiguously from a nucleotide sequence corresponding to the 5' end of said sequence of SEQ ID NO:35 from nucleotide 93 to nucleotide 1481, to a nucleotide sequence corresponding to the 3' end of said sequence of SEQ ID NO:35 from nucleotide 93 to nucleotide 1481.

In other embodiments, the present invention provides a composition comprising a protein, wherein said protein comprises an amino acid sequence selected from the group consisting of:

(a) the amino acid sequence of SEQ ID NO:36;

(b) a fragment of the amino acid sequence of SEQ ID NO:36, the fragment comprising eight contiguous amino acids of SEQ ID NO:36; and (c) the amino acid sequence encoded by the cDNA insert of clone yc29_1 deposited under accession number ATCC 98834;

the protein being substantially free from other mammalian proteins. Preferably such protein comprises the amino acid sequence of SEQ ID NO:36. In further preferred embodiments, the present invention provides a protein comprising a fragment of the amino acid sequence of SEQ ID NO:36 having biological activity, the fragment preferably comprising eight (more preferably twenty, most preferably thirty) contiguous amino acids of SEQ ID NO:36, or a protein comprising a fragment of the amino acid sequence of SEQ ID NO:36 having biological activity, the fragment comprising the amino acid sequence from amino acid 226 to amino acid 235 of SEQ ID NO:36.

In one embodiment, the present invention provides a composition comprising an isolated polynucleotide selected from the group consisting of:

(a) a polynucleotide comprising the nucleotide sequence of SEQ ID NO:37;

(b) a polynucleotide comprising the nucleotide sequence of SEQ ID NO:37 from nucleotide 482 to nucleotide 751;

(c) a polynucleotide comprising the nucleotide sequence of SEQ ID NO:37 from nucleotide 611 to nucleotide 751;

(d) a polynucleotide comprising the nucleotide sequence of the full-length protein coding sequence of clone yc40_1 deposited under accession number ATCC 98834;

(e) a polynucleotide encoding the full-length protein encoded by the cDNA insert of clone yc40_1 deposited under accession number ATCC 98834;

(f) a polynucleotide comprising the nucleotide sequence of a mature protein coding sequence of clone yc40_1 deposited under accession number ATCC 98834;

(g) a polynucleotide encoding a mature protein encoded by the cDNA insert of clone yc40_1 deposited under accession number ATCC 98834;

(h) a polynucleotide encoding a protein comprising the amino acid sequence of SEQ ID NO:38;

(i) a polynucleotide encoding a protein comprising a fragment of the amino acid sequence of SEQ ID NO:38 having biological activity, the fragment comprising eight contiguous amino acids of SEQ ID NO:38;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:37.

Preferably, such polynucleotide comprises the nucleotide sequence of SEQ ID NO:37 from nucleotide 482 to nucleotide 751; the nucleotide sequence of SEQ ID NO:37 from nucleotide 611 to nucleotide 751; the nucleotide sequence of the full-length protein coding sequence of clone yc40_1 deposited under accession number ATCC 98834; or the nucleotide sequence of a mature protein coding sequence of clone yc40_1 deposited under accession number ATCC 98834. In other preferred embodiments, the polynucleotide encodes the full-length or a mature protein encoded by the cDNA insert of clone yc40_1 deposited under accession number ATCC 98834. In further preferred embodiments, the present invention provides a polynucleotide encoding a protein comprising a fragment of the amino acid sequence of SEQ ID NO:38 having biological activity, the fragment preferably comprising eight (more preferably twenty, most preferably thirty) contiguous amino acids of SEQ ID NO:38, or a polynucleotide encoding a protein comprising a fragment of the amino acid sequence of SEQ ID NO:38 having biological activity, the fragment comprising the amino acid sequence from amino acid 40 to amino acid 49 of SEQ ID NO:38.

Other embodiments provide the gene corresponding to the cDNA sequence of SEQ ID NO:37.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:37, but excluding the poly(A) tail at the 3' end of SEQ ID NO:37; and
    (ab) the nucleotide sequence of the cDNA insert of clone yc40_1 deposited under accession number ATCC 98834;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:37, but excluding the poly(A) tail at the 3' end of SEQ ID NO:37; and
    (bb) the nucleotide sequence of the cDNA insert of clone yc40_1 deposited under accession number ATCC 98834;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:37, and extending contiguously from a nucleotide sequence corresponding to the 5' end of SEQ ID NO:37 to a nucleotide sequence corresponding to the 3' end of SEQ ID NO:37, but excluding the poly(A) tail at the 3' end of SEQ ID NO:37. Also preferably the polynucleotide isolated according to the above process comprises a nucleotide sequence corresponding to the cDNA sequence of SEQ ID NO:37 from nucleotide 482 to nucleotide 751, and extending contiguously from a nucleotide sequence corresponding to the 5' end of said sequence of SEQ ID NO:37 from nucleotide 482 to nucleotide 751, to a nucleotide sequence corresponding to the 3' end of said sequence of SEQ ID NO:37 from nucleotide 482 to nucleotide 751. Also preferably the polynucleotide isolated according to the above process comprises a nucleotide sequence corresponding to the cDNA sequence of SEQ ID NO:37 from nucleotide 611 to nucleotide 751, and extending contiguously from a nucleotide sequence corresponding to the 5' end of said sequence of SEQ ID NO:37 from nucleotide 611 to nucleotide 751, to a nucleotide sequence corresponding to the 3' end of said sequence of SEQ ID NO:37 from nucleotide 611 to nucleotide 751.

In other embodiments, the present invention provides a composition comprising a protein, wherein said protein comprises an amino acid sequence selected from the group consisting of:
  (a) the amino acid sequence of SEQ ID NO:38;
  (b) a fragment of the amino acid sequence of SEQ ID NO:38, the fragment comprising eight contiguous amino acids of SEQ ID NO:38; and
  (c) the amino acid sequence encoded by the cDNA insert of clone yc40_1 deposited under accession number ATCC 98834;
the protein being substantially free from other mammalian proteins. Preferably such protein comprises the amino acid sequence of SEQ ID NO:38. In further preferred embodiments, the present invention provides a protein comprising a fragment of the amino acid sequence of SEQ ID NO:38 having biological activity, the fragment preferably comprising eight (more preferably twenty, most preferably thirty) contiguous amino acids of SEQ ID NO:38, or a protein comprising a fragment of the amino acid sequence of SEQ ID NO:38 having biological activity, the fragment comprising the amino acid sequence from amino acid 40 to amino acid 49 of SEQ ID NO:38.

In one embodiment, the present invention provides a composition comprising an isolated polynucleotide selected from the group consisting of:
  (a) a polynucleotide comprising the nucleotide sequence of SEQ ID NO:39;
  (b) a polynucleotide comprising the nucleotide sequence of SEQ ID NO:39 from nucleotide 179 to nucleotide 601;
  (c) a polynucleotide comprising the nucleotide sequence of SEQ ID NO:39 from nucleotide 356 to nucleotide 601;
  (d) a polynucleotide comprising the nucleotide sequence of the full-length protein coding sequence of clone yd10_1 deposited under accession number ATCC 98834;
  (e) a polynucleotide encoding the full-length protein encoded by the cDNA insert of clone yd10_1 deposited under accession number ATCC 98834;
  (f) a polynucleotide comprising the nucleotide sequence of a mature protein coding sequence of clone yd10_1 deposited under accession number ATCC 98834;
  (g) a polynucleotide encoding a mature protein encoded by the cDNA insert of clone yd10_1 deposited under accession number ATCC 98834;
  (h) a polynucleotide encoding a protein comprising the amino acid sequence of SEQ ID NO:40;
  (i) a polynucleotide encoding a protein comprising a fragment of the amino acid sequence of SEQ ID NO:40 having biological activity, the fragment comprising eight contiguous amino acids of SEQ ID NO:40;
  (j) a polynucleotide which is an allelic variant of a polynucleotide of (a)–(g) above;
  (k) a polynucleotide which encodes a species homologue of the protein of (h) or (i) above;
  (l) a polynucleotide that hybridizes under stringent conditions to any one of the polynucleotides specified in (a)–(i); and
  (m) a polynucleotide that hybridizes under stringent conditions to any one of the polynucleotides specified in (a)–(i) and that has a length that is at least 25% of the length of SEQ ID NO:39.

Preferably, such polynucleotide comprises the nucleotide sequence of SEQ ID NO:39 from nucleotide 179 to nucleotide 601; the nucleotide sequence of SEQ ID NO:39 from nucleotide 356 to nucleotide 601; the nucleotide sequence of the full-length protein coding sequence of clone yd10_1 deposited under accession number ATCC 98834; or the nucleotide sequence of a mature protein coding sequence of clone yd10_1 deposited under accession number ATCC 98834. In other preferred embodiments, the polynucleotide encodes the full-length or a mature protein encoded by the cDNA insert of clone yd10_1 deposited under accession number ATCC 98834. In further preferred embodiments, the present invention provides a polynucleotide encoding a protein comprising a fragment of the amino acid sequence of SEQ ID NO:40 having biological activity, the fragment preferably comprising eight (more preferably twenty, most preferably thirty) contiguous amino acids of SEQ ID NO:40, or a polynucleotide encoding a protein comprising a fragment of the amino acid sequence of SEQ ID NO:40 having biological activity, the fragment comprising the amino acid sequence from amino acid 65 to amino acid 74 of SEQ ID NO:40.

Other embodiments provide the gene corresponding to the cDNA sequence of SEQ ID NO:39.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:39, but excluding the poly(A) tail at the 3' end of SEQ ID NO:39; and
      (ab) the nucleotide sequence of the cDNA insert of clone yd10_1 deposited under accession number ATCC 98834;
    (ii) hybridizing said probe(s) to human genomic DNA in conditions at least as stringent as 4×SSC at 50 degrees C.; and
    (iii) isolating the DNA polynucleotides detected with the probe(s);
  and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:39, but excluding the poly(A) tail at the 3' end of SEQ ID NO:39; and
      (bb) the nucleotide sequence of the cDNA insert of clone yd10_1 deposited under accession number ATCC 98834;

(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:39, and extending contiguously from a nucleotide sequence corresponding to the 5' end of SEQ ID NO:39 to a nucleotide sequence corresponding to the 3' end of SEQ ID NO:39, but excluding the poly(A) tail at the 3' end of SEQ ID NO:39. Also preferably the polynucleotide isolated according to the above process comprises a nucleotide sequence corresponding to the cDNA sequence of SEQ ID NO:39 from nucleotide 179 to nucleotide 601, and extending contiguously from a nucleotide sequence corresponding to the 5' end of said sequence of SEQ ID NO:39 from nucleotide 179 to nucleotide 601, to a nucleotide sequence corresponding to the 3' end of said sequence of SEQ ID NO:39 from nucleotide 179 to nucleotide 601. Also preferably the polynucleotide isolated according to the above process comprises a nucleotide sequence corresponding to the cDNA sequence of SEQ ID NO:39 from nucleotide 356 to nucleotide 601, and extending contiguously from a nucleotide sequence corresponding to the 5' end of said sequence of SEQ ID NO:39 from nucleotide 356 to nucleotide 601, to a nucleotide sequence corresponding to the 3' end of said sequence of SEQ ID NO:39 from nucleotide 356 to nucleotide 601.

In other embodiments, the present invention provides a composition comprising a protein, wherein said protein comprises an amino acid sequence selected from the group consisting of:
(a) the amino acid sequence of SEQ ID NO:40;
(b) a fragment of the amino acid sequence of SEQ ID NO:40, the fragment comprising eight contiguous amino acids of SEQ ID NO:40; and
(c) the amino acid sequence encoded by the cDNA insert of clone yd10_1 deposited under accession number ATCC 98834;

the protein being substantially free from other mammalian proteins. Preferably such protein comprises the amino acid sequence of SEQ ID NO:40. In further preferred embodiments, the present invention provides a protein comprising a fragment of the amino acid sequence of SEQ ID NO:40 having biological activity, the fragment preferably comprising eight (more preferably twenty, most preferably thirty) contiguous amino acids of SEQ ID NO:40, or a protein comprising a fragment of the amino acid sequence of SEQ ID NO:40 having biological activity, the fragment comprising the amino acid sequence from amino acid 65 to amino acid 74 of SEQ ID NO:40.

In one embodiment, the present invention provides a composition comprising an isolated polynucleotide selected from the group consisting of:
(a) a polynucleotide comprising the nucleotide sequence of SEQ ID NO:41;
(b) a polynucleotide comprising the nucleotide sequence of SEQ ID NO:41 from nucleotide 324 to nucleotide 1559;
(c) a polynucleotide comprising the nucleotide sequence of SEQ ID NO:41 from nucleotide 387 to nucleotide 1559;
(d) a polynucleotide comprising the nucleotide sequence of the full-length protein coding sequence of clone yf5_1 deposited under accession number ATCC 98834;
(e) a polynucleotide encoding the full-length protein encoded by the cDNA insert of clone yf5_1 deposited under accession number ATCC 98834;
(f) a polynucleotide comprising the nucleotide sequence of a mature protein coding sequence of clone yf5_1 deposited under accession number ATCC 98834;
(g) a polynucleotide encoding a mature protein encoded by the cDNA insert of clone yf5_1 deposited under accession number ATCC 98834;
(h) a polynucleotide encoding a protein comprising the amino acid sequence of SEQ ID NO:42;
(i) a polynucleotide encoding a protein comprising a fragment of the amino acid sequence of SEQ ID NO:42 having biological activity, the fragment comprising eight contiguous amino acids of SEQ ID NO:42;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:41.

Preferably, such polynucleotide comprises the nucleotide sequence of SEQ ID NO:41 from nucleotide 324 to nucleotide 1559; the nucleotide sequence of SEQ ID NO:41 from nucleotide 387 to nucleotide 1559; the nucleotide sequence of the full-length protein coding sequence of clone yf5_1 deposited under accession number ATCC 98834; or the nucleotide sequence of a mature protein coding sequence of clone yf5_1 deposited under accession number ATCC 98834. In other preferred embodiments, the polynucleotide encodes the full-length or a mature protein encoded by the cDNA insert of clone yf5_1 deposited under accession number ATCC 98834. In further preferred embodiments, the present invention provides a polynucleotide encoding a protein comprising a fragment of the amino acid sequence of SEQ ID NO:42 having biological activity, the fragment preferably comprising eight (more preferably twenty, most preferably thirty) contiguous amino acids of SEQ ID NO:42, or a polynucleotide encoding a protein comprising a fragment of the amino acid sequence of SEQ ID NO:42 having biological activity, the fragment comprising the amino acid sequence from amino acid 201 to amino acid 210 of SEQ ID NO:42.

Other embodiments provide the gene corresponding to the cDNA sequence of SEQ ID NO:41.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:41, but excluding the poly(A) tail at the 3' end of SEQ ID NO:41; and
(ab) the nucleotide sequence of the cDNA insert of clone yf5_1 deposited under accession number ATCC 98834;
(ii) hybridizing said probe(s) to human genomic DNA in conditions at least as stringent as 4×SSC at 50 degrees C.; and
(iii) isolating the DNA polynucleotides detected with the probe(s);

and
(b) a process comprising the steps of:
(i) preparing one or more polynucleotide primers that hybridize in 6×SSC at 65 degrees C. to a nucleotide sequence selected from the group consisting of:
(ba) SEQ ID NO:41, but excluding the poly(A) tail at the 3' end of SEQ ID NO:41; and
(bb) the nucleotide sequence of the cDNA insert of clone yf5_1 deposited under accession number ATCC 98834;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:41, and extending contiguously from a nucleotide sequence corresponding to the 5' end of SEQ ID NO:41 to a nucleotide sequence corresponding to the 3' end of SEQ ID. NO:41, but excluding the poly(A) tail at the 3' end of SEQ ID NO:41. Also preferably the polynucleotide isolated according to the above process comprises a nucleotide sequence corresponding to the cDNA sequence of SEQ ID NO:41 from nucleotide 324 to nucleotide 1559, and extending contiguously from a nucleotide sequence corresponding to the 5' end of said sequence of SEQ ID NO:41 from nucleotide 324 to nucleotide 1559, to a nucleotide sequence corresponding to the 3' end of said sequence of SEQ ID NO:41 from nucleotide 324 to nucleotide 1559. Also preferably the polynucleotide isolated according to the above process comprises a nucleotide sequence corresponding to the cDNA sequence of SEQ ID NO:41 from nucleotide 387 to nucleotide 1559, and extending contiguously from a nucleotide sequence corresponding to the 5' end of said sequence of SEQ ID NO:41 from nucleotide 387 to nucleotide 1559, to a nucleotide sequence corresponding to the 3' end of said sequence of SEQ ID NO:41 from nucleotide 387 to nucleotide 1559.

In other embodiments, the present invention provides a composition comprising a protein, wherein said protein comprises an amino acid sequence selected from the group consisting of:
(a) the amino acid sequence of SEQ ID NO:42;
(b) a fragment of the amino acid sequence of SEQ ID NO:42, the fragment comprising eight contiguous amino acids of SEQ ID NO:42; and
(c) the amino acid sequence encoded by the cDNA insert of clone yf5_1 deposited under accession number ATCC 98834;
the protein being substantially free from other mammalian proteins. Preferably such protein comprises the amino acid sequence of SEQ ID NO:42. In further preferred embodiments, the present invention provides a protein comprising a fragment of the amino acid sequence of SEQ ID NO:42 having biological activity, the fragment preferably comprising eight (more preferably twenty, most preferably thirty) contiguous amino acids of SEQ ID NO:42, or a protein comprising a fragment of the amino acid sequence of SEQ ID NO:42 having biological activity, the fragment comprising the amino acid sequence from amino acid 201 to amino acid 210 of SEQ ID NO:42.

In one embodiment, the present invention provides a composition comprising an isolated polynucleotide selected from the group consisting of:
(a) a polynucleotide comprising the nucleotide sequence of SEQ ID NO:43;
(b) a polynucleotide comprising the nucleotide sequence of SEQ ID NO:43 from nucleotide 257 to nucleotide 649;
(c) a polynucleotide comprising the nucleotide sequence of SEQ ID NO:43 from nucleotide 335 to nucleotide 649;
(d) a polynucleotide comprising the nucleotide sequence of the full-length protein coding sequence of clone ya67_1 deposited under accession number ATCC 98864;
(e) a polynucleotide encoding the full-length protein encoded by the cDNA insert of clone ya67_1 deposited under accession number ATCC 98864;
(f) a polynucleotide comprising the nucleotide sequence of a mature protein coding sequence of clone ya67_1 deposited under accession number ATCC 98864;
(g) a polynucleotide encoding a mature protein encoded by the cDNA insert of clone ya67_1 deposited under accession number ATCC 98864;
(h) a polynucleotide encoding a protein comprising the amino acid sequence of SEQ ID NO:44;
(i) a polynucleotide encoding a protein comprising a fragment of the amino acid sequence of SEQ ID NO:44 having biological activity, the fragment comprising eight contiguous amino acids of SEQ ID NO:44;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:43.

Preferably, such polynucleotide comprises the nucleotide sequence of SEQ ID NO:43 from nucleotide 257 to nucleotide 649; the nucleotide sequence of SEQ ID NO:43 from nucleotide 335 to nucleotide 649; the nucleotide sequence of the full-length protein coding sequence of done ya67_1 deposited under accession number ATCC 98864; or the nucleotide sequence of a mature protein coding sequence of clone ya67_1 deposited under accession number ATCC 98864. In other preferred embodiments, the polynucleotide encodes the full-length or a mature protein encoded by the cDNA insert of clone ya67_1 deposited under accession number ATCC 98864. In further preferred embodiments, the present invention provides a polynucleotide encoding a protein comprising a fragment of the amino acid sequence of SEQ ID NO:44 having biological activity, the fragment preferably comprising eight (more preferably twenty, most preferably thirty) contiguous amino acids of SEQ ID NO:44, or a polynucleotide encoding a protein comprising a fragment of the amino acid sequence of SEQ ID NO:44 having biological activity, the fragment comprising the amino acid sequence from amino acid 60 to amino acid 69 of SEQ ID NO:44.

Other embodiments provide the gene corresponding to the cDNA sequence of SEQ ID NO:43.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:

(aa) SEQ ID NO:43, but excluding the poly(A) tail at the 3' end of SEQ ID NO:43; and
(ab) the nucleotide sequence of the cDNA insert of clone ya67_1 deposited under accession number ATCC 98864;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:43, but excluding the poly(A) tail at the 3' end of SEQ ID NO:43; and
(bb) the nucleotide sequence of the cDNA insert of clone ya67_1 deposited under accession number ATCC 98864;
(j) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:43, and extending contiguously from a nucleotide sequence corresponding to the 5' end of SEQ ID NO:43 to a nucleotide sequence corresponding to the 3' end of SEQ ID NO:43, but excluding the poly(A) tail at the 3' end of SEQ ID NO:43. Also preferably the polynucleotide isolated according to the above process comprises a nucleotide sequence corresponding to the cDNA sequence of SEQ ID NO:43 from nucleotide 257 to nucleotide 649, and extending contiguously from a nucleotide sequence corresponding to the 5' end of said sequence of SEQ ID NO:43 from nucleotide 257 to nucleotide 649, to a nucleotide sequence corresponding to the 3' end of said sequence of SEQ ID NO:43 from nucleotide 257 to nucleotide 649. Also preferably the polynucleotide isolated according to the above process comprises a nucleotide sequence corresponding to the cDNA sequence of SEQ ID NO:43 from nucleotide 335 to nucleotide 649, and extending contiguously from a nucleotide sequence corresponding to the 5' end of said sequence of SEQ ID NO:43 from nucleotide 335 to nucleotide 649, to a nucleotide sequence corresponding to the 3' end of said sequence of SEQ ID NO:43 from nucleotide 335 to nucleotide 649.

In other embodiments, the present invention provides a composition comprising a protein, wherein said protein comprises an amino acid sequence selected from the group consisting of:
(a) the amino acid sequence of SEQ ID NO:44;
(b) a fragment of the amino acid sequence of SEQ ID NO:44, the fragment comprising eight contiguous amino acids of SEQ ID NO:44; and
(c) the amino acid sequence encoded by the cDNA insert of clone ya67_1 deposited under accession number ATCC 98864;
the protein being substantially free from other mammalian proteins. Preferably such protein comprises the amino acid sequence of SEQ ID NO:44. In further preferred embodiments, the present invention provides a protein comprising a fragment of the amino acid sequence of SEQ ID NO:44 having biological activity, the fragment preferably comprising eight (more preferably twenty, most preferably thirty) contiguous amino acids of SEQ ID NO:44, or a protein comprising a fragment of the amino acid sequence of SEQ ID NO:44 having biological activity, the fragment comprising the amino acid sequence from amino acid 60 to amino acid 69 of SEQ ID NO:44.

In one embodiment, the present invention provides a composition comprising an isolated polynucleotide selected from the group consisting of:
(a) a polynucleotide comprising the nucleotide sequence of SEQ ID NO:45;
(b) a polynucleotide comprising the nucleotide sequence of SEQ ID NO:45 from nucleotide 89 to nucleotide 787;
(c) a polynucleotide comprising the nucleotide sequence of the full-length protein coding sequence of clone ya70_1 deposited under accession number ATCC 98864;
(d) a polynucleotide encoding the full-length protein encoded by the cDNA insert of clone ya70_1 deposited under accession number ATCC 98864;
(e) a polynucleotide comprising the nucleotide sequence of a mature protein coding sequence of clone ya70_1 deposited under accession number ATCC 98864;
(f) a polynucleotide encoding a mature protein encoded by the cDNA insert of clone ya70_1 deposited under accession number ATCC 98864;
(g) a polynucleotide encoding a protein comprising the amino acid sequence of SEQ ID NO:46;
(h) a polynucleotide encoding a protein comprising a fragment of the amino acid sequence of SEQ ID NO:46 having biological activity, the fragment comprising eight contiguous amino acids of SEQ ID NO:46;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:45.

Preferably, such polynucleotide comprises the nucleotide sequence of SEQ ID NO:45 from nucleotide 89 to nucleotide 787; the nucleotide sequence of the full-length protein coding sequence of clone ya70_1 deposited under accession number ATCC 98864; or the nucleotide sequence of a mature protein coding sequence of clone ya70_1 deposited under accession number ATCC 98864. In other preferred embodiments, the polynucleotide encodes the full-length or a mature protein encoded by the cDNA insert of clone ya70_1 deposited under accession number ATCC 98864. In further preferred embodiments, the present invention provides a polynucleotide encoding a protein comprising a fragment of the amino acid sequence of SEQ ID NO:46 having biological activity, the fragment preferably comprising eight (more preferably twenty, most preferably thirty) contiguous amino acids of SEQ ID NO:46, or a polynucleotide encoding a protein comprising a fragment of the amino acid sequence of SEQ ID NO:46 having biological activity, the fragment comprising the amino acid sequence from amino acid 111 to amino acid 120 of SEQ ID NO:46.

Other embodiments provide the gene corresponding to the cDNA sequence of SEQ ID NO:45.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:45, but excluding the poly(A) tail at the 3' end of SEQ ID NO:45; and
(ab) the nucleotide sequence of the cDNA insert of clone ya70_1 deposited under accession number ATCC 98864;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:45, but excluding the poly(A) tail at the 3' end of SEQ ID NO:45; and
(bb) the nucleotide sequence of the cDNA insert of clone ya70_1 deposited under accession number ATCC 98864;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:45, and extending contiguously from a nucleotide sequence corresponding to the 5' end of SEQ ID NO:45 to a nucleotide sequence corresponding to the 3' end of SEQ ID NO:45, but excluding the poly(A) tail at the 3' end of SEQ ID NO:45. Also preferably the polynucleotide isolated according to the above process comprises a nucleotide sequence corresponding to the cDNA sequence of SEQ ID NO:45 from nucleotide 89 to nucleotide 787, and extending contiguously from a nucleotide sequence corresponding to the 5' end of said sequence of SEQ ID NO:45 from nucleotide 89 to nucleotide 787, to a nucleotide sequence corresponding to the 3' end of said sequence of SEQ ID NO:45 from nucleotide 89 to nucleotide 787.

In other embodiments, the present invention provides a composition comprising a protein, wherein said protein comprises an amino acid sequence selected from the group consisting of:

(a) the amino acid sequence of SEQ ID NO:46;
(b) a fragment of the amino acid sequence of SEQ ID NO:46, the fragment comprising eight contiguous amino acids of SEQ ID NO:46; and
(c) the amino acid sequence encoded by the cDNA insert of clone ya70_1 deposited under accession number ATCC 98864;

the protein being substantially free from other mammalian proteins. Preferably such protein comprises the amino acid sequence of SEQ ID NO:46. In further preferred embodiments, the present invention provides a protein comprising a fragment of the amino acid sequence of SEQ ID NO:46 having biological activity, the fragment preferably comprising eight (more preferably twenty, most preferably thirty) contiguous amino acids of SEQ ID NO:46, or a protein comprising a fragment of the amino acid sequence of SEQ ID NO:46 having biological activity, the fragment comprising the amino acid sequence from amino acid 111 to amino acid 120 of SEQ ID NO:46.

In one embodiment, the present invention provides a composition comprising an isolated polynucleotide selected from the group consisting of:

(a) a polynucleotide comprising the nucleotide sequence of SEQ ID NO:47;
(b) a polynucleotide comprising the nucleotide sequence of SEQ ID NO:47 from nucleotide 1017 to nucleotide 1265;
(c) a polynucleotide comprising the nucleotide sequence of SEQ ID NO:47 from nucleotide 1068 to nucleotide 1265;
(d) a polynucleotide comprising the nucleotide sequence of the full-length protein coding sequence of clone yb51_1 deposited under accession number ATCC 98864;
(e) a polynucleotide encoding the full-length protein encoded by the cDNA insert of clone yb51_1 deposited under accession number ATCC 98864;
(f) a polynucleotide comprising the nucleotide sequence of a mature protein coding sequence of clone yb51_1 deposited under accession number ATCC 98864;
(g) a polynucleotide encoding a mature protein encoded by the cDNA insert of clone yb51_1 deposited under accession number ATCC 98864;
(h) a polynucleotide encoding a protein comprising the amino acid sequence of SEQ ID NO:48;
(i) a polynucleotide encoding a protein comprising a fragment of the amino acid sequence of SEQ ID NO:48 having biological activity, the fragment comprising eight contiguous amino acids of SEQ ID NO:48;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:47.

Preferably, such polynucleotide comprises the nucleotide sequence of SEQ ID NO:47 from nucleotide 1017 to nucleotide 1265; the nucleotide sequence of SEQ ID NO:47 from nucleotide 1068 to nucleotide 1265; the nucleotide sequence of the full-length protein coding sequence of clone yb51_1 deposited under accession number ATCC 98864; or the nucleotide sequence of a mature protein coding sequence of clone yb51_1 deposited under accession number ATCC 98864. In other preferred embodiments, the polynucleotide encodes the full-length or a mature protein encoded by the cDNA insert of clone yb51_1 deposited under accession number ATCC 98864. In further preferred embodiments, the present invention provides a polynucleotide encoding a protein comprising a fragment of the amino acid sequence of SEQ ID NO:48 having biological activity, the fragment preferably comprising eight (more preferably twenty, most preferably thirty) contiguous amino acids of SEQ ID NO:48, or a polynucleotide encoding a protein comprising a fragment of the amino acid sequence of SEQ ID NO:48 having biological activity, the fragment comprising the amino acid sequence from amino acid 36 to amino acid 45 of SEQ ID NO:48.

Other embodiments provide the gene corresponding to the cDNA sequence of SEQ ID NO:47.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:47, but excluding the poly(A) tail at the 3' end of SEQ ID NO:47; and
      (ab) the nucleotide sequence of the cDNA insert of clone yb51_1 deposited under accession number ATCC 98864;
    (ii) hybridizing said probe(s) to human genomic DNA in conditions at least as stringent as 4×SSC at 50 degrees C.; and
    (iii) isolating the DNA polynucleotides detected with the probe(s);
and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:47, but excluding the poly(A) tail at the 3' end of SEQ ID NO:47; and
      (bb) the nucleotide sequence of the cDNA insert of clone yb51_1 deposited under accession number ATCC 98864;
    (ii) hybridizing said primer(s) to human genomic DNA in conditions at least as stringent as 4×SSC at 50 degrees C.;
    (iii) amplifying human DNA sequences; and
    (iv) isolating the polynucleotide products of step (b) (iii).

Preferably the polynucleotide isolated according to the above process comprises a nucleotide sequence corresponding to the cDNA sequence of SEQ ID NO:47, and extending contiguously from a nucleotide sequence corresponding to the 5' end of SEQ ID NO:47 to a nucleotide sequence corresponding to the 3' end of SEQ ID NO:47, but excluding the poly(A) tail at the 3' end of SEQ ID NO:47. Also preferably the polynucleotide isolated according to the above process comprises a nucleotide sequence corresponding to the cDNA sequence of SEQ ID NO:47 from nucleotide 1017 to nucleotide 1265, and extending contiguously from a nucleotide sequence corresponding to the 5' end of said sequence of SEQ ID NO:47 from nucleotide 1017 to nucleotide 1265, to a nucleotide sequence corresponding to the 3' end of said sequence of SEQ ID NO:47 from nucleotide 1017 to nucleotide 1265. Also preferably the polynucleotide isolated according to the above process comprises a nucleotide sequence corresponding to the cDNA sequence of SEQ ID NO:47 from nucleotide 1068 to nucleotide 1265, and extending contiguously from a nucleotide sequence corresponding to the 5' end of said sequence of SEQ ID NO:47 from nucleotide 1068 to nucleotide 1265, to a nucleotide sequence corresponding to the 3' end of said sequence of SEQ ID NO:47 from nucleotide 1068 to nucleotide 1265.

In other embodiments, the present invention provides a composition comprising a protein, wherein said protein comprises an amino acid sequence selected from the group consisting of:

(a) the amino acid sequence of SEQ ID NO:48;
  (b) a fragment of the amino acid sequence of SEQ ID NO:48, the fragment comprising eight contiguous amino acids of SEQ ID NO:48; and
  (c) the amino acid sequence encoded by the cDNA insert of clone yb51_1 deposited under accession number ATCC 98864;
the protein being substantially free from other mammalian proteins. Preferably such protein comprises the amino acid sequence of SEQ ID NO:48. In further preferred embodiments, the present invention provides a protein comprising a fragment of the amino acid sequence of SEQ ID NO:48 having biological activity, the fragment preferably comprising eight (more preferably twenty, most preferably thirty) contiguous amino acids of SEQ ID NO:48, or a protein comprising a fragment of the amino acid sequence of SEQ ID NO:48 having biological activity, the fragment comprising the amino acid sequence from amino acid 36 to amino acid 45 of SEQ ID NO:48.

In one embodiment, the present invention provides a composition comprising an isolated polynucleotide selected from the group consisting of:
  (a) a polynucleotide comprising the nucleotide sequence of SEQ ID NO:49;
  (b) a polynucleotide comprising the nucleotide sequence of SEQ ID NO:49 from nucleotide 13 to nucleotide 306;
  (c) a polynucleotide comprising the nucleotide sequence of the full-length protein coding sequence of clone yb101_1 deposited under accession number ATCC 98864;
  (d) a polynucleotide encoding the full-length protein encoded by the cDNA insert of clone yb101_1 deposited under accession number ATCC 98864;
  (e) a polynucleotide comprising the nucleotide sequence of a mature protein coding sequence of clone yb101_1 deposited under accession number ATCC 98864;
  (f) a polynucleotide encoding a mature protein encoded by the cDNA insert of clone yb101_1 deposited under accession number ATCC 98864;
  (g) a polynucleotide encoding a protein comprising the amino acid sequence of SEQ ID NO:50;
  (h) a polynucleotide encoding a protein comprising a fragment of the amino acid sequence of SEQ ID NO:50 having biological activity, the fragment comprising eight contiguous amino acids of SEQ ID NO:50;
  (i) a polynucleotide which is an allelic variant of a polynucleotide of (a)–(f) above;
  (j) a polynucleotide which encodes a species homologue of the protein of (g) or (h) above;
  (k) a polynucleotide that hybridizes under stringent conditions to any one of the polynucleotides specified in (a)–(h); and
  (l) a polynucleotide that hybridizes under stringent conditions to any one of the polynucleotides specified in (a)–(h) and that has a length that is at least 25% of the length of SEQ ID NO:49.

Preferably, such polynucleotide comprises the nucleotide sequence of SEQ ID NO:49 from nucleotide 13 to nucleotide 306; the nucleotide sequence of the full-length protein coding sequence of clone yb101_1 deposited under accession number ATCC 98864; or the nucleotide sequence of a mature protein coding sequence of clone yb101_1 deposited under accession number ATCC 98864. In other preferred embodiments, the polynucleotide encodes the full-length or a mature protein encoded by the cDNA insert of clone yb101_1 deposited under accession number ATCC 98864. In further preferred embodiments, the present invention provides a polynucleotide encoding a protein comprising a fragment of the amino acid sequence of SEQ ID NO:50 having biological activity, the fragment preferably comprising eight (more preferably twenty, most preferably thirty) contiguous amino acids of SEQ ID NO:50, or a polynucleotide encoding a protein comprising a fragment of the amino acid sequence of SEQ ID NO:50 having biological activity, the fragment comprising the amino acid sequence from amino acid 44 to amino acid 53 of SEQ ID NO:50.

Other embodiments provide the gene corresponding to the cDNA sequence of SEQ ID NO:49.

Further embodiments of the invention provide isolated polynucleotides produced according to a process selected from the group consisting of:
(a) a process comprising the steps of:
 (i) preparing one or more polynucleotide probes that hybridize in 6×SSC at 65 degrees C. to a nucleotide sequence selected from the group consisting of:
  (aa) SEQ ID NO:49, but excluding the poly(A) tail at the 3' end of SEQ ID NO:49; and
  (ab) the nucleotide sequence of the cDNA insert of clone yb101_1 deposited under accession number ATCC 98864;
 (ii) hybridizing said probe(s) to human genomic DNA in conditions at least as stringent as 4×SSC at 50 degrees C.; and
 (iii) isolating the DNA polynucleotides detected with the probe(s);
and
(b) a process comprising the steps of:
 (i) preparing one or more polynucleotide primers that hybridize in 6×SSC at 65 degrees C. to a nucleotide sequence selected from the group consisting of:
  (ba) SEQ ID NO:49, but excluding the poly(A) tail at the 3' end of SEQ ID NO:49; and
  (bb) the nucleotide sequence of the cDNA insert of clone yb101_1 deposited under accession number ATCC 98864;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b)(iii).

Preferably the polynucleotide isolated according to the above process comprises a nucleotide sequence corresponding to the cDNA sequence of SEQ ID NO:49, and extending contiguously from a nucleotide sequence corresponding to the 5' end of SEQ ID NO:49 to a nucleotide sequence corresponding to the 3' end of SEQ ID NO:49, but excluding the poly(A) tail at the 3' end of SEQ ID NO:49. Also preferably the polynucleotide isolated according to the above process comprises a nucleotide sequence corresponding to the cDNA sequence of SEQ ID NO:49 from nucleotide 13 to nucleotide 306, and extending contiguously from a nucleotide sequence corresponding to the 5' end of said sequence of SEQ ID NO:49 from nucleotide 13 to nucleotide 306, to a nucleotide sequence corresponding to the 3' end of said sequence of SEQ ID NO:49 from nucleotide 13 to nucleotide 306.

In other embodiments, the present invention provides a composition comprising a protein, wherein said protein comprises an amino add sequence selected from the group consisting of:

(a) the amino acid sequence of SEQ ID NO:50;
(b) a fragment of the amino acid sequence of SEQ ID NO:50, the fragment comprising eight contiguous amino acids of SEQ ID NO:50; and
(c) the amino acid sequence encoded by the cDNA insert of clone yb101_1 deposited under accession number ATCC 98864;
the protein being substantially free from other mammalian proteins. Preferably such protein comprises the amino add sequence of SEQ ID NO:50. In further preferred embodiments, the present invention provides a protein comprising a fragment of the amino add sequence of SEQ ID NO:50 having biological activity, the fragment preferably comprising eight (more preferably twenty, most preferably thirty) contiguous amino acids of SEQ ID NO:50, or a protein comprising a fragment of the amino acid sequence of SEQ ID NO:50 having biological activity, the fragment comprising the amino acid sequence from amino acid 44 to amino acid 53 of SEQ ID NO:50.

In one embodiment, the present invention provides a composition comprising an isolated polynucleotide selected from the group consisting of:
(a) a polynucleotide comprising the nucleotide sequence of SEQ ID NO:51;
(b) a polynucleotide comprising the nucleotide sequence of SEQ ID NO:51 from nucleotide 284 to nucleotide 706;
(c) a polynucleotide comprising the nucleotide sequence of the full-length protein coding sequence of clone yb124_1 deposited under accession number ATCC 98864;
(d) a polynucleotide encoding the full-length protein encoded by the cDNA insert of clone yb124_1 deposited under accession number ATCC 98864;
(e) a polynucleotide comprising the nucleotide sequence of a mature protein coding sequence of clone yb124_1 deposited under accession number ATCC 98864;
(f) a polynucleotide encoding a mature protein encoded by the cDNA insert of clone yb124_1 deposited under accession number ATCC 98864;
(g) a polynucleotide encoding a protein comprising the amino acid sequence of SEQ ID NO:52;
(h) a polynucleotide encoding a protein comprising a fragment of the amino acid sequence of SEQ ID NO:52 having biological activity, the fragment comprising eight contiguous amino acids of SEQ ID NO:52;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:51.

Preferably, such polynucleotide comprises the nucleotide sequence of SEQ ID NO:51 from nucleotide 284 to nucleotide 706; the nucleotide sequence of the full-length protein coding sequence of clone yb124_1 deposited under accession number ATCC 98864; or the nucleotide sequence of a mature protein coding sequence of clone yb124_1 deposited under accession number ATCC 98864. In other preferred embodiments, the polynucleotide encodes the full-length or a mature protein encoded by the cDNA insert of clone yb124_1 deposited under accession number ATCC 98864. In further preferred embodiments, the present invention provides a polynucleotide encoding a protein comprising a fragment of the amino acid sequence of SEQ ID NO:52 having biological activity, the fragment preferably comprising eight (more preferably twenty, most preferably thirty) contiguous amino acids of SEQ ID NO:52, or a polynucleotide encoding a protein comprising a fragment of the amino acid sequence of SEQ ID NO:52 having biological activity, the fragment comprising the amino acid sequence from amino acid 65 to amino acid 74 of SEQ ID NO:52.

Other embodiments provide the gene corresponding to the cDNA sequence of SEQ ID NO:51.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:51, but excluding the poly(A) tail at the 3' end of SEQ ID NO:51; and
    (ab) the nucleotide sequence of the cDNA insert of clone yb124_1 deposited under accession number ATCC 98864;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:51, but excluding the poly(A) tail at the 3' end of SEQ ID NO:51; and
    (bb) the nucleotide sequence of the cDNA insert of clone yb124_1 deposited under accession number ATCC 98864;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:51, and extending contiguously from a nucleotide sequence corresponding to the 5' end of SEQ ID NO:51 to a nucleotide sequence corresponding to the 3' end of SEQ ID NO:51, but excluding the poly(A) tail at the 3' end of SEQ ID NO:51. Also preferably the polynucleotide isolated according to the above process comprises a nucleotide sequence corresponding to the cDNA sequence of SEQ ID NO:51 from nucleotide 284 to nucleotide 706, and extending contiguously from a nucleotide sequence corresponding to the 5' end of said sequence of SEQ ID NO:51 from nucleotide 284 to nucleotide 706, to a nucleotide sequence corresponding to the 3' end of said sequence of SEQ ID NO:51 from nucleotide 284 to nucleotide 706.

In other embodiments, the present invention provides a composition comprising a protein, wherein said protein comprises an amino acid sequence selected from the group consisting of:

(a) the amino acid sequence of SEQ ID NO:52;
(b) a fragment of the amino acid sequence of SEQ ID NO:52, the fragment comprising eight contiguous amino acids of SEQ ID NO:52; and
(c) the amino acid sequence encoded by the cDNA insert of clone yb124_1 deposited under accession number ATCC 98864;

the protein being substantially free from other mammalian proteins. Preferably such protein comprises the amino acid sequence of SEQ ID NO:52. In further preferred embodiments, the present invention provides a protein comprising a fragment of the amino acid sequence of SEQ ID NO:52 having biological activity, the fragment preferably comprising eight (more preferably twenty, most preferably thirty) contiguous amino acids of SEQ ID NO:52, or a protein comprising a fragment of the amino acid sequence of SEQ ID NO:52 having biological activity, the fragment comprising the amino acid sequence from amino acid 65 to amino acid 74 of SEQ ID NO:52.

In one embodiment, the present invention provides a composition comprising an isolated polynucleotide selected from the group consisting of:

(a) a polynucleotide comprising the nucleotide sequence of SEQ ID NO:53;
(b) a polynucleotide comprising the nucleotide sequence of SEQ ID NO:53 from nucleotide 1106 to nucleotide 1447;
(c) a polynucleotide comprising the nucleotide sequence of SEQ ID NO:53 from nucleotide 1187 to nucleotide 1447;
(d) a polynucleotide comprising the nucleotide sequence of the full-length protein coding sequence of clone yb125_1 deposited under accession number ATCC 98864;
(e) a polynucleotide encoding the full-length protein encoded by the cDNA insert of clone yb125_1 deposited under accession number ATCC 98864;
(e) a polynucleotide comprising the nucleotide sequence of a mature protein coding sequence of clone yb125_1 deposited under accession number ATCC 98864;
(g) a polynucleotide encoding a mature protein encoded by the cDNA insert of clone yb125_1 deposited under accession number ATCC 98864;
(h) a polynucleotide encoding a protein comprising the amino acid sequence of SEQ ID NO:54;
(i) a polynucleotide encoding a protein comprising a fragment of the amino acid sequence of SEQ ID NO:54 having biological activity, the fragment comprising eight contiguous amino acids of SEQ ID NO:54;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:53.

Preferably, such polynucleotide comprises the nucleotide sequence of SEQ ID NO:53 from nucleotide 1106 to nucleotide 1447; the nucleotide sequence of SEQ ID NO:53 from nucleotide 1187 to nucleotide 1447; the nucleotide sequence of the full-length protein coding sequence of clone yb125_1 deposited under accession number ATCC 98864; or the nucleotide sequence of a mature protein coding sequence of clone yb125_1 deposited under accession number ATCC 98864. In other preferred embodiments, the polynucleotide encodes the full-length or a mature protein encoded by the cDNA insert of clone yb125_1 deposited under accession number ATCC 98864. In further preferred embodiments, the present invention provides a polynucleotide encoding a protein comprising a fragment of the amino acid sequence of SEQ ID NO:54 having biological activity, the fragment preferably comprising eight (more preferably twenty, most preferably thirty) contiguous amino acids of SEQ ID NO:54, or a polynucleotide encoding a protein comprising a fragment of the amino acid sequence of SEQ ID NO:54 having biological activity, the fragment comprising the amino acid sequence from amino acid 52 to amino acid 61 of SEQ ID NO:54.

Other embodiments provide the gene corresponding to the cDNA sequence of SEQ ID NO:53.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:53, but excluding the poly(A) tail at the 3' end of SEQ ID NO:53; and
    (ab) the nucleotide sequence of the cDNA insert of clone yb125_1 deposited under accession number ATCC 98864;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:53, but excluding the poly(A) tail at the 3' end of SEQ ID NO:53; and
    (bb) the nucleotide sequence of the cDNA insert of clone yb125_1 deposited under accession number ATCC 98864;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:53, and extending contiguously from a nucleotide sequence corresponding to the 5' end of SEQ ID NO:53 to a nucleotide sequence corresponding to the 3' end of SEQ ID NO:53, but excluding the poly(A) tail at the 3' end of SEQ ID NO:53. Also preferably the polynucleotide isolated according to the above process comprises a nucleotide sequence corresponding to the cDNA sequence of SEQ ID NO:53 from nucleotide 1106 to nucleotide 1447, and extending contiguously from a nucleotide sequence corresponding to the 5' end of said sequence of SEQ ID NO:53 from nucleotide 1106 to nucleotide 1447, to a nucleotide sequence corresponding to the 3' end of said sequence of SEQ ID NO:53 from nucleotide 1106 to nucleotide 1447. Also preferably the polynucleotide isolated according to the above process comprises a nucleotide sequence corresponding to the cDNA sequence of SEQ ID NO:53 from nucleotide 1187 to nucleotide 1447, and extending contiguously from a nucleotide sequence corresponding to the 5' end of said sequence of SEQ ID NO:53 from nucleotide 1187 to nucleotide 1447, to a nucleotide sequence corresponding to the 3' end of said sequence of SEQ ID NO:53 from nucleotide 1187 to nucleotide 1447.

In other embodiments, the present invention provides a composition comprising a protein, wherein said protein comprises an amino acid sequence selected from the group consisting of:
(a) the amino acid sequence of SEQ ID NO:54;
(b) a fragment of the amino acid sequence of SEQ ID NO:54, the fragment comprising eight contiguous amino acids of SEQ ID NO:54; and
(c) the amino acid sequence encoded by the cDNA insert of clone yb125_1 deposited under accession number ATCC 98864;
the protein being substantially free from other mammalian proteins. Preferably such protein comprises the amino acid sequence of SEQ ID NO:54. In further preferred embodiments, the present invention provides a protein comprising a fragment of the amino acid sequence of SEQ ID NO:54 having biological activity, the fragment preferably comprising eight (more preferably twenty, most preferably thirty) contiguous amino acids of SEQ ID NO:54, or a protein comprising a fragment of the amino acid sequence of SEQ ID NO:54 having biological activity, the fragment comprising the amino acid sequence from amino acid 52 to amino acid 61 of SEQ ID NO:54.

In one embodiment, the present invention provides a composition comprising an isolated polynucleotide selected from the group consisting of:
(a) a polynucleotide comprising the nucleotide sequence of SEQ ID NO:55;
(b) a polynucleotide comprising the nucleotide sequence of SEQ ID NO:55 from nucleotide 28 to nucleotide 417;
(c) a polynucleotide comprising the nucleotide sequence of the full-length protein coding sequence of clone yb179_1 deposited under accession number ATCC 98864;
(d) a polynucleotide encoding the full-length protein encoded by the cDNA insert of clone yb179_1 deposited under accession number ATCC 98864;
(e) a polynucleotide comprising the nucleotide sequence of a mature protein coding sequence of clone yb179_1 deposited under accession number ATCC 98864;
(f) a polynucleotide encoding a mature protein encoded by the cDNA insert of clone yb179_1 deposited under accession number ATCC 98864;
(g) a polynucleotide encoding a protein comprising the amino acid sequence of SEQ ID NO:56;
(h) a polynucleotide encoding a protein comprising a fragment of the amino acid sequence of SEQ ID NO:56 having biological activity, the fragment comprising eight contiguous amino acids of SEQ ID NO:56;
(i) a polynucleotide which is an allelic variant of a polynucleotide of (a)–(f) above;
(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:55.

Preferably, such polynucleotide comprises the nucleotide sequence of SEQ ID NO:55 from nucleotide 28 to nucleotide 417; the nucleotide sequence of the full-length protein coding sequence of clone yb179_1 deposited under accession number ATCC 98864; or the nucleotide sequence of a mature protein coding sequence of clone yb179_1 deposited under accession number ATCC 98864. In other preferred embodiments, the polynucleotide encodes the full-length or a mature protein encoded by the cDNA insert of clone yb179_1 deposited under accession number ATCC 98864. In further preferred embodiments, the present invention provides a polynucleotide encoding a protein comprising a fragment of the amino acid sequence of SEQ ID NO:56 having biological activity, the fragment preferably comprising eight (more preferably twenty, most preferably thirty) contiguous amino acids of SEQ ID NO:56, or a polynucleotide encoding a protein comprising a fragment of the amino acid sequence of SEQ ID NO:56 having biological activity, the fragment comprising the amino acid sequence from amino acid 60 to amino acid 69 of SEQ ID NO:56.

Other embodiments provide the gene corresponding to the cDNA sequence of SEQ ID NO:55.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:55, but excluding the poly(A) tail at the 3' end of SEQ ID NO:55; and
    (ab) the nucleotide sequence of the cDNA insert of clone yb179_1 deposited under accession number ATCC 98864;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:55, but excluding the poly(A) tail at the 3' end of SEQ ID NO:55; and
    (bb) the nucleotide sequence of the cDNA insert of clone yb179_1 deposited under accession number ATCC 98864;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:55, and extending contiguously from a nucleotide sequence corresponding to the 5' end of SEQ ID NO:55 to a nucleotide sequence corresponding to the 3' end of SEQ ID NO:55, but excluding the poly(A) tail at the 3' end of SEQ ID NO:55. Also preferably the polynucleotide isolated according to the above process comprises a nucleotide sequence corresponding to the cDNA sequence of SEQ ID NO:55 from nucleotide 28 to nucleotide 417, and extending contiguously from a nucleotide sequence corresponding to the 5' end of said sequence of SEQ ID NO:55 from nucleotide 28 to nucleotide 417, to a nucleotide sequence corresponding to the 3' end of said sequence of SEQ ID NO:55 from nucleotide 28 to nucleotide 417.

In other embodiments, the present invention provides a composition comprising a protein, wherein said protein comprises an amino acid sequence selected from the group consisting of:

(a) the amino acid sequence of SEQ ID NO:56;
(b) a fragment of the amino acid sequence of SEQ ID NO:56, the fragment comprising eight contiguous amino acids of SEQ ID NO:56; and
(c) the amino acid sequence encoded by the cDNA insert of clone yb179_1 deposited under accession number ATCC 98864;

the protein being substantially free from other mammalian proteins. Preferably such protein comprises the amino acid sequence of SEQ ID NO:56. In further preferred embodiments, the present invention provides a protein comprising a fragment of the amino acid sequence of SEQ ID NO:56 having biological activity, the fragment preferably comprising eight (more preferably twenty, most preferably thirty) contiguous amino acids of SEQ ID NO:56, or a protein comprising a fragment of the amino acid sequence of SEQ ID NO:56 having biological activity, the fragment comprising the amino acid sequence from amino acid 60 to amino acid 69 of SEQ ID NO:56.

In one embodiment, the present invention provides a composition comprising an isolated polynucleotide selected from the group consisting of:

(a) a polynucleotide comprising the nucleotide sequence of SEQ ID NO:57;
(b) a polynucleotide comprising the nucleotide sequence of SEQ ID NO:57 from nucleotide 56 to nucleotide 1084;
(c) a polynucleotide comprising the nucleotide sequence of SEQ ID NO:57 from nucleotide 107 to nucleotide 1084;
(d) a polynucleotide comprising the nucleotide sequence of the full-length protein coding sequence of clone yc48_1 deposited under accession number ATCC 98864;
(e) a polynucleotide encoding the full-length protein encoded by the cDNA insert of clone yc48_1 deposited under accession number ATCC 98864;
(f) a polynucleotide comprising the nucleotide sequence of a mature protein coding sequence of clone yc48_1 deposited under accession number ATCC 98864;
(g) a polynucleotide encoding a mature protein encoded by the cDNA insert of clone yc48_1 deposited under accession number ATCC 98864;
(h) a polynucleotide encoding a protein comprising the amino acid sequence of SEQ ID NO:58;
(i) a polynucleotide encoding a protein comprising a fragment of the amino acid sequence of SEQ ID NO:58 having biological activity, the fragment comprising eight contiguous amino acids of SEQ ID NO:58;
(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:57.

Preferably, such polynucleotide comprises the nucleotide sequence of SEQ ID NO:57 from nucleotide 56 to nucleotide 1084; the nucleotide sequence of SEQ ID NO:57 from nucleotide 107 to nucleotide 1084; the nucleotide sequence of the full-length protein coding sequence of clone yc48_1 deposited under accession number ATCC 98864; or the nucleotide sequence of a mature protein coding sequence of clone yc48_1 deposited under accession number ATCC 98864. In other preferred embodiments, the polynucleotide encodes the full-length or a mature protein encoded by the cDNA insert of clone yc48_1 deposited under accession number ATCC 98864. In further preferred embodiments, the present invention provides a polynucleotide encoding a protein comprising a fragment of the amino acid sequence of SEQ ID NO:58 having biological activity, the fragment preferably comprising eight (more preferably twenty, most preferably thirty) contiguous amino acids of SEQ ID NO:58, or a polynucleotide encoding a protein comprising a fragment of the amino acid sequence of SEQ ID NO:58 having biological activity, the fragment comprising the amino acid sequence from amino acid 166 to amino acid 175 of SEQ ID NO:58.

Other embodiments provide the gene corresponding to the cDNA sequence of SEQ ID NO:57.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:57, but excluding the poly(A) tail at the 3' end of SEQ ID NO:57; and
    (ab) the nucleotide sequence of the cDNA insert of clone yc48_1 deposited under accession number ATCC 98864;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:57, but excluding the poly(A) tail at the 3' end of SEQ ID NO:57; and
    (bb) the nucleotide sequence of the cDNA insert of done yc48_1 deposited under accession number ATCC 98864;
  (ii) hybridizing said primer(s) to human genomic DNA in conditions at least as stringent as 4×SSC at 50 degrees C.;
  (ii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:57, and extending contiguously from a nucleotide sequence corresponding to the 5' end of SEQ ID NO:57 to a nucleotide sequence corresponding to the 3' end of SEQ ID NO:57, but excluding the poly(A) tail at the 3' end of SEQ ID NO:57. Also preferably the polynucleotide isolated according to the above process comprises a nucleotide sequence corresponding to the cDNA sequence of SEQ ID NO:57 from nucleotide 56 to nucleotide 1084, and extending contiguously from a nucleotide sequence corresponding to the 5' end of said sequence of SEQ ID NO:57 from nucleotide 56 to nucleotide 1084, to a nucleotide sequence corresponding to the 3' end of said sequence of SEQ ID NO:57 from nucleotide 56 to nucleotide 1084. Also preferably the polynucleotide isolated according to the above process comprises a nucleotide sequence corresponding to the cDNA sequence of SEQ ID NO:57 from nucleotide 107 to nucleotide 1084, and extending contiguously from a nucleotide sequence corresponding to the 5' end of said sequence of SEQ ID NO:57 from nucleotide 107 to nucleotide 1084, to a nucleotide sequence corresponding to the 3' end of said sequence of SEQ. ID NO:57 from nucleotide 107 to nucleotide 1084.

In other embodiments, the present invention provides a composition comprising a protein, wherein said protein comprises an amino acid sequence selected from the group consisting of:

(a) the amino acid sequence of SEQ ID NO:58;

(b) a fragment of the amino acid sequence of SEQ ID NO:58, the fragment comprising eight contiguous amino acids of SEQ ID NO:58; and (c) the amino acid sequence encoded by the cDNA insert of clone yc48_1 deposited under accession number ATCC 98864;

the protein being substantially free from other mammalian proteins. Preferably such protein comprises the amino acid sequence of SEQ ID NO:58. In further preferred embodiments, the present invention provides a protein comprising a fragment of the amino acid sequence of SEQ ID NO:58 having biological activity, the fragment preferably comprising eight (more preferably twenty, most preferably thirty) contiguous amino acids of SEQ ID NO:58, or a protein comprising a fragment of the amino acid sequence of SEQ ID NO:58 having biological activity, the fragment comprising the amino acid sequence from amino acid 166 to amino acid 175 of SEQ ID NO:58.

In one embodiment, the present invention provides a composition comprising an isolated polynucleotide selected from the group consisting of:

(a) a polynucleotide comprising the nucleotide sequence of SEQ ID NO:59;

(b) a polynucleotide comprising the nucleotide sequence of SEQ ID NO:59 from nucleotide 373 to nucleotide 660;

(c) a polynucleotide comprising the nucleotide sequence of SEQ ID NO:59 from nucleotide 436 to nucleotide 660;

(d) a polynucleotide comprising the nucleotide sequence of the full-length protein coding sequence of clone ye21_1 deposited under accession number ATCC 98864;

(e) a polynucleotide encoding the full-length protein encoded by the cDNA insert of clone ye21_1 deposited under accession number ATCC 98864;

(f) a polynucleotide comprising the nucleotide sequence of a mature protein coding sequence of clone ye21_1 deposited under accession number ATCC 98864;

(g) a polynucleotide encoding a mature protein encoded by the cDNA insert of clone ye21_1 deposited under accession number ATCC 98864;
(h) a polynucleotide encoding a protein comprising the amino acid sequence of SEQ ID NO:60;
(i) a polynucleotide encoding a protein comprising a fragment of the amino acid sequence of SEQ ID NO:60 having biological activity, the fragment comprising eight contiguous amino acids of SEQ ID NO:60;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:59.

Preferably, such polynucleotide comprises the nucleotide sequence of SEQ ID NO:59 from nucleotide 373 to nucleotide 660; the nucleotide sequence of SEQ ID NO:59 from nucleotide 436 to nucleotide 660; the nucleotide sequence of the full-length protein coding sequence of clone ye21_1 deposited under accession number ATCC 98864; or the nucleotide sequence of a mature protein coding sequence of clone ye21_1 deposited under accession number ATCC 98864. In other preferred embodiments, the polynucleotide encodes the full-length or a mature protein encoded by the cDNA insert of clone ye21_1 deposited under accession number ATCC 98864. In further preferred embodiments, the present invention provides a polynucleotide encoding a protein comprising a fragment of the amino acid sequence of SEQ ID NO:60 having biological activity, the fragment preferably comprising eight (more preferably twenty, most preferably thirty) contiguous amino acids of SEQ ID NO:60, or a polynucleotide encoding a protein comprising a fragment of the amino acid sequence of SEQ ID NO:60 having biological activity, the fragment comprising the amino acid sequence from amino acid 43 to amino acid 52 of SEQ ID NO:60.

Other embodiments provide the gene corresponding to the cDNA sequence of SEQ ID NO:59.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:59, but excluding the poly(A) tail at the 3' end of SEQ ID NO:59; and
    (ab) the nucleotide sequence of the cDNA insert of clone ye21_1 deposited under accession number ATCC 98864;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:59, but excluding the poly(A) tail at the 3' end of SEQ ID NO:59; and
    (bb) the nucleotide sequence of the cDNA insert of clone ye21_1 deposited under accession number ATCC 98864;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:59, and extending contiguously from a nucleotide sequence corresponding to the 5' end of SEQ ID NO:59 to a nucleotide sequence corresponding to the 3' end of SEQ ID NO:59, but excluding the poly(A) tail at the 3' end of SEQ ID NO:59. Also preferably the polynucleotide isolated according to the above process comprises a nucleotide sequence corresponding to the cDNA sequence of SEQ ID NO:59 from nucleotide 373 to nucleotide 660, and extending contiguously from a nucleotide sequence corresponding to the 5' end of said sequence of SEQ ID NO:59 from nucleotide 373 to nucleotide 660, to a nucleotide sequence corresponding to the 3' end of said sequence of SEQ ID NO:59 from nucleotide 373 to nucleotide 660. Also preferably the polynucleotide isolated according to the above process comprises a nucleotide sequence corresponding to the cDNA sequence of SEQ ID NO:59 from nucleotide 436 to nucleotide 660, and extending contiguously from a nucleotide sequence corresponding to the 5' end of said sequence of SEQ ID NO:59 from nucleotide 436 to nucleotide 660, to a nucleotide sequence corresponding to the 3' end of said sequence of SEQ ID NO:59 from nucleotide 436 to nucleotide 660.

In other embodiments, the present invention provides a composition comprising a protein, wherein said protein comprises an amino acid sequence selected from the group consisting of:
(a) the amino acid sequence of SEQ ID NO:60;
(b) a fragment of the amino acid sequence of SEQ ID NO:60, the fragment comprising eight contiguous amino acids of SEQ ID NO:60; and
(c) the amino acid sequence encoded by the cDNA insert of clone ye21_1 deposited under accession number ATCC 98864;

the protein being substantially free from other mammalian proteins. Preferably such protein comprises the amino acid sequence of SEQ ID NO:60. In further preferred embodiments, the present invention provides a protein comprising a fragment of the amino acid sequence of SEQ ID NO:60 having biological activity, the fragment preferably comprising eight (more preferably twenty, most preferably thirty) contiguous amino acids of SEQ ID NO:60, or a protein comprising a fragment of the amino acid sequence of SEQ ID NO:60 having biological activity, the fragment comprising the amino acid sequence from amino acid 43 to amino acid 52 of SEQ ID NO:60.

In one embodiment, the present invention provides a composition comprising an isolated polynucleotide selected from the group consisting of:
(a) a polynucleotide comprising the nucleotide sequence of SEQ ID NO:61;
(b) a polynucleotide comprising the nucleotide sequence of SEQ ID NO:61 from nucleotide 119 to nucleotide 466;

(c) a polynucleotide comprising the nucleotide sequence of the full-length protein coding sequence of clone ye22_1 deposited under accession number ATCC 98864;

(d) a polynucleotide encoding the full-length protein encoded by the cDNA insert of clone ye22_1 deposited under accession number ATCC 98864;

(e) a polynucleotide comprising the nucleotide sequence of a mature protein coding sequence of clone ye22_1 deposited under accession number ATCC 98864;

(f) a polynucleotide encoding a mature protein encoded by the cDNA insert of clone ye22_1 deposited under accession number ATCC 98864;

(g) a polynucleotide encoding a protein comprising the amino acid sequence of SEQ ID NO:62;

(h) a polynucleotide encoding a protein comprising a fragment of the amino acid sequence of SEQ ID NO:62 having biological activity, the fragment comprising eight contiguous amino acids of SEQ ID NO:62;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:61.

Preferably, such polynucleotide comprises the nucleotide sequence of SEQ ID NO:61 from nucleotide 119 to nucleotide 466; the nucleotide sequence of the full-length protein coding sequence of clone ye22_1 deposited under accession number ATCC 98864; or the nucleotide sequence of a mature protein coding sequence of clone ye22_1 deposited under accession number ATCC 98864. In other preferred embodiments, the polynucleotide encodes the full-length or a mature protein encoded by the cDNA insert of clone ye22_1 deposited under accession number ATCC 98864. In further preferred embodiments, the present invention provides a polynucleotide encoding a protein comprising a fragment of the amino acid sequence of SEQ ID NO:62 having biological activity, the fragment preferably comprising eight (more preferably twenty, most preferably thirty) contiguous amino acids of SEQ ID NO:62, or a polynucleotide encoding a protein comprising a fragment of the amino acid sequence of SEQ ID NO:62 having biological activity, the fragment comprising the amino acid sequence from amino acid 53 to amino acid 62 of SEQ ID NO:62.

Other embodiments provide the gene corresponding to the cDNA sequence of SEQ ID NO:61.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:61, but excluding the poly(A) tail at the 3' end of SEQ ID NO:61; and
    (ab) the nucleotide sequence of the cDNA insert of clone ye22_1 deposited under accession number ATCC 98864;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:61, but excluding the poly(A) tail at the 3' end of SEQ ID NO:61; and
    (bb) the nucleotide sequence of the cDNA insert of clone ye22_1 deposited under accession number ATCC 98864;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:61, and extending contiguously from a nucleotide sequence corresponding to the 5' end of SEQ ID NO:61 to a nucleotide sequence corresponding to the 3' end of SEQ ID NO:61, but excluding the poly(A) tail at the 3' end of SEQ ID NO:61. Also preferably the polynucleotide isolated according to the above process comprises a nucleotide sequence corresponding to the cDNA sequence of SEQ ID NO:61 from nucleotide 119 to nucleotide 466, and extending contiguously from a nucleotide sequence corresponding to the 5' end of said sequence of SEQ ID NO:61 from nucleotide 119 to nucleotide 466, to a nucleotide sequence corresponding to the 3' end of said sequence of SEQ ID NO:61 from nucleotide 119 to nucleotide 466.

In other embodiments, the present invention provides a composition comprising a protein, wherein said protein comprises an amino acid sequence selected from the group consisting of:

(a) the amino acid sequence of SEQ ID NO:62;

(b) a fragment of the amino acid sequence of SEQ ID NO:62, the fragment comprising eight contiguous amino acids of SEQ ID NO:62; and (c) the amino acid sequence encoded by the cDNA insert of clone ye22_1 deposited under accession number ATCC 98864;

the protein being substantially free from other mammalian proteins. Preferably such protein comprises the amino acid sequence of SEQ ID NO:62. In further preferred embodiments, the present invention provides a protein comprising a fragment of the amino acid sequence of SEQ ID NO:62 having biological activity, the fragment preferably comprising eight (more preferably twenty, most preferably thirty) contiguous amino acids of SEQ ID NO:62, or a protein comprising a fragment of the amino acid sequence of SEQ ID NO:62 having biological activity, the fragment comprising the amino acid sequence from amino acid 53 to amino acid 62 of SEQ ID NO:62.

In one embodiment, the present invention provides a composition comprising an isolated polynucleotide selected from the group consisting of:

(a) a polynucleotide comprising the nucleotide sequence of SEQ ID NO:63;

(b) a polynucleotide comprising the nucleotide sequence of SEQ ID NO:63 from nucleotide 1212 to nucleotide 1502;

(c) a polynucleotide comprising the nucleotide sequence of the full-length protein coding sequence of clone ye39_1 deposited under accession number ATCC 98861;

(d) a polynucleotide encoding the full-length protein encoded by the cDNA insert of clone ye39_1 deposited under accession number ATCC 98861;

(e) a polynucleotide comprising the nucleotide sequence of a mature protein coding sequence of clone ye39_1 deposited under accession number ATCC 98861;

(f) a polynucleotide encoding a mature protein encoded by the cDNA insert of clone ye39_1 deposited under accession number ATCC 98861;

(g) a polynucleotide encoding a protein comprising the amino acid sequence of SEQ ID NO:64;

(h) a polynucleotide encoding a protein comprising a fragment of the amino acid sequence of SEQ ID NO:64 having biological activity, the fragment comprising eight contiguous amino acids of SEQ ID NO:64;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:63.

Preferably, such polynucleotide comprises the nucleotide sequence of SEQ ID NO:63 from nucleotide 1212 to nucleotide 1502; the nucleotide sequence of the full-length protein coding sequence of clone ye39_1 deposited under accession number ATCC 98861; or the nucleotide sequence of a mature protein coding sequence of clone ye39_1 deposited under accession number ATCC 98861. In other preferred embodiments, the polynucleotide encodes the full-length or a mature protein encoded by the cDNA insert of clone ye39_1 deposited under accession number ATCC 98861. In further preferred embodiments, the present invention provides a polynucleotide encoding a protein comprising a fragment of the amino acid sequence of SEQ ID NO:64 having biological activity, the fragment preferably comprising eight (more preferably twenty, most preferably thirty) contiguous amino acids of SEQ ID NO:64, or a polynucleotide encoding a protein comprising a fragment of the amino acid sequence of SEQ ID NO:64 having biological activity, the fragment comprising the amino acid sequence from amino acid 43 to amino acid 52 of SEQ ID NO:64.

Other embodiments provide the gene corresponding to the cDNA sequence of SEQ ID NO:63.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:63, but excluding the poly(A) tail at the 3' end of SEQ ID NO:63; and
    (ab) the nucleotide sequence of the cDNA insert of clone ye39_1 deposited under accession number ATCC 98861;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:63, but excluding the poly(A) tail at the 3' end of SEQ ID NO:63; and
    (bb) the nucleotide sequence of the cDNA insert of clone ye39_1 deposited under accession number ATCC 98861;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:63, and extending contiguously from a nucleotide sequence corresponding to the 5' end of SEQ ID NO:63 to a nucleotide sequence corresponding to the 3' end of SEQ ID NO:63, but excluding the poly(A) tail at the 3' end of SEQ ID NO:63. Also preferably the polynucleotide isolated according to the above process comprises a nucleotide sequence corresponding to the cDNA sequence of SEQ ID NO:63 from nucleotide 1212 to nucleotide 1502, and extending contiguously from a nucleotide sequence corresponding to the 5' end of said sequence of SEQ ID NO:63 from nucleotide 1212 to nucleotide 1502, to a nucleotide sequence corresponding to the 3' end of said sequence of SEQ ID NO:63 from nucleotide 1212 to nucleotide 1502.

In other embodiments, the present invention provides a composition comprising a protein, wherein said protein comprises an amino acid sequence selected from the group consisting of:

(a) the amino acid sequence of SEQ ID NO:64;

(b) a fragment of the amino acid sequence of SEQ ID NO:64, the fragment comprising eight contiguous amino acids of SEQ ID NO:64; and (c) the amino acid sequence encoded by the cDNA insert of clone ye39_1 deposited under accession number ATCC 98861;

the protein being substantially free from other mammalian proteins. Preferably such protein comprises the amino acid sequence of SEQ ID NO:64. In further preferred embodiments, the present invention provides a protein comprising a fragment of the amino acid sequence of SEQ ID NO:64 having biological activity, the fragment preferably comprising eight (more preferably twenty, most preferably thirty) contiguous amino acids of SEQ ID NO:64, or a protein comprising a fragment of the amino acid sequence of SEQ ID NO:64 having biological activity, the fragment comprising the amino acid sequence from amino acid 43 to amino acid 52 of SEQ ID NO:64.

In one embodiment, the present invention provides a composition comprising an isolated polynucleotide selected from the group consisting of:

(a) a polynucleotide comprising the nucleotide sequence of SEQ ID NO:65;

(b) a polynucleotide comprising the nucleotide sequence of SEQ ID NO:65 from nucleotide 81 to nucleotide 887;

(c) a polynucleotide comprising the nucleotide sequence of the full-length protein coding sequence of clone yf9_1 deposited under accession number ATCC 98861;

(d) a polynucleotide encoding the full-length protein encoded by the cDNA insert of clone yf9_1 deposited under accession number ATCC 98861;

(e) a polynucleotide comprising the nucleotide sequence of a mature protein coding sequence of clone yf9_1 deposited under accession number ATCC 98861;

(f) a polynucleotide encoding a mature protein encoded by the cDNA insert of clone yf9_1 deposited under accession number ATCC 98861;

(g) a polynucleotide encoding a protein comprising the amino acid sequence of SEQ ID NO:66;

(h) a polynucleotide encoding a protein comprising a fragment of the amino acid sequence of SEQ ID NO:66 having biological activity, the fragment comprising eight contiguous amino acids of SEQ ID NO:66;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:65.

Preferably, such polynucleotide comprises the nucleotide sequence of SEQ ID NO:65 from nucleotide 81 to nucleotide 887; the nucleotide sequence of the full-length protein coding sequence of clone yf9_1 deposited under accession number ATCC 98861; or the nucleotide sequence of a mature protein coding sequence of clone yf9_1 deposited under accession number ATCC 98861. In other preferred embodiments, the polynucleotide encodes the full-length or a mature protein encoded by the cDNA insert of clone yf9_1 deposited under accession number ATCC 98861. In further preferred embodiments, the present invention provides a polynucleotide encoding a protein comprising a fragment of the amino acid sequence of SEQ ID NO:66 having biological activity, the fragment preferably comprising eight (more preferably twenty, most preferably thirty) contiguous amino acids of SEQ ID NO:66, or a polynucleotide encoding a protein comprising a fragment of the amino acid sequence of SEQ ID NO:66 having biological activity, the fragment comprising the amino acid sequence from amino acid 129 to amino acid 138 of SEQ ID NO:66.

Other embodiments provide the gene corresponding to the cDNA sequence of SEQ ID NO:65.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:65; and
(ab) the nucleotide sequence of the cDNA insert of clone yf9_1 deposited under accession number ATCC 98861;
(ii) hybridizing said probe(s) to human genomic DNA in conditions at least as stringent as 4×SSC at 50 degrees C.; and
(iii) isolating the DNA polynucleotides detected with the probe(s);

and
(b) a process comprising the steps of:
(i) preparing one or more polynucleotide primers that hybridize in 6×SSC at 65 degrees C. to a nucleotide sequence selected from the group consisting of:
(ba) SEQ ID NO:65; and
(bb) the nucleotide sequence of the cDNA insert of clone yf9_1 deposited under accession number ATCC 98861;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:65, land extending contiguously from a nucleotide sequence corresponding to the 5' end of SEQ ID NO:65 to a nucleotide sequence corresponding to the 3' end of SEQ ID NO:65. Also preferably the polynucleotide isolated according to the above process comprises a nucleotide sequence corresponding to the cDNA sequence of SEQ ID NO:65 from nucleotide 81 to nucleotide 887, and extending contiguously from a nucleotide sequence corresponding to the 5' end of said sequence of SEQ ID NO:65 from nucleotide 81 to nucleotide 887, to a nucleotide sequence corresponding to the 3' end of said sequence of SEQ ID NO:65 from nucleotide 81 to nucleotide 887.

In other embodiments, the present invention provides a composition comprising a protein, wherein said protein comprises an amino acid sequence selected from the group consisting of:

(a) the amino acid sequence of SEQ ID NO:66;
(b) a fragment of the amino acid sequence of SEQ ID NO:66, the fragment comprising eight contiguous amino acids of SEQ ID NO:66; and
(c) the amino acid sequence encoded by the cDNA insert of clone yf9_1 deposited under accession number ATCC 98861;

the protein being substantially free from other mammalian proteins. Preferably such protein comprises the amino acid sequence of SEQ ID NO:66. In further preferred embodiments, the present invention provides a protein comprising a fragment of the amino acid sequence of SEQ ID NO:66 having biological activity, the fragment preferably comprising eight (more preferably twenty, most preferably thirty) contiguous amino acids of SEQ ID NO:66, or a protein comprising a fragment of the amino acid sequence of SEQ ID NO:66 having biological activity, the fragment comprising the amino acid sequence from amino acid 129 to amino acid 138 of SEQ ID NO:66.

In one embodiment, the present invention provides a composition comprising an isolated polynucleotide selected from the group consisting of:

(a) a polynucleotide comprising the nucleotide sequence of SEQ ID NO:67;

(b) a polynucleotide comprising the nucleotide sequence of SEQ ID NO:67 from nucleotide 63 to nucleotide 305;

(c) a polynucleotide comprising the nucleotide sequence of the full-length protein coding sequence of done yh4_1 deposited under accession number ATCC 98861;

(d) a polynucleotide encoding the full-length protein encoded by the cDNA insert of clone yh4_1 deposited under accession number ATCC 98861;

(e) a polynucleotide comprising the nucleotide sequence of a mature protein coding sequence of clone yh4_1 deposited under accession number ATCC 98861;
(f) a polynucleotide encoding a mature protein encoded by the cDNA insert of clone yh4_1 deposited under accession number ATCC 98861;
(g) a polynucleotide encoding a protein comprising the amino acid sequence of SEQ ID NO:68;
(h) a polynucleotide encoding a protein comprising a fragment of the amino acid sequence of SEQ ID NO:68 having biological activity, the fragment comprising eight contiguous amino acids of SEQ ID NO 68;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:67.

Preferably, such polynucleotide comprises the nucleotide sequence of SEQ ID NO:67 from nucleotide 63 to nucleotide 305; the nucleotide sequence of the full-length protein coding sequence of clone yh4_1 deposited under accession number ATCC 98861; or the nucleotide sequence of a mature protein coding sequence of clone yh4_1 deposited under accession number ATCC 98861. In other preferred embodiments, the polynucleotide encodes the full-length or a mature protein encoded by the cDNA insert of clone yh4_1 deposited under accession number ATCC 98861. In further preferred embodiments, the present invention provides a polynucleotide encoding a protein comprising a fragment of the amino acid sequence of SEQ ID NO:68 having biological activity, the fragment preferably comprising eight (more preferably twenty, most preferably thirty) contiguous amino acids of SEQ ID NO:68, or a polynucleotide encoding a protein comprising a fragment of the amino acid sequence of SEQ ID NO:68 having biological activity, the fragment comprising the amino acid sequence from amino acid 35 to amino acid 44 of SEQ ID NO:68.

Other embodiments provide the gene corresponding to the cDNA sequence of SEQ ID NO:67.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:67, but excluding the poly(A) tail at the 3' end of SEQ ID NO:67; and
(ab) the nucleotide sequence of the cDNA insert of clone yh4_1 deposited under accession number ATCC 98861;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:67, but excluding the poly(A) tail at the 3' end of SEQ ID NO:67; and
(bb) the nucleotide sequence of the cDNA insert of clone yh4_1 deposited under accession number ATCC 98861;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:67, and extending contiguously from a nucleotide sequence corresponding to the 5' end of SEQ ID NO:67 to a nucleotide sequence corresponding to the 3' end of SEQ ID NO:67, but excluding the poly(A) tail at the 3' end of SEQ ID NO:67. Also preferably the polynucleotide isolated according to the above process comprises a nucleotide sequence corresponding to the cDNA sequence of SEQ ID NO:67 from nucleotide 63 to nucleotide 305, and extending contiguously from a nucleotide sequence corresponding to the 5' end of said sequence of SEQ ID NO:67 from nucleotide 63 to nucleotide 305, to a nucleotide sequence corresponding to the 3' end of said sequence of SEQ ID NO:67 from nucleotide 63 to nucleotide 305.

In other embodiments, the present invention provides a composition comprising a protein, wherein said protein comprises an amino acid sequence selected from the group consisting of:
(a) the amino acid sequence of SEQ ID NO:68;
(b) a fragment of the amino acid sequence of SEQ ID NO:68, the fragment comprising eight contiguous amino acids of SEQ ID NO:68; and
(c) the amino acid sequence encoded by the cDNA insert of clone yh4_1 deposited under accession number ATCC 98861;
the protein being substantially free from other mammalian proteins. Preferably such protein comprises the amino acid sequence of SEQ ID NO:68. In further preferred embodiments, the present invention provides a protein comprising a fragment of the amino acid sequence of SEQ ID NO:68 having biological activity, the fragment preferably comprising eight (more preferably twenty, most preferably thirty) contiguous amino acids of SEQ ID NO:68, or a protein comprising a fragment of the amino acid sequence of SEQ ID NO:68 having biological activity, the fragment comprising the amino acid sequence from amino acid 35 to amino acid 44 of SEQ ID NO:68.

In one embodiment, the present invention provides a composition comprising an isolated polynucleotide selected from the group consisting of:
(a) a polynucleotide comprising the nucleotide sequence of SEQ ID NO:69;
(b) a polynucleotide comprising the nucleotide sequence of SEQ ID NO:69 from nucleotide 332 to nucleotide 685;
(c) a polynucleotide comprising the nucleotide sequence of SEQ ID NO:69 from nucleotide 422 to nucleotide 685;
(d) a polynucleotide comprising the nucleotide sequence of the full-length protein coding sequence of clone yi4_1 deposited under accession number ATCC 98861;
(e) a polynucleotide encoding the full-length protein encoded by the cDNA insert of clone yi4_1 deposited under accession number ATCC 98861;

(f) a polynucleotide comprising the nucleotide sequence of a mature protein coding sequence of clone yi4_1 deposited under accession number ATCC 98861;

(g) a polynucleotide encoding a mature protein encoded by the cDNA insert of clone yi4_1 deposited under accession number ATCC 98861;

(h) a polynucleotide encoding a protein comprising the amino acid sequence of SEQ ID NO:70;

(i) a polynucleotide encoding a protein comprising a fragment of the amino acid sequence of SEQ ID NO:70 having biological activity, the fragment comprising eight contiguous amino acids of SEQ ID NO:70;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:69.

Preferably, such polynucleotide comprises the nucleotide sequence of SEQ ID NO:69 from nucleotide 332 to nucleotide 685; the nucleotide sequence of SEQ ID NO:69 from nucleotide 422 to nucleotide 685; the nucleotide sequence of the full-length protein coding sequence of clone yi4_1 deposited under accession number ATCC 98861; or the nucleotide sequence of a mature protein coding sequence of clone yi4_1 deposited under accession number ATCC 98861. In other preferred embodiments, the polynucleotide encodes the full-length or a mature protein encoded by the cDNA insert of clone yi4_1 deposited under accession number ATCC 98861. In further preferred embodiments, the present invention provides a polynucleotide encoding a protein comprising a fragment of the amino acid sequence of SEQ ID NO:70 having biological activity, the fragment preferably comprising eight (more preferably twenty, most preferably thirty) contiguous amino acids of SEQ ID NO:70, or a polynucleotide encoding a protein comprising a fragment of the amino acid sequence of SEQ ID NO:70 having biological activity, the fragment comprising the amino acid sequence from amino acid 54 to amino acid 63 of SEQ ID NO:70.

Other embodiments provide the gene corresponding to the cDNA sequence of SEQ ID NO:69.

Further embodiments of the invention provide isolated polynucleotides produced according to a process selected from the group consisting of:

(a) a process comprising the steps of:
   (i) preparing one or more polynucleotide probes that hybridize in 6×SSC at 65 degrees C. to a nucleotide sequence selected from the group consisting of:
      (aa) SEQ ID NO:69, but excluding the poly(A) tail at the 3' end of SEQ ID NO:69; and
      (ab) the nucleotide sequence of the cDNA insert of done yi4_1 deposited under accession number ATCC 98861;
   (ii) hybridizing said probe(s) to human genomic DNA in conditions at least as stringent as 4×SSC at 50 degrees C.; and
   (iii) isolating the DNA polynucleotides detected with the probe(s);

and (b) a process comprising the steps of:
   (i) preparing one or more polynucleotide primers that hybridize in 6×SSC at 65 degrees C. to a nucleotide sequence selected from the group consisting of:
      (ba) SEQ ID NO:69, but excluding the poly(A) tail at the 3' end of SEQ ID NO:69; and
      (bb) the nucleotide sequence of the cDNA insert of clone yi4_1 deposited under accession number ATCC 98861;
   (ii) hybridizing said primer(s) to human genomic DNA in conditions at least as stringent as 4×SSC at 50 degrees C.;
   (iii) amplifying human DNA sequences; and
   (iv) isolating the polynucleotide products of step (b) (iii).

Preferably the polynucleotide isolated according to the above process comprises a nucleotide sequence corresponding to the cDNA sequence of SEQ ID NO:69, and extending contiguously from a nucleotide sequence corresponding to the 5' end of SEQ ID NO:69 to a nucleotide sequence corresponding to the 3' end of SEQ ID NO:69, but excluding the poly(A) tail at the 3' end of SEQ ID NO:69. Also preferably the polynucleotide isolated according to the above process comprises a nucleotide sequence corresponding to the cDNA sequence of SEQ ID NO:69 from nucleotide 332 to nucleotide 685, and extending contiguously from a nucleotide sequence corresponding to the 5' end of said sequence of SEQ ID NO:69 from nucleotide 332 to nucleotide 685, to a nucleotide sequence corresponding to the 3' end of said sequence of SEQ ID NO:69 from nucleotide 332 to nucleotide 685. Also preferably the polynucleotide isolated according to the above process comprises a nucleotide sequence corresponding to the cDNA sequence of SEQ ID NO:69 from nucleotide 422 to nucleotide 685, and extending contiguously from a nucleotide sequence corresponding to the 5' end of said sequence of SEQ ID NO:69 from nucleotide 422 to nucleotide 685, to a nucleotide sequence corresponding to the 3' end of said sequence of SEQ ID NO:69 from nucleotide 422 to nucleotide 685.

In other embodiments, the present invention provides a composition comprising a protein, wherein said protein comprises an amino acid sequence selected from the group consisting of:

(a) the amino acid sequence of SEQ ID NO:70;

(b) a fragment of the amino acid sequence of SEQ ID NO:70, the fragment comprising eight contiguous amino acids of SEQ ID NO:70; and (c) the amino acid sequence encoded by the cDNA insert of clone yi4_1 deposited under accession number ATCC 98861;

the protein being substantially free from other mammalian proteins. Preferably such protein comprises the amino acid sequence of SEQ ID NO:70. In further preferred embodiments, the present invention provides a protein comprising a fragment of the amino acid sequence of SEQ ID NO:70 having biological activity, the fragment preferably comprising eight (more preferably twenty, most preferably thirty) contiguous amino acids of SEQ ID NO:70, or a protein comprising a fragment of the amino acid sequence of SEQ ID NO:70 having biological activity, the fragment comprising the amino acid sequence from amino acid 54 to amino acid 63 of SEQ ID NO:70.

In one embodiment, the present invention provides a composition comprising an isolated polynucleotide selected from the group consisting of:

(a) a polynucleotide comprising the nucleotide sequence of SEQ ID NO:71;

(b) a polynucleotide comprising the nucleotide sequence of SEQ ID NO:71 from nucleotide 143 to nucleotide 502;

(c) a polynucleotide comprising the nucleotide sequence of SEQ ID NO:71 from nucleotide 203 to nucleotide 502;

(d) a polynucleotide comprising the nucleotide sequence of the full-length protein coding sequence of clone yj3_1 deposited under accession number ATCC 98861;

(e) a polynucleotide encoding the full-length protein encoded by the cDNA insert of clone yj3_1 deposited under accession number ATCC 98861;

(f) a polynucleotide comprising the nucleotide sequence of a mature protein coding sequence of clone yj3_1 deposited under accession number ATCC 98861;

(g) a polynucleotide encoding a mature protein encoded by the cDNA insert of clone yj3_1 deposited under accession number ATCC 98861;

(h) a polynucleotide encoding a protein comprising the amino acid sequence of SEQ ID NO:72;

(i) a polynucleotide encoding a protein comprising a fragment of the amino acid sequence of SEQ ID NO:72 having biological activity, the fragment comprising eight contiguous amino acids of SEQ ID NO:72;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:71.

Preferably, such polynucleotide comprises the nucleotide sequence of SEQ ID NO:71 from nucleotide 143 to nucleotide 502; the nucleotide sequence of SEQ ID NO:71 from nucleotide 203 to nucleotide 502; the nucleotide sequence of the full-length protein coding sequence of clone yj3_1 deposited under accession number ATCC 98861; or the nucleotide sequence of a mature protein coding sequence of clone yj3_1 deposited under accession number ATCC 98861. In other preferred embodiments, the polynucleotide encodes the full-length or a mature protein encoded by the cDNA insert of clone yj3_1 deposited under accession number ATCC 98861. In further preferred embodiments, the present invention provides a polynucleotide encoding a protein comprising a fragment of the amino acid sequence of SEQ ID NO:72 having biological activity, the fragment preferably comprising eight (more preferably twenty, most preferably thirty) contiguous amino acids of SEQ ID NO:72, or a polynucleotide encoding a protein comprising a fragment of the amino acid sequence of SEQ ID NO:72 having biological activity, the fragment comprising the amino acid sequence from amino acid 55 to amino acid 64 of SEQ ID NO:72.

Other embodiments provide the gene corresponding to the cDNA sequence of SEQ ID NO:71.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:71, but excluding the poly(A) tail at the 3' end of SEQ ID NO:71; and
    (ab) the nucleotide sequence of the cDNA insert of clone yj3_1 deposited under accession number ATCC 98861;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:71, but excluding the poly(A) tail at the 3' end of SEQ ID NO:71; and
    (bb) the nucleotide sequence of the cDNA insert of clone yj3_1 deposited under accession number ATCC 98861;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:71, and extending contiguously from a nucleotide sequence corresponding to the 5' end of SEQ ID NO:71 to a nucleotide sequence corresponding to the 3' end of SEQ ID NO:71, but excluding the poly(A) tail at the 3' end of SEQ ID NO:71. Also preferably the polynucleotide isolated according to the above process comprises a nucleotide sequence corresponding to the cDNA sequence of SEQ ID NO:71 from nucleotide 143 to nucleotide 502, and extending contiguously from a nucleotide sequence corresponding to the 5' end of said sequence of SEQ ID NO:71 from nucleotide 143 to nucleotide 502, to a nucleotide sequence corresponding to the 3' end of said sequence of SEQ ID NO:71 from nucleotide 143 to nucleotide 502. Also preferably the polynucleotide isolated according to the above process comprises a nucleotide sequence corresponding to the cDNA sequence of SEQ ID NO:71 from nucleotide 203 to nucleotide 502, and extending contiguously from a nucleotide sequence corresponding to the 5' end of said sequence of SEQ ID NO:71 from nucleotide 203 to nucleotide 502, to a nucleotide sequence corresponding to the 3' end of said sequence of SEQ ID NO:71 from nucleotide 203 to nucleotide 502.

In other embodiments, the present invention provides a composition comprising a protein, wherein said protein comprises an amino acid sequence selected from the group consisting of:

(a) the amino acid sequence of SEQ ID NO:72;

(b) a fragment of the amino acid sequence of SEQ ID NO:72, the fragment comprising eight contiguous amino acids of SEQ ID NO:72; and (c) the amino acid sequence encoded by the cDNA insert of clone yj3_1 deposited under accession number ATCC 98861;

the protein being substantially free from other mammalian proteins. Preferably such protein comprises the amino acid sequence of SEQ ID NO:72. In further preferred embodiments, the present invention provides a protein comprising a fragment of the amino acid sequence of SEQ ID NO:72 having biological activity, the fragment preferably comprising eight (more preferably twenty, most preferably thirty) contiguous amino acids of SEQ ID NO:72, or a protein comprising a fragment of the amino acid sequence of SEQ ID NO:72 having biological activity, the fragment comprising the amino acid sequence from amino acid 55 to amino acid 64 of SEQ ID NO:72.

In one embodiment, the present invention provides a composition comprising an isolated polynucleotide selected from the group consisting of:

(a) a polynucleotide comprising the nucleotide sequence of SEQ ID NO:73;

(b) a polynucleotide comprising the nucleotide sequence of SEQ ID NO:73 from nucleotide 30 to nucleotide 1004;

(c) a polynucleotide comprising the nucleotide sequence of SEQ ID NO:73 from nucleotide 129 to nucleotide 1004;

(d) a polynucleotide comprising the nucleotide sequence of the full-length protein coding sequence of clone yj7_1 deposited under accession number ATCC 98861;

(e) a polynucleotide encoding the full-length protein encoded by the cDNA insert of clone yj7_1 deposited under accession number ATCC 98861;

(f) a polynucleotide comprising the nucleotide sequence of a mature protein coding sequence of clone yj7_1 deposited under accession number ATCC 98861;

(g) a polynucleotide encoding a mature protein encoded by the cDNA insert of clone yj7_1 deposited under accession number ATCC 98861;

(h) a polynucleotide encoding a protein comprising the amino acid sequence of SEQ ID NO:74;

(i) a polynucleotide encoding a protein comprising a fragment of the amino acid sequence of SEQ ID NO:74 having biological activity, the fragment comprising eight contiguous amino acids of SEQ ID NO:74;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:73.

Preferably, such polynucleotide comprises the nucleotide sequence of SEQ ID NO:73 from nucleotide 30 to nucleotide 1004; the nucleotide sequence of SEQ ID NO:73 from nucleotide 129 to nucleotide 1004; the nucleotide sequence of the full-length protein coding sequence of clone yj7_1 deposited under accession number ATCC 98861; or the nucleotide sequence of a mature protein coding sequence of clone yj7_1 deposited under accession number ATCC 98861. In other preferred embodiments, the polynucleotide encodes the full-length or a mature protein encoded by the cDNA insert of clone yj7_1 deposited under accession number ATCC 98861. In further preferred embodiments, the present invention provides a polynucleotide encoding a protein comprising a fragment of the amino acid sequence of SEQ ID NO:74 having biological activity, the fragment preferably comprising eight (more preferably twenty, most preferably thirty) contiguous amino acids of SEQ ID NO:74, or a polynucleotide encoding a protein comprising a fragment of the amino acid sequence of SEQ ID NO:74 having biological activity, the fragment comprising the amino acid sequence from amino acid 157 to amino acid 166 of SEQ ID NO:74.

Other embodiments provide the gene corresponding to the cDNA sequence of SEQ ID NO:73.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:73, but excluding the poly(A) tail at the 3' end of SEQ ID NO:73; and
(ab) the nucleotide sequence of the cDNA insert of clone yj7_1 deposited under accession number ATCC 98861;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:73, but excluding the poly(A) tail at the 3' end of SEQ ID NO:73; and
(bb) the nucleotide sequence of the cDNA insert of clone yj7_1 deposited under accession number ATCC 98861;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:73, and extending contiguously from a nucleotide sequence corresponding to the 5' end of SEQ ID NO:73 to a nucleotide sequence corresponding to the 3' end of SEQ ID NO:73, but excluding the poly(A) tail at the 3' end of SEQ ID NO:73. Also preferably the polynucleotide isolated according to the above process comprises a nucleotide sequence corresponding to the cDNA sequence of SEQ ID NO:73 from nucleotide 30 to nucleotide 1004, and extending contiguously from a nucleotide sequence corresponding to the 5' end of said sequence of SEQ ID NO:73 from nucleotide 30 to nucleotide 1004, to a nucleotide sequence corresponding to the 3' end of said sequence of SEQ ID NO:73 from nucleotide 30 to nucleotide 1004. Also preferably the polynucleotide isolated according to the above process comprises a nucleotide sequence corresponding to the cDNA sequence of SEQ ID NO:73 from nucleotide 129 to nucleotide 1004, and extending contiguously from a nucleotide sequence corresponding to the 5' end of said sequence of SEQ ID NO:73 from nucleotide 129 to nucleotide 1004, to a nucleotide sequence corresponding to the 3' end of said sequence of SEQ ID NO:73 from nucleotide 129 to nucleotide 1004.

In other embodiments, the present invention provides a composition comprising a protein, wherein said protein comprises an amino acid sequence selected from the group consisting of:

(a) the amino acid sequence of SEQ ID NO:74;
(b) a fragment of the amino acid sequence of SEQ ID NO:74, the fragment comprising eight contiguous amino acids of SEQ ID NO:74; and
(c) the amino acid sequence encoded by the cDNA insert of clone yj7_1 deposited under accession number ATCC 98861;

the protein being substantially free from other mammalian proteins. Preferably such protein comprises the amino acid sequence of SEQ ID NO:74. In further preferred embodiments, the present invention provides a protein comprising a fragment of the amino acid sequence of SEQ ID NO:74 having biological activity, the fragment preferably comprising eight (more preferably twenty, most preferably thirty) contiguous amino acids of SEQ ID NO:74, or a protein comprising a fragment of the amino acid sequence of SEQ ID NO:74 having biological activity, the fragment comprising the amino acid sequence from amino acid 157 to amino acid 166 of SEQ ID NO:74.

In one embodiment, the present invention provides a composition comprising an isolated polynucleotide selected from the group consisting of:
(a) a polynucleotide comprising the nucleotide sequence of SEQ ID NO:75;
(b) a polynucleotide comprising the nucleotide sequence of SEQ ID NO:75 from nucleotide 109 to nucleotide 1047;
(c) a polynucleotide comprising the nucleotide sequence of the full-length protein coding sequence of clone yj10_1 deposited under accession number ATCC 98861;
(d) a polynucleotide encoding the full-length protein encoded by the cDNA insert of clone yj10_1 deposited under accession number ATCC 98861;
(e) a polynucleotide comprising the nucleotide sequence of a mature protein coding sequence of clone yj10_1 deposited under accession number ATCC 98861;
(f) a polynucleotide encoding a mature protein encoded by the cDNA insert of clone yj10_1 deposited under accession number ATCC 98861;
(g) a polynucleotide encoding a protein comprising the amino acid sequence of SEQ ID NO:76;
(h) a polynucleotide encoding a protein comprising a fragment of the amino acid sequence of SEQ ID NO:76 having biological activity, the fragment comprising eight contiguous amino acids of SEQ ID NO:76;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:75.

Preferably, such polynucleotide comprises the nucleotide sequence of SEQ ID NO:75 from nucleotide 109 to nucleotide 1047; the nucleotide sequence of the full-length protein coding sequence of done yj10_1 deposited under accession number ATCC 98861; or the nucleotide sequence of a mature protein coding sequence of clone yj10_1 deposited under accession number ATCC 98861. In other preferred embodiments, the polynucleotide encodes the full-length or a mature protein encoded by the cDNA insert of clone yj10_1 deposited under accession number ATCC 98861. In further preferred embodiments, the present invention provides a polynucleotide encoding a protein comprising a fragment of the amino acid sequence of SEQ ID NO:76 having biological activity, the fragment preferably comprising eight (more preferably twenty, most preferably thirty) contiguous amino acids of SEQ ID NO:76, or a polynucleotide encoding a protein comprising a fragment of the amino acid sequence of SEQ ID NO:76 having biological activity, the fragment comprising the amino acid sequence from amino acid 151 to amino acid 160 of SEQ ID NO:76.

Other embodiments provide the gene corresponding to the cDNA sequence of SEQ ID NO:75.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:75, but excluding the poly(A) tail at the 3' end of SEQ ID NO:75; and
(ab) the nucleotide sequence of the cDNA insert of clone yj10_1 deposited under accession number ATCC 98861;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:75, but excluding the poly(A) tail at the 3' end of SEQ ID NO:75; and
(bb) the nucleotide sequence of the cDNA insert of clone yj10_1 deposited under accession number ATCC 98861;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:75, and extending contiguously from a nucleotide sequence corresponding to the 5' end of SEQ ID NO:75 to a nucleotide sequence corresponding to the 3' end of SEQ ID NO:75, but excluding the poly(A) tail at the 3' end of SEQ ID NO:75. Also preferably the polynucleotide isolated according to the above process comprises a nucleotide sequence corresponding to the cDNA sequence of SEQ ID NO:75 from nucleotide 109 to nucleotide 1047, and extending contiguously from a nucleotide sequence corresponding to the 5' end of said sequence of SEQ ID NO:75 from nucleotide 109 to nucleotide 1047, to a nucleotide sequence corresponding to the 3' end of said sequence of SEQ ID NO:75 from nucleotide 109 to nucleotide 1047.

In other embodiments, the present invention provides a composition comprising a protein, wherein said protein comprises an amino acid sequence selected from the group consisting of:

(a) the amino acid sequence of SEQ ID NO:76;
(b) a fragment of the amino acid sequence of SEQ ID NO:76, the fragment comprising eight contiguous amino acids of SEQ ID NO:76; and
(c) the amino acid sequence encoded by the cDNA insert of clone yj10_1 deposited under accession number ATCC 98861;
the protein being substantially free from other mammalian proteins. Preferably such protein comprises the amino acid sequence of SEQ ID NO:76. In further preferred embodiments, the present invention provides a protein comprising a fragment of the amino acid sequence of SEQ ID NO:76 having biological activity, the fragment preferably comprising eight (more preferably twenty, most preferably thirty) contiguous amino acids of SEQ ID NO:76, or a protein comprising a fragment of the amino acid sequence of SEQ ID NO:76 having biological activity, the fragment comprising the amino acid sequence from amino acid 151 to amino acid 160 of SEQ ID NO:76.

In one embodiment, the present invention provides a composition comprising an isolated polynucleotide selected from the group consisting of:
(a) a polynucleotide comprising the nucleotide sequence of SEQ ID NO:77;
(b) a polynucleotide comprising the nucleotide sequence of SEQ ID NO:77 from nucleotide 42 to nucleotide 1196;
(c) a polynucleotide comprising the nucleotide sequence of SEQ ID NO:77 from nucleotide 558 to nucleotide 1196;
(d) a polynucleotide comprising the nucleotide sequence of the full-length protein coding sequence of clone yj28_1 deposited under accession number ATCC 98861;
(e) a polynucleotide encoding the full-length protein encoded by the cDNA insert of clone yj28_1 deposited under accession number ATCC 98861;
(f) a polynucleotide comprising the nucleotide sequence of a mature protein coding sequence of clone yj28_1 deposited under accession number ATCC 98861;
(g) a polynucleotide encoding a mature protein encoded by the cDNA insert of clone yj28_1 deposited under accession number ATCC 98861;
(h) a polynucleotide encoding a protein comprising the amino acid sequence of SEQ ID NO:78;
(i) a polynucleotide encoding a protein comprising a fragment of the amino acid sequence of SEQ ID NO:78 having biological activity, the fragment comprising eight contiguous amino acids of SEQ ID NO:78;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:77.

Preferably, such polynucleotide comprises the nucleotide sequence of SEQ ID NO:77 from nucleotide 42 to nucleotide 1196; the nucleotide sequence of SEQ ID NO:77 from nucleotide 558 to nucleotide 1196; the nucleotide sequence of the full-length protein coding sequence of clone yj28_1 deposited under accession number ATCC 98861; or the nucleotide sequence of a mature protein coding sequence of clone yj28_1 deposited under accession number ATCC 98861. In other preferred embodiments, the polynucleotide encodes the full-length or a mature protein encoded by the cDNA insert of clone yj28_1 deposited under accession number ATCC 98861. In further preferred embodiments, the present invention provides a polynucleotide encoding a protein comprising a fragment of the amino acid sequence of SEQ ID NO:78 having biological activity, the fragment preferably comprising eight (more preferably twenty, most preferably thirty) contiguous amino acids of SEQ ID NO:78, or a polynucleotide encoding a protein comprising a fragment of the amino acid sequence of SEQ ID NO:78 having biological activity, the fragment comprising the amino acid sequence from amino acid 187 to amino acid 196 of SEQ ID NO:78.

Other embodiments provide the gene corresponding to the cDNA sequence of SEQ ID NO:77.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:77, but excluding the poly(A) tail at the 3' end of SEQ ID NO:77; and
    (ab) the nucleotide sequence of the cDNA insert of clone yj28_1 deposited under accession number ATCC 98861;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:77, but excluding the poly(A) tail at the 3' end of SEQ ID NO:77; and
    (bb) the nucleotide sequence of the cDNA insert of clone yj28_1 deposited under accession number ATCC 98861;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:77, and extending contiguously from a nucleotide sequence corresponding to the 5' end of SEQ ID NO:77 to a nucleotide sequence corresponding to the 3' end of SEQ ID NO:77, but excluding the poly(A) tail at the 3' end of SEQ ID NO:77. Also preferably the polynucleotide isolated according to the above process comprises a nucleotide sequence corresponding to the cDNA sequence of SEQ ID NO:77 from nucleotide 42 to nucleotide 1196, and extending contiguously from a nucleotide sequence corresponding to the 5' end of said sequence of SEQ ID NO:77 from nucleotide 42 to nucleotide 1196, to a nucleotide sequence corresponding to the 3' end of said sequence of SEQ ID NO:77 from nucleotide 42 to nucleotide 1196. Also preferably the polynucleotide isolated according to the above process comprises a nucleotide sequence corresponding to the cDNA sequence of SEQ ID NO:77 from nucleotide 558 to nucleotide 1196, and extending contiguously from a nucleotide sequence corresponding to the 5' end of said sequence of SEQ ID NO:77 from nucleotide 558 to nucleotide 1196, to a nucleotide sequence corresponding to the 3' end of said sequence of SEQ ID NO:77 from nucleotide 558 to nucleotide 1196.

In other embodiments, the present invention provides a composition comprising a protein, wherein said protein comprises an amino acid sequence selected from the group consisting of:

(a) the amino acid sequence of SEQ ID NO:78;

(b) a fragment of the amino acid sequence of SEQ ID NO:78, the fragment comprising eight contiguous amino acids of SEQ ID NO:78; and (c) the amino acid sequence encoded by the cDNA insert of clone yj28_1 deposited under accession number ATCC 98861;

the protein being substantially free from other mammalian proteins. Preferably such protein comprises the amino acid sequence of SEQ ID NO:78. In further preferred embodiments, the present invention provides a protein comprising a fragment of the amino acid sequence of SEQ ID NO:78 having biological activity, the fragment preferably comprising eight (more preferably twenty, most preferably thirty) contiguous amino acids of SEQ ID NO:78, or a protein comprising a fragment of the amino acid sequence of SEQ ID NO:78 having biological activity, the fragment comprising the amino acid sequence from amino acid 187 to amino acid 196 of SEQ ID NO:78.

In one embodiment, the present invention provides a composition comprising an isolated polynucleotide selected from the group consisting of:

(a) a polynucleotide comprising the nucleotide sequence of SEQ ID NO:79;

(b) a polynucleotide comprising the nucleotide sequence of SEQ ID NO:79 from nucleotide 29 to nucleotide 1156;

(c) a polynucleotide comprising the nucleotide sequence of SEQ ID NO:79 from nucleotide 995 to nucleotide 1156;

(d) a polynucleotide comprising the nucleotide sequence of the full-length protein coding sequence of clone yj29_1 deposited under accession number ATCC 98861;

(e) a polynucleotide encoding the full-length protein encoded by the cDNA insert of clone yj29_1 deposited under accession number ATCC 98861;

(f) a polynucleotide comprising the nucleotide sequence of a mature protein coding sequence of done yj29_1 deposited under accession number ATCC 98861;

(g) a polynucleotide encoding a mature protein encoded by the cDNA insert of clone yj29_1 deposited under accession number ATCC 98861;

(h) a polynucleotide encoding a protein comprising the amino acid sequence of SEQ ID NO:80;

(i) a polynucleotide encoding a protein comprising a fragment of the amino acid sequence of SEQ ID NO:80 having biological activity, the fragment comprising eight contiguous amino acids of SEQ ID NO:80;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:79.

Preferably, such polynucleotide comprises the nucleotide sequence of SEQ ID NO:79 from nucleotide 29 to nucleotide 1156; the nucleotide sequence of SEQ ID NO:79 from nucleotide 995 to nucleotide 1156; the nucleotide sequence of the full-length protein coding sequence of clone yj29_1 deposited under accession number ATCC 98861; or the nucleotide sequence of a mature protein coding sequence of clone yj29_1 deposited under accession number ATCC 98861. In other preferred embodiments, the polynucleotide encodes the full-length or a mature protein encoded by the cDNA insert of clone yj29_1 deposited under accession number ATCC 98861. In further preferred embodiments, the present invention provides a polynucleotide encoding a protein comprising a fragment of the amino acid sequence of SEQ ID NO:80 having biological activity, the fragment preferably comprising eight (more preferably twenty, most preferably thirty) contiguous amino acids of SEQ ID NO:80, or a polynucleotide encoding a protein comprising a fragment of the amino acid sequence of SEQ ID NO:80 having biological activity, the fragment comprising the amino acid sequence from amino acid 183 to amino acid 192 of SEQ ID NO:80.

Other embodiments provide the gene corresponding to the cDNA sequence of SEQ ID NO:79.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:79, but excluding the poly(A) tail at the 3' end of SEQ ID NO:79; and
    (ab) the nucleotide sequence of the cDNA insert of clone yj29_1 deposited under accession number ATCC 98861;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:79, but excluding the poly(A) tail at the 3' end of SEQ ID NO:79; and
    (bb) the nucleotide sequence of the cDNA insert of clone yj29_1 deposited under accession number ATCC 98861;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:79, and extending contiguously from a nucleotide sequence corresponding to the 5' end of SEQ ID NO:79 to a nucleotide sequence corresponding to the 3' end of SEQ ID NO:79, but excluding the poly(A) tail at the 3' end of SEQ ID NO:79. Also preferably the polynucleotide isolated according to the above process comprises a nucleotide sequence corresponding to the cDNA sequence of SEQ ID NO:79 from nucleotide 29 to nucleotide 1156, and extending contiguously from a nucleotide sequence corresponding to the 5' end of said sequence of SEQ ID NO:79 from nucleotide 29 to nucleotide 1156, to a nucleotide sequence corresponding to the 3' end of said sequence of SEQ ID NO:79_1 from nucleotide 29 to nucleotide 1156. Also preferably the polynucleotide isolated according to the above process comprises a nucleotide sequence corresponding to the cDNA sequence of SEQ ID NO:79 from nucleotide 995 to nucleotide 1156, and extending contiguously from a nucleotide sequence corresponding to the 5' end of said sequence of SEQ ID NO:79 from nucleotide 995 to nucleotide 1156, to a nucleotide sequence corresponding to the 3' end of said sequence of SEQ ID NO:79 from nucleotide 995 to nucleotide 1156.

In other embodiments, the present invention provides a composition comprising a protein, wherein said protein comprises an amino acid sequence selected from the group consisting of:

(a) the amino acid sequence of SEQ ID NO:80;

(b) a fragment of the amino acid sequence of SEQ ID NO:80, the fragment comprising eight contiguous amino acids of SEQ ID NO:80; and (c) the amino acid sequence encoded by the cDNA insert of clone yj29_1 deposited under accession number ATCC 98861;

the protein being substantially free from other mammalian proteins. Preferably such protein comprises the amino acid sequence of SEQ ID NO:80. In further preferred embodiments, the present invention provides a protein comprising a fragment of the amino acid sequence of SEQ ID NO:80 having biological activity, the fragment preferably comprising eight (more preferably twenty, most preferably thirty) contiguous amino acids of SEQ ID NO:80, or a protein comprising a fragment of the amino acid sequence of SEQ ID NO:80 having biological activity, the fragment comprising the amino acid sequence from amino acid 183 to amino acid 192 of SEQ ID NO:80.

In one embodiment, the present invention provides a composition comprising an isolated polynucleotide selected from the group consisting of:

(a) a polynucleotide comprising the nucleotide sequence of SEQ ID NO:81;

(b) a polynucleotide comprising the nucleotide sequence of SEQ ID NO:81 from nucleotide 93 to nucleotide 398;

(c) a polynucleotide comprising the nucleotide sequence of SEQ ID NO:81 from nucleotide 321 to nucleotide 398;

(d) a polynucleotide comprising the nucleotide sequence of the full-length protein coding sequence of clone yj32_1 deposited under accession number ATCC 98861;

(e) a polynucleotide encoding the full-length protein encoded by the cDNA insert of clone yj32_1 deposited under accession number ATCC 98861;

(f) a polynucleotide comprising the nucleotide sequence of a mature protein coding sequence of clone yj32_1 deposited under accession number ATCC 98861;

(g) a polynucleotide encoding a mature protein encoded by the cDNA insert of clone yj32_1 deposited under accession number ATCC 98861;

(h) a polynucleotide encoding a protein comprising the amino acid sequence of SEQ ID NO:82;

(i) a polynucleotide encoding a protein comprising a fragment of the amino acid sequence of SEQ ID NO:82 having biological activity, the fragment comprising eight contiguous amino acids of SEQ ID NO:82;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:81.

Preferably, such polynucleotide comprises the nucleotide sequence of SEQ ID NO:81 from nucleotide 93 to nucleotide 398; the nucleotide sequence of SEQ ID NO:81 from nucleotide 321 to nucleotide 398; the nucleotide sequence of the full-length protein coding sequence of clone yj32_1 deposited under accession number ATCC 98861; or the nucleotide sequence of a mature protein coding sequence of clone yj32_1 deposited under accession number ATCC 98861. In other preferred embodiments, the polynucleotide encodes the full-length or a mature protein encoded by the cDNA insert of clone yj32_1 deposited under accession number ATCC 98861. In further preferred embodiments, the present invention provides a polynucleotide encoding a protein comprising a fragment of the amino acid sequence of SEQ ID NO:82 having biological activity, the fragment preferably comprising eight (more preferably twenty, most preferably thirty) contiguous amino acids of SEQ ID NO:82, or a polynucleotide encoding a protein comprising a fragment of the amino acid sequence of SEQ ID NO:82 having biological activity, the fragment comprising the amino acid sequence from amino acid 46 to amino acid 55 of SEQ ID NO:82.

Other embodiments provide the gene corresponding to the cDNA sequence of SEQ ID NO:81.

Further embodiments of the invention provide isolated polynucleotides produced according to a process selected from the group consisting of:

(a) a process comprising the steps of:
 (i) preparing one or more polynucleotide probes that hybridize in 6xSSC at 65 degrees C. to a nucleotide sequence selected from the group consisting of:
  (aa) SEQ ID NO:81, but excluding the poly(A) tail at the 3' end of SEQ ID NO:81; and
  (ab) the nucleotide sequence of the cDNA insert of clone yj32_1 deposited under accession number ATCC 98861;
 (ii) hybridizing said probe(s) to human genomic DNA in conditions at least as stringent as 4xSSC at 50 degrees C.; and
 (iii) isolating the DNA polynucleotides detected with the probe(s);

and (b) a process comprising the steps of:
 (i) preparing one or more polynucleotide primers that hybridize in 6xSSC at 65 degrees C. to a nucleotide sequence selected from the group consisting of:

(ba) SEQ ID NO:81, but excluding the poly(A) tail at the 3' end of SEQ ID NO:81; and (bb) the nucleotide sequence of the cDNA insert of clone yj32_1 deposited under accession number ATCC 98861;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:81, and extending contiguously from a nucleotide sequence corresponding to the 5' end of SEQ ID NO:81 to a nucleotide sequence corresponding to the 3' end of SEQ ID NO:81, but excluding the poly(A) tail at the 3' end of SEQ ID NO:81. Also preferably the polynucleotide isolated according to the above process comprises a nucleotide sequence corresponding to the cDNA sequence of SEQ ID NO:81 from nucleotide 93 to nucleotide 398, and extending contiguously from a nucleotide sequence corresponding to the 5' end of said sequence of SEQ ID NO:81 from nucleotide 93 to nucleotide 398, to a nucleotide sequence corresponding to the 3' end of said sequence of SEQ ID NO:81 from nucleotide 93 to nucleotide 398. Also preferably the polynucleotide isolated according to the above process comprises a nucleotide sequence corresponding to the cDNA sequence of SEQ ID NO:81 from nucleotide 321 to nucleotide 398, and extending contiguously from a nucleotide sequence corresponding to the 5' end of said sequence of SEQ ID NO:81 from nucleotide 321 to nucleotide 398, to a nucleotide sequence corresponding to the 3' end of said sequence of SEQ ID NO:81 from nucleotide 321 to nucleotide 398.

In other embodiments, the present invention provides a composition comprising a protein, wherein said protein comprises an amino acid sequence selected from the group consisting of:

(a) the amino acid sequence of SEQ ID NO:82;

(b) a fragment of the amino acid sequence of SEQ ID NO:82, the fragment comprising eight contiguous amino acids of SEQ ID NO:82; and (c) the amino acid sequence encoded by the cDNA insert of clone yj32_1 deposited under accession number ATCC 98861;

the protein being substantially free from other mammalian proteins. Preferably such protein comprises the amino acid sequence of SEQ ID NO:82. In further preferred embodiments, the present invention provides a protein comprising a fragment of the amino acid sequence of SEQ ID NO:82 having biological activity, the fragment preferably comprising eight (more preferably twenty, most preferably thirty) contiguous amino acids of SEQ ID NO:82, or a protein comprising a fragment of the amino acid sequence of SEQ ID NO:82 having biological activity, the fragment comprising the amino acid sequence from amino acid 46 to amino acid 55 of SEQ ID NO:82.

In one embodiment, the present invention provides a composition comprising an isolated polynucleotide selected from the group consisting of:

(a) a polynucleotide comprising the nucleotide sequence of SEQ ID NO:83;

(b) a polynucleotide comprising the nucleotide sequence of SEQ ID NO:83 from nucleotide 167 to nucleotide 1264;

(c) a polynucleotide comprising the nucleotide sequence of SEQ ID NO:83 from nucleotide 233 to nucleotide 1264;

(d) a polynucleotide comprising the nucleotide sequence of the full-length protein coding sequence of clone yb186_1 deposited under accession number ATCC 98872;

(e) a polynucleotide encoding the full-length protein encoded by the cDNA insert of clone yb186_1 deposited under accession number ATCC 98872;

(f) a polynucleotide comprising the nucleotide sequence of a mature protein coding sequence of clone yb186_1 deposited under accession number ATCC 98872;

(g) a polynucleotide encoding a mature protein encoded by the cDNA insert of clone yb186_1 deposited under accession number ATCC 98872;

(h) a polynucleotide encoding a protein comprising the amino acid sequence of SEQ ID NO:84;

(i) a polynucleotide encoding a protein comprising a fragment of the amino acid sequence of SEQ ID NO:84 having biological activity, the fragment comprising eight contiguous amino acids of SEQ ID NO:84;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:83.

Preferably, such polynucleotide comprises the nucleotide sequence of SEQ ID NO:83 from nucleotide 167 to nucleotide 1264; the nucleotide sequence of SEQ ID NO:83 from nucleotide 233 to nucleotide 1264; the nucleotide sequence of the full-length protein coding sequence of clone yb186_1 deposited under accession number ATCC 98872; or the nucleotide sequence of a mature protein coding sequence of clone yb186_1 deposited under accession number ATCC 98872. In other preferred embodiments, the polynucleotide encodes the full-length or a mature protein encoded by the cDNA insert of clone yb186_1 deposited under accession number ATCC 98872. In further preferred embodiments, the present invention provides a polynucleotide encoding a protein comprising a fragment of the amino acid sequence of SEQ ID NO:84 having biological activity, the fragment preferably comprising eight (more preferably twenty, most preferably thirty) contiguous amino acids of SEQ ID NO:84, or a polynucleotide encoding a protein comprising a fragment of the amino acid sequence of SEQ ID NO:84 having biological activity, the fragment comprising the amino acid sequence from amino acid 178 to amino acid 187 of SEQ ID NO:84.

Other embodiments provide the gene corresponding to the cDNA sequence of SEQ ID NO:83.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:83, but excluding the poly(A) tail at the 3' end of SEQ ID NO:83; and (ab) the nucleotide sequence of the cDNA insert of clone yb186_1 deposited under accession number ATCC 98872;

(ii) hybridizing said probe(s) to human genomic DNA in conditions at least as stringent as 4×SSC at 50 degrees C.; and (iii) isolating the DNA polynucleotides detected with the probe(s);

and (b) a process comprising the steps of:

(i) preparing one or more polynucleotide primers that hybridize in 6×SSC at 65 degrees C. to a nucleotide sequence selected from the group consisting of:

(ba) SEQ ID NO:83, but excluding the poly(A) tail at the 3' end of SEQ ID NO:83; and (bb) the nucleotide sequence of the cDNA insert of clone yb186_1 deposited under accession number ATCC 98872;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:83, and extending contiguously from a nucleotide sequence corresponding to the 5' end of SEQ ID NO:83 to a nucleotide sequence corresponding to the 3' end of SEQ ID NO:83, but excluding the poly(A) tail at the 3' end of SEQ ID NO:83. Also preferably the polynucleotide isolated according to the above process comprises a nucleotide sequence corresponding to the cDNA sequence of SEQ ID NO:83 from nucleotide 167 to nucleotide 1264, and extending contiguously from a nucleotide sequence corresponding to the 5' end of said sequence of SEQ ID NO:83 from nucleotide 167 to nucleotide 1264, to a nucleotide sequence corresponding to the 3' end of said sequence of SEQ ID NO:83 from nucleotide 167 to nucleotide 1264. Also preferably the polynucleotide isolated according to the above process comprises a nucleotide sequence corresponding to the cDNA sequence of SEQ ID NO:83 from nucleotide 233 to nucleotide 1264, and extending contiguously from a nucleotide sequence corresponding to the 5' end of said sequence of SEQ ID NO:83 from nucleotide 233 to nucleotide 1264, to a nucleotide sequence corresponding to the 3' end of said sequence of SEQ ID NO:83 from nucleotide 233 to nucleotide 1264.

In other embodiments, the present invention provides a composition comprising a protein, wherein said protein comprises an amino acid sequence selected from the group consisting of:

(a) the amino acid sequence of SEQ ID NO:84;

(b) a fragment of the amino acid sequence of SEQ ID NO:84, the fragment comprising eight contiguous amino acids of SEQ ID NO:84; and (c) the amino acid sequence encoded by the cDNA insert of clone yb186_1 deposited under accession number ATCC 98872;

the protein being substantially free from other mammalian proteins. Preferably such protein comprises the amino acid sequence of SEQ ID NO:84. In further preferred embodiments, the present invention provides a protein comprising a fragment of the amino acid sequence of SEQ ID NO:84 having biological activity, the fragment preferably comprising eight (more preferably twenty, most preferably thirty) contiguous amino acids of SEQ ID NO:84, or a protein comprising a fragment of the amino acid sequence of SEQ ID NO:84 having biological activity, the fragment comprising the amino acid sequence from amino acid 178 to amino acid 187 of SEQ ID NO:84.

In one embodiment, the present invention provides a composition comprising an isolated polynucleotide selected from the group consisting of:

(a) a polynucleotide comprising the nucleotide sequence of SEQ ID NO:85;

(b) a polynucleotide comprising the nucleotide sequence of SEQ ID NO:85 from nucleotide 832 to nucleotide 1416;

(c) a polynucleotide comprising the nucleotide sequence of the full-length protein coding sequence of clone yb226_1 deposited under accession number ATCC 98872;

(d) a polynucleotide encoding the full-length protein encoded by the cDNA insert of clone yb226_1 deposited under accession number ATCC 98872;

(e) a polynucleotide comprising the nucleotide sequence of a mature protein coding sequence of clone yb226_1 deposited under accession number ATCC 98872;

(f) a polynucleotide encoding a mature protein encoded by the cDNA insert of clone yb226_1 deposited under accession number ATCC 98872;

(g) a polynucleotide encoding a protein comprising the amino acid sequence of SEQ ID NO:86;

(h) a polynucleotide encoding a protein comprising a fragment of the amino acid sequence of SEQ ID NO:86 having biological activity, the fragment comprising eight contiguous amino acids of SEQ ID NO:86;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:85.

Preferably, such polynucleotide comprises the nucleotide sequence of SEQ ID NO:85 from nucleotide 832 to nucleotide 1416; the nucleotide sequence of the full-length protein coding sequence of clone yb226_1 deposited under accession number ATCC 98872; or the nucleotide sequence of a mature protein coding sequence of clone yb226_1 deposited under accession number ATCC 98872. In other preferred embodiments, the polynucleotide encodes the full-length or a mature protein encoded by the cDNA insert of clone yb226_1 deposited under accession number ATCC 98872. In further preferred embodiments, the present invention provides a polynucleotide encoding a protein comprising a fragment of the amino acid sequence of SEQ ID NO:86 having biological activity, the fragment preferably comprising eight (more preferably twenty, most preferably thirty) contiguous amino acids of SEQ ID NO:86, or a polynucleotide encoding a protein comprising a fragment of the amino acid sequence of SEQ ID NO:86 having biological activity, the fragment comprising the amino acid sequence from amino acid 92 to amino acid 101 of SEQ ID NO:86.

Other embodiments provide the gene corresponding to the cDNA sequence of SEQ ID NO:85.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:85, but excluding the poly(A) tail at the 3' end of SEQ ID NO:85; and
    (ab) the nucleotide sequence of the cDNA insert of clone yb226_1 deposited under accession number ATCC 98872;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:85, but excluding the poly(A) tail at the 3' end of SEQ ID NO:85; and
    (bb) the nucleotide sequence of the cDNA insert of clone yb226_1 deposited under accession number ATCC 98872;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:85, and extending contiguously from a nucleotide sequence corresponding to the 5' end of SEQ ID NO:85 to a nucleotide sequence corresponding to the 3' end of SEQ ID NO:85, but excluding the poly(A) tail at the 3' end of SEQ ID NO:85. Also preferably the polynucleotide isolated according to the above process comprises a nucleotide sequence corresponding to the cDNA sequence of SEQ ID NO:85 from nucleotide 832 to nucleotide 1416, and extending contiguously from a nucleotide sequence corresponding to the 5' end of said sequence of SEQ ID NO:85 from nucleotide 832 to nucleotide 1416, to a nucleotide sequence corresponding to the 3' end of said sequence of SEQ ID NO:85 from nucleotide 832 to nucleotide 1416.

In other embodiments, the present invention provides a composition comprising a protein, wherein said protein comprises an amino acid sequence selected from the group consisting of:
  (a) the amino acid sequence of SEQ ID NO:86;
  (b) a fragment of the amino acid sequence of SEQ ID NO:86, the fragment comprising eight contiguous amino acids of SEQ ID NO:86; and
  (c) the amino acid sequence encoded by the cDNA insert of clone yb226_1 deposited under accession number ATCC 98872;
the protein being substantially free from other mammalian proteins. Preferably such protein comprises the amino acid sequence of SEQ ID NO:86. In further preferred embodiments, the present invention provides a protein comprising a fragment of the amino acid sequence of SEQ ID NO:86 having biological activity, the fragment preferably comprising eight (more preferably twenty, most preferably thirty) contiguous amino acids of SEQ ID NO:86, or a protein comprising a fragment of the amino acid sequence of SEQ ID NO:86 having biological activity, the fragment comprising the amino acid sequence from amino acid 92 to amino acid 101 of SEQ ID NO:86.

In one embodiment, the present invention provides a composition comprising an isolated polynucleotide selected from the group consisting of:
  (a) a polynucleotide comprising the nucleotide sequence of SEQ ID NO:87;
  (b) a polynucleotide comprising the nucleotide sequence of SEQ ID NO:87 from nucleotide 155 to nucleotide 745;
  (c) a polynucleotide comprising the nucleotide sequence of the full-length protein coding sequence of clone yd50_1 deposited under accession number ATCC 98872;
  (d) a polynucleotide encoding the full-length protein encoded by the cDNA insert of clone yd50_1 deposited under accession number ATCC 98872;
  (e) a polynucleotide comprising the nucleotide sequence of a mature protein coding sequence of clone yd50_1 deposited under accession number ATCC 98872;
  (f) a polynucleotide encoding a mature protein encoded by the cDNA insert of clone yd50_1 deposited under accession number ATCC 98872;
  (g) a polynucleotide encoding a protein comprising the amino acid sequence of SEQ ID NO:88;
  (h) a polynucleotide encoding a protein comprising a fragment of the amino acid sequence of SEQ ID NO:88 having biological activity, the fragment comprising eight contiguous amino acids of SEQ ID NO:88;
  (i) a polynucleotide which is an allelic variant of a polynucleotide of (a)–(f) above;
  (j) a polynucleotide which encodes a species homologue of the protein of (g) or (h) above;
  (k) a polynucleotide that hybridizes under stringent conditions to any one of the polynucleotides specified in (a)–(h); and
  (l) a polynucleotide that hybridizes under stringent conditions to any one of the polynucleotides specified in (a)–(h) and that has a length that is at least 25% of the length of SEQ ID NO:87.

Preferably, such polynucleotide comprises the nucleotide sequence of SEQ ID NO:87 from nucleotide 155 to nucleotide 745; the nucleotide sequence of the full-length protein coding sequence of clone yd50_1 deposited under accession number ATCC 98872; or the nucleotide sequence of a mature protein coding sequence of clone yd50_1 deposited under accession number ATCC 98872. In other preferred embodiments, the polynucleotide encodes the full-length or a mature protein encoded by the cDNA insert of clone yd50_1 deposited under accession number ATCC 98872. In further preferred embodiments, the present invention provides a polynucleotide encoding a protein comprising a fragment of the amino acid sequence of SEQ ID NO:88 having biological activity, the fragment preferably comprising eight (more preferably twenty, most preferably thirty) contiguous amino acids of SEQ ID NO:88, or a polynucleotide encoding a protein comprising a fragment of the amino acid sequence of SEQ ID NO:88 having biological activity, the fragment comprising the amino acid sequence from amino acid 93 to amino acid 102 of SEQ ID NO:88.

Other embodiments provide the gene corresponding to the cDNA sequence of SEQ ID NO:87.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:87, but excluding the poly(A) tail at the 3' end of SEQ ID NO:87; and
    (ab) the nucleotide sequence of the cDNA insert of clone yd50_1 deposited under accession number ATCC 98872;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:87, but excluding the poly(A) tail at the 3' end of SEQ ID NO:87; and
    (bb) the nucleotide sequence of the cDNA insert of done yd50_1 deposited under accession number ATCC 98872;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:87, and extending contiguously from a nucleotide sequence corresponding to the 5' end of SEQ ID NO:87 to a nucleotide sequence corresponding to the 3' end of SEQ ID NO:87, but excluding the poly(A) tail at the 3' end of SEQ ID NO:87. Also preferably the polynucleotide isolated according to the above process comprises a nucleotide sequence corresponding to the cDNA sequence of SEQ ID NO:87 from nucleotide 155 to nucleotide 745, and extending contiguously from a nucleotide sequence corresponding to the 5' end of said sequence of SEQ ID NO:87 from nucleotide 155 to nucleotide 745, to a nucleotide sequence corresponding to the 3' end of said sequence of SEQ ID NO:87 from nucleotide 155 to nucleotide 745.

In other embodiments, the present invention provides a composition comprising a protein, wherein said protein comprises an amino acid sequence selected from the group consisting of:
  (a) the amino acid sequence of SEQ ID NO:88;
  (b) a fragment of the amino acid sequence of SEQ ID NO:88, the fragment comprising eight contiguous amino acids of SEQ ID NO:88; and
  (c) the amino acid sequence encoded by the cDNA insert of clone yd50_1 deposited under accession number ATCC 98872;
the protein being substantially free from other mammalian proteins. Preferably such protein comprises the amino acid sequence of SEQ ID NO:88. In further preferred embodiments, the present invention provides a protein comprising a fragment of the amino acid sequence of SEQ ID NO:88 having biological activity, the fragment preferably comprising eight (more preferably twenty, most preferably thirty) contiguous amino acids of SEQ ID NO:88, or a protein comprising a fragment of the amino acid sequence of SEQ ID NO:88 having biological activity, the fragment comprising the amino acid sequence from amino acid 93 to amino acid 102 of SEQ ID NO:88.

In one embodiment, the present invention provides a composition comprising an isolated polynucleotide selected from the group consisting of:
  (a) a polynucleotide comprising the nucleotide sequence of SEQ ID NO:89;
  (b) a polynucleotide comprising the nucleotide sequence of SEQ ID NO:89 from nucleotide 42 to nucleotide 317;
  (c) a polynucleotide comprising the nucleotide sequence of SEQ ID NO:89 from nucleotide 111 to nucleotide 317;
  (d) a polynucleotide comprising the nucleotide sequence of the full-length protein coding sequence of clone yd51_1 deposited under accession number ATCC 98872;
  (e) a polynucleotide encoding the full-length protein encoded by the cDNA insert of clone yd51_1 deposited under accession number ATCC 98872;
  (f) a polynucleotide comprising the nucleotide sequence of a mature protein coding sequence of clone yd51_1 deposited under accession number ATCC 98872;
  (g) a polynucleotide encoding a mature protein encoded by the cDNA insert of clone yd51_1 deposited under accession number ATCC 98872;
  (h) a polynucleotide encoding a protein comprising the amino acid sequence of SEQ ID NO:90;
  (i) a polynucleotide encoding a protein comprising a fragment of the amino acid sequence of SEQ ID NO:90 having biological activity, the fragment comprising eight contiguous amino acids of SEQ ID NO:90;
  (j) a polynucleotide which is an allelic variant of a polynucleotide of (a)–(g) above;
  (k) a polynucleotide which encodes a species homologue of the protein of (h) or (i) above;
  (l) a polynucleotide that hybridizes under stringent conditions to any one of the polynucleotides specified in (a)–(i); and
  (m) a polynucleotide that hybridizes under stringent conditions to any one of the polynucleotides specified in (a)–(i) and that has a length that is at least 25% of the length of SEQ ID NO:89.

Preferably, such polynucleotide comprises the nucleotide sequence of SEQ ID NO:89 from nucleotide 42 to nucleotide 317; the nucleotide sequence of SEQ ID NO:89 from nucleotide 111 to nucleotide 317; the nucleotide sequence of the full-length protein coding sequence of clone yd51_1 deposited under accession number ATCC 98872; or the nucleotide sequence of a mature protein coding sequence of clone yd51_1 deposited under accession number ATCC 98872. In other preferred embodiments, the polynucleotide encodes the full-length or a mature protein encoded by the cDNA insert of clone yd51_1 deposited under accession number ATCC 98872. In further preferred embodiments, the present invention provides a polynucleotide encoding a protein comprising a fragment of the amino acid sequence of SEQ ID NO:90 having biological activity, the fragment preferably comprising eight (more preferably twenty, most preferably thirty) contiguous amino acids of SEQ ID NO:90, or a polynucleotide encoding a protein comprising a fragment of the amino acid sequence of SEQ ID NO:90 having biological activity, the fragment comprising the amino acid sequence from amino acid 41 to amino acid 50 of SEQ ID NO:90.

Other embodiments provide the gene corresponding to the cDNA sequence of SEQ ID NO:89.

Further embodiments of the invention provide isolated polynucleotides produced according to a process selected from the group consisting of:

(a) a process comprising the steps of:
   (i) preparing one or more polynucleotide probes that hybridize in 6×SSC at 65 degrees C. to a nucleotide sequence selected from the group consisting of:
      (aa) SEQ ID NO:89, but excluding the poly(A) tail at the 3' end of SEQ ID NO:89; and
      (ab) the nucleotide sequence of the cDNA insert of clone yd51_1 deposited under accession number ATCC 98872;
   (ii) hybridizing said probe(s) to human genomic DNA in conditions at least as stringent as 4×SSC at 50 degrees C.; and
   (iii) isolating the DNA polynucleotides detected with the probe(s);
and
(b) a process comprising the steps of:
   (i) preparing one or more polynucleotide primers that hybridize in 6×SSC at 65 degrees C. to a nucleotide sequence selected from the group consisting of:
      (ba) SEQ ID NO:89, but excluding the poly(A) tail at the 3' end of SEQ ID NO:89; and
      (bb) the nucleotide sequence of the cDNA insert of clone yd51_1 deposited under accession number ATCC 98872;
   (ii) hybridizing said primer(s) to human genomic DNA in conditions at least as stringent as 4×SSC at 50 degrees C.;
   (iii) amplifying human DNA sequences; and
   (iv) isolating the polynucleotide products of step (b)(iii).

Preferably the polynucleotide isolated according to the above process comprises a nucleotide sequence corresponding to the cDNA sequence of SEQ ID NO:89, and extending contiguously from a nucleotide sequence corresponding to the 5' end of SEQ ID NO:89 to a nucleotide sequence corresponding to the 3' end of SEQ ID NO:89, but excluding the poly(A) tail at the 3' end of SEQ ID NO:89. Also preferably the polynucleotide isolated according to the above process comprises a nucleotide sequence corresponding to the cDNA sequence of SEQ ID NO:89 from nucleotide 42 to nucleotide 317, and extending contiguously from a nucleotide sequence corresponding to the 5' end of said sequence of SEQ ID NO:89 from nucleotide 42 to nucleotide 317, to a nucleotide sequence corresponding to the 3' end of said sequence of SEQ ID NO:89 from nucleotide 42 to nucleotide 317. Also preferably the polynucleotide isolated according to the above process comprises a nucleotide sequence corresponding to the cDNA sequence of SEQ ID NO:89 from nucleotide 111 to nucleotide 317, and extending contiguously from a nucleotide sequence corresponding to the 5' end of said sequence of SEQ ID NO:89 from nucleotide 111 to nucleotide 317, to a nucleotide sequence corresponding to the 3' end of said sequence of SEQ ID NO:89 from nucleotide 111 to nucleotide 317.

In other embodiments, the present invention provides a composition comprising a protein, wherein said protein comprises an amino acid sequence selected from the group consisting of:

(a) the amino acid sequence of SEQ ID NO:90;
(b) a fragment of the amino acid sequence of SEQ ID NO:90; the fragment comprising eight contiguous amino acids of SEQ ID NO:90; and
(c) the amino acid sequence encoded by the cDNA insert of clone yd51_1 deposited under accession number ATCC 98872;

the protein being substantially free from other mammalian proteins. Preferably such protein comprises the amino acid sequence of SEQ ID NO:90. In further preferred embodiments, the present invention provides a protein comprising a fragment of the amino acid sequence of SEQ ID NO:90 having biological activity, the fragment preferably comprising eight (more preferably twenty, most preferably thirty) contiguous amino acids of SEQ ID NO:90, or a protein comprising a fragment of the amino acid sequence of SEQ ID NO:90 having biological activity, the fragment comprising the amino acid sequence from amino acid 41 to amino acid 50 of SEQ ID NO:90.

In one embodiment, the present invention provides a composition comprising an isolated polynucleotide selected from the group consisting of:

(a) a polynucleotide comprising the nucleotide sequence of SEQ ID NO:91;
(b) a polynucleotide comprising the nucleotide sequence of SEQ ID NO:91 from nucleotide 7 to nucleotide 603;
(c) a polynucleotide comprising the nucleotide sequence of SEQ ID NO:91 from nucleotide 244 to nucleotide 603;
(d) a polynucleotide comprising the nucleotide sequence of the full-length protein coding sequence of clone yd73_1 deposited under accession number ATCC 98872;
(e) a polynucleotide encoding the full-length protein encoded by the cDNA insert of clone yd73_1 deposited under accession number ATCC 98872;
(f) a polynucleotide comprising the nucleotide sequence of a mature protein coding sequence of clone yd73_1 deposited under accession number ATCC 98872;
(g) a polynucleotide encoding a mature protein encoded by the cDNA insert of clone yd73_1 deposited under accession number ATCC 98872;
(h) a polynucleotide encoding a protein comprising the amino acid sequence of SEQ ID NO:92;
(i) a polynucleotide encoding a protein comprising a fragment of the amino acid sequence of SEQ ID NO:92 having biological activity, the fragment comprising eight contiguous amino acids of SEQ ID NO:92;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:91.

Preferably, such polynucleotide comprises the nucleotide sequence of SEQ ID NO:91 from nucleotide 7 to nucleotide 603; the nucleotide sequence of SEQ ID NO:91 from nucleotide 244 to nucleotide 603; the nucleotide sequence of the full-length protein coding sequence of clone yd73_1 deposited under accession number ATCC 98872; or the nucleotide sequence of a mature protein coding sequence of clone yd73_1 deposited under accession number ATCC 98872. In other preferred embodiments, the polynucleotide encodes the full-length or a mature protein encoded by the cDNA insert of clone yd73_1 deposited under accession number ATCC 98872. In further preferred embodiments, the present invention provides a polynucleotide encoding a protein comprising a fragment of the amino acid sequence of SEQ ID NO:92 having biological activity, the fragment preferably comprising eight (more preferably twenty, most preferably thirty) contiguous amino acids of SEQ ID NO:92, or a polynucleotide encoding a protein comprising a fragment of the amino acid sequence of SEQ ID NO:92 having biological activity, the fragment comprising the amino acid sequence from amino acid 94 to amino acid 103 of SEQ ID NO:92.

Other embodiments provide the gene corresponding to the cDNA sequence of SEQ ID NO:91.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:91, but excluding the poly(A) tail at the 3' end of SEQ ID NO:91; and
    (ab) the nucleotide sequence of the cDNA insert of clone yd73_1 deposited under accession number ATCC 98872;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:91, but excluding the poly(A) tail at the 3' end of SEQ ID NO:91; and
    (bb) the nucleotide sequence of the cDNA insert of clone yd73_1 deposited under accession number ATCC 98872;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:91, and extending contiguously from a nucleotide sequence corresponding to the 5' end of SEQ ID NO:91 to a nucleotide sequence corresponding to the 3' end of SEQ ID NO:91, but excluding the poly(A) tail at the 3' end of SEQ ID NO:91. Also preferably the polynucleotide isolated according to the above process comprises a nucleotide sequence corresponding to the cDNA sequence of SEQ ID NO:91 from nucleotide 7 to nucleotide 603, and extending contiguously from a nucleotide sequence corresponding to the 5' end of said sequence of SEQ ID NO:91 from nucleotide 7 to nucleotide 603, to a nucleotide sequence corresponding to the 3' end of said sequence of SEQ ID NO:91 from nucleotide 7 to nucleotide 603. Also preferably the polynucleotide isolated according to the above process comprises a nucleotide sequence corresponding to the cDNA sequence of SEQ ID NO:91 from nucleotide 244 to nucleotide 603, and extending contiguously from a nucleotide sequence corresponding to the 5' end of said sequence of SEQ ID NO:91 from nucleotide 244 to nucleotide 603, to a nucleotide sequence corresponding to the 3' end of said sequence of SEQ ID NO:91 from nucleotide 244 to nucleotide 603.

In other embodiments, the present invention provides a composition comprising a protein, wherein said protein comprises an amino acid sequence selected from the group consisting of:
(a) the amino acid sequence of SEQ ID NO:92;
(b) a fragment of the amino acid sequence of SEQ ID NO:92, the fragment comprising eight contiguous amino acids of SEQ ID NO:92; and
(c) the amino acid sequence encoded by the cDNA insert of clone yd73_1 deposited under accession number ATCC 98872;
the protein being substantially free from other mammalian proteins. Preferably such protein comprises the amino acid sequence of SEQ ID NO:92. In further preferred embodiments, the present invention provides a protein comprising a fragment of the amino acid sequence of SEQ ID NO:92 having biological activity, the fragment preferably comprising eight (more preferably twenty, most preferably thirty) contiguous amino acids of SEQ ID NO:92, or a protein comprising a fragment of the amino acid sequence of SEQ ID NO:92 having biological activity, the fragment comprising the amino acid sequence from amino acid 94 to amino acid 103 of SEQ ID NO:92.

In one embodiment, the present invention provides a composition comprising an isolated polynucleotide selected from the group consisting of:
(a) a polynucleotide comprising the nucleotide sequence of SEQ ID NO:93;
(b) a polynucleotide comprising the nucleotide sequence of SEQ ID NO:93 from nucleotide 367 to nucleotide 747;
(c) a polynucleotide comprising the nucleotide sequence of SEQ ID NO:93 from nucleotide 667 to nucleotide 747;
(d) a polynucleotide comprising the nucleotide sequence of the full-length protein coding sequence of clone ye43_1 deposited under accession number ATCC 98872;
(e) a polynucleotide encoding the full-length protein encoded by the cDNA insert of clone ye43_1 deposited under accession number ATCC 98872;
(f) a polynucleotide comprising the nucleotide sequence of a mature protein coding sequence of clone ye43_1 deposited under accession number ATCC 98872;
(g) a polynucleotide encoding a mature protein encoded by the cDNA insert of clone ye43_1 deposited under accession number ATCC 98872;
(h) a polynucleotide encoding a protein comprising the amino acid sequence of SEQ ID NO:94;
(i) a polynucleotide encoding a protein comprising a fragment of the amino acid sequence of SEQ ID NO:94 having biological activity, the fragment comprising eight contiguous amino acids of SEQ ID NO:94;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:93.

Preferably, such polynucleotide comprises the nucleotide sequence of SEQ ID NO:93 from nucleotide 367 to nucleotide 747; the nucleotide sequence of SEQ ID NO:93 from nucleotide 667 to nucleotide 747; the nucleotide sequence of the full-length protein coding sequence of clone ye43_1 deposited under accession number ATCC 98872; or the nucleotide sequence of a mature protein coding sequence of clone ye43_1 deposited under accession number ATCC 98872. In other preferred embodiments, the polynucleotide encodes the full-length or a mature protein encoded by the cDNA insert of clone ye43_1 deposited under accession number ATCC 98872. In further preferred embodiments, the present invention provides a polynucleotide encoding a protein comprising a fragment of the amino acid sequence of SEQ ID NO:94 having biological activity, the fragment preferably comprising eight (more preferably twenty, most preferably thirty) contiguous amino acids of SEQ ID NO:94, or a polynucleotide encoding a protein comprising a fragment of the amino acid sequence of SEQ ID NO:94 having biological activity, the fragment comprising the amino acid sequence from amino acid 58 to amino acid 67 of SEQ ID NO:94.

Other embodiments provide the gene corresponding to the cDNA sequence of SEQ ID NO:93.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:93, but excluding the poly(A) tail at the 3' end of SEQ ID NO:93; and
    (ab) the nucleotide sequence of the cDNA insert of clone ye43_1 deposited under accession number ATCC 98872;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:93, but excluding the poly(A) tail at the 3' end of SEQ ID NO:93; and
    (bb) the nucleotide sequence of the cDNA insert of clone ye43_1 deposited under accession number ATCC 98872;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:93, and extending contiguously from a nucleotide sequence corresponding to the 5' end of SEQ ID NO:93 to a nucleotide sequence corresponding to the 3' end of SEQ ID NO:93, but excluding the poly(A) tail at the 3' end of SEQ ID NO:93. Also preferably the polynucleotide isolated according to the above process comprises a nucleotide sequence corresponding to the cDNA sequence of SEQ ID NO:93 from nucleotide 367 to nucleotide 747, and extending contiguously from a nucleotide sequence corresponding to the 5' end of said sequence of SEQ ID NO:93 from nucleotide 367 to nucleotide 747, to a nucleotide sequence corresponding to the 3' end of said sequence of SEQ ID NO:93 from nucleotide 367 to nucleotide 747. Also preferably the polynucleotide isolated according to the above process comprises a nucleotide sequence corresponding to the cDNA sequence of SEQ ID NO:93 from nucleotide 667 to nucleotide 747, and extending contiguously from a nucleotide sequence corresponding to the 5' end of said sequence of SEQ ID NO:93 from nucleotide 667 to nucleotide 747, to a nucleotide sequence corresponding to the 3' end of said sequence of SEQ ID NO:93 from nucleotide 667 to nucleotide 747.

In other embodiments, the present invention provides a composition comprising a protein, wherein said protein comprises an amino acid sequence selected from the group consisting of:

(a) the amino acid sequence of SEQ ID NO:94;
(b) a fragment of the amino acid sequence of SEQ ID NO:94, the fragment comprising eight contiguous amino acids of SEQ ID NO:94; and
(c) the amino acid sequence encoded by the cDNA insert of clone ye43_1 deposited under accession number ATCC 98872;

the protein being substantially free from other mammalian proteins. Preferably such protein comprises the amino acid sequence of SEQ ID NO:94. In further preferred embodiments, the present invention provides a protein comprising a fragment of the amino acid sequence of SEQ ID NO:94 having biological activity, the fragment preferably comprising eight (more preferably twenty, most preferably thirty) contiguous amino acids of SEQ ID NO:94, or a protein comprising a fragment of the amino acid sequence of SEQ ID NO:94 having biological activity, the fragment comprising the amino acid sequence from amino acid 58 to amino acid 67 of SEQ ID NO:94.

In one embodiment, the present invention provides a composition comprising an isolated polynucleotide selected from the group consisting of:

(a) a polynucleotide comprising the nucleotide sequence of SEQ ID NO:95;
(b) a polynucleotide comprising the nucleotide sequence of SEQ ID NO:95 from nucleotide 632 to nucleotide 1492;
(c) a polynucleotide comprising the nucleotide sequence of SEQ ID NO:95 from nucleotide 1460 to nucleotide 1492;
(d) a polynucleotide comprising the nucleotide sequence of the full-length protein coding sequence of clone yh71_1 deposited under accession number ATCC 98872;
(e) a polynucleotide encoding the full-length protein encoded by the cDNA insert of clone yh71_1 deposited under accession number ATCC 98872;
(f) a polynucleotide comprising the nucleotide sequence of a mature protein coding sequence of clone yh71_1 deposited under accession number ATCC 98872;
(g) a polynucleotide encoding a mature protein encoded by the cDNA insert of clone yh71_1 deposited under accession number ATCC 98872;

(h) a polynucleotide encoding a protein comprising the amino acid sequence of SEQ ID NO:96;

(i) a polynucleotide encoding a protein comprising a fragment of the amino acid sequence of SEQ ID NO:96 having biological activity, the fragment comprising eight contiguous amino acids of SEQ ID NO:96;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:95.

Preferably, such polynucleotide comprises the nucleotide sequence of SEQ ID NO:95 from nucleotide 632 to nucleotide 1492; the nucleotide sequence of SEQ ID NO:95 from nucleotide 1460 to nucleotide 1492; the nucleotide sequence of the full-length protein coding sequence of clone yh71_1 deposited under accession number ATCC 98872; or the nucleotide sequence of a mature protein coding sequence of clone yh71_1 deposited under accession number ATCC 98872. In other preferred embodiments, the polynucleotide encodes the full-length or a mature protein encoded by the cDNA insert of clone yh71_1 deposited under accession number ATCC 98872. In further preferred embodiments, the present invention provides a polynucleotide encoding a protein comprising a fragment of the amino acid sequence of SEQ ID NO:96 having biological activity, the fragment preferably comprising eight (more preferably twenty, most preferably thirty) contiguous amino acids of SEQ ID NO:96, or a polynucleotide encoding a protein comprising a fragment of the amino acid sequence of SEQ ID NO:96 having biological activity, the fragment comprising the amino acid sequence from amino acid 138 to amino acid 147 of SEQ ID NO:96.

Other embodiments provide the gene corresponding to the cDNA sequence of SEQ ID NO:95.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:95, but excluding the poly(A) tail at the 3' end of SEQ ID NO:95; and
    (ab) the nucleotide sequence of the cDNA insert of clone yh71_1 deposited under accession number ATCC 98872;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:95, but excluding the poly(A) tail at the 3' end of SEQ ID NO:95; and
    (bb) the nucleotide sequence of the cDNA insert of clone yh71_1 deposited under accession number ATCC 98872;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:95, and extending contiguously from a nucleotide sequence corresponding to the 5' end of SEQ ID NO:95 to a nucleotide sequence corresponding to the 3' end of SEQ ID NO:95, but excluding the poly(A) tail at the 3' end of SEQ ID NO:95. Also preferably the polynucleotide isolated according to the above process comprises a nucleotide sequence corresponding to the cDNA sequence of SEQ ID NO:95 from nucleotide 632 to nucleotide 1492, and extending contiguously from a nucleotide sequence corresponding to the 5' end of said sequence of SEQ ID NO:95 from nucleotide 632 to nucleotide 1492, to a nucleotide sequence corresponding to the 3' end of said sequence of SEQ ID NO:95 from nucleotide 632 to nucleotide 1492. Also preferably the polynucleotide isolated according to the above process comprises a nucleotide sequence corresponding to the cDNA sequence of SEQ ID NO:95 from nucleotide 1460 to nucleotide 1492, and extending contiguously from a nucleotide sequence corresponding to the 5' end of said sequence of SEQ ID NO:95 from nucleotide 1460 to nucleotide 1492, to a nucleotide sequence corresponding to the 3' end of said sequence of SEQ ID NO:95 from nucleotide 1460 to nucleotide 1492.

In other embodiments, the present invention provides a composition comprising a protein, wherein said protein comprises an amino acid sequence selected from the group consisting of:

(a) the amino acid sequence of SEQ ID NO:96;

(b) a fragment of the amino acid sequence of SEQ ID NO:96, the fragment comprising eight contiguous amino acids of SEQ ID NO:96; and (c) the amino acid sequence encoded by the cDNA insert of clone yh71_1 deposited under accession number ATCC 98872;

the protein being substantially free from other mammalian proteins. Preferably such protein comprises the amino acid sequence of SEQ ID NO:96. In further preferred embodiments, the present invention provides a protein comprising a fragment of the amino acid sequence of SEQ ID NO:96 having biological activity, the fragment preferably comprising eight (more preferably twenty, most preferably thirty) contiguous amino acids of SEQ ID NO:96, or a protein comprising a fragment of the amino acid sequence of SEQ ID NO:96 having biological activity, the fragment comprising the amino acid sequence from amino acid 138 to amino acid 147 of SEQ ID NO:96.

In one embodiment, the present invention provides a composition comprising an isolated polynucleotide selected from the group consisting of:

(a) a polynucleotide comprising the nucleotide sequence of SEQ ID NO:97;

(b) a polynucleotide comprising the nucleotide sequence of SEQ ID NO:97 from nucleotide 349 to nucleotide 771;

(c) a polynucleotide comprising the nucleotide sequence of SEQ ID NO:97 from nucleotide 490 to nucleotide 771;

(d) a polynucleotide comprising the nucleotide sequence of the full-length protein coding sequence of clone yh100_1 deposited under accession number ATCC 98872;

(e) a polynucleotide encoding the full-length protein encoded by the cDNA insert of clone yh100_1 deposited under accession number ATCC 98872;
(f) a polynucleotide comprising the nucleotide sequence of a mature protein coding sequence of clone yh100_1 deposited under accession number ATCC 98872;
(g) a polynucleotide encoding a mature protein encoded by the cDNA insert of clone yh100_1 deposited under accession number ATCC 98872;
(h) a polynucleotide encoding a protein comprising the amino acid sequence of SEQ ID NO:98;
(i) a polynucleotide encoding a protein comprising a fragment of the amino acid sequence of SEQ ID NO:98 having biological activity, the fragment comprising eight contiguous amino acids of SEQ ID NO:98;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:97.

Preferably, such polynucleotide comprises the nucleotide sequence of SEQ ID NO:97 from nucleotide 349 to nucleotide 771; the nucleotide sequence of SEQ ID NO:97 from nucleotide 490 to nucleotide 771; the nucleotide sequence of the full-length protein coding sequence of clone yh100_1 deposited under accession number ATCC 98872; or the nucleotide sequence of a mature protein coding sequence of clone yh100_1 deposited under accession number ATCC 98872. In other preferred embodiments, the polynucleotide encodes the full-length or a mature protein encoded by the cDNA insert of clone yh100_1 deposited under accession number ATCC 98872. In further preferred embodiments, the present invention provides a polynucleotide encoding a protein comprising a fragment of the amino acid sequence of SEQ ID NO:98 having biological activity, the fragment preferably comprising eight (more preferably twenty, most preferably thirty) contiguous amino acids of SEQ ID NO:98, or a polynucleotide encoding a protein comprising a fragment of the amino acid sequence of SEQ ID NO:98 having biological activity, the fragment comprising the amino acid sequence from amino acid 65 to amino acid 74 of SEQ ID NO:98.

Other embodiments provide the gene corresponding to the cDNA sequence of SEQ ID NO:97.

Further embodiments of the invention provide isolated polynucleotides produced according to a process selected from the group consisting of:
(a) a process comprising the steps of:
 (i) preparing one or more polynucleotide probes that hybridize in 6×SSC at 65 degrees C. to a nucleotide sequence selected from the group consisting of:
  (aa) SEQ ID NO:97, but excluding the poly(A) tail at the 3' end of SEQ ID NO:97; and
  (ab) the nucleotide sequence of the cDNA insert of clone yh100_1 deposited under accession number ATCC 98872;
 (ii) hybridizing said probe(s) to human genomic DNA in conditions at least as stringent as 4×SSC at 50 degrees C.; and
 (iii) isolating the DNA polynucleotides detected with the probe(s);
and
(b) a process comprising the steps of:
 (i) preparing one or more polynucleotide primers that hybridize in 6×SSC at 65 degrees C. to a nucleotide sequence selected from the group consisting of:
  (ba) SEQ ID NO:97, but excluding the poly(A) tail at the 3' end of SEQ ID NO:97; and
  (bb) the nucleotide sequence of the cDNA insert of clone yh100_1 deposited under accession number ATCC 98872;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b) (iii).

Preferably the polynucleotide isolated according to the above process comprises a nucleotide sequence corresponding to the cDNA sequence of SEQ ID NO:97, and extending contiguously from a nucleotide sequence corresponding to the 5' end of SEQ ID NO:97 to a nucleotide sequence corresponding to the 3' end of SEQ ID NO:97, but excluding the poly(A) tail at the 3' end of SEQ ID NO:97. Also preferably the polynucleotide isolated according to the above process comprises a nucleotide sequence corresponding to the cDNA sequence of SEQ ID NO:97 from nucleotide 349 to nucleotide 771, and extending contiguously from a nucleotide sequence corresponding to the 5' end of said sequence of SEQ ID NO:97 from nucleotide 349 to nucleotide 771, to a nucleotide sequence corresponding to the 3' end of said sequence of SEQ ID NO:97 from nucleotide 349 to nucleotide 771. Also preferably the polynucleotide isolated according to the above process comprises a nucleotide sequence corresponding to the cDNA sequence of SEQ ID NO:97 from nucleotide 490 to nucleotide 771, and extending contiguously from a nucleotide sequence corresponding to the 5' end of said sequence of SEQ ID NO:97 from nucleotide 490 to nucleotide 771, to a nucleotide sequence corresponding to the 3' end of said sequence of SEQ ID NO:97 from nucleotide 490 to nucleotide 771.

In other embodiments, the present invention provides a composition comprising a protein, wherein said protein comprises an amino acid sequence selected from the group consisting of:
(a) the amino acid sequence of SEQ ID NO:98;
(b) a fragment of the amino acid sequence of SEQ ID NO:98, the fragment comprising eight contiguous amino acids of SEQ ID NO:98; and
(c) the amino acid sequence encoded by the cDNA insert of clone yh100_1 deposited under accession number ATCC 98872;
the protein being substantially free from other mammalian proteins. Preferably such protein comprises the amino acid sequence of SEQ ID NO:98. In further preferred embodiments, the present invention provides a protein comprising a fragment of the amino acid sequence of SEQ ID NO:98 having biological activity, the fragment preferably comprising eight (more preferably twenty, most preferably thirty) contiguous amino acids of SEQ ID NO:98, or a protein comprising a fragment of the amino acid sequence of SEQ ID NO:98 having biological activity, the fragment comprising the amino acid sequence from amino acid 65 to amino acid 74 of SEQ ID NO:98.

In one embodiment, the present invention provides a composition comprising an isolated polynucleotide selected from the group consisting of:
(a) a polynucleotide comprising the nucleotide sequence of SEQ ID NO:99;

(b) a polynucleotide comprising the nucleotide sequence of SEQ ID NO:99 from nucleotide 165 to nucleotide 416;

(c) a polynucleotide comprising the nucleotide sequence of SEQ ID NO:99 from nucleotide 261 to nucleotide 416;

(d) a polynucleotide comprising the nucleotide sequence of the full-length protein coding sequence of clone yi3_1 deposited under accession number ATCC 98872;

(e) a polynucleotide encoding the full-length protein encoded by the cDNA insert of clone yi3_1 deposited under accession number ATCC 98872;

(f) a polynucleotide comprising the nucleotide sequence of a mature protein coding sequence of clone yi3_1 deposited under accession number ATCC 98872;

(g) a polynucleotide encoding a mature protein encoded by the cDNA insert of clone yi3_1 deposited under accession number ATCC 98872;

(h) a polynucleotide encoding a protein comprising the amino acid sequence of SEQ ID NO:100;

(i) a polynucleotide encoding a protein comprising a fragment of the amino acid sequence of SEQ ID NO:100 having biological activity, the fragment comprising eight contiguous amino acids of SEQ ID NO:100;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:99.

Preferably, such polynucleotide comprises the nucleotide sequence of SEQ ID NO:99 from nucleotide 165 to nucleotide 416; the nucleotide sequence of SEQ ID NO:99 from nucleotide 261 to nucleotide 416; the nucleotide sequence of the full-length protein coding sequence of clone yi3_1 deposited under accession number ATCC 98872; or the nucleotide sequence of a mature protein coding sequence of clone yi3_1 deposited under accession number ATCC 98872. In other preferred embodiments, the polynucleotide encodes the full-length or a mature protein encoded by the cDNA insert of clone yi3_1 deposited under accession number ATCC 98872. In further preferred embodiments, the present invention provides a polynucleotide encoding a protein comprising a fragment of the amino acid sequence of SEQ ID NO:100 having biological activity, the fragment preferably comprising eight (more preferably twenty, most preferably thirty) contiguous amino acids of SEQ ID NO:100, or a polynucleotide encoding a protein comprising a fragment of the amino acid sequence of SEQ ID NO:100 having biological activity, the fragment comprising the amino acid sequence from amino acid 37 to amino acid 46 of SEQ ID NO:100.

Other embodiments provide the gene corresponding to the cDNA sequence of SEQ ID NO:99.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:99, but excluding the poly(A) tail at the 3' end of SEQ ID NO:99; and
(ab) the nucleotide sequence of the cDNA insert of clone yi3_1 deposited under accession number ATCC 98872;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:99, but excluding the poly(A) tail at the 3' end of SEQ ID NO:99; and
(bb) the nucleotide sequence of the cDNA insert of clone yi3_1 deposited under accession number ATCC 98872;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:99, and extending contiguously from a nucleotide sequence corresponding to the 5' end of SEQ ID NO:99 to a nucleotide sequence corresponding to the 3' end of SEQ ID NO:99, but excluding the poly(A) tail at the 3' end of SEQ ID NO:99. Also preferably the polynucleotide isolated according to the above process comprises a nucleotide sequence corresponding to the cDNA sequence of SEQ ID NO:99 from nucleotide 165 to nucleotide 416, and extending contiguously from a nucleotide sequence corresponding to the 5' end of said sequence of SEQ ID NO:99 from nucleotide 165 to nucleotide 416, to a nucleotide sequence corresponding to the 3' end of said sequence of SEQ ID NO:99 from nucleotide 165 to nucleotide 416. Also preferably the polynucleotide isolated according to the above process comprises a nucleotide sequence corresponding to the cDNA sequence of SEQ ID NO:99 from nucleotide 261 to nucleotide 416, and extending contiguously from a nucleotide sequence corresponding to the 5' end of said sequence of SEQ ID NO:99 from nucleotide 261 to nucleotide 416, to a nucleotide sequence corresponding to the 3' end of said sequence of SEQ ID NO:99 from nucleotide 261 to nucleotide 416.

In other embodiments, the present invention provides a composition comprising a protein, wherein said protein comprises an amino acid sequence selected from the group consisting of:

(a) the amino acid sequence of SEQ ID NO:100;
(b) a fragment of the amino acid sequence of SEQ ID NO:100, the fragment comprising eight contiguous amino acids of SEQ ID NO:100; and
(c) the amino acid sequence encoded by the cDNA insert of clone yi3_1 deposited under accession number ATCC 98872;

the protein being substantially free from other mammalian proteins. Preferably such protein comprises the amino acid sequence of SEQ ID NO:100. In further preferred embodiments, the present invention provides a protein comprising a fragment of the amino acid sequence of SEQ ID NO:100 having biological activity, the fragment preferably comprising eight (more preferably twenty, most preferably thirty) contiguous amino acids of SEQ ID NO:100, or a protein comprising a fragment of the amino acid sequence of SEQ ID NO:100 having biological activity, the fragment comprising the amino acid sequence from amino acid 37 to amino acid 46 of SEQ ID NO:100.

In one embodiment, the present invention provides a composition comprising an isolated polynucleotide selected from the group consisting of:

(a) a polynucleotide comprising the nucleotide sequence of SEQ ID NO:101;

(b) a polynucleotide comprising the nucleotide sequence of SEQ ID NO:101 from nucleotide 141 to nucleotide 995;

(c) a polynucleotide comprising the nucleotide sequence of SEQ ID NO:101 from nucleotide 213 to nucleotide 995;

(d) a polynucleotide comprising the nucleotide sequence of the full-length protein coding sequence of clone yj23_1 deposited under accession number ATCC 98872;

(e) a polynucleotide encoding the full-length protein encoded by the cDNA insert of clone yj23_1 deposited under accession number ATCC 98872;

(f) a polynucleotide comprising the nucleotide sequence of a mature protein coding sequence of clone yj23_1 deposited under accession number ATCC 98872;

(g) a polynucleotide encoding a mature protein encoded by the cDNA insert of clone yj23_1 deposited under accession number ATCC 98872;

(h) a polynucleotide encoding a protein comprising the amino acid sequence of SEQ ID NO:102;

(i) a polynucleotide encoding a protein comprising a fragment of the amino acid sequence of SEQ ID NO:102 having biological activity, the fragment comprising eight contiguous amino acids of SEQ ID NO:102;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:101.

Preferably, such polynucleotide comprises the nucleotide sequence of SEQ ID NO:101 from nucleotide 141 to nucleotide 995; the nucleotide sequence of SEQ ID NO:101 from nucleotide 213 to nucleotide 995; the nucleotide sequence of the full-length protein coding sequence of clone yj23_1 deposited under accession number ATCC 98872; or the nucleotide sequence of a mature protein coding sequence of clone yj23_1 deposited under accession number ATCC 98872. In other preferred embodiments, the polynucleotide encodes the full-length or a mature protein encoded by the cDNA insert of clone yj23_1 deposited under accession number ATCC 98872. In further preferred embodiments, the present invention provides a polynucleotide encoding a protein comprising a fragment of the amino acid sequence of SEQ ID NO:102 having biological activity, the fragment preferably comprising eight (more preferably twenty, most preferably thirty) contiguous amino acids of SEQ ID NO:102, or a polynucleotide encoding a protein comprising a fragment of the amino acid sequence of SEQ ID NO:102 having biological activity, the fragment comprising the amino acid sequence from amino acid 137 to amino acid 146 of SEQ ID NO:102.

Other embodiments provide the gene corresponding to the cDNA sequence of SEQ ID NO:101.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:101, but excluding the poly(A) tail at the 3' end of SEQ ID NO:101; and
    (ab) the nucleotide sequence of the cDNA insert of clone yj23_1 deposited under accession number ATCC 98872;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:101, but excluding the poly(A) tail at the 3' end of SEQ ID NO:101; and
    (bb) the nucleotide sequence of the cDNA insert of clone yj23_1 deposited under accession number ATCC 98872;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:101, and extending contiguously from a nucleotide sequence corresponding to the 5' end of SEQ ID NO:101 to a nucleotide sequence corresponding to the 3' end of SEQ ID NO:101, but excluding the poly(A) tail at the 3' end of SEQ ID NO:101. Also preferably the polynucleotide isolated according to the above process comprises a nucleotide sequence corresponding to the cDNA sequence of SEQ ID NO:101 from nucleotide 141 to nucleotide 995, and extending contiguously from a nucleotide sequence corresponding to the 5' end of said sequence of SEQ ID NO:101 from nucleotide 141 to nucleotide 995, to a nucleotide sequence corresponding to the 3' end of said sequence of SEQ ID NO:101 from nucleotide 141 to nucleotide 995. Also preferably the polynucleotide isolated according to the above process comprises a nucleotide sequence corresponding to the cDNA sequence of SEQ ID NO:101 from nucleotide 213 to nucleotide 995, and extending contiguously from a nucleotide sequence corresponding to the 5' end of said sequence of SEQ ID NO:101 from nucleotide 213 to nucleotide 995, to a nucleotide sequence corresponding to the 3' end of said sequence of SEQ ID NO:101 from nucleotide 213 to nucleotide 995.

In other embodiments, the present invention provides a composition comprising a protein, wherein said protein comprises an amino acid sequence selected from the group consisting of:

(a) the amino acid sequence of SEQ ID NO:102;

(b) a fragment of the amino acid sequence of SEQ ID NO:102, the fragment comprising eight contiguous amino acids of SEQ ID NO:102; and (c) the amino acid sequence encoded by the cDNA insert of clone yj23_1 deposited under accession number ATCC 98872;

the protein being substantially free from other mammalian proteins. Preferably such protein comprises the amino acid sequence of SEQ ID NO:102. In further preferred embodiments, the present invention provides a protein comprising a fragment of the amino acid sequence of SEQ ID NO:102 having biological activity, the fragment preferably comprising eight (more preferably twenty, most preferably thirty) contiguous amino acids of SEQ ID NO:102, or a protein comprising a fragment of the amino acid sequence of SEQ ID NO:102 having biological activity, the fragment comprising the amino acid sequence from amino acid 137 to amino acid 146 of SEQ ID NO:102.

In one embodiment, the present invention provides a composition comprising an isolated polynucleotide selected from the group consisting of:

(a) a polynucleotide comprising the nucleotide sequence of SEQ ID NO:103;

(b) a polynucleotide comprising the nucleotide sequence of SEQ ID NO:103 from nucleotide 13 to nucleotide 747;

(c) a polynucleotide comprising the nucleotide sequence of SEQ ID NO:103 from nucleotide 67 to nucleotide 747;

(d) a polynucleotide comprising the nucleotide sequence of the full-length protein coding sequence of clone yl9_1 deposited under accession number ATCC 98872;

(e) a polynucleotide encoding the full-length protein encoded by the cDNA insert of clone yl9_1 deposited under accession number ATCC 98872;

(f) a polynucleotide comprising the nucleotide sequence of a mature protein coding sequence of clone yl9_1 deposited under accession number ATCC 98872;

(g) a polynucleotide encoding a mature protein encoded by the cDNA insert of clone yl9_1 deposited under accession number ATCC 98872;

(h) a polynucleotide encoding a protein comprising the amino acid sequence of SEQ ID NO:104;

(i) a polynucleotide encoding a protein comprising a fragment of the amino acid sequence of SEQ ID NO:104 having biological activity, the fragment comprising eight contiguous amino acids of SEQ ID NO:104;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:103.

Preferably, such polynucleotide comprises the nucleotide sequence of SEQ ID NO:103 from nucleotide 13 to nucleotide 747; the nucleotide sequence of SEQ ID NO:103 from nucleotide 67 to nucleotide 747; the nucleotide sequence of the full-length protein coding sequence of clone yl9_1 deposited under accession number ATCC 98872; or the nucleotide sequence of a mature protein coding sequence of clone yl9_1 deposited under accession number ATCC 98872. In other preferred embodiments, the polynucleotide encodes the full-length or a mature protein encoded by the cDNA insert of clone yl9_1 deposited under accession number ATCC 98872. In further preferred embodiments, the present invention provides a polynucleotide encoding a protein comprising a fragment of the amino acid sequence of SEQ ID NO:104 having biological activity, the fragment preferably comprising eight (more preferably twenty, most preferably thirty) contiguous amino acids of SEQ ID NO:104, or a polynucleotide encoding a protein comprising a fragment of the amino acid sequence of SEQ ID NO:104 having biological activity, the fragment comprising the amino acid sequence from amino acid 117 to amino acid 126 of SEQ ID NO:104.

Other embodiments provide the gene corresponding to the cDNA sequence of SEQ ID NO:103.

Further embodiments of the invention provide isolated polynucleotides produced according to a process selected from the group consisting of:

(a) a process comprising the steps of:
 (i) preparing one or more polynucleotide probes that hybridize in 6×SSC at 65 degrees C. to a nucleotide sequence selected from the group consisting of:
  (aa) SEQ ID NO:103, but excluding the poly(A) tail at the 3' end of SEQ ID NO:103; and
  (ab) the nucleotide sequence of the cDNA insert of clone yl9_1 deposited under accession number ATCC 98872;
 (ii) hybridizing said probe(s) to human genomic DNA in conditions at least as stringent as 4×SSC at 50 degrees C.; and
 (iii) isolating the DNA polynucleotides detected with the probe(s);
and (b) a process comprising the steps of:
 (i) preparing one or more polynucleotide primers that hybridize in 6×SSC at 65 degrees C. to a nucleotide sequence selected from the group consisting of:
  (ba) SEQ ID NO:103, but excluding the poly(A) tail at the 3' end of SEQ ID NO:103; and
  (bb) the nucleotide sequence of the cDNA insert of clone yl9_1 deposited under accession number ATCC 98872;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b) (iii).

Preferably the polynucleotide isolated according to the above process comprises a nucleotide sequence corresponding to the cDNA sequence of SEQ ID NO:103, and extending contiguously from a nucleotide sequence corresponding to the 5' end of SEQ ID NO:103 to a nucleotide sequence corresponding to the 3' end of SEQ ID NO:103, but excluding the poly(A) tail at the 3' end of SEQ ID NO:103. Also preferably the polynucleotide isolated according to the above process comprises a nucleotide sequence corresponding to the cDNA sequence of SEQ ID NO:103 from nucleotide 13 to nucleotide 747, and extending contiguously from a nucleotide sequence corresponding to the 5' end of said sequence of SEQ ID NO:103 from nucleotide 13 to nucleotide 747, to a nucleotide sequence corresponding to the 3' end of said sequence of SEQ ID NO:103 from nucleotide 13 to nucleotide 747. Also preferably the polynucleotide isolated according to the above process comprises a nucleotide sequence corresponding to the cDNA sequence of SEQ ID NO:103 from nucleotide 67 to nucleotide 747, and extending contiguously from a nucleotide sequence corresponding to the 5' end of said sequence of SEQ ID NO:103 from nucleotide 67 to nucleotide 747, to a nucleotide sequence corresponding to the 3' end of said sequence of SEQ ID NO:103 from nucleotide 67 to nucleotide 747.

In other embodiments, the present invention provides a composition comprising a protein, wherein said protein comprises an amino acid sequence selected from the group consisting of:

(a) the amino acid sequence of SEQ ID NO:104;

(b) a fragment of the amino acid sequence of SEQ ID NO:104, the fragment comprising eight contiguous amino acids of SEQ ID NO:104; and (c) the amino acid sequence encoded by the cDNA insert of clone yl9_1 deposited under accession number ATCC 98872;

the protein being substantially free from other mammalian proteins. Preferably such protein comprises the amino acid sequence of SEQ ID NO:104. In further preferred embodiments, the present invention provides a protein comprising a fragment of the amino acid sequence of SEQ ID NO:104 having biological activity, the fragment preferably comprising eight (more preferably twenty, most preferably thirty) contiguous amino acids of SEQ ID NO:104, or a protein comprising a fragment of the amino acid sequence of SEQ ID NO:104 having biological activity, the fragment comprising the amino acid sequence from amino acid 117 to amino acid 126 of SEQ ID NO:104.

In one embodiment, the present invention provides a composition comprising an isolated polynucleotide selected from the group consisting of:

(a) a polynucleotide comprising the nucleotide sequence of SEQ ID NO:105;

(b) a polynucleotide comprising the nucleotide sequence of SEQ ID NO:105 from nucleotide 375 to nucleotide 728;

(c) a polynucleotide comprising the nucleotide sequence of the full-length protein coding sequence of clone ya66_1 deposited under accession number ATCC 98887;

(d) a polynucleotide encoding the full-length protein encoded by the cDNA insert of clone ya66_1 deposited under accession number ATCC 98887;

(e) a polynucleotide comprising the nucleotide sequence of a mature protein coding sequence of clone ya66_1 deposited under accession number ATCC 98887;

(f) a polynucleotide encoding a mature protein encoded by the cDNA insert of clone ya66_1 deposited under accession number ATCC 98887;

(g) a polynucleotide encoding a protein comprising the amino acid sequence of SEQ ID NO:106;

(h) a polynucleotide encoding a protein comprising a fragment of the amino acid sequence of SEQ ID NO:106 having biological activity, the fragment comprising eight contiguous amino acids of SEQ ID NO:106;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:105.

Preferably, such polynucleotide comprises the nucleotide sequence of SEQ ID NO:105 from nucleotide 375 to nucleotide 728; the nucleotide sequence of the full-length protein coding sequence of clone ya66_1 deposited under accession number ATCC 98887; or the nucleotide sequence of a mature protein coding sequence of clone ya66_1 deposited under accession number ATCC 98887. In other preferred embodiments, the polynucleotide encodes the full-length or a mature protein encoded by the cDNA insert of clone ya66_1 deposited under accession number ATCC 98887. In further preferred embodiments, the present invention provides a polynucleotide encoding a protein comprising a fragment of the amino acid sequence of SEQ ID NO:106 having biological activity, the fragment preferably comprising eight (more preferably twenty, most preferably thirty) contiguous amino acids of SEQ ID NO:106, or a polynucleotide encoding a protein comprising a fragment of the amino acid sequence of SEQ ID NO:106 having biological activity, the fragment comprising the amino acid sequence from amino acid 54 to amino acid 63 of SEQ ID NO:106.

Other embodiments provide the gene corresponding to the cDNA sequence of SEQ ID NO:105.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:105, but excluding the poly(A) tail at the 3' end of SEQ ID NO:105; and (ab) the nucleotide sequence of the cDNA insert of clone ya66_1 deposited under accession number ATCC 98887;

(ii) hybridizing said probe(s) to human genomic DNA in conditions at least as stringent as 4×SSC at 50 degrees C.; and (iii) isolating the DNA polynucleotides detected with the probe(s);

and (b) a process comprising the steps of:

(i) preparing one or more polynucleotide primers that hybridize in 6×SSC at 65 degrees C. to a nucleotide sequence selected from the group consisting of:

(ba) SEQ ID NO:105, but excluding the poly(A) tail at the 3' end of SEQ ID NO:105; and (bb) the nucleotide sequence of the cDNA insert of clone ya66_1 deposited under accession number ATCC 98887;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:105, and extending contiguously from a nucleotide sequence corresponding to the 5' end of SEQ ID NO:105 to a nucleotide sequence corresponding to the 3' end of SEQ ID NO:105, but excluding the poly(A) tail at the 3' end of SEQ ID NO:105. Also preferably the polynucleotide isolated according to the above process comprises a nucleotide sequence corresponding to the cDNA sequence of SEQ ID NO:105 from nucleotide 375 to nucleotide 728, and extending contiguously from a nucleotide sequence corresponding to the 5' end of said sequence of SEQ ID NO:105 from nucleotide 375 to nucleotide 728, to a nucleotide sequence corresponding to the 3' end of said sequence of SEQ ID NO:105 from nucleotide 375 to nucleotide 728.

In other embodiments, the present invention provides a composition comprising a protein, wherein said protein comprises an amino acid sequence selected from the group consisting of:

(a) the amino acid sequence of SEQ ID NO:106;
(b) a fragment of the amino acid sequence of SEQ ID NO:106, the fragment comprising eight contiguous amino acids of SEQ ID NO:106; and
(c) the amino acid sequence encoded by the cDNA insert of clone ya66_1 deposited under accession number ATCC 98887;

the protein being substantially free from other mammalian proteins. Preferably such protein comprises the amino acid sequence of SEQ ID NO:106. In further preferred embodiments, the present invention provides a protein comprising a fragment of the amino acid sequence of SEQ ID NO:106 having biological activity, the fragment preferably comprising eight (more preferably twenty, most preferably thirty) contiguous amino acids of SEQ ID NO:106, or a protein comprising a fragment of the amino acid sequence of SEQ ID NO:106 having biological activity, the fragment comprising the amino acid sequence from amino acid 54 to amino acid 63 of SEQ ID NO:106.

In one embodiment, the present invention provides a composition comprising an isolated polynucleotide selected from the group consisting of:

(a) a polynucleotide comprising the nucleotide sequence of SEQ ID NO:107;
(b) a polynucleotide comprising the nucleotide sequence of SEQ ID NO:107 from nucleotide 131 to nucleotide 457;
(c) a polynucleotide comprising the nucleotide sequence of the full-length protein coding sequence of clone yb187_1 deposited under accession number ATCC 98887;
(d) a polynucleotide encoding the full-length protein encoded by the cDNA insert of clone yb187_1 deposited under accession number ATCC 98887;
(e) a polynucleotide comprising the nucleotide sequence of a mature protein coding sequence of clone yb187_1 deposited under accession number ATCC 98887;
(f) a polynucleotide encoding a mature protein encoded by the cDNA insert of clone yb187_1 deposited under accession number ATCC 98887;
(g) a polynucleotide encoding a protein comprising the amino acid sequence of SEQ ID NO:108;
(h) a polynucleotide encoding a protein comprising a fragment of the amino acid sequence of SEQ ID NO:108 having biological activity, the fragment comprising eight contiguous amino acids of SEQ ID NO:108;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:107.

Preferably, such polynucleotide comprises the nucleotide sequence of SEQ ID NO:107 from nucleotide 131 to nucleotide 457; the nucleotide sequence of the full-length protein coding sequence of clone yb187_1 deposited under accession number ATCC 98887; or the nucleotide sequence of a mature protein coding sequence of clone yb187_1 deposited under accession number ATCC 98887. In other preferred embodiments, the polynucleotide encodes the full-length or a mature protein encoded by the cDNA insert of clone yb187_1 deposited under accession number ATCC 98887. In further preferred embodiments, the present invention provides a polynucleotide encoding a protein comprising a fragment of the amino acid sequence of SEQ ID NO:108 having biological activity, the fragment preferably comprising eight (more preferably twenty, most preferably thirty) contiguous amino acids of SEQ ID NO:108, or a polynucleotide encoding a protein comprising a fragment of the amino acid sequence of SEQ ID NO:108 having biological activity, the fragment comprising the amino acid sequence from amino acid 49 to amino acid 58 of SEQ ID NO:108.

Other embodiments provide the gene corresponding to the cDNA sequence of SEQ ID NO:107.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:107, but excluding the poly(A) tail at the 3' end of SEQ ID NO:107; and
(ab) the nucleotide sequence of the cDNA insert of clone yb187_1 deposited under accession number ATCC 98887;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:107, but excluding the poly(A) tail at the 3' end of SEQ ID NO:107; and
(bb) the nucleotide sequence of the cDNA insert of clone yb187_1 deposited under accession number ATCC 98887;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:107, and extending contiguously from a nucleotide sequence corresponding to the 5' end of SEQ ID NO:107 to a nucleotide sequence corresponding to the 3' end of SEQ ID NO:107, but excluding the poly(A) tail at the 3' end of SEQ ID NO:107. Also preferably the polynucleotide isolated according to the above process comprises a nucleotide sequence corresponding to the cDNA sequence of SEQ ID NO:107 from nucleotide 131 to nucleotide 457, and extending contiguously from a nucleotide sequence corresponding to the 5' end of said sequence of SEQ ID NO:107 from nucleotide 131 to nucleotide 457, to a nucleotide sequence corresponding to the 3' end of said sequence of SEQ ID NO:107 from nucleotide 131 to nucleotide 457.

In other embodiments, the present invention provides a composition comprising a protein, wherein said protein comprises an amino acid sequence selected from the group consisting of:

(a) the amino acid sequence of SEQ ID NO:108;

(b) a fragment of the amino acid sequence of SEQ ID NO:108, the fragment comprising eight contiguous amino acids of SEQ ID NO:108; and (c) the amino acid sequence encoded by the cDNA insert of clone yb187_1 deposited under accession number ATCC 98887;

the protein being substantially free from other mammalian proteins. Preferably such protein comprises the amino acid sequence of SEQ ID NO:108. In further preferred embodiments, the present invention provides a protein comprising a fragment of the amino acid sequence of SEQ ID NO:108 having biological activity, the fragment preferably comprising eight (more preferably twenty, most preferably thirty) contiguous amino acids of SEQ ID NO:108, or a protein comprising a fragment of the amino acid sequence of SEQ ID NO:108 having biological activity, the fragment comprising the amino acid sequence from amino acid 49 to amino acid 58 of SEQ ID NO:108.

In one embodiment, the present invention provides a composition comprising an isolated polynucleotide selected from the group consisting of:

(a) a polynucleotide comprising the nucleotide sequence of SEQ ID NO:109;

(b) a polynucleotide comprising the nucleotide sequence of SEQ ID NO:109 from nucleotide 458 to nucleotide 676;

(c) a polynucleotide comprising the nucleotide sequence of SEQ ID NO:109 from nucleotide 503 to nucleotide 676;

(d) a polynucleotide comprising the nucleotide sequence of the full-length protein coding sequence of clone yb219_1 deposited under accession number ATCC 98887;

(e) a polynucleotide encoding the full-length protein encoded by the cDNA insert of clone yb219_1 deposited under accession number ATCC 98887;

(f) a polynucleotide comprising the nucleotide sequence of a mature protein coding sequence of clone yb219_1 deposited under accession number ATCC 98887;

(g) a polynucleotide encoding a mature protein encoded by the cDNA insert of clone yb219_1 deposited under accession number ATCC 98887;

(h) a polynucleotide encoding a protein comprising the amino acid sequence of SEQ ID NO:110;

(i) a polynucleotide encoding a protein comprising a fragment of the amino acid sequence of SEQ ID NO:110 having biological activity, the fragment comprising eight contiguous amino acids of SEQ ID NO:110;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:109.

Preferably, such polynucleotide comprises the nucleotide sequence of SEQ ID NO:109 from nucleotide 458 to nucleotide 676; the nucleotide sequence of SEQ ID NO:109 from nucleotide 503 to nucleotide 676; the nucleotide sequence of the full-length protein coding sequence of clone yb219_1 deposited under accession number ATCC 98887; or the nucleotide sequence of a mature protein coding sequence of clone yb219_1 deposited under accession number ATCC 98887. In other preferred embodiments, the polynucleotide encodes the full-length or a mature protein encoded by the cDNA insert of clone yb219_1 deposited under accession number ATCC 98887. In further preferred embodiments, the present invention provides a polynucleotide encoding a protein comprising a fragment of the amino acid sequence of SEQ ID NO:110 having biological activity, the fragment preferably comprising eight (more preferably twenty, most preferably thirty) contiguous amino acids of SEQ ID NO:110, or a polynucleotide encoding a protein comprising a fragment of the amino acid sequence of SEQ ID NO:110 having biological activity, the fragment comprising the amino acid sequence from amino acid 31 to amino acid 40 of SEQ ID NO:110.

Other embodiments provide the gene corresponding to the cDNA sequence of SEQ ID NO:109.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:109, but excluding the poly(A) tail at the 3' end of SEQ ID NO:109; and
    (ab) the nucleotide sequence of the cDNA insert of clone yb219_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:109, but excluding the poly(A) tail at the 3' end of SEQ ID NO:109; and
    (bb) the nucleotide sequence of the cDNA insert of clone yb219_1 deposited under accession number ATCC 98887;

(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:109, and extending contiguously from a nucleotide sequence corresponding to the 5' end of SEQ ID NO:109 to a nucleotide sequence corresponding to the 3' end of SEQ ID NO:109, but excluding the poly(A) tail at the 3' end of SEQ ID NO:109. Also preferably the polynucleotide isolated according to the above process comprises a nucleotide sequence corresponding to the cDNA sequence of SEQ ID NO:109 from nucleotide 458 to nucleotide 676, and extending contiguously from a nucleotide sequence corresponding to the 5' end of said sequence of SEQ ID NO:109 from nucleotide 458 to nucleotide 676, to a nucleotide sequence corresponding to the 3' end of said sequence of SEQ ID NO:109 from nucleotide 458 to nucleotide 676. Also preferably the polynucleotide isolated according to the above process comprises a nucleotide sequence corresponding to the cDNA sequence of SEQ ID NO:109 from nucleotide 503 to nucleotide 676, and extending contiguously from a nucleotide sequence corresponding to the 5' end of said sequence of SEQ ID NO:109 from nucleotide 503 to nucleotide 676, to a nucleotide sequence corresponding to the 3' end of said sequence of SEQ ID NO:109 from nucleotide 503 to nucleotide 676.

In other embodiments, the present invention provides a composition comprising a protein, wherein said protein comprises an amino acid sequence selected from the group consisting of:
(a) the amino acid sequence of SEQ ID NO:110;
(b) a fragment of the amino acid sequence of SEQ ID NO:110, the fragment comprising eight contiguous amino acids of SEQ ID NO:110; and
(c) the amino acid sequence encoded by the cDNA insert of clone yb219_1 deposited under accession number ATCC 98887;
the protein being substantially free from other mammalian proteins. Preferably such protein comprises the amino acid sequence of SEQ ID NO:110. In further preferred embodiments, the present invention provides a protein comprising a fragment of the amino acid sequence of SEQ ID NO:110 having biological activity, the fragment preferably comprising eight (more preferably twenty, most preferably thirty) contiguous amino acids of SEQ ID NO:110, or a protein comprising a fragment of the amino acid sequence of SEQ ID NO:110 having biological activity, the fragment comprising the amino acid sequence from amino acid 31 to amino acid 40 of SEQ ID NO:110.

In one embodiment, the present invention provides a composition comprising an isolated polynucleotide selected from the group consisting of:
(a) a polynucleotide comprising the nucleotide sequence of SEQ ID NO:111;
(b) a polynucleotide comprising the nucleotide sequence of SEQ ID NO:111 from nucleotide 238 to nucleotide 396;
(c) a polynucleotide comprising the nucleotide sequence of SEQ ID NO:111 from nucleotide 277 to nucleotide 396;
(d) a polynucleotide comprising the nucleotide sequence of the full-length protein coding sequence of clone yb228_1 deposited under accession number ATCC 98887;
(e) a polynucleotide encoding the full-length protein encoded by the cDNA insert of clone yb228_1 deposited under accession number ATCC 98887;
(f) a polynucleotide comprising the nucleotide sequence of a mature protein coding sequence of clone yb228_1 deposited under accession number ATCC 98887;
(g) a polynucleotide encoding a mature protein encoded by the cDNA insert of clone yb228_1 deposited under accession number ATCC 98887;
(h) a polynucleotide encoding a protein comprising the amino acid sequence of SEQ ID NO:112;
(i) a polynucleotide encoding a protein comprising a fragment of the amino acid sequence of SEQ ID NO:112 having biological activity, the fragment comprising eight contiguous amino acids of SEQ ID NO:112;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:111.

Preferably, such polynucleotide comprises the nucleotide sequence of SEQ ID NO:111 from nucleotide 238 to nucleotide 396; the nucleotide sequence of SEQ ID NO:111 from nucleotide 277 to nucleotide 396; the nucleotide sequence of the full-length protein coding sequence of clone yb228_1 deposited under accession number ATCC 98887; or the nucleotide sequence of a mature protein coding sequence of clone yb228_1 deposited under accession number ATCC 98887. In other preferred embodiments, the polynucleotide encodes the full-length or a mature protein encoded by the cDNA insert of clone yb228_1 deposited under accession number ATCC 98887. In further preferred embodiments, the present invention provides a polynucleotide encoding a protein comprising a fragment of the amino acid sequence of SEQ ID NO:112 having biological activity, the fragment preferably comprising eight (more preferably twenty, most preferably thirty) contiguous amino acids of SEQ ID NO:112, or a polynucleotide encoding a protein comprising a fragment of the amino acid sequence of SEQ ID NO:112 having biological activity, the fragment comprising the amino acid sequence from amino acid 21 to amino acid 30 of SEQ ID NO:112.

Other embodiments provide the gene corresponding to the cDNA sequence of SEQ ID NO:111.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:111, but excluding the poly(A) tail at the 3' end of SEQ ID NO:111; and
(ab) the nucleotide sequence of the cDNA insert of clone yb228_1 deposited under accession number ATCC 98887;
(ii) hybridizing said probe(s) to human genomic DNA in conditions at least as stringent as 4×SSC at 50 degrees C.; and (iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:111, but excluding the poly(A) tail at the 3' end of SEQ ID NO:111; and
(bb) the nucleotide sequence of the cDNA insert of clone yb228_1 deposited under accession number ATCC 98887;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:111, and extending contiguously from a nucleotide sequence corresponding to the 5' end of SEQ ID NO:111 to a nucleotide sequence corresponding to the 3' end of SEQ ID NO:111, but excluding the poly(A) tail at the 3' end of SEQ ID NO:111. Also preferably the polynucleotide isolated according to the above process comprises a nucleotide sequence corresponding to the cDNA sequence of SEQ ID NO:111 from nucleotide 238 to nucleotide 396, and extending contiguously from a nucleotide sequence corresponding to the 5' end of said sequence of SEQ ID NO:111 from nucleotide 238 to nucleotide 396, to a nucleotide sequence corresponding to the 3' end of said sequence of SEQ ID NO:111 from nucleotide 238 to nucleotide 396. Also preferably the polynucleotide isolated according to the above process comprises a nucleotide sequence corresponding to the cDNA sequence of SEQ ID NO:111 from nucleotide 277 to nucleotide 396, and extending contiguously from a nucleotide sequence corresponding to the 5' end of said sequence of SEQ ID NO:111 from nucleotide 277 to nucleotide 396, to a nucleotide sequence corresponding to the 3' end of said sequence of SEQ ID NO:111 from nucleotide 277 to nucleotide 396.

In other embodiments, the present invention provides a composition comprising a protein, wherein said protein comprises an amino acid sequence selected from the group consisting of:
(a) the amino acid sequence of SEQ ID NO:112;
(b) a fragment of the amino acid sequence of SEQ ID NO:112, the fragment comprising eight contiguous amino acids of SEQ ID NO:112; and
(c) the amino acid sequence encoded by the cDNA insert of clone yb228_1 deposited under accession number ATCC 98887;
the protein being substantially free from other mammalian proteins. Preferably such protein comprises the amino acid sequence of SEQ ID NO:112. In further preferred embodiments, the present invention provides a protein comprising a fragment of the amino acid sequence of SEQ ID NO:112 having biological activity, the fragment preferably comprising eight (more preferably twenty, most preferably thirty) contiguous amino acids of SEQ ID NO:112, or a protein comprising a fragment of the amino acid sequence of SEQ ID NO:112 having biological activity, the fragment comprising the amino acid sequence from amino acid 21 to amino acid 30 of SEQ ID NO:112.

In one embodiment, the present invention provides a composition comprising an isolated polynucleotide selected from the group consisting of:

(a) a polynucleotide comprising the nucleotide sequence of SEQ ID NO:113;
(b) a polynucleotide comprising the nucleotide sequence of SEQ ID NO:113 from nucleotide 6 to nucleotide 722;
(c) a polynucleotide comprising the nucleotide sequence of SEQ ID NO:113 from nucleotide 375 to nucleotide 722;
(d) a polynucleotide comprising the nucleotide sequence of the full-length protein coding sequence of clone yc27_1 deposited under accession number ATCC 98887;
(e) a polynucleotide encoding the full-length protein encoded by the cDNA insert of clone yc27_1 deposited under accession number ATCC 98887;
(f) a polynucleotide comprising the nucleotide sequence of a mature protein coding sequence of clone yc27_1 deposited under accession number ATCC 98887;
(g) a polynucleotide encoding a mature protein encoded by the cDNA insert of clone yc27_1 deposited under accession number ATCC 98887;
(h) a polynucleotide encoding a protein comprising the amino acid sequence of SEQ ID NO:114;
(i) a polynucleotide encoding a protein comprising a fragment of the amino acid sequence of SEQ ID NO:114 having biological activity, the fragment comprising eight contiguous amino acids of SEQ ID NO:114;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:113.

Preferably, such polynucleotide comprises the nucleotide sequence of SEQ ID NO:113 from nucleotide 6 to nucleotide 722; the nucleotide sequence of SEQ ID NO:113 from nucleotide 375 to nucleotide 722; the nucleotide sequence of the full-length protein coding sequence of clone yc27_1 deposited under accession number ATCC 98887; or the nucleotide sequence of a mature protein coding sequence of clone yc27_1 deposited under accession number ATCC 98887. In other preferred embodiments, the polynucleotide encodes the full-length or a mature protein encoded by the cDNA insert of clone yc27_1 deposited under accession number ATCC 98887. In further preferred embodiments, the present invention provides a polynucleotide encoding a protein comprising a fragment of the amino acid sequence of SEQ ID NO:114 having biological activity, the fragment preferably comprising eight (more preferably twenty, most preferably thirty) contiguous amino acids of SEQ ID NO:114, or a polynucleotide encoding a protein comprising a fragment of the amino acid sequence of SEQ ID NO:114 having biological activity, the fragment comprising the amino acid sequence from amino acid 114 to amino acid 123 of SEQ ID NO:114.

Other embodiments provide the gene corresponding to the cDNA sequence of SEQ ID NO:113.

Further embodiments of the invention provide isolated polynucleotides produced according to a process selected from the group consisting of:

(a) a process comprising the steps of:
   (i) preparing one or more polynucleotide probes that hybridize in 6×SSC at 65 degrees C. to a nucleotide sequence selected from the group consisting of:
      (aa) SEQ ID NO:113, but excluding the poly(A) tail at the 3' end of SEQ ID NO:113; and
      (ab) the nucleotide sequence of the cDNA insert of clone yc27_1 deposited under accession number ATCC 98887;
   (ii) hybridizing said probe(s) to human genomic DNA in conditions at least as stringent as 4×SSC at 50 degrees C.; and
   (iii) isolating the DNA polynucleotides detected with the probe(s);
and
(b) a process comprising the steps of:
   (i) preparing one or more polynucleotide primers that hybridize in 6×SSC at 65 degrees C. to a nucleotide sequence selected from the group consisting of:
      (ba) SEQ ID NO:113, but excluding the poly(A) tail at the 3' end of SEQ ID NO:113; and
      (bb) the nucleotide sequence of the cDNA insert of clone yc27_1 deposited under accession number ATCC 98887;
   (ii) hybridizing said primer(s) to human genomic DNA in conditions at least as stringent as 4×SSC at 50 degrees C.;
   (iii) amplifying human DNA sequences; and
   (iv) isolating the polynucleotide products of step (b)(iii).

Preferably the polynucleotide isolated according to the above process comprises a nucleotide sequence corresponding to the cDNA sequence of SEQ ID NO:113, and extending contiguously from a nucleotide sequence corresponding to the 5' end of SEQ ID NO:113 to a nucleotide sequence corresponding to the 3' end of SEQ ID NO:113, but excluding the poly(A) tail at the 3' end of SEQ ID NO:113. Also preferably the polynucleotide isolated according to the above process comprises a nucleotide sequence corresponding to the cDNA sequence of SEQ ID NO:113 from nucleotide 6 to nucleotide. 722, and extending contiguously from a nucleotide sequence corresponding to the 5' end of said sequence of SEQ ID NO:113 from nucleotide 6 to nucleotide 722, to a nucleotide sequence corresponding to the 3' end of said sequence of SEQ ID NO:113 from nucleotide 6 to nucleotide 722. Also preferably the polynucleotide isolated according to the above process comprises a nucleotide sequence corresponding to the cDNA sequence of SEQ ID NO:113 from nucleotide 375 to nucleotide 722, and extending contiguously from a nucleotide sequence corresponding to the 5' end of said sequence of SEQ ID NO:113 from nucleotide 375 to nucleotide 722, to a nucleotide sequence corresponding to the 3' end of said sequence of SEQ ID NO:113 from nucleotide 375 to nucleotide 722.

In other embodiments, the present invention provides a composition comprising a protein, wherein said protein comprises an amino acid sequence selected from the group consisting of:
   (a) the amino acid sequence of SEQ ID NO:114;
   (b) a fragment of the amino acid sequence of SEQ ID NO:114, the fragment comprising eight contiguous amino acids of SEQ ID NO:114; and
   (c) the amino acid sequence encoded by the cDNA insert of clone yc27_1 deposited under accession number ATCC 98887;
the protein being substantially free from other mammalian proteins. Preferably such protein comprises the amino acid sequence of SEQ ID NO:114. In further preferred embodiments, the present invention provides a protein comprising a fragment of the amino acid sequence of SEQ ID NO:114 having biological activity, the fragment preferably comprising eight (more preferably twenty, most preferably thirty) contiguous amino acids of SEQ ID NO:114, or a protein comprising a fragment of the amino acid sequence of SEQ ID NO:114 having biological activity, the fragment comprising the amino acid sequence from amino acid 114 to amino acid 123 of SEQ ID NO:114.

In one embodiment, the present invention provides a composition comprising an isolated polynucleotide selected from the group consisting of:
   (a) a polynucleotide comprising the nucleotide sequence of SEQ ID NO:115;
   (b) a polynucleotide comprising the nucleotide sequence of SEQ ID NO:115 from nucleotide 382 to nucleotide 681;
   (c) a polynucleotide comprising the nucleotide sequence of the full-length protein coding sequence of clone yc49_1 deposited under accession number ATCC 98887;
   (d) a polynucleotide encoding the full-length protein encoded by the cDNA insert of clone yc49_1 deposited under accession number ATCC 98887;
   (e) a polynucleotide comprising the nucleotide sequence of a mature protein coding sequence of clone yc49_1 deposited under accession number ATCC 98887;
   (f) a polynucleotide encoding a mature protein encoded by the cDNA insert of clone yc49_1 deposited under accession number ATCC 98887;
   (g) a polynucleotide encoding a protein comprising the amino acid sequence of SEQ ID NO:116;
   (h) a polynucleotide encoding a protein comprising a fragment of the amino acid sequence of SEQ ID NO:116 having biological activity, the fragment comprising eight contiguous amino acids of SEQ ID NO:116;
   (i) a polynucleotide which is an allelic variant of a polynucleotide of (a)–(f) above;
   (j) a polynucleotide which encodes a species homologue of the protein of (g) or (h) above;
   (k) a polynucleotide that hybridizes under stringent conditions to any one of the polynucleotides specified in (a)–(h); and
   (l) a polynucleotide that hybridizes under stringent conditions to any one of the polynucleotides specified in (a)–(h) and that has a length that is at least 25% of the length of SEQ ID NO:115.

Preferably, such polynucleotide comprises the nucleotide sequence of SEQ ID NO:115 from nucleotide 382 to nucleotide 681; the nucleotide sequence of the full-length protein coding sequence of clone yc49_1 deposited under accession number ATCC 98887; or the nucleotide sequence of a mature protein coding sequence of clone yc49_1 deposited under accession number ATCC 98887. In other preferred embodiments, the polynucleotide encodes the full-length or a mature protein encoded by the cDNA insert of clone yc49_1 deposited under accession number ATCC 98887. In further preferred embodiments, the present invention provides a polynucleotide encoding a protein comprising a fragment of the amino acid sequence of SEQ ID NO:116 having biological activity, the fragment preferably comprising eight (more preferably twenty, most preferably thirty) contiguous amino acids of SEQ ID NO:116, or a polynucleotide encoding a protein comprising a fragment of the amino acid sequence of SEQ ID NO:116 having biological activity, the fragment comprising the amino acid sequence from amino acid 45 to amino acid 54 of SEQ ID NO:116.

Other embodiments provide the gene corresponding to the cDNA sequence of SEQ ID NO:115.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:115, but excluding the poly(A) tail at the 3' end of SEQ ID NO:115; and
    (ab) the nucleotide sequence of the cDNA insert of clone yc49_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO: 15, but excluding the poly(A) tail at the 3' end of SEQ ID NO:115; and
    (bb) the nucleotide sequence of the cDNA insert of clone yc49_1 deposited under accession number ATCC 98887;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:115, and extending contiguously from a nucleotide sequence corresponding to the 5' end of SEQ ID NO:115 to a nucleotide sequence corresponding to the 3' end of SEQ ID NO:115, but excluding the poly(A) tail at the 3' end of SEQ ID NO:115. Also preferably the polynucleotide isolated according to the above process comprises a nucleotide sequence corresponding to the cDNA sequence of SEQ ID NO:115 from nucleotide 382 to nucleotide 681, and extending contiguously from a nucleotide sequence corresponding to the 5' end of said sequence of SEQ ID NO:115 from nucleotide 382 to nucleotide 681, to a nucleotide sequence corresponding to the 3' end of said sequence of SEQ ID NO:115 from nucleotide 382 to nucleotide 681.

In other embodiments, the present invention provides a composition comprising a protein, wherein said protein comprises an amino acid sequence selected from the group consisting of:

(a) the amino acid sequence of SEQ ID NO:116;
(b) a fragment of the amino acid sequence of SEQ ID NO:116, the fragment comprising eight contiguous amino acids of SEQ ID NO:116; and
(c) the amino acid sequence encoded by the cDNA insert of clone yc49_1 deposited under accession number ATCC 98887;

the protein being substantially free from other mammalian proteins. Preferably such protein comprises the amino acid sequence of SEQ ID NO:116. In further preferred embodiments, the present invention provides a protein comprising a fragment of the amino acid sequence of SEQ ID NO:116 having biological activity, the fragment preferably comprising eight (more preferably twenty, most preferably thirty) contiguous amino acids of SEQ ID NO:116, or a protein comprising a fragment of the amino acid sequence of SEQ ID NO:116 having biological activity, the fragment comprising the amino acid sequence from amino acid 45 to amino acid 54 of SEQ ID NO:116.

In one embodiment, the present invention provides a composition comprising an isolated polynucleotide selected from the group consisting of:

(a) a polynucleotide comprising the nucleotide sequence of SEQ ID NO:117;
(b) a polynucleotide comprising the nucleotide sequence of SEQ ID NO:117 from nucleotide 71 to nucleotide 364;
(c) a polynucleotide comprising the nucleotide sequence of the full-length protein coding sequence of clone yd40_1 deposited under accession number ATCC 98887;
(d) a polynucleotide encoding the full-length protein encoded by the cDNA insert of clone yd40_1 deposited under accession number ATCC 98887;
(e) a polynucleotide comprising the nucleotide sequence of a mature protein coding sequence of clone yd40_1 deposited under accession number ATCC 98887;
(f) a polynucleotide encoding a mature protein encoded by the cDNA insert of clone yd40_1 deposited under accession number ATCC 98887;
(g) a polynucleotide encoding a protein comprising the amino acid sequence of SEQ ID NO:118;
(h) a polynucleotide encoding a protein comprising a fragment of the amino acid sequence of SEQ ID NO:118 having biological activity, the fragment comprising eight contiguous amino acids of SEQ ID NO:118;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:117.

Preferably, such polynucleotide comprises the nucleotide sequence of SEQ ID NO:117 from nucleotide 71 to nucleotide 364; the nucleotide sequence of the full-length protein coding sequence of clone yd40_1 deposited under accession number ATCC 98887; or the nucleotide sequence of a mature protein coding sequence of clone yd40_1 deposited under accession number ATCC 98887. In other preferred embodiments, the polynucleotide encodes the full-length or a mature protein encoded by the cDNA insert of clone yd40_1 deposited under accession number ATCC 98887. In further preferred embodiments, the present invention provides a polynucleotide encoding a protein comprising a fragment of the amino acid sequence of SEQ ID NO:118 having biological activity, the fragment preferably comprising eight (more preferably twenty, most preferably thirty) contiguous amino acids of SEQ ID NO:118, or a polynucleotide encoding a protein comprising a fragment of the amino acid sequence of SEQ ID NO:118 having biological activity, the fragment comprising the amino acid sequence from amino acid 44 to amino acid 53 of SEQ ID NO:118.

Other embodiments provide the gene corresponding to the cDNA sequence of SEQ ID NO:117.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:117, but excluding the poly(A) tail at the 3' end of SEQ ID NO:117; and
(ab) the nucleotide sequence of the cDNA insert of clone yd40_1 deposited under accession number ATCC 98887;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:117, but excluding the poly(A) tail at the 3' end of SEQ ID NO:117; and
(bb) the nucleotide sequence of the cDNA insert of clone yd40_1 deposited under accession number ATCC 98887;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:117, and extending contiguously from a nucleotide sequence corresponding to the 5' end of SEQ ID NO:117 to a nucleotide sequence corresponding to the 3' end of SEQ ID NO:117, but excluding the poly(A) tail at the 3' end of SEQ ID NO:117. Also preferably the polynucleotide isolated according to the above process comprises a nucleotide sequence corresponding to the cDNA sequence of SEQ ID NO:117 from nucleotide 71 to nucleotide 364, and extending contiguously from a nucleotide sequence corresponding to the 5' end of said sequence of SEQ ID NO:117 from nucleotide 71 to nucleotide 364, to a nucleotide sequence corresponding to the 3' end of said sequence of SEQ ID NO:117 from nucleotide 71 to nucleotide 364.

In other embodiments, the present invention provides a composition comprising a protein, wherein said protein comprises an amino acid sequence selected from the group consisting of:

(a) the amino acid sequence of SEQ ID NO:118;
(b) a fragment of the amino acid sequence of SEQ ID NO:118, the fragment comprising eight contiguous amino acids of SEQ ID NO:118; and
(c) the amino acid sequence encoded by the cDNA insert of clone yd40_1 deposited under accession number ATCC 98887;

the protein being substantially free from other mammalian proteins. Preferably such protein comprises the amino acid sequence of SEQ ID NO:118. In further preferred embodiments, the present invention provides a protein comprising a fragment of the amino acid sequence of SEQ ID NO:118 having biological activity, the fragment preferably comprising eight (more preferably twenty, most preferably thirty) contiguous amino acids of SEQ ID NO:118, or a protein comprising a fragment of the amino acid sequence of SEQ ID NO:118 having biological activity, the fragment comprising the amino acid sequence from amino acid 44 to amino acid 53 of SEQ ID NO:118.

In one embodiment, the present invention provides a composition comprising an isolated polynucleotide selected from the group consisting of:

(a) a polynucleotide comprising the nucleotide sequence of SEQ ID NO:119;
(b) a polynucleotide comprising the nucleotide sequence of SEQ ID NO:119 from nucleotide 75 to nucleotide 725;
(c) a polynucleotide comprising the nucleotide sequence of the full-length protein coding sequence of clone yd64_1 deposited under accession number ATCC 98887;
(d) a polynucleotide encoding the full-length protein encoded by the cDNA insert of clone yd64_1 deposited under accession number ATCC 98887;
(e) a polynucleotide comprising the nucleotide sequence of a mature protein coding sequence of clone yd64_1 deposited under accession number ATCC 98887;
(f) a polynucleotide encoding a mature protein encoded by the cDNA insert of clone yd64_1 deposited under accession number ATCC 98887;
(g) a polynucleotide encoding a protein comprising the amino acid sequence of SEQ ID NO:120;
(h) a polynucleotide encoding a protein comprising a fragment of the amino acid sequence of SEQ ID NO:120 having biological activity, the fragment comprising eight contiguous amino acids of SEQ ID NO:120;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:119.

Preferably, such polynucleotide comprises the nucleotide sequence of SEQ ID NO:119 from nucleotide 75 to nucleotide 725; the nucleotide sequence of the full-length protein coding sequence of clone yd64_1 deposited under accession number ATCC 98887; or the nucleotide sequence of a mature protein coding sequence of clone yd64_1 deposited under accession number ATCC 98887. In other preferred embodiments, the polynucleotide encodes the full-length or a mature protein encoded by the cDNA insert of clone yd64_1 deposited under accession number ATCC 98887. In further preferred embodiments, the present invention provides a polynucleotide encoding a protein comprising a fragment of the amino acid sequence of SEQ ID NO:120 having biological activity, the fragment preferably comprising eight (more preferably twenty, most preferably thirty) contiguous amino acids of SEQ ID NO:120, or a polynucleotide encoding a protein comprising a fragment of the amino acid sequence of SEQ ID NO:120 having biological activity, the fragment comprising the amino acid sequence from amino acid 103 to amino acid 112 of SEQ ID NO:120.

Other embodiments provide the gene corresponding to the cDNA sequence of SEQ ID NO:119.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:119, but excluding the poly(A) tail at the 3' end of SEQ ID NO:119; and
    (ab) the nucleotide sequence of the cDNA insert of clone yd64_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:119, but excluding the poly(A) tail at the 3' end of SEQ ID NO:119; and
    (bb) the nucleotide sequence of the cDNA insert of clone yd64_1 deposited under accession number ATCC 98887;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:119, and extending contiguously from a nucleotide sequence corresponding to the 5' end of SEQ ID NO:119 to a nucleotide sequence corresponding to the 3' end of SEQ ID NO:119, but excluding the poly(A) tail at the 3' end of SEQ ID NO:119. Also preferably the polynucleotide isolated according to the above process comprises a nucleotide sequence corresponding to the cDNA sequence of SEQ ID NO:119 from nucleotide 75 to nucleotide 725, and extending contiguously from a nucleotide sequence corresponding to the 5' end of said sequence of SEQ ID NO:119 from nucleotide 75 to nucleotide 725, to a nucleotide sequence corresponding to the 3' end of said sequence of SEQ ID NO:119 from nucleotide 75 to nucleotide 725.

In other embodiments, the present invention provides a composition comprising a protein, wherein said protein comprises an amino acid sequence selected from the group consisting of:

(a) the amino acid sequence of SEQ ID NO:120;
(b) a fragment of the amino acid sequence of SEQ ID NO:120, the fragment comprising eight contiguous amino acids of SEQ ID NO:120; and
(c) the amino acid sequence encoded by the cDNA insert of clone yd64_1 deposited under accession number ATCC 98887;

the protein being substantially free from other mammalian proteins. Preferably such protein comprises the amino acid sequence of SEQ ID NO:120. In further preferred embodiments, the present invention provides a protein comprising a fragment of the amino acid sequence of SEQ ID NO:120 having biological activity, the fragment preferably comprising eight (more preferably twenty, most preferably thirty) contiguous amino acids of SEQ ID NO:120, or a protein comprising a fragment of the amino acid sequence of SEQ ID NO:120 having biological activity, the fragment comprising the amino acid sequence from amino acid 103 to amino acid 112 of SEQ ID NO:120.

In one embodiment, the present invention provides a composition comprising an isolated polynucleotide selected from the group consisting of:

(a) a polynucleotide comprising the nucleotide sequence of SEQ ID NO:121;
(b) a polynucleotide comprising the nucleotide sequence of SEQ ID NO:121 from nucleotide 256 to nucleotide 780;
(c) a polynucleotide comprising the nucleotide sequence of SEQ ID NO:121 from nucleotide 412 to nucleotide 780;
(d) a polynucleotide comprising the nucleotide sequence of the full-length protein coding sequence of clone ye47_1 deposited under accession number ATCC 98887;
(e) a polynucleotide encoding the full-length protein encoded by the cDNA insert of clone ye47_1 deposited under accession number ATCC 98887;
(f) a polynucleotide comprising the nucleotide sequence of a mature protein coding sequence of clone ye47_1 deposited under accession number ATCC 98887;
(g) a polynucleotide encoding a mature protein encoded by the cDNA insert of clone ye47_1 deposited under accession number ATCC 98887;
(h) a polynucleotide encoding a protein comprising the amino acid sequence of SEQ ID NO:122;
(i) a polynucleotide encoding a protein comprising a fragment of the amino acid sequence of SEQ ID NO:122 having biological activity, the fragment comprising eight contiguous amino acids of SEQ ID NO:122;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:121.

Preferably, such polynucleotide comprises the nucleotide sequence of SEQ ID NO:121 from nucleotide 256 to nucleotide 780; the nucleotide sequence of SEQ ID NO:121 from nucleotide 412 to nucleotide 780; the nucleotide sequence of the full-length protein coding sequence of clone ye47_1 deposited under accession number ATCC 98887; or the nucleotide sequence of a mature protein coding sequence of clone ye47_1 deposited under accession number ATCC 98887. In other preferred embodiments, the polynucleotide encodes the full-length or a mature protein encoded by the cDNA insert of clone ye47_1 deposited under accession number ATCC 98887. In further preferred embodiments, the present invention provides a polynucleotide encoding a protein comprising a fragment of the amino acid sequence of SEQ ID NO:122 having biological activity, the fragment preferably comprising eight (more preferably twenty, most preferably thirty) contiguous amino acids of SEQ ID NO:122, or a polynucleotide encoding a protein comprising a fragment of the amino acid sequence of SEQ ID NO:122 having biological activity, the fragment comprising the amino acid sequence from amino acid 82 to amino acid 91 of SEQ ID NO:122.

Other embodiments provide the gene corresponding to the cDNA sequence of SEQ ID NO:121.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:121, but excluding the poly(A) tail at the 3' end of SEQ ID NO:121; and
    (ab) the nucleotide sequence of the cDNA insert of clone ye47_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:121, but excluding the poly(A) tail at the 3' end of SEQ ID NO:121; and
    (bb) the nucleotide sequence of the cDNA insert of clone ye47_1 deposited under accession number ATCC 98887;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:121, and extending contiguously from a nucleotide sequence corresponding to the 5' end of SEQ ID NO:121 to a nucleotide sequence corresponding to the 3' end of SEQ ID NO:121, but excluding the poly(A) tail at the 3' end of SEQ ID NO:121. Also preferably the ;polynucleotide isolated according to the above process comprises a nucleotide sequence corresponding to the cDNA sequence of SEQ ID NO:12 from nucleotide 256 to nucleotide 780, and extending contiguously from a nucleotide sequence corresponding to the 5' end of said sequence of SEQ ID NO:121 from nucleotide 256 to nucleotide 780, to a nucleotide sequence corresponding to the 3' end of said sequence of SEQ ID NO:121 from nucleotide 256 to nucleotide 780. Also preferably the polynucleotide isolated according to the above process comprises a nucleotide sequence corresponding to the cDNA sequence of SEQ ID NO:121 from nucleotide 412 to nucleotide 780, and extending contiguously from a nucleotide sequence corresponding to the 5' end of said sequence of SEQ ID NO:121 from nucleotide 412 to nucleotide 780, to a nucleotide sequence corresponding to the 3' end of said sequence of SEQ ID NO:121 from nucleotide 412 to nucleotide 780.

In other embodiments, the present invention provides a composition comprising a protein, wherein said protein comprises an amino acid sequence selected from the group consisting of:

(a) the amino acid sequence of SEQ ID NO:122;
(b) a fragment of the amino acid sequence of SEQ ID NO:122, the fragment comprising eight contiguous amino acids of SEQ ID NO:122; and
(c) the amino acid sequence encoded by the cDNA insert of clone ye47_1 deposited under accession number ATCC 98887;

the protein being substantially free from other mammalian proteins. Preferably such protein comprises the amino acid sequence of SEQ ID NO:122. In further preferred embodiments, the present invention provides a protein comprising a fragment of the amino acid sequence of SEQ ID NO:122 having biological activity, the fragment preferably comprising eight (more preferably twenty, most preferably thirty) contiguous amino acids of SEQ ID NO:122, or a protein comprising a fragment of the amino acid sequence of SEQ ID NO:22 having biological activity, the fragment comprising the amino acid sequence from amino acid 82 to amino acid 9 of SEQ ID NO:122.

In one embodiment, the present invention provides a composition comprising an isolated polynucleotide selected from the group consisting of:

(a) a polynucleotide comprising the nucleotide sequence of SEQ ID NO:123;
(b) a polynucleotide comprising the nucleotide sequence of SEQ ID NO:123 from nucleotide 127 to nucleotide 405;
(c) a polynucleotide comprising the nucleotide sequence of SEQ ID NO:123 from nucleotide 268 to nucleotide 405;
(d) a polynucleotide comprising the nucleotide sequence of the full-length protein coding sequence of clone yh50_1 deposited under accession number ATCC 98887;
(e) a polynucleotide encoding the full-length protein encoded by the cDNA insert of clone yh50_1 deposited under accession number ATCC 98887;
(f) a polynucleotide comprising the nucleotide sequence of a mature protein coding sequence of clone yh50_1 deposited under accession number ATCC 98887;
(g) a polynucleotide encoding a mature protein encoded by the cDNA insert of clone yh50_1 deposited under accession number ATCC 98887;
(h) a polynucleotide encoding a protein comprising the amino acid sequence of SEQ ID NO:124;
(i) a polynucleotide encoding a protein comprising a fragment of the amino acid sequence of SEQ ID NO:124 having biological activity, the fragment comprising eight contiguous amino acids of SEQ ID NO:124;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:123.

Preferably, such polynucleotide comprises the nucleotide sequence of SEQ ID NO:123 from nucleotide 127 to nucleotide 405; the nucleotide sequence of SEQ ID NO:123 from nucleotide 268 to nucleotide 405; the nucleotide sequence of the full-length protein coding sequence of clone yh50_1 deposited under accession number ATCC 98887; or the nucleotide sequence of a mature protein coding sequence of clone yh50_1 deposited under accession number ATCC 98887. In other preferred embodiments, the polynucleotide encodes the full-length or a mature protein encoded by the cDNA insert of clone yh50_1 deposited under accession number ATCC 98887. In further preferred embodiments, the present invention provides a polynucleotide encoding a protein comprising a fragment of the amino acid sequence of SEQ ID NO:124 having biological activity, the fragment preferably comprising eight (more preferably twenty, most preferably thirty) contiguous amino acids of SEQ ID NO:124, or a polynucleotide encoding a protein comprising a fragment of the amino acid sequence of SEQ ID NO:124 having biological activity, the fragment comprising the amino acid sequence from amino acid 41 to amino acid 50 of SEQ ID NO:124.

Other embodiments provide the gene corresponding to the cDNA sequence of SEQ ID NO:123.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:123, but excluding the poly(A) tail at the 3' end of SEQ ID NO:123; and
    (ab) the nucleotide sequence of the cDNA insert of clone yh50_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:123, but excluding the poly(A) tail at the 3' end of SEQ ID NO:123; and
    (bb) the nucleotide sequence of the cDNA insert of clone yh50_1 deposited under accession number ATCC 98887;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:123, and extending contiguously from a nucleotide sequence corresponding to the 5' end of SEQ ID NO:123 to a nucleotide sequence corresponding to the 3' end of SEQ ID NO:123, but excluding the poly(A) tail at the 3' end of SEQ ID NO:123. Also preferably the polynucleotide isolated according to the above process comprises a nucleotide sequence corresponding to the cDNA sequence of SEQ ID NO:123 from nucleotide 127 to nucleotide 405, and extending contiguously from a nucleotide sequence corresponding to the 5' end of said sequence of SEQ ID NO:123 from nucleotide 127 to nucleotide 405, to a nucleotide sequence corresponding to the 3' end of said sequence of SEQ ID NO:123 from nucleotide 127 to nucleotide 405. Also preferably the polynucleotide isolated according to the above process comprises a nucleotide sequence corresponding to the cDNA sequence of SEQ ID NO:123 from nucleotide 268 to nucleotide 405, and extending contiguously from a nucleotide sequence corresponding to the 5' end of said sequence of SEQ ID NO:123 from nucleotide 268 to nucleotide 405, to a nucleotide sequence corresponding to the 3' end of said sequence of SEQ ID NO:123 from nucleotide 268 to nucleotide 405.

In other embodiments, the present invention provides a composition comprising a protein, wherein said protein comprises an amino acid sequence selected from the group consisting of:

(a) the amino acid sequence of SEQ ID NO:124;
(b) a fragment of the amino acid sequence of SEQ ID NO:124, the fragment comprising eight contiguous amino acids of SEQ ID NO:124; and
(c) the amino acid sequence encoded by the cDNA insert of clone yh50_1 deposited under accession number ATCC 98887;

the protein being substantially free from other mammalian proteins. Preferably such protein comprises the amino acid sequence of SEQ ID NO:124. In further preferred embodiments, the present invention provides a protein comprising a fragment of the amino acid sequence of SEQ ID NO:124 having biological activity, the fragment preferably comprising eight (more preferably twenty, most preferably thirty) contiguous amino acids of SEQ ID NO:124, or a protein comprising a fragment of the amino acid sequence of SEQ ID NO:124 having biological activity, the fragment comprising the amino acid sequence from amino acid 41 to amino acid 50 of SEQ ID NO:124.

In one embodiment, the present invention provides a composition comprising an isolated polynucleotide selected from the group consisting of:

(a) a polynucleotide comprising the nucleotide sequence of SEQ ID NO:125;
(b) a polynucleotide comprising the nucleotide sequence of SEQ ID NO:125 from nucleotide 1175 to nucleotide 1480;
(c) a polynucleotide comprising the nucleotide sequence of the full-length protein coding sequence of clone yh53_1 deposited under accession number ATCC 98887;
(d) a polynucleotide encoding the full-length protein encoded by the cDNA insert of clone yh53_1 deposited under accession number ATCC 98887;
(e) a polynucleotide comprising the nucleotide sequence of a mature protein coding sequence of clone yh53_1 deposited under accession number ATCC 98887;
(f) a polynucleotide encoding a mature protein encoded by the cDNA insert of clone yh53_1 deposited under accession number ATCC 98887;
(g) a polynucleotide encoding a protein comprising the amino acid sequence of SEQ ID NO:126;

(h) a polynucleotide encoding a protein comprising a fragment of the amino acid sequence of SEQ ID NO:126 having biological activity, the fragment comprising eight contiguous amino acids of SEQ ID NO:126;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:125.

Preferably, such polynucleotide comprises the nucleotide sequence of SEQ ID NO:125 from nucleotide 1175 to nucleotide 1480; the nucleotide sequence of the full-length protein coding sequence of clone yh53_1 deposited under accession number ATCC 98887; or the nucleotide sequence of a mature protein coding sequence of clone yh53_1 deposited under accession number ATCC 98887. In other preferred embodiments, the polynucleotide encodes the full-length or a mature protein encoded by the cDNA insert of clone yh53_1 deposited under accession number ATCC 98887. In further preferred embodiments, the present invention provides a polynucleotide encoding a protein comprising a fragment of the amino acid sequence of SEQ ID NO:126 having biological activity, the fragment preferably comprising eight (more preferably twenty, most preferably thirty) contiguous amino acids of SEQ ID NO:126, or a polynucleotide encoding a protein comprising a fragment of the amino acid sequence of SEQ ID NO:126 having biological activity, the fragment comprising the amino acid sequence from amino acid 46 to amino acid 55 of SEQ ID NO:126.

Other embodiments provide the gene corresponding to the cDNA sequence of SEQ ID NO:125.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:125, but excluding the poly(A) tail at the 3' end of SEQ ID NO:125; and
    (ab) the nucleotide sequence of the cDNA insert of clone yh53_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:125, but excluding the poly(A) tail at the 3' end of SEQ ID NO:125; and
    (bb) the nucleotide sequence of the cDNA insert of clone yh53_1 deposited under accession number ATCC 98887;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:125, and extending contiguously from a nucleotide sequence corresponding to the 5' end of SEQ ID NO:125 to a nucleotide sequence corresponding to the 3' end of SEQ ID NO:125, but excluding the poly(A) tail at the 3' end of SEQ ID NO:125. Also preferably the polynucleotide isolated according to the above process comprises a nucleotide sequence corresponding to the cDNA sequence of SEQ ID NO:125 from nucleotide 1175 to nucleotide 1480, and extending contiguously from a nucleotide sequence corresponding to the 5' end of said sequence of SEQ ID NO:125 from nucleotide 1175 to nucleotide 1480, to a nucleotide sequence corresponding to the 3' end of said sequence of SEQ ID NO:125 from nucleotide 1175 to nucleotide 1480.

In other embodiments, the present invention provides a composition comprising a protein, wherein said protein comprises an amino acid sequence selected from the group consisting of:

(a) the amino acid sequence of SEQ ID NO:126;

(b) a fragment of the amino acid sequence of SEQ ID NO:126, the fragment comprising eight contiguous amino acids of SEQ ID NO:126; and (c) the amino acid sequence encoded by the cDNA insert of clone yh53_1 deposited under accession number ATCC 98887;

the protein being substantially free from other mammalian proteins. Preferably such protein comprises the amino acid sequence of SEQ ID NO:126. In further preferred embodiments, the present invention provides a protein comprising a fragment of the amino acid sequence of SEQ ID NO:126 having biological activity, the fragment preferably comprising eight (more preferably twenty, most preferably thirty) contiguous amino acids of SEQ ID NO:126, or a protein comprising a fragment of the amino acid sequence of SEQ ID NO:126 having biological activity, the fragment comprising the amino acid sequence from amino acid 46 to amino acid 55 of SEQ ID NO:126.

In one embodiment, the present invention provides a composition comprising an isolated polynucleotide selected from the group consisting of:

(a) a polynucleotide comprising the nucleotide sequence of SEQ ID NO:127;

(b) a polynucleotide comprising the nucleotide sequence of SEQ ID NO:127 from nucleotide 65 to nucleotide 319;

(c) a polynucleotide comprising the nucleotide sequence of SEQ ID NO:127 from nucleotide 173 to nucleotide 319;

(d) a polynucleotide comprising the nucleotide sequence of the full-length protein coding sequence of clone yh98_1 deposited under accession number ATCC 98887;

(e) a polynucleotide encoding the full-length protein encoded by the cDNA insert of clone yh98_1 deposited under accession number ATCC 98887;

(f) a polynucleotide comprising the nucleotide sequence of a mature protein coding sequence of clone yh98_1 deposited under accession number ATCC 98887;

(g) a polynucleotide encoding a mature protein encoded by the cDNA insert of clone yh98_1 deposited under accession number ATCC 98887;

(h) a polynucleotide encoding a protein comprising the amino acid sequence of SEQ ID NO:128;

(i) a polynucleotide encoding a protein comprising a fragment of the amino acid sequence of SEQ ID NO:128 having biological activity, the fragment comprising eight contiguous amino acids of SEQ ID NO:128;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:127.

Preferably, such polynucleotide comprises the nucleotide sequence of SEQ ID NO:127 from nucleotide 65 to nucleotide 319; the nucleotide sequence of SEQ ID NO:127 from nucleotide 173 to nucleotide 319; the nucleotide sequence of the full-length protein coding sequence of clone yh98_1 deposited under accession number ATCC 98887; or the nucleotide sequence of a mature protein coding sequence of clone yh98_1 deposited under accession number ATCC 98887. In other preferred embodiments, the polynucleotide encodes the full-length or a mature protein encoded by the cDNA insert of clone yh98_1 deposited under accession number ATCC 98887. In further preferred embodiments, the present invention provides a polynucleotide encoding a protein comprising a fragment of the amino acid sequence of SEQ ID NO:128 having biological activity, the fragment preferably comprising eight (more preferably twenty, most preferably thirty) contiguous amino acids of SEQ ID NO:128, or a polynucleotide encoding a protein comprising a fragment of the amino acid sequence of SEQ ID NO:128 having biological activity, the fragment comprising the amino acid sequence from amino acid 37 to amino acid 46 of SEQ ID NO:128.

Other embodiments provide the gene corresponding to the cDNA sequence of SEQ ID NO:127.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:127, but excluding the poly(A) tail at the 3' end of SEQ ID NO:127; and
    (ab) the nucleotide sequence of the cDNA insert of clone yh98_1 deposited under accession number ATCC 98887;
  (ii) hybridizing said probe(s) to human genomic DNA in conditions at least as stringent as 4×SSC at 50 degrees C.; and
  (iii) isolating the DNA polynucleotides detected with the probe(s);
and (b) a process comprising the steps of:
  (i) preparing one or more polynucleotide primers that hybridize in 6×SSC at 65 degrees C. to a nucleotide sequence selected from the group consisting of:
    (ba) SEQ ID NO:127, but excluding the poly(A) tail at the 3' end of SEQ ID NO:127; and
    (bb) the nucleotide sequence of the cDNA insert of clone yh98_1 deposited under accession number ATCC 98887;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:127, and extending contiguously from a nucleotide sequence corresponding to the 5' end of SEQ ID NO:127 to a nucleotide sequence corresponding to the 3' end of SEQ ID NO:127, but excluding the poly(A) tail at the 3' end of SEQ ID NO:127. Also preferably the polynucleotide isolated according to the above process comprises a nucleotide sequence corresponding to the cDNA sequence of SEQ ID NO:127 from nucleotide 65 to nucleotide 319, and extending contiguously from a nucleotide sequence corresponding to the 5' end of said sequence of SEQ ID NO:127 from nucleotide 65 to nucleotide 319, to a nucleotide sequence corresponding to the 3' end of said sequence of SEQ ID NO:127 from nucleotide 65 to nucleotide 319. Also preferably the polynucleotide isolated according to the above process comprises a nucleotide sequence corresponding to the cDNA sequence of SEQ ID NO:127 from nucleotide 173 to nucleotide 319, and extending contiguously from a nucleotide sequence corresponding to the 5' end of said sequence of SEQ ID NO:127 from nucleotide 173 to nucleotide 319, to a nucleotide sequence corresponding to the 3' end of said sequence of SEQ ID NO:127 from nucleotide 173 to nucleotide 319.

In other embodiments, the present invention provides a composition comprising a protein, wherein said protein comprises an amino acid sequence selected from the group consisting of:

(a) the amino acid sequence of SEQ ID NO:128;

(b) a fragment of the amino acid sequence of SEQ ID NO:128, the fragment comprising eight contiguous amino acids of SEQ ID NO:128; and (c) the amino acid sequence encoded by the cDNA insert of clone yh98_1 deposited under accession number ATCC 98887;

the protein being substantially free from other mammalian proteins. Preferably such protein comprises the amino acid sequence of SEQ ID NO:128. In further preferred embodiments, the present invention provides a protein comprising a fragment of the amino acid sequence of SEQ ID NO:128 having biological activity, the fragment preferably comprising eight (more preferably twenty, most preferably thirty) contiguous amino acids of SEQ ID NO:128, or a protein comprising a fragment of the amino acid sequence of SEQ ID NO:128 having biological activity, the fragment comprising the amino acid sequence from amino acid 37 to amino acid 46 of SEQ ID NO:128.

In one embodiment, the present invention provides a composition comprising an isolated polynucleotide selected from the group consisting of:

(a) a polynucleotide comprising the nucleotide sequence of SEQ ID NO:129;

(b) a polynucleotide comprising the nucleotide sequence of SEQ ID NO:129 from nucleotide 122 to nucleotide 469;

(c) a polynucleotide comprising the nucleotide sequence of SEQ ID NO:129 from nucleotide 263 to nucleotide 469;

(d) a polynucleotide comprising the nucleotide sequence of the full-length protein coding sequence of clone ya69_1 deposited under accession number ATCC 98915;

(e) a polynucleotide encoding the full-length protein encoded by the cDNA insert of clone ya69_1 deposited under accession number ATCC 98915;

(f) a polynucleotide comprising the nucleotide sequence of a mature protein coding sequence of clone ya69_1 deposited under accession number ATCC 98915;

(g) a polynucleotide encoding a mature protein encoded by the cDNA insert of clone ya69_1 deposited under accession number ATCC 98915;

(h) a polynucleotide encoding a protein comprising the amino acid sequence of SEQ ID NO:130;

(i) a polynucleotide encoding a protein comprising a fragment of the amino acid sequence of SEQ ID NO:130 having biological activity, the fragment comprising eight contiguous amino acids of SEQ ID NO:130;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:129.

Preferably, such polynucleotide comprises the nucleotide sequence of SEQ ID NO:129 from nucleotide 122 to nucleotide 469; the nucleotide sequence of SEQ ID NO:129 from nucleotide 263 to nucleotide 469; the nucleotide sequence of the full-length protein coding sequence of clone ya69_1 deposited under accession number ATCC 98915; or the nucleotide sequence of a mature protein coding sequence of clone ya69_1 deposited under accession number ATCC 98915. In other preferred embodiments, the polynucleotide encodes the full-length or a mature protein encoded by the cDNA insert of clone ya69_1 deposited under accession number ATCC 98915. In further preferred embodiments, the present invention provides a polynucleotide encoding a protein comprising a fragment of the amino acid sequence of SEQ ID NO:130 having biological activity, the fragment preferably comprising eight (more preferably twenty, most preferably thirty) contiguous amino acids of SEQ ID NO:130, or a polynucleotide encoding a protein comprising a fragment of the amino acid sequence of SEQ ID NO:130 having biological activity, the fragment comprising the amino acid sequence from amino acid 53 to amino acid 62 of SEQ ID NO:130.

Other embodiments provide the gene corresponding to the cDNA sequence of SEQ ID NO:129.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:

(aa) SEQ ID NO:129, but excluding the poly(A) tail at the 3' end of SEQ ID NO:129; and (ab) the nucleotide sequence of the cDNA insert of clone ya69_1 deposited under accession number ATCC 98915;

(ii) hybridizing said probe(s) to human genomic DNA in conditions at least as stringent as 4×SSC at 50 degrees C.; and (iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:

(ba) SEQ ID NO:129, but excluding the poly(A) tail at the 3' end of SEQ ID NO:129; and (bb) the nucleotide sequence of the cDNA insert of clone ya69_1 deposited under accession number ATCC 98915;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:129, and extending contiguously from a nucleotide sequence corresponding to the 5' end of SEQ ID NO:129 to a nucleotide sequence corresponding to the 3' end of SEQ ID NO:129, but excluding the poly(A) tail at the 3' end of SEQ ID NO:129. Also preferably the polynucleotide isolated according to the above process comprises a nucleotide sequence corresponding to the cDNA sequence of SEQ ID NO:129 from nucleotide 122 to nucleotide 469, and extending contiguously from a nucleotide sequence corresponding to the 5' end of said sequence of SEQ ID NO:129 from nucleotide 122 to nucleotide 469, to a nucleotide sequence corresponding to the 3' end of said sequence of SEQ ID NO:129 from nucleotide 122 to nucleotide 469. Also preferably the polynucleotide isolated according to the above process comprises a nucleotide sequence corresponding to the cDNA sequence of SEQ ID NO:129 from nucleotide 263 to nucleotide 469, and extending contiguously from a nucleotide sequence corresponding to the 5' end of said sequence of SEQ ID NO:129 from nucleotide 263 to nucleotide 469, to a nucleotide sequence corresponding to the 3' end of said sequence of SEQ ID NO:129 from nucleotide 263 to nucleotide 469.

In other embodiments, the present invention provides a composition comprising a protein, wherein said protein comprises an amino acid sequence selected from the group consisting of:

(a) the amino acid sequence of SEQ ID NO:130;

(b) a fragment of the amino acid sequence of SEQ ID NO:130, the fragment comprising eight contiguous amino acids of SEQ ID NO:130; and (c) the amino acid sequence encoded by the cDNA insert of clone ya69_1 deposited under accession number ATCC 98915;

the protein being substantially free from other mammalian proteins. Preferably such protein comprises the amino acid sequence of SEQ ID NO:130. In further preferred embodiments, the present invention provides a protein comprising a fragment of the amino acid sequence of SEQ ID NO:130 having biological activity, the fragment preferably comprising eight (more preferably twenty, most preferably thirty) contiguous amino acids of SEQ ID NO:130, or a protein comprising a fragment of the amino acid sequence of SEQ ID NO:130 having biological activity, the fragment comprising the amino acid sequence from amino acid 53 to amino acid 62 of SEQ ID NO:130.

In one embodiment, the present invention provides a composition comprising an isolated polynucleotide selected from the group consisting of:

(a) a polynucleotide comprising the nucleotide sequence of SEQ ID NO:131;

(b) a polynucleotide comprising the nucleotide sequence of SEQ ID NO:131 from nucleotide 36 to nucleotide 554;

(c) a polynucleotide comprising the nucleotide sequence of SEQ ID NO:131 from nucleotide 183 to nucleotide 554;

(d) a polynucleotide comprising the nucleotide sequence of the full-length protein coding sequence of clone yd107_1 deposited under accession number ATCC 98915;

(e) a polynucleotide encoding the full-length protein encoded by the cDNA insert of clone yd107_1 deposited under accession number ATCC 98915;

(f) a polynucleotide comprising the nucleotide sequence of a mature protein coding sequence of clone yd107_1 deposited under accession number ATCC 98915;

(g) a polynucleotide encoding a mature protein encoded by the cDNA insert of clone yd107_1 deposited under accession number ATCC 98915;

(h) a polynucleotide encoding a protein comprising the amino acid sequence of SEQ ID NO:132;

(i) a polynucleotide encoding a protein comprising a fragment of the amino acid sequence of SEQ ID NO:132 having biological activity, the fragment comprising eight contiguous amino acids of SEQ ID NO:132;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:131.

Preferably, such polynucleotide comprises the nucleotide sequence of SEQ ID NO:131 from nucleotide 36 to nucleotide 554; the nucleotide sequence of SEQ ID NO:131 from nucleotide 183 to nucleotide 554; the nucleotide sequence of the full-length protein coding sequence of clone yd107_1 deposited under accession number ATCC 98915; or the nucleotide sequence of a mature protein coding sequence of clone yd107_1 deposited under accession number ATCC 98915. In other preferred embodiments, the polynucleotide encodes the full-length or a mature protein encoded by the cDNA insert of clone yd107_1 deposited under accession number ATCC 98915. In further preferred embodiments, the present invention provides a polynucleotide encoding a protein comprising a fragment of the amino acid sequence of SEQ ID NO:132 having biological activity, the fragment preferably comprising eight (more preferably twenty, most preferably thirty) contiguous amino acids of SEQ ID NO:132, or a polynucleotide encoding a protein comprising a fragment of the amino acid sequence of SEQ ID NO:132 having biological activity, the fragment comprising the amino acid sequence from amino acid 81 to amino acid 90 of SEQ ID NO:132.

Other embodiments provide the gene corresponding to the cDNA sequence of SEQ ID NO:131.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:131, but excluding the poly(A) tail at the 3' end of SEQ ID NO:131; and
    (ab) the nucleotide sequence of the cDNA insert of clone yd107_1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:131, but excluding the poly(A) tail at the 3' end of SEQ ID NO:131; and
    (bb) the nucleotide sequence of the cDNA insert of clone yd107_1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:131, and extending contiguously from a nucleotide sequence corresponding to the 5' end of SEQ ID NO:131 to a nucleotide sequence corresponding to the 3' end of SEQ ID NO:131, but excluding the poly(A) tail at the 3' end of SEQ ID NO:131. Also preferably the polynucleotide isolated according to the above process comprises a nucleotide sequence corresponding to the cDNA sequence of SEQ ID NO:131 from nucleotide 36 to nucleotide 554, and extending contiguously from a nucleotide sequence corresponding to the 5' end of said sequence of SEQ ID NO:131 from nucleotide 36 to nucleotide 554, to a nucleotide sequence corresponding to the 3' end of said sequence of SEQ ID NO:131 from nucleotide 36 to nucleotide 554. Also preferably the polynucleotide isolated according to the above process comprises a nucleotide sequence corresponding to the cDNA sequence of SEQ ID NO:131 from nucleotide 183 to nucleotide 554, and extending contiguously from a nucleotide sequence corresponding to the 5' end of said sequence of SEQ ID NO:131 from nucleotide 183 to nucleotide 554, to a nucleotide sequence corresponding to the 3' end of said sequence of SEQ ID NO:131 from nucleotide 183 to nucleotide 554.

In other embodiments, the present invention provides a composition comprising a protein, wherein said protein comprises an amino acid sequence selected from the group consisting of:

(a) the amino acid sequence of SEQ ID NO:132;

(b) a fragment of the amino acid sequence of SEQ ID NO:132, the fragment comprising eight contiguous amino acids of SEQ ID NO:132; and (c) the amino acid sequence encoded by the cDNA insert of clone yd107_1 deposited under accession number ATCC 98915;

the protein being substantially free from other mammalian proteins. Preferably such protein comprises the amino acid sequence of SEQ ID NO:132. In further preferred embodiments, the present invention provides a protein comprising a fragment of the amino acid sequence of SEQ ID NO:132 having biological activity, the fragment preferably comprising eight (more preferably twenty, most preferably thirty) contiguous amino acids of SEQ ID NO:132, or a protein comprising a fragment of the amino acid sequence of SEQ ID NO:132 having biological activity, the fragment comprising the amino acid sequence from amino acid 81 to amino acid 90 of SEQ ID NO:132.

In one embodiment, the present invention provides a composition comprising an isolated polynucleotide selected from the group consisting of:

(a) a polynucleotide comprising the nucleotide sequence of SEQ ID NO:133;

(b) a polynucleotide comprising the nucleotide sequence of SEQ ID NO:133 from nucleotide 8 to nucleotide 493;

(c) a polynucleotide comprising the nucleotide sequence of SEQ ID NO:133 from nucleotide 53 to nucleotide 493;

(d) a polynucleotide comprising the nucleotide sequence of the full-length protein coding sequence of clone yd145_1 deposited under accession number ATCC 98915;

(e) a polynucleotide encoding the full-length protein encoded by the cDNA insert of clone yd145_1 deposited under accession number ATCC 98915;

(f) a polynucleotide comprising the nucleotide sequence of a mature protein coding sequence of clone yd145_1 deposited under accession number ATCC 98915;

(g) a polynucleotide encoding a mature protein encoded by the cDNA insert of clone yd145_1 deposited under accession number ATCC 98915;

(h) a polynucleotide encoding a protein comprising the amino acid sequence of SEQ ID NO:134;

(i) a polynucleotide encoding a protein comprising a fragment of the amino acid sequence of SEQ ID NO:134 having biological activity, the fragment comprising eight contiguous amino acids of SEQ ID NO:134;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:133.

Preferably, such polynucleotide comprises the nucleotide sequence of SEQ ID NO:133 from nucleotide 8 to nucleotide 493; the nucleotide sequence of SEQ ID NO:133 from nucleotide 53 to nucleotide 493; the nucleotide sequence of the full-length protein coding sequence of clone yd145_1 deposited under accession number ATCC 98915; or the nucleotide sequence of a mature protein coding sequence of clone yd145_1 deposited under accession number ATCC 98915. In other preferred embodiments, the polynucleotide encodes the full-length or a mature protein encoded by the cDNA insert of clone yd145_1 deposited under accession number ATCC 98915. In further preferred embodiments, the present invention provides a polynucleotide encoding a protein comprising a fragment of the amino acid sequence of SEQ ID NO:134 having biological activity, the fragment preferably comprising eight (more preferably twenty, most preferably thirty) contiguous amino acids of SEQ ID NO:134, or a polynucleotide encoding a protein comprising a fragment of the amino acid sequence of SEQ ID NO:134 having biological activity, the fragment comprising the amino acid sequence from amino acid 76 to amino acid 85 of SEQ ID NO:134.

Other embodiments provide the gene corresponding to the cDNA sequence of SEQ ID NO:133.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:133, but excluding the poly(A) tail at the 3' end of SEQ ID NO:133; and
    (ab) the nucleotide sequence of the cDNA insert of clone yd145_1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:133, but excluding the poly(A) tail at the 3' end of SEQ ID NO:133; and
    (bb) the nucleotide sequence of the cDNA insert of clone yd145_1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:133, and extending contiguously from a nucleotide sequence corresponding to the 5' end of SEQ ID NO:133 to a nucleotide sequence corresponding to the 3' end of SEQ ID NO:133, but excluding the poly(A) tail at the 3' end of SEQ ID NO:133. Also preferably the polynucleotide isolated according to the above process comprises a nucleotide sequence corresponding to the cDNA sequence of SEQ ID NO:133 from nucleotide 8 to nucleotide 493, and extending contiguously from a nucleotide sequence corresponding to the 5' end of said sequence of SEQ ID NO:133 from nucleotide 8 to nucleotide 493, to a nucleotide sequence corresponding to the 3' end of said sequence of SEQ ID NO:133 from nucleotide 8 to nucleotide 493. Also preferably the polynucleotide isolated according to the above process comprises a nucleotide sequence corresponding to the cDNA sequence of SEQ ID NO:133 from nucleotide 53 to nucleotide 493, and extending contiguously from a nucleotide sequence corresponding to the 5' end of said sequence of SEQ ID NO:133 from nucleotide 53 to nucleotide 493, to a nucleotide sequence corresponding to the 3' end of said sequence of SEQ ID NO:133 from nucleotide 53 to nucleotide 493.

In other embodiments, the present invention provides a composition comprising a protein, wherein said protein comprises an amino acid sequence selected from the group consisting of:
   (a) the amino acid sequence of SEQ ID NO:134;
   (b) a fragment of the amino acid sequence of SEQ ID NO:134, the fragment comprising eight contiguous amino acids of SEQ ID NO:134; and
   (c) the amino acid sequence encoded by the cDNA insert of clone yd145_1 deposited under accession number ATCC 98915;
the protein being substantially free from other mammalian proteins. Preferably such protein comprises the amino acid sequence of SEQ ID NO:134. In further preferred embodiments, the present invention provides a protein comprising a fragment of the amino acid sequence of SEQ ID NO:134 having biological activity, the fragment preferably comprising eight (more preferably twenty, most preferably thirty) contiguous amino acids of SEQ ID NO:134, or a protein comprising a fragment of the amino acid sequence of SEQ ID NO:134 having biological activity, the fragment comprising the amino acid sequence from amino acid 76 to amino acid 85 of SEQ ID NO:134.

In one embodiment, the present invention provides a composition comprising an isolated polynucleotide selected from the group consisting of:
   (a) a polynucleotide comprising the nucleotide sequence of SEQ ID NO:135;
   (b) a polynucleotide comprising the nucleotide sequence of SEQ ID NO:135 from nucleotide 21 to nucleotide 308;
   (c) a polynucleotide comprising the nucleotide sequence of the full-length protein coding sequence of clone yh24_1 deposited under accession number ATCC 98915;
   (d) a polynucleotide encoding the full-length protein encoded by the cDNA insert of clone yh24_1 deposited under accession number ATCC 98915;
   (e) a polynucleotide comprising the nucleotide sequence of a mature protein coding sequence of clone yh24_1 deposited under accession number ATCC 98915;
   (f) a polynucleotide encoding a mature protein encoded by the cDNA insert of clone yh24_1 deposited under accession number ATCC 98915;
   (g) a polynucleotide encoding a protein comprising the amino acid sequence of SEQ ID NO:136;
   (h) a polynucleotide encoding a protein comprising a fragment of the amino acid sequence of SEQ ID NO:136 having biological activity, the fragment comprising eight contiguous amino acids of SEQ ID NO:136;
   (i) a polynucleotide which is an allelic variant of a polynucleotide of (a)–(f) above;
   (j) a polynucleotide which encodes a species homologue of the protein of (g) or (h) above;
   (k) a polynucleotide that hybridizes under stringent conditions to any one of the polynucleotides specified in (a)–(h); and
   (l) a polynucleotide that hybridizes under stringent conditions to any one of the polynucleotides specified in (a)–(h) and that has a length that is at least 25% of the length of SEQ ID NO:135.

Preferably, such polynucleotide comprises the nucleotide sequence of SEQ ID NO:135 from nucleotide 21 to nucleotide 308; the nucleotide sequence of the full-length protein coding sequence of clone yh24_1 deposited under accession number ATCC 98915; or the nucleotide sequence of a mature protein coding sequence of clone yh24_1 deposited under accession number ATCC 98915. In other preferred embodiments, the polynucleotide encodes the full-length or a mature protein encoded by the cDNA insert of clone yh24_1 deposited under accession number ATCC 98915. In further preferred embodiments, the present invention provides a polynucleotide encoding a protein comprising a fragment of the amino acid sequence of SEQ ID NO:136 having biological activity, the fragment preferably comprising eight (more preferably twenty, most preferably thirty) contiguous amino acids of SEQ ID NO:136, or a polynucleotide encoding a protein comprising a fragment of the amino acid sequence of SEQ ID NO:136 having biological activity, the fragment comprising the amino acid sequence from amino acid 43 to amino acid 52 of SEQ ID NO:136.

Other embodiments provide the gene corresponding to the cDNA sequence of SEQ ID NO:135.

Further embodiments of the invention provide isolated polynucleotides produced according to a process selected from the group consisting of:
   (a) a process comprising the steps of:
      (i) preparing one or more polynucleotide probes that hybridize in 6×SSC at 65 degrees C. to a nucleotide sequence selected from the group consisting of:
         (aa) SEQ ID NO:135, but excluding the poly(A) tail at the 3' end of SEQ ID NO:135; and
         (ab) the nucleotide sequence of the cDNA insert of clone yh24_1 deposited under accession number ATCC 98915;
      (ii) hybridizing said probe(s) to human genomic DNA in conditions at least as stringent as 4×SSC at 50 degrees C.; and
      (iii) isolating the DNA polynucleotides detected with the probe(s);
   and
   (b) a process comprising the steps of:
      (i) preparing one or more polynucleotide primers that hybridize in 6×SSC at 65 degrees C. to a nucleotide sequence selected from the group consisting of:
         (ba) SEQ ID NO:135, but excluding the poly(A) tail at the 3' end of SEQ ID NO:135; and
         (bb) the nucleotide sequence of the cDNA insert of clone yh24_1 deposited under accession number ATCC 98915;
      (ii) hybridizing said primer(s) to human genomic DNA in conditions at least as stringent as 4×SSC at 50 degrees C.;
      (iii) amplifying human DNA sequences; and
      (iv) isolating the polynucleotide products of step (b) (iii).

Preferably the polynucleotide isolated according to the above process comprises a nucleotide sequence corresponding to the cDNA sequence of SEQ ID NO:135, and extending contiguously from a nucleotide sequence corresponding to the 5' end of SEQ ID NO:135 to a nucleotide sequence corresponding to the 3' end of SEQ ID NO:135, but excluding the poly(A) tail at the 3' end of SEQ ID NO:135. Also preferably the polynucleotide isolated according to the above process comprises a nucleotide sequence corresponding to the cDNA sequence of SEQ ID NO:135 from nucleotide 21 to nucleotide 308, and extending contiguously from a nucleotide sequence corresponding to the 5' end of said sequence of SEQ ID NO:135 from nucleotide 21 to nucleotide 308, to a nucleotide sequence corresponding to the 3' end of said sequence of SEQ ID NO:135 from nucleotide 21 to nucleotide 308.

In other embodiments, the present invention provides a composition comprising a protein, wherein said protein comprises an amino acid sequence selected from the group consisting of:

(a) the amino acid sequence of SEQ ID NO:136;

(b) a fragment of the amino acid sequence of SEQ ID NO:136, the fragment comprising eight contiguous amino acids of SEQ ID NO:136; and (c) the amino acid sequence encoded by the cDNA insert of clone yh24_1 deposited under accession number ATCC 98915;

the protein being substantially free from other mammalian proteins. Preferably such protein comprises the amino acid sequence of SEQ ID NO:136. In further preferred embodiments, the present invention provides a protein comprising a fragment of the amino acid sequence of SEQ ID NO:136 having biological activity, the fragment preferably comprising eight (more preferably twenty, most preferably thirty) contiguous amino acids of SEQ ID NO:136, or a protein comprising a fragment of the amino acid sequence of SEQ ID NO:136 having biological activity, the fragment comprising the amino acid sequence from amino acid 43 to amino acid 52 of SEQ ID NO:136.

In one embodiment, the present invention provides a composition comprising an isolated polynucleotide selected from the group consisting of:

(a) a polynucleotide comprising the nucleotide sequence of SEQ ID. NO:137;

(b) a polynucleotide comprising the nucleotide sequence of SEQ ID NO:137 from nucleotide 214 to nucleotide 735;

(c) a polynucleotide comprising the nucleotide sequence of SEQ ID NO:137 from nucleotide 634 to nucleotide 735;

(d) a polynucleotide comprising the nucleotide sequence of the full-length protein coding sequence of clone yi11_1 deposited under accession number ATCC 98915;

(e) a polynucleotide encoding the full-length protein encoded by the cDNA insert of clone yi11_1 deposited under accession number ATCC 98915;

(f) a polynucleotide comprising the nucleotide sequence of a mature protein coding sequence of clone yi11_1 deposited under accession number ATCC 98915;

(g) a polynucleotide encoding a mature protein encoded by the cDNA insert of clone yi11_1 deposited under accession number ATCC 98915;

(h) a polynucleotide encoding a protein comprising the amino acid sequence of SEQ ID NO:138;

(i) a polynucleotide encoding a protein comprising a fragment of the amino acid sequence of SEQ ID NO:138 having biological activity, the fragment comprising eight contiguous amino acids of SEQ ID NO:138;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:137.

Preferably, such polynucleotide comprises the nucleotide sequence of SEQ ID NO:137 from nucleotide 214 to nucleotide 735; the nucleotide sequence of SEQ ID NO:137 from nucleotide 634 to nucleotide 735; the nucleotide sequence of the full-length protein coding sequence of clone yi11_1 deposited under accession number ATCC 98915; or the nucleotide sequence of a mature protein coding sequence of clone yi11_1 deposited under accession number ATCC 98915. In other preferred embodiments, the polynucleotide encodes the full-length or a mature protein encoded by the cDNA insert of clone yi11_1 deposited under accession number ATCC 98915. In further preferred embodiments, the present invention provides a polynucleotide encoding a protein comprising a fragment of the amino acid sequence of SEQ ID NO:138 having biological activity, the fragment preferably comprising eight (more preferably twenty, most preferably thirty) contiguous amino acids of SEQ ID NO:138, or a polynucleotide encoding a protein comprising a fragment of the amino acid sequence of SEQ ID NO:138 having biological activity, the fragment comprising the amino acid sequence from amino acid 82 to amino acid 91 of SEQ ID NO:138.

Other embodiments provide the gene corresponding to the cDNA sequence of SEQ ID NO:137.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:137, but excluding the poly(A) tail at the 3' end of SEQ ID NO:137; and
(ab) the nucleotide sequence of the cDNA insert of clone yi11_1 deposited under accession number ATCC 98915;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:137, but excluding the poly(A) tail at the 3' end of SEQ ID NO:137; and
(bb) the nucleotide sequence of the cDNA insert of clone yi11_1 deposited under accession number ATCC 98915;
(j) hybridizing said primer(s) to human genomic DNA in conditions at least as stringent as 4×SSC at 50 degrees C.;

(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:137, and extending contiguously from a nucleotide sequence corresponding to the 5' end of SEQ ID NO:137 to a nucleotide sequence corresponding to the 3' end of SEQ ID NO:137, but excluding the poly(A) tail at the 3' end of SEQ ID NO:137. Also preferably the polynucleotide isolated according to the above process comprises a nucleotide sequence corresponding to the cDNA sequence of SEQ ID NO:137 from nucleotide 214 to nucleotide 735, and extending contiguously from a nucleotide sequence corresponding to the 5' end of said sequence of SEQ ID NO:137 from nucleotide 214 to nucleotide 735, to a nucleotide sequence corresponding to the 3' end of said sequence of SEQ ID NO:137 from nucleotide 214 to nucleotide 735. Also preferably the polynucleotide isolated according to the above process comprises a nucleotide sequence corresponding to the cDNA sequence of SEQ ID NO:137 from nucleotide 634 to nucleotide 735, and extending contiguously from a nucleotide sequence corresponding to the 5' end of said sequence of SEQ ID NO:137 from nucleotide 634 to nucleotide 735, to a nucleotide sequence corresponding to the 3' end of said sequence of SEQ ID NO:137 from nucleotide 634 to nucleotide 735.

In other embodiments, the present invention provides a composition comprising a protein, wherein said protein comprises an amino acid sequence selected from the group consisting of:

(a) the amino acid sequence of SEQ ID NO:138;
(b) a fragment of the amino acid sequence of SEQ ID NO:138, the fragment comprising eight contiguous amino acids of SEQ ID NO:138; and
(c) the amino acid sequence encoded by the cDNA insert of clone yi11_1 deposited under accession number ATCC 98915;

the protein being substantially free from other mammalian proteins. Preferably such protein comprises the amino acid sequence of SEQ ID NO:138. In further preferred embodiments, the present invention provides a protein comprising a fragment of the amino acid sequence of SEQ ID NO:138 having biological activity, the fragment preferably comprising eight (more preferably twenty, most preferably thirty) contiguous amino acids of SEQ ID NO:138, or a protein comprising a fragment of the amino acid sequence of SEQ ID NO:138 having biological activity, the fragment comprising the amino acid sequence from amino acid 82 to amino acid 91 of SEQ ID NO:138.

In one embodiment, the present invention provides a composition comprising an isolated polynucleotide selected from the group consisting of:

(a) a polynucleotide comprising the nucleotide sequence of SEQ ID NO:139;
(b) a polynucleotide comprising the nucleotide sequence of SEQ ID NO:139 from nucleotide 668 to nucleotide 937;
(c) a polynucleotide comprising the nucleotide sequence of SEQ ID NO:139 from nucleotide 848 to nucleotide 937;
(d) a polynucleotide comprising the nucleotide sequence of the full-length protein coding sequence of clone yi18_1 deposited under accession number ATCC 98915;
(e) a polynucleotide encoding the full-length protein encoded by the cDNA insert of clone yi18_1 deposited under accession number ATCC 98915;
(f) a polynucleotide comprising the nucleotide sequence of a mature protein coding sequence of clone yi18_1 deposited under accession number ATCC 98915;
(g) a polynucleotide encoding a mature protein encoded by the cDNA insert of clone yi18_1 deposited under accession number ATCC 98915;
(h) a polynucleotide encoding a protein comprising the amino acid sequence of SEQ ID NO:140;
(i) a polynucleotide encoding a protein comprising a fragment of the amino acid sequence of SEQ ID NO:140 having biological activity, the fragment comprising eight contiguous amino acids of SEQ ID NO:140;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:139.

Preferably, such polynucleotide comprises the nucleotide sequence of SEQ ID NO:139 from nucleotide 668 to nucleotide 937; the nucleotide sequence of SEQ ID NO:139 from nucleotide 848 to nucleotide 937; the nucleotide sequence of the full-length protein coding sequence of clone yi18_1 deposited under accession number ATCC 98915; or the nucleotide sequence of a mature protein coding sequence of clone yi18_1 deposited under accession number ATCC 98915. In other preferred embodiments, the polynucleotide encodes the full-length or a mature protein encoded by the cDNA insert of clone yi18_1 deposited under accession number ATCC 98915. In further preferred embodiments, the present invention provides a polynucleotide encoding a protein comprising a fragment of the amino acid sequence of SEQ ID NO:140 having biological activity, the fragment preferably comprising eight (more preferably twenty, most preferably thirty) contiguous amino acids of SEQ ID NO:140, or a polynucleotide encoding a protein comprising a fragment of the amino acid sequence of SEQ ID NO:140 having biological activity, the fragment comprising the amino acid sequence from amino acid 40 to amino acid 49 of SEQ ID NO:140.

Other embodiments provide the gene corresponding to the cDNA sequence of SEQ ID NO:139.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:139, but excluding the poly(A) tail at the 3' end of SEQ ID NO:139; and
    (ab) the nucleotide sequence of the cDNA insert of clone yi18_1 deposited under accession number ATCC 98915;
  (ii) hybridizing said probe(s) to human genomic DNA in conditions at least as stringent as 4×SSC at 50 degrees C.; and (iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:139, but excluding the poly(A) tail at the 3' end of SEQ ID NO:139; and
(bb) the nucleotide sequence of the cDNA insert of clone yi18_1 deposited under accession number ATCC 98915;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:139, and extending contiguously from a nucleotide sequence corresponding to the 5' end of SEQ ID NO:139 to a nucleotide sequence corresponding to the 3' end of SEQ ID NO:139, but excluding the poly(A) tail at the 3' end of SEQ ID NO:139. Also preferably the polynucleotide isolated according to the above process comprises a nucleotide sequence corresponding to the cDNA sequence of SEQ ID NO:139 from nucleotide 668 to nucleotide 937, and extending contiguously from a nucleotide sequence corresponding to the 5' end of said sequence of SEQ ID NO:139 from nucleotide 668 to nucleotide 937, to a nucleotide sequence corresponding to the 3' end of said sequence of SEQ ID NO:139 from nucleotide 668 to nucleotide 937. Also preferably the polynucleotide isolated according to the above process comprises a nucleotide sequence corresponding to the cDNA sequence of SEQ ID NO:139 from nucleotide 848 to nucleotide 937, and extending contiguously from a nucleotide sequence corresponding to the 5' end of said sequence of SEQ ID NO:139 from nucleotide 848 to nucleotide 937, to a nucleotide sequence corresponding to the 3' end of said sequence of SEQ ID NO:139 from nucleotide 848 to nucleotide 937.

In other embodiments, the present invention provides a composition comprising a protein, wherein said protein comprises an amino acid sequence selected from the group consisting of:
(a) the amino acid sequence of SEQ ID NO: 140;
(b) a fragment of the amino acid sequence of SEQ ID NO:140, the fragment comprising eight contiguous amino acids of SEQ ID NO:140; and
(c) the amino acid sequence encoded by the cDNA insert of clone yi18_1 deposited under accession number ATCC 98915;
the protein being substantially free from other mammalian proteins. Preferably such protein comprises the amino acid sequence of SEQ ID NO:140. In further preferred embodiments, the present invention provides a protein comprising a fragment of the amino acid sequence of SEQ ID NO:140 having biological activity, the fragment preferably comprising eight (more preferably twenty, most preferably thirty) contiguous amino acids of SEQ ID NO:140, or a protein comprising a fragment of the amino acid sequence of SEQ ID NO:140 having biological activity, the fragment comprising the amino acid sequence from amino acid 40 to amino acid 49 of SEQ ID NO:140.

In one embodiment, the present invention provides a composition comprising an isolated polynucleotide selected from the group consisting of:

(a) a polynucleotide comprising the nucleotide sequence of SEQ ID NO:141;
(b) a polynucleotide comprising the nucleotide sequence of SEQ ID NO:141 from nucleotide 171 to nucleotide 407;
(c) a polynucleotide comprising the nucleotide sequence of SEQ ID NO:141 from nucleotide 258 to nucleotide 407;
(d) a polynucleotide comprising the nucleotide sequence of the full-length protein coding sequence of clone yk14_1 deposited under accession number ATCC 98915;
(e) a polynucleotide encoding the full-length protein encoded by the cDNA insert of clone yk14_1 deposited under accession number ATCC 98915;
(f) a polynucleotide comprising the nucleotide sequence of a mature protein coding sequence of clone yk14_1 deposited under accession number ATCC 98915;
(g) a polynucleotide encoding a mature protein encoded by the cDNA insert of clone yk14_1 deposited under accession number ATCC 98915;
(h) a polynucleotide encoding a protein comprising the amino acid sequence of SEQ ID NO:142;
(i) a polynucleotide encoding a protein comprising a fragment of the amino acid sequence of SEQ ID NO:142 having biological activity, the fragment comprising eight contiguous amino acids of SEQ ID NO:142;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:141.

Preferably, such polynucleotide comprises the nucleotide sequence of SEQ ID NO:141 from nucleotide 171 to nucleotide 407; the nucleotide sequence of SEQ ID NO:141 from nucleotide 258 to nucleotide 407; the nucleotide sequence of the full-length protein coding sequence of clone yk14_1 deposited under accession number ATCC 98915; or the nucleotide sequence of a mature protein coding sequence of clone yk14_1 deposited under accession number ATCC 98915. In other preferred embodiments, the polynucleotide encodes the full-length or a mature protein encoded by the cDNA insert of clone yk14_1 deposited under accession number ATCC 98915. In further preferred embodiments, the present invention provides a polynucleotide encoding a protein comprising a fragment of the amino acid sequence of SEQ ID NO:142 having biological activity, the fragment preferably comprising eight (more preferably twenty, most preferably thirty) contiguous amino acids of SEQ ID NO:142, or a polynucleotide encoding a protein comprising a fragment of the amino acid sequence of SEQ ID NO:142 having biological activity, the fragment comprising the amino acid sequence from amino acid 34 to amino acid 43 of SEQ ID NO:142.

Other embodiments provide the gene corresponding to the cDNA sequence of SEQ ID NO:141.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:141, but excluding the poly(A) tail at the 3' end of SEQ ID NO:141; and
    (ab) the nucleotide sequence of the cDNA insert of clone yk14_1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:141, but excluding the poly(A) tail at the 3' end of SEQ ID NO:141; and
    (bb) the nucleotide sequence of the cDNA insert of clone yk14_1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:141, and extending contiguously from a nucleotide sequence corresponding to the 5' end of SEQ ID NO:141 to a nucleotide sequence corresponding to the 3' end of SEQ ID NO:141, but excluding the poly(A) tail at the 3' end of SEQ ID NO:141. Also preferably the polynucleotide isolated according to the above process comprises a nucleotide sequence corresponding to the cDNA sequence of SEQ ID NO:141 from nucleotide 171 to nucleotide 407, and extending contiguously from a nucleotide sequence corresponding to the 5' end of said sequence of SEQ ID NO:141 from nucleotide 171 to nucleotide 407, to a nucleotide sequence corresponding to the 3' end of said sequence of SEQ ID NO:141 from nucleotide 171 to nucleotide 407. Also preferably the polynucleotide isolated according to the above process comprises a nucleotide sequence corresponding to the cDNA sequence of SEQ ID NO:141 from nucleotide 258 to nucleotide 407, and extending contiguously from a nucleotide sequence corresponding to the 5' end of said sequence of SEQ ID NO:141 from nucleotide 258 to nucleotide 407, to a nucleotide sequence corresponding to the 3' end of said sequence of SEQ ID NO:141 from nucleotide 258 to nucleotide 407.

In other embodiments, the present invention provides a composition comprising a protein, wherein said protein comprises an amino acid sequence selected from the group consisting of:
  (a) the amino acid sequence of SEQ ID NO:142;
  (b) a fragment of the amino acid sequence of SEQ ID NO:142, the fragment comprising eight contiguous amino acids of SEQ ID NO:142; and
  (c) the amino acid sequence encoded by the cDNA insert of clone yk14_1 deposited under accession number ATCC 98915;
the protein being substantially free from other mammalian proteins. Preferably such protein comprises the amino acid sequence of SEQ ID NO:142. In further preferred embodiments, the present invention provides a protein comprising a fragment of the amino acid sequence of SEQ ID NO:142 having biological activity, the fragment preferably comprising eight (more preferably twenty, most preferably thirty) contiguous amino acids of SEQ ID NO:142, or a protein comprising a fragment of the amino acid sequence of SEQ ID NO:142 having biological activity, the fragment comprising the amino acid sequence from amino acid 34 to amino acid 43 of SEQ ID NO:142.

In one embodiment, the present invention provides a composition comprising an isolated polynucleotide selected from the group consisting of:
  (a) a polynucleotide comprising the nucleotide sequence of SEQ ID NO:143;
  (b) a polynucleotide comprising the nucleotide sequence of SEQ ID NO:143 from nucleotide 164 to nucleotide 457;
  (c) a polynucleotide comprising the nucleotide sequence of the full-length protein coding sequence of clone yk39_1 deposited under accession number ATCC 98915;
  (d) a polynucleotide encoding the full-length protein encoded by the cDNA insert of clone yk39_1 deposited under accession number ATCC 98915;
  (e) a polynucleotide comprising the nucleotide sequence of a mature protein coding sequence of clone yk39_1 deposited under accession number ATCC 98915;
  (f) a polynucleotide encoding a mature protein encoded by the cDNA insert of clone yk39_1 deposited under accession number ATCC 98915;
  (g) a polynucleotide encoding a protein comprising the amino acid sequence of SEQ ID NO:144;
  (h) a polynucleotide encoding a protein comprising a fragment of the amino acid sequence of SEQ ID NO:144 having biological activity, the fragment comprising eight contiguous amino acids of SEQ ID NO:144;
  (i) a polynucleotide which is an allelic variant of a polynucleotide of (a)–(f) above;
  (j) a polynucleotide which encodes a species homologue of the protein of (g) or (h) above;
  (k) a polynucleotide that hybridizes under stringent conditions to any one of the polynucleotides specified in (a)–(h); and
  (l) a polynucleotide that hybridizes under stringent conditions to any one of the polynucleotides specified in (a)–(h) and that has a length that is at least 25% of the length of SEQ ID NO:143.

Preferably, such polynucleotide comprises the nucleotide sequence of SEQ ID NO:143 from nucleotide 164 to nucleotide 457; the nucleotide sequence of the full-length protein coding sequence of clone yk39_1 deposited under accession number ATCC 98915; or the nucleotide sequence of a mature protein coding sequence of clone yk39_1 deposited under accession number ATCC 98915. In other preferred embodiments, the polynucleotide encodes the full-length or a mature protein encoded by the cDNA insert of clone yk39_1 deposited under accession number ATCC 98915. In further preferred embodiments, the present invention provides a polynucleotide encoding a protein comprising a fragment of the amino acid sequence of SEQ ID NO:144 having biological activity, the fragment preferably comprising eight (more preferably twenty, most preferably thirty) contiguous amino acids of SEQ ID NO:144, or a polynucleotide encoding a protein comprising a fragment of the amino acid sequence of SEQ ID NO:144 having biological activity, the fragment comprising the amino acid sequence from amino acid 44 to amino acid 53 of SEQ ID NO:144.

Other embodiments provide the gene corresponding to the cDNA sequence of SEQ ID NO:143.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:143, but excluding the poly(A) tail at the 3' end of SEQ ID NO:143; and
    (ab) the nucleotide sequence of the cDNA insert of clone yk39__1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:143, but excluding the poly(A) tail at the 3' end of SEQ ID NO:143; and
    (bb) the nucleotide sequence of the cDNA insert of clone yk39__1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:143, and extending contiguously from a nucleotide sequence corresponding to the 5' end of SEQ ID NO:143 to a nucleotide sequence corresponding to the 3' end of SEQ ID NO:143, but excluding the poly(A) tail at the 3' end of SEQ ID NO:143. Also preferably the polynucleotide isolated according to the above process comprises a nucleotide sequence corresponding to the cDNA sequence of SEQ ID NO:143 from nucleotide 164 to nucleotide 457, and extending contiguously from a nucleotide sequence corresponding to the 5' end of said sequence of SEQ ID NO:143 from nucleotide 164 to nucleotide 457, to a nucleotide sequence corresponding to the 3' end of said sequence of SEQ ID NO:143 from nucleotide 164 to nucleotide 457.

In other embodiments, the present invention provides a composition comprising a protein, wherein said protein comprises an amino acid sequence selected from the group consisting of:

(a) the amino acid sequence of SEQ ID NO:144;
(b) a fragment of the amino acid sequence of SEQ ID NO:144, the fragment comprising eight contiguous amino acids of SEQ ID NO:144; and
(c) the amino acid sequence encoded by the cDNA insert of clone yk39__1 deposited under accession number ATCC 98915;

the protein being substantially free from other mammalian proteins. Preferably such protein comprises the amino acid sequence of SEQ ID NO:144. In further preferred embodiments, the present invention provides a protein comprising a fragment of the amino acid sequence of SEQ ID NO:144 having biological activity, the fragment preferably comprising eight (more preferably twenty, most preferably thirty) contiguous amino acids of SEQ ID NO:144, or a protein comprising a fragment of the amino acid sequence of SEQ ID NO:144 having biological activity, the fragment comprising the amino acid sequence from amino acid 44 to amino acid 53 of SEQ ID NO:144.

In one embodiment, the present invention provides a composition comprising an isolated polynucleotide selected from the group consisting of:

(a) a polynucleotide comprising the nucleotide sequence of SEQ ID NO:145;
(b) a polynucleotide comprising the nucleotide sequence of SEQ ID NO:145 from nucleotide 72 to nucleotide 500;
(c) a polynucleotide comprising the nucleotide sequence of SEQ ID NO: 145 from nucleotide 255 to nucleotide 500;
(d) a polynucleotide comprising the nucleotide sequence of the full-length protein coding sequence of clone yk91__1 deposited under accession number ATCC 98915;
(e) a polynucleotide encoding the full-length protein encoded by the cDNA insert of clone yk91__1 deposited under accession number ATCC 98915;
(f) a polynucleotide comprising the nucleotide sequence of a mature protein coding sequence of clone yk91__1 deposited under accession number ATCC 98915;
(g) a polynucleotide encoding a mature protein encoded by the cDNA insert of clone yk91__1 deposited under accession number ATCC 98915;
(h) a polynucleotide encoding a protein comprising the amino acid sequence of SEQ ID NO:146;
(i) a polynucleotide encoding a protein comprising a fragment of the amino acid sequence of SEQ ID NO:146 having biological activity, the fragment comprising eight contiguous amino acids of SEQ ID NO:146;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:145.

Preferably, such polynucleotide comprises the nucleotide sequence of SEQ ID NO:145 from nucleotide 72 to nucleotide 500; the nucleotide sequence of SEQ ID NO:145 from nucleotide 255 to nucleotide 500; the nucleotide sequence of the full-length protein coding sequence of clone yk91__1 deposited under accession number ATCC 98915; or the nucleotide sequence of a mature protein coding sequence of clone yk91__1 deposited under accession number ATCC 98915. In other preferred embodiments, the polynucleotide encodes the full-length or a mature protein encoded by the cDNA insert of clone yk91__1 deposited under accession number ATCC 98915. In further preferred embodiments, the present invention provides a polynucleotide encoding a protein comprising a fragment of the amino acid sequence of SEQ ID NO:146 having biological activity, the fragment preferably comprising eight (more preferably twenty, most preferably thirty) contiguous amino acids of SEQ ID NO:146, or a polynucleotide encoding a protein comprising a fragment of the amino acid sequence of SEQ ID NO:146 having biological activity, the fragment comprising the amino acid sequence from amino acid 66 to amino acid 75 of SEQ ID NO:146.

Other embodiments provide the gene corresponding to the cDNA sequence of SEQ ID NO:145.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:145, but excluding the poly(A) tail at the 3' end of SEQ ID NO:145; and
    (ab) the nucleotide sequence of the cDNA insert of clone yk91_1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:145, but excluding the poly(A) tail at the 3' end of SEQ ID NO:145; and
    (bb) the nucleotide sequence of the cDNA insert of clone yk91_1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:145, and extending contiguously from a nucleotide sequence corresponding to the 5' end of SEQ ID NO:145 to a nucleotide sequence corresponding to the 3' end of SEQ ID NO:145, but excluding the poly(A) tail at the 3' end of SEQ ID NO:145. Also preferably the polynucleotide isolated according to the above process comprises a nucleotide sequence corresponding to the cDNA sequence of SEQ ID NO:145 from nucleotide 72 to nucleotide 500, and extending contiguously from a nucleotide sequence corresponding to the 5' end of said sequence of SEQ ID NO:145 from nucleotide 72 to nucleotide 500, to a nucleotide sequence corresponding to the 3' end of said sequence of SEQ ID NO:145 from nucleotide 72 to nucleotide 500. Also preferably the polynucleotide isolated according to the above process comprises a nucleotide sequence corresponding to the cDNA sequence of SEQ ID NO:145 from nucleotide 255 to nucleotide 500, and extending contiguously from a nucleotide sequence corresponding to the 5' end of said sequence of SEQ ID NO:145 from nucleotide 255 to nucleotide 500, to a nucleotide sequence corresponding to the 3' end of said sequence of SEQ ID NO:145 from nucleotide 255 to nucleotide 500.

In other embodiments, the present invention provides a composition comprising a protein, wherein said protein comprises an amino acid sequence selected from the group consisting of:

(a) the amino acid sequence of SEQ ID NO:146;
(b) a fragment of the amino acid sequence of SEQ ID NO:146, the fragment comprising eight contiguous amino acids of SEQ ID NO:146; and
(c) the amino acid sequence encoded by the cDNA insert of clone yk91_1 deposited under accession number ATCC 98915;

the protein being substantially free from other mammalian proteins. Preferably such protein comprises the amino acid sequence of SEQ ID NO:146. In further preferred embodiments, the present invention provides a protein comprising a fragment of the amino acid sequence of SEQ ID NO:146 having biological activity, the fragment preferably comprising eight (more preferably twenty, most preferably thirty) contiguous amino acids of SEQ ID NO:146, or a protein comprising a fragment of the amino acid sequence of SEQ ID NO:146 having biological activity, the fragment comprising the amino acid sequence from amino acid 66 to amino acid 75 of SEQ ID NO:146.

In one embodiment, the present invention provides a composition comprising an isolated polynucleotide selected from the group consisting of:

(a) a polynucleotide comprising the nucleotide sequence of SEQ ID NO:147;
(b) a polynucleotide comprising the nucleotide sequence of SEQ ID NO:147 from nucleotide 174 to nucleotide 620;
(c) a polynucleotide comprising the nucleotide sequence of SEQ ID NO:147 from nucleotide 240 to nucleotide 620;
(d) a polynucleotide comprising the nucleotide sequence of the full-length protein coding sequence of clone yk199_1 deposited under accession number ATCC 98915;
(e) a polynucleotide encoding the full-length protein encoded by the cDNA insert of clone yk199_1 deposited under accession number ATCC 98915;
(f) a polynucleotide comprising the nucleotide sequence of a mature protein coding sequence of clone yk199_1 deposited under accession number ATCC 98915;
(g) a polynucleotide encoding a mature protein encoded by the cDNA insert of clone yk199_1 deposited under accession number ATCC 98915;
(h) a polynucleotide encoding a protein comprising the amino acid sequence of SEQ ID NO:148;
(i) a polynucleotide encoding a protein comprising a fragment of the amino acid sequence of SEQ ID NO:148 having biological activity, the fragment comprising eight contiguous amino acids of SEQ ID NO:148;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:147.

Preferably, such polynucleotide comprises the nucleotide sequence of SEQ ID NO:147 from nucleotide 174 to nucleotide 620; the nucleotide sequence of SEQ ID NO:147 from nucleotide 240 to nucleotide 620; the nucleotide sequence of the full-length protein coding sequence of clone yk199_1 deposited under accession number ATCC 98915; or the nucleotide sequence of a mature protein coding sequence of clone yk199_1 deposited under accession number ATCC 98915. In other preferred embodiments, the polynucleotide encodes the full-length or a mature protein encoded by the cDNA insert of done yk199_1 deposited under accession number ATCC 98915. In further preferred embodiments, the present invention provides a polynucleotide encoding a protein comprising a fragment of the amino acid sequence of SEQ ID NO:148 having biological activity, the fragment preferably comprising eight (more preferably twenty, most preferably thirty) contiguous amino acids of SEQ ID NO:148, or a polynucleotide encoding a protein comprising a fragment of the amino acid sequence of SEQ ID NO:148 having biological activity, the fragment comprising the amino acid sequence from amino acid 69 to amino acid 78 of SEQ ID NO:148.

Other embodiments provide the gene corresponding to the cDNA sequence of SEQ ID NO:147.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:147, but excluding the poly(A) tail at the 3' end of SEQ ID NO:147; and
    (ab) the nucleotide sequence of the cDNA insert of clone yk199_1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:147, but excluding the poly(A) tail at the 3' end of SEQ ID NO:147; and
    (bb) the nucleotide sequence of the cDNA insert of clone yk199_1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:147, and extending contiguously from a nucleotide sequence corresponding to the 5' end of SEQ ID NO:147 to a nucleotide sequence corresponding to the 3' end of SEQ ID NO:147, but excluding the poly(A) tail at the 3' end of SEQ ID NO:147. Also preferably the polynucleotide isolated according to the above process comprises a nucleotide sequence corresponding to the cDNA sequence of SEQ ID NO:147 from nucleotide 174 to nucleotide 620, and extending contiguously from a nucleotide sequence corresponding to the 5' end of said sequence of SEQ ID NO:147 from nucleotide 174 to nucleotide 620, to a nucleotide sequence corresponding to the 3' end of said sequence of SEQ ID NO:147 from nucleotide 174 to nucleotide 620. Also preferably the polynucleotide isolated according to the above process comprises a nucleotide sequence corresponding to the cDNA sequence of SEQ ID NO:147 from nucleotide 240 to nucleotide 620, and extending contiguously from a nucleotide sequence corresponding to the 5' end of said sequence of SEQ ID NO:147 from nucleotide 240 to nucleotide 620, to a nucleotide sequence corresponding to the 3' end of said sequence of SEQ ID NO:147 from nucleotide 240 to nucleotide 620.

In other embodiments, the present invention provides a composition comprising a protein, wherein said protein comprises an amino acid sequence selected from the group consisting of:

(a) the amino acid sequence of SEQ ID NO:148;
(b) a fragment of the amino acid sequence of SEQ ID NO:148, the fragment comprising eight contiguous amino acids of SEQ ID NO:148; and
(c) the amino acid sequence encoded by the cDNA insert of clone yk199_1 deposited under accession number ATCC 98915;

the protein being substantially free from other mammalian proteins. Preferably such protein comprises the amino acid sequence of SEQ ID NO:148. In further preferred embodiments, the present invention provides a protein comprising a fragment of the amino acid sequence of SEQ ID NO:148 having biological activity, the fragment preferably comprising eight (more preferably twenty, most preferably thirty) contiguous amino acids of SEQ ID NO:148, or a protein comprising a fragment of the amino acid sequence of SEQ ID NO:148 having biological activity, the fragment comprising the amino acid sequence from amino acid 69 to amino acid 78 of SEQ ID NO:148.

In one embodiment, the present invention provides a composition comprising an isolated polynucleotide selected from the group consisting of:

(a) a polynucleotide comprising the nucleotide sequence of SEQ ID NO:149;
(b) a polynucleotide comprising the nucleotide sequence of SEQ ID NO:149 from nucleotide 325 to nucleotide 984;
(c) a polynucleotide comprising the nucleotide sequence of SEQ ID NO:149 from nucleotide 973 to nucleotide 984;
(d) a polynucleotide comprising the nucleotide sequence of the full-length protein coding sequence of clone yl4_1 deposited under accession number ATCC 98915;
(e) a polynucleotide encoding the full-length protein encoded by the cDNA insert of clone yl4_1 deposited under accession number ATCC 98915;
(f) a polynucleotide comprising the nucleotide sequence of a mature protein coding sequence of clone yl4_1 deposited under accession number ATCC 98915;
(g) a polynucleotide encoding a mature protein encoded by the cDNA insert of clone yl4_1 deposited under accession number ATCC 98915;

(h) a polynucleotide encoding a protein comprising the amino acid sequence of SEQ ID NO:150;

(i) a polynucleotide encoding a protein comprising a fragment of the amino acid sequence of SEQ ID NO:150 having biological activity, the fragment comprising eight contiguous amino acids of SEQ ID NO:150;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:149.

Preferably, such polynucleotide comprises the nucleotide sequence of SEQ ID NO:149 from nucleotide 325 to nucleotide 984; the nucleotide sequence of SEQ ID NO:149 from nucleotide 973 to nucleotide 984; the nucleotide sequence of the full-length protein coding sequence of clone yl4_1 deposited under accession number ATCC 98915; or the nucleotide sequence of a mature protein coding sequence of clone yl4_1 deposited under accession number ATCC 98915. In other preferred embodiments, the polynucleotide encodes the full-length or a mature protein encoded by the cDNA insert of clone yl4_1 deposited under accession number ATCC 98915. In further preferred embodiments, the present invention provides a polynucleotide encoding a protein comprising a fragment of the amino acid sequence of SEQ ID NO:150 having biological activity, the fragment preferably comprising eight (more preferably twenty, most preferably thirty) contiguous amino acids of SEQ ID NO:150, or a polynucleotide encoding a protein comprising a fragment of the amino acid sequence of SEQ ID NO:150 having biological activity, the fragment comprising the amino acid sequence from amino acid 105 to amino acid 114 of SEQ ID NO:150.

Other embodiments provide the gene corresponding to the cDNA sequence of SEQ ID NO:149.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:149, but excluding the poly(A) tail at the 3' end of SEQ ID NO:149; and
    (ab) the nucleotide sequence of the cDNA insert of clone yl4_1 deposited under accession number ATCC 98915;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:149, but excluding the poly(A) tail at the 3' end of SEQ ID NO:149; and
    (bb) the nucleotide sequence of the cDNA insert of clone yl4_1 deposited under accession number ATCC 98915;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:149, and extending contiguously from a nucleotide sequence corresponding to the 5' end of SEQ ID NO:149 to a nucleotide sequence corresponding to the 3' end of SEQ ID NO:149, but excluding the poly(A) tail at the 3' end of SEQ ID NO:149. Also preferably the polynucleotide isolated according to the above process comprises a nucleotide sequence corresponding to the cDNA sequence of SEQ ID NO:149 from nucleotide 325 to nucleotide 984, and extending contiguously from a nucleotide sequence corresponding to the 5' end of said sequence of SEQ ID NO:149 from nucleotide 325 to nucleotide 984, to a nucleotide sequence corresponding to the 3' end of said sequence of SEQ ID NO:149 from nucleotide 325 to nucleotide 984. Also preferably the polynucleotide isolated according to the above process comprises a nucleotide sequence corresponding to the cDNA sequence of SEQ ID NO:149 from nucleotide 973 to nucleotide 984, and extending contiguously from a nucleotide sequence corresponding to the 5' end of said sequence of SEQ ID NO:149 from nucleotide 973 to nucleotide 984, to a nucleotide sequence corresponding to the 3' end of said sequence of SEQ ID NO: 149 from nucleotide 973 to nucleotide 984.

In other embodiments, the present invention provides a composition comprising a protein, wherein said protein comprises an amino acid sequence selected from the group consisting of:

(a) the amino acid sequence of SEQ ID NO:150;

(b) a fragment of the amino acid sequence of SEQ ID NO:150, the fragment comprising eight contiguous amino acids of SEQ ID NO:150; and (c) the amino acid sequence encoded by the cDNA insert of clone yl4_1 deposited under accession number ATCC 98915;

the protein being substantially free from other mammalian proteins. Preferably such protein comprises the amino acid sequence of SEQ ID NO:150. In further preferred embodiments, the present invention provides a protein comprising a fragment of the amino acid sequence of SEQ ID NO:150 having biological activity, the fragment preferably comprising eight (more preferably twenty, most preferably thirty) contiguous amino acids of SEQ ID NO:150, or a protein comprising a fragment of the amino acid sequence of SEQ ID NO:150 having biological activity, the fragment comprising the amino acid sequence from amino acid 105 to amino acid 114 of SEQ ID NO:150.

In one embodiment, the present invention provides a composition comprising an isolated polynucleotide selected from the group consisting of:

(a) a polynucleotide comprising the nucleotide sequence of SEQ ID NO:151;

(b) a polynucleotide comprising the nucleotide sequence of SEQ ID NO:151 from nucleotide 119 to nucleotide 415;

(c) a polynucleotide comprising the nucleotide sequence of the full-length protein coding sequence of clone yl14_1 deposited under accession number ATCC 98915;

(d) a polynucleotide encoding the full-length protein encoded by the cDNA insert of clone yl14_1 deposited under accession number ATCC 98915;
(e) a polynucleotide comprising the nucleotide sequence of a mature protein coding sequence of clone yl14_1 deposited under accession number ATCC 98915;
(f) a polynucleotide encoding a mature protein encoded by the cDNA insert of clone yl14_1 deposited under accession number ATCC 98915;
(g) a polynucleotide encoding a protein comprising the amino acid sequence of SEQ ID NO:152;
(h) a polynucleotide encoding a protein comprising a fragment of the amino acid sequence of SEQ ID NO:152 having biological activity, the fragment comprising eight contiguous amino acids of SEQ ID NO:152;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:151.

Preferably, such polynucleotide comprises the nucleotide sequence of SEQ ID NO:151 from nucleotide 119 to nucleotide 415; the nucleotide sequence of the full-length protein coding sequence of clone yl14_1 deposited under accession number ATCC 98915; or the nucleotide sequence of a mature protein coding sequence of clone yl14_1 deposited under accession number ATCC 98915. In other preferred embodiments, the polynucleotide encodes the full-length or a mature protein encoded by the cDNA insert of clone yl14_1 deposited under accession number ATCC 98915. In further preferred embodiments, the present invention provides a polynucleotide encoding a protein comprising a fragment of the amino acid sequence of SEQ ID NO:152 having biological activity, the fragment preferably comprising eight (more preferably twenty, most preferably thirty) contiguous amino acids of SEQ ID NO:152, or a polynucleotide encoding a protein comprising a fragment of the amino acid sequence of SEQ ID NO:152 having biological activity, the fragment comprising the amino acid sequence from amino acid 44 to amino acid 53 of SEQ ID NO:152.

Other embodiments provide the gene corresponding to the cDNA sequence of SEQ ID NO:151.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:151, but excluding the poly(A) tail at the 3' end of SEQ ID NO:151; and
      (ab) the nucleotide sequence of the cDNA insert of clone yl14_1 deposited under accession number ATCC 98915;
    (ii) hybridizing said probe(s) to human genomic DNA in conditions at least as stringent as 4×SSC at 50 degrees C.; and
    (iii) isolating the DNA polynucleotides detected with the probe(s);
  and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:151, but excluding the poly(A) tail at the 3' end of SEQ ID NO:151; and
      (bb) the nucleotide sequence of the cDNA insert of clone yl14_1 deposited under accession number ATCC 98915;
    (ii) hybridizing said primer(s) to human genomic DNA in conditions at least as stringent as 4×SSC at 50 degrees C.;
    (iii) amplifying human DNA sequences; and
    (iv) isolating the polynucleotide products of step (b) (iii).

Preferably the polynucleotide isolated according to the above process comprises a nucleotide sequence corresponding to the cDNA sequence of SEQ ID NO:151, and extending contiguously from a nucleotide sequence corresponding to the 5' end of SEQ ID NO:151 to a nucleotide sequence corresponding to the 3' end of SEQ ID NO:151, but excluding the poly(A) tail at the 3' end of SEQ ID NO:151. Also preferably the polynucleotide isolated according to the above process comprises a nucleotide sequence corresponding to the cDNA sequence of SEQ ID NO:151 from nucleotide 119 to nucleotide 415, and extending contiguously from a nucleotide sequence corresponding to the 5' end of said sequence of SEQ ID NO:151 from nucleotide 119 to nucleotide 415, to a nucleotide sequence corresponding to the 3' end of said sequence of SEQ ID NO:151 from nucleotide 119 to nucleotide 415.

In other embodiments, the present invention provides a composition comprising a protein, wherein said protein comprises an amino acid sequence selected from the group consisting of:
  (a) the amino acid sequence of SEQ ID NO:152;
  (b) a fragment of the amino acid sequence of SEQ ID NO:152, the fragment comprising eight contiguous amino acids of SEQ ID NO:152; and
  (c) the amino acid sequence encoded by the cDNA insert of clone yl14_1 deposited under accession number ATCC 98915;
the protein being substantially free from other mammalian proteins. Preferably such protein comprises the amino acid sequence of SEQ ID NO:152. In further preferred embodiments, the present invention provides a protein comprising a fragment of the amino acid sequence of SEQ ID NO:152 having biological activity, the fragment preferably comprising eight (more preferably twenty, most preferably thirty) contiguous amino acids of SEQ ID NO:152, or a protein comprising a fragment of the amino acid sequence of SEQ ID NO:152 having biological activity, the fragment comprising the amino acid sequence from amino acid 44 to amino acid 53 of SEQ ID NO:152.

In one embodiment, the present invention provides a composition comprising an isolated polynucleotide selected from the group consisting of:
  (a) a polynucleotide comprising the nucleotide sequence of SEQ ID NO:153;
  (b) a polynucleotide comprising the nucleotide sequence of SEQ ID NO:153 from nucleotide 96 to nucleotide 377;
  (c) a polynucleotide comprising the nucleotide sequence of SEQ ID NO:153 from nucleotide 225 to nucleotide 377;

(d) a polynucleotide comprising the nucleotide sequence of the full-length protein coding sequence of clone ya80_1 deposited under accession number ATCC 98925;

(e) a polynucleotide encoding the full-length protein encoded by the cDNA insert of clone ya80_1 deposited under accession number ATCC 98925;

(f) a polynucleotide comprising the nucleotide sequence of a mature protein coding sequence of clone ya80_1 deposited under accession number ATCC 98925;

(g) a polynucleotide encoding a mature protein encoded by the cDNA insert of clone ya80_1 deposited under accession number ATCC 98925;

(h) a polynucleotide encoding a protein comprising the amino acid sequence of SEQ ID NO:154;

(i) a polynucleotide encoding a protein comprising a fragment of the amino acid sequence of SEQ ID NO:154 having biological activity, the fragment comprising eight contiguous amino acids of SEQ ID NO:154;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:153.

Preferably, such polynucleotide comprises the nucleotide sequence of SEQ ID NO:153 from nucleotide 96 to nucleotide 377; the nucleotide sequence of SEQ ID NO:153 from nucleotide 225 to nucleotide 377; the nucleotide sequence of the full-length protein coding sequence of clone ya80_1 deposited under accession number ATCC 98925; or the nucleotide sequence of a mature protein coding sequence of clone ya80_1 deposited under accession number ATCC 98925. In other preferred embodiments, the polynucleotide encodes the full-length or a mature protein encoded by the cDNA insert of clone ya80_1 deposited under accession number ATCC 98925. In further preferred embodiments, the present invention provides a polynucleotide encoding a protein comprising a fragment of the amino acid sequence of SEQ ID NO:154 having biological activity, the fragment preferably comprising eight (more preferably twenty, most preferably thirty) contiguous amino acids of SEQ ID NO:154, or a polynucleotide encoding a protein comprising a fragment of the amino acid sequence of SEQ ID NO:154 having biological activity, the fragment comprising the amino acid sequence from amino acid 42 to amino acid 51 of SEQ ID NO:154.

Other embodiments provide the gene corresponding to the cDNA sequence of SEQ ID NO:153.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:153, but excluding the poly(A) tail at the 3' end of SEQ ID NO:153; and
(ab) the nucleotide sequence of the cDNA insert of done ya80_1 deposited under accession number ATCC 98925;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:153, but excluding the poly(A) tail at the 3' end of SEQ ID NO:153; and
(bb) the nucleotide sequence of the cDNA insert of clone ya80_1 deposited under accession number ATCC 98925;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:153, and extending contiguously from a nucleotide sequence corresponding to the 5' end of SEQ ID NO:153 to a nucleotide sequence corresponding to the 3' end of SEQ ID NO:153, but excluding the poly(A) tail at the 3' end of SEQ ID NO:153. Also preferably the polynucleotide isolated according to the above process comprises a nucleotide sequence corresponding to the cDNA sequence of SEQ ID NO:153 from nucleotide 96 to nucleotide 377, and extending contiguously from a nucleotide sequence corresponding to the 5' end of said sequence of SEQ ID NO:153 from nucleotide 96 to nucleotide 377, to a nucleotide sequence corresponding to the 3' end of said sequence of SEQ ID NO:153 from nucleotide 96 to nucleotide 377. Also preferably the polynucleotide isolated according to the above process comprises a nucleotide sequence corresponding to the cDNA sequence of SEQ ID NO:153 from nucleotide 225 to nucleotide 377, and extending contiguously from a nucleotide sequence corresponding to the 5' end of said sequence of SEQ ID NO:153 from nucleotide 225 to nucleotide 377, to a nucleotide sequence corresponding to the 3' end of said sequence of SEQ ID NO:153 from nucleotide 225 to nucleotide 377.

In other embodiments, the present invention provides a composition comprising a protein, wherein said protein comprises an amino acid sequence selected from the group consisting of:

(a) the amino acid sequence of SEQ ID NO:154;

(b) a fragment of the amino acid sequence of SEQ ID NO:154, the fragment comprising eight contiguous amino acids of SEQ ID NO:154; and (c) the amino acid sequence encoded by the cDNA insert of clone ya80_1 deposited under accession number ATCC 98925;

the protein being substantially free from other mammalian proteins. Preferably such protein comprises the amino acid sequence of SEQ ID NO:154. In further preferred embodiments, the present invention provides a protein comprising a fragment of the amino acid sequence of SEQ ID NO:154 having biological activity, the fragment preferably comprising eight (more preferably twenty, most preferably thirty) contiguous amino acids of SEQ ID NO:154, or a protein comprising a fragment of the amino acid sequence of SEQ ID NO:154 having biological activity, the fragment comprising the amino acid sequence from amino acid 42 to amino acid 51 of SEQ ID NO:154.

In one embodiment, the present invention provides a composition comprising an isolated polynucleotide selected from the group consisting of:

(a) a polynucleotide comprising the nucleotide sequence of SEQ ID NO:155;

(b) a polynucleotide comprising the nucleotide sequence of SEQ ID NO:155 from nucleotide 118 to nucleotide 681;

(c) a polynucleotide comprising the nucleotide sequence of SEQ ID NO:155 from nucleotide 622 to nucleotide 681;

(d) a polynucleotide comprising the nucleotide sequence of the full-length protein coding sequence of clone yd61_1 deposited under accession number ATCC 98925;

(e) a polynucleotide encoding the full-length protein encoded by the cDNA insert of clone yd61_1 deposited under accession number ATCC 98925;

(f) a polynucleotide comprising the nucleotide sequence of a mature protein coding sequence of clone yd61_1 deposited under accession number ATCC 98925;

(g) a polynucleotide encoding a mature protein encoded by the cDNA insert of clone yd61_1 deposited under accession number ATCC 98925;

(h) a polynucleotide encoding a protein comprising the amino acid sequence of SEQ ID NO:156;

(i) a polynucleotide encoding a protein comprising a fragment of the amino acid sequence of SEQ ID NO:156 having biological activity, the fragment comprising eight contiguous amino acids of SEQ ID NO:156;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:155.

Preferably, such polynucleotide comprises the nucleotide sequence of SEQ ID NO:155 from nucleotide 118 to nucleotide 681; the nucleotide sequence of SEQ ID NO:155 from nucleotide 622 to nucleotide 681; the nucleotide sequence of the full-length protein coding sequence of clone yd61_1 deposited under accession number ATCC 98925; or the nucleotide sequence of a mature protein coding sequence of clone yd61_1 deposited under accession number ATCC 98925. In other preferred embodiments, the polynucleotide encodes the full-length or a mature protein encoded by the cDNA insert of clone yd61_1 deposited under accession number ATCC 98925. In further preferred embodiments, the present invention provides a polynucleotide encoding a protein comprising a fragment of the amino acid sequence of SEQ ID NO:156 having biological activity, the fragment preferably comprising eight (more preferably twenty, most preferably thirty) contiguous amino acids of SEQ ID NO:156, or a polynucleotide encoding a protein comprising a fragment of the amino acid sequence of SEQ ID NO:156 having biological activity, the fragment comprising the amino acid sequence from amino acid 89 to amino acid 98 of SEQ ID NO:156.

Other embodiments provide the gene corresponding to the cDNA sequence of SEQ ID NO:155.

Further embodiments of the invention provide isolated polynucleotides produced according to a process selected from the group consisting of:

(a) a process comprising the steps of:
 (i) preparing one or more polynucleotide probes that hybridize in 6×SSC at 65 degrees C. to a nucleotide sequence selected from the group consisting of:
  (aa) SEQ ID NO:155, but excluding the poly(A) tail at the 3' end of SEQ ID NO:155; and
  (ab) the nucleotide sequence of the cDNA insert of clone yd61_1 deposited under accession number ATCC 98925;
 (ii) hybridizing said probe(s) to human genomic DNA in conditions at least as stringent as 4×SSC at 50 degrees C.; and
 (iii) isolating the DNA polynucleotides detected with the probe(s);

and (b) a process comprising the steps of:
 (i) preparing one or more polynucleotide primers that hybridize in 6×SSC at 65 degrees C. to a nucleotide sequence selected from the group consisting of:
  (ba) SEQ ID NO:155, but excluding the poly(A) tail at the 3' end of SEQ ID NO:155; and
  (bb) the nucleotide sequence of the cDNA insert of clone yd61_1 deposited under accession number ATCC 98925;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b)(iii).

Preferably the polynucleotide isolated according to the above process comprises a nucleotide sequence corresponding to the cDNA sequence of SEQ ID NO:155, and extending contiguously from a nucleotide sequence corresponding to the 5' end of SEQ ID NO:155 to a nucleotide sequence corresponding to the 3' end of SEQ ID NO:155, but excluding the poly(A) tail at the 3' end of SEQ ID NO:155. Also preferably the polynucleotide isolated according to the above process comprises a nucleotide sequence corresponding to the cDNA sequence of SEQ ID NO:155 from nucleotide 118 to nucleotide 681, and extending contiguously from a nucleotide sequence corresponding to the 5' end of said sequence of SEQ ID NO:155 from nucleotide 118 to nucleotide 681, to a nucleotide sequence corresponding to the 3' end of said sequence of SEQ ID NO:155 from nucleotide 118 to nucleotide 681. Also preferably the polynucleotide isolated according to the above process comprises a nucleotide sequence corresponding to the cDNA sequence of SEQ ID NO:155 from nucleotide 622 to nucleotide 681, and extending contiguously from a nucleotide sequence corresponding to the 5' end of said sequence of SEQ ID NO:155 from nucleotide 622 to nucleotide 681, to a nucleotide sequence corresponding to the 3' end of said sequence of SEQ ID NO:155 from nucleotide 622 to nucleotide 681.

In other embodiments, the present invention provides a composition comprising a protein, wherein said protein comprises an amino acid sequence selected from the group consisting of:

(a) the amino acid sequence of SEQ ID NO:156;

(b) a fragment of the amino acid sequence of SEQ ID NO:156, the fragment comprising eight contiguous amino acids of SEQ ID NO:156; and (c) the amino acid sequence encoded by the cDNA insert of clone yd61_1 deposited under accession number ATCC 98925;

the protein being substantially free from other mammalian proteins. Preferably such protein comprises the amino acid sequence of SEQ ID NO:156. In further preferred embodiments, the present invention provides a protein comprising a fragment of the amino acid sequence of SEQ ID NO:156 having biological activity, the fragment preferably comprising eight (more preferably twenty, most preferably thirty) contiguous amino acids of SEQ ID NO:156, or a protein comprising a fragment of the amino acid sequence of SEQ ID NO:156 having biological activity, the fragment comprising the amino acid sequence from amino acid 89 to amino acid 98 of SEQ ID NO:156.

In one embodiment, the present invention provides a composition comprising an isolated polynucleotide selected from the group consisting of:

(a) a polynucleotide comprising the nucleotide sequence of SEQ ID NO:157;

(b) a polynucleotide comprising the nucleotide sequence of SEQ ID NO:157 from nucleotide 261 to nucleotide 614;

(c) a polynucleotide comprising the nucleotide sequence of the full-length protein coding sequence of clone yd88_1 deposited under accession number ATCC 98925;

(d) a polynucleotide encoding the full-length protein encoded by the cDNA insert of clone yd88_1 deposited under accession number ATCC 98925;

(e) a polynucleotide comprising the nucleotide sequence of a mature protein coding sequence of clone yd88_1 deposited under accession number ATCC 98925;

(f) a polynucleotide encoding a mature protein encoded by the cDNA insert of clone yd88_1 deposited under accession number ATCC 98925;

(g) a polynucleotide encoding a protein comprising the amino acid sequence of SEQ ID NO:158;

(h) a polynucleotide encoding a protein comprising a fragment of the amino acid sequence of SEQ ID NO:158 having biological activity, the fragment comprising eight contiguous amino acids of SEQ ID NO:158;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:157.

Preferably, such polynucleotide comprises the nucleotide sequence of SEQ ID NO:157 from nucleotide 261 to nucleotide 614; the nucleotide sequence of the full-length protein coding sequence of clone yd88_1 deposited under accession number ATCC 98925; or the nucleotide sequence of a mature protein coding sequence of clone yd88_1 deposited under accession number ATCC 98925. In other preferred embodiments, the polynucleotide encodes the full-length or a mature protein encoded by the cDNA insert of clone yd88_1 deposited under accession number ATCC 98925. In further preferred embodiments, the present invention provides a polynucleotide encoding a protein comprising a fragment of the amino acid sequence of SEQ ID NO:158 having biological activity, the fragment preferably comprising eight (more preferably twenty, most preferably thirty) contiguous amino acids of SEQ ID NO:158, or a polynucleotide encoding a protein comprising a fragment of the amino acid sequence of SEQ ID NO:158 having biological activity, the fragment comprising the amino acid sequence from amino acid 54 to amino acid 63 of SEQ ID NO:158.

Other embodiments provide the gene corresponding to the cDNA sequence of SEQ ID NO:157.

Further embodiments of the invention provide isolated polynucleotides produced according to a process selected from the group consisting of:

(a) a process comprising the steps of:
 (i) preparing one or more polynucleotide probes that hybridize in 6×SSC at 65 degrees C. to a nucleotide sequence selected from the group consisting of:
  (aa) SEQ ID NO:157, but excluding the poly(A) tail at the 3' end of SEQ ID NO:157; and
  (ab) the nucleotide sequence of the cDNA insert of clone yd88_1 deposited under accession number ATCC 98925;
 (ii) hybridizing said probe(s) to human genomic DNA in conditions at least as stringent as 4×SSC at 50 degrees C.; and
 (iii) isolating the DNA polynucleotides detected with the probe(s);

and (b) a process comprising the steps of:
 (i) preparing one or more polynucleotide primers that hybridize in 6×SSC at 65 degrees C. to a nucleotide sequence selected from the group consisting of:
  (ba) SEQ ID NO:157, but excluding the poly(A) tail at the 3' end of SEQ ID NO:157; and
  (bb) the nucleotide sequence of the cDNA insert of clone yd88_1 deposited under accession number ATCC 98925;
 (ii) hybridizing said primer(s) to human genomic DNA in conditions at least as stringent as 4×SSC at 50 degrees C.;
 (iii) amplifying human DNA sequences; and
 (iv) isolating the polynucleotide products of step (b) (iii).

Preferably the polynucleotide isolated according to the above process comprises a nucleotide sequence corresponding to the cDNA sequence of SEQ ID NO:157, and extending contiguously from a nucleotide sequence corresponding to the 5' end of SEQ ID NO:157 to a nucleotide sequence corresponding to the 3' end of SEQ ID NO:157, but excluding the poly(A) tail at the 3' end of SEQ ID NO:157. Also preferably the polynucleotide isolated according to the above process comprises a nucleotide sequence corresponding to the cDNA sequence of SEQ ID NO:157 from nucleotide 261 to nucleotide 614, and extending contiguously from a nucleotide sequence corresponding to the 5' end of said sequence of SEQ ID NO:157 from nucleotide 261 to nucleotide 614, to a nucleotide sequence corresponding to the 3' end of said sequence of SEQ ID NO:157 from nucleotide 261 to nucleotide 614.

In other embodiments, the present invention provides a composition comprising a protein, wherein said protein comprises an amino acid sequence selected from the group consisting of:

(a) the amino acid sequence of SEQ ID NO:158;

(b) a fragment of the amino acid sequence of SEQ ID NO:158, the fragment comprising eight contiguous amino acids of SEQ ID NO:158; and (c) the amino acid sequence encoded by the cDNA insert of clone yd88_1 deposited under accession number ATCC 98925;

the protein being substantially free from other mammalian proteins. Preferably such protein comprises the amino acid sequence of SEQ ID NO:158. In further preferred embodiments, the present invention provides a protein comprising a fragment of the amino acid sequence of SEQ ID NO:158 having biological activity, the fragment preferably comprising eight (more preferably twenty, most preferably thirty) contiguous amino acids of SEQ ID NO:158, or a protein comprising a fragment of the amino acid sequence of SEQ ID NO:158 having biological activity, the fragment comprising the amino acid sequence from amino acid 54 to amino acid 63 of SEQ ID NO:158.

In one embodiment, the present invention provides a composition comprising an isolated polynucleotide selected from the group consisting of:
- (a) a polynucleotide comprising the nucleotide sequence of SEQ ID NO:159;
- (b) a polynucleotide comprising the nucleotide sequence of SEQ ID NO:159 from nucleotide 26 to nucleotide 475;
- (c) a polynucleotide comprising the nucleotide sequence of the full-length protein coding sequence of clone yd109_1 deposited under accession number ATCC 98925;
- (d) a polynucleotide encoding the full-length protein encoded by the cDNA insert of clone yd109_1 deposited under accession number ATCC 98925;
- (e) a polynucleotide comprising the nucleotide sequence of a mature protein coding sequence of clone yd109_1 deposited under accession number ATCC 98925;
- (f) a polynucleotide encoding a mature protein encoded by the cDNA insert of clone yd109_1 deposited under accession number ATCC 98925;
- (g) a polynucleotide encoding a protein comprising the amino acid sequence of SEQ ID NO:160;
- (h) a polynucleotide encoding a protein comprising a fragment of the amino acid sequence of SEQ ID NO:160 having biological activity, the fragment comprising eight contiguous amino acids of SEQ ID NO:160;
- (i) a polynucleotide which is an allelic variant of a polynucleotide of (a)–(f) above;
- (j) a polynucleotide which encodes a species homologue of the protein of (g) or (h) above;
- (k) a polynucleotide that hybridizes under stringent conditions to any one of the polynucleotides specified in (a)–(h); and
- (l) a polynucleotide that hybridizes under stringent conditions to any one of the polynucleotides specified in (a)–(h) and that has a length that is at least 25% of the length of SEQ ID NO:159.

Preferably, such polynucleotide comprises the nucleotide sequence of SEQ ID NO:159 from nucleotide 26 to nucleotide 475; the nucleotide sequence of the full-length protein coding sequence of clone yd109_1 deposited under accession number ATCC 98925; or the nucleotide sequence of a mature protein coding sequence of clone yd109_1 deposited under accession number ATCC 98925. In other preferred embodiments, the polynucleotide encodes the full-length or a mature protein encoded by the cDNA insert of clone yd109_1 deposited under accession number ATCC 98925. In further preferred embodiments, the present invention provides a polynucleotide encoding a protein comprising a fragment of the amino acid sequence of SEQ ID NO:160 having biological activity, the fragment preferably comprising eight (more preferably twenty, most preferably thirty) contiguous amino acids of SEQ ID NO:160, or a polynucleotide encoding a protein comprising a fragment of the amino acid sequence of SEQ ID NO:160 having biological activity, the fragment comprising the amino acid sequence from amino acid 70 to amino acid 79 of SEQ ID NO:160.

Other embodiments provide the gene corresponding to the cDNA sequence of SEQ ID NO:159.

Further embodiments of the invention provide isolated polynucleotides produced according to a process selected from the group consisting of:
- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:159, but excluding the poly(A) tail at the 3' end of SEQ ID NO:159; and
    - (ab) the nucleotide sequence of the cDNA insert of clone yd109_1 deposited under accession number ATCC 98925;
  - (ii) hybridizing said probe(s) to human genomic DNA in conditions at least as stringent as 4×SSC at 50 degrees C.; and
  - (iii) isolating the DNA polynucleotides detected with the probe(s);

and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:159, but excluding the poly(A) tail at the 3' end of SEQ ID NO:159; and
    - (bb) the nucleotide sequence of the cDNA insert of done yd109_1 deposited under accession number ATCC 98925;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b) (iii).

Preferably the polynucleotide isolated according to the above process comprises a nucleotide sequence corresponding to the cDNA sequence of SEQ ID NO:159, and extending contiguously from a nucleotide sequence corresponding to the 5' end of SEQ ID NO:159 to a nucleotide sequence corresponding to the 3' end of SEQ ID NO:159, but excluding the poly(A) tail at the 3' end of SEQ ID NO:159. Also preferably the polynucleotide isolated according to the above process comprises a nucleotide sequence corresponding to the cDNA sequence of SEQ ID NO:159 from nucleotide 26 to nucleotide 475, and extending contiguously from a nucleotide sequence corresponding to the 5' end of said sequence of SEQ ID NO:159 from nucleotide 26 to nucleotide 475, to a nucleotide sequence corresponding to the 3' end of said sequence of SEQ ID NO:159 from nucleotide 26 to nucleotide 475.

In other embodiments, the present invention provides a composition comprising a protein, wherein said protein comprises an amino acid sequence selected from the group consisting of:
- (a) the amino acid sequence of SEQ ID NO:160;
- (b) a fragment of the amino acid sequence of SEQ ID NO:160, the fragment comprising eight contiguous amino acids of SEQ ID NO:160; and
- (c) the amino acid sequence encoded by the cDNA insert of clone yd109_1 deposited under accession number ATCC 98925;

the protein being substantially free from other mammalian proteins. Preferably such protein comprises the amino acid sequence of SEQ ID NO:160. In further preferred embodiments, the present invention provides a protein comprising a fragment of the amino acid sequence of SEQ ID NO:160 having biological activity, the fragment preferably comprising eight (more preferably twenty, most preferably thirty) contiguous amino acids of SEQ ID NO:160, or a protein comprising a fragment of the amino acid sequence of SEQ ID NO:160 having biological activity, the fragment comprising the amino acid sequence from amino acid 70 to amino acid 79 of SEQ ID NO:160.

In one embodiment, the present invention provides a composition comprising an isolated polynucleotide selected from the group consisting of:
- (a) a polynucleotide comprising the nucleotide sequence of SEQ ID NO:161;
- (b) a polynucleotide comprising the nucleotide sequence of SEQ ID NO:161 from nucleotide 79 to nucleotide 474;
- (c) a polynucleotide comprising the nucleotide sequence of the full-length protein coding sequence of clone yd141_1 deposited under accession number ATCC 98925;
- (d) a polynucleotide encoding the full-length protein encoded by the cDNA insert of clone yd141_1 deposited under accession number ATCC 98925;
- (e) a polynucleotide comprising the nucleotide sequence of a mature protein coding sequence of clone yd141_1 deposited under accession number ATCC 98925;
- (f) a polynucleotide encoding a mature protein encoded by the cDNA insert of clone yd141_1 deposited under accession number ATCC 98925;
- (g) a polynucleotide encoding a protein comprising the amino acid sequence of SEQ ID NO:162;
- (h) a polynucleotide encoding a protein comprising a fragment of the amino acid sequence of SEQ ID NO:162 having biological activity, the fragment comprising eight contiguous amino acids of SEQ ID NO:162;
- (i) a polynucleotide which is an allelic variant of a polynucleotide of (a)–(f) above;
- (j) a polynucleotide which encodes a species homologue of the protein of (g) or (h) above;
- (k) a polynucleotide that hybridizes under stringent conditions to any one of the polynucleotides specified in (a)–(h); and
- (l) a polynucleotide that hybridizes under stringent conditions to any one of the polynucleotides specified in (a)–(h) and that has a length that is at least 25% of the length of SEQ ID NO:161.

Preferably, such polynucleotide comprises the nucleotide sequence of SEQ ID NO:161 from nucleotide 79 to nucleotide 474; the nucleotide sequence of the full-length protein coding sequence of clone yd141_1 deposited under accession number ATCC 98925; or the nucleotide sequence of a mature protein coding sequence of clone yd141_1 deposited under accession number ATCC 98925. In other preferred embodiments, the polynucleotide encodes the full-length or a mature protein encoded by the cDNA insert of clone yd141_1 deposited under accession number ATCC 98925. In further preferred embodiments, the present invention provides a polynucleotide encoding a protein comprising a fragment of the amino acid sequence of SEQ ID NO:162 having biological activity, the fragment preferably comprising eight (more preferably twenty, most preferably thirty) contiguous amino acids of SEQ ID NO:162, or a polynucleotide encoding a protein comprising a fragment of the amino acid sequence of SEQ ID NO:162 having biological activity, the fragment comprising the amino acid sequence from amino acid 61 to amino acid 70 of SEQ ID NO:162.

Other embodiments provide the gene corresponding to the cDNA sequence of SEQ ID NO:161.

Further embodiments of the invention provide isolated polynucleotides produced according to a process selected from the group consisting of:
- (a) a process comprising the steps of:
  - (i) preparing one or more polynucleotide probes that hybridize in 6×SSC at 65 degrees C. to a nucleotide sequence selected from the group consisting of:
    - (aa) SEQ ID NO:161, but excluding the poly(A) tail at the 3' end of SEQ ID NO:161; and
    - (ab) the nucleotide sequence of the cDNA insert of done yd141_1 deposited under accession number ATCC 98925;
  - (ii) hybridizing said probe(s) to human genomic DNA in conditions at least as stringent as 4×SSC at 50 degrees C.; and
  - (iii) isolating the DNA polynucleotides detected with the probe(s);

and
- (b) a process comprising the steps of:
  - (i) preparing one or more polynucleotide primers that hybridize in 6×SSC at 65 degrees C. to a nucleotide sequence selected from the group consisting of:
    - (ba) SEQ ID NO:161, but excluding the poly(A) tail at the 3' end of SEQ ID NO:161; and
    - (bb) the nucleotide sequence of the cDNA insert of done yd141_1 deposited under accession number ATCC 98925;
  - (ii) hybridizing said primer(s) to human genomic DNA in conditions at least as stringent as 4×SSC at 50 degrees C.;
  - (iii) amplifying human DNA sequences; and
  - (iv) isolating the polynucleotide products of step (b) (iii).

Preferably the polynucleotide isolated according to the above process comprises a nucleotide sequence corresponding to the cDNA sequence of SEQ ID NO:161, and extending contiguously from a nucleotide sequence corresponding to the 5' end of SEQ ID NO:161 to a nucleotide sequence corresponding to the 3' end of SEQ ID NO:161, but excluding the poly(A) tail at the 3' end of SEQ ID NO:161. Also preferably the polynucleotide isolated according to the above process comprises a nucleotide sequence corresponding to the cDNA sequence of SEQ ID NO:161 from nucleotide 79 to nucleotide 474, and extending contiguously from a nucleotide sequence corresponding to the 5' end of said sequence of SEQ ID NO:161 from nucleotide 79 to nucleotide 474, to a nucleotide sequence corresponding to the 3' end of said sequence of SEQ ID NO:161 from nucleotide 79 to nucleotide 474.

In other embodiments, the present invention provides a composition comprising a protein, wherein said protein comprises an amino acid sequence selected from the group consisting of:
- (a) the amino acid sequence of SEQ ID NO:162;
- (b) a fragment of the amino acid sequence of SEQ ID NO:162, the fragment comprising eight contiguous amino acids of SEQ ID NO:162; and
- (c) the amino acid sequence encoded by the cDNA insert of clone yd141_1 deposited under accession number ATCC 98925;

the protein being substantially free from other mammalian proteins. Preferably such protein comprises the amino acid sequence of SEQ ID NO:162. In further preferred embodiments, the present invention provides a protein comprising a fragment of the amino acid sequence of SEQ ID NO:162 having biological activity, the fragment preferably comprising eight (more preferably twenty, most preferably thirty) contiguous amino acids of SEQ ID NO:162, or a protein comprising a fragment of the amino acid sequence of SEQ ID NO:162 having biological activity, the fragment comprising the amino acid sequence from amino acid 61 to amino acid 70 of SEQ ID NO:162.

In one embodiment, the present invention provides a composition comprising an isolated polynucleotide selected from the group consisting of:

(a) a polynucleotide comprising the nucleotide sequence of SEQ ID NO:163;

(b) a polynucleotide comprising the nucleotide sequence of SEQ ID NO:163 from nucleotide 45 to nucleotide 347;

(c) a polynucleotide comprising the nucleotide sequence of SEQ ID NO:163 from nucleotide 135 to nucleotide 347;

(d) a polynucleotide comprising the nucleotide sequence of the full-length protein coding sequence of clone yd153_1 deposited under accession number ATCC 98925;

(e) a polynucleotide encoding the full-length protein encoded by the cDNA insert of clone yd153_1 deposited under accession number ATCC 98925;

(f) a polynucleotide comprising the nucleotide sequence of a mature protein coding sequence of clone yd153_1 deposited under accession number ATCC 98925;

(g) a polynucleotide encoding a mature protein encoded by the cDNA insert of clone yd153_1 deposited under accession number ATCC 98925;

(h) a polynucleotide encoding a protein comprising the amino acid sequence of SEQ ID NO:164;

(i) a polynucleotide encoding a protein comprising a fragment of the amino acid sequence of SEQ ID NO:164 having biological activity, the fragment comprising eight contiguous amino acids of SEQ ID NO:164;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:163.

Preferably, such polynucleotide comprises the nucleotide sequence of SEQ ID NO:163 from nucleotide 45 to nucleotide 347; the nucleotide sequence of SEQ ID NO:163 from nucleotide 135 to nucleotide 347; the nucleotide sequence of the full-length protein coding sequence of clone yd153_1 deposited under accession number ATCC 98925; or the nucleotide sequence of a mature protein coding sequence of clone yd153_1 deposited under accession number ATCC 98925. In other preferred embodiments, the polynucleotide encodes the full-length or a mature protein encoded by the cDNA insert of clone yd153_1 deposited under accession number ATCC 98925. In further preferred embodiments, the present invention provides a polynucleotide encoding a protein comprising a fragment of the amino acid sequence of SEQ ID NO:164 having biological activity, the fragment preferably comprising eight (more preferably twenty, most preferably thirty) contiguous amino acids of SEQ ID NO:164, or a polynucleotide encoding a protein comprising a fragment of the amino acid sequence of SEQ ID NO:164 having biological activity, the fragment comprising the amino acid sequence from amino acid 45 to amino acid 54 of SEQ ID NO:164.

Other embodiments provide the gene corresponding to the cDNA sequence of SEQ ID NO:163.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:163, but excluding the poly(A) tail at the 3' end of SEQ ID NO:163; and
(ab) the nucleotide sequence of the cDNA insert of clone yd153_1 deposited under accession number ATCC 98925;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:163, but excluding the poly(A) tail at the 3' end of SEQ ID NO:163; and
(bb) the nucleotide sequence of the cDNA insert of clone yd153_1 deposited under accession number ATCC 98925;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:163, and extending contiguously from a nucleotide sequence corresponding to the 5' end of SEQ ID NO:163 to a nucleotide sequence corresponding to the 3' end of SEQ ID NO:163, but excluding the poly(A) tail at the 3' end of SEQ ID NO:163. Also preferably the polynucleotide isolated according to the above process comprises a nucleotide sequence corresponding to the cDNA sequence of SEQ ID NO:163 from nucleotide 45 to nucleotide 347, and extending contiguously from a nucleotide sequence corresponding to the 5' end of said sequence of SEQ ID NO:163 from nucleotide 45 to nucleotide 347, to a nucleotide sequence corresponding to the 3' end of said sequence of SEQ ID NO:163 from nucleotide 45 to nucleotide 347. Also preferably the polynucleotide isolated according to the above process comprises a nucleotide sequence corresponding to the cDNA sequence of SEQ ID NO:163 from nucleotide 135 to nucleotide 347, and extending contiguously from a nucleotide sequence corresponding to the 5' end of said sequence of SEQ ID NO:163 from nucleotide 135 to nucleotide 347, to a nucleotide sequence corresponding to the 3' end of said sequence of SEQ ID NO:163 from nucleotide 135 to nucleotide 347.

In other embodiments, the present invention provides a composition comprising a protein, wherein said protein comprises an amino acid sequence selected from the group consisting of:

(a) the amino acid sequence of SEQ ID NO:164;

(b) a fragment of the amino acid sequence of SEQ ID NO:164, the fragment comprising eight contiguous amino acids of SEQ ID NO:164; and (c) the amino acid sequence encoded by the cDNA insert of clone yd153_1 deposited under accession number ATCC 98925;

the protein being substantially free from other mammalian proteins. Preferably such protein comprises the amino acid sequence of SEQ ID NO:164. In further preferred embodiments, the present invention provides a protein comprising a fragment of the amino acid sequence of SEQ ID NO:164 having biological activity, the fragment preferably comprising eight (more preferably twenty, most preferably thirty) contiguous amino acids of SEQ ID NO:164, or a protein comprising a fragment of the amino acid sequence of SEQ ID NO:164 having biological activity, the fragment comprising the amino acid sequence from amino acid 45 to amino acid 54 of SEQ ID NO:164.

In one embodiment, the present invention provides a composition comprising an isolated polynucleotide selected from the group consisting of:

(a) a polynucleotide comprising the nucleotide sequence of SEQ ID NO:165;

(b) a polynucleotide comprising the nucleotide sequence of SEQ ID NO:165 from nucleotide 114 to nucleotide 470;

(c) a polynucleotide comprising the nucleotide sequence of the full-length protein coding sequence of clone yd165_1 deposited under accession number ATCC 98925;

(d) a polynucleotide encoding the full-length protein encoded by the cDNA insert of clone yd165_1 deposited under accession number ATCC 98925;

(e) a polynucleotide comprising the nucleotide sequence of a mature protein coding sequence of clone yd165_1 deposited under accession number ATCC 98925;

(f) a polynucleotide encoding a mature protein encoded by the cDNA insert of clone yd165_1 deposited under accession number ATCC 98925;

(g) a polynucleotide encoding a protein comprising the amino acid sequence of SEQ ID NO:166;

(h) a polynucleotide encoding a protein comprising a fragment of the amino acid sequence of SEQ ID NO:166 having biological activity, the fragment comprising eight contiguous amino acids of SEQ ID NO:166;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:165.

Preferably, such polynucleotide comprises the nucleotide sequence of SEQ ID NO:165 from nucleotide 114 to nucleotide 470; the nucleotide sequence of the full-length protein coding sequence of clone yd165_1 deposited under accession number ATCC 98925; or the nucleotide sequence of a mature protein coding sequence of clone yd165_1 deposited under accession number ATCC 98925. In other preferred embodiments, the polynucleotide encodes the full-length or a mature protein encoded by the cDNA insert of clone yd165_1 deposited under accession number ATCC 98925. In further preferred embodiments, the present invention provides a polynucleotide encoding a protein comprising a fragment of the amino acid sequence of SEQ ID NO:166 having biological activity, the fragment preferably comprising eight (more preferably twenty, most preferably thirty) contiguous amino acids of SEQ ID NO:166, or a polynucleotide encoding a protein comprising a fragment of the amino acid sequence of SEQ ID NO:166 having biological activity, the fragment comprising the amino acid sequence from amino acid 54 to amino acid 63 of SEQ ID NO:166.

Other embodiments provide the gene corresponding to the cDNA sequence of SEQ ID NO:165.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:165, but excluding the poly(A) tail at the 3' end of SEQ ID NO:165; and
    (ab) the nucleotide sequence of the cDNA insert of clone yd165_1 deposited under accession number ATCC 98925;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:165, but excluding the poly(A) tail at the 3' end of SEQ ID NO:165; and
    (bb) the nucleotide sequence of the cDNA insert of clone yd165_1 deposited under accession number ATCC 98925;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:165, and extending contiguously from a nucleotide sequence corresponding to the 5' end of SEQ ID NO:165 to a nucleotide sequence corresponding to the 3' end of SEQ ID NO:165, but excluding the poly(A) tail at the 3' end of SEQ ID NO:165. Also preferably the polynucleotide isolated according to the above process comprises a nucleotide sequence corresponding to the cDNA sequence of SEQ ID NO:165 from nucleotide 114 to nucleotide 470, and extending contiguously from a nucleotide sequence corresponding to the 5' end of said sequence of SEQ ID NO:165 from nucleotide 114 to nucleotide 470, to a nucleotide sequence corresponding to the 3' end of said sequence of SEQ ID NO:165 from nucleotide 114 to nucleotide 470.

In other embodiments, the present invention provides a composition comprising a protein, wherein said protein comprises an amino acid sequence selected from the group consisting of:

(a) the amino acid sequence of SEQ ID NO:166;
(b) a fragment of the amino acid sequence of SEQ ID NO:166, the fragment comprising eight contiguous amino acids of SEQ ID NO:166; and
(c) the amino acid sequence encoded by the cDNA insert of clone yd165_1 deposited under accession number ATCC 98925;

the protein being substantially free from other mammalian proteins. Preferably such protein comprises the amino acid sequence of SEQ ID NO:166. In further preferred embodiments, the present invention provides a protein comprising a fragment of the amino acid sequence of SEQ ID NO:166 having biological activity, the fragment preferably comprising eight (more preferably twenty, most preferably thirty) contiguous amino acids of SEQ ID NO:166, or a protein comprising a fragment of the amino acid sequence of SEQ ID NO:166 having biological activity, the fragment comprising the amino acid sequence from amino acid 54 to amino acid 63 of SEQ ID NO:166.

In one embodiment, the present invention provides a composition comprising an isolated polynucleotide selected from the group consisting of:

(a) a polynucleotide comprising the nucleotide sequence of SEQ ID NO:167;
(b) a polynucleotide comprising the nucleotide sequence of SEQ ID NO:167 from nucleotide 82 to nucleotide 663;
(c) a polynucleotide comprising the nucleotide sequence of SEQ ID NO:167 from nucleotide 139 to nucleotide 663;
(d) a polynucleotide comprising the nucleotide sequence of the full-length protein coding sequence of clone yd178_1 deposited under accession number ATCC 98925;
(e) a polynucleotide encoding the full-length protein encoded by the cDNA insert of clone yd178_1 deposited under accession number ATCC 98925;
(f) a polynucleotide comprising the nucleotide sequence of a mature protein coding sequence of clone yd178_1 deposited under accession number ATCC 98925;
(g) a polynucleotide encoding a mature protein encoded by the cDNA insert of clone yd178_1 deposited under accession number ATCC 98925;
(h) a polynucleotide encoding a protein comprising the amino acid sequence of SEQ ID NO:168;
(i) a polynucleotide encoding a protein comprising a fragment of the amino acid sequence of SEQ ID NO:168 having biological activity, the fragment comprising eight contiguous amino acids of SEQ ID NO:168;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:167.

Preferably, such polynucleotide comprises the nucleotide sequence of SEQ ID NO:167 from nucleotide 82 to nucleotide 663; the nucleotide sequence of SEQ ID NO:167 from nucleotide 139 to nucleotide 663; the nucleotide sequence of the full-length protein coding sequence of clone yd178_1 deposited under accession number ATCC 98925; or the nucleotide sequence of a mature protein coding sequence of clone yd178_1 deposited under accession number ATCC 98925. In other preferred embodiments, the polynucleotide encodes the full-length or a mature protein encoded by the cDNA insert of clone yd178_1 deposited under accession number ATCC 98925. In further preferred embodiments, the present invention provides a polynucleotide encoding a protein comprising a fragment of the amino acid sequence of SEQ ID NO:168 having biological activity, the fragment preferably comprising eight (more preferably twenty, most preferably thirty) contiguous amino acids of SEQ ID NO:168, or a polynucleotide encoding a protein comprising a fragment of the amino acid sequence of SEQ ID NO:168 having biological activity, the fragment comprising the amino acid sequence from amino acid 92 to amino acid 101 of SEQ ID NO:168.

Other embodiments provide the gene corresponding to the cDNA sequence of SEQ ID NO:167.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:167, but excluding the poly(A) tail at the 3' end of SEQ ID NO:167; and
(ab) the nucleotide sequence of the cDNA insert of clone yd178_1 deposited under accession number ATCC 98925;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:167, but excluding the poly(A) tail at the 3' end of SEQ ID NO:167; and
(bb) the nucleotide sequence of the cDNA insert of clone yd178_1 deposited under accession number ATCC 98925;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:167, and extending contiguously from a nucleotide sequence corresponding to the 5' end of SEQ ID NO:167 to a nucleotide sequence corresponding to the 3' end of SEQ ID NO:167, but excluding the poly(A) tail at the 3' end of SEQ ID NO:167. Also preferably the polynucleotide isolated according to the above process comprises a nucleotide sequence corresponding to the cDNA sequence of SEQ ID NO:167 from nucleotide 82 to nucleotide 663, and extending contiguously from a nucleotide sequence corresponding to the 5' end of said sequence of SEQ ID NO:167 from nucleotide 82 to nucleotide 663, to a nucleotide sequence corresponding to the 3' end of said sequence of SEQ ID NO:167 from nucleotide 82 to nucleotide 663. Also preferably the polynucleotide isolated according to the above process comprises a nucleotide sequence corresponding to the cDNA sequence of SEQ ID NO:167 from nucleotide 139 to nucleotide 663, and extending contiguously from a nucleotide sequence corresponding to the 5' end of said sequence of SEQ ID NO:167 from nucleotide 139 to nucleotide 663, to a nucleotide sequence corresponding to the 3' end of said sequence of SEQ ID NO:167 from nucleotide 139 to nucleotide 663.

In other embodiments, the present invention provides a composition comprising a protein, wherein said protein comprises an amino acid sequence selected from the group consisting of:

(a) the amino acid sequence of SEQ ID NO:168;
(b) a fragment of the amino acid sequence of SEQ ID NO:168, the fragment comprising eight contiguous amino acids of SEQ ID NO:168; and
(c) the amino acid sequence encoded by the cDNA insert of clone yd178_1 deposited under accession number ATCC 98925;

the protein being substantially free from other mammalian proteins. Preferably such protein comprises the amino acid sequence of SEQ ID NO:168. In further preferred embodiments, the present invention provides a protein comprising a fragment of the amino acid sequence of SEQ ID NO:168 having biological activity, the fragment preferably comprising eight (more preferably twenty, most preferably thirty) contiguous amino acids of SEQ ID NO:168, or a protein comprising a fragment of the amino acid sequence of SEQ ID NO:168 having biological activity, the fragment comprising the amino acid sequence from amino acid 92 to amino acid 101 of SEQ ID NO:168.

In one embodiment, the present invention provides a composition comprising an isolated polynucleotide selected from the group consisting of:

(a) a polynucleotide comprising the nucleotide sequence of SEQ ID NO:169;
(b) a polynucleotide comprising the nucleotide sequence of SEQ ID NO:169 from nucleotide 121 to nucleotide 450;
(c) a polynucleotide comprising the nucleotide sequence of the full-length protein coding sequence of clone yd191_1 deposited under accession number ATCC 98925;
(d) a polynucleotide encoding the full-length protein encoded by the cDNA insert of clone yd191_1 deposited under accession number ATCC 98925;
(e) a polynucleotide comprising the nucleotide sequence of a mature protein coding sequence of clone yd191_1 deposited under accession number ATCC 98925;
(f) a polynucleotide encoding a mature protein encoded by the cDNA insert of clone yd191_1 deposited under accession number ATCC 98925;
(g) a polynucleotide encoding a protein comprising the amino acid sequence of SEQ ID NO: 170;
(h) a polynucleotide encoding a protein comprising a fragment of the amino acid sequence of SEQ ID NO:170 having biological activity, the fragment comprising eight contiguous amino acids of SEQ ID NO:170;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:169.

Preferably, such polynucleotide comprises the nucleotide sequence of SEQ ID NO: 169 from nucleotide 121 to nucleotide 450; the nucleotide sequence of the full length protein coding sequence of clone yd191_1 deposited under accession number ATCC 98925; or the nucleotide sequence of a mature protein coding sequence of clone yd191_1 deposited under accession number ATCC 98925. In other preferred embodiments, the polynucleotide encodes the full length or a mature protein encoded by the cDNA insert of clone yd191_1 deposited under accession number ATCC 98925. In further preferred embodiments, the present invention provides a polynucleotide encoding a protein comprising a fragment of the amino acid sequence of SEQ ID NO:170 having biological activity, the fragment preferably comprising eight (more preferably twenty, most preferably thirty) contiguous amino acids of SEQ ID NO:170, or a polynucleotide encoding a protein comprising a fragment of the amino acid sequence of SEQ ID NO:170 having biological activity, the fragment comprising the amino acid sequence from amino acid 50 to amino acid 59 of SEQ ID NO:170.

Other embodiments provide the gene corresponding to the cDNA sequence of SEQ ID NO:169.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:169, but excluding the poly(A) tail at the 3' end of SEQ ID NO:169; and
    (ab) the nucleotide sequence of the cDNA insert of clone yd191_1 deposited under accession number ATCC 98925;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:169, but excluding the poly(A) tail at the 3' end of SEQ ID NO:169; and
    (bb) the nucleotide sequence of the cDNA insert of clone yd191_1 deposited under accession number ATCC 98925;
  (ii) hybridizing said primer(s) to human genomic DNA in conditions at least as stringent as 4×SSC at 50 degrees C.;

(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:169, and extending contiguously from a nucleotide sequence corresponding to the 5' end of SEQ ID NO:169 to a nucleotide sequence corresponding to the 3' end of SEQ ID NO:169, but excluding the poly(A) tail at the 3' end of SEQ ID NO:169. Also preferably the polynucleotide isolated according to the above process comprises a nucleotide sequence corresponding to the cDNA sequence of SEQ ID NO:169 from nucleotide 121 to nucleotide 450, and extending contiguously from a nucleotide sequence corresponding to the 5' end of said sequence of SEQ ID NO:169 from nucleotide 121 to nucleotide 450, to a nucleotide sequence corresponding to the 3' end of said sequence of SEQ ID NO:169 from nucleotide 121 to nucleotide 450.

In other embodiments, the present invention provides a composition comprising a protein, wherein said protein comprises an amino acid sequence selected from the group consisting of:

(a) the amino acid sequence of SEQ ID NO:170;
(b) a fragment of the amino acid sequence of SEQ ID NO:170, the fragment comprising eight contiguous amino acids of SEQ ID NO:170; and
(c) the amino acid sequence encoded by the cDNA insert of clone yd191_1 deposited under accession number ATCC 98925;

the protein being substantially free from other mammalian proteins. Preferably such protein comprises the amino acid sequence of SEQ ID NO:170. In further preferred embodiments, the present invention provides a protein comprising a fragment of the amino acid sequence of SEQ ID NO:170 having biological activity, the fragment preferably comprising eight (more preferably twenty, most preferably thirty) contiguous amino acids of SEQ ID NO:170, or a protein comprising a fragment of the amino acid sequence of SEQ ID NO:170 having biological activity, the fragment comprising the amino acid sequence from amino acid 50 to amino acid 59 of SEQ ID NO:170.

In one embodiment, the present invention provides a composition comprising an isolated polynucleotide selected from the group consisting of:

(a) a polynucleotide comprising the nucleotide sequence of SEQ ID NO:171;
(b) a polynucleotide comprising the nucleotide sequence of SEQ ID NO:171 from nucleotide 33 to nucleotide 494;
(c) a polynucleotide comprising the nucleotide sequence of the full-length protein coding sequence of clone ye7_1 deposited under accession number ATCC 98924;
(d) a polynucleotide encoding the full-length protein encoded by the cDNA insert of clone ye7_1 deposited under accession number ATCC 98924;
(e) a polynucleotide comprising the nucleotide sequence of a mature protein coding sequence of clone ye7_1 deposited under accession number ATCC 98924;
(f) a polynucleotide encoding a mature protein encoded by the cDNA insert of clone ye7_1 deposited under accession number ATCC 98924;
(g) a polynucleotide encoding a protein comprising the amino acid sequence of SEQ ID NO:172;
(h) a polynucleotide encoding a protein comprising a fragment of the amino acid sequence of SEQ ID NO:172 having biological activity, the fragment comprising eight contiguous amino acids of SEQ ID NO:172;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:171.

Preferably, such polynucleotide comprises the nucleotide sequence of SEQ ID NO:171 from nucleotide 33 to nucleotide 494; the nucleotide sequence of the full-length protein coding sequence of clone ye7_1 deposited under accession number ATCC 98924; or the nucleotide sequence of a mature protein coding sequence of clone ye7_1 deposited under accession number ATCC 98924. In other preferred embodiments, the polynucleotide encodes the full-length or a mature protein encoded by the cDNA insert of clone ye7_1 deposited under accession number ATCC 98924. In further preferred embodiments, the present invention provides a polynucleotide encoding a protein comprising a fragment of the amino acid sequence of SEQ ID NO:172 having biological activity, the fragment preferably comprising eight (more preferably twenty, most preferably thirty) contiguous amino acids of SEQ ID NO:172, or a polynucleotide encoding a protein comprising a fragment of the amino acid sequence of SEQ ID NO:172 having biological activity, the fragment comprising the amino acid sequence from amino acid 72 to amino acid 81 of SEQ ID NO:172.

Other embodiments provide the gene corresponding to the cDNA sequence of SEQ ID NO:171.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:171, but excluding the poly(A) tail at the 3' end of SEQ ID NO:171; and
(ab) the nucleotide sequence of the cDNA insert of done ye7_1 deposited under accession number ATCC 98924;
(ii) hybridizing said probe(s) to human genomic DNA in conditions at least as stringent as 4×SSC at 50 degrees C.; and
(iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:171, but excluding the poly(A) tail at the 3' end of SEQ ID NO:171; and
(bb) the nucleotide sequence of the cDNA insert of clone ye7_1 deposited under accession number ATCC 98924;
(ii) hybridizing said primer(s) to human genomic DNA in conditions at least as stringent as 4×SSC at 50 degrees C.;

(iii) amplifying human DNA sequences; and
(iv) isolating the polynucleotide products of step (b)(iii).

Preferably the polynucleotide isolated according to the above process comprises a nucleotide sequence corresponding to the cDNA sequence of SEQ ID NO:171, and extending contiguously from a nucleotide sequence corresponding to the 5' end of SEQ ID NO:171 to a nucleotide sequence corresponding to the 3' end of SEQ ID NO:171, but excluding the poly(A) tail at the 3' end of SEQ ID NO:171. Also preferably the polynucleotide isolated according to the above process comprises a nucleotide sequence corresponding to the cDNA sequence of SEQ ID NO:171 from nucleotide 33 to nucleotide 494, and extending contiguously from a nucleotide sequence corresponding to the 5' end of said sequence of SEQ ID NO:171 from nucleotide 33 to nucleotide 494, to a nucleotide sequence corresponding to the 3' end of said sequence of SEQ ID NO:171 from nucleotide 33 to nucleotide 494.

In other embodiments, the present invention provides a composition comprising a protein, wherein said protein comprises an amino acid sequence selected from the group consisting of:
(a) the amino acid sequence of SEQ ID NO:172;
(b) a fragment of the amino acid sequence of SEQ ID NO:172, the fragment comprising eight contiguous amino acids of SEQ ID NO:172; and
(c) the amino acid sequence encoded by the cDNA insert of clone ye7_1 deposited under accession number ATCC 98924;
the protein being substantially free from other mammalian proteins. Preferably such protein comprises the amino acid sequence of SEQ ID NO:172. In further preferred embodiments, the present invention provides a protein comprising a fragment of the amino acid sequence of SEQ ID NO:172 having biological activity, the fragment preferably comprising eight (more preferably twenty, most preferably thirty) contiguous amino acids of SEQ ID NO:172, or a protein comprising a fragment of the amino acid sequence of SEQ ID NO:172 having biological activity, the fragment comprising the amino acid sequence from amino acid 72 to amino acid 81 of SEQ ID NO:172.

In one embodiment, the present invention provides a composition comprising an isolated polynucleotide selected from the group consisting of:
(a) a polynucleotide comprising the nucleotide sequence of SEQ ID NO:173;
(b) a polynucleotide comprising the nucleotide sequence of SEQ ID NO:173 from nucleotide 1251 to nucleotide 1625;
(c) a polynucleotide comprising the nucleotide sequence of SEQ ID NO:173 from nucleotide 1395 to nucleotide 1625;
(d) a polynucleotide comprising the nucleotide sequence of the full-length protein coding sequence of clone yf33_1 deposited under accession number ATCC 98924;
(e) a polynucleotide encoding the full-length protein encoded by the cDNA insert of clone yf33_1 deposited under accession number ATCC 98924;
(f) a polynucleotide comprising the nucleotide sequence of a mature protein coding sequence of clone yf33_1 deposited under accession number ATCC 98924;
(g) a polynucleotide encoding a mature protein encoded by the cDNA insert of clone yf33_1 deposited under accession number ATCC 98924;
(h) a polynucleotide encoding a protein comprising the amino acid sequence of SEQ ID NO:174;
(i) a polynucleotide encoding a protein comprising a fragment of the amino acid sequence of SEQ ID NO:174 having biological activity, the fragment comprising eight contiguous amino acids of SEQ ID NO:174;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:173.

Preferably, such polynucleotide comprises the nucleotide sequence of SEQ ID NO:173 from nucleotide 1251 to nucleotide 1625; the nucleotide sequence of SEQ ID NO:173 from nucleotide 1395 to nucleotide 1625; the nucleotide sequence of the full-length protein coding sequence of clone yf33_1 deposited under accession number ATCC 98924; or the nucleotide sequence of a mature protein coding sequence of clone yf33_1 deposited under accession number ATCC 98924. In other preferred embodiments, the polynucleotide encodes the full-length or a mature protein encoded by the cDNA insert of clone yf33_1 deposited under accession number ATCC 98924. In further preferred embodiments, the present invention provides a polynucleotide encoding a protein comprising a fragment of the amino acid sequence of SEQ ID NO:174 having biological activity, the fragment preferably comprising eight (more preferably twenty, most preferably thirty) contiguous amino acids of SEQ ID NO:174, or a polynucleotide encoding a protein comprising a fragment of the amino acid sequence of SEQ ID NO:174 having biological activity, the fragment comprising the amino acid sequence from amino acid 57 to amino acid 66 of SEQ ID NO:174.

Other embodiments provide the gene corresponding to the cDNA sequence of SEQ ID NO:173.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:173, but excluding the poly(A) tail at the 3' end of SEQ ID NO:173; and
(ab) the nucleotide sequence of the cDNA insert of clone yf33_1 deposited under accession number ATCC 98924;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:173, but excluding the poly(A) tail at the 3' end of SEQ ID NO:173; and (bb) the nucleotide sequence of the cDNA insert of clone yf33_1 deposited under accession number ATCC 98924;

(ii) hybridizing said primer(s) to human genomic DNA in conditions at least as stringent as 4×SSC at 50 degrees C.;

(iii) amplifying human DNA sequences; and (iv) isolating the polynucleotide products of step (b)(iii).

Preferably the polynucleotide isolated according to the above process comprises a nucleotide sequence corresponding to the cDNA sequence of SEQ ID NO:173, and extending contiguously from a nucleotide sequence corresponding to the 5' end of SEQ ID NO:173 to a nucleotide sequence corresponding to the 3' end of SEQ ID NO:173, but excluding the poly(A) tail at the 3' end of SEQ ID NO:173. Also preferably the polynucleotide isolated according to the above process comprises a nucleotide sequence corresponding to the cDNA sequence of SEQ ID NO:173 from nucleotide 1251 to nucleotide 1625, and extending contiguously from a nucleotide sequence corresponding to the 5' end of said sequence of SEQ ID NO:173 from nucleotide 1251 to nucleotide 1625, to a nucleotide sequence corresponding to the 3' end of said sequence of SEQ ID NO:173 from nucleotide 1251 to nucleotide 1625. Also preferably the polynucleotide isolated according to the above process comprises a nucleotide sequence corresponding to the cDNA sequence of SEQ ID NO:173 from nucleotide 1395 to nucleotide 1625, and extending contiguously from a nucleotide sequence corresponding to the 5' end of said sequence of SEQ ID NO:173 from nucleotide 1395 to nucleotide 1625, to a nucleotide sequence corresponding to the 3' end of said sequence of SEQ ID NO:173 from nucleotide 1395 to nucleotide 1625.

In other embodiments, the present invention provides a composition comprising a protein, wherein said protein comprises an amino acid sequence selected from the group consisting of:

(a) the amino acid sequence of SEQ ID NO:174;

(b) a fragment of the amino acid sequence of SEQ ID NO:174, the fragment comprising eight contiguous amino acids of SEQ ID NO:174; and (c) the amino acid sequence encoded by the cDNA insert of clone yf33_1 deposited under accession number ATCC 98924;

the protein being substantially free from other mammalian proteins. Preferably such protein comprises the amino acid sequence of SEQ ID NO:174. In further preferred embodiments, the present invention provides a protein comprising a fragment of the amino acid sequence of SEQ ID NO:174 having biological activity, the fragment preferably comprising eight (more preferably twenty, most preferably thirty) contiguous amino acids of SEQ ID NO:174, or a protein comprising a fragment of the amino acid sequence of SEQ ID NO:174 having biological activity, the fragment comprising the amino acid sequence from amino acid 57 to amino acid 66 of SEQ ID NO:174.

In one embodiment, the present invention provides a composition comprising an isolated polynucleotide selected from the group consisting of:

(a) a polynucleotide comprising the nucleotide sequence of SEQ ID NO:175;

(b) a polynucleotide comprising the nucleotide sequence of SEQ ID NO:175 from nucleotide 1299 to nucleotide 1640;

(c) a polynucleotide comprising the nucleotide sequence of the full-length protein coding sequence of clone yi15_1 deposited under accession number ATCC 98924;

(d) a polynucleotide encoding the full-length protein encoded by the cDNA insert of clone yi15_1 deposited under accession number ATCC 98924;

(e) a polynucleotide comprising the nucleotide sequence of a mature protein coding sequence of clone yi15_1 deposited under accession number ATCC 98924;

(f) a polynucleotide encoding a mature protein encoded by the cDNA insert of clone yi15_1 deposited under accession number ATCC 98924;

(g) a polynucleotide encoding a protein comprising the amino acid sequence of SEQ ID NO:176;

(h) a polynucleotide encoding a protein comprising a fragment of the amino acid sequence of SEQ ID NO:176 having biological activity, the fragment comprising eight contiguous amino acids of SEQ ID NO:176;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:175.

Preferably, such polynucleotide comprises the nucleotide sequence of SEQ ID NO:175 from nucleotide 1299 to nucleotide 1640; the nucleotide sequence of the full-length protein coding sequence of clone yi15_1 deposited under accession number ATCC 98924; or the nucleotide sequence of a mature protein coding sequence of clone yi15_1 deposited under accession number ATCC 98924. In other preferred embodiments, the polynucleotide encodes the full-length or a mature protein encoded by the cDNA insert of clone yi15_1 deposited under accession number ATCC 98924. In further preferred embodiments, the present invention provides a polynucleotide encoding a protein comprising a fragment of the amino acid sequence of SEQ ID NO:176 having biological activity, the fragment preferably comprising eight (more preferably twenty, most preferably thirty) contiguous amino acids of SEQ ID NO:176, or a polynucleotide encoding a protein comprising a fragment of the amino acid sequence of SEQ ID NO:176 having biological activity, the fragment comprising the amino acid sequence from amino acid 52 to amino acid 61 of SEQ ID NO:176.

Other embodiments provide the gene corresponding to the cDNA sequence of SEQ ID NO:175.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:175, but excluding the poly(A) tail at the 3' end of SEQ ID NO:175; and (ab) the nucleotide sequence of the cDNA insert of clone yi15_1 deposited under accession number ATCC 98924;

(ii) hybridizing said probe(s) to human genomic DNA in conditions at least as stringent as 4×SSC at 50 degrees C.; and (iii) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:175, but excluding the poly(A) tail at the 3' end of SEQ ID NO:175; and
(bb) the nucleotide sequence of the cDNA insert of clone yi15_1 deposited under accession number ATCC 98924;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:175, and extending contiguously from a nucleotide sequence corresponding to the 5' end of SEQ ID NO:175 to a nucleotide sequence corresponding to the 3' end of SEQ ID NO:175, but excluding the poly(A) tail at the 3' end of SEQ ID NO:175. Also preferably the polynucleotide isolated according to the above process comprises a nucleotide sequence corresponding to the cDNA sequence of SEQ ID NO:175 from nucleotide 1299 to nucleotide 1640, and extending contiguously from a nucleotide sequence corresponding to the 5' end of said sequence of SEQ ID NO:175 from nucleotide 1299 to nucleotide 1640, to a nucleotide sequence corresponding to the 3' end of said sequence of SEQ ID NO:175 from nucleotide 1299 to nucleotide 1640.

In other embodiments, the present invention provides a composition comprising a protein, wherein said protein comprises an amino acid sequence selected from the group consisting of:

(a) the amino acid sequence of SEQ ID NO:176;
(b) a fragment of the amino acid sequence of SEQ ID NO:176, the fragment comprising eight contiguous amino acids of SEQ ID NO:176; and
(c) the amino acid sequence encoded by the cDNA insert of clone yi15_1 deposited under accession number ATCC 98924;

the protein being substantially free from other mammalian proteins. Preferably such protein comprises the amino acid sequence of SEQ ID NO:176. In further preferred embodiments, the present invention provides a protein comprising a fragment of the amino acid sequence of SEQ ID NO:176 having biological activity, the fragment preferably comprising eight (more preferably twenty, most preferably thirty) contiguous amino acids of SEQ ID NO:176, or a protein comprising a fragment of the amino acid sequence of SEQ ID NO:176 having biological activity, the fragment comprising the amino acid sequence from amino acid 52 to amino acid 61 of SEQ ID NO:176.

In one embodiment, the present invention provides a composition comprising an isolated polynucleotide selected from the group consisting of:

(a) a polynucleotide comprising the nucleotide sequence of SEQ ID NO:177;
(b) a polynucleotide comprising the nucleotide sequence of SEQ ID NO:177 from nucleotide 85 to nucleotide 1377;
(c) a polynucleotide comprising the nucleotide sequence of SEQ ID NO:177 from nucleotide 139 to nucleotide 1377;
(d) a polynucleotide comprising the nucleotide sequence of the full-length protein coding sequence of done yi17_1 deposited under accession number ATCC 98924;
(e) a polynucleotide encoding the full-length protein encoded by the cDNA insert of clone yi17_1 deposited under accession number ATCC 98924;
(f) a polynucleotide comprising the nucleotide sequence of a mature protein coding sequence of clone yi17_1 deposited under accession number ATCC 98924;
(g) a polynucleotide encoding a mature protein encoded by the cDNA insert of clone yi17_1 deposited under accession number ATCC 98924;
(h) a polynucleotide encoding a protein comprising the amino acid sequence of SEQ ID NO:178;
(i) a polynucleotide encoding a protein comprising a fragment of the amino acid sequence of SEQ ID NO:178 having biological activity, the fragment comprising eight contiguous amino acids of SEQ ID NO:178;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:177.

Preferably, such polynucleotide comprises the nucleotide sequence of SEQ ID NO:177 from nucleotide 85 to nucleotide 1377; the nucleotide sequence of SEQ ID NO:177 from nucleotide 139 to nucleotide 1377; the nucleotide sequence of the full-length protein coding sequence of clone yi17_1 deposited under accession number ATCC 98924; or the nucleotide sequence of a mature protein coding sequence of clone yi17_1 deposited under accession number ATCC 98924. In other preferred embodiments, the polynucleotide encodes the full-length or a mature protein encoded by the cDNA insert of clone yi17_1 deposited under accession number ATCC 98924. In further preferred embodiments, the present invention provides a polynucleotide encoding a protein comprising a fragment of the amino acid sequence of SEQ ID NO:178 having biological activity, the fragment preferably comprising eight (more preferably twenty, most preferably thirty) contiguous amino acids of SEQ ID NO:178, or a polynucleotide encoding a protein comprising a fragment of the amino acid sequence of SEQ ID NO:178 having biological activity, the fragment comprising the amino acid sequence from amino acid 210 to amino acid 219 of SEQ ID NO:178.

Other embodiments provide the gene corresponding to the cDNA sequence of SEQ ID NO:177.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:177, but excluding the poly(A) tail at the 3' end of SEQ ID NO:177; and
(ab) the nucleotide sequence of the cDNA insert of clone yi17_1 deposited under accession number ATCC 98924;

(ii) hybridizing said probe(s) to human genomic DNA in conditions at least as stringent as 4×SSC at 50 degrees C.; and (iii) isolating the DNA polynucleotides detected with the probe(s);

and (b) a process comprising the steps of:

(i) preparing one or more polynucleotide primers that hybridize in 6×SSC at 65 degrees C. to a nucleotide sequence selected from the group consisting of:

(ba) SEQ ID NO:177, but excluding the poly(A) tail at the 3' end of SEQ ID NO:177; and (bb) the nucleotide sequence of the cDNA insert of clone yi17_1 deposited under accession number ATCC 98924;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:177, and extending contiguously from a nucleotide sequence corresponding to the 5' end of SEQ ID NO:177 to a nucleotide sequence corresponding to the 3' end of SEQ ID NO:177, but excluding the poly(A) tail at the 3' end of SEQ ID NO:177. Also preferably the polynucleotide isolated according to the above process comprises a nucleotide sequence corresponding to the cDNA sequence of SEQ ID NO:177 from nucleotide 85 to nucleotide 1377, and extending contiguously from a nucleotide sequence corresponding to the 5' end of said sequence of SEQ ID NO:177 from nucleotide 85 to nucleotide 1377, to a nucleotide sequence corresponding to the 3' end of said sequence of SEQ ID NO:177 from nucleotide 85 to nucleotide 1377. Also preferably the polynucleotide isolated according to the above process comprises a nucleotide sequence corresponding to the cDNA sequence of SEQ ID NO:177 from nucleotide 139 to nucleotide 1377, and extending contiguously from a nucleotide sequence corresponding to the 5' end of said sequence of SEQ ID NO:177 from nucleotide 139 to nucleotide 1377, to a nucleotide sequence corresponding to the 3' end of said sequence of SEQ ID NO:177 from nucleotide 139 to nucleotide 1377.

In other embodiments, the present invention provides a composition comprising a protein, wherein said protein comprises an amino acid sequence selected from the group consisting of:

(a) the amino acid sequence of SEQ ID NO:178;

(b) a fragment of the amino acid sequence of SEQ ID NO:178, the fragment comprising eight contiguous amino acids of SEQ ID NO:178; and (c) the amino acid sequence encoded by the cDNA insert of clone yi17_1 deposited under accession number ATCC 98924;

the protein being substantially free from other mammalian proteins. Preferably such protein comprises the amino acid sequence of SEQ ID NO:178. In further preferred embodiments, the present invention provides a protein comprising a fragment of the amino acid sequence of SEQ ID NO:178 having biological activity, the fragment preferably comprising eight (more preferably twenty, most preferably thirty) contiguous amino acids of SEQ ID NO:178, or a protein comprising a fragment of the amino acid sequence of SEQ ID NO:178 having biological activity, the fragment comprising the amino acid sequence from amino acid 210 to amino acid 219 of SEQ ID NO:178.

In one embodiment, the present invention provides a composition comprising an isolated polynucleotide selected from the group consisting of:

(a) a polynucleotide comprising the nucleotide sequence of SEQ ID NO:179;

(b) a polynucleotide comprising the nucleotide sequence of SEQ ID NO:179 from nucleotide 50 to nucleotide 1075;

(c) a polynucleotide comprising the nucleotide sequence of SEQ ID NO:179 from nucleotide 215 to nucleotide 1075;

(d) a polynucleotide comprising the nucleotide sequence of the full-length protein coding sequence of clone yk38_1 deposited under accession number ATCC 98924;

(e) a polynucleotide encoding the full-length protein encoded by the cDNA insert of clone yk38_1 deposited under accession number ATCC 98924;

(f) a polynucleotide comprising the nucleotide sequence of a mature protein coding sequence of clone yk38_1 deposited under accession number ATCC 98924;

(g) a polynucleotide encoding a mature protein encoded by the cDNA insert of clone yk38_1 deposited under accession number ATCC 98924;

(h) a polynucleotide encoding a protein comprising the amino acid sequence of SEQ ID NO:180;

(i) a polynucleotide encoding a protein comprising a fragment of the amino acid sequence of SEQ ID NO:180 having biological activity, the fragment comprising eight contiguous amino acids of SEQ ID NO:180;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:179.

Preferably, such polynucleotide comprises the nucleotide sequence of SEQ ID NO:179 from nucleotide 50 to nucleotide 1075; the nucleotide sequence of SEQ ID NO:179 from nucleotide 215 to nucleotide 1075; the nucleotide sequence of the full-length protein coding sequence of clone yk38_1 deposited under accession number ATCC 98924; or the nucleotide sequence of a mature protein coding sequence of clone yk38_1 deposited under accession number ATCC 98924. In other preferred embodiments, the polynucleotide encodes the full-length or a mature protein encoded by the cDNA insert of clone yk38_1 deposited under accession number ATCC 98924. In further preferred embodiments, the present invention provides a polynucleotide encoding a protein comprising a fragment of the amino acid sequence of SEQ ID NO:180 having biological activity, the fragment preferably comprising eight (more preferably twenty, most preferably thirty) contiguous amino acids of SEQ ID NO:180, or a polynucleotide encoding a protein comprising a fragment of the amino acid sequence of SEQ ID NO:180 having biological activity, the fragment comprising the amino acid sequence from amino acid 166 to amino acid 175 of SEQ ID NO:180.

Other embodiments provide the gene corresponding to the cDNA sequence of SEQ ID NO:179.

Further embodiments of the invention provide isolated polynucleotides produced according to a process selected from the group consisting of:
(a) a process comprising the steps of:
   (i) preparing one or more polynucleotide probes that hybridize in 6×SSC at 65 degrees C. to a nucleotide sequence selected from the group consisting of:
      (aa) SEQ ID NO:179, but excluding the poly(A) tail at the 3' end of SEQ ID NO:179; and
      (ab) the nucleotide sequence of the cDNA insert of clone yk38_1 deposited under accession number ATCC 98924;
   (ii) hybridizing said probe(s) to human genomic DNA in conditions at least as stringent as 4×SSC at 50 degrees C.; and
   (iii) isolating the DNA polynucleotides detected with the probe(s);
and
(b) a process comprising the steps of:
   (i) preparing one or more polynucleotide primers that hybridize in 6×SSC at 65 degrees C. to a nucleotide sequence selected from the group consisting of:
      (ba) SEQ ID NO:179, but excluding the poly(A) tail at the 3' end of SEQ ID NO:179; and
      (bb) the nucleotide sequence of the cDNA insert of clone yk38_1 deposited under accession number ATCC 98924;
   (ii) hybridizing said primer(s) to human genomic DNA in conditions at least as stringent as 4×SSC at 50 degrees C.;
   (iii) amplifying human DNA sequences; and
   (iv) isolating the polynucleotide products of step (b)(iii).

Preferably the polynucleotide isolated according to the above process comprises a nucleotide sequence corresponding to the cDNA sequence of SEQ ID NO:179, and extending contiguously from a nucleotide sequence corresponding to the 5' end of SEQ ID NO:179 to a nucleotide sequence corresponding to the 3' end of SEQ ID NO:179, but excluding the poly(A) tail at the 3' end of SEQ ID NO:179. Also preferably the polynucleotide isolated according to the above process comprises a nucleotide sequence corresponding to the cDNA sequence of SEQ ID NO:179 from nucleotide 50 to nucleotide 1075, and extending contiguously from a nucleotide sequence corresponding to the 5' end of said sequence of SEQ ID NO:179 from nucleotide 50 to nucleotide 1075, to a nucleotide sequence corresponding to the 3' end of said sequence of SEQ ID NO:179 from nucleotide 50 to nucleotide 1075. Also preferably the polynucleotide isolated according to the above process comprises a nucleotide sequence corresponding to the cDNA sequence of SEQ ID NO:179 from nucleotide 215 to nucleotide 1075, and extending contiguously from a nucleotide sequence corresponding to the 5' end of said sequence of SEQ ID NO:179 from nucleotide 215 to nucleotide 1075, to a nucleotide sequence corresponding to the 3' end of said sequence of SEQ ID NO:179 from nucleotide 215 to nucleotide 1075.

In other embodiments, the present invention provides a composition comprising a protein, wherein said protein comprises an amino acid sequence selected from the group consisting of:
(a) the amino acid sequence of SEQ ID NO:180;
(b) a fragment of the amino acid sequence of SEQ ID NO:180, the fragment comprising eight contiguous amino acids of SEQ ID NO:180; and
(c) the amino acid sequence encoded by the cDNA insert of clone yk38_1 deposited under accession number ATCC 98924;

the protein being substantially free from other mammalian proteins. Preferably such protein comprises the amino acid sequence of SEQ ID NO:180. In further preferred embodiments, the present invention provides a protein comprising a fragment of the amino acid sequence of SEQ ID NO:180 having biological activity, the fragment preferably comprising eight (more preferably twenty, most preferably thirty) contiguous amino acids of SEQ ID NO:180, or a protein comprising a fragment of the amino acid sequence of SEQ ID NO:180 having biological activity, the fragment comprising the amino acid sequence from amino acid 166 to amino acid 175 of SEQ ID NO:180.

In one embodiment, the present invention provides a composition comprising an isolated polynucleotide selected from the group consisting of:
(a) a polynucleotide comprising the nucleotide sequence of SEQ ID NO:181;
(b) a polynucleotide comprising the nucleotide sequence of SEQ ID NO:181 from nucleotide 76 to nucleotide 348;
(c) a polynucleotide comprising the nucleotide sequence of SEQ ID NO:181 from nucleotide 139 to nucleotide 348;
(d) a polynucleotide comprising the nucleotide sequence of the full-length protein coding sequence of clone yk51_1 deposited under accession number ATCC 98924;
(e) a polynucleotide encoding the full-length protein encoded by the cDNA insert of clone yk51_1 deposited under accession number ATCC 98924;
(f) a polynucleotide comprising the nucleotide sequence of a mature protein coding sequence of clone yk51_1 deposited under accession number ATCC 98924;
(g) a polynucleotide encoding a mature protein encoded by the cDNA insert of clone yk51_1 deposited under accession number ATCC 98924;
(h) a polynucleotide encoding a protein comprising the amino acid sequence of SEQ ID NO:182;
(i) a polynucleotide encoding a protein comprising a fragment of the amino acid sequence of SEQ ID NO:182 having biological activity, the fragment comprising eight contiguous amino acids of SEQ ID NO:182;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:181.

Preferably, such polynucleotide comprises the nucleotide sequence of SEQ ID NO:181 from nucleotide 76 to nucleotide 348; the nucleotide sequence of SEQ ID NO:181 from nucleotide 139 to nucleotide 348; the nucleotide sequence of the full-length protein coding sequence of clone yk51_1 deposited under accession number ATCC 98924; or the nucleotide sequence of a mature protein coding sequence of clone yk51_1 deposited under accession ATCC 98924. In other preferred embodiments, the polynucleotide encodes the full-length or a mature protein encoded by the cDNA insert of clone yk51_1 deposited under accession number ATCC 98924. In further preferred embodiments, the present invention provides a polynucleotide encoding a protein comprising a fragment of the amino acid sequence of SEQ ID NO:182 having biological activity, the fragment preferably comprising eight (more preferably twenty, most preferably thirty) contiguous amino acids of SEQ ID NO:182, or a polynucleotide encoding a protein comprising a fragment of the amino acid sequence of SEQ ID NO:182 having biological activity, the fragment comprising the amino acid sequence from amino acid 40 to amino acid 49 of SEQ ID NO:182.

Other embodiments provide the gene corresponding to the cDNA sequence of SEQ ID NO:181.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:181, but excluding the poly(A) tail at the 3' end of SEQ ID NO:181; and
    (ab) the nucleotide sequence of the cDNA insert of clone yk51_1 deposited under accession number ATCC 98924;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:181, but excluding the poly(A) tail at the 3' end of SEQ ID NO:181; and
    (bb) the nucleotide sequence of the cDNA insert of clone yk51_1 deposited under accession number ATCC 98924;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:181, and extending contiguously from a nucleotide sequence corresponding to the 5' end of SEQ ID NO:181 to a nucleotide sequence corresponding to the 3' end of SEQ ID NO:181, but excluding the poly(A) tail at the 3' end of SEQ ID NO:181. Also preferably the polynucleotide isolated according to the above process comprises a nucleotide sequence corresponding to the cDNA sequence of SEQ ID NO:181 from nucleotide 76 to nucleotide 348, and extending contiguously from a nucleotide sequence corresponding to the 5' end of said sequence of SEQ ID NO:181 from nucleotide 76 to nucleotide 348, to a nucleotide sequence corresponding to the 3' end of said sequence of SEQ ID NO:181 from nucleotide 76 to nucleotide 348. Also preferably the polynucleotide isolated according to the above process comprises a nucleotide sequence corresponding to the cDNA sequence of SEQ ID NO:181 from nucleotide 139 to nucleotide 348, and extending contiguously from a nucleotide sequence corresponding to the 5' end of said sequence of SEQ ID NO:181 from nucleotide 139 to nucleotide 348, to a nucleotide sequence corresponding to the 3' end of said sequence of SEQ ID NO:181 from nucleotide 139 to nucleotide 348.

In other embodiments, the present invention provides a composition comprising a protein, wherein said protein comprises an amino acid sequence selected from the group consisting of:

(a) the amino acid sequence of SEQ ID NO:182;
(b) a fragment of the amino acid sequence of SEQ ID NO:182, the fragment comprising eight contiguous amino acids of SEQ ID NO:182; and
(c) the amino acid sequence encoded by the cDNA insert of clone yk51_1 deposited under accession number ATCC 98924;

the protein being substantially free from other mammalian proteins. Preferably such protein comprises the amino acid sequence of SEQ ID NO:182. In further preferred embodiments, the present invention provides a protein comprising a fragment of the amino acid sequence of SEQ ID NO:182 having biological activity, the fragment preferably comprising eight (more preferably twenty, most preferably thirty) contiguous amino acids of SEQ ID NO:182, or a protein comprising a fragment of the amino acid sequence of SEQ ID NO:182 having biological activity, the fragment comprising the amino acid sequence from amino acid 40 to amino acid 49 of SEQ ID NO:182.

In one embodiment, the present invention provides a composition comprising an isolated polynucleotide selected from the group consisting of:

(a) a polynucleotide comprising the nucleotide sequence of SEQ ID NO:183;
(b) a polynucleotide comprising the nucleotide sequence of SEQ ID NO:183 from nucleotide 203 to nucleotide 577;
(c) a polynucleotide comprising the nucleotide sequence of the full-length protein coding sequence of clone yk74_1 deposited under accession number ATCC 98924;
(d) a polynucleotide encoding the full-length protein encoded by the cDNA insert of clone yk74_1 deposited under accession number ATCC 98924;
(e) a polynucleotide comprising the nucleotide sequence of a mature protein coding sequence of clone yk74_1 deposited under accession number ATCC 98924;
(f) a polynucleotide encoding a mature protein encoded by the cDNA insert of clone yk74_1 deposited under accession number ATCC 98924;
(g) a polynucleotide encoding a protein comprising the amino acid sequence of SEQ ID NO:184;
(h) a polynucleotide encoding a protein comprising a fragment of the amino acid sequence of SEQ ID NO:184 having biological activity, the fragment comprising eight contiguous amino acids of SEQ ID NO:184;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:183.

Preferably, such polynucleotide comprises the nucleotide sequence of SEQ ID NO:183 from nucleotide 203 to nucleotide 577; the nucleotide sequence of the full-length protein coding sequence of clone yk74_1 deposited under accession number ATCC 98924; or the nucleotide sequence of a mature protein coding sequence of clone yk74_1 deposited under accession number ATCC 98924. In other preferred embodiments, the polynucleotide encodes the full-length or a mature protein encoded by the cDNA insert of clone yk74_1 deposited under accession number ATCC 98924. In further preferred embodiments, the present invention provides a polynucleotide encoding a protein comprising a fragment of the amino acid sequence of SEQ ID NO:184 having biological activity, the fragment preferably comprising eight (more preferably twenty, most preferably thirty) contiguous amino acids of SEQ ID NO:184, or a polynucleotide encoding a protein comprising a fragment of the amino acid sequence of SEQ ID NO:184 having biological activity, the fragment comprising the amino acid sequence from amino acid 57 to amino acid 66 of SEQ ID NO:184.

Other embodiments provide the gene corresponding to the cDNA sequence of SEQ ID NO:183.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:183, but excluding the poly(A) tail at the 3' end of SEQ ID NO:183; and
    (ab) the nucleotide sequence of the cDNA insert of clone yk74_1 deposited under accession number ATCC 98924;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:183, but excluding the poly(A) tail at the 3' end of SEQ ID NO:183; and
    (bb) the nucleotide sequence of the cDNA insert of clone yk74_1 deposited under accession number ATCC 98924;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:183, and extending contiguously from a nucleotide sequence corresponding to the 5' end of SEQ ID NO:183 to a nucleotide sequence corresponding to the 3' end of SEQ ID NO:183, but excluding the poly(A) tail at the 3' end of SEQ ID NO:183. Also preferably the polynucleotide isolated according to the above process comprises a nucleotide sequence corresponding to the cDNA sequence of SEQ ID NO:183 from nucleotide 203 to nucleotide 577, and extending contiguously from a nucleotide sequence corresponding to the 5' end of said sequence of SEQ ID NO:183 from nucleotide 203 to nucleotide 577, to a nucleotide sequence corresponding to the 3' end of said sequence of SEQ ID NO:183 from nucleotide 203 to nucleotide 577.

In other embodiments, the present invention provides a composition comprising a protein, wherein said protein comprises an amino acid sequence selected from the group consisting of:

(a) the amino acid sequence of SEQ ID NO:184;
(b) a fragment of the amino acid sequence of SEQ ID NO:184, the fragment comprising eight contiguous amino acids of SEQ ID NO:184; and
(c) the amino acid sequence encoded by the cDNA insert of clone yk74_1 deposited under accession number ATCC 98924;

the protein being substantially free from other mammalian proteins. Preferably such protein comprises the amino acid sequence of SEQ ID NO:184. In further preferred embodiments, the present invention provides a protein comprising a fragment of the amino acid sequence of SEQ ID NO:184 having biological activity, the fragment preferably comprising eight (more preferably twenty, most preferably thirty) contiguous amino acids of SEQ ID NO:184, or a protein comprising a fragment of the amino acid sequence of SEQ ID NO:184 having biological activity, the fragment comprising the amino acid sequence from amino acid 57 to amino acid 66 of SEQ ID NO:184.

In one embodiment, the present invention provides a composition comprising an isolated polynucleotide selected from the group consisting of:

(a) a polynucleotide comprising the nucleotide sequence of SEQ ID NO:185;
(b) a polynucleotide comprising the nucleotide sequence of SEQ ID NO:185 from nucleotide 38 to nucleotide 2170;
(c) a polynucleotide comprising the nucleotide sequence of the full-length protein coding sequence of clone yk89_1 deposited under accession number ATCC 98924;
(d) a polynucleotide encoding the full-length protein encoded by the cDNA insert of clone yk89_1 deposited under accession number ATCC 98924;
(e) a polynucleotide comprising the nucleotide sequence of a mature protein coding sequence of clone yk89_1 deposited under accession number ATCC 98924;
(f) a polynucleotide encoding a mature protein encoded by the cDNA insert of clone yk89_1 deposited under accession number ATCC 98924;
(g) a polynucleotide encoding a protein comprising the amino acid sequence of SEQ ID NO:186;
(h) a polynucleotide encoding a protein comprising a fragment of the amino acid sequence of SEQ ID NO:186 having biological activity, the fragment comprising eight contiguous amino acids of SEQ ID NO:186;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:185.

Preferably, such polynucleotide comprises the nucleotide sequence of SEQ ID NO:185 from nucleotide 38 to nucleotide 2170; the nucleotide sequence of the full-length protein coding sequence of clone yk89_1 deposited under accession number ATCC 98924; or the nucleotide sequence of a mature protein coding sequence of clone yk89_1 deposited under accession number ATCC 98924. In other preferred embodiments, the polynucleotide encodes the full-length or a mature protein encoded by the cDNA insert of clone yk89_1 deposited under accession number ATCC 98924. In further preferred embodiments, the present invention provides a polynucleotide encoding a protein comprising a fragment of the amino acid sequence of SEQ ID NO:186 having biological activity, the fragment preferably comprising eight (more preferably twenty, most preferably thirty) contiguous amino acids of SEQ ID NO:186, or a polynucleotide encoding a protein comprising a fragment of the amino acid sequence of SEQ ID NO:186 having biological activity, the fragment comprising the amino acid sequence from amino acid 350 to amino acid 359 of SEQ ID NO:186.

Other embodiments provide the gene corresponding to the cDNA sequence of SEQ ID NO:185.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:185, but excluding the poly(A) tail at the 3' end of SEQ ID NO:185; and
    (ab) the nucleotide sequence of the cDNA insert of clone yk89_1 deposited under accession number ATCC 98924;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:185, but excluding the poly(A) tail at the 3' end of SEQ ID NO:185; and
    (bb) the nucleotide sequence of the cDNA insert of clone yk89_1 deposited under accession number ATCC 98924;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:185, and extending contiguously from a nucleotide sequence corresponding to the 5' end of SEQ ID NO:185 to a nucleotide sequence corresponding to the 3' end of SEQ ID NO:185, but excluding the poly(A) tail at the 3' end of SEQ ID NO:185. Also preferably the polynucleotide isolated according to the above process comprises a nucleotide sequence corresponding to the cDNA sequence of SEQ ID NO:185 from nucleotide 38 to nucleotide 2170, and extending contiguously from a nucleotide sequence corresponding to the 5' end of said sequence of SEQ ID NO:185 from nucleotide 38 to nucleotide 2170, to a nucleotide sequence corresponding to the 3' end of said sequence of SEQ ID NO:185 from nucleotide 38 to nucleotide 2170.

In other embodiments, the present invention provides a composition comprising a protein, wherein said protein comprises an amino acid sequence selected from the group consisting of:

(a) the amino acid sequence of SEQ ID NO:186;
(b) a fragment of the amino acid sequence of SEQ ID NO:186, the fragment comprising eight contiguous amino acids of SEQ ID NO:186; and
(c) the amino acid sequence encoded by the cDNA insert of clone yk89_1 deposited under accession number ATCC 98924;

the protein being substantially free from other mammalian proteins. Preferably such protein comprises the amino acid sequence of SEQ ID NO:186. In further preferred embodiments, the present invention provides a protein comprising a fragment of the amino acid sequence of SEQ ID NO:186 having biological activity, the fragment preferably comprising eight (more preferably twenty, most preferably thirty) contiguous amino acids of SEQ ID NO:186, or a protein comprising a fragment of the amino acid sequence of SEQ ID NO:186 having biological activity, the fragment comprising the amino acid sequence from amino acid 350 to amino acid 359 of SEQ ID NO:186.

In one embodiment, the present invention provides a composition comprising an isolated polynucleotide selected from the group consisting of:

(a) a polynucleotide comprising the nucleotide sequence of SEQ ID NO:187;
(b) a polynucleotide comprising the nucleotide sequence of SEQ ID NO:187 from nucleotide 14 to nucleotide 742;
(c) a polynucleotide comprising the nucleotide sequence of SEQ ID NO:187 from nucleotide 89 to nucleotide 742;
(d) a polynucleotide comprising the nucleotide sequence of the full-length protein coding sequence of done yl18_1 deposited under accession number ATCC 98924;
(e) a polynucleotide encoding the full-length protein encoded by the cDNA insert of clone yl18_1 deposited under accession number ATCC 98924;
(f) a polynucleotide comprising the nucleotide sequence of a mature protein coding sequence of clone yl18_1 deposited under accession number ATCC 98924;
(g) a polynucleotide encoding a mature protein encoded by the cDNA insert of clone yl18_1 deposited under accession number ATCC 98924;
(h) a polynucleotide encoding a protein comprising the amino acid sequence of SEQ ID NO:188;
(i) a polynucleotide encoding a protein comprising a fragment of the amino acid sequence of SEQ ID NO:188 having biological activity, the fragment comprising eight contiguous amino acids of SEQ ID NO:188;
(j) a polynucleotide which is an allelic variant of a polynucleotide of (a)–(g) above;
(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:187.

Preferably, such polynucleotide comprises the nucleotide sequence of SEQ ID NO:187 from nucleotide 14 to nucleotide 742; the nucleotide sequence of SEQ ID NO:187 from nucleotide 89 to nucleotide 742; the nucleotide sequence of the full-length protein coding sequence of clone yl18_1 deposited under accession number ATCC 98924; or the nucleotide sequence of a mature protein coding sequence of clone yl18_1 deposited under accession number ATCC 98924. In other preferred embodiments, the polynucleotide encodes the full-length or a mature protein encoded by the cDNA insert of clone yl18_1 deposited under accession number ATCC 98924. In further preferred embodiments, the present invention provides a polynucleotide encoding a protein comprising a fragment of the amino acid sequence of SEQ ID NO:188 having biological activity, the fragment preferably comprising eight (more preferably twenty, most preferably thirty) contiguous amino acids of SEQ ID NO:188, or a polynucleotide encoding a protein comprising a fragment of the amino acid sequence of SEQ ID NO:188 having biological activity, the fragment comprising the amino acid sequence from amino acid 116 to amino acid 125 of SEQ ID NO:188.

Other embodiments provide the gene corresponding to the cDNA sequence of SEQ ID NO:187.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:187, but excluding the poly(A) tail at the 3' end of SEQ ID NO:187; and
    (ab) the nucleotide sequence of the cDNA insert of clone yl18_1 deposited under accession number ATCC 98924;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:187, but excluding the poly(A) tail at the 3' end of SEQ ID NO:187; and
    (bb) the nucleotide sequence of the cDNA insert of clone yl18_1 deposited under accession number ATCC 98924;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:187, and extending contiguously from a nucleotide sequence corresponding to the 5' end of SEQ ID NO:187 to a nucleotide sequence corresponding to the 3' end of SEQ ID NO:187, but excluding the poly(A) tail at the 3' end of SEQ ID NO:187. Also preferably the polynucleotide isolated according to the above process comprises a nucleotide sequence corresponding to the cDNA sequence of SEQ ID NO:187 from nucleotide 14 to nucleotide 742, and extending contiguously from a nucleotide sequence corresponding to the 5' end of said sequence of SEQ ID NO:187 from nucleotide 14 to nucleotide 742, to a nucleotide sequence corresponding to the 3' end of said sequence of SEQ ID NO:187 from nucleotide 14 to nucleotide 742. Also preferably the polynucleotide isolated according to the above process comprises a nucleotide sequence corresponding to the cDNA sequence of SEQ ID NO:187 from nucleotide 89 to nucleotide 742, and extending contiguously from a nucleotide sequence corresponding to the 5' end of said sequence of SEQ ID NO:187 from nucleotide 89 to nucleotide 742, to a nucleotide sequence corresponding to the 3' end of said sequence of SEQ ID NO:187 from nucleotide 89 to nucleotide 742.

In other embodiments, the present invention provides a composition comprising a protein, wherein said protein comprises an amino acid sequence selected from the group consisting of:

(a) the amino acid sequence of SEQ ID NO:188;
(b) a fragment of the amino acid sequence of SEQ ID NO:188, the fragment comprising eight contiguous amino acids of SEQ ID NO:188; and
(c) the amino acid sequence encoded by the cDNA insert of clone yl18_1 deposited under accession number ATCC 98924;

the protein being substantially free from other mammalian proteins. Preferably such protein comprises the amino acid sequence of SEQ ID NO:188. In further preferred embodiments, the present invention provides a protein comprising a fragment of the amino acid sequence of SEQ ID NO:188 having biological activity, the fragment preferably comprising eight (more preferably twenty, most preferably thirty) contiguous amino acids of SEQ ID NO:188, or a protein comprising a fragment of the amino acid sequence of SEQ ID NO:188 having biological activity, the fragment comprising the amino acid sequence from amino acid 116 to amino acid 125 of SEQ ID NO:188.

In one embodiment, the present invention provides a composition comprising an isolated polynucleotide selected from the group consisting of:

(a) a polynucleotide comprising the nucleotide sequence of SEQ ID NO:189;
(b) a polynucleotide comprising the nucleotide sequence of SEQ ID NO:189 from nucleotide 280 to nucleotide 615;
(c) a polynucleotide comprising the nucleotide sequence of SEQ ID NO:189 from nucleotide 325 to nucleotide 615;
(d) a polynucleotide comprising the nucleotide sequence of the full-length protein coding sequence of clone yb325_1 deposited under accession number ATCC 98958;
(e) a polynucleotide encoding the full-length protein encoded by the cDNA insert of clone yb325_1 deposited under accession number ATCC 98958;
(f) a polynucleotide comprising the nucleotide sequence of a mature protein coding sequence of clone yb325_1 deposited under accession number ATCC 98958;
(g) a polynucleotide encoding a mature protein encoded by the cDNA insert of clone yb325_1 deposited under accession number ATCC 98958;

(h) a polynucleotide encoding a protein comprising the amino acid sequence of SEQ ID NO:190;

(i) a polynucleotide encoding a protein comprising a fragment of the amino acid sequence of SEQ ID NO:190 having biological activity, the fragment comprising eight contiguous amino acids of SEQ ID NO:190;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:189.

Preferably, such polynucleotide comprises the nucleotide sequence of SEQ ID NO:189 from nucleotide 280 to nucleotide 615; the nucleotide sequence of SEQ ID NO:189 from nucleotide 325 to nucleotide 615; the nucleotide sequence of the full-length protein coding sequence of clone yb325_1 deposited under accession number ATCC 98958; or the nucleotide sequence of a mature protein coding sequence of clone yb325_1 deposited under accession number ATCC 98958. In other preferred embodiments, the polynucleotide encodes the full-length or a mature protein encoded by the cDNA insert of clone yb325_1 deposited under accession number ATCC 98958. In further preferred embodiments, the present invention provides a polynucleotide encoding a protein comprising a fragment of the amino acid sequence of SEQ ID NO:190 having biological activity, the fragment preferably comprising eight (more preferably twenty, most preferably thirty) contiguous amino acids of SEQ ID NO:190, or a polynucleotide encoding a protein comprising a fragment of the amino acid sequence of SEQ ID NO:190 having biological activity, the fragment comprising the amino acid sequence from amino acid 51 to amino acid 60 of SEQ ID NO:190.

Other embodiments provide the gene corresponding to the cDNA sequence of SEQ ID NO:189.

Further embodiments of the invention provide isolated polynucleotides produced according to a process selected from the group consisting of:

(a) a process comprising the steps of:
(i) preparing one or more polynucleotide probes that hybridize in 6×SSC at 65 degrees C. to a nucleotide sequence selected from the group consisting of:
(aa) SEQ ID NO:189; and
(ab) the nucleotide sequence of the cDNA insert of clone yb325_1 deposited under accession number ATCC 98958;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:189; and
(bb) the nucleotide sequence of the cDNA insert of clone yb325_1 deposited under accession number ATCC 98958;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:189, and extending contiguously from a nucleotide sequence corresponding to the 5' end of SEQ ID NO:189 to a nucleotide sequence corresponding to the 3' end of SEQ ID NO:189. Also preferably the polynucleotide isolated according to the above process comprises a nucleotide sequence corresponding to the cDNA sequence of SEQ ID NO:189 from nucleotide 280 to nucleotide 615, and extending contiguously from a nucleotide sequence corresponding to the 5' end of said sequence of SEQ ID NO:189 from nucleotide 280 to nucleotide 615, to a nucleotide sequence corresponding to the 3' end of said sequence of SEQ ID NO:189 from nucleotide 280 to nucleotide 615. Also preferably the polynucleotide isolated according to the above process comprises a nucleotide sequence corresponding to the cDNA sequence of SEQ ID NO:189 from nucleotide 325 to nucleotide 615, and extending contiguously from a nucleotide sequence corresponding to the 5' end of said sequence of SEQ ID NO:189 from nucleotide 325 to nucleotide 615, to a nucleotide sequence corresponding to the 3' end of said sequence of SEQ ID NO:189 from nucleotide 325 to nucleotide 615.

In other embodiments, the present invention provides a composition comprising a protein, wherein said protein comprises an amino acid sequence selected from the group consisting of:

(a) the amino acid sequence of SEQ ID NO:190;
(b) a fragment of the amino acid sequence of SEQ ID NO:190, the fragment comprising eight contiguous amino acids of SEQ ID NO:190; and
(c) the amino acid sequence encoded by the cDNA insert of clone yb325_1 deposited under accession number ATCC 98958;

the protein being substantially free from other mammalian proteins. Preferably such protein comprises the amino acid sequence of SEQ ID NO:190. In further preferred embodiments, the present invention provides a protein comprising a fragment of the amino acid sequence of SEQ ID NO:190 having biological activity, the fragment preferably comprising eight (more preferably twenty, most preferably thirty) contiguous amino acids of SEQ ID NO:190, or a protein comprising a fragment of the amino acid sequence of SEQ ID NO:190 having biological activity, the fragment comprising the amino acid sequence from amino acid 51 to amino acid 60 of SEQ ID NO:190.

In one embodiment, the present invention provides a composition comprising an isolated polynucleotide selected from the group consisting of:

(a) a polynucleotide comprising the nucleotide sequence of SEQ ID NO:191;
(b) a polynucleotide comprising the nucleotide sequence of SEQ ID NO:191 from nucleotide 163 to nucleotide 429;
(c) a polynucleotide comprising the nucleotide sequence of SEQ ID NO:191 from nucleotide 274 to nucleotide 429;
(d) a polynucleotide comprising the nucleotide sequence of the full-length protein coding sequence of clone yd261_1 deposited under accession number ATCC 98958;

(e) a polynucleotide encoding the full-length protein encoded by the cDNA insert of clone yd261_1 deposited under accession number ATCC 98958;
(f) a polynucleotide comprising the nucleotide sequence of a mature protein coding sequence of clone yd261_1 deposited under accession number ATCC 98958;
(g) a polynucleotide encoding a mature protein encoded by the cDNA insert of clone yd261_1 deposited under accession number ATCC 98958;
(h) a polynucleotide encoding a protein comprising the amino acid sequence of SEQ ID NO:192;
(i) a polynucleotide encoding a protein comprising a fragment of the amino acid sequence of SEQ ID NO:192 having biological activity, the fragment comprising eight contiguous amino acids of SEQ ID NO:192;
(j) a polynucleotide which is an allelic variant of a polynucleotide of (a)–(g) above;
(k) a polynucleotide which encodes a species homologue of the protein of (h) or (i) above;
(l) a polynucleotide that hybridizes under stringent conditions to any one of the polynucleotides specified in (a)–(i); and
(m) a polynucleotide that hybridizes under stringent conditions to any one of the polynucleotides specified in (a)–(i) and that has a length that is at least 25% of the length of SEQ ID NO:191.

Preferably, such polynucleotide comprises the nucleotide sequence of SEQ ID NO:191 from nucleotide 163 to nucleotide 429; the nucleotide sequence of SEQ ID NO:191 from nucleotide 274 to nucleotide 429; the nucleotide sequence of the full-length protein coding sequence of clone yd261_1 deposited under accession number ATCC 98958; or the nucleotide sequence of a mature protein coding sequence of clone yd261_1 deposited under accession number ATCC 98958. In other preferred embodiments, the polynucleotide encodes the full-length or a mature protein encoded by the cDNA insert of clone yd261_1 deposited under accession number ATCC 98958. In further preferred embodiments, the present invention provides a polynucleotide encoding a protein comprising a fragment of the amino acid sequence of SEQ ID NO:192 having biological activity, the fragment preferably comprising eight (more preferably twenty, most preferably thirty) contiguous amino acids of SEQ ID NO:192, or a polynucleotide encoding a protein comprising a fragment of the amino acid sequence of SEQ ID NO:192 having biological activity, the fragment comprising the amino acid sequence from amino acid 39 to amino acid 48 of SEQ ID NO:192.

Other embodiments provide the gene corresponding to the cDNA sequence of SEQ ID NO:191.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:191, but excluding the poly(A) tail at the 3' end of SEQ ID NO:191; and
(ab) the nucleotide sequence of the cDNA insert of clone yd261_1 deposited under accession number ATCC 98958;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:191, but excluding the poly(A) tail at the 3' end of SEQ ID NO:191; and
(bb) the nucleotide sequence of the cDNA insert of clone yd261_1 deposited under accession number ATCC 98958;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:191, and extending contiguously from a nucleotide sequence corresponding to the 5' end of SEQ ID NO:191 to a nucleotide sequence corresponding to the 3' end of SEQ ID NO:191, but excluding the poly(A) tail at the 3' end of SEQ ID NO:191. Also preferably the polynucleotide isolated according to the above process comprises a nucleotide sequence corresponding to the cDNA sequence of SEQ ID NO:191 from nucleotide 163 to nucleotide 429, and extending contiguously from a nucleotide sequence corresponding to the 5' end of said sequence of SEQ ID NO:191 from nucleotide 163 to nucleotide 429, to a nucleotide sequence corresponding to the 3' end of said sequence of SEQ ID NO:191 from nucleotide 163 to nucleotide 429. Also preferably the polynucleotide isolated according to the above process comprises a nucleotide sequence corresponding to the cDNA sequence of SEQ ID NO:191 from nucleotide 274 to nucleotide 429, and extending contiguously from a nucleotide sequence corresponding to the 5' end of said sequence of SEQ ID NO:191 from nucleotide 274 to nucleotide 429, to a nucleotide sequence corresponding to the 3' end of said sequence of SEQ ID NO:191 from nucleotide 274 to nucleotide 429.

In other embodiments, the present invention provides a composition comprising a protein, wherein said protein comprises an amino acid sequence selected from the group consisting of:
(a) the amino acid sequence of SEQ ID NO:192;
(b) a fragment of the amino acid sequence of SEQ ID NO:192, the fragment comprising eight contiguous amino acids of SEQ ID NO:192; and
(c) the amino acid sequence encoded by the cDNA insert of clone yd261_1 deposited under accession number ATCC 98958;

the protein being substantially free from other mammalian proteins. Preferably such protein comprises the amino acid sequence of SEQ ID NO:192. In further preferred embodiments, the present invention provides a protein comprising a fragment of the amino acid sequence of SEQ ID NO:192 having biological activity, the fragment preferably comprising eight (more preferably twenty, most preferably thirty) contiguous amino acids of SEQ ID NO:192, or a protein comprising a fragment of the amino acid sequence of SEQ ID NO:192 having biological activity, the fragment comprising the amino acid sequence from amino acid 39 to amino acid 48 of SEQ ID NO:192.

In one embodiment, the present invention provides a composition comprising an isolated polynucleotide selected from the group consisting of:

(a) a polynucleotide comprising the nucleotide sequence of SEQ ID NO:193;
(b) a polynucleotide comprising the nucleotide sequence of SEQ ID NO:193 from nucleotide 1262 to nucleotide 1858;
(c) a polynucleotide comprising the nucleotide sequence of the full-length protein coding sequence of clone yh33_1 deposited under accession number ATCC 98958;
(d) a polynucleotide encoding the full-length protein encoded by the cDNA insert of clone yh33_1 deposited under accession number ATCC 98958;
(e) a polynucleotide comprising the nucleotide sequence of a mature protein coding sequence of clone yh33_1 deposited under accession number ATCC 98958;
(f) a polynucleotide encoding a mature protein encoded by the cDNA insert of clone yh33_1 deposited under accession number ATCC 98958;
(g) a polynucleotide encoding a protein comprising the amino acid sequence of SEQ ID NO:194;
(h) a polynucleotide encoding a protein comprising a fragment of the amino acid sequence of SEQ ID NO:194 having biological activity, the fragment comprising eight contiguous amino acids of SEQ ID NO:194;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:193.

Preferably, such polynucleotide comprises the nucleotide sequence of SEQ ID NO:193 from nucleotide 1262 to nucleotide 1858; the nucleotide sequence of the full-length protein coding sequence of clone yh33_1 deposited under accession number ATCC 98958; or the nucleotide sequence of a mature protein coding sequence of clone yh33_1 deposited under accession number ATCC 98958. In other preferred embodiments, the polynucleotide encodes the full-length or a mature protein encoded by the cDNA insert of clone yh33_1 deposited under accession number ATCC 98958. In further preferred embodiments, the present invention provides a polynucleotide encoding a protein comprising a fragment of the amino acid sequence of SEQ ID NO:194 having biological activity, the fragment preferably comprising eight (more preferably twenty, most preferably thirty) contiguous amino acids of SEQ ID NO:194, or a polynucleotide encoding a protein comprising a fragment of the amino acid sequence of SEQ ID NO:194 having biological activity, the fragment comprising the amino acid sequence from amino acid 94 to amino acid 103 of SEQ ID NO:194.

Other embodiments provide the gene corresponding to the cDNA sequence of SEQ ID NO:193.

Further embodiments of the invention provide isolated polynucleotides produced according to a process selected from the group consisting of:
(a) a process comprising the steps of:
(i) preparing one or more polynucleotide probes that hybridize in 6×SSC at 65 degrees C. to a nucleotide sequence selected from the group consisting of:
(aa) SEQ ID NO:193, but excluding the poly(A) tail at the 3' end of SEQ ID NO:193; and
(ab) the nucleotide sequence of the cDNA insert of clone yh33_1 deposited under accession number ATCC 98958;
(ii) hybridizing said probe(s) to human genomic DNA in conditions at least as stringent as 4×SSC at 50 degrees C.; and
(iii) isolating the DNA polynucleotides detected with the probe(s);
and
(b) a process comprising the steps of:
(i) preparing one or more polynucleotide primers that hybridize in 6×SSC at 65 degrees C. to a nucleotide sequence selected from the group consisting of:
(ba) SEQ ID NO:193, but excluding the poly(A) tail at the 3' end of SEQ ID NO:193; and
(bb) the nucleotide sequence of the cDNA insert of clone yh33_1 deposited under accession number ATCC 98958;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:193, and extending contiguously from a nucleotide sequence corresponding to the 5' end of SEQ ID NO:193 to a nucleotide sequence corresponding to the 3' end of SEQ ID NO:193, but excluding the poly(A) tail at the 3' end of SEQ ID NO:193. Also preferably the polynucleotide isolated according to the above process comprises a nucleotide sequence corresponding to the cDNA sequence of SEQ ID NO:193 from nucleotide 1262 to nucleotide 1858, and extending contiguously from a nucleotide sequence corresponding to the 5' end of said sequence of SEQ ID NO:193 from nucleotide 1262 to nucleotide 1858, to a nucleotide sequence corresponding to the 3' end of said sequence of SEQ ID NO:193 from nucleotide 1262 to nucleotide 1858.

In other embodiments, the present invention provides a composition comprising a protein, wherein said protein comprises an amino acid sequence selected from the group consisting of:
(a) the amino acid sequence of SEQ ID NO:194;
(b) a fragment of the amino acid sequence of SEQ ID NO:194, the fragment comprising eight contiguous amino acids of SEQ ID NO:194; and
(c) the amino acid sequence encoded by the cDNA insert of clone yh33_1 deposited under accession number ATCC 98958;

the protein being substantially free from other mammalian proteins. Preferably such protein comprises the amino acid sequence of SEQ ID NO:194. In further preferred embodiments; the present invention provides a protein comprising a fragment of the amino acid sequence of SEQ ID NO:194 having biological activity, the fragment preferably comprising eight (more preferably twenty, most preferably thirty) contiguous amino acids of SEQ ID NO:194, or a protein comprising a fragment of the amino acid sequence of SEQ ID NO:194 having biological activity, the fragment comprising the amino acid sequence from amino acid 94 to amino acid 103 of SEQ ID NO:194.

In one embodiment, the present invention provides a composition comprising an isolated polynucleotide selected from the group consisting of:

(a) a polynucleotide comprising the nucleotide sequence of SEQ ID NO:195;

(b) a polynucleotide comprising the nucleotide sequence of SEQ ID NO:195 from nucleotide 25 to nucleotide 1851;

(c) a polynucleotide comprising the nucleotide sequence of SEQ ID NO:195 from nucleotide 250 to nucleotide 1851;

(d) a polynucleotide comprising the nucleotide sequence of the full-length protein coding sequence of clone yi16_1 deposited under accession number ATCC 98958;

(e) a polynucleotide encoding the full-length protein encoded by the cDNA insert of clone yi16_1 deposited under accession number ATCC 98958;

(f) a polynucleotide comprising the nucleotide sequence of a mature protein coding sequence of clone yi16_1 deposited under accession number ATCC 98958;

(g) a polynucleotide encoding a mature protein encoded by the cDNA insert of clone yi16_1 deposited under accession number ATCC 98958;

(h) a polynucleotide encoding a protein comprising the amino acid sequence of SEQ ID NO:196;

(i) a polynucleotide encoding a protein comprising a fragment of the amino acid sequence of SEQ ID NO:196 having biological activity, the fragment comprising eight contiguous amino acids of SEQ ID NO:196;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:195.

Preferably, such polynucleotide comprises the nucleotide sequence of SEQ ID NO:195 from nucleotide 25 to nucleotide 1851; the nucleotide sequence of SEQ ID NO:195 from nucleotide 250 to nucleotide 1851; the nucleotide sequence of the full-length protein coding sequence of clone yi16_1 deposited under accession number ATCC 98958; or the nucleotide sequence of a mature protein coding sequence of clone yi16_1 deposited under accession number ATCC 98958. In other preferred embodiments, the polynucleotide encodes the full-length or a mature protein encoded by the cDNA insert of clone yi16_1 deposited under accession number ATCC 98958. In further preferred embodiments, the present invention provides a polynucleotide encoding a protein comprising a fragment of the amino acid sequence of SEQ ID NO:196 having biological activity, the fragment preferably comprising eight (more preferably twenty, most preferably thirty) contiguous amino acids of SEQ ID NO:196, or a polynucleotide encoding a protein comprising a fragment of the amino acid sequence of SEQ ID NO:196 having biological activity, the fragment comprising the amino acid sequence from amino acid 299 to amino acid 308 of SEQ ID NO:196.

Other embodiments provide the gene corresponding to the cDNA sequence of SEQ ID NO:195.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:195, but excluding the poly(A) tail at the 3' end of SEQ ID NO:195; and
    (ab) the nucleotide sequence of the cDNA insert of clone yi16_1 deposited under accession number ATCC 98958;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:195, but excluding the poly(A) tail at the 3' end of SEQ ID NO:195; and
    (bb) the nucleotide sequence of the cDNA insert of clone yi16_1 deposited under accession number ATCC 98958;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:195, and extending contiguously from a nucleotide sequence corresponding to the 5' end of SEQ ID NO:195 to a nucleotide sequence corresponding to the 3' end of SEQ ID NO:195, but excluding the poly(A) tail at the 3' end of SEQ ID NO:195. Also preferably the polynucleotide isolated according to the above process comprises a nucleotide sequence corresponding to the cDNA sequence of SEQ ID NO:195 from nucleotide 25 to nucleotide 1851, and extending contiguously from a nucleotide sequence corresponding to the 5' end of said sequence of SEQ ID NO:195 from nucleotide 25 to nucleotide 1851, to a nucleotide sequence corresponding to the 3' end of said sequence of SEQ ID NO:195 from nucleotide to nucleotide 1851. Also preferably the polynucleotide isolated according to the above process comprises a nucleotide sequence corresponding to the cDNA sequence of SEQ ID NO:195 from nucleotide 250 to nucleotide 1851, and extending contiguously from a nucleotide sequence corresponding to the 5' end of said sequence of SEQ ID NO:195 from nucleotide 250 to nucleotide 1851, to a nucleotide sequence corresponding to the 3' end of said sequence of SEQ ID NO:195 from nucleotide 250 to nucleotide 1851.

In other embodiments, the present invention provides a composition comprising a protein, wherein said protein comprises an amino acid sequence selected from the group consisting of:

(a) the amino acid sequence of SEQ ID NO:196;

(b) a fragment of the amino acid sequence of SEQ ID NO:196, the fragment comprising eight contiguous amino acids of SEQ ID NO:196; and (c) the amino acid sequence encoded by the cDNA insert of clone yi16_1 deposited under accession number ATCC 98958;

the protein being substantially free from other mammalian proteins. Preferably such protein comprises the amino acid sequence of SEQ ID NO:196. In further preferred embodiments, the present invention provides a protein comprising a fragment of the amino acid sequence of SEQ ID NO:196 having biological activity, the fragment preferably comprising eight (more preferably twenty, most preferably thirty) contiguous amino acids of SEQ ID NO:196, or a protein comprising a fragment of the amino acid sequence of SEQ ID NO:196 having biological activity, the fragment comprising the amino acid sequence from amino acid 299 to amino acid 308 of SEQ ID NO:196.

In one embodiment, the present invention provides a composition comprising an isolated polynucleotide selected from the group consisting of:

(a) a polynucleotide comprising the nucleotide sequence of SEQ ID NO:197;

(b) a polynucleotide comprising the nucleotide sequence of SEQ ID NO:197 from nucleotide 739 to nucleotide 996;

(c) a polynucleotide comprising the nucleotide sequence of the full-length protein coding sequence of clone yk46_1 deposited under accession number ATCC 98958;

(d) a polynucleotide encoding the full-length protein encoded by the cDNA insert of clone yk46_1 deposited under accession number ATCC 98958;

(e) a polynucleotide comprising the nucleotide sequence of a mature protein coding sequence of clone yk46_1 deposited under accession number ATCC 98958;

(f) a polynucleotide encoding a mature protein encoded by the cDNA insert of clone yk46_1 deposited under accession number ATCC 98958;

(g) a polynucleotide encoding a protein comprising the amino acid sequence of SEQ ID NO:198;

(h) a polynucleotide encoding a protein comprising a fragment of the amino acid sequence of SEQ ID NO:198 having biological activity, the fragment comprising eight contiguous amino acids of SEQ ID NO:198;

(i) a polynucleotide which is an allelic variant of a polynucleotide of (a)–(f) above;

(j) a polynucleotide which encodes a species homologue of the protein of (g) or (h) above;

(k) a polynucleotide that hybridizes under stringent conditions to any one of the polynucleotides specified in (a)–(h); and (l) a polynucleotide that hybridizes under stringent conditions to any one of the polynucleotides specified in (a)–(h) and that has a length that is at least 25% of the length of SEQ ID NO:197.

Preferably, such polynucleotide comprises the nucleotide sequence of SEQ ID NO:197 from nucleotide 739 to nucleotide 996; the nucleotide sequence of the full-length protein coding sequence of clone yk46_1 deposited under accession number ATCC 98958; or the nucleotide sequence of a mature protein coding sequence of clone yk46_1 deposited under accession number ATCC 98958. In other preferred embodiments, the polynucleotide encodes the full-length or a mature protein encoded by the cDNA insert of clone yk46_1 deposited under accession number ATCC 98958. In further preferred embodiments, the present invention provides a polynucleotide encoding a protein comprising a fragment of the amino acid sequence of SEQ ID NO:198 having biological activity, the fragment preferably comprising eight (more preferably twenty, most preferably thirty) contiguous amino acids of SEQ ID NO:198, or a polynucleotide encoding a protein comprising a fragment of the amino acid sequence of SEQ ID NO:198 having biological activity, the fragment comprising the amino acid sequence from amino acid 38 to amino acid 47 of SEQ ID NO:198.

Other embodiments provide the gene corresponding to the cDNA sequence of SEQ ID NO:197.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:197, but excluding the poly(A) tail at the 3' end of SEQ ID NO:197; and
    (ab) the nucleotide sequence of the cDNA insert of clone yk46_1 deposited under accession number ATCC 98958;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:197, but excluding the poly(A) tail at the 3' end of SEQ ID NO:197; and
    (bb) the nucleotide sequence of the cDNA insert of clone yk46_1 deposited under accession number ATCC 98958;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:197, and extending contiguously from a nucleotide sequence corresponding to the 5' end of SEQ ID NO:197 to a nucleotide sequence corresponding to the 3' end of SEQ ID NO:197, but excluding the poly(A) tail at the 3' end of SEQ ID NO:197. Also preferably the polynucleotide isolated according to the above process comprises a nucleotide sequence corresponding to the cDNA sequence of SEQ ID NO:197 from nucleotide 739 to nucleotide 996, and extending contiguously from a nucleotide sequence corresponding to the 5' end of said sequence of SEQ ID NO:197 from nucleotide 739 to nucleotide 996, to a nucleotide sequence corresponding to the 3' end of said sequence of SEQ ID NO:197 from nucleotide 739 to nucleotide 996.

In other embodiments, the present invention provides a composition comprising a protein, wherein said protein comprises an amino acid sequence selected from the group consisting of:

(a) the amino acid sequence of SEQ ID NO:198;

(b) a fragment of the amino acid sequence of SEQ ID NO:198, the fragment comprising eight contiguous amino acids of SEQ ID NO:198; and (c) the amino acid sequence encoded by the cDNA insert of clone yk46_1 deposited under accession number ATCC 98958;

the protein being substantially free from other mammalian proteins. Preferably such protein comprises the amino acid sequence of SEQ ID NO:198. In further preferred embodiments, the present invention provides a protein comprising a fragment of the amino acid sequence of SEQ ID NO:198 having biological activity, the fragment preferably comprising eight (more preferably twenty, most preferably thirty) contiguous amino acids of SEQ ID NO:198, or a protein comprising a fragment of the amino acid sequence of SEQ ID NO:198 having biological activity, the fragment comprising the amino acid sequence from amino acid 38 to amino acid 47 of SEQ ID NO:198.

In one embodiment, the present invention provides a composition comprising an isolated polynucleotide selected from the group consisting of:

(a) a polynucleotide comprising the nucleotide sequence of SEQ ID NO:199;

(b) a polynucleotide comprising the nucleotide sequence of SEQ ID NO:199 from nucleotide 222 to nucleotide 605;

(c) a polynucleotide comprising the nucleotide sequence of SEQ ID NO:199 from nucleotide 366 to nucleotide 605;

(d) a polynucleotide comprising the nucleotide sequence of the full-length protein coding sequence of clone yk84_1 deposited under accession number ATCC 98958;

(e) a polynucleotide encoding the full-length protein encoded by the cDNA insert of clone yk84_1 deposited under accession number ATCC 98958;

(f) a polynucleotide comprising the nucleotide sequence of a mature protein coding sequence of clone yk84_1 deposited under accession number ATCC 98958;

(g) a polynucleotide encoding a mature protein encoded by the cDNA insert of clone yk84_1 deposited under accession number ATCC 98958;

(h) a polynucleotide encoding a protein comprising the amino acid sequence of SEQ ID NO:200;

(i) a polynucleotide encoding a protein comprising a fragment of the amino acid sequence of SEQ ID NO:200 having biological activity, the fragment comprising eight contiguous amino acids of SEQ ID NO:200;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:199.

Preferably, such polynucleotide comprises the nucleotide sequence of SEQ ID NO:199 from nucleotide 222 to nucleotide 605; the nucleotide sequence of SEQ ID NO:199 from nucleotide 366 to nucleotide 605; the nucleotide sequence of the full-length protein coding sequence of clone yk84_1 deposited under accession number ATCC 98958; or the nucleotide sequence of a mature protein coding sequence of clone yk84_1 deposited under accession number ATCC 98958. In other preferred embodiments, the polynucleotide encodes the full-length or a mature protein encoded by the cDNA insert of clone yk84_1 deposited under accession number ATCC 98958. In further preferred embodiments, the present invention provides a polynucleotide encoding a protein comprising a fragment of the amino acid sequence of SEQ ID NO:200 having biological activity, the fragment preferably comprising eight (more preferably twenty, most preferably thirty) contiguous amino acids of SEQ ID NO:200, or a polynucleotide encoding a protein comprising a fragment of the amino acid sequence of SEQ ID NO:200 having biological activity, the fragment comprising the amino acid sequence from amino acid 59 to amino acid 68 of SEQ ID NO:200.

Other embodiments provide the gene corresponding to the cDNA sequence of SEQ ID NO:199.

Further embodiments of the invention provide isolated polynucleotides produced according to a process selected from the group consisting of:

(a) a process comprising the steps of:
  (i) preparing one or more polynucleotide probes that hybridize in 6×SSC at 65 degrees C. to a nucleotide sequence selected from the group consisting of:
    (aa) SEQ ID NO:199, but excluding the poly(A) tail at the 3' end of SEQ ID NO:199; and
    (ab) the nucleotide sequence of the cDNA insert of clone yk84_1 deposited under accession number ATCC 98958;
  (ii) hybridizing said probe(s) to human genomic DNA in conditions at least as stringent as 4×SSC at 50 degrees C.; and
  (iii) isolating the DNA polynucleotides detected with the probe(s);

and (b) a process comprising the steps of:
  (i) preparing one or more polynucleotide primers that hybridize in 6×SSC at 65 degrees C. to a nucleotide sequence selected from the group consisting of:
    (ba) SEQ ID NO:199, but excluding the poly(A) tail at the 3' end of SEQ ID NO:199; and
    (bb) the nucleotide sequence of the cDNA insert of clone yk84_1 deposited under accession number ATCC 98958;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:199, and extending contiguously from a nucleotide sequence corresponding to the 5' end of SEQ ID NO:199 to a nucleotide sequence corresponding to the 3' end of SEQ ID NO:199, but excluding the poly(A) tail at the 3' end of SEQ ID NO:199. Also preferably the polynucleotide isolated according to the above process comprises a nucleotide sequence corresponding to the cDNA sequence of SEQ ID NO:199 from nucleotide 222 to nucleotide 605, and extending contiguously from a nucleotide sequence corresponding to the 5' end of said sequence of SEQ ID NO:199 from nucleotide 222 to nucleotide 605, to a nucleotide sequence corresponding to the 3' end of said sequence of SEQ ID NO:199 from nucleotide 222 to nucleotide 605. Also preferably the polynucleotide isolated according to the above process comprises a nucleotide sequence corresponding to the cDNA sequence of SEQ ID NO:199 from nucleotide 366 to nucleotide 605, and extending contiguously from a nucleotide sequence corresponding to the 5' end of said sequence of SEQ ID NO:199 from nucleotide 366 to nucleotide 605, to a nucleotide sequence corresponding to the 3' end of said sequence of SEQ ID NO:199 from nucleotide 366 to nucleotide 605.

In other embodiments, the present invention provides a composition comprising a protein, wherein said protein comprises an amino acid sequence selected from the group consisting of:
 (a) the amino acid sequence of SEQ ID NO:200;
 (b) a fragment of the amino acid sequence of SEQ ID NO:200, the fragment comprising eight contiguous amino acids of SEQ ID NO:200; and
 (c) the amino acid sequence encoded by the cDNA insert of clone yk84_1 deposited under accession number ATCC 98958;
the protein being substantially free from other mammalian proteins. Preferably such protein comprises the amino acid sequence of SEQ ID NO:200. In further preferred embodiments, the present invention provides a protein comprising a fragment of the amino acid sequence of SEQ ID NO:200 having biological activity, the fragment preferably comprising eight (more preferably twenty, most preferably thirty) contiguous amino acids of SEQ ID NO:200, or a protein comprising a fragment of the amino acid sequence of SEQ ID NO:200 having biological activity, the fragment comprising the amino acid sequence from amino acid 59 to amino acid 68 of SEQ ID NO:200.

In one embodiment, the present invention provides a composition comprising an isolated polynucleotide selected from the group consisting of:
 (a) a polynucleotide comprising the nucleotide sequence of SEQ ID NO:201;
 (b) a polynucleotide comprising the nucleotide sequence of SEQ ID NO:201 from nucleotide 140 to nucleotide 1036;
 (c) a polynucleotide comprising the nucleotide sequence of SEQ ID NO:201 from nucleotide 269 to nucleotide 1036;
 (d) a polynucleotide comprising the nucleotide sequence of the full-length protein coding sequence of clone yk143_1 deposited under accession number ATCC 98958;
 (e) a polynucleotide encoding the full-length protein encoded by the cDNA insert of clone yk143_1 deposited under accession number ATCC 98958;
 (f) a polynucleotide comprising the nucleotide sequence of a mature protein coding sequence of clone yk143_1 deposited under accession number ATCC 98958;
 (g) a polynucleotide encoding a mature protein encoded by the cDNA insert of clone yk143_1 deposited under accession number ATCC 98958;
 (h) a polynucleotide encoding a protein comprising the amino acid sequence of SEQ ID NO:202;
 (i) a polynucleotide encoding a protein comprising a fragment of the amino acid sequence of SEQ ID NO:202 having biological activity, the fragment comprising eight contiguous amino acids of SEQ ID NO:202;
 (j) a polynucleotide which is an allelic variant of a polynucleotide of (a)–(g) above;
 (k) a polynucleotide which encodes a species homologue of the protein of (h) or (i) above;
 (l) a polynucleotide that hybridizes under stringent conditions to any one of the polynucleotides specified in (a)–(i); and
 (m) a polynucleotide that hybridizes under stringent conditions to any one of the polynucleotides specified in (a)–(i) and that has a length that is at least 25% of the length of SEQ ID NO:201.

Preferably, such polynucleotide comprises the nucleotide sequence of SEQ ID NO:201 from nucleotide 140 to nucleotide 1036; the nucleotide sequence of SEQ ID NO:201 from nucleotide 269 to nucleotide 1036; the nucleotide sequence of the full-length protein coding sequence of clone yk143_1 deposited under accession number ATCC 98958; or the nucleotide sequence of a mature protein coding sequence of clone yk143_1 deposited under accession number ATCC 98958. In other preferred embodiments, the polynucleotide encodes the full-length or a mature protein encoded by the cDNA insert of clone yk143_1 deposited under accession number ATCC 98958. In further preferred embodiments, the present invention provides a polynucleotide encoding a protein comprising a fragment of the amino acid sequence of SEQ ID NO:202 having biological activity, the fragment preferably comprising eight (more preferably twenty, most preferably thirty) contiguous amino acids of SEQ ID NO:202, or a polynucleotide encoding a protein comprising a fragment of the amino acid sequence of SEQ ID NO:202 having biological activity, the fragment comprising the amino acid sequence from amino acid 144 to amino acid 153 of SEQ ID NO:202.

Other embodiments provide the gene corresponding to the cDNA sequence of SEQ ID NO:201.

Further embodiments of the invention provide isolated polynucleotides produced according to a process selected from the group consisting of:
 (a) a process comprising the steps of:
  (i) preparing one or more polynucleotide probes that hybridize in 6×SSC at 65 degrees C. to a nucleotide sequence selected from the group consisting of:
   (aa) SEQ ID NO:201, but excluding the poly(A) tail at the 3' end of SEQ ID NO:201; and
   (ab) the nucleotide sequence of the cDNA insert of clone yk143_1 deposited under accession number ATCC 98958;
  (ii) hybridizing said probe(s) to human genomic DNA in conditions at least as stringent as 4×SSC at 50 degrees C.; and
  (iii) isolating the DNA polynucleotides detected with the probe(s);
and
 (b) a process comprising the steps of:
  (i) preparing one or more polynucleotide primers that hybridize in 6×SSC at 65 degrees C. to a nucleotide sequence selected from the group consisting of:
   (ba) SEQ ID NO:201, but excluding the poly(A) tail at the 3' end of SEQ ID NO:201; and
   (bb) the nucleotide sequence of the cDNA insert of clone yk143_1 deposited under accession number ATCC 98958;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b) (iii).

Preferably the polynucleotide isolated according to the above process comprises a nucleotide sequence corresponding to the cDNA sequence of SEQ ID NO:201, and extending contiguously from a nucleotide sequence corresponding to the 5' end of SEQ ID NO:201 to a nucleotide sequence corresponding to the 3' end of SEQ ID NO:201, but excluding the poly(A) tail at the 3' end of SEQ ID NO:201. Also preferably the polynucleotide isolated according to the above process comprises a nucleotide sequence corresponding to the cDNA sequence of SEQ ID NO:201 from nucleotide 140 to nucleotide 1036, and extending contiguously from a nucleotide sequence corresponding to the 5' end of said sequence of SEQ ID NO:201 from nucleotide 140 to nucleotide 1036, to a nucleotide sequence corresponding to the 3' end of said sequence of SEQ ID NO:201 from nucleotide 140 to nucleotide 1036. Also preferably the polynucleotide isolated according to the above process comprises a nucleotide sequence corresponding to the cDNA sequence of SEQ ID NO:201 from nucleotide 269 to nucleotide 1036, and extending contiguously from a nucleotide sequence corresponding to the 5' end of said sequence of SEQ ID NO:201 from nucleotide 269 to nucleotide 1036, to a nucleotide sequence corresponding to the 3' end of said sequence of SEQ ID NO:201 from nucleotide 269 to nucleotide 1036.

In other embodiments, the present invention provides a composition comprising a protein, wherein said protein comprises an amino acid sequence selected from the group consisting of:
  (a) the amino acid sequence of SEQ ID NO:202;
  (b) a fragment of the amino acid sequence of SEQ ID NO:202, the fragment comprising eight contiguous amino acids of SEQ ID NO:202; and
  (c) the amino acid sequence encoded by the cDNA insert of clone yk143_1 deposited under accession number ATCC 98958;
the protein being substantially free from other mammalian proteins. Preferably such protein comprises the amino acid sequence of SEQ ID NO:202. In further preferred embodiments, the present invention provides a protein comprising a fragment of the amino acid sequence of SEQ ID NO:202 having biological activity, the fragment preferably comprising eight (more preferably twenty, most preferably thirty) contiguous amino acids of SEQ ID NO:202, or a protein comprising a fragment of the amino acid sequence of SEQ ID NO:202 having biological activity, the fragment comprising the amino acid sequence from amino acid 144 to amino acid 153 of SEQ ID NO:202.

In one embodiment, the present invention provides a composition comprising an isolated polynucleotide selected from the group consisting of:
  (a) a polynucleotide comprising the nucleotide sequence of SEQ ID NO:203;
  (b) a polynucleotide comprising the nucleotide sequence of SEQ ID NO:203 from nucleotide 304 to nucleotide 636;
  (c) a polynucleotide comprising the nucleotide sequence of SEQ ID NO:203 from nucleotide 415 to nucleotide 636;
  (d) a polynucleotide comprising the nucleotide sequence of the full-length protein coding sequence of clone yk156_1 deposited under accession number ATCC 98958;
  (e) a polynucleotide encoding the full-length protein encoded by the cDNA insert of clone yk156_1 deposited under accession number ATCC 98958;
  (f) a polynucleotide comprising the nucleotide sequence of a mature protein coding sequence of clone yk156_1 deposited under accession number ATCC 98958;
  (g) a polynucleotide encoding a mature protein encoded by the cDNA insert of clone yk156_1 deposited under accession number ATCC 98958;
  (h) a polynucleotide encoding a protein comprising the amino acid sequence of SEQ ID NO:204;
  (i) a polynucleotide encoding a protein comprising a fragment of the amino acid sequence of SEQ ID NO:204 having biological activity, the fragment comprising eight contiguous amino acids of SEQ ID NO:204;
  (j) a polynucleotide which is an allelic variant of a polynucleotide of (a)–(g) above;
  (k) a polynucleotide which encodes a species homologue of the protein of (h) or (i) above;
  (l) a polynucleotide that hybridizes under stringent conditions to any one of the polynucleotides specified in (a)–(i); and
  (m) a polynucleotide that hybridizes under stringent conditions to any one of the polynucleotides specified in (a)–(i) and that has a length that is at least 25% of the length of SEQ ID NO:203.

Preferably, such polynucleotide comprises the nucleotide sequence of SEQ ID NO:203 from nucleotide 304 to nucleotide 636; the nucleotide sequence of SEQ ID NO:203 from nucleotide 415 to nucleotide 636; the nucleotide sequence of the full-length protein coding sequence of clone yk156_1 deposited under accession number ATCC 98958; or the nucleotide sequence of a mature protein coding sequence of clone yk156_1 deposited under accession number ATCC 98958. In other preferred embodiments, the polynucleotide encodes the full-length or a mature protein encoded by the cDNA insert of clone yk156_1 deposited under accession number ATCC 98958. In further preferred embodiments, the present invention provides a polynucleotide encoding a protein comprising a fragment of the amino acid sequence of SEQ ID NO:204 having biological activity, the fragment preferably comprising eight (more preferably twenty, most preferably thirty) contiguous amino acids of SEQ ID NO:204, or a polynucleotide encoding a protein comprising a fragment of the amino acid sequence of SEQ ID NO:204 having biological activity, the fragment comprising the amino acid sequence from amino acid 50 to amino acid 59 of SEQ ID NO:204.

Other embodiments provide the gene corresponding to the cDNA sequence of SEQ ID NO:203.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:203, but excluding the poly(A) tail at the 3' end of SEQ ID NO:203; and
      (ab) the nucleotide sequence of the cDNA insert of clone yk156_1 deposited under accession number ATCC 98958;
    (i) hybridizing said probe(s) to human genomic DNA in conditions at least as stringent as 4×SSC at 50 degrees C.; and
    (iii) isolating the DNA polynucleotides detected with the probe(s);
and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:203, but excluding the poly(A) tail at the 3' end of SEQ ID NO:203; and (bb) the nucleotide sequence of the cDNA insert of clone yk156_1 deposited under accession number ATCC 98958;

(ii) hybridizing said primer(s) to human genomic DNA in conditions at least as stringent as 4×SSC at 50 degrees C.;

(iii) amplifying human DNA sequences; and (iv) isolating the polynucleotide products of step (b) (iii).

Preferably the polynucleotide isolated according to the above process comprises a nucleotide sequence corresponding to the cDNA sequence of SEQ ID NO:203, and extending contiguously from a nucleotide sequence corresponding to the 5' end of SEQ ID NO:203 to a nucleotide sequence corresponding to the 3' end of SEQ ID NO:203 but excluding the poly(A) tail at the 3' end of SEQ ID NO:203. Also preferably the polynucleotide isolated according to the above process comprises a nucleotide sequence corresponding to the cDNA sequence of SEQ ID NO:203 from nucleotide 304 to nucleotide 636, and extending contiguously from a nucleotide sequence corresponding to the 5' end of said sequence of SEQ ID NO:203 from nucleotide 304 to nucleotide 636, to a nucleotide sequence corresponding to the 3' end of said sequence of SEQ ID NO:203 from nucleotide 304 to nucleotide 636. Also preferably the polynucleotide isolated according to the above process comprises a nucleotide sequence corresponding to the cDNA sequence of SEQ ID NO:203 from nucleotide 415 to nucleotide 636, and extending contiguously from a nucleotide sequence corresponding to the 5' end of said sequence of SEQ ID NO:203 from nucleotide 415 to nucleotide 636, to a nucleotide sequence corresponding to the 3' end of said sequence of SEQ ID NO:203 from nucleotide 415 to nucleotide 636.

In other embodiments, the present invention provides a composition comprising a protein, wherein said protein comprises an amino acid sequence selected from the group consisting of:

(a) the amino acid sequence of SEQ ID NO:204;

(b) a fragment of the amino acid sequence of SEQ ID NO:204, the fragment comprising eight contiguous amino acids of SEQ ID NO:204; and (c) the amino acid sequence encoded by the cDNA insert of clone yk156_1 deposited under accession number ATCC 98958;

the protein being substantially free from other mammalian proteins. Preferably such protein comprises the amino acid sequence of SEQ ID NO:204. In further preferred embodiments, the present invention provides a protein comprising a fragment of the amino acid sequence of SEQ ID NO:204 having biological activity, the fragment preferably comprising eight (more preferably twenty, most preferably thirty) contiguous amino acids of SEQ ID NO:204, or a protein comprising a fragment of the amino acid sequence of SEQ ID NO:204 having biological activity, the fragment comprising the amino acid sequence from amino acid 50 to amino acid 59 of SEQ ID NO:204.

In one embodiment, the present invention provides a composition comprising an isolated polynucleotide selected from the group consisting of:

(a) a polynucleotide comprising the nucleotide sequence of SEQ ID NO:205;

(b) a polynucleotide comprising the nucleotide sequence of SEQ ID NO:205 from nucleotide 571 to nucleotide 891;

(c) a polynucleotide comprising the nucleotide sequence of SEQ ID NO:205 from nucleotide 745 to nucleotide 891;

(d) a polynucleotide comprising the nucleotide sequence of the full-length protein coding sequence of clone yk204_1 deposited under accession number ATCC 98958;

(e) a polynucleotide encoding the full-length protein encoded by the cDNA insert of clone yk204_1 deposited under accession number ATCC 98958;

(f) a polynucleotide comprising the nucleotide sequence of a mature protein coding sequence of clone yk204_1 deposited under accession number ATCC 98958;

(g) a polynucleotide encoding a mature protein encoded by the cDNA insert of clone yk204_1 deposited under accession number ATCC 98958;

(h) a polynucleotide encoding a protein comprising the amino acid sequence of SEQ ID NO:206;

(i) a polynucleotide encoding a protein comprising a fragment of the amino acid sequence of SEQ ID NO:206 having biological activity, the fragment comprising eight contiguous amino acids of SEQ ID NO:206;

(j) a polynucleotide which is an allelic variant of a polynucleotide of (a)–(g) above;

(k) a polynucleotide which encodes a species homologue of the protein of (h) or (i) above;

(l) a polynucleotide that hybridizes under stringent conditions to any one of the polynucleotides specified in (a)–(i); and (m) a polynucleotide that hybridizes under stringent conditions to any one of the polynucleotides specified in (a)–(i) and that has a length that is at least 25% of the length of SEQ ID NO:205.

Preferably, such polynucleotide comprises the nucleotide sequence of SEQ ID NO:205 from nucleotide 571 to nucleotide 891; the nucleotide sequence of SEQ ID NO:205 from nucleotide 745 to nucleotide 891; the nucleotide sequence of the full-length protein coding sequence of clone yk204_1 deposited under accession number ATCC 98958; or the nucleotide sequence of a mature protein coding sequence of clone yk204_1 deposited under accession number ATCC 98958. In other preferred embodiments, the polynucleotide encodes the full-length or a mature protein encoded by the cDNA insert of clone yk204_1 deposited under accession number ATCC 98958. In further preferred embodiments, the present invention provides a polynucleotide encoding a protein comprising a fragment of the amino acid sequence of SEQ ID NO:206 having biological activity, the fragment preferably comprising eight (more preferably twenty, most preferably thirty) contiguous amino acids of SEQ ID NO:206, or a polynucleotide encoding a protein comprising a fragment of the amino acid sequence of SEQ ID NO:206 having biological activity, the fragment comprising the amino acid sequence from amino acid 48 to amino acid 57 of SEQ ID NO:206.

Other embodiments provide the gene corresponding to the cDNA sequence of SEQ ID NO:205.

Further embodiments of the invention provide isolated polynucleotides produced according to a process selected from the group consisting of:

(a) a process comprising the steps of:

(i) preparing one or more polynucleotide probes that hybridize in 6×SSC at 65 degrees C. to a nucleotide sequence selected from the group consisting of:

(aa) SEQ ID NO:205, but excluding the poly(A) tail at the 3' end of SEQ ID NO:205; and (ab) the nucleotide sequence of the cDNA insert of clone yk204_1 deposited under accession number ATCC 98958;

(ii) hybridizing said probe(s) to human genomic DNA in conditions at least as stringent as 4×SSC at 50 degrees C.; and (j) isolating the DNA polynucleotides detected with the probe(s);

and (b) a process comprising the steps of:
(i) preparing one or more polynucleotide primers that hybridize in 6×SSC at 65 degrees C. to a nucleotide sequence selected from the group consisting of:
(ba) SEQ ID NO:205, but excluding the poly(A) tail at the 3' end of SEQ ID NO:205; and
(bb) the nucleotide sequence of the cDNA insert of clone yk204_1 deposited under accession number ATCC 98958;
(ii) hybridizing said primer(s) to human genomic DNA in conditions at least as stringent as 4×SSC at 50 degrees C.;
(iii) amplifying human DNA sequences; and
(iv) isolating the polynucleotide products of step (b) (iii).

Preferably the polynucleotide isolated according to the above process comprises a nucleotide sequence corresponding to the cDNA sequence of SEQ ID NO:205, and extending contiguously from a nucleotide sequence corresponding to the 5' end of SEQ ID NO:205 to a nucleotide sequence corresponding to the 3' end of SEQ ID NO:205, but excluding the poly(A) tail at the 3' end of SEQ ID NO:205. Also preferably the polynucleotide isolated according to the above process comprises a nucleotide sequence corresponding to the cDNA sequence of SEQ ID NO:205 from nucleotide 571 to nucleotide 891, and extending contiguously from a nucleotide sequence corresponding to the 5' end of said sequence of SEQ ID NO:205 from nucleotide 571 to nucleotide 891, to a nucleotide sequence corresponding to the 3' end of said sequence of SEQ ID NO:205 from nucleotide 571 to nucleotide 891. Also preferably the polynucleotide isolated according to the above process comprises a nucleotide sequence corresponding to the cDNA sequence of SEQ ID NO:205 from nucleotide 745 to nucleotide 891, and extending contiguously from a nucleotide sequence corresponding to the 5' end of said sequence of SEQ ID NO:205 from nucleotide 745 to nucleotide 891, to a nucleotide sequence corresponding to the 3' end of said sequence of SEQ ID NO:205 from nucleotide 745 to nucleotide 891.

In other embodiments, the present invention provides a composition comprising a protein, wherein said protein comprises an amino acid sequence selected from the group consisting of:

(a) the amino acid sequence of SEQ ID NO:206;
(b) a fragment of the amino acid sequence of SEQ ID NO:206, the fragment comprising eight contiguous amino acids of SEQ ID NO:206; and
(c) the amino acid sequence encoded by the cDNA insert of clone yk204_1 deposited under accession number ATCC 98958;

the protein being substantially free from other mammalian proteins. Preferably such protein comprises the amino acid sequence of SEQ ID NO:206. In further preferred embodiments, the present invention provides a protein comprising a fragment of the amino acid sequence of SEQ ID NO:206 having biological activity, the fragment preferably comprising eight (more preferably twenty, most preferably thirty) contiguous amino acids of SEQ ID NO:206, or a protein comprising a fragment of the amino acid sequence of SEQ ID NO:206 having biological activity, the fragment comprising the amino acid sequence from amino acid 48 to amino acid 57 of SEQ ID NO:206.

In one embodiment, the present invention provides a composition comprising an isolated polynucleotide selected from the group consisting of:

(a) a polynucleotide comprising the nucleotide sequence of SEQ ID NO:207;
(b) a polynucleotide comprising the nucleotide sequence of SEQ ID NO:207 from nucleotide 283 to nucleotide 1560;
(c) a polynucleotide comprising the nucleotide sequence of the full-length protein coding sequence of clone yk224_1 deposited under accession number ATCC 98958;
(d) a polynucleotide encoding the full-length protein encoded by the cDNA insert of clone yk224_1 deposited under accession number ATCC 98958;
(e) a polynucleotide comprising the nucleotide sequence of a mature protein coding sequence of clone yk224_1 deposited under accession number ATCC 98958;
(f) a polynucleotide encoding a mature protein encoded by the cDNA insert of clone yk224_1 deposited under accession number ATCC 98958;,
(g) a polynucleotide encoding a protein comprising the amino acid sequence of SEQ ID NO:208;
(h) a polynucleotide encoding a protein comprising a fragment of the amino acid sequence of SEQ ID NO:208 having biological activity, the fragment comprising eight contiguous amino acids of SEQ ID NO:208;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:207.

Preferably, such polynucleotide comprises the nucleotide sequence of SEQ ID NO:207 from nucleotide 283 to nucleotide 1560; the nucleotide sequence of the full-length protein coding sequence of clone yk224_1 deposited under accession number ATCC 98958; or the nucleotide sequence of a mature protein coding sequence of clone yk224_1 deposited under accession number ATCC 98958. In other preferred embodiments, the polynucleotide encodes the full-length or a mature protein encoded by the cDNA insert of done yk224_1 deposited under accession number ATCC 98958. In further preferred embodiments, the present invention provides a polynucleotide encoding a protein comprising a fragment of the amino acid sequence of SEQ ID NO:208 having biological activity, the fragment preferably comprising eight (more preferably twenty, most preferably thirty) contiguous amino acids of SEQ ID NO:208, or a polynucleotide encoding a protein comprising a fragment of the amino acid sequence of SEQ ID NO:208 having biological activity, the fragment comprising the amino acid sequence from amino acid 208 to amino acid 217 of SEQ ID NO:208.

Other embodiments provide the gene corresponding to the cDNA sequence of SEQ ID NO:207.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:207, but excluding the poly(A) tail at the 3' end of SEQ ID NO:207; and
      (ab) the nucleotide sequence of the cDNA insert of clone yk224_1 deposited under accession number ATCC 98958;
    (ii) hybridizing said probe(s) to human genomic DNA in conditions at least as stringent as 4×SSC at 50 degrees C.; and
    (iii) isolating the DNA polynucleotides detected with the probe(s);
and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:207, but excluding the poly(A) tail at the 3' end of SEQ ID NO:207; and
      (bb) the nucleotide sequence of the cDNA insert of clone yk224_1 deposited under accession number ATCC 98958;
    (ii) hybridizing said primer(s) to human genomic DNA in conditions at least as stringent as 4×SSC at 50 degrees C.;
    (iii) amplifying human DNA sequences; and
    (iv) isolating the polynucleotide products of step (b)(iii).

Preferably the polynucleotide isolated according to the above process comprises a nucleotide sequence corresponding to the cDNA sequence of SEQ ID NO:207, and extending contiguously from a nucleotide sequence corresponding to the 5' end of SEQ ID NO:207 to a nucleotide sequence corresponding to the 3' end of SEQ ID NO:207, but excluding the poly(A) tail at the 3' end of SEQ ID NO:207. Also preferably the polynucleotide isolated according to the above process comprises a nucleotide sequence corresponding to the cDNA sequence of SEQ ID NO:207 from nucleotide 283 to nucleotide 1560, and extending contiguously from a nucleotide sequence corresponding to the 5' end of said sequence of SEQ ID NO:207 from nucleotide 283 to nucleotide 1560, to a nucleotide sequence corresponding to the 3' end of said sequence of SEQ ID NO:207 from nucleotide 283 to nucleotide 1560.

In other embodiments, the present invention provides a composition comprising a protein, wherein said protein comprises an amino acid sequence selected from the group consisting of:
  (a) the amino acid sequence of SEQ ID NO:208;
  (b) a fragment of the amino acid sequence of SEQ ID NO:208, the fragment comprising eight contiguous amino acids of SEQ ID NO:208; and
  (c) the amino acid sequence encoded by the cDNA insert of clone yk224_1 deposited under accession number ATCC 98958;
the protein being substantially free from other mammalian proteins. Preferably such protein comprises the amino acid sequence of SEQ ID NO:208. In further preferred embodiments, the present invention provides a protein comprising a fragment of the amino acid sequence of SEQ ID NO:208 having biological activity, the fragment preferably comprising eight (more preferably twenty, most preferably thirty) contiguous amino acids of SEQ ID NO:208, or a protein comprising a fragment of the amino acid sequence of SEQ ID NO:208 having biological activity, the fragment comprising the amino acid sequence from amino acid 208 to amino acid 217 of SEQ ID NO:208.

In one embodiment, the present invention provides a composition comprising an isolated polynucleotide selected from the group consisting of:
  (a) a polynucleotide comprising the nucleotide sequence of SEQ ID NO:209;
  (b) a polynucleotide comprising the nucleotide sequence of SEQ ID NO:209 from nucleotide 485 to nucleotide 1465;
  (c) a polynucleotide comprising the nucleotide sequence of SEQ ID NO:209 from nucleotide 560 to nucleotide 1465;
  (d) a polynucleotide comprising the nucleotide sequence of the full-length protein coding sequence of clone yk261_1 deposited under accession number ATCC 98958;
  (e) a polynucleotide encoding the full-length protein encoded by the cDNA insert of clone yk261_1 deposited under accession number ATCC 98958;
  (f) a polynucleotide comprising the nucleotide sequence of a mature protein coding sequence of clone yk261_1 deposited under accession number ATCC 98958;
  (g) a polynucleotide encoding a mature protein encoded by the cDNA insert of clone yk261_1 deposited under accession number ATCC 98958;
  (h) a polynucleotide encoding a protein comprising the amino acid sequence of SEQ ID NO:210;
  (i) a polynucleotide encoding a protein comprising a fragment of the amino acid sequence of SEQ ID NO:210 having biological activity, the fragment comprising eight contiguous amino acids of SEQ ID NO:210;
  (j) a polynucleotide which is an allelic variant of a polynucleotide of (a)–(g) above;
  (k) a polynucleotide which encodes a species homologue of the protein of (h) or (i) above;
  (l) a polynucleotide that hybridizes under stringent conditions to any one of the polynucleotides specified in (a)–(i); and
  (m) a polynucleotide that hybridizes under stringent conditions to any one of the polynucleotides specified in (a)–(i) and that has a length that is at least 25% of the length of SEQ ID NO:209.

Preferably, such polynucleotide comprises the nucleotide sequence of SEQ ID NO:209 from nucleotide 485 to nucleotide 1465; the nucleotide sequence of SEQ ID NO:209 from nucleotide 560 to nucleotide 1465; the nucleotide sequence of the full-length protein coding sequence of clone yk261_1 deposited under accession number ATCC 98958; or the nucleotide sequence of a mature protein coding sequence of clone yk261_1 deposited under accession number ATCC 98958. In other preferred embodiments, the polynucleotide encodes the full-length or a mature protein encoded by the cDNA insert of clone yk261_1 deposited under accession number ATCC 98958. In further preferred embodiments, the present invention provides a polynucleotide encoding a protein comprising a fragment of the amino acid sequence of SEQ ID NO:210 having biological activity, the fragment preferably comprising eight (more preferably twenty, most preferably thirty) contiguous amino acids of SEQ ID NO:210, or a polynucleotide encoding a protein comprising a fragment of the amino acid sequence of SEQ ID NO:210 having biological activity, the fragment comprising the amino acid sequence from amino acid 158 to amino acid 167 of SEQ ID NO:210.

Other embodiments provide the gene corresponding to the cDNA sequence of SEQ ID NO:209.

Further embodiments of the invention provide isolated polynucleotides produced according to a process selected from the group consisting of:
(a) a process comprising the steps of:
  (i) preparing one or more polynucleotide probes that hybridize in 6×SSC at 65 degrees C. to a nucleotide sequence selected from the group consisting of:
    (aa) SEQ ID NO:209, but excluding the poly(A) tail at the 3' end of SEQ ID NO:209; and
    (ab) the nucleotide sequence of the cDNA insert of clone yk261_1 deposited under accession number ATCC 98958;
  (ii) hybridizing said probe(s) to human genomic DNA in conditions at least as stringent as 4×SSC at 50 degrees C.; and
  (iii) isolating the DNA polynucleotides detected with the probe(s);
and
(b) a process comprising the steps of:
  (i) preparing one or more polynucleotide primers that hybridize in 6×SSC at 65 degrees C. to a nucleotide sequence selected from the group consisting of:
    (ba) SEQ ID NO:209, but excluding the poly(A) tail at the 3' end of SEQ ID NO:209; and
    (bb) the nucleotide sequence of the cDNA insert of clone yk261_1 deposited under accession number ATCC 98958;
  (ii) hybridizing said primer(s) to human genomic DNA in conditions at least as stringent as 4×SSC at 50 degrees C.;
  (iii) amplifying human DNA sequences; and
  (iv) isolating the polynucleotide products of step (b)(iii).

Preferably the polynucleotide isolated according to the above process comprises a nucleotide sequence corresponding to the cDNA sequence of SEQ ID NO:209, and extending contiguously from a nucleotide sequence corresponding to the 5' end of SEQ ID NO:209 to a nucleotide sequence corresponding to the 3' end of SEQ ID NO:209, but excluding the poly(A) tail at the 3' end of SEQ ID NO:209. Also preferably the polynucleotide isolated according to the above process comprises a nucleotide sequence corresponding to the cDNA sequence of SEQ ID NO:209 from nucleotide 485 to nucleotide 1465, and extending contiguously from a nucleotide sequence corresponding to the 5' end of said sequence of SEQ ID NO:209 from nucleotide 485 to nucleotide 1465, to a nucleotide sequence corresponding to the 3' end of said sequence of SEQ ID NO:209 from nucleotide 485 to nucleotide 1465. Also preferably the polynucleotide isolated according to the above process comprises a nucleotide sequence corresponding to the cDNA sequence of SEQ ID NO:209 from nucleotide 560 to nucleotide 1465, and extending contiguously from a nucleotide sequence corresponding to the 5' end of said sequence of SEQ ID NO:209 from nucleotide 560 to nucleotide 1465, to a nucleotide sequence corresponding to the 3' end of said sequence of SEQ ID NO:209 from nucleotide 560 to nucleotide 1465.

In other embodiments, the present invention provides a composition comprising a protein, wherein said protein comprises an amino acid sequence selected from the group consisting of:

(a) the amino acid sequence of SEQ ID NO:210;
(b) a fragment of the amino acid sequence of SEQ ID NO:210, the fragment comprising eight contiguous amino acids of SEQ ID NO:210; and
(c) the amino acid sequence encoded by the cDNA insert of clone yk261_1 deposited under accession number ATCC 98958;

the protein being substantially free from other mammalian proteins. Preferably such protein comprises the amino acid sequence of SEQ ID NO:210. In further preferred embodiments, the present invention provides a protein comprising a fragment of the amino acid sequence of SEQ ID NO:210 having biological activity, the fragment preferably comprising eight (more preferably twenty, most preferably thirty) contiguous amino acids of SEQ ID NO:210, or a protein comprising a fragment of the amino acid sequence of SEQ ID NO:210 having biological activity, the fragment comprising the amino acid sequence from amino acid 158 to amino acid 167 of SEQ ID NO:210.

In one embodiment, the present invention provides a composition comprising an isolated polynucleotide selected from the group consisting of:

(a) a polynucleotide comprising the nucleotide sequence of SEQ ID NO:211;
(b) a polynucleotide comprising the nucleotide sequence of SEQ ID NO:211 from nucleotide 96 to nucleotide 821;
(c) a polynucleotide comprising the nucleotide sequence of the full-length protein coding sequence of clone ys3_1 deposited under accession number ATCC 98958;
(d) a polynucleotide encoding the full-length protein encoded by the cDNA insert of clone ys3_1 deposited under accession number ATCC 98958;
(e) a polynucleotide comprising the nucleotide sequence of a mature protein coding sequence of clone ys3_1 deposited under accession number ATCC 98958;
(f) a polynucleotide encoding a mature protein encoded by the cDNA insert of clone ys3_1 deposited under accession number ATCC 98958;
(g) a polynucleotide encoding a protein comprising the amino acid sequence of SEQ ID NO:212;
(h) a polynucleotide encoding a protein comprising a fragment of the amino acid sequence of SEQ ID NO:212 having biological activity, the fragment comprising eight contiguous amino acids of SEQ ID NO:212;
(i) a polynucleotide which is an allelic variant of a polynucleotide of (a)–(f) above;
(j) a polynucleotide which encodes a species homologue of the protein of (g) or (h) above;
(k) a polynucleotide that hybridizes under stringent conditions to any one of the polynucleotides specified in (a)–(h); and
(l) a polynucleotide that hybridizes under stringent conditions to any one of the polynucleotides specified in (a)–(h) and that has a length that is at least 25% of the length of SEQ ID NO:211.

Preferably, such polynucleotide comprises the nucleotide sequence of SEQ ID NO:211 from nucleotide 96 to nucleotide 821; the nucleotide sequence of the full-length protein coding sequence of clone ys3_1 deposited under accession number ATCC 98958; or the nucleotide sequence of a mature protein coding sequence of clone ys3_1 deposited under accession number ATCC 98958. In other preferred embodiments, the polynucleotide encodes the full-length or a mature protein encoded by the cDNA insert of clone ys3_1 deposited under accession number ATCC 98958. In further preferred embodiments, the present invention provides a polynucleotide encoding a protein comprising a fragment of the amino acid sequence of SEQ ID NO:212 having biological activity, the fragment preferably comprising eight (more preferably twenty, most preferably thirty) contiguous amino acids of SEQ ID NO:212, or a polynucleotide encoding a protein comprising a fragment of the amino acid sequence of SEQ ID NO:212 having biological activity, the fragment comprising the amino acid sequence from amino acid 116 to amino acid 125 of SEQ ID NO:212.

Other embodiments provide the gene corresponding to the cDNA sequence of SEQ ID NO:211.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:211, but excluding the poly(A) tail at the 3' end of SEQ ID NO:211; and
      (ab) the nucleotide sequence of the cDNA insert of clone ys3_1 deposited under accession number ATCC 98958;
    (ii) hybridizing said probe(s) to human genomic DNA in conditions at least as stringent as 4×SSC at 50 degrees C.; and
    (iii) isolating the DNA polynucleotides detected with the probe(s);
and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:211, but excluding the poly(A) tail at the 3' end of SEQ ID NO:211; and
      (bb) the nucleotide sequence of the cDNA insert of clone y53_1 deposited under accession number ATCC 98958;
    (ii) hybridizing said primer(s) to human genomic DNA in conditions at least as stringent as 4×SSC at 50 degrees C.;
    (iii) amplifying human DNA sequences; and
    (iv) isolating the polynucleotide products of step (b) (iii).

Preferably the polynucleotide isolated according to the above process comprises a nucleotide sequence corresponding to the cDNA sequence of SEQ ID NO:211, and extending contiguously from a nucleotide sequence corresponding to the 5' end of SEQ ID NO:211 to a nucleotide sequence corresponding to the 3' end of SEQ ID NO:211, but excluding the poly(A) tail at the 3' end of SEQ ID NO:211. Also preferably the polynucleotide isolated according to the above process comprises a nucleotide sequence corresponding to the cDNA sequence of SEQ ID NO:211 from nucleotide 96 to nucleotide 821, and extending contiguously from a nucleotide sequence corresponding to the 5' end of said sequence of SEQ ID NO:211 from nucleotide 96 to nucleotide 821, to a nucleotide sequence corresponding to the 3' end of said sequence of SEQ ID NO:211 from nucleotide 96 to nucleotide 821.

In other embodiments, the present invention provides a composition comprising a protein, wherein said protein comprises an amino acid sequence selected from the group consisting of:

(a) the amino acid sequence of SEQ ID NO:212;
  (b) a fragment of the amino acid sequence of SEQ ID NO:212, the fragment comprising eight contiguous amino acids of SEQ ID NO:212; and
  (c) the amino acid sequence encoded by the cDNA insert of clone ys3_1 deposited under accession number ATCC 98958;
the protein being substantially free from other mammalian proteins. Preferably such protein comprises the amino acid sequence of SEQ ID NO:212. In further preferred embodiments, the present invention provides a protein comprising a fragment of the amino acid sequence of SEQ ID NO:212 having biological activity, the fragment preferably comprising eight (more preferably twenty, most preferably thirty) contiguous amino acids of SEQ ID NO:212, or a protein comprising a fragment of the amino acid sequence of SEQ ID NO:212 having biological activity, the fragment comprising the amino acid sequence from amino acid 116 to amino acid 125 of SEQ ID NO:212.

In one embodiment, the present invention provides a composition comprising an isolated polynucleotide selected from the group consisting of:
  (a) a polynucleotide comprising the nucleotide sequence of SEQ ID NO:213;
  (b) a polynucleotide comprising the nucleotide sequence of SEQ ID NO:213 from nucleotide 191 to nucleotide 499;
  (c) a polynucleotide comprising the nucleotide sequence of SEQ ID NO:213 from nucleotide 317 to nucleotide 499;
  (d) a polynucleotide comprising the nucleotide sequence of the full-length protein coding sequence of clone ys10_1 deposited under accession number ATCC 98958;
  (e) a polynucleotide encoding the full-length protein encoded by the cDNA insert of clone ys10_1 deposited under accession number ATCC 98958;
  (f) a polynucleotide comprising the nucleotide sequence of a mature protein coding sequence of clone ys10_1 deposited under accession number ATCC 98958;
  (g) a polynucleotide encoding a mature protein encoded by the cDNA insert of clone ys10_1 deposited under accession number ATCC 98958;
  (h) a polynucleotide encoding a protein comprising the amino acid sequence of SEQ ID NO:214;
  (i) a polynucleotide encoding a protein comprising a fragment of the amino acid sequence of SEQ ID NO:214 having biological activity, the fragment comprising eight contiguous amino acids of SEQ ID NO:214;
  (j) a polynucleotide which is an allelic variant of a polynucleotide of (a)–(g) above;
  (k) a polynucleotide which encodes a species homologue of the protein of (h) or (i) above;
  (l) a polynucleotide that hybridizes under stringent conditions to any one of the polynucleotides specified in (a)–(i); and
  (m) a polynucleotide that hybridizes under stringent conditions to any one of the polynucleotides specified in (a)–(i) and that has a length that is at least 25% of the length of SEQ ID NO:213.

Preferably, such polynucleotide comprises the nucleotide sequence of SEQ ID NO:213 from nucleotide 191 to nucleotide 499; the nucleotide sequence of SEQ ID NO:213 from nucleotide 317 to nucleotide 499; the nucleotide sequence of the full-length protein coding sequence of clone ys10_1 deposited under accession number ATCC 98958; or the nucleotide sequence of a mature protein coding sequence of clone ys10_1 deposited under accession number ATCC 98958. In other preferred embodiments, the polynucleotide encodes the full-length or a mature protein encoded by the cDNA insert of clone ys10_1 deposited under accession number ATCC 98958. In further preferred embodiments, the present invention provides a polynucleotide encoding a protein comprising a fragment of the amino acid sequence of SEQ ID NO:214 having biological activity, the fragment preferably comprising eight (more preferably twenty, most preferably thirty) contiguous amino acids of SEQ ID NO:214, or a polynucleotide encoding a protein comprising a fragment of the amino acid sequence of SEQ ID NO:214 having biological activity, the fragment comprising the amino acid sequence from amino acid 46 to amino acid 55 of SEQ ID NO:214.

Other embodiments provide the gene corresponding to the cDNA sequence of SEQ ID NO:213.

Further embodiments of the invention provide isolated polynucleotides produced according to a process selected from the group consisting of:
  (a) a process comprising the steps of:
    (i) preparing one or more polynucleotide probes that hybridize in 6×SSC at 65 degrees C. to a nucleotide sequence selected from the group consisting of:
      (aa) SEQ ID NO:213, but excluding the poly(A) tail at the 3' end of SEQ ID NO:213; and
      (ab) the nucleotide sequence of the cDNA insert of clone ys10_1 deposited under accession number ATCC 98958;
    (ii) hybridizing said probe(s) to human genomic DNA in conditions at least as stringent as 4×SSC at 50 degrees C.; and
    (iii) isolating the DNA polynucleotides detected with the probe(s);
and
  (b) a process comprising the steps of:
    (i) preparing one or more polynucleotide primers that hybridize in 6×SSC at 65 degrees C. to a nucleotide sequence selected from the group consisting of:
      (ba) SEQ ID NO:213, but excluding the poly(A) tail at the 3' end of SEQ ID NO:213; and
      (bb) the nucleotide sequence of the cDNA insert of clone ys10_1 deposited under accession number ATCC 98958;
    (ii) hybridizing said primer(s) to human genomic DNA in conditions at least as stringent as 4×SSC at 50 degrees C.;
    (iii) amplifying human DNA sequences; and
    (iv) isolating the polynucleotide products of step (b) (iii).

Preferably the polynucleotide isolated according to the above process comprises a nucleotide sequence corresponding to the cDNA sequence of SEQ ID NO:213, and extending contiguously from a nucleotide sequence corresponding to the 5' end of SEQ ID NO:213 to a nucleotide sequence corresponding to the 3' end of SEQ ID NO:213, but excluding the poly(A) tail at the 3' end of SEQ ID NO:213. Also preferably the polynucleotide isolated according to the above process comprises a nucleotide sequence corresponding to the cDNA sequence of SEQ ID NO:213 from nucleotide 191 to nucleotide 499, and extending contiguously from a nucleotide sequence corresponding to the 5' end of said sequence of SEQ ID NO:213 from nucleotide 191 to nucleotide 499, to a nucleotide sequence corresponding to the 3' end of said sequence of SEQ ID NO:213 from nucleotide 191 to nucleotide 499. Also preferably the polynucleotide isolated according to the above process comprises a nucleotide sequence corresponding to the cDNA sequence of SEQ ID NO:213 from nucleotide 317 to nucleotide 499, and extending contiguously from a nucleotide sequence corresponding to the 5' end of said sequence of SEQ ID NO:213 from nucleotide 317 to nucleotide 499, to a nucleotide sequence corresponding to the 3' end of said sequence of SEQ ID NO:213 from nucleotide 317 to nucleotide 499.

In other embodiments, the present invention provides a composition comprising a protein, wherein said protein comprises an amino acid sequence selected from the group consisting of:
  (a) the amino acid sequence of SEQ ID NO:214;
  (b) a fragment of the amino acid sequence of SEQ ID NO:214, the fragment comprising eight contiguous amino acids of SEQ ID NO:214; and
  (c) the amino acid sequence encoded by the cDNA insert of clone ys10_1 deposited under accession number ATCC 98958;
the protein being substantially free from other mammalian proteins. Preferably such protein comprises the amino acid sequence of SEQ ID NO:214. In further preferred embodiments, the present invention provides a protein comprising a fragment of the amino acid sequence of SEQ ID NO:214 having biological activity, the fragment preferably comprising eight (more preferably twenty, most preferably thirty) contiguous amino acids of SEQ ID NO:214, or a protein comprising a fragment of the amino acid sequence of SEQ ID NO:214 having biological activity, the fragment comprising the amino acid sequence from amino acid 46 to amino acid 55 of SEQ ID NO:214.

In certain preferred embodiments, the polynucleotide is operably linked to an expression control sequence. The invention also provides a host cell, including bacterial, yeast, insect and mammalian cells, transformed with such polynucleotide compositions. Also provided by the present invention are organisms that have enhanced, reduced, or modified expression of the gene(s) corresponding to the polynucleotide sequences disclosed herein.

Processes are also provided for producing a protein, which comprise:
  (a) growing a culture of the host cell transformed with such polynucleotide compositions in a suitable culture medium; and
  (b) purifying the protein from the culture.

The protein produced according to such methods is also provided by the present invention.

Protein compositions of the present invention may further comprise a pharmaceutically acceptable carrier. Compositions comprising an antibody which specifically reacts with such protein are also provided by the present invention.

Methods are also provided for preventing, treating or ameliorating a medical condition which comprises administering to a mammalian subject a therapeutically effective amount of a composition comprising a protein of the present invention and a pharmaceutically acceptable carrier.

Figure 1A:
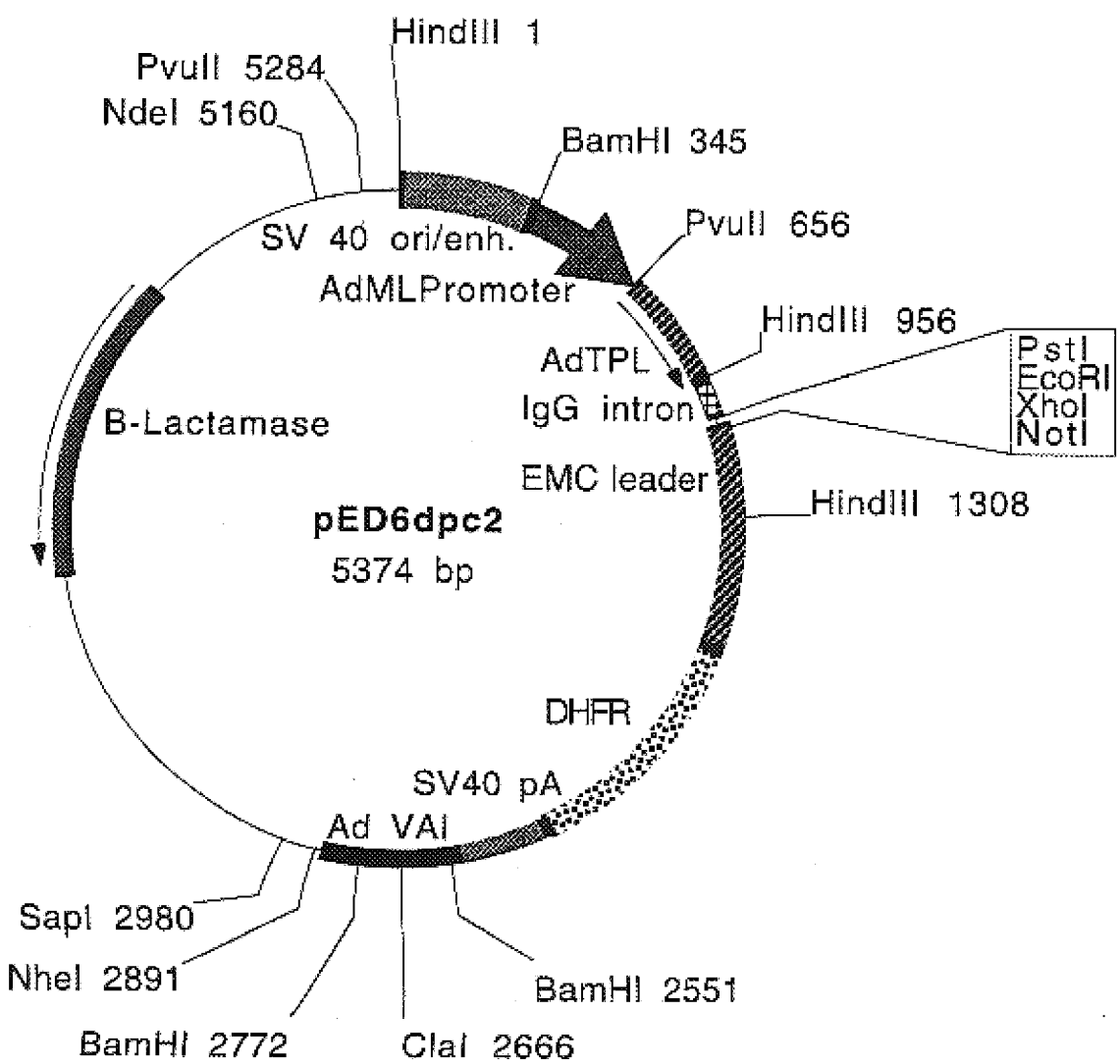
FIGS. 1A and 1B are schematic representations of the pED6 and pNOTs vectors, respectively, used for deposit of clones disclosed herein.

DETAILED DESCRIPTION
ISOLATED PROTEINS AND POLYNUCLEOTIDES

Nucleotide and amino acid sequences, as presently determined, are reported below for each clone and protein disclosed in the present application. The nucleotide sequence of each clone can readily be determined by sequencing of the deposited clone in accordance with known methods. The predicted amino acid sequence (both full-length and mature forms) can then be determined from such nucleotide sequence. The amino acid sequence of the protein encoded by a particular clone can also be determined by expression of the clone in a suitable host cell, collecting the protein and determining its sequence. For each disclosed protein applicants have identified what they have determined to be the reading frame best identifiable with sequence information available at the time of filing.

As used herein a "secreted" protein is one which, when expressed in a suitable host cell, is transported across or through a membrane, including transport as a result of signal sequences in its amino acid sequence. "Secreted" proteins include without limitation proteins secreted wholly (e.g., soluble proteins) or partially (e.g., receptors) from the cell in which they are expressed. "Secreted" proteins also include without limitation proteins which are transported across the membrane of the endoplasmic reticulum.

Clone "ya15_1"

A polynucleotide of the present invention has been identified as clone "ya15_1". ya15_1 was isolated from a human adult testes cDNA library and was identified as encoding a secreted or transmembrane protein on the basis of computer analysis of the amino acid sequence of the encoded protein. ya15_1 is a full-length clone, including the entire coding sequence of a secreted protein (also referred to herein as "ya15_1 protein").

The nucleotide sequence of ya15_1 as presently determined is reported in SEQ ID NO:1, and includes a poly(A) tail. What applicants presently believe to be the proper reading frame and the predicted amino acid sequence of the ya15_1 protein corresponding to the foregoing nucleotide sequence is reported in SEQ ID NO:2. Amino acids 8 to 20 of SEQ ID NO:2 are a possible leader/signal sequence, with the predicted mature amino acid sequence beginning at amino acid 21. Due to the hydrophobic nature of the predicted leader/signal sequence, it is likely to act as a transmembrane domain should the predicted leader/signal sequence not be separated from the remainder of the ya15_1 protein.

The EcoRI/NotI restriction fragment obtainable from the deposit containing clone ya15_1 should be approximately 1100 bp.

The nucleotide sequence disclosed herein for ya15_1 was searched against the GenBank and GeneSeq nucleotide sequence databases using BLASTN/BLASTX and FASTA search protocols. ya15_1 demonstrated at least some similarity with sequences identified as Z94056 (Human DNA sequence from PAC 436M11 on chromosome Xp22.11-22.2; contains a serine threonine protein phosphatase gene, ESTs and STSs). Based upon sequence similarity, ya15_1 proteins and each similar protein or peptide may share at least some activity. The TopPredII computer program predicts a potential transmembrane domain within the ya15_1 protein sequence centered around amino acid 40 of SEQ ID NO:2. The nucleotide sequence of ya15_1 indicates that it may contain an Alu repetitive element.

Clone "ya24_1"

A polynucleotide of the present invention has been identified as clone "ya24_1". ya24_1 was isolated from a human adult testes cDNA library and was identified as encoding a secreted or transmembrane protein on the basis of computer analysis of the amino acid sequence of the encoded protein. ya24_1 is a full-length clone, including the entire coding sequence of a secreted protein (also referred to herein as "ya24_1 protein").

The nucleotide sequence of ya24_1 as presently determined is reported in SEQ ID NO:3, and includes a poly(A) tail. What applicants presently believe to be the proper reading frame and the predicted amino acid sequence of the ya24_1 protein corresponding to the foregoing nucleotide sequence is reported in SEQ ID NO:4. Amino acids 3 to 15 of SEQ ID NO:4 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the ya24_1 protein.

The EcoRI/NotI restriction fragment obtainable from the deposit containing clone ya24_1 should be approximately 750 bp.

The nucleotide sequence disclosed herein for ya24_1 was searched against the GenBank and GeneSeq nucleotide sequence databases using BLASTN/BLASTX and FASTA search protocols. ya24_1 demonstrated at least some similarity with sequences identified as AA537299 (vk46d03.r1 Soares mouse mammary gland NbMMG *Mus musculus* cDNA clone 949637 5'). Based upon sequence similarity, ya24_1 proteins and each similar protein or peptide may share at least some activity.

Clone "yb42_1"

A polynucleotide of the present invention has been identified as clone "yb42_1". yb42_1 was isolated from a human fetal brain cDNA library and was identified as encoding a secreted or transmembrane protein on the basis of computer analysis of the amino acid sequence of the encoded protein. yb42_1 is a full-length clone, including the entire coding sequence of a secreted protein (also referred to herein as "yb42_1 protein").

The nucleotide sequence of yb42_1 as presently determined is reported in SEQ ID NO:5, and includes a poly(A) tail. What applicants presently believe to be the proper reading frame and the predicted amino acid sequence of the yb42_1 protein corresponding to the foregoing nucleotide sequence is reported in SEQ ID NO:6. Amino acids 41 to 53 of SEQ ID NO:6 are a predicted leader/signal sequence, with the predicted mature amino acid sequence beginning at amino acid 54. Due to the hydrophobic nature of the predicted leader/signal sequence, it is likely to act as a transmembrane domain should the predicted leader/signal sequence not be separated from the remainder of the yb42_1 protein.

Another potential yb42_1 reading frame and predicted amino acid sequence is encoded by basepairs 1879 to 2220 of SEQ ID NO:5 and is reported in SEQ ID NO:265; amino acids 54 to 66 of SEQ ID NO:265 are a predicted leader/signal sequence, with the predicted mature amino acid sequence beginning at amino acid 67 of SEQ ID NO:265. Due to the hydrophobic nature of this predicted leader/signal sequence, it is likely to act as a transmembrane domain should the predicted leader/signal sequence not be separated from the remainder of the protein of SEQ ID NO:265.

The EcoRI/NotI restriction fragment obtainable from the deposit containing clone yb42_1 should be approximately 3900 bp.

The nucleotide sequence disclosed herein for yb42_1 was searched against the GenBank and GeneSeq nucleotide sequence databases using BLASTN/BLASTX and FASTA search protocols. yb42_1 demonstrated at least some similarity with sequences identified as AA213992 (zn58d08.s1 Stratagene muscle 937209 Homo sapiens cDNA clone 562383 3'). Based upon sequence similarity, yb42_1 proteins and each similar protein or peptide may share at least some activity. The nucleotide sequence of yb42_1 indicates that it may contain at least one MIR repeat sequence.

Clone "yc9_1"

A polynucleotide of the present invention has been identified as clone "yc9_1". yc9_1 was isolated from a human fetal kidney (293 cell line) cDNA library and was identified as encoding a secreted or transmembrane protein on the basis of computer analysis of the amino acid sequence of the encoded protein. yc9_1 is a full-length clone, including the entire coding sequence of a secreted protein (also referred to herein as "yc9_1 protein").

The nucleotide sequence of yc9_1 as presently determined is reported in SEQ ID NO:7, and includes a poly(A) tail. What applicants presently believe to be the proper reading frame and the predicted amino acid sequence of the yc9_1 protein corresponding to the foregoing nucleotide sequence is reported in SEQ ID NO:8.

The EcoRI/NotI restriction fragment obtainable from the deposit containing clone yc9_1 should be approximately 3300 bp.

The nucleotide sequence disclosed herein for yc9_1 was searched against the GenBank and GeneSeq nucleotide sequence databases using BLASTN/BLASTX and FASTA search protocols. yc9_1 demonstrated at least some similarity with sequences identified as AA588539 (nm94a07.s1 NCI_CGAP_Co9 Homo sapiens cDNA clone IMAGE:1075860) and N47418 (yy88e12.r1 Homo sapiens cDNA clone 280654 5'). The predicted amino acid sequence disclosed herein for yc9_1 was searched against the GenPept and GeneSeq amino acid sequence databases using the BLASTX search protocol. The predicted yc9_1 protein demonstrated at least some similarity to sequences identified as X97196 (*D. melanogaster* X gene). Based upon sequence similarity, yc9_1 proteins and each similar protein or peptide may share at least some activity. The TopPredII computer program predicts two potential transmembrane domains within the yc9_1 protein sequence, centered around amino acids 80 and 200 of SEQ ID NO:8, respectively.

Clone "yc19_1"

A polynucleotide of the present invention has been identified as clone "yc19_1". yc19_1 was isolated from a human fetal kidney (293 cell line) cDNA library and was identified as encoding a secreted or transmembrane protein on the basis of computer analysis of the amino acid sequence of the encoded protein. yc19_1 is a full-length clone, including the entire coding sequence of a secreted protein (also referred to herein as "yc19_1 protein").

The nucleotide sequence of yc19_1 as presently determined is reported in SEQ ID NO:9, and includes a poly(A) tail. What applicants presently believe to be the proper reading frame and the predicted amino acid sequence of the yc19_1 protein corresponding to the foregoing nucleotide sequence is reported in SEQ ID NO:10. Amino acids 106 to 118 of SEQ ID NO:10 are a predicted leader/signal sequence, with the predicted mature amino acid sequence beginning at amino acid 119. Due to the hydrophobic nature of the predicted leader/signal sequence, it is likely to act as a transmembrane domain should the predicted leader/signal sequence not be separated from the remainder of the yc19_1 protein.

The EcoRI/NotI restriction fragment obtainable from the deposit containing clone yc19_1 should be approximately 1400 bp.

The nucleotide sequence disclosed herein for yc19_1 was searched against the GenBank and GeneSeq nucleotide sequence databases using BLASTN/BLASTX and FASTA search protocols. yc19_1 demonstrated at least some similarity with sequences identified as AA126002 (zl85a08.s1 Stratagene colon (#937204) Homo sapiens cDNA clone 511382 3') and AA307000 (EST177917 Colon carcinoma (HCC) cell line *Homo sapiens* cDNA 5' end). The predicted amino acid sequence disclosed herein for yc19_1 was searched against the GenPept and GeneSeq amino acid sequence databases using the BLASTX search protocol. The predicted yc19_1 protein demonstrated at least some similarity to sequences identified as X83742 (MAP kinase phosphotase [*Xenopus laevis*]), and to several tyrosine phosphatases from other species. Based upon sequence similarity, yc19_1 proteins and each similar protein or peptide may share at least some activity. The TopPredII computer program predicts an additional potential transmembrane domain within the yc19_1 protein sequence centered around amino acid 43 of SEQ ID NO:10; this region (amino acids 30 to 42 of SEQ ID NO:10) may also be a leader/signal sequence, with the predicted mature amino acid sequence beginning at amino acid 43.

yc19_1 protein was expressed in a COS cell expression system, and an expressed protein band of approximately 23 kDa was detected in conditioned medium and membrane fractions using SDS polyacrylamide gel electrophoresis.

Clone "yc20_1"

A polynucleotide of the present invention has been identified as clone "yc20_1". yc20_1 was isolated from a human fetal kidney (293 cell line) cDNA library and was identified as encoding a secreted or transmembrane protein on the basis of computer analysis of the amino acid sequence of the encoded protein. yc20_1 is a full-length clone, including the entire coding sequence of a secreted protein (also referred to herein as "yc20_1 protein").

The nucleotide sequence of yc20_1 as presently determined is reported in SEQ ID NO:11, and includes a poly(A) tail. What applicants presently believe to be the proper reading frame and the predicted amino acid sequence of the yc20_1 protein corresponding to the foregoing nucleotide sequence is reported in SEQ ID NO:12.

The EcoRI/NotI restriction fragment obtainable from the deposit containing clone yc20_1 should be approximately 1450 bp.

The nucleotide sequence disclosed herein for yc20_1 was searched against the GenBank and GeneSeq nucleotide sequence databases using BLASTN/BLASTX and FASTA search protocols. yc20_1 demonstrated at least some similarity with sequences identified as AA447839 (aa18c12.r1 Soares NhHMPu S1 *Homo sapiens* cDNA clone 813622 5'), N33405 (yy41e10.s1 *Homo sapiens* cDNA clone 273834 3'), and T19519 (Human gene signature HUMGS00580). Based upon sequence similarity, yc20_1 proteins and each similar protein or peptide may share at least some activity.

Clone "ya9_1"

A polynucleotide of the present invention has been identified as clone "ya9_1". ya9_1 was isolated from a human adult testes cDNA library and was identified as encoding a secreted or transmembrane protein on the basis of computer analysis of the amino acid sequence of the encoded protein. ya9_1 is a full-length clone, including the entire coding sequence of a secreted protein (also referred to herein as "ya9_1 protein").

The nucleotide sequence of ya9_1 as presently determined is reported in SEQ ID NO:13, and includes a poly(A) tail. What applicants presently believe to be the proper reading frame and the predicted amino acid sequence of the ya9_1 protein corresponding to the foregoing nucleotide sequence is reported in SEQ ID NO:14. Amino acids 15 to 27 of SEQ ID NO:14 are a predicted leader/signal sequence, with the predicted mature amino acid sequence beginning at amino acid 28. Due to the hydrophobic nature of the predicted leader/signal sequence, it is likely to act as a transmembrane domain should the predicted leader/signal sequence not be separated from the remainder of the ya9_1 protein.

The EcoRI/NotI restriction fragment obtainable from the deposit containing clone ya9_1 should be approximately 950 bp.

The nucleotide sequence disclosed herein for ya9_1 was searched against the GenBank and GeneSeq nucleotide sequence databases using BLASTN/BLASTX and FASTA search protocols. ya9_1 demonstrated at least some similarity with sequences identified as AA442366 (zv62c04.r1 Soares testis NHT *Homo sapiens* cDNA clone 758214 5') and AA609166 (af12a08.s1 Soares testis NHT *Homo sapiens* cDNA clone 1031414 3'). Based upon sequence similarity, ya9_1 proteins and each similar protein or peptide may share at least some activity. The TopPredII computer program predicts an additional potential transmembrane domain within the ya9_1 protein sequence, centered around amino acid 62 of SEQ ID NO:14.

Clone "ya11_1"

A polynucleotide of the present invention has been identified as clone "ya11_1". ya11_1 was isolated from a human adult testes cDNA library and was identified as encoding a secreted or transmembrane protein on the basis of computer analysis of the amino acid sequence of the encoded protein. ya11_1 is a full-length clone, including the entire coding sequence of a secreted protein (also referred to herein as "ya11_1 protein").

The nucleotide sequence of ya11_1 as presently determined is reported in SEQ ID NO:15, and includes a poly(A) tail. What applicants presently believe to be the proper reading frame and the predicted amino acid sequence of the ya11_1 protein corresponding to the foregoing nucleotide sequence is reported in SEQ ID NO:16. Amino acids 36 to 48 of SEQ ID NO:16 are a predicted leader/signal sequence, with the predicted mature amino acid sequence beginning at amino acid 49. Due to the hydrophobic nature of the predicted leader/signal sequence, it is likely to act as a transmembrane domain should the predicted leader/signal sequence not be separated from the remainder of the ya11_1 protein.

The EcoRI/NotI restriction fragment obtainable from the deposit containing done ya11_1 should be approximately 500 bp.

The nucleotide sequence disclosed herein for ya11_1 was searched against the GenBank and GeneSeq nucleotide sequence databases using BLASTN/BLASTX and FASTA search protocols. ya11_1 demonstrated at least some similarity with sequences identified as Z68274 (Human DNA sequence from cosmid L129H7, Huntington's Disease Region, chromosome 4p16.3 contains Pseudogene and CpG island). Based upon sequence similarity, ya11_1 proteins and each similar protein or peptide may share at least some activity. The TopPredII computer program predicts an additional potential transmembrane domain within the ya11_1 protein sequence, centered around amino acid 81 of SEQ ID NO:16.

Clone "ya28_1"

A polynucleotide of the present invention has been identified as clone "ya28_1". ya28_1 was isolated from a human adult testes cDNA library and was identified as encoding a secreted or transmembrane protein on the basis of computer analysis of the amino acid sequence of the encoded protein. ya28_1 is a full-length clone, including the entire coding sequence of a secreted protein (also referred to herein as "ya28_1 protein").

The nucleotide sequence of ya28_1 as presently determined is reported in SEQ ID NO:17, and includes a poly(A) tail. What applicants presently believe to be the proper reading frame and the predicted amino acid sequence of the ya28_1 protein corresponding to the foregoing nucleotide sequence is reported in SEQ ID NO:18. Amino acids 41 to 53 of SEQ ID NO:18 are a predicted leader/signal sequence, with the predicted mature amino acid sequence beginning at amino acid 54. Due to the hydrophobic nature of the predicted leader/signal sequence, it is likely to act as a transmembrane domain should the predicted leader/signal sequence not be separated from the remainder of the ya28_1 protein.

The EcoRI/NotI restriction fragment obtainable from the deposit containing clone ya28_1 should be approximately 300 bp.

The nucleotide sequence disclosed herein for ya28_1 was searched against the GenBank and GeneSeq nucleotide sequence databases using BLASTN/BLASTX and FASTA search protocols. ya28_1 demonstrated at least some similarity with sequences identified as AA576255 (nm62b09.s1 NCI_CGAP_Br3 *Homo sapiens* cDNA clone IMAGE:1072793). Based upon sequence similarity, ya28_1 proteins and each similar protein or peptide may share at least some activity.

ya28_1 protein was expressed in a COS cell expression system, and an expressed protein band of approximately 23 kDa was detected in membrane fractions using SDS polyacrylamide gel electrophoresis.

Clone "yb81_1"

A polynucleotide of the present invention has been identified as clone "yb81_1". yb81_1 was isolated from a human fetal brain cDNA library and was identified as encoding a secreted or transmembrane protein on the basis of computer analysis of the amino acid sequence of the encoded protein. yb81_1 is a full-length clone, including the entire coding sequence of a secreted protein (also referred to herein as "yb81_1 protein").

The nucleotide sequence of yb81_1 as presently determined is reported in SEQ ID NO:19, and includes a poly(A) tail. What applicants presently believe to be the proper reading frame and the predicted amino acid sequence of the yb81_1 protein corresponding to the foregoing nucleotide sequence is reported in SEQ ID NO:20.

The EcoRI/NotI restriction fragment obtainable from the deposit containing clone yb81_1 should be approximately 1200 bp.

The nucleotide sequence disclosed herein for yb81_1 was searched against the GenBank and GeneSeq nucleotide sequence databases using BLASTN/BLASTX and FASTA search protocols. yb81_1 demonstrated at least some similarity with sequences identified as T67164 (Human alpha-N-acetylglucosaminidase gene). Based upon sequence similarity, yb81_1 proteins and each similar protein or peptide may share at least some activity. The TopPredII computer program predicts a potential transmembrane domain within the yb81_1 protein sequence centered around amino acid 73 of SEQ ID NO:20.

Clone "yc14_1"

A polynucleotide of the present invention has been identified as clone "yc14_1". yc14_1 was isolated from a human fetal kidney (293 cell line) cDNA library and was identified as encoding a secreted or transmembrane protein on the basis of computer analysis of the amino acid sequence of the encoded protein. yc14_1 is a full-length clone, including the entire coding sequence of a secreted protein (also referred to herein as "yc14_1 protein").

The nucleotide sequence of yc14_1 as presently determined is reported in SEQ ID NO:21, and includes a poly(A) tail. What applicants presently believe to be the proper reading frame and the predicted amino acid sequence of the yc14_1 protein corresponding to the foregoing nucleotide sequence is reported in SEQ ID NO:22. Amino acids 388 to 400 of SEQ ID NO:22 are a predicted leader/signal sequence, with the predicted mature amino acid sequence beginning at amino acid 401. Due to the hydrophobic nature of the predicted leader/signal sequence, it is likely to act as a transmembrane domain should the predicted leader/signal sequence not be separated from the remainder of the yc14_1 protein.

The EcoRI/NotI restriction fragment obtainable from the deposit containing clone yc14_1 should be approximately 3000 bp.

The nucleotide sequence disclosed herein for yc14_1 was searched against the GenBank and GeneSeq nucleotide sequence databases using BLASTN/BLASTX and FASTA search protocols. yc14_1 demonstrated at least some similarity with sequences identified as AA007392 (zh99a08.r1 Soares fetal liver spleen 1NFLS S1 *Homo sapiens* cDNA clone 429398 5'), AA573120 (nj41e10.s1 NCI_CGAP_AA1 *Homo sapiens* cDNA clone IMAGE 995082 similar to TR G285999 G285999 ORF, COMPLETE CDS), and D13642 (Human mRNA for KIAA0017 gene, complete cds). The predicted amino acid sequence disclosed herein for yc14_1 was searched against the GenPept and GeneSeq amino acid sequence databases using the BLASTX search protocol. The predicted yc14_1 protein demonstrated at least some similarity to sequences identified as D13642 (KIAA0017 [*Homo sapiens*]) and Z47816 (unknown [*Saccharomyces cerevisiae*] (*S. cerevisiae* chromosome M cosmid 9827, and translated products)). The yc14_1 protein contains the immunoglobulin and major histocompatibility complex protein signature at its extreme N-terminus (starting at amino acid 3 of SEQ ID NO:22). Based upon sequence similarity, yc14_1 proteins and each similar protein or peptide may share at least some activity. The TopPredII computer program predicts four additional potential transmembrane domains within the yc14_1 protein sequence, centered around amino acids 50, 200, 210, and 830 of SEQ ID NO:22, respectively.

yc14_1 protein was expressed in a COS cell expression system, and an expressed protein band of approximately 92 kDa was detected in membrane fractions using SDS polyacrylamide gel electrophoresis.

Clone "yc24_1"

A polynucleotide of the present invention has been identified as clone "yc24_1". yc24_1 was isolated from a human fetal kidney (293 cell line) cDNA library and was identified as encoding a secreted or transmembrane protein on the basis of computer analysis of the amino acid sequence of the encoded protein. yc24_1 is a full-length clone, including the entire coding sequence of a secreted protein (also referred to herein as "yc24_1 protein").

The nucleotide sequence of yc24_1 as presently determined is reported in SEQ ID NO:23, and includes a poly(A) tail. What applicants presently believe to be the proper reading frame and the predicted amino acid sequence of the yc24_1 protein corresponding to the foregoing nucleotide sequence is reported in SEQ ID NO:24. Amino acids 50 to 62 of SEQ ID NO:24 are a possible leader/signal sequence, with the predicted mature amino acid sequence beginning at amino acid 63. Due to the hydrophobic nature of the predicted leader/signal sequence, it is likely to act as a transmembrane domain should the predicted leader/signal sequence not be separated from the remainder of the yc24_1 protein.

The EcoRI/NotI restriction fragment obtainable from the deposit containing clone yc24_1 should be approximately 1650 bp.

The nucleotide sequence disclosed herein for yc24_1 was searched against the GenBank and GeneSeq nucleotide sequence databases using BLASTN/BLASTX and FASTA search protocols. yc24_1 demonstrated at least some similarity with sequences identified as AA172170 (zp29b07.s1 Stratagene neuroepithellum (#937231) *Homo sapiens* cDNA clone 610837 3' similar to gb L10240 BASIGIN PRECURSOR (HUMAN), AA756004 (vv37a04.r1 Stratagene mouse heart (#937316) *Mus musculus* cDNA clone 1224558 5' similar to TR:Q14134 Q14134 ATAXIA-TELANGIECTASIA GROUP D-ASSOCIATED PROTEIN, mRNA sequence), D48379 (Rice cDNA, partial sequence (S145461A), mRNA sequence), E07941 (cDNA encoding human basigin1), L20471 (Human extracellular matrix metalloproteinase inducer gene, complete cds), Q71341 (Human basigin I immunoglobulin gene), and X64364 (*H.sapiens* mRNA for M6 antigen). The M6 antigen has been localized in all leucocyte lines examined (including lymphocytes, monocytes, and granulocytes) and is implicated in interacting with cytokine factors like GM-CSF and interferon gamma. A protein that is at least very similar to M6 antigen, extracellular matrix metalloproteinase inducer (EMMPRIN), has been localized to the surface of tumor cells and is implicated in stimulating several matrix metalloproteinases in the fibroblasts. Based upon sequence similarity, yc24_1 proteins and each similar protein or peptide may share at least some activity. The TopPredII computer program predicts a potential transmembrane domain within the yc24_1 protein sequence near the N-terminus of SEQ ID NO:24.

Clone "yc25_1"

A polynucleotide of the present invention has been identified as clone "yc25_1". yc25_1 was isolated from a human fetal kidney (293 cell line) cDNA library and was identified as encoding a secreted or transmembrane protein on the basis of computer analysis of the amino acid sequence of the encoded protein. yc25_1 is a full-length clone, including the entire coding sequence of a secreted protein (also referred to herein as "yc25_1 protein").

The nucleotide sequence of yc25_1 as presently determined is reported in SEQ ID NO:25, and includes a poly(A) tail. What applicants presently believe to be the proper reading frame and the predicted amino acid sequence of the yc25_1 protein corresponding to the foregoing nucleotide sequence is reported in SEQ ID NO:26. Amino acids 6 to 18 of SEQ ID NO:26 are a predicted leader/signal sequence, with the predicted mature amino acid sequence beginning at amino acid 19. Due to the hydrophobic nature of the predicted leader/signal sequence, it is likely to act as a transmembrane domain should the predicted leader/signal sequence not be separated from the remainder of the yc25_1 protein.

The EcoRI/NotI restriction fragment obtainable from the deposit containing clone yc25_1 should be approximately 1800 bp.

The nucleotide sequence disclosed herein for yc25_1 was searched against the GenBank and GeneSeq nucleotide sequence databases using BLASTN/BLASTX and FASTA search protocols. yc25_1 demonstrated at least some similarity with sequences identified as AA332406 (EST36341 Embryo, 8 week I *Homo sapiens* cDNA 5' end), T20094 (Human gene signature HUMGS01237), and W73912 (zd71a11.s1 Soares fetal heart NbHH19W *Homo sapiens* cDNA clone 346076 3'). Based upon sequence similarity, yc25_1 proteins and each similar protein or peptide may share at least some activity.

Clone "ye2_1"

A polynucleotide of the present invention has been identified as clone "ye2_1". ye2_1 was isolated from a human fetal brain cDNA library and was identified as encoding a secreted or transmembrane protein on the basis of computer analysis of the amino acid sequence of the encoded protein. ye2_1 is a full-length clone, including the entire coding sequence of a secreted protein (also referred to herein as "ye2_1 protein").

The nucleotide sequence of ye2_1 as presently determined is reported in SEQ ID NO:27, and includes a poly(A) tail. What applicants presently believe to be the proper reading frame and the predicted amino acid sequence of the ye2_1 protein corresponding to the foregoing nucleotide sequence is reported in SEQ ID NO:28. Amino acids 30 to 42 of SEQ ID NO:28 are a possible leader/signal sequence, with the predicted mature amino acid sequence beginning at amino acid 43. Due to the hydrophobic nature of the predicted leader/signal sequence, it is likely to act as a transmembrane domain should the predicted leader/signal sequence not be separated from the remainder of the ye2_1 protein.

The EcoRI/NotI restriction fragment obtainable from the deposit containing clone ye2_1 should be approximately 1500 bp.

The nucleotide sequence disclosed herein for ye2_1 was searched against the GenBank and GeneSeq nucleotide sequence databases using BLASTN/BLASTX and FASTA search protocols. ye2_1 demonstrated at least some similarity with sequences identified as AA354797 (EST63132 Jurkat T-cells V *Homo sapiens* cDNA 5' end) and Z43858 (*H. sapiens* partial cDNA sequence; clone c-1md12). Based upon sequence similarity, ye2_1 proteins and each similar protein or peptide may share at least some activity. The TopPredII computer program predicts an additional potential transmembrane domain within the ye2_1 protein sequence centered around amino acid 70 of SEQ ID NO:28.

Clone "ya65_1"

A polynucleotide of the present invention has been identified as clone "ya65_1". ya65_1 was isolated from a human adult testes cDNA library and was identified as encoding a secreted or transmembrane protein on the basis of computer analysis of the amino acid sequence of the encoded protein. ya65_1 is a full-length clone, including the entire coding sequence of a secreted protein (also referred to herein as "ya65_1 protein").

The nucleotide sequence of ya65_1 as presently determined is reported in SEQ ID NO:29, and includes a poly(A) tail. What applicants presently believe to be the proper reading frame and the predicted amino acid sequence of the ya65_1 protein corresponding to the foregoing nucleotide sequence is reported in SEQ ID NO:30.

The EcoRI/NotI restriction fragment obtainable from the deposit containing clone ya65_1 should be approximately 550 bp.

The nucleotide sequence disclosed herein for ya65_1 was searched against the GenBank and GeneSeq nucleotide sequence databases using BLASTN/BLASTX and FASTA search protocols. ya65_1 demonstrated at least some similarity with sequences identified as AI005084 (ou08g10.x1 Soares_NFL_T_GBC_S1 *Homo sapiens* cDNA clone IMAGE:1625730 3', mRNA sequence). Based upon sequence similarity, ya65_1 proteins and each similar protein or peptide may share at least some activity. The TopPredII computer program predicts a potential transmembrane domain within the ya65_1 protein sequence centered around amino acid 87 of SEQ ID NO:30.

Clone "yb60_1"

A polynucleotide of the present invention has been identified as clone "yb60_1". yb60_1 was isolated from a human fetal brain cDNA library and was identified as encoding a secreted or transmembrane protein on the basis of computer analysis of the amino acid sequence of the encoded protein. yb60_1 is a full-length clone, including the entire coding sequence of a secreted protein (also referred to herein as "yb60_1 protein").

The nucleotide sequence of yb60_1 as presently determined is reported in SEQ ID NO:31, and includes a poly(A) tail. What applicants presently believe to be the proper reading frame and the predicted amino acid sequence of the yb60_1 protein corresponding to the foregoing nucleotide sequence is reported in SEQ ID NO:32. Amino acids 46 to 58 of SEQ ID NO:32 are a possible leader/signal sequence, with the predicted mature amino acid sequence beginning at amino acid 59. Due to the hydrophobic nature of the predicted leader/signal sequence, it is likely to act as a transmembrane domain should the predicted leader/signal sequence not be separated from the remainder of the yb60_1 protein.

The EcoRI/NotI restriction fragment obtainable from the deposit containing clone yb60_1 should be approximately 2500 bp.

The nucleotide sequence disclosed herein for yb60_1 was searched against the GenBank and GeneSeq nucleotide sequence databases using BLASTN/BLASTX and FASTA search protocols. yb60_1 demonstrated at least some similarity with sequences identified as AA505869 (nh99f02.s1 NCI_CGAP_Br2 *Homo sapiens* cDNA clone IMAGE:966651), H29487 (ym60a10.r1 *Homo sapiens* cDNA clone 52621 5'), and T24510 (Human gene signature HUMGS06552; standard; cDNA to mRNA). Based upon sequence similarity, yb60_1 proteins and each similar protein or peptide may share at least some activity.

Clone "yb139_1"

A polynucleotide of the present invention has been identified as clone "yb139_1". yb139_1 was isolated from a human fetal brain cDNA library and was identified as encoding a secreted or transmembrane protein on the basis of computer analysis of the amino acid sequence of the encoded protein. yb139_1 is a full-length clone, including the entire coding sequence of a secreted protein (also referred to herein as "yb139_1 protein").

The nucleotide sequence of yb139_1 as presently determined is reported in SEQ ID NO:33, and includes a poly(A) tail. What applicants presently believe to be the proper reading frame and the predicted amino acid sequence of the yb139_1 protein corresponding to the foregoing nucleotide sequence is reported in SEQ ID NO:34. Amino acids 101 to 113 of SEQ ID NO:34 are a predicted leader/signal sequence, with the predicted mature amino acid sequence beginning at amino acid 114. Due to the hydrophobic nature of the predicted leader/signal sequence, it is likely to act as a transmembrane domain should the predicted leader/signal sequence not be separated from the remainder of the yb139_1 protein.

The EcoRI/NotI restriction fragment obtainable from the deposit containing clone yb139_1 should be approximately 1000 bp.

The nucleotide sequence disclosed herein for yb139_1 was searched against the GenBank and GeneSeq nucleotide sequence databases using BLASTN/BLASTX and FASTA search protocols. yb139_1 demonstrated at least some similarity with sequences identified as AA332206 (EST36115 Embryo, 8 week I *Homo sapiens* cDNA 5' end, mRNA sequence). Based upon sequence similarity, yb139_1 proteins and each similar protein or peptide may share at least some activity. The TopPredII computer program predicts an additional potential transmembrane domain within the yb139_1 protein sequence centered around amino acid 42 of SEQ ID NO:34. The nucleotide acid sequence of yb139_1 indicates that it may contain sequences similar to a primate simple repeat and to the *M. serrator* retropseudogene-like repetitive element I.

Clone "yc29_1"

A polynucleotide of the present invention has been identified as clone "yc29_1". yc29_1 was isolated from a human fetal kidney (293 cell line) cDNA library and was identified as encoding a secreted or transmembrane protein on the basis of computer analysis of the amino acid sequence of the encoded protein. yc29_1 is a full-length clone, including the entire coding sequence of a secreted protein (also referred to herein as "yc29_1 protein").

The nucleotide sequence of yc29_1 as presently determined is reported in SEQ ID NO:35, and includes a poly(A) tail. What applicants presently believe to be the proper reading frame and the predicted amino acid sequence of the yc29_1 protein corresponding to the foregoing nucleotide sequence is reported in SEQ ID NO:36.

The EcoRI/NotI restriction fragment obtainable from the deposit containing clone yc29_1 should be approximately 2100 bp.

The nucleotide sequence disclosed herein for yc29_1 was searched against the GenBank and GeneSeq nucleotide sequence databases using BLASTN/BLASTX and FASTA search protocols. yc29_1 demonstrated at least some similarity with sequences identified as AA195033 (zr35a12.s1 Soares NhHMPu S1 *Homo sapiens* cDNA clone 665374 3', mRNA sequence), AF046001 (*Homo sapiens* zinc finger transcription factor (ZNF207) mRNA, complete cds), and T23300 (Human gene signature HUMGS05114; standard; cDNA to mRNA). The predicted amino acid sequence disclosed herein for yc29_1 was searched against the GenPept and GeneSeq amino acid sequence databases using the BLASTX search protocol. The predicted yc29_1 protein demonstrated at least some similarity to the sequence identified as AF046001 (zinc finger transcription factor [*Homo sapiens*]). The presence of zinc fingers in a protein may indicate that the protein has a DNA-binding function, but zinc fingers may also be protein-protein interaction domains.

Based upon sequence similarity, yc29_1 proteins and each similar protein or peptide may share at least some activity. The TopPredII computer program predicts two potential transmembrane domains within the yc29_1 protein sequence, one centered around amino acid 175 and another around amino acid 210 of SEQ ID NO:36.

yc29_1 protein was expressed in a COS cell expression system, and an expressed protein band of approximately 56 kDa was detected in membrane fractions using SDS polyacrylamide gel electrophoresis.

Clone "yc40_1"

A polynucleotide of the present invention has been identified as clone "yc40_1". yc40_1 was isolated from a human fetal kidney (293 cell line) cDNA library and was identified as encoding a secreted or transmembrane protein on the basis of computer analysis of the amino acid sequence of the encoded protein. yc40_1 is a full-length clone, including the entire coding sequence of a secreted protein (also referred to herein as "yc40_1 protein").

The nucleotide sequence of yc40_1 as presently determined is reported in SEQ ID NO:37, and includes a poly(A) tail. What applicants presently believe to be the proper reading frame and the predicted amino acid sequence of the yc40_1 protein corresponding to the foregoing nucleotide sequence is reported in SEQ ID NO:38. Amino acids 31 to 43 of SEQ ID NO:38 are a predicted leader/signal sequence, with the predicted mature amino acid sequence beginning at amino acid 44. Due to the hydrophobic nature of the predicted leader/signal sequence, it is likely to act as a transmembrane domain should the predicted leader/signal sequence not be separated from the remainder of the yc40_1 protein.

The EcoRI/NotI restriction fragment obtainable from the deposit containing clone yc40_1 should be approximately 1400 bp.

The nucleotide sequence disclosed herein for yc40_1 was searched against the GenBank and GeneSeq nucleotide sequence databases using BLASTN/BLASTX and FASTA search protocols. yc40_1 demonstrated at least some similarity with sequences identified as D62445 (Human aorta cDNA 5'-end GEN-286A10, mRNA sequence) and T25162 (Human gene signature HUMGS07322; standard; DNA). Based upon sequence similarity, yc40_1 proteins and each similar protein or peptide may share at least some activity. The TopPredII computer program predicts a potential transmembrane domain within the yc40_1 protein sequence centered around amino acid 50 of SEQ ID NO:38.

Clone "yd10_1"

A polynucleotide of the present invention has been identified as clone "yd10_1". yd10_1 was isolated from a human adult brain cDNA library and was identified as encoding a secreted or transmembrane protein on the basis of computer analysis of the amino acid sequence of the encoded protein. yd10_1 is a full-length clone, including the entire coding sequence of a secreted protein (also referred to herein as "yd10_1 protein").

The nucleotide sequence of yd10_1 as presently determined is reported in SEQ ID NO:39, and includes a poly(A) tail. What applicants presently believe to be the proper reading frame and the predicted amino acid sequence of the yd10_1 protein corresponding to the foregoing nucleotide sequence is reported in SEQ ID NO:40. Amino acids 47 to 59 of SEQ ID NO:40 are a predicted leader/signal sequence, with the predicted mature amino acid sequence beginning at amino acid 60. Due to the hydrophobic nature of the predicted leader/signal sequence, it is likely to act as a transmembrane domain should the predicted leader/signal sequence not be separated from the remainder of the yd10_1 protein.

The EcoRI/NotI restriction fragment obtainable from the deposit containing clone yd10_1 should be approximately 825 bp.

The nucleotide sequence disclosed herein for yd10_1 was searched against the GenBank and GeneSeq nucleotide sequence databases using BLASTN/BLASTX and FASTA search protocols. yd10_1 demonstrated at least some similarity with sequences identified as AA587270 (nn70g03.s1 NCI_CGAP_Lar1 *Homo sapiens* cDNA clone IMAGE:1089268 similar to contains Alu repetitive element-;contains element PTR5 repetitive element; mRNA sequence). Based upon sequence similarity, yd10_1 proteins and each similar protein or peptide may share at least some activity. The nucleotide sequence of yd10_1 indicates that it may contain an Alu repetitive element.

Clone "yf5_1"

A polynucleotide of the present invention has been identified as clone "yf5_1". yf5_1 was isolated from a human fetal brain cDNA library and was identified as encoding a secreted or transmembrane protein on the basis of computer analysis of the amino acid sequence of the encoded protein. yf5_1 is a full-length clone, including the entire coding sequence of a secreted protein (also referred to herein as "yf5_1 protein").

The nucleotide sequence of yf5_1 as presently determined is reported in SEQ ID NO:41, and includes a poly(A) tail. What applicants presently believe to be the proper reading frame and the predicted amino acid sequence of the yf5_1 protein corresponding to the foregoing nucleotide sequence is reported in SEQ ID NO:42. Amino acids 9 to 21 of SEQ ID NO:42 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the yf5_1 protein.

The EcoRI/NotI restriction fragment obtainable from the deposit containing clone yf5_1 should be approximately 1800 bp.

The nucleotide sequence disclosed herein for yf5_1 was searched against the GenBank and GeneSeq nucleotide sequence databases using BLASTN/BLASTX and FASTA search protocols. yf5_1 demonstrated at least some similarity with sequences identified as AA181631 (zp52a03.s1 Stratagene HeLa cell s3 937216 *Homo sapiens* cDNA clone 613036 3', mRNA sequence) and U49082 (Human transporter protein (g17) mRNA, complete cds). The predicted amino acid sequence disclosed herein for yf5_1 was searched against the GenPept and GeneSeq amino acid sequence databases using the BLASTX search protocol. The predicted yf5_1 protein demonstrated at least some similarity to the sequence identified as U49082 (transporter protein [*Homo sapiens*]). Based upon sequence similarity, yf5_1 proteins and each similar protein or peptide may share at least some activity. The TopPredII computer program predicts ten additional potential transmembrane domains within the yf5_1 protein sequence, centered around amino acids 36, 84, 130, 154, 213, 249, 292, 330, 353, and 389 of SEQ ID NO:42, respectively. The nucleotide sequence of yf5_1 indicates that it may contain a MIR repeat region.

Clone "ya67_1"

A polynucleotide of the present invention has been identified as clone "ya67_1". ya67_1 was isolated from a human adult testes cDNA library and was identified as encoding a secreted or transmembrane protein on the basis of computer analysis of the amino acid sequence of the encoded protein. ya67_1 is a full-length clone, including the entire coding sequence of a secreted protein (also referred to herein as "ya67_1 protein").

The nucleotide sequence of ya67_1 as presently determined is reported in SEQ ID NO:43, and includes a poly(A) tail. What applicants presently believe to be the proper reading frame and the predicted amino acid sequence of the ya67_1 protein corresponding to the foregoing nucleotide sequence is reported in SEQ ID NO:44. Amino acids 14 to 26 of SEQ ID NO:44 are a predicted leader/signal sequence, with the predicted mature amino acid sequence beginning at amino acid 27. Amino acids 16 to 28 are also a predicted leader/signal sequence, with the predicted mature amino acid sequence beginning at amino acid 29. Due to the hydrophobic nature of the predicted leader/signal sequences, each is likely to act as a transmembrane domain should it not be separated from the remainder of the ya67_1 protein.

The EcoRI/NotI restriction fragment obtainable from the deposit containing clone ya67_1 should be approximately 800 bp.

The nucleotide sequence disclosed herein for ya67_1 was searched against the GenBank and GeneSeq nucleotide sequence databases using BLASTN/BLASTX and FASTA search protocols. ya67_1 demonstrated at least some similarity with sequences identified as AC002042 (* SEQUENCING IN PROGRESS * *Homo sapiens* chromosome 16p11.2 BAC clone CIT987SK-A-180G2; HTGS phase 1, 5 unordered pieces). Based upon sequence similarity, ya67_1 proteins and each similar protein or peptide may share at least some activity. The nucleotide sequence of ya67_1 indicates that it may contain an MIR repeat sequence.

ya67_1 protein was expressed in a COS cell expression system, and an expressed protein band of approximately 21 kDa was detected in membrane fractions using SDS polyacrylamide gel electrophoresis.

Clone "ya70_1"

A polynucleotide of the present invention has been identified as clone "ya70_1". ya70_1 was isolated from a human adult testes cDNA library and was identified as encoding a secreted or transmembrane protein on the basis of computer analysis of the amino acid sequence of the encoded protein. ya70_1 is a full-length clone, including the entire coding sequence of a secreted protein (also referred to herein as "ya70_1 protein").

The nucleotide sequence of ya70_1 as presently determined is reported in SEQ ID NO:45, and includes a poly(A) tail. What applicants presently believe to be the proper reading frame and the predicted amino acid sequence of the ya70_1 protein corresponding to the foregoing nucleotide sequence is reported in SEQ ID NO:46.

The EcoRI/NotI restriction fragment obtainable from the deposit containing clone ya70_1 should be approximately 1500 bp.

The nucleotide sequence disclosed herein for ya70_1 was searched against the GenBank and GeneSeq nucleotide sequence databases using BLASTN/BLASTX and FASTA search protocols. ya70_1 demonstrated at least some similarity with sequences identified as AA813657 (ai69c03.s1 Soares testis NHT *Homo sapiens* cDNA clone 1376068 3', mRNA sequence) and U84408 (Human IL-1 receptor related protein MyD88 mRNA, complete cds). The predicted amino acid sequence disclosed herein for ya70_1 was searched against the GenPept and GeneSeq amino acid sequence databases using the BLASTX search protocol. The predicted ya70_1 protein demonstrated at least some similarity to the sequences identified as U84408 (MyD88 [*Homo sapiens*]). Human MyD88, an IL-6 primary response gene, encodes a protein containing an N-terminal death domain and a C-terminal region that exhibits homology to human IL-1Rp80 and drosophila Toll (IL-1Rp80 and Toll are homologs). Based upon sequence similarity, ya70_1 proteins and each similar protein or peptide may share at least some activity. The TopPredII computer program predicts two potential transmembrane domains within the ya70_1 protein sequence, one centered around amino acid 90 and another around amino acid 175 of SEQ ID NO:46.

Clone "yb51_1"

A polynucleotide of the present invention has been identified as clone "yb51_1". yb51_1 was isolated from a human fetal brain cDNA library and was identified as encoding a secreted or transmembrane protein on the basis of computer analysis of the amino acid sequence of the encoded protein. yb51_1 is a full-length clone, including the entire coding sequence of a secreted protein (also referred to herein as "yb51_1 protein").

The nucleotide sequence of yb51_1 as presently determined is reported in SEQ ID NO:47, and includes a poly(A) tail. What applicants presently believe to be the proper reading frame and the predicted amino acid sequence of the yb51_1 protein corresponding to the foregoing nucleotide sequence is reported in SEQ ID NO:48. Amino acids 5 to 17 of SEQ ID NO:48 are a predicted leader/signal sequence, with the predicted mature amino acid sequence beginning at amino acid 18. Due to the hydrophobic nature of the predicted leader/signal sequence, it is likely to act as a transmembrane domain should the predicted leader/signal sequence not be separated from the remainder of the yb51_1 protein.

The EcoRI/NotI restriction fragment obtainable from the deposit containing clone yb51_1 should be approximately 1400 bp.

The nucleotide sequence disclosed herein for yb51_1 was searched against the GenBank and GeneSeq nucleotide sequence databases using BLASTN/BLASTX and FASTA search protocols. yb51_1 demonstrated at least some similarity with sequences identified as AA058715 (zk70c03.s1 Soares pregnant uterus NbHPU *Homo sapiens* cDNA clone 488164 3' similar to contains Alu repetitive element; contains element MER1 repetitive element) and Z44795 (*H. sapiens* partial cDNA sequence; clone c-29d08). Based upon sequence similarity, yb51_1 proteins and each similar protein or peptide may share at least some activity. The TopPredII computer program predicts an additional potential transmembrane domain within the yb51_1 protein sequence centered around amino acid 59 of SEQ ID NO:48. The nucleotide sequence of yb51_1 indicates that it may contain at least one repetitive element.

Clone "yb101_1"

A polynucleotide of the present invention has been identified as clone "yb101_1". yb101_1 was isolated from a human fetal brain cDNA library and was identified as encoding a secreted or transmembrane protein on the basis of computer analysis of the amino acid sequence of the encoded protein. yb101_1 is a full-length clone, including the entire coding sequence of a secreted protein (also referred to herein as "yb101_1 protein").

The nucleotide sequence of yb101_1 as presently determined is reported in SEQ ID NO:49, and includes a poly(A) tail. What applicants presently believe to be the proper reading frame and the predicted amino acid sequence of the yb101_1 protein corresponding to the foregoing nucleotide sequence is reported in SEQ ID NO:50.

The EcoRI/NotI restriction fragment obtainable from the deposit containing clone yb101_1 should be approximately 1050 bp.

The nucleotide sequence disclosed herein for yb101_1 was searched against the GenBank and GeneSeq nucleotide sequence databases using BLASTN/BLASTX and FASTA search protocols. yb101_1 demonstrated at least some similarity with sequences identified as AC005060 (*Homo sapiens* clone RG086D03; HTGS phase 1, 3 unordered pieces) and D60925 (Human fetal brain cDNA 5'-end GEN-139D01, mRNA sequence). Based upon sequence similarity, yb1011 proteins and each similar protein or peptide may share at least some activity. The TopPredII computer program predicts a potential transmembrane domain within the yb101_1 protein sequence centered around amino acid 11 of SEQ ID NO:50.

yb11_1 protein was expressed in a COS cell expression system, and an expressed protein band of approximately 8 kDa was detected in membrane fractions using SDS polyacrylamide gel electrophoresis.

Clone "yb124_1"

A polynucleotide of the present invention has been identified as clone "yb124_1". yb124_1 was isolated from a human fetal brain cDNA library and was identified as encoding a secreted or transmembrane protein on the basis of computer analysis of the amino acid sequence of the encoded protein. yb124_1 is a full-length clone, including the entire coding sequence of a secreted protein (also referred to herein as "yb124_1 protein").

The nucleotide sequence of yb124_1 as presently determined is reported in SEQ ID NO:51, and includes a poly(A) tail. What applicants presently believe to be the proper reading frame and the predicted amino acid sequence of the yb124_1 protein corresponding to the foregoing nucleotide sequence is reported in SEQ ID NO:52.

The EcoRI/NotI restriction fragment obtainable from the deposit containing clone yb124_1 should be approximately 1700 bp.

The nucleotide sequence disclosed herein for yb124_1 was searched against the GenBank and GeneSeq nucleotide sequence databases using BLASTN/BLASTX and FASTA search protocols. yb124_1 demonstrated at least some similarity with sequences identified as AA430306 (zw68g03.r1 Soares testis NHT *Homo sapiens* cDNA clone 781396 5', mRNA sequence). Based upon sequence similarity, yb124_1 proteins and each similar protein or peptide may share at least some activity. The TopPredII computer program predicts three potential transmembrane domains within the yb124_1 protein sequence, centered around amino acids 30, 84, and 134 of SEQ ID NO:52, respectively. Amino acids 128 to 140 of SEQ ID NO:52 also have characteristics indicative of a leader/signal sequence.

Clone "yb125_1"

A polynucleotide of the present invention has been identified as clone "yb125_1". yb125_1 was isolated from a human fetal brain cDNA library and was identified as encoding a secreted or transmembrane protein on the basis of computer analysis of the amino acid sequence of the encoded protein. yb125_1 is a full-length clone, including the entire coding sequence of a secreted protein (also referred to herein as "yb125_1 protein").

The nucleotide sequence of yb125_1 as presently determined is reported in SEQ ID NO:53, and includes a poly(A) tail. What applicants presently believe to be the proper reading frame and the predicted amino acid sequence of the yb125_1 protein corresponding to the foregoing nucleotide sequence is reported in SEQ ID NO:54. Amino acids 15 to 27 of SEQ ID NO:54 are a predicted leader/signal sequence, with the predicted mature amino acid sequence beginning at amino acid 28. Due to the hydrophobic nature of the predicted leader/signal sequence, it is likely to act as a transmembrane domain should the predicted leader/signal sequence not be separated from the remainder of the yb125_1 protein.

The EcoRI/NotI restriction fragment obtainable from the deposit containing clone yb125_1 should be approximately 2000 bp.

The nucleotide sequence disclosed herein for yb125_1 was searched against the GenBank and GeneSeq nucleotide sequence databases using BLASTN/BLASTX and FASTA search protocols. yb125_1 demonstrated at least some similarity with sequences identified as AA340207 (EST45465 Fetal brain m *Homo sapiens* cDNA 5' end, mRNA sequence) and Q92781 (Human thymopoietin gene fragment; standard; DNA). Based upon sequence similarity, yb125_1 proteins and each similar protein or peptide may share at least some activity. The nucleotide sequence of yb125_1 indicates that it may contain an Alu repetitive element.

Clone "yb179_1"

A polynucleotide of the present invention has been identified as clone "yb179_1". yb179_1 was isolated from a human fetal brain cDNA library and was identified as encoding a secreted or transmembrane protein on the basis of computer analysis of the amino acid sequence of the encoded protein. yb179_1 is a full-length clone, including the entire coding sequence of a secreted protein (also referred to herein as "yb179_1 protein").

The nucleotide sequence of yb179_1 as presently determined is reported in SEQ ID NO:55, and includes a poly(A) tail. What applicants presently believe to be the proper reading frame and the predicted amino acid sequence of the yb179_1 protein corresponding to the foregoing nucleotide sequence is reported in SEQ ID NO:56.

The EcoRI/NotI restriction fragment obtainable from the deposit containing clone yb179_1 should be approximately 1500 bp.

The nucleotide sequence disclosed herein for yb179_1 was searched against the GenBank and GeneSeq nucleotide sequence databases using BLASTN/BLASTX and FASTA search protocols. yb179_1 demonstrated at least some similarity with sequences identified as AA398428 (zt62a1.s1 Soares testis NHT *Homo sapiens* cDNA clone 726908 3', mRNA sequence). Based upon sequence similarity, yb179_1 proteins and each similar protein or peptide may share at least some activity. The TopPredII computer program predicts a potential transmembrane domain within the yb179_1 protein sequence centered around amino acid 100 of SEQ ID NO:56. Amino acids 97 to 109 of SEQ ID NO:56 are also a possible leader/signal sequence, with the predicted mature amino acid sequence beginning at amino acid 110.

Clone "yc48_1"

A polynucleotide of the present invention has been identified as clone "yc48_1". yc48_1 was isolated from a human fetal kidney (293 cell line) cDNA library and was identified as encoding a secreted or transmembrane protein on the basis of computer analysis of the amino acid sequence of the encoded protein. yc48_1 is a full-length clone, including the entire coding sequence of a secreted protein (also referred to herein as "yc48_1 protein").

The nucleotide sequence of yc48_1 as presently determined is reported in SEQ ID NO:57, and includes a poly(A) tail. What applicants presently believe to be the proper reading frame and the predicted amino acid sequence of the yc48_1 protein corresponding to the foregoing nucleotide sequence is reported in SEQ ID NO:58. Amino acids 5 to 17 of SEQ ID NO:58 are a predicted leader/signal sequence, with the predicted mature amino acid sequence beginning at amino acid 18. Due to the hydrophobic nature of the predicted leader/signal sequence, it is likely to act as a transmembrane domain should the predicted leader/signal sequence not be separated from the remainder of the yc48_1 protein.

The EcoRI/NotI restriction fragment obtainable from the deposit containing clone yc48_1 should be approximately 1400 bp.

The nucleotide sequence disclosed herein for yc48_1 was searched against the GenBank and GeneSeq nucleotide sequence databases using BLASTN/BLASTX and FASTA search protocols. yc48_1 demonstrated at least some similarity with sequences identified as AI009170 (EST203621 Normalized rat embryo, Bento Soares Rattus sp. cDNA clone REMBJ87 3' end, mRNA sequence). Based upon sequence similarity, yc48_1 proteins and each similar protein or peptide may share at least some activity. The TopPredII computer program predicts two additional potential transmembrane domains within the yc48_1 protein sequence, one centered around amino acid 110 and another around amino acid 180 of SEQ ID NO:58.

Clone "ye21_1"

A polynucleotide of the present invention has been identified as clone "ye21_1". ye21_1 was isolated from a human fetal brain cDNA library and was identified as encoding a secreted or transmembrane protein on the basis of computer analysis of the amino acid sequence of the encoded protein. ye21_1 is a full-length clone, including the entire coding sequence of a secreted protein (also referred to herein as "ye21_1 protein").

The nucleotide sequence of ye21_1 as presently determined is reported in SEQ ID NO:59, and includes a poly(A) tail. What applicants presently believe to be the proper reading frame and the predicted amino acid sequence of the ye21_1 protein corresponding to the foregoing nucleotide sequence is reported in SEQ ID NO:60. Amino acids 9 to 21 of SEQ ID NO:60 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the ye21_1 protein.

The EcoRI/NotI restriction fragment obtainable from the deposit containing clone ye21_1 should be approximately 1550 bp.

The nucleotide sequence disclosed herein for ye21_1 was searched against the GenBank and GeneSeq nucleotide sequence databases using BLASTN/BLASTX and FASTA search protocols. No significant hits were found in the databases. The TopPredII computer program predicts a potential transmembrane domain within the ye21_1 protein sequence centered around amino acid 66 of SEQ ID NO:60. The nucleotide sequence of ye21_1 indicates that it may contain an Alu repetitive element.

Clone "ye22_1"

A polynucleotide of the present invention has been identified as clone "ye22_1". ye22_1 was isolated from a human fetal brain cDNA library and was identified as encoding a secreted or transmembrane protein on the basis of computer analysis of the amino acid sequence of the encoded protein. ye22_1 is a full-length clone, including the entire coding sequence of a secreted protein (also referred to herein as "ye22_1 protein").

The nucleotide sequence of ye22_1 as presently determined is reported in SEQ ID NO:61, and includes a poly(A) tail. What applicants presently believe to be the proper reading frame and the predicted amino acid sequence of the ye22_1 protein corresponding to the foregoing nucleotide sequence is reported in SEQ ID NO:62.

The EcoRI/NotI restriction fragment obtainable from the deposit containing clone ye22_1 should be approximately 1600 bp.

The nucleotide sequence disclosed herein for ye22_1 was searched against the GenBank and GeneSeq nucleotide sequence databases using BLASTN/BLASTX and FASTA search protocols. ye22_1 demonstrated at least some similarity with sequences identified as AJ002553 (* SEQUENCING IN PROGRESS * *Homo sapiens* genomic DNA (PAC 1118i22) from chromosome 11; HTGS phase 1) and T19813 (Human gene signature HUMGS00891; standard; cDNA to mRNA). The predicted amino acid sequence disclosed herein for ye22_1 was searched against the GenPept and GeneSeq amino acid sequence databases using the BLASTX search protocol. The predicted ye22_1 protein demonstrated at least some similarity to the sequence identified as AF003145 (No definition line found [*Caenorhabditis elegans*]). Based upon sequence similarity, ye22_1 proteins and each similar protein or peptide may share at least some activity. The TopPredII computer program predicts a potential transmembrane domain within the ye22_1 protein sequence centered around amino acid 77 of SEQ ID NO:62. The nucleotide sequence of ye22_1 indicates that it may contain repetitive elements.

Clone "ye39_1"

A polynucleotide of the present invention has been identified as clone "ye39_1". ye39_1 was isolated from a human fetal brain cDNA library and was identified as encoding a secreted or transmembrane protein on the basis of computer analysis of the amino acid sequence of the encoded protein. ye39_1 is a full-length clone, including the entire coding sequence of a secreted protein (also referred to herein as "ye39_1 protein").

The nucleotide sequence of ye39_1 as presently determined is reported in SEQ ID NO:63, and includes a poly(A) tail. What applicants presently believe to be the proper reading frame and the predicted amino acid sequence of the ye39_1 protein corresponding to the foregoing nucleotide sequence is reported in SEQ ID NO:64.

The EcoRI/NotI restriction fragment obtainable from the deposit containing done ye39_1 should be approximately 1700 bp.

The nucleotide sequence disclosed herein for ye39_1 was searched against the GenBank and GeneSeq nucleotide sequence databases using BLASTN/BLASTX and FASTA search protocols. ye39_1 demonstrated at least some similarity with sequences identified as AA360300 (EST69467 Liver II *Homo sapiens* cDNA 5' end, mRNA sequence). Based upon sequence similarity, ye39_1 proteins and each similar protein or peptide may share at least some activity. The TopPredII computer program predicts two potential transmembrane domains within the ye39_1 protein sequence, one centered around amino acid 20 and another around amino acid 45 of SEQ ID NO:64.

Clone "yf9_1"

A polynucleotide of the present invention has been identified as clone "yf9_1". yf9_1 was isolated from a human fetal brain cDNA library and was identified as encoding a secreted or transmembrane protein on the basis of computer analysis of the amino acid sequence of the encoded protein. yf9_1 is a full-length clone, including the entire coding sequence of a secreted protein (also referred to herein as "yf9_1 protein").

The nucleotide sequence of yf9_1 as presently determined is reported in SEQ ID NO:65. What applicants presently believe to be the proper reading frame and the predicted amino acid sequence of the yf9_1 protein corresponding to the foregoing nucleotide sequence is reported in SEQ ID NO:66.

The EcoRI/NotI restriction fragment obtainable from the deposit containing clone yf9_1 should be approximately 950 bp.

The nucleotide sequence disclosed herein for yf9_1 was searched against the GenBank and GeneSeq nucleotide sequence databases using BLASTN/BLASTX and FASTA search protocols. yf9_1 demonstrated at least some similarity with sequences identified as AA747796 (nx86a03.s1 NCI_CGAP_GCB1 *Homo sapiens* cDNA clone IMAGE 1269100, mRNA sequence) and AF009426 (*Homo sapiens* clone 22 mRNA, alternative splice variant beta-1, complete cds). The predicted amino acid sequence disclosed herein for yf9_1 was searched against the GenPept and GeneSeq amino acid sequence databases using the BLASTX search protocol. The predicted yf9_1 protein demonstrated at least some similarity to the sequence identified as AF009426 (clone 22 [*Homo sapiens*]). Based upon sequence similarity, yf9_1 proteins and each similar protein or peptide may share at least some activity. Clone 22 mRNA was identified from brain transcripts and the corresponding gene has been localized to chromosome 18; the chromosome regions 18p and 18q where the transcripts cluster are candidate regions for bipolar disorder. The protein products of the clone 22 mRNA variants are predicted to be membrane spanning. (Yoshikawa et al., 1997, *Am. J. Med. Genet*. 74(2): 140–149, which is incorporated by reference herein). The predicted yf9_1 protein appears to be a novel splice variant expressed from the clone 22 gene. The TopPredII computer program predicts a potential transmembrane domain within the yf9_1 protein sequence centered around amino acid 39 of SEQ ID NO:66.

yf9_1 protein was expressed in a COS cell expression system, and an expressed protein band of approximately 24 kDa was detected in conditioned medium and membrane fractions using SDS polyacrylamide gel electrophoresis.

Clone "yh4_1"

A polynucleotide of the present invention has been identified as clone "yh4_1". yh4_1 was isolated from a human brain (fetal and adult) cDNA library and was identified as encoding a secreted or transmembrane protein on the basis of computer analysis of the amino acid sequence of the encoded protein. yh4_1 is a full-length clone, including the entire coding sequence of a secreted protein (also referred to herein as "yh4_1 protein").

The nucleotide sequence of yh4_1 as presently determined is reported in SEQ ID NO:67, and includes a poly(A) tail. What applicants presently believe to be the proper reading frame and the predicted amino acid sequence of the yh4_1 protein corresponding to the foregoing nucleotide sequence is reported in SEQ ID NO:68.

The EcoRI/NotI restriction fragment obtainable from the deposit containing clone yh4_1 should be approximately 1500 bp.

The nucleotide sequence disclosed herein for yh4_1 was searched against the GenBank and GeneSeq nucleotide sequence databases using BLASTN/BLASTX and FASTA search protocols. No significant hits were found in the databases. The TopPredII computer program predicts a potential transmembrane domain within the yh4_1 protein sequence centered around amino acid 80 of SEQ ID NO:68. The nucleotide sequence of yh4_1 indicates that it may contain an Alu repetitive element.

Clone "yi4_1"

A polynucleotide of the present invention has been identified as clone "yi4_1". yi4_1 was isolated from a human brain cDNA library and was identified as encoding a secreted or transmembrane protein on the basis of computer analysis of the amino acid sequence of the encoded protein. yi4_1 is a full-length clone, including the entire coding sequence of a secreted protein (also referred to herein as "yi4_1 protein").

The nucleotide sequence of yi4_1 as presently determined is reported in SEQ ID NO:69, and includes a poly(A)

tail. What applicants presently believe to be the proper reading frame and the predicted amino acid sequence of the yi4_1 protein corresponding to the foregoing nucleotide sequence is reported in SEQ ID NO:70. Amino acids 18 to 30 of SEQ ID NO:70 are a predicted leader/signal sequence, with the predicted mature amino acid sequence beginning at amino acid 31. Due to the hydrophobic nature of the predicted leader/signal sequence, it is likely to act as a transmembrane domain should the predicted leader/signal sequence not be separated from the remainder of the yi4_1 protein.

The EcoRI/NotI restriction fragment obtainable from the deposit containing clone yi4_1 should be approximately 1400 bp.

The nucleotide sequence disclosed herein for yi4_1 was searched against the GenBank and GeneSeq nucleotide sequence databases using BLASTN/BLASTX and FASTA search protocols. yi4_1 demonstrated at least some similarity with sequences identified as AA553835 (nk94f03.s1 NCI_CGAP_Co11 *Homo sapiens* cDNA clone IMAGE:1028477, mRNA sequence) and T22931 (Human gene signature HUMGS04656; standard; cDNA to mRNA). Based upon sequence similarity, yi4_1 proteins and each similar protein or peptide may share at least some activity. The nucleotide sequence of yi4_1 indicates that it may contain simple nucleotide repeat sequences.

Clone "yj3_1"

A polynucleotide of the present invention has been identified as clone "yj3_1". yj3_1 was isolated from a human fetal kidney (293 cell line) cDNA library and was identified as encoding a secreted or transmembrane protein on the basis of computer analysis of the amino acid sequence of the encoded protein. yj3_1 is a full-length clone, including the entire coding sequence of a secreted protein (also referred to herein as "yj3_1 protein").

The nucleotide sequence of yj3_1 as presently determined is reported in SEQ ID NO:71, and includes a poly(A) tail. What applicants presently believe to be the proper reading frame and the predicted amino acid sequence of the yj3_1 protein corresponding to the foregoing nucleotide sequence is reported in SEQ ID NO:72. Amino acids 8 to 20 of SEQ ID NO:72 are a predicted leader/signal sequence, with the predicted mature amino acid sequence beginning at amino acid 21. Due to the hydrophobic nature of the predicted leader/signal sequence, it is likely to act as a transmembrane domain should the predicted leader/signal sequence not be separated from the remainder of the yj3_1 protein.

The EcoRI/NotI restriction fragment obtainable from the deposit containing clone yj3_1 should be approximately 900 bp.

The nucleotide sequence disclosed herein for yj3_1 was searched against the GenBank and GeneSeq nucleotide sequence databases using BLASTN/BLASTX and FASTA search protocols. yj3_1 demonstrated at least some similarity with sequences identified as AC004955 (*Homo sapiens* clone DJ1087M19; HTGS phase 1, 7 unordered pieces) and W37665 (zc12f05.r1 Soares parathyroid tumor NbHPA *Homo sapiens* cDNA clone 322113 5', mRNA sequence). Based upon sequence similarity, yj3_1 proteins and each similar protein or peptide may share at least some activity. The TopPredII computer program predicts four additional potential transmembrane domains within the yj3_1 protein sequence, centered around amino acids 17, 45, 87, and 110 of SEQ ID NO:72, respectively.

Clone "yj7_1"

A polynucleotide of the present invention has been identified as clone "yj7_1". yj7_1 was isolated from a human fetal kidney (293 cell line) cDNA library and was identified as encoding a secreted or transmembrane protein on the basis of computer analysis of the amino acid sequence of the encoded protein. yj7_1 is a full-length clone, including the entire coding sequence of a secreted protein (also referred to herein as "yj7_1 protein").

The nucleotide sequence of yj7_1 as presently determined is reported in SEQ ID NO:73, and includes a poly(A) tail. What applicants presently believe to be the proper reading frame and the predicted amino acid sequence of the yj7_1 protein corresponding to the foregoing nucleotide sequence is reported in SEQ ID NO:74. Amino acids 21 to 33 of SEQ ID NO:74 are a predicted leader/signal sequence, with the predicted mature amino acid sequence beginning at amino acid 34. Due to the hydrophobic nature of the predicted leader/signal sequence, it is likely to act as a transmembrane domain should the predicted leader/signal sequence not be separated from the remainder of the yj7_1 protein.

The EcoRI/NotI restriction fragment obtainable from the deposit containing clone yj7_1 should be approximately 1159 bp.

The nucleotide sequence disclosed herein for yj7_1 was searched against the GenBank and GeneSeq nucleotide sequence databases using BLASTN/BLASTX and FASTA search protocols. yj7_1 demonstrated at least some similarity with sequences identified as AA827998 (of10c11.s1 NCI_CGAP_Co12 *Homo sapiens* cDNA clone IMAGE:1420724 3', mRNA sequence), C80074 (*Mus musculus* 3.5-dpc blastocyst cDNA 3'-end sequence, mRNA sequence), and T25792 (Human gene signature HUMGS08020; standard; cDNA to mRNA). The predicted amino acid sequence disclosed herein for yj7_1 was searched against the GenPept and GeneSeq amino acid sequence databases using the BLASTX search protocol. The predicted yj7_1 protein demonstrated at least some similarity to sequences identified as R61477 (Clavulanic acid dehydrogenase sequence), U43283 (similar to the insect-type alcohol dehydrogenase/ribitol dehydrogenase family [*Caenorhabditis elegans*]), and Z99116 (similar to ketoacyl reductase [*Bacillus subtilus*]).

Based upon sequence similarity, yj7_1 proteins and each similar protein or peptide may share at least some activity. Motifs search revealed the short-chain alcohol dehydrogenase family signature. These dehydrogenases and reductases are cytoplasmic, however, the amino acid similarity alignment is more consistent with domain/motif sharing. Also, the predicted yj7_1 protein demonstrates similarity to proteins that are only "similar to" these dehydrogenase and reductase enzymes; the predicted yj7_1 protein exhibits less amino acid similarity to the enzymes themselves. Therefore, the predicted yj7_1 protein might be a novel, secreted form of alcohol dehydrogenase.

yj7_1 protein was expressed in a COS cell expression system, and an expressed protein band of approximately 32 kDa was detected in membrane fractions using SDS polyacrylamide gel electrophoresis.

Clone "yj10_1"

A polynucleotide of the present invention has been identified as clone "yj10_1". yj10_1 was isolated from a human fetal kidney (293 cell line) cDNA library and was identified as encoding a secreted or transmembrane protein on the basis of computer analysis of the amino acid sequence of the encoded protein. yj10_1 is a full-length clone, including the entire coding sequence of a secreted protein (also referred to herein as "yj10_1 protein").

The nucleotide sequence of yj10_1 as presently determined is reported in SEQ ID NO:75, and includes a poly(A)

tail. What applicants presently believe to be the proper reading frame and the predicted amino acid sequence of the yj10_1 protein corresponding to the foregoing nucleotide sequence is reported in SEQ ID NO:76.

The EcoRI/NotI restriction fragment obtainable from the deposit containing clone yj10_1 should be approximately 1600 bp.

The nucleotide sequence disclosed herein for yj10_1 was searched against the GenBank and GeneSeq nucleotide sequence databases using BLASTN/BLASTX and FASTA search protocols. yj10_1 demonstrated at least some similarity with sequences identified as AF072860 (*Homo sapiens* protein activator of the interferon-induced protein kinase (PACT) mRNA, complete cds), AI056368 (oy48c07.x1 NCI_CGAP_Brn23 *Homo sapiens* cDNA clone IMAGE 1669068 3' similar to TR Q91836 Q91836 RNA BINDING PROTEIN; mRNA sequence) and T24520 (Human gene signature HUMGS06564; standard; cDNA to mRNA). The predicted amino acid sequence disclosed herein for yj10_1 was searched against the GenPept and GeneSeq amino acid sequence databases using the BLASTX search protocol. The predicted yj10_1 protein demonstrated at least some similarity to the sequence identified as AF072860 (protein activator of the interferon-induced protein kinase [*Homo sapiens*]). Based upon sequence similarity, yj10_1 proteins and each similar protein or peptide may share at least some activity.

Clone "yj28_1"

A polynucleotide of the present invention has been identified as clone "yj28_1". yj28_1 was isolated from a human fetal kidney (293 cell line) cDNA library and was identified as encoding a secreted or transmembrane protein on the basis of computer analysis of the amino acid sequence of the encoded protein. yj28_1 is a full-length clone, including the entire coding sequence of a secreted protein (also referred to herein as "yj28_1 protein").

The nucleotide sequence of yj28_1 as presently determined is reported in SEQ ID NO:77, and includes a poly(A) tail. What applicants presently believe to be the proper reading frame and the predicted amino acid sequence of the yj28_1 protein corresponding to the foregoing nucleotide sequence is reported in SEQ ID NO:78. Amino acids 160 to 172 of SEQ ID NO:78 are a predicted leader/signal sequence, with the predicted mature amino acid sequence beginning at amino acid 173. Due to the hydrophobic nature of the predicted leader/signal sequence, it is likely to act as a transmembrane domain should the predicted leader/signal sequence not be separated from the remainder of the yj28_1 protein.

The EcoRI/NotI restriction fragment obtainable from the deposit containing done yj28_1 should be approximately 1250 bp.

The nucleotide sequence disclosed herein for yj28_1 was searched against the GenBank and GeneSeq nucleotide sequence databases using BLASTN/BLASTX and FASTA search protocols. yj28_1 demonstrated at least some similarity with sequences identified as AA402090 (zu53f03.r1 Soares ovary tumor NbHOT *Homo sapiens* cDNA clone 741725 5', mRNA sequence) and AJ009691 (*Podocoryne carnea* mRNA for SMC2orf protein, partial). The predicted amino acid sequence disclosed herein for yj28_1 was searched against the GenPept and GeneSeq amino acid sequence databases using the BLASTX search protocol. The predicted yj28_1 protein demonstrated at least some similarity to the sequence identified as AJ009691 (SMC2orf [*Podocoryne carnea*]). Based upon sequence similarity, yj28_1 proteins and each similar protein or peptide may share at least some activity. The TopPredII computer program predicts an additional potential transmembrane domain within the yj28_1 protein sequence centered around amino acid 348 of SEQ ID NO:78.

Clone "yj29_1"

A polynucleotide of the present invention has been identified as clone "yj29_1". yj29_1 was isolated from a human fetal kidney (293 cell line) cDNA library and was identified as encoding a secreted or transmembrane protein on the basis of computer analysis of the amino acid sequence of the encoded protein. yj29_1 is a full-length clone, including the entire coding sequence of a secreted protein (also referred to herein as "yj29_1 protein").

The nucleotide sequence of yj29_1 as presently determined is reported in SEQ ID NO:79, and includes a poly(A) tail. What applicants presently believe to be the proper reading frame and the predicted amino acid sequence of the yj29_1 protein corresponding to the foregoing nucleotide sequence is reported in SEQ ID NO:80. Amino acids 310 to 322 of SEQ ID NO:80 are a predicted leader/signal sequence, with the predicted mature amino acid sequence beginning at amino acid 323. Due to the hydrophobic nature of the predicted leader/signal sequence, it is likely to act as a transmembrane domain should the predicted leader/signal sequence not be separated from the remainder of the yj29_1 protein.

The EcoRI/NotI restriction fragment obtainable from the deposit containing clone yj29_1 should be approximately 1600 bp.

The nucleotide sequence disclosed herein for yj29_1 was searched against the GenBank and GeneSeq nucleotide sequence databases using BLASTN/BLASTX and FASTA search protocols. yj29_1 demonstrated at least some similarity with sequences identified as AA156900 (zl20c06.r1 Soares pregnant uterus NbHPU *Homo sapiens* cDNA clone 502474 5' similar to WP:T06D8.8 CE02329; mRNA sequence), AF015416 (*Homo sapiens* chromosome 11 from 11p15.5 region, complete sequence), and T23342 Human gene signature HUMGS05162; standard; cDNA to mRNA). The predicted amino acid sequence disclosed herein for yj29_1 was searched against the GenPept and GeneSeq amino acid sequence databases using the BLASTX search protocol. The predicted yj29_1 protein demonstrated at least some similarity to the sequence identified as Z49130 (T06D8.8 [*Caenorhabditis elegans*]). Based upon sequence similarity, yj29_1 proteins and each similar protein or peptide may share at least some activity. The TopPredII computer program predicts an additional potential transmembrane domain within the yj29_1 protein sequence centered around amino acid 207 of SEQ ID NO:80.

Clone "yj32_1"

A polynucleotide of the present invention has been identified as clone "yj32_1". yj32_1 was isolated from a human fetal kidney (293 cell line) cDNA library and was identified as encoding a secreted or transmembrane protein on the basis of computer analysis of the amino acid sequence of the encoded protein. yj32_1 is a full-length clone, including the entire coding sequence of a secreted protein (also referred to herein as "yj32_1 protein").

The nucleotide sequence of yj32_1 as presently determined is reported in SEQ ID NO:81, and includes a poly(A) tail. What applicants presently believe to be the proper reading frame and the predicted amino acid sequence of the yj32_1 protein corresponding to the foregoing nucleotide sequence is reported in SEQ ID NO:82. Amino acids 64 to 76 of SEQ ID NO:82 are a predicted leader/signal sequence, with the predicted mature amino acid sequence beginning at amino acid 77. Due to the hydrophobic nature of the predicted leader/signal sequence, it is likely to act as a transmembrane domain should the predicted leader/signal sequence not be separated from the remainder of the yj32_1 protein.

The EcoRI/NotI restriction fragment obtainable from the deposit containing clone yj32_1 should be approximately 1450 bp.

The nucleotide sequence disclosed herein for yj32_1 was searched against the GenBank and GeneSeq nucleotide sequence databases using BLASTN/BLASTX and FASTA search protocols. No significant hits were found in the databases. The TopPredII computer program predicts an additional potential transmembrane domain within the yj32_1 protein sequence, near the N-terminus of SEQ ID NO:82. The nucleotide sequence of yj32_1 indicates that it may contain an Alu repetitive element. yj32_1 protein was expressed in a COS cell expression system, and an expressed protein band of approximately 10 kDa was detected in conditioned medium using SDS polyacrylamide gel electrophoresis.

Clone "yb186_1"

A polynucleotide of the present invention has been identified as clone "yb186_1". yb186_1 was isolated from a human fetal brain cDNA library and was identified as encoding a secreted or transmembrane protein on the basis of computer analysis of the amino acid sequence of the encoded protein. yb186_1 is a full-length clone, including the entire coding sequence of a secreted protein (also referred to herein as "yb186_1 protein").

The nucleotide sequence of yb186_1 as presently determined is reported in SEQ ID NO:83, and includes a poly(A) tail. What applicants presently believe to be the proper reading frame and the predicted amino acid sequence of the yb186_1 protein corresponding to the foregoing nucleotide sequence is reported in SEQ ID NO:84. Amino acids 10 to 22 of SEQ ID NO:84 are a predicted leader/signal sequence, with the predicted mature amino acid sequence beginning at amino acid 23. Amino acids 14 to 26 of SEQ ID NO:84 are also a predicted leader/signal sequence, with the predicted mature amino acid sequence beginning in this case at amino acid 27. Due to the hydrophobic nature of the predicted leader/signal sequences, each is likely to act as a transmembrane domain should it not be separated from the remainder of the yb186_1 protein.

The EcoRI/NotI restriction fragment obtainable from the deposit containing clone yb186_1 should be approximately 2700 bp.

The nucleotide sequence disclosed herein for yb186_1 was searched against the GenBank and GeneSeq nucleotide sequence databases using BLASTN/BLASTX and FASTA search protocols. yb186_1 demonstrated at least some similarity with sequences identified as T25270 (Human gene signature HUMGS07432; standard; cDNA to mRNA) and W73738 (zd50d05.s1 Soares fetal heart NbHH19W *Homo sapiens* cDNA clone 344073 3', mRNA sequence). Based upon sequence similarity, yb186_1 proteins and each similar protein or peptide may share at least some activity. The TopPredII computer program predicts an additional potential transmembrane domain within the yb186_1 protein sequence centered around amino acid 243 of SEQ ID NO:84.

Clone "yb226_1"

A polynucleotide of the present invention has been identified as clone "yb226_1". yb226_1 was isolated from a human fetal brain cDNA library and was identified as encoding a secreted or transmembrane protein on the basis of computer analysis of the amino acid sequence of the encoded protein. yb226_1 is a full-length done, including the entire coding sequence of a secreted protein (also referred to herein as "yb226_1 protein").

The nucleotide sequence of yb226_1 as presently determined is reported in SEQ ID NO:85, and includes a poly(A) tail. What applicants presently believe to be the proper reading frame and the predicted amino acid sequence of the yb226_1 protein corresponding to the foregoing nucleotide sequence is reported in SEQ ID NO:86.

The EcoRI/NotI restriction fragment obtainable from the deposit containing clone yb226_1 should be approximately 1800 bp.

The nucleotide sequence disclosed herein for yb226_1 was searched against the GenBank and GeneSeq nucleotide sequence databases using BLASTN/BLASTX and FASTA search protocols. yb226_1 demonstrated at least some similarity with sequences identified as N72056 (yv29f11.r1 Soares fetal liver spleen 1NFLS *Homo sapiens* cDNA clone 244173 5', mRNA sequence). Based upon sequence similarity, yb226_1 proteins and each similar protein or peptide may share at least some activity. The TopPredII computer program predicts two potential transmembrane domains within the yb226_1 protein sequence, one around amino acid 54 and another around amino acid 122 of SEQ ID NO:86. Amino acids 45 to 57 and 77 to 89 of SEQ ID NO:86 are also possible leader/signal sequences, with the predicted mature amino acid sequences beginning at amino acids 58 and 90, respectively.

Clone "yd50_1"

A polynucleotide of the present invention has been identified as clone "yd50_1". yd50_1 was isolated from a human adult brain cDNA library and was identified as encoding a secreted or transmembrane protein on the basis of computer analysis of the amino acid sequence of the encoded protein. yd50_1 is a full-length clone, including the entire coding sequence of a secreted protein (also referred to herein as "yd50_1 protein").

The nucleotide sequence of yd50_1 as presently determined is reported in SEQ ID NO:87, and includes a poly(A) tail. What applicants presently believe to be the proper reading frame and the predicted amino acid sequence of the yd50_1 protein corresponding to the foregoing nucleotide sequence is reported in SEQ ID NO:88.

The EcoRI/NotI restriction fragment obtainable from the deposit containing clone yd50_1 should be approximately 900 bp.

The nucleotide sequence disclosed herein for yd50_1 was searched against the GenBank and GeneSeq nucleotide sequence databases using BLASTN/BLASTX and FASTA search protocols. yd50_1 demonstrated at least some similarity with sequences identified as AA037761 (zk38c07.s1 Soares pregnant uterus NbHPU *Homo sapiens* cDNA clone 485100 3', mRNA sequence), AA312218 (EST182969 Jurkat T-cells VI *Homo sapiens* cDNA 5' end, mRNA sequence), and T24178 (Human gene signature HUMGS06183; standard; cDNA to mRNA). The predicted amino acid sequence disclosed herein for yd50_1 was searched against the GenPept and GeneSeq amino acid sequence databases using the BLASTX search protocol. The predicted yd50_1 protein demonstrated at least some similarity to sequences identified as AF038613 (undefined protein [*Caenorhabditis elegans*]) and AL023286 (hypothetical protein [*Schizosaccharomyces pombe*]). Based upon sequence similarity, yd50_1 proteins and each similar protein or peptide may share at least some activity. The TopPredII computer program predicts a potential transmembrane domain within the yd50_1 protein sequence centered around amino acid 45 of SEQ ID NO:88.

Clone "yd51_1"

A polynucleotide of the present invention has been identified as clone "yd51_1". yd51_1 was isolated from a human adult brain cDNA library and was identified as encoding a secreted or transmembrane protein on the basis of computer analysis of the amino acid sequence of the encoded protein. yd51_1 is a full-length clone, including the entire coding sequence of a secreted protein (also referred to herein as "yd51_1 protein").

The nucleotide sequence of yd51_1 as presently determined is reported in SEQ ID NO:89, and includes a poly(A) tail. What applicants presently believe to be the proper reading frame and the predicted amino acid sequence of the yd51_1 protein corresponding to the foregoing nucleotide sequence is reported in SEQ ID NO:90. Amino acids 11 to 23 of SEQ ID NO:90 are a predicted leader/signal sequence, with the predicted mature amino acid sequence beginning at amino acid 24. Due to the hydrophobic nature of the predicted leader/signal sequence, it is likely to act as a transmembrane domain should the predicted leader/signal sequence not be separated from the remainder of the yd51_1 protein.

The EcoRI/NotI restriction fragment obtainable from the deposit containing clone yd51_1 should be approximately 800 bp.

The nucleotide sequence disclosed herein for yd51_1 was searched against the GenBank and GeneSeq nucleotide sequence databases using BLASTN/BLASTX and FASTA search protocols. yd51_1 demonstrated at least some similarity with sequences identified as AA205661 (zq68g09.s1 Stratagene neuroepithelium (#937231) *Homo sapiens* cDNA clone 646816 3', mRNA sequence). Based upon sequence similarity, yd51_1 proteins and each similar protein or peptide may share at least some activity.

yd51_1 protein was expressed in a COS cell expression system, and an expressed protein band of approximately 24 kDa was detected in conditioned medium and membrane fractions using SDS polyacrylamide gel electrophoresis.

Clone "yd73_1"

A polynucleotide of the present invention has been identified as clone "yd73_1". yd73_1 was isolated from a human adult brain cDNA library and was identified as encoding a secreted or transmembrane protein on the basis of computer analysis of the amino acid sequence of the encoded protein. yd73_1 is a full-length clone, including the entire coding sequence of a secreted protein (also referred to herein as "yd73_1 protein").

The nucleotide sequence of yd73_1 as presently determined is reported in SEQ ID NO:91, and includes a poly(A) tail. What applicants presently believe to be the proper reading frame and the predicted amino acid sequence of the yd73_1 protein corresponding to the foregoing nucleotide sequence is reported in SEQ ID NO:92. Amino acids 67 to 79 of SEQ ID NO:92 are a predicted leader/signal sequence, with the predicted mature amino acid sequence beginning at amino acid 80. Due to the hydrophobic nature of the predicted leader/signal sequence, it is likely to act as a transmembrane domain should the predicted leader/signal sequence not be separated from the remainder of the yd73_1 protein.

The EcoRI/NotI restriction fragment obtainable from the deposit containing clone yd73_1 should be approximately 1000 bp.

The nucleotide sequence disclosed herein for yd73_1 was searched against the GenBank and GeneSeq nucleotide sequence databases using BLASTN/BLASTX and FASTA search protocols. yd73_1 demonstrated at least some similarity with sequences identified as AA587100 (nn81g06.s1 NCI_CGAP_Co9 *Homo sapiens* cDNA clone IMAGE:1090330, mRNA sequence) and T51192 (Human breast specific gene BSG10 partial cDNA clone HBGDM44; standard; cDNA). The predicted amino acid sequence disclosed herein for yd73_1 was searched against the GenPept and GeneSeq amino acid sequence databases using the BLASTX search protocol. The predicted yd73_1 protein demonstrated at least some similarity to the sequence identified as AF000198 (No definition line found (T28F2.2) [*Caenorhabditis elegans*]). Based upon sequence similarity, yd73_1 proteins and each similar protein or peptide may share at least some activity. The TopPredII computer program predicts two potential transmembrane domains within the yd73_1 protein sequence, one centered around amino acid 74 and another around amino acid 169 of SEQ ID NO:92.

yd73_1 protein was expressed in a COS cell expression system, and an expressed protein band of approximately 23 kDa was detected in membrane fractions using SDS polyacrylamide gel electrophoresis.

Clone "ye43_1"

A polynucleotide of the present invention has been identified as clone "ye43_1". ye43_1 was isolated from a human fetal brain cDNA library and was identified as encoding a secreted or transmembrane protein on the basis of computer analysis of the amino acid sequence of the encoded protein. ye43_1 is a full-length clone, including the entire coding sequence of a secreted protein (also referred to herein as "ye43_1 protein").

The nucleotide sequence of ye43_1 as presently determined is reported in SEQ ID NO:93, and includes a poly(A) tail. What applicants presently believe to be the proper reading frame and the predicted amino acid sequence of the ye43_1 protein corresponding to the foregoing nucleotide sequence is reported in SEQ ID NO:94. Amino acids 88 to 100 of SEQ ID NO:94 are a predicted leader/signal sequence, with the predicted mature amino acid sequence beginning at amino acid 101. Due to the hydrophobic nature of the predicted leader/signal sequence, it is likely to act as a transmembrane domain should the predicted leader/signal sequence not be separated from the remainder of the ye43_1 protein.

The EcoRI/NotI restriction fragment obtainable from the deposit containing clone ye43_1 should be approximately 1500 bp.

The nucleotide sequence disclosed herein for ye43_1 was searched against the GenBank and GeneSeq nucleotide sequence databases using BLASTN/BLASTX and FASTA search protocols. ye43_1 demonstrated at least some similarity with sequences identified as T23444 (Human gene signature HUMGS05282; standard; cDNA to mRNA) and Z99353 (*Homo sapiens* mRNA; expressed sequence tag; clone DKFZphamy1_1a12, 3' read, mRNA sequence). Based upon sequence similarity, ye43_1 proteins and each similar protein or peptide may share at least some activity. The TopPredII computer program predicts two potential transmembrane domains within the ye43_1 protein sequence, one centered around amino acid 51 and another around amino acid 89 of SEQ ID NO:94.

Clone "yh71_1"

A polynucleotide of the present invention has been identified as clone "yh71_1". yh71_1 was isolated from a human brain (fetal and adult) cDNA library and was identified as encoding a secreted or transmembrane protein on the basis of computer analysis of the amino acid sequence of the encoded protein. yh71_1 is a full-length clone, including the entire coding sequence of a secreted protein (also referred to herein as "yh71_1 protein").

The nucleotide sequence of yh71_1 as presently determined is reported in SEQ ID NO:95, and includes a poly(A) tail. What applicants presently believe to be the proper reading frame and the predicted amino acid sequence of the yh71_1 protein corresponding to the foregoing nucleotide sequence is reported in SEQ ID NO:96. Amino acids 264 to 276 of SEQ ID NO:96 are a predicted leader/signal sequence, with the predicted mature amino acid sequence beginning at amino acid 277. Due to the hydrophobic nature of the predicted leader/signal sequence, it is likely to act as a transmembrane domain should the predicted leader/signal sequence not be separated from the remainder of the yh71_1 protein.

The EcoRI/NotI restriction fragment obtainable from the deposit containing clone yh71_1 should be approximately 1891 bp.

The nucleotide sequence disclosed herein for yh71_1 was searched against the GenBank and GeneSeq nucleotide sequence databases using BLASTN/BLASTX and FASTA search protocols. yh71_1 demonstrated at least some similarity with sequences identified as H10493 (yl90h09.r1 *Homo sapiens* cDNA clone 45675 5'), T39809 (Mouse H74 gene; standard; DNA), and X85124 (*M.musculus* pacsin gene). Based upon sequence similarity, yh71_1 proteins and each similar protein or peptide may share at least some activity. The TopPredII computer program predicts two additional potential transmembrane domains within the yh71_1 protein sequence, one centered around amino acid 122 and another around amino acid 190 of SEQ ID NO:96.

Clone "yh100_1"

A polynucleotide of the present invention has been identified as clone "yh100_1". yh100_1 was isolated from a human brain (fetal and adult) cDNA library and was identified as encoding a secreted or transmembrane protein on the basis of computer analysis of the amino acid sequence of the encoded protein. yh100_1 is a full-length clone, including the entire coding sequence of a secreted protein (also referred to herein as "yh100_1 protein").

The nucleotide sequence of yh100_1 as presently determined is reported in SEQ ID NO:97, and includes a poly(A) tail. What applicants presently believe to be the proper reading frame and the predicted amino acid sequence of the yh100_1 protein corresponding to the foregoing nucleotide sequence is reported in SEQ ID NO:98. Amino acids 35 to 47 of SEQ ID NO:98 are a predicted leader/signal sequence, with the predicted mature amino acid sequence beginning at amino add 48. Due to the hydrophobic nature of the predicted leader/signal sequence, it is likely to act as a transmembrane domain should the predicted leader/signal sequence not be separated from the remainder of the yh100_1 protein.

The EcoRI/NotI restriction fragment obtainable from the deposit containing clone yh100_1 should be approximately 2200 bp.

The nucleotide sequence disclosed herein for yh100_1 was searched against the GenBank and GeneSeq nucleotide sequence databases using BLASTN/BLASTX and FASTA search protocols. No significant hits were found in the database. The TopPredII computer program predicts an additional potential transmembrane domain within the yh100_1 protein sequence, around amino acid 73 of SEQ ID NO:98. The nucleotide sequence of yh100_1 indicates that it may contain an Alu repetitive element.

Clone "yi3_1"

A polynucleotide of the present invention has been identified as clone "yi3_1". yi3_1 was isolated from a human brain cDNA library and was identified as encoding a secreted or transmembrane protein on the basis of computer analysis of the amino acid sequence of the encoded protein. yi3_1 is a full-length clone, including the entire coding sequence of a secreted protein (also referred to herein as "yi3_1 protein").

The nucleotide sequence of yi3_1 as presently determined is reported in SEQ ID NO:99, and includes a poly(A) tail. What applicants presently believe to be the proper reading frame and the predicted amino acid sequence of the yi3_1 protein corresponding to the foregoing nucleotide sequence is reported in SEQ ID NO:100. Amino acids 20 to 32 of SEQ ID NO:100 are a predicted leader/signal sequence, with the predicted mature amino acid sequence beginning at amino acid 33. Due to the hydrophobic nature of the predicted leader/signal sequence, it is likely to act as a transmembrane domain should the predicted leader/signal sequence not be separated from the remainder of the yi3_1 protein.

The EcoRI/NotI restriction fragment obtainable from the deposit containing clone yi3_1 should be approximately 2000 bp.

The nucleotide sequence disclosed herein for yi3_1 was searched against the GenBank and GeneSeq nucleotide sequence databases using BLASTN/BLASTX and FASTA search protocols. yi3_1 demonstrated at least some similarity with sequences identified as N22677 (yx64a05.s1 *Homo sapiens* cDNA clone 266480 3'). Based upon sequence similarity, yi3_1 proteins and each similar protein or peptide may share at least some activity.

Clone "yj23_1"

A polynucleotide of the present invention has been identified as clone "yj23_1". yj23_1 was isolated from a human fetal kidney (293 cell line) cDNA library and was identified as encoding a secreted or transmembrane protein on the basis of computer analysis of the amino acid sequence of the encoded protein. yj23_1 is a full-length clone, including the entire coding sequence of a secreted protein (also referred to herein as "yj23_1 protein").

The nucleotide sequence of yj23_1 as presently determined is reported in SEQ ID NO:101, and includes a poly(A) tail. What applicants presently believe to be the proper reading frame and the predicted amino acid sequence of the yj23_1 protein corresponding to the foregoing nucleotide sequence is reported in SEQ ID NO:102. Amino acids 12 to 24 of SEQ ID NO:102 are a predicted leader/signal sequence, with the predicted mature amino acid sequence beginning at amino acid 25. Amino acids 15 to 27 of SEQ ID NO:102 are also a possible leader/signal sequence, with the predicted mature amino acid sequence beginning in this case at amino acid 28, or are a transmembrane domain. Due to the hydrophobic nature of the predicted leader/signal sequences, each is likely to act as a transmembrane domain should it not be separated from the remainder of the yj23_1 protein.

The EcoRI/NotI restriction fragment obtainable from the deposit containing clone yj23_1 should be approximately 1400 bp.

The nucleotide sequence disclosed herein for yj23_1 was searched against the GenBank and GeneSeq nucleotide sequence databases using BLASTN/BLASTX and FASTA search protocols. yj23_1 demonstrated at least some similarity with sequences identified as A1096483 (qa03c12.x1 NCI_CGAP_Brn23 *Homo sapiens* cDNA clone IMAGE:1685686 3' similar to TR:Q04386 Q04386 HYPOTHETICAL 29.1 KD PROTEIN IN RPII140 5' REGION; mRNA sequence) and T19036 (Human gene signature HUMGS00043; standard; cDNA to mRNA). Based upon sequence similarity, yj23_1 proteins and each similar protein or peptide may share at least some activity. The TopPredII computer program predicts two additional potential transmembrane domains within the yj23_1 protein sequence, one centered around amino acid 90 and another around amino acid 199 of SEQ ID NO:102.

Clone "yl9_1"

A polynucleotide of the present invention has been identified as clone "yl9_1". yl9_1 was isolated from a human adult spleen cDNA library and was identified as encoding a secreted or transmembrane protein on the basis of computer analysis of the amino acid sequence of the encoded protein. yl9_1 is a full-length clone, including the entire coding sequence of a secreted protein (also referred to herein as "yl9_1 protein").

The nucleotide sequence of yl9_1 as presently determined is reported in SEQ ID NO:103, and includes a poly(A) tail. What applicants presently believe to be the proper reading frame and the predicted amino acid sequence of the yl9_1 protein corresponding to the foregoing nucleotide sequence is reported in SEQ ID NO:104. Amino acids 6 to 18 of SEQ ID NO:104 are a predicted leader/signal sequence, with the predicted mature amino acid sequence beginning at amino acid 19. Due to the hydrophobic nature of the predicted leader/signal sequence, it is likely to act as a transmembrane domain should the predicted leader/signal sequence not be separated from the remainder of the yl9_1 protein.

The EcoRI/NotI restriction fragment obtainable from the deposit containing clone yl9_1 should be approximately 1100 bp.

The nucleotide sequence disclosed herein for yl9_1 was searched against the GenBank and GeneSeq nucleotide sequence databases using BLASTN/BLASTX and FASTA search protocols. yl9_1 demonstrated at least some similarity with sequences identified as AA902287 (ok69g10.s1 NCI_CGAP_GC4 Homo sapiens cDNA clone IMAGE 1519266 3' similar to SW C1QA_HUMAN P02745 COMPLEMENT C1Q SUBCOMPONENT, A CHAIN PRECURSOR; mRNA sequence) and X58861 (Mouse mRNA for complement subcomponent C1Q alpha-chain). The predicted amino acid sequence disclosed herein for yl9_1 was searched against the GenPept and GeneSeq amino acid sequence databases using the BLASTX search protocol. The predicted yl9_1 protein demonstrated at least some similarity to sequences identified as R22265 (New collagen type protein from chipmunk blood), W09108 (Human adipocyte complement related protein Acrp30), and X58861 (complement subcomponent C1Q A-chain precursor [Mus musculus]). Based upon sequence similarity, yl9_1 proteins and each similar protein or peptide may share at least some activity. The predicted yl9_1 protein has at least some similarity to human, mouse, and rat complement subcomponent C1Q, and motifs and profile hidden markov model analysis of the predicted yl9_1 protein have revealed the presence of a C1Q domain signature at amino acids 116 to 241 of SEQ ID NO:104. C1Q is a subunit of the C1 enzyme complex that activates the serum complement system. The collagen-like regions of C1Q interact with the Ca(2+)-Dependent C1R(2)/C1S(2) proenzyme complex, and efficient activation of C1 takes place on interaction of the globular heads of C1Q with the Fc regions of IgG or IgM antibody present in immune complexes. The C1Q domain has been found in the C-terminus of vertebrate secreted or membrane-bound proteins which are mostly short-chain collagens and collagen-like molecules. The predicted yl9_1 protein appears to encode a novel member of the C1 enzyme complex, having the highest degree of similarity to the A-chain of the complex. The TopPredII computer program predicts a potential transmembrane domain within the yl9_1 protein sequence centered around amino acid 160 of SEQ ID NO:104.

yl9_1 protein was expressed in a COS cell expression system, and an expressed protein band of approximately 23 kDa was detected in membrane fractions using SDS polyacrylamide gel electrophoresis.

Clone "ya66_1"

A polynucleotide of the present invention has been identified as clone "ya66_1". ya66_1 was isolated from a human adult testes cDNA library and was identified as encoding a secreted or transmembrane protein on the basis of computer analysis of the amino acid sequence of the encoded protein. ya66_1 is a full-length clone, including the entire coding sequence of a secreted protein (also referred to herein as "ya66_1 protein").

The nucleotide sequence of ya66_1 as presently determined is reported in SEQ ID NO:105, and includes a poly(A) tail. What applicants presently believe to be the proper reading frame and the predicted amino acid sequence of the ya66_1 protein corresponding to the foregoing nucleotide sequence is reported in SEQ ID NO:106.

The EcoRI/NotI restriction fragment obtainable from the deposit containing clone ya66_1 should be approximately 1050 bp.

The nucleotide sequence disclosed herein for ya66_1 was searched against the GenBank and GeneSeq nucleotide sequence databases using BLASTN/BLASTX and FASTA search protocols. ya66_1 demonstrated at least some similarity with sequences identified as AI096636 (qb57c12.x1 NCI_CGAP_Brn23 Homo sapiens cDNA clone IMAGE:1704214 3', mRNA sequence) and T20099 (Human gene signature HUMGS01242; standard; cDNA to mRNA). Based upon sequence similarity, ya66_1 proteins and each similar protein or peptide may share at least some activity. The TopPredII computer program predicts a potential transmembrane domain within the ya66_1 protein sequence centered around amino acid 106 of SEQ ID NO:106.

Clone "yb187_1"

A polynucleotide of the present invention has been identified as clone "yb187_1". yb187_1 was isolated from a human fetal brain cDNA library and was identified as encoding a secreted or transmembrane protein on the basis of computer analysis of the amino acid sequence of the encoded protein. yb187_1 is a full-length clone, including the entire coding sequence of a secreted protein (also referred to herein as "yb187_1 protein").

The nucleotide sequence of yb187_1 as presently determined is reported in SEQ ID NO:107, and includes a poly(A) tail. What applicants presently believe to be the proper reading frame and the predicted amino acid sequence of the yb187_1 protein corresponding to the foregoing nucleotide sequence is reported in SEQ ID NO:108.

The EcoRI/NotI restriction fragment obtainable from the deposit containing clone yb187_1 should be approximately 1800 bp.

The nucleotide sequence disclosed herein for yb187_1 was searched against the GenBank and GeneSeq nucleotide sequence databases using BLASTN/BLASTX and FASTA search protocols. yb187_1 demonstrated at least some similarity with sequences identified as AA846805 (aj99f04.s1

Soares parathyroid tumor NbHPA *Homo sapiens* cDNA clone IMAGE:1404607 3', mRNA sequence) and Q61039 (Human brain Expressed Sequence Tag EST01102; standard; DNA). Based upon sequence similarity, yb187_1 proteins and each similar protein or peptide may share at least some activity. The TopPredII computer program predicts a potential transmembrane domain within the yb187_1 protein sequence centered around amino acid 58 of SEQ ID NO:108; amino acids 58 to 70 of SEQ ID NO:108 are also a possible leader/signal sequence, with the predicted mature amino acid sequence beginning at amino acid 71.

Clone "yb219_1"

A polynucleotide of the present invention has been identified as clone "yb219_1". yb219_1 was isolated from a human fetal brain cDNA library and was identified as encoding a secreted or transmembrane protein on the basis of computer analysis of the amino acid sequence of the encoded protein. yb219_1 is a full-length clone, including the entire coding sequence of a secreted protein (also referred to herein as "yb219_1 protein").

The nucleotide sequence of yb219_1 as presently determined is reported in SEQ ID NO:109, and includes a poly(A) tail. What applicants presently believe to be the proper reading frame and the predicted amino acid sequence of the yb219_1 protein corresponding to the foregoing nucleotide sequence is reported in SEQ ID NO:110. Amino acids 3 to 15 of SEQ ID NO:110 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the yb219_1 protein.

The EcoRI/NotI restriction fragment obtainable from the deposit containing clone yb219_1 should be approximately 1600 bp.

The nucleotide sequence disclosed herein for yb219_1 was searched against the GenBank and GeneSeq nucleotide sequence databases using BLASTN/BLASTX and FASTA search protocols. No significant hits were found in the database.

Clone "yb228_1"

A polynucleotide of the present invention has been identified as clone "yb228_1". yb228_1 was isolated from a human fetal brain cDNA library and was identified as encoding a secreted or transmembrane protein on the basis of computer analysis of the amino acid sequence of the encoded protein. yb228_1 is a full-length clone, including the entire coding sequence of a secreted protein (also referred to herein as "yb228_1 protein").

The nucleotide sequence of yb228_1 as presently determined is reported in SEQ ID NO:111, and includes a poly(A) tail. What applicants presently believe to be the proper reading frame and the predicted amino acid sequence of the yb228_1 protein corresponding to the foregoing nucleotide sequence is reported in SEQ ID NO:112. Amino acids 1 to 13 of SEQ ID NO:112 are a predicted leader/signal sequence, with the predicted mature amino acid sequence beginning at amino acid 14. Due to the hydrophobic nature of the predicted leader/signal sequence, it is likely to act as a transmembrane domain should the predicted leader/signal sequence not be separated from the remainder of the yb228_1 protein.

The EcoRI/NotI restriction fragment obtainable from the deposit containing clone yb228_1 should be approximately 650 bp.

The nucleotide sequence disclosed herein for yb228_1 was searched against the GenBank and GeneSeq nucleotide sequence databases using BLASTN/BLASTX and FASTA search protocols. No hits were found in the database. The TopPredII computer program predicts a potential transmembrane domain within the yb228_1 protein sequence centered around amino acid 31 of SEQ ID NO:112.

Clone "yc27_1"

A polynucleotide of the present invention has been identified as clone "yc27_1". yc27_1 was isolated from a human fetal kidney (293 embryonal carcinoma cell line) cDNA library and was identified as encoding a secreted or transmembrane protein on the basis of computer analysis of the amino acid sequence of the encoded protein. yc27_1 is a full-length clone, including the entire coding sequence of a secreted protein (also referred to herein as "yc27_1 protein").

The nucleotide sequence of yc27_1 as presently determined is reported in SEQ ID NO:113, and includes a poly(A) tail. What applicants presently believe to be the proper reading frame and the predicted amino acid sequence of the yc27_1 protein corresponding to the foregoing nucleotide sequence is reported in SEQ ID NO:114. Amino acids 111 to 123 of SEQ ID NO:114 are a predicted leader/signal sequence, with the predicted mature amino add sequence beginning at amino add 124. Due to the hydrophobic nature of the predicted leader/signal sequence, it is likely to act as a transmembrane domain should the predicted leader/signal sequence not be separated from the remainder of the yc27_1 protein.

The EcoRI/NotI restriction fragment obtainable from the deposit containing clone yc27_1 should be approximately 1300 bp.

The nucleotide sequence disclosed herein for yc27_1 was searched against the GenBank and GeneSeq nucleotide sequence databases using BLASTN/BLASTX and FASTA search protocols. yc27_1 demonstrated at least some similarity with sequences identified as T23290 (Human gene signature HUMGS05104; standard; cDNA to mRNA) and W60958 (zc98d11.s1 Pancreatic Islet *Homo sapiens* cDNA clone 339189 3', mRNA sequence). The predicted amino acid sequence disclosed herein for yc27_1 was searched against the GenPept and GeneSeq amino acid sequence databases using the BLASTX search protocol. The predicted yc27_1 protein demonstrated at least some similarity to sequences identified as AL021890 (undefined protein [*Arabidopsis thaliana*]) and U00036 (R151.6 [*Caenorhabditis elegans*]). Based upon sequence similarity, yc27_1 proteins and each similar protein or peptide may share at least some activity. The TopPredII computer program predicts three potential transmembrane domains within the yc27_1 protein sequence, centered around amino acids 68, 107, and 161 of SEQ ID NO:114, respectively.

yc27_1 protein was expressed in a COS cell expression system, and an expressed protein band of approximately 23 kDa was detected in membrane fractions using SDS polyacrylamide gel electrophoresis.

Clone "yc49_1"

A polynucleotide of the present invention has been identified as clone "yc49_1". yc49_1 was isolated from a human fetal kidney (293 embryonal carcinoma cell line) cDNA library and was identified as encoding a secreted or transmembrane protein on the basis of computer analysis of the amino acid sequence of the encoded protein. yc49_1 is a full-length clone, including the entire coding sequence of a secreted protein (also referred to herein as "yc49_1 protein").

The nucleotide sequence of yc49_1 as presently determined is reported in SEQ ID NO:115, and includes a poly(A) tail. What applicants presently believe to be the proper reading frame and the predicted amino acid sequence of the yc49_1 protein corresponding to the foregoing nucleotide sequence is reported in SEQ ID NO:116.

The EcoRI/NotI restriction fragment obtainable from the deposit containing clone yc49_1 should be approximately 1000 bp.

The nucleotide sequence disclosed herein for yc49_1 was searched against the GenBank and GeneSeq nucleotide sequence databases using BLASTN/BLASTX and FASTA search protocols. yc49_1 demonstrated at least some similarity with sequences identified as AF052113 (*Homo sapiens* clone 23675 mRNA sequence), N28761 (yx69b12.r1 *Homo sapiens* cDNA clone 266975 5'), and T20571 (Human gene signature HUMGS01786; standard; cDNA to mRNA). Based upon sequence similarity, yc49_1 proteins and each similar protein or peptide may share at least some activity. The TopPredII computer program predicts two potential transmembrane domains within the yc49_1 protein sequence, one centered around amino acid 48 and another around amino acid 75 of SEQ ID NO:116. Amino acids 38 to 50 of SEQ ID NO:116 are also a possible leader/signal sequence, with the predicted mature amino acid sequence beginning at amino acid 51.

Clone "yd40_1"

A polynucleotide of the present invention has been identified as clone "yd40_1". yd40_1 was isolated from a human adult brain cDNA library and was identified as encoding a secreted or transmembrane protein on the basis of computer analysis of the amino acid sequence of the encoded protein. yd40_1 is a full-length clone, including the entire coding sequence of a secreted protein (also referred to herein as "yd40_1 protein").

The nucleotide sequence of yd40_1 as presently determined is reported in SEQ ID NO:117, and includes a poly(A) tail. What applicants presently believe to be the proper reading frame and the predicted amino acid sequence of the yd40_1 protein corresponding to the foregoing nucleotide sequence is reported in SEQ ID NO:118.

The EcoRI/NotI restriction fragment obtainable from the deposit containing clone yd40_1 should be approximately 900 bp.

The nucleotide sequence disclosed herein for yd40_1 was searched against the GenBank and GeneSeq nucleotide sequence databases using BLASTN/BLASTX and FASTA search protocols. No significant hits were found in the database. The TopPredII computer program predicts three potential transmembrane domains within the yd40_1 protein sequence, centered around amino acids 19, 60, and 86 of SEQ ID NO:118, respectively. The nucleotide sequence of yd40_1 indicates that it may contain a MIR repetitive element.

Clone "yd64_1"

A polynucleotide of the present invention has been identified as clone "yd64_1". yd64_1 was isolated from a human adult brain cDNA library and was identified as encoding a secreted or transmembrane protein on the basis of computer analysis of the amino acid sequence of the encoded protein. yd64_1 is a full-length clone, including the entire coding sequence of a secreted protein (also referred to herein as "yd64_1 protein").

The nucleotide sequence of yd64_1 as presently determined is reported in SEQ ID NO:119, and includes a poly(A) tail. What applicants presently believe to be the proper reading frame and the predicted amino acid sequence of the yd64_1 protein corresponding to the foregoing nucleotide sequence is reported in SEQ ID NO:120.

The EcoRI/NotI restriction fragment obtainable from the deposit containing clone yd64_1 should be approximately 1000 bp.

The nucleotide sequence disclosed herein for yd64_1 was searched against the GenBank and GeneSeq nucleotide sequence databases using BLASTN/BLASTX and FASTA search protocols. yd64_1 demonstrated at least some similarity with sequences identified as N59133 (yz62c12.s1 Soares multiple sclerosis 2NbHMSP *Homo sapiens* cDNA clone 287638 3', mRNA sequence). The predicted amino acid sequence disclosed herein for yd64_1 was searched against the GenPept and GeneSeq amino acid sequence databases using the BLASTX search protocol. The predicted yd64_1 protein demonstrated at least some similarity to sequences identified as M98529 (21 kDa protein [*Homo sapiens*]). Based upon sequence similarity, yd64_1 proteins and each similar protein or peptide may share at least some activity. The TopPredII computer program predicts a potential transmembrane domains within the yd64_1 protein sequence centered around amino acid 96 of SEQ ID NO:120.

yd64_1 protein was expressed in a COS cell expression system, and an expressed protein band of approximately 23 kDa was detected in conditioned medium using SDS polyacrylamide gel electrophoresis.

Clone "ye47_1"

A polynucleotide of the present invention has been identified as clone "ye47_1". ye47_1 was isolated from a human fetal brain cDNA library and was identified as encoding a secreted or transmembrane protein on the basis of computer analysis of the amino acid sequence of the encoded protein. ye47_1 is a full-length clone, including the entire coding sequence of a secreted protein (also referred to herein as "ye471 protein").

The nucleotide sequence of ye471 as presently determined is reported in SEQ ID NO:121, and includes a poly(A) tail. What applicants presently believe to be the proper reading frame and the predicted amino acid sequence of the ye47_1 protein corresponding to the foregoing nucleotide sequence is reported in SEQ ID NO:122. Amino acids 40 to 52 of SEQ ID NO:122 are a predicted leader/signal sequence, with the predicted mature amino acid sequence beginning at amino acid 53. Due to the hydrophobic nature of the predicted leader/signal sequence, it is likely to act as a transmembrane domain should the predicted leader/signal sequence not be separated from the remainder of the ye47_1 protein.

The EcoRI/NotI restriction fragment obtainable from the deposit containing clone ye47_1 should be approximately 1600 bp.

The nucleotide sequence disclosed herein for ye47_1 was searched against the GenBank and GeneSeq nucleotide sequence databases using BLASTN/BLASTX and FASTA search protocols. ye47_1 demonstrated at least some similarity with sequences identified as AC000105 (* SEQUENCING IN PROGRESS * *Homo sapiens* Chromosome 22q11.2 MDR Region; HTGS phase 2, 6 ordered pieces). Based upon sequence similarity, ye47_1 proteins and each similar protein or peptide may share at least some activity. The TopPredII computer program predicts an additional potential transmembrane domain within the ye47_1 protein sequence centered around amino acid 42 of SEQ ID NO:122. The nucleotide sequence of ye47_1 indicates that it may contain one or more of the following repetitive elements: Alu, MIR.

ye47_1 protein was expressed in a COS cell expression system, and an expressed protein band of approximately 24 kDa was detected in membrane fractions using SDS polyacrylamide gel electrophoresis.

Clone "yh50_1"

A polynucleotide of the present invention has been identified as clone "yh50_1". yh50_1 was isolated from a human brain (fetal and adult) cDNA library and was identified as encoding a secreted or transmembrane protein on the basis of computer analysis of the amino acid sequence of the encoded protein. yh50_1 is a full-length clone, including the entire coding sequence of a secreted protein (also referred to herein as "yh50_1 protein").

The nucleotide sequence of yh50_1 as presently determined is reported in SEQ ID NO:123, and includes a poly(A) tail. What applicants presently believe to be the proper reading frame and the predicted amino acid sequence of the yh50_1 protein corresponding to the foregoing nucleotide sequence is reported in SEQ ID NO:124. Amino acids 35 to 47 of SEQ ID NO:124 are a predicted leader/signal sequence, with the predicted mature amino acid sequence beginning at amino acid 48. Due to the hydrophobic nature of the predicted leader/signal sequence, it is likely to act as a transmembrane domain should the predicted leader/signal sequence not be separated from the remainder of the yh50_1 protein.

The EcoRI/NotI restriction fragment obtainable from the deposit containing clone yh50_1 should be approximately 2515 bp.

The nucleotide sequence disclosed herein for yh50_1 was searched against the GenBank and GeneSeq nucleotide sequence databases using BLASTN/BLASTX and FASTA search protocols. yh50_1 demonstrated at least some similarity with sequences identified as N49425 (yv21c11.r1 Homo sapiens cDNA clone 243380 5' similar to contains Alu repetitive element), Q90512 (CEA clone HindIII-Sau3A fragment; standard; DNA), and R98218 (yq75a05.r1 Homo sapiens cDNA clone 201584 5' similar to contains Alu repetitive element). Based upon sequence similarity, yh50_1 proteins and each similar protein or peptide may share at least some activity. The nucleotide sequence of yh50_1 indicates that it may contain an Alu repetitive element.

Clone "yh53_1"

A polynucleotide of the present invention has been identified as clone "yh53_1". yh53_1 was isolated from a human brain (fetal and adult) cDNA library and was identified as encoding a secreted or transmembrane protein on the basis of computer analysis of the amino acid sequence of the encoded protein. yh53_1 is a full-length clone, including the entire coding sequence of a secreted protein (also referred to herein as "yh53_1 protein").

The nucleotide sequence of yh53_1 as presently determined is reported in SEQ ID NO:125, and includes a poly(A) tail. What applicants presently believe to be the proper reading frame and the predicted amino acid sequence of the yh53_1 protein corresponding to the foregoing nucleotide sequence is reported in SEQ ID NO:126.

The EcoRI/NotI restriction fragment obtainable from the deposit containing clone yh53_1 should be approximately 1763 bp.

The nucleotide sequence disclosed herein for yh53_1 was searched against the GenBank and GeneSeq nucleotide sequence databases using BLASTN/BLASTX and FASTA search protocols. yh53_1 demonstrated at least some similarity with sequences identified as T23683 (Human gene signature HUMGS05558; standard; cDNA to mRNA) and W52762 (zd13a08.r1 Soares fetal heart NbHH19W Homo sapiens cDNA clone 340502 5', mRNA sequence). Based upon sequence similarity, yh53_1 proteins and each similar protein or peptide may share at least some activity. The TopPredII computer program predicts a potential transmembrane domain within the yh53_1 protein sequence centered around amino acid 23 of SEQ ID NO:126.

Clone "yh98_1"

A polynucleotide of the present invention has been identified as clone "yh98_1". yh98_1 was isolated from a human brain (fetal and adult) cDNA library and was identified as encoding a secreted or transmembrane protein on the basis of computer analysis of the amino acid sequence of the encoded protein. yh98_1 is a full-length clone, including the entire coding sequence of a secreted protein (also referred to herein as "yh98_1 protein").

The nucleotide sequence of yh98_1 as presently determined is reported in SEQ ID NO:127, and includes a poly(A) tail. What applicants presently believe to be the proper reading frame and the predicted amino acid sequence of the yh98_1 protein corresponding to the foregoing nucleotide sequence is reported in SEQ ID NO:128. Amino acids 24 to 36 of SEQ ID NO:128 are a predicted leader/signal sequence, with the predicted mature amino acid sequence beginning at amino acid 37. Due to the hydrophobic nature of the predicted leader/signal sequence, it is likely to act as a transmembrane domain should the predicted leader/signal sequence not be separated from the remainder of the yh98_1 protein.

Another potential yh98_1 reading frame and predicted amino acid sequence that could be encoded by basepairs 1381 to 1635 of SEQ ID NO:127 is reported in SEQ ID NO:266. Amino acids 64 to 76 of SEQ ID NO:266 are a predicted leader/signal sequence, with the predicted mature amino acid sequence beginning at amino acid 77. Due to the hydrophobic nature of the predicted leader/signal sequence, it is likely to act as a transmembrane domain should the predicted leader/signal sequence not be separated from the remainder of the protein of SEQ ID NO:266.

The EcoRI/NotI restriction fragment obtainable from the deposit containing clone yh98_1 should be approximately 1000 bp.

The nucleotide sequence disclosed herein for yh98_1 was searched against the GenBank and GeneSeq nucleotide sequence databases using BLASTN/BLASTX and FASTA search protocols. yh98_1 demonstrated at least some similarity with sequences identified as AA187630 (zp73e04.s1 Stratagene HeLa cell s3 937216 Homo sapiens cDNA clone 625854 3', mRNA sequence), AA632023 (np74d10.s1 NCI_CGAP_Br2 Homo sapiens cDNA clone IMAGE:1132051, mRNA sequence), AA837470 (od20e11.s1 NCI_CGAP_GCB1 Homo sapiens cDNA clone IMAGE:1368524, mRNA sequence), AF034176 (Homo sapiens ntcon5 contig mRNA, partial sequence, mRNA sequence), AF052101 (Homo sapiens clone 23872 mRNA sequence), AI092946 (qa81c03.x1 Soares_fetal_heart_NbHH19W Homo sapiens cDNA clone IMAGE:1693156 3', mRNA sequence), and Q76621 (Human genome fragment (Preferred); standard; DNA). Based upon sequence similarity, yh98_1 proteins and each similar protein or peptide may share at least some activity.

Clone "ya69_1"

A polynucleotide of the present invention has been identified as clone "ya69_1". ya69_1 was isolated from a human adult testes cDNA library and was identified as encoding a secreted or transmembrane protein on the basis of computer analysis of the amino acid sequence of the encoded protein. ya69_1 is a full-length clone, including the entire coding sequence of a secreted protein (also referred to herein as "ya69_1 protein").

The nucleotide sequence of ya69_1 as presently determined is reported in SEQ ID NO:129, and includes a poly(A) tail. What applicants presently believe to be the proper reading frame and the predicted amino acid sequence of the ya69_1 protein corresponding to the foregoing nucleotide sequence is reported in SEQ ID NO:130. Amino acids 35 to 47 of SEQ ID NO:130 are a predicted leader/signal sequence, with the predicted mature amino acid sequence beginning at amino acid 48. Due to the hydrophobic nature of the predicted leader/signal sequence, it is likely to act as a transmembrane domain should the predicted leader/signal sequence not be separated from the remainder of the ya69_1 protein.

The EcoRI/NotI restriction fragment obtainable from the deposit containing clone ya69_1 should be approximately 2000 bp.

The nucleotide sequence disclosed herein for ya69_1 was searched against the GenBank and GeneSeq nucleotide sequence databases using BLASTN/BLASTX and FASTA search protocols. ya69_1 demonstrated at least some similarity with sequences identified as A1075196 (oy96c08.x1 Soares_fetal_liver_spleen_1NFLS_S1 *Homo sapiens* cDNA clone IMAGE:1673678 3', mRNA sequence). Based upon sequence similarity, ya69_1 proteins and each similar protein or peptide may share at least some activity. The TopPredII computer program predicts a potential transmembrane domain within the ya69_1 protein sequence, centered around amino acid 40 of SEQ ID NO:130.

Clone "yd107_1"

A polynucleotide of the present invention has been identified as clone "yd107_1". yd107_1 was isolated from a human adult brain cDNA library and was identified as encoding a secreted or transmembrane protein on the basis of computer analysis of the amino acid sequence of the encoded protein. yd107_1 is a full-length clone, including the entire coding sequence of a secreted protein (also referred to herein as "yd107_1 protein").

The nucleotide sequence of yd107_1 as presently determined is reported in SEQ ID NO:131, and includes a poly(A) tail. What applicants presently believe to be the proper reading frame and the predicted amino acid sequence of the yd107_1 protein corresponding to the foregoing nucleotide sequence is reported in SEQ ID NO:132. Amino acids 37 to 49 of SEQ ID NO:132 are a predicted leader/signal sequence, with the predicted mature amino acid sequence beginning at amino acid 50. Due to the hydrophobic nature of the predicted leader/signal sequence, it is likely to act as a transmembrane domain should the predicted leader/signal sequence not be separated from the remainder of the yd107_1 protein.

The EcoRI/NotI restriction fragment obtainable from the deposit containing clone yd107_1 should be approximately 1000 bp.

The nucleotide sequence disclosed herein for yd107_1 was searched against the GenBank and GeneSeq nucleotide sequence databases using BLASTN/BLASTX and FASTA search protocols. yd107_1 demonstrated at least some similarity with sequences identified as AA910935 (ok85f02.s1 NCI_CGAP_Kid3 *Homo sapiens* cDNA clone IMAGE:1520763 3' similar to WP:R05D11.5 CE06240; mRNA sequence) and T26576 (Human gene signature HUMGS08822; standard; cDNA to mRNA). The predicted amino acid sequence disclosed herein for yd107_1 was searched against the GenPept and GeneSeq amino acid sequence databases using the BLASTX search protocol. The predicted yd107_1 protein demonstrated at least some similarity to sequences identified as Z75546 (R05D11.5 [*Caenorhabditis elegans*]). Based upon sequence similarity, yd107_1 proteins and each similar protein or peptide may share at least some activity. The TopPredII computer program predicts two potential transmembrane domains within the yd107_1 protein sequence, one centered around amino acid 48 and another around amino acid 121 of SEQ ID NO:132.

Clone "yd145_1"

A polynucleotide of the present invention has been identified as clone "yd145_1". yd145_1 was isolated from a human adult brain cDNA library and was identified as encoding a secreted or transmembrane protein on the basis of computer analysis of the amino acid sequence of the encoded protein. yd145_1 is a full-length clone, including the entire coding sequence of a secreted protein (also referred to herein as "yd145_1 protein").

The nucleotide sequence of yd145_1 as presently determined is reported in SEQ ID NO:133, and includes a poly(A) tail. What applicants presently believe to be the proper reading frame and the predicted amino acid sequence of the yd145_1 protein corresponding to the foregoing nucleotide sequence is reported in SEQ ID NO:134. Amino acids 3 to 15 of SEQ ID NO:134 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the yd145_1 protein.

The EcoRI/NotI restriction fragment obtainable from the deposit containing clone yd145_1 should be approximately 750 bp.

The nucleotide sequence disclosed herein for yd145_1 was searched against the GenBank and GeneSeq nucleotide sequence databases using BLASTN/BLASTX and FASTA search protocols. yd145_1 demonstrated at least some similarity with sequences identified as AA432034 (zw80e01.r1 Soares testis NHT *Homo sapiens* cDNA clone 782520 5', mRNA sequence) and X87489 (*H.sapiens* genomic DNA (chromosome 3; clone NL1243D)). Based upon sequence similarity, yd145_1 proteins and each similar protein or peptide may share at least some activity. The TopPredII computer program predicts an additional potential transmembrane domain within the yd145_1 protein sequence centered around amino acid 45 of SEQ ID NO:134.

Clone "yh24_1"

A polynucleotide of the present invention has been identified as clone "yh24_1". yh24_1 was isolated from a human brain (fetal and adult) cDNA library and was identified as encoding a secreted or transmembrane protein on the basis of computer analysis of the amino acid sequence of the encoded protein. yh24_1 is a full-length clone, including the entire coding sequence of a secreted protein (also referred to herein as "yh24_1 protein").

The nucleotide sequence of yh24_1 as presently determined is reported in SEQ ID NO:135, and includes a poly(A) tail. What applicants presently believe to be the proper reading frame and the predicted amino acid sequence of the yh24_1 protein corresponding to the foregoing nucleotide sequence is reported in SEQ ID NO:136. Another potential yh24_1 reading frame and predicted amino acid sequence that could be encoded by basepairs 676 to 939 of SEQ ID NO:135 is reported in SEQ ID NO:267.

The EcoRI/NotI restriction fragment obtainable from the deposit containing done yh24_1 should be approximately 1000 bp.

The nucleotide sequence disclosed herein for yh24_1 was searched against the GenBank and GeneSeq nucleotide sequence databases using BLASTN/BLASTX and FASTA search protocols. yh24_1 demonstrated at least some similarity with sequences identified as AA129061 (zo11f12.r1 Stratagene neuroepithelium NT2RAMI 937234 *Homo sapiens* cDNA clone 567407 5' similar to TR:G439877 G439877 REVERSE TRANSCRIPTASE; mRNA sequence). Based upon sequence similarity, yh24_1 proteins and each similar protein or peptide may share at least some activity. The TopPredII computer program predicts two potential transmembrane domains within the yh24_1 protein sequence of SEQ ID NO:136, one centered around amino acid 52 and another near the N-terminus of SEQ ID NO:136, the latter domain also being a possible signal/leader sequence. Analysis of the possible yh24_1 amino acid sequence of SEQ ID NO:267 reveals a binding-protein-dependent transport systems inner membrane component signature. This signature is present in the integral inner-membrane proteins superfamily which translocate substrates across the membrane.

Clone "yi11_1"

A polynucleotide of the present invention has been identified as clone "yi11_1". yi11_1 was isolated from a human brain cDNA library and was identified as encoding a secreted or transmembrane protein on the basis of computer analysis of the amino acid sequence of the encoded protein. yi11_1 is a full-length clone, including the entire coding sequence of a secreted protein (also referred to herein as "yi11_1 protein").

The nucleotide sequence of yi11_1 as presently determined is reported in SEQ ID NO:137, and includes a poly(A) tail. What applicants presently believe to be the proper reading frame and the predicted amino add sequence of the yi11_1 protein corresponding to the foregoing nucleotide sequence is reported in SEQ ID NO:138. Amino acids 128 to 140 of SEQ ID NO:138 are a predicted leader/signal sequence, with the predicted mature amino acid sequence beginning at amino acid 141. Due to the hydrophobic nature of the predicted leader/signal sequence, it is likely to act as a transmembrane domain should the predicted leader/signal sequence not be separated from the remainder of the yi11_1 protein.

The EcoRI/NotI restriction fragment obtainable from the deposit containing clone yi11_1 should be approximately 1550 bp.

The nucleotide sequence disclosed herein for yi11_1 was searched against the GenBank and GeneSeq nucleotide sequence databases using BLASTN/BLASTX and FASTA search protocols. yi11_1 demonstrated at least some similarity with sequences identified as AA772340 (ai43c02.s1 Soares parathyroid tumor NbHPA *Homo sapiens* cDNA clone 1359746 3', mRNA sequence), T26648 (Human gene signature HUMGS08895; standard; cDNA to mRNA), and U48972 (*Mus musculus* spindlin (Spin) mRNA, complete cds). Based upon sequence similarity, yi11_1 proteins and each similar protein or peptide may share at least some activity. The TopPredII computer program predicts four potential transmembrane domains within the yi11_1 protein sequence, centered around amino acids 20, 45, 90, and 136 of SEQ ID NO:138, respectively, with the most N-terminal domain also being a possible signal/leader sequence.

Clone "yi18_1"

A polynucleotide of the present invention has been identified as clone "yi18_1". yi18_1 was isolated from a human brain cDNA library and was identified as encoding a secreted or transmembrane protein on the basis of computer analysis of the amino acid sequence of the encoded protein. yi18_1 is a full-length clone, including the entire coding sequence of a secreted protein (also referred to herein as "yi18_1 protein").

The nucleotide sequence of yi18_1 as presently determined is reported in SEQ ID NO:139, and includes a poly(A) tail. What applicants presently believe to be the proper reading frame and the predicted amino acid sequence of the yi18_1 protein corresponding to the foregoing nucleotide sequence is reported in SEQ ID NO:140. Amino acids 48 to 60 of SEQ ID NO:140 are a predicted leader/signal sequence, with the predicted mature amino acid sequence beginning at amino acid 61. Due to the hydrophobic nature of the predicted leader/signal sequence, it is likely to act as a transmembrane domain should the predicted leader/signal sequence not be separated from the remainder of the yi18_1 protein.

The EcoRI/NotI restriction fragment obtainable from the deposit containing clone yi18_1 should be approximately 1850 bp.

The nucleotide sequence disclosed herein for yi18_1 was searched against the GenBank and GeneSeq nucleotide sequence databases using BLASTN/BLASTX and FASTA search protocols. yi18_1 demonstrated at least some similarity with sequences identified as AC003086 Human BAC clone RG104F04 from 7q21-q22, complete sequence), T81349 (yd27c10.s1 *Homo sapiens* cDNA clone 109458 3'), and T81524 (yd27c10.r1 *Homo sapiens* cDNA clone 109458 5'). Based upon sequence similarity, yi18_1 proteins and each similar protein or peptide may share at least some activity.

Clone "yk14_1"

A polynucleotide of the present invention has been identified as clone "yk14_1". yk14_1 was isolated from a human adult thymus cDNA library and was identified as encoding a secreted or transmembrane protein on the basis of computer analysis of the amino acid sequence of the encoded protein. yk14_1 is a full-length clone, including the entire coding sequence of a secreted protein (also referred to herein as "yk14_1 protein").

The nucleotide sequence of yk14_1 as presently determined is reported in SEQ ID NO:141, and includes a poly(A) tail. What applicants presently believe to be the proper reading frame and the predicted amino acid sequence of the yk14_1 protein corresponding to the foregoing nucleotide sequence is reported in SEQ ID NO:142. Amino acids 17 to 29 of SEQ ID NO:142 are a predicted leader/signal sequence, with the predicted mature amino acid sequence beginning at amino acid 30. Due to the hydrophobic nature of the predicted leader/signal sequence, it is likely to act as a transmembrane domain should the predicted leader/signal sequence not be separated from the remainder of the yk14_1 protein.

The EcoRI/NotI restriction fragment obtainable from the deposit containing clone yk14_1 should be approximately 1067 bp.

The nucleotide sequence disclosed herein for yk14_1 was searched against the GenBank and GeneSeq nucleotide sequence databases using BLASTN/BLASTX and FASTA search protocols. yk14_1 demonstrated at least some similarity with sequences identified as AA576618 (nm74f07.s1 NCI_CGAP_Co9 *Homo sapiens* cDNA clone IMAGE:1073989, mRNA sequence). Based upon sequence similarity, yk14_1 proteins and each similar protein or peptide may share at least some activity. The TopPredII computer program predicts an additional potential transmembrane domains within the yk14_1 protein sequence centered around amino acid 61 of SEQ ID NO:142.

Clone "yk39_1"

A polynucleotide of the present invention has been identified as clone "yk39_1". yk39_1 was isolated from a human adult thymus cDNA library and was identified as encoding a secreted or transmembrane protein on the basis of computer analysis of the amino acid sequence of the encoded protein. yk39_1 is a full-length clone, including the entire coding sequence of a secreted protein (also referred to herein as "yk39_1 protein").

The nucleotide sequence of yk39_1 as presently determined is reported in SEQ ID NO:143, and includes a poly(A) tail. What applicants presently believe to be the proper reading frame and the predicted amino acid sequence of the yk39_1 protein corresponding to the foregoing nucleotide sequence is reported in SEQ ID NO:144.

The EcoRI/NotI restriction fragment obtainable from the deposit containing clone yk39_1 should be approximately 1300 bp.

The nucleotide sequence disclosed herein for yk39_1 was searched against the GenBank and GeneSeq nucleotide sequence databases using BLASTN/BLASTX and FASTA search protocols. No significant hits were found in the database. The TopPredII computer program predicts two potential transmembrane domains within the yk39_1 protein sequence, one centered around amino acid 18 and another around amino acid 44 of SEQ ID NO:144. The nucleotide sequence of yk39_1 indicates that it may contain a MIR repeat region.

Clone "yk91_1"

A polynucleotide of the present invention has been identified as clone "yk91_1". yk91_1 was isolated from a human adult thymus cDNA library and was identified as encoding a secreted or transmembrane protein on the basis of computer analysis of the amino acid sequence of the encoded protein. yk91_1 is a full-length clone, including the entire coding sequence of a secreted protein (also referred to herein as "yk91_1 protein").

The nucleotide sequence of yk91_1 as presently determined is reported in SEQ ID NO:145, and includes a poly(A) tail. What applicants presently believe to be the proper reading frame and the predicted amino acid sequence of the yk91_1 protein corresponding to the foregoing nucleotide sequence is reported in SEQ ID NO:146. Amino acids 49 to 61 of SEQ ID NO:146 are a predicted leader/signal sequence, with the predicted mature amino acid sequence beginning at amino acid 62. Due to the hydrophobic nature of the predicted leader/signal sequence, it is likely to act as a transmembrane domain should the predicted leader/signal sequence not be separated from the remainder of the yk91_1 protein.

The EcoRI/NotI restriction fragment obtainable from the deposit containing clone yk91_1 should be approximately 1150 bp.

The nucleotide sequence disclosed herein for yk91_1 was searched against the GenBank and GeneSeq nucleotide sequence databases using BLASTN/BLASTX and FASTA search protocols. No significant hits were found in the database. The TopPredII computer program predicts an additional potential transmembrane domain within the yk91_1 protein sequence centered around amino acid 80 of SEQ ID NO:146. The nucleotide sequence of yk91_1 indicates that it may contain an Alu repetitive element.

Clone "yk199_1"

A polynucleotide of the present invention has been identified as clone "yk199_1". yk199_1 was isolated from a human adult thymus cDNA library and was identified as encoding a secreted or transmembrane protein on the basis of computer analysis of the amino acid sequence of the encoded protein. yk199_1 is a full-length clone, including the entire coding sequence of a secreted protein (also referred to herein as "yk199_1 protein").

The nucleotide sequence of yk199_1 as presently determined is reported in SEQ ID NO:147, and includes a poly(A) tail. What applicants presently believe to be the proper reading frame and the predicted amino acid sequence of the yk199_1 protein corresponding to the foregoing nucleotide sequence is reported in SEQ ID NO:148. Amino acids 10 to 22 of SEQ ID NO:148 are a predicted leader/signal sequence, with the predicted mature amino acid sequence beginning at amino acid 23. Due to the hydrophobic nature of the predicted leader/signal sequence, it is likely to act as a transmembrane domain should the predicted leader/signal sequence not be separated from the remainder of the yk199_1 protein.

The EcoRI/NotI restriction fragment obtainable from the deposit containing clone yk199_1 should be approximately 1700 bp.

The nucleotide sequence disclosed herein for yk199_1 was searched against the GenBank and GeneSeq nucleotide sequence databases using BLASTN/BLASTX and FASTA search protocols. yk199_1 demonstrated at least some similarity with sequences identified as AI039293 (ox33e12.s1 Soares_total_fetus_Nb2HF8_9w *Homo sapiens* cDNA clone IMAGE:1658158 3', mRNA sequence). Based upon sequence similarity, yk199_1 proteins and each similar protein or peptide may share at least some activity. The TopPredII computer program predicts a potential transmembrane domain within the yk199_1 protein sequence, around amino acid 132 of SEQ ID NO:148. The nucleotide sequence and the predicted amino acid sequence of yk199_1 indicate that it may contain human TAR1 (telomere-associated repeat 1) sequence.

Clone "yl4_1"

A polynucleotide of the present invention has been identified as clone "yl4_1". yl4_1 was isolated from a human adult spleen cDNA library and was identified as encoding a secreted or transmembrane protein on the basis of computer analysis of the amino acid sequence of the encoded protein. yl4_1 is a full-length clone, including the entire coding sequence of a secreted protein (also referred to herein as "yl4_1 protein").

The nucleotide sequence of yl4_1 as presently determined is reported in SEQ ID NO:149, and includes a poly(A) tail. What applicants presently believe to be the proper reading frame and the predicted amino acid sequence of the yl4_1 protein corresponding to the foregoing nucleotide sequence is reported in SEQ ID NO:150. Amino acids 204 to 216 of SEQ ID NO:150 are a predicted leader/signal sequence, with the predicted mature amino acid sequence beginning at amino acid 217. Due to the hydrophobic nature of the predicted leader/signal sequence, it is likely to act as a transmembrane domain should the predicted leader/signal sequence not be separated from the remainder of the yl4_1 protein.

The EcoRI/NotI restriction fragment obtainable from the deposit containing clone yl4_1 should be approximately 1250 bp.

The nucleotide sequence disclosed herein for yl4_1 was searched against the GenBank and GeneSeq nucleotide sequence databases using BLASTN/BLASTX and FASTA search protocols. yl4_1 demonstrated at least some similarity with sequences identified as AA283813 (zt19g10.s1 Soares ovary tumor NbHOT *Homo sapiens* cDNA clone 713634 3', mRNA sequence). Based upon sequence similarity, yl4_1 proteins and each similar protein or peptide may share at least some activity. The TopPredII computer program predicts an additional potential transmembrane domain within the yl4_1 protein sequence centered around amino acid 108 of SEQ ID NO:150.

Clone "yl14_1"

A polynucleotide of the present invention has been identified as clone "yl14_1". yl14_1 was isolated from a human adult spleen cDNA library and was identified as encoding a secreted or transmembrane protein on the basis of computer analysis of the amino acid sequence of the encoded protein. yl14_1 is a full-length clone, including the entire coding sequence of a secreted protein (also referred to herein as "yl14_1 protein").

The nucleotide sequence of yl14_1 as presently determined is reported in SEQ ID NO:151, and includes a poly(A) tail. What applicants presently believe to be the proper reading frame and the predicted amino acid sequence of the yl14_1 protein corresponding to the foregoing nucleotide sequence is reported in SEQ ID NO:152.

The EcoRI/NotI restriction fragment obtainable from the deposit containing clone yl14_1 should be approximately 1000 bp.

The nucleotide sequence disclosed herein for yl14_1 was searched against the GenBank and GeneSeq nucleotide sequence databases using BLASTN/BLASTX and FASTA search protocols. yl14_1 demonstrated at least some similarity with sequences identified as AF034174 (*Homo sapiens* ntcon3 contig mRNA, partial sequence, mRNA sequence) and T03943 (human thrombopoietin genomic coding sequence). Based upon sequence similarity, yl14_1 proteins and each similar protein or peptide may share at least some activity. The TopPredII computer program predicts two potential transmembrane domains within the yl14_1 protein sequence, one centered around amino acid 18 and another around amino acid 69 of SEQ ID NO:152; amino acids 61 to 73 are also a possible leader/signal sequence, with the predicted mature amino acid sequence beginning at amino acid 74 of SEQ ID NO:152. The nucleotide sequence of yl14_1 indicates that it may contain an Alu repetitive element.

Clone "ya80_1"

A polynucleotide of the present invention has been identified as clone "ya80_1". ya80_1 was isolated from a human adult testes cDNA library and was identified as encoding a secreted or transmembrane protein on the basis of computer analysis of the amino acid sequence of the encoded protein. ya80_1 is a full-length clone, including the entire coding sequence of a secreted protein (also referred to herein as "ya80_1 protein").

The nucleotide sequence of ya80_1 as presently determined is reported in SEQ ID NO:153, and includes a poly(A) tail. What applicants presently believe to be the proper reading frame and the predicted amino acid sequence of the ya80_1 protein corresponding to the foregoing nucleotide sequence is reported in SEQ ID NO:154. Amino acids 31 to 43 of SEQ ID NO:154 are a predicted leader/signal sequence, with the predicted mature amino acid sequence beginning at amino acid 44. Due to the hydrophobic nature of the predicted leader/signal sequence, it is likely to act as a transmembrane domain should the predicted leader/signal sequence not be separated from the remainder of the ya80_1 protein.

The EcoRI/NotI restriction fragment obtainable from the deposit containing clone ya80_1 should be approximately 600 bp.

The nucleotide sequence disclosed herein for ya80_1 was searched against the GenBank and GeneSeq nucleotide sequence databases using BLASTN/BLASTX and FASTA search protocols. No significant hits were found in the database. The TopPredII computer program predicts a potential transmembrane domain within the ya80_1 protein sequence centered around amino acid 30 of SEQ ID NO:154.

Clone "yd61_1"

A polynucleotide of the present invention has been identified as clone "yd61_1". yd61_1 was isolated from a human adult brain cDNA library and was identified as encoding a secreted or transmembrane protein on the basis of computer analysis of the amino acid sequence of the encoded protein. yd61_1 is a full-length clone, including the entire coding sequence of a secreted protein (also referred to herein as "yd61_1 protein").

The nucleotide sequence of yd61_1 as presently determined is reported in SEQ ID NO:155, and includes a poly(A) tail. What applicants presently believe to be the proper reading frame and the predicted amino acid sequence of the yd61_1 protein corresponding to the foregoing nucleotide sequence is reported in SEQ ID NO:156. Amino acids 156 to 168 of SEQ ID NO:156 are a predicted leader/signal sequence, with the predicted mature amino acid sequence beginning at amino acid 169. Due to the hydrophobic nature of the predicted leader/signal sequence, it is likely to act as a transmembrane domain should the predicted leader/signal sequence not be separated from the remainder of the yd61_1 protein.

The EcoRI/NotI restriction fragment obtainable from the deposit containing clone yd61_1 should be approximately 950 bp.

The nucleotide sequence disclosed herein for yd61_1 was searched against the GenBank and GeneSeq nucleotide sequence databases using BLASTN/BLASTX and FASTA search protocols. yd61_1 demonstrated at least some similarity with sequences identified as AI017161 (ou28a07.x1 Soares_NFL_T_GBC_S1 *Homo sapiens* cDNA clone IMAGE:1627572 3' similar to TR:Q15040 Q15040 mRNA ;contains TAR1.t1 MSR1 repetitive element; mRNA sequence) and D31884 (Human mRNA for KIAA0063 gene, complete cds). The predicted amino acid sequence disclosed herein for yd61_1 was searched against the GenPept and GeneSeq amino acid sequence databases using the BLASTX search protocol. The predicted yd61_1 protein demonstrated at least some similarity to the sequence identified as D31884 (KIAA0063 [*Homo sapiens*]). Based upon sequence similarity, yd61_1 proteins and each similar protein or peptide may share at least some activity. The TopPredII computer program predicts two potential transmembrane domains within the yd61_1 protein sequence, one centered around amino acid 78 and another around amino acid 11 of SEQ ID NO:156.

Clone "yd88_1"

A polynucleotide of the present invention has been identified as clone "yd88_1". yd88_1 was isolated from a human adult brain cDNA library and was identified as encoding a secreted or transmembrane protein on the basis of computer analysis of the amino acid sequence of the encoded protein. yd88_1 is a full-length clone, including the entire coding sequence of a secreted protein (also referred to herein as "yd88_1 protein").

The nucleotide sequence of yd88_1 as presently determined is reported in SEQ ID NO:157, and includes a poly(A) tail. What applicants presently believe to be the proper reading frame and the predicted amino acid sequence of the yd88_1 protein corresponding to the foregoing nucleotide sequence is reported in SEQ ID NO:158.

The EcoRI/NotI restriction fragment obtainable from the deposit containing clone yd88_1 should be approximately 1000 bp.

The nucleotide sequence disclosed herein for yd88_1 was searched against the GenBank and GeneSeq nucleotide sequence databases using BLASTN/BLASTX and FASTA search protocols. yd88_1 demonstrated at least some similarity with sequences identified as W22362 (66B4 Human retina cDNA Tsp509I-cleaved sublibrary *Homo sapiens* cDNA not directional, mRNA sequence). Based upon sequence similarity, yd88_1 proteins and each similar protein or peptide may share at least some activity. The TopPredII computer program predicts a potential transmembrane domains within the yd88_1 protein sequence, around amino acid 60 of SEQ ID NO:158.

Clone "yd109_1"

A polynucleotide of the present invention has been identified as clone "yd109_1". yd109_1 was isolated from a human adult brain cDNA library and was identified as encoding a secreted or transmembrane protein on the basis of computer analysis of the amino acid sequence of the encoded protein. yd109_1 is a full-length clone, including the entire coding sequence of a secreted protein (also referred to herein as "yd109_1 protein").

The nucleotide sequence of yd109_1 as presently determined is reported in SEQ ID NO:159, and includes a poly(A) tail. What applicants presently believe to be the proper reading frame and the predicted amino acid sequence of the yd109_1 protein corresponding to the foregoing nucleotide sequence is reported in SEQ ID NO:160.

The EcoRI/NotI restriction fragment obtainable from the deposit containing clone yd109_1 should be approximately 550 bp.

The nucleotide sequence disclosed herein for yd109_1 was searched against the GenBank and GeneSeq nucleotide sequence databases using BLASTN/BLASTX and FASTA search protocols. yd109_1 demonstrated at least some similarity with sequences identified as AA809139 (nw17h06.s1 NCI_CGAP_GCBO *Homo sapiens* cDNA clone IMAGE:1240763, mRNA sequence) and T21990 (Human gene signature HUMGS03533; standard; cDNA to mRNA). The predicted amino acid sequence disclosed herein for yd109_1 was searched against the GenPept and GeneSeq amino acid sequence databases using the BLASTX search protocol. The predicted yd109_1 protein demonstrated at least some similarity to the sequence identified as U80438 (coded for by *C. elegans* cDNA CEESD64F; similar to a short region of DNAJ proteins in part of the DNAJ-like domain [*Caenorhabditis elegans*]). Based upon sequence similarity, yd109_1 proteins and each similar protein or peptide may share at least some activity. The TopPredII computer program predicts a potential transmembrane domain within the yd109_1 protein sequence, centered around a position between amino acid 50 and amino acid 54 of SEQ ID NO:160.

Clone "yd141_1"

A polynucleotide of the present invention has been identified as clone "yd141_1". yd141_1 was isolated from a human adult brain cDNA library and was identified as encoding a secreted or transmembrane protein on the basis of computer analysis of the amino acid sequence of the encoded protein. yd141_1 is a full-length clone, including the entire coding sequence of a secreted protein (also referred to herein as "yd141_1 protein").

The nucleotide sequence of yd141_1 as presently determined is reported in SEQ ID NO:161, and includes a poly(A) tail. What applicants presently believe to be the proper reading frame and the predicted amino acid sequence of the yd141_1 protein corresponding to the foregoing nucleotide sequence is reported in SEQ ID NO:162.

The EcoRI/NotI restriction fragment obtainable from the deposit containing clone yd141_1 should be approximately 650 bp.

The nucleotide sequence disclosed herein for yd141_1 was searched against the GenBank and GeneSeq nucleotide sequence databases using BLASTN/BLASTX and FASTA search protocols. yd141_1 demonstrated at least some similarity with sequences identified as AA974564 (op28f05.s1 Soares_NFL_T_GBC_S1 *Homo sapiens* cDNA clone IMAGE 1578177 3', mRNA sequence) and AC004789 (*Homo sapiens* chromosome 16, cosmid clone RT140 (LANL), complete sequence). Based upon sequence similarity, yd141_1 proteins and each similar protein or peptide may share at least some activity. The TopPredII computer program predicts six potential transmembrane domains within the yd141_1 protein sequence, one centered around amino acid 46 and others around amino acids 10, 35, 70, 93 and 100 of SEQ ID NO:162, respectively.

yd141_1 protein was expressed in a COS cell expression system, and an expressed protein band of approximately 13 kDa was detected in membrane fractions using SDS polyacrylamide gel electrophoresis.

Clone "yd153_1"

A polynucleotide of the present invention has been identified as clone "yd153_1". yd153_1 was isolated from a human adult brain cDNA library and was identified as encoding a secreted or transmembrane protein on the basis of computer analysis of the amino acid sequence of the encoded protein. yd153_1 is a full-length clone, including the entire coding sequence of a secreted protein (also referred to herein as "yd153_1 protein").

The nucleotide sequence of yd153_1 as presently determined is reported in SEQ ID NO:163, and includes a poly(A) tail. What applicants presently believe to be the proper reading frame and the predicted amino acid sequence of the yd153_1 protein corresponding to the foregoing nucleotide sequence is reported in SEQ ID NO:164. Amino acids 18 to 30 of SEQ ID NO:164 are a predicted leader/signal sequence, with the predicted mature amino acid sequence beginning at amino acid 31. Due to the hydrophobic nature of the predicted leader/signal sequence, it is likely to act as a transmembrane domain should the predicted leader/signal sequence not be separated from the remainder of the yd153_1 protein.

Another potential yd153_1 reading frame and predicted amino acid sequence is encoded by basepairs 68 to 244 of SEQ ID NO:163 and is reported in SEQ ID NO:268.

The EcoRI/NotI restriction fragment obtainable from the deposit containing clone yd153_1 should be approximately 650 bp.

The nucleotide sequence disclosed herein for yd153_1 was searched against the GenBank and GeneSeq nucleotide sequence databases using BLASTN/BLASTX and FASTA search protocols. yd153_1 demonstrated at least some similarity with sequences identified as AA309873 (EST180736 Jurkat T-cells V *Homo sapiens* cDNA 5' end, mRNA sequence) and T26022 (Human gene signature HUMGS08258; standard; cDNA to mRNA). Based upon sequence similarity, yd153_1 proteins and each similar protein or peptide may share at least some activity.

Clone "yd165_1"

A polynucleotide of the present invention has been identified as clone "yd165_1". yd165_1 was isolated from a human adult brain cDNA library and was identified as encoding a secreted or transmembrane protein on the basis of computer analysis of the amino acid sequence of the encoded protein. yd165_1 is a full-length clone, including the entire coding sequence of a secreted protein (also referred to herein as "yd165_1 protein").

The nucleotide sequence of yd165_1 as presently determined is reported in SEQ ID NO:165, and includes a poly(A) tail. What applicants presently believe to be the proper reading frame and the predicted amino acid sequence of the yd165_1 protein corresponding to the foregoing nucleotide sequence is reported in SEQ ID NO:166.

The EcoRI/NotI restriction fragment obtainable from the deposit containing clone yd165_1 should be approximately 650 bp.

The nucleotide sequence disclosed herein for yd165_1 was searched against the GenBank and GeneSeq nucleotide sequence databases using BLASTN/BLASTX and FASTA search protocols. yd165_1 demonstrated at least some similarity with sequences identified as AA873304 (oh75h10.s1 NCI_CGAP_Kid5 Homo sapiens cDNA clone IMAGE 1472899 3' similar to SW INI7_HUMAN P40305 INTERFERON-ALPHA INDUCED 11.5 KD PROTEIN; mRNA sequence), V24016 (Human interferon-inducible protein, HIFI, coding sequence; standard; cDNA), and X67325 (*H.sapiens* p27 mRNA). The predicted amino acid sequence disclosed herein for yd165_1 was searched against the GenPept and GeneSeq amino acid sequence databases using the BLASTX search protocol. The predicted yd165_1 protein demonstrated at least some similarity to sequences identified as U22970 (interferon-inducible peptide precursor [*Homo sapiens*]), W54040 (Human interferon-inducible protein, HIFI), and X67325 (p27 gene product [*Homo sapiens*]). Based upon sequence similarity, yd165_1 proteins and each similar protein or peptide may share at least some activity. The TopPredII computer program predicts three potential transmembrane domains within the yd165_1 protein sequence, centered around amino acids 43, 77, and 107 of SEQ ID NO:166, respectively.

Clone "yd178_1"

A polynucleotide of the present invention has been identified as clone "yd178_1". yd178_1 was isolated from a human adult brain cDNA library and was identified as encoding a secreted or transmembrane protein on the basis of computer analysis of the amino acid sequence of the encoded protein. yd178_1 is a full-length clone, including the entire coding sequence of a secreted protein (also referred to herein as "yd178_1 protein").

The nucleotide sequence of yd178_1 as presently determined is reported in SEQ ID NO:167, and includes a poly(A) tail. What applicants presently believe to be the proper reading frame and the predicted amino acid sequence of the yd178_1 protein corresponding to the foregoing nucleotide sequence is reported in SEQ ID NO:168. Amino acids 7 to 19 of SEQ ID NO:168 are a predicted leader/signal sequence, with the predicted mature amino acid sequence beginning at amino acid 20. Due to the hydrophobic nature of the predicted leader/signal sequence, it is likely to act as a transmembrane domain should the predicted leader/signal sequence not be separated from the remainder of the yd178_1 protein.

The EcoRI/NotI restriction fragment obtainable from the deposit containing clone yd178_1 should be approximately 900 bp.

The nucleotide sequence disclosed herein for yd178_1 was searched against the GenBank and GeneSeq nucleotide sequence databases using BLASTN/BLASTX and FASTA search protocols. yd178_1 demonstrated at least some similarity with sequences identified as AI141062 (oz43g12.x1 Soares_NhHMPu_S1 *Homo sapiens* cDNA clone IMAGE:1678150 3' similar to SW:LYG_ANSAN P00718 LYSOZYME G; mRNA sequence) and X61002 (*G.gallus* mRNA for goose-type lysozyme). The predicted amino acid sequence disclosed herein for yd178_1 was searched against the GenPept and GeneSeq amino acid sequence databases using the BLASTX search protocol. The predicted yd178_1 protein demonstrated at least some similarity to the sequence identified as X61002 (lysozyme [*Gallus gallus*]), and chicken "goose-type" lysozymes. Based upon sequence similarity, yd178_1 proteins and each similar protein or peptide may share at least some activity.

yd178_1 protein was expressed in a COS cell expression system, and an expressed protein band of approximately 23 kDa was detected in conditioned medium and membrane fractions using SDS polyacrylamide gel electrophoresis.

Clone "yd191_1"

A polynucleotide of the present invention has been identified as clone "yd191_1". yd191_1 was isolated from a human adult brain cDNA library and was identified as encoding a secreted or transmembrane protein on the basis of computer analysis of the amino acid sequence of the encoded protein. yd191_1 is a full-length done, including the entire coding sequence of a secreted protein (also referred to herein as "yd191_1 protein").

The nucleotide sequence of yd191_1 as presently determined is reported in SEQ ID NO:169, and includes a poly(A) tail. What applicants presently believe to be the proper reading frame and the predicted amino acid sequence of the yd191_1 protein corresponding to the foregoing nucleotide sequence is reported in SEQ ID NO:170.

The EcoRI/NotI restriction fragment obtainable from the deposit containing clone yd191_1 should be approximately 550 bp.

The nucleotide sequence disclosed herein for yd191_1 was searched against the GenBank and GeneSeq nucleotide sequence databases using BLASTN/BLASTX and FASTA search protocols. yd191_1 demonstrated at least some similarity with sequences identified as H98768 (yx13d09.s1 *Homo sapiens* cDNA clone 261617 3'). Based upon sequence similarity, yd191_1 proteins and each similar protein or peptide may share at least some activity. The TopPredII computer program predicts two potential transmembrane domains within the yd191_1 protein sequence, one centered around amino acid 55 and another around amino acid 68 of SEQ ID NO:170.

Clone "ye7_1"

A polynucleotide of the present invention has been identified as clone "ye7_1". ye7_1 was isolated from a human fetal brain cDNA library and was identified as encoding a secreted or transmembrane protein on the basis of computer analysis of the amino acid sequence of the encoded protein. ye7_1 is a full-length clone, including the entire coding sequence of a secreted protein (also referred to herein as "ye7_1 protein").

The nucleotide sequence of ye7_1 as presently determined is reported in SEQ ID NO:171, and includes a poly(A) tail. What applicants presently believe to be the proper reading frame and the predicted amino acid sequence of the ye7_1 protein corresponding to the foregoing nucleotide sequence is reported in SEQ ID NO:172.

The EcoRI/NotI restriction fragment obtainable from the deposit containing clone ye7_1 should be approximately 2400 bp.

The nucleotide sequence disclosed herein for ye7_1 was searched against the GenBank and GeneSeq nucleotide sequence databases using BLASTN/BLASTX and FASTA search protocols. ye7_1 demonstrated at least some similarity with sequences identified as AI017060 (ov01d06.x1 NCI_CGAP_Kid3 *Homo sapiens* cDNA clone IMAGE:1636043 3', mRNA sequence). Based upon sequence similarity, ye7_1 proteins and each similar protein or peptide may share at least some activity. The TopPredII computer program predicts two potential transmembrane domains within the ye7_1 protein sequence, one centered around amino acid 65 and another around amino acid 105 of SEQ ID NO:172.

Clone "yf33_1"

A polynucleotide of the present invention has been identified as clone "yf33_1". yf33_1 was isolated from a human fetal brain cDNA library and was identified as encoding a secreted or transmembrane protein on the basis of computer analysis of the amino acid sequence of the encoded protein. yf33_1 is a full-length clone, including the entire coding sequence of a secreted protein (also referred to herein as "yf33_1 protein").

The nucleotide sequence of yf33_1 as presently determined is reported in SEQ ID NO:173, and includes a poly(A) tail. What applicants presently believe to be the proper reading frame and the predicted amino acid sequence of the yf33_1 protein corresponding to the foregoing nucleotide sequence is reported in SEQ ID NO:174. Amino acids 36 to 48 of SEQ ID NO:174 are a predicted leader/signal sequence, with the predicted mature amino acid sequence beginning at amino acid 49. Due to the hydrophobic nature of the predicted leader/signal sequence, it is likely to act as a transmembrane domain should the predicted leader/signal sequence not be separated from the remainder of the yf33_1 protein.

The EcoRI/NotI restriction fragment obtainable from the deposit containing done yf33_1 should be approximately 2500 bp.

The nucleotide sequence disclosed herein for yf33_1 was searched against the GenBank and GeneSeq nucleotide sequence databases using BLASTN/BLASTX and FASTA search protocols. No significant hits were found in the database. The TopPredII computer program predicts a potential transmembrane domain within the yf33_1 protein sequence centered around amino acids 93 of SEQ ID NO:174. The nucleotide sequence of yf33_1 indicates that it may contain an Alu repetitive element.

Clone "yi15_1"

A polynucleotide of the present invention has been identified as clone "yi15_1". yi15_1 was isolated from a human brain cDNA library and was identified as encoding a secreted or transmembrane protein on the basis of computer analysis of the amino acid sequence of the encoded protein. yi15_1 is a full-length clone, including the entire coding sequence of a secreted protein (also referred to herein as "yi15_1 protein").

The nucleotide sequence of yi15_1 as presently determined is reported in SEQ ID NO:175, and includes a poly(A) tail. What applicants presently believe to be the proper reading frame and the predicted amino acid sequence of the yi15_1 protein corresponding to the foregoing nucleotide sequence is reported in SEQ ID NO:176. Amino acids 52 to 64 of SEQ ID NO:176 are a possible leader/signal sequence, with the predicted mature amino acid sequence beginning at amino acid 65. Due to the hydrophobic nature of the predicted leader/signal sequence, it is likely to act as a transmembrane domain should the predicted leader/signal sequence not be separated from the remainder of the yi15_1 protein.

The EcoRI/NotI restriction fragment obtainable from the deposit containing clone yi15_1 should be approximately 2500 bp.

The nucleotide sequence disclosed herein for yi15_1 was searched against the GenBank and GeneSeq nucleotide sequence databases using BLASTN/BLASTX and FASTA search protocols. yi15_1 demonstrated at least some similarity with sequences identified as AA290994 (zs45d07.r1 NCI_CGAP_GCB1 *Homo sapiens* cDNA clone IMAGE 700429 5', mRNA sequence) and AF010235 (*Homo sapiens* mRNA from chromosome 5q31-33 region). Based upon sequence similarity, yi15_1 proteins and each similar protein or peptide may share at least some activity. The TopPredII computer program predicts four potential transmembrane domains within the yi15_1 protein sequence, centered around amino adds 30,60,70, and 100 of SEQ ID NO:176, respectively.

Clone "yi17_1"

A polynucleotide of the present invention has been identified as clone "yi17_1". yi17_1 was isolated from a human brain cDNA library and was identified as encoding a secreted or transmembrane protein on the basis of computer analysis of the amino acid sequence of the encoded protein. yi17_1 is a full-length clone, including the entire coding sequence of a secreted protein (also referred to herein as "yi17_1 protein").

The nucleotide sequence of yi17_1 as presently determined is reported in SEQ ID NO:177, and includes a poly(A) tail. What applicants presently believe to be the proper reading frame and the predicted amino acid sequence of the yi17_1 protein corresponding to the foregoing nucleotide sequence is reported in SEQ ID NO:178. Amino acids 6 to 18 of SEQ ID NO:178 are a predicted leader/signal sequence, with the predicted mature amino acid sequence beginning at amino acid 19. Due to the hydrophobic nature of the predicted leader/signal sequence, it is likely to act as a transmembrane domain should the predicted leader/signal sequence not be separated from the remainder of the yi17_1 protein.

The EcoRI/NotI restriction fragment obtainable from the deposit containing clone yi17_1 should be approximately 1700 bp.

The nucleotide sequence disclosed herein for yi17_1 was searched against the GenBank and GeneSeq nucleotide sequence databases using BLASTN/BLASTX and FASTA search protocols. yi17_1 demonstrated at least some similarity with sequences identified as AA418852 (zw01f10.s1 Soares NhHMPu S1 *Homo sapiens* cDNA clone 768043 3', mRNA sequence). Based upon sequence similarity, yi17_1 proteins and each similar protein or peptide may share at least some activity.

Clone "yk38_1"

A polynucleotide of the present invention has been identified as clone "yk38_1". yk38_1 was isolated from a human adult thymus cDNA library and was identified as encoding a secreted or transmembrane protein on the basis of computer analysis of the amino acid sequence of the encoded protein. yk38_1 is a full-length clone, including the entire coding sequence of a secreted protein (also referred to herein as "yk38_1 protein").

The nucleotide sequence of yk38_1 as presently determined is reported in SEQ ID NO:179, and includes a poly(A) tail. What applicants presently believe to be the proper reading frame and the predicted amino acid sequence of the yk38_1 protein corresponding to the foregoing nucleotide sequence is reported in SEQ ID NO:180. Amino acids 43 to 55 of SEQ ID NO:180 are a predicted leader/signal sequence, with the predicted mature amino acid sequence beginning at amino acid 56. Due to the hydrophobic nature of the predicted leader/signal sequence, it is likely to act as a transmembrane domain should the predicted leader/signal sequence not be separated from the remainder of the yk38_1 protein.

The EcoRI/NotI restriction fragment obtainable from the deposit containing clone yk38_1 should be approximately 2050 bp.

The nucleotide sequence disclosed herein for yk38_1 was searched against the GenBank and GeneSeq nucleotide sequence databases using BLASTN/BLASTX and FASTA search protocols. yk38_1 demonstrated at least some similarity with sequences identified as AA477698 (zu44c09.r1 Soares ovary tumor NbHOT Homo sapiens cDNA clone 740848 5', mRNA sequence), AF052183 (Homo sapiens clone 24804 mRNA sequence), and T26733 (Human gene signature HUMGS08983; standard; cDNA to mRNA). Based upon sequence similarity, yk38_1 proteins and each similar protein or peptide may share at least some activity. The TopPredII computer program predicts four potential transmembrane domains within the yk38_1 protein sequence, centered around amino acids 50, 135, 210 and 260 of SEQ ID NO:180, respectively. Hidden markov model and motifs analysis have revealed the presence of two WD-40 (beta transducin/G-beta) repeats at amino acids 118–153 and 157–196 of SEQ ID NO:180. The WD40 domain is thought to mediate protein-protein interactions.

Clone "yk51_1"

A polynucleotide of the present invention has been identified as clone "yk51_1". yk51_1 was isolated from a human adult thymus cDNA library and was identified as encoding a secreted or transmembrane protein on the basis of computer analysis of the amino acid sequence of the encoded protein. yk51_1 is a full-length clone, including the entire coding sequence of a secreted protein (also referred to herein as "yk51_1 protein").

The nucleotide sequence of yk51_1 as presently determined is reported in SEQ ID NO:181, and includes a poly(A) tail. What applicants presently believe to be the proper reading frame and the predicted amino acid sequence of the yk51_1 protein corresponding to the foregoing nucleotide sequence is reported in SEQ ID NO:182. Amino acids 9 to 21 of SEQ ID NO:182 are a predicted leader/signal sequence, with the predicted mature amino acid sequence beginning at amino acid 22. Due to the hydrophobic nature of the predicted leader/signal sequence, it is likely to act as a transmembrane domain should the predicted leader/signal sequence not be separated from the remainder of the yk51_1 protein.

The EcoRI/NotI restriction fragment obtainable from the deposit containing clone yk51_1 should be approximately 1350 bp.

The nucleotide sequence disclosed herein for yk51_1 was searched against the GenBank and GeneSeq nucleotide sequence databases using BLASTN/BLASTX and FASTA search protocols. yk51_1 demonstrated at least some similarity with sequences identified as Z93014 (Human DNA sequence * SEQUENCING IN PROGRESS * from clone 167P19; HTGS phase 1). Based upon sequence similarity, yk51_1 proteins and each similar protein or peptide may share at least some activity. The TopPredII computer program predicts two additional potential transmembrane domains within the yk51_1 protein sequence, one centered around amino acid 65 and another around amino acid 81 of SEQ ID NO:182.

Clone "yk74_1"

A polynucleotide of the present invention has been identified as clone "yk74_1". yk74_1 was isolated from a human adult thymus cDNA library and was identified as encoding a secreted or transmembrane protein on the basis of computer analysis of the amino acid sequence of the encoded protein. yk74_1 is a full-length clone, including the entire coding sequence of a secreted protein (also referred to herein as "yk74_1 protein").

The nucleotide sequence of yk74_1 as presently determined is reported in SEQ ID NO:183, and includes a poly(A) tail. What applicants presently believe to be the proper reading frame and the predicted amino acid sequence of the yk74_1 protein corresponding to the foregoing nucleotide sequence is reported in SEQ ID NO:184.

The EcoRI/NotI restriction fragment obtainable from the deposit containing clone yk74_1 should be approximately 1500 bp.

The nucleotide sequence disclosed herein for yk74_1 was searched against the GenBank and GeneSeq nucleotide sequence databases using BLASTN/BLASTX and FASTA search protocols. yk74_1 demonstrated at least some similarity with sequences identified as AA910887:(ok87e02.s1 NCI_CGAP_Lu5 Homo sapiens cDNA clone IMAGE:1520954 3', mRNA sequence). Based upon sequence similarity, yk74_1 proteins and each similar protein or peptide may share at least some activity. The TopPredII computer program predicts three potential transmembrane domains within the yk74_1 protein sequence, centered around amino acids 15, 75, and 105 of SEQ ID NO:184, respectively. The nucleotide sequence of yk74_1 indicates that it may contain an Alu repetitive element.

Clone "yk89_1"

A polynucleotide of the present invention has been identified as clone "yk89_1". yk89_1 was isolated from a human adult thymus cDNA library and was identified as encoding a secreted or transmembrane protein on the basis of computer analysis of the amino acid sequence of the encoded protein. yk89_1 is a full-length clone, including the entire coding sequence of a secreted protein (also referred to herein as "yk89_1 protein").

The nucleotide sequence of yk89_1 as presently determined is reported in SEQ ID NO:185, and includes a poly(A) tail. What applicants presently believe to be the proper reading frame and the predicted amino acid sequence of the yk89_1 protein corresponding to the foregoing nucleotide sequence is reported in SEQ ID NO:186.

The EcoRI/NotI restriction fragment obtainable from the deposit containing clone yk89_1 should be approximately 2800 bp.

The nucleotide sequence disclosed herein for yk89_1 was searched against the GenBank and GeneSeq nucleotide sequence databases using BLASTN/BLASTX and FASTA search protocols. yk89_1 demonstrated at least some similarity with sequences identified as AA524431 (ng44e05.s1 NCI_CGAP_Co3 Homo sapiens cDNA clone IMAGE 937664, mRNA sequence), AF045607 (Xenopus laevis origin recognition complex associated protein p81 mRNA, complete cds), U50950 (Human infant brain unknown product mRNA, complete cds), and V23269 (Human latheo protein encoding est cDNA; standard; cDNA). The predicted amino acid sequence disclosed herein for yk89_1 was searched against the GenPept and GeneSeq amino acid sequence databases using the BLASTX search protocol. The predicted yk89_1 protein demonstrated at least some similarity to sequences identified as U50950 (unknown [Homo sapiens]), W53458 and W53460 (latheo protein [Drosophila]), W53459 (Human latheo protein sequence), and W53461 (Human latheo protein internal reading protein sequence). The latheo gene encodes a protein of ~70 kD which lacks sequence or domain homology to known proteins. In situ staining with a polyclonal antibody raised against the Latheo protein reveals protein expression in the larval central nervous system (CNS), and specific localization in presynaptic boutons at roughly half the neuromuscular junctions in 3rd-instar larvae, consistent with a role for Latheo protein in synaptic function. (Rohrbough, Pinto, and Tully, Center for Learning and Memory, Cold Spring Harbor Laboratory; and K. S. Broadie, Dept. of Biology, University of Utah, Salt Lake City Utah 84112.) Based upon sequence similarity, yk89_1 proteins and each similar protein or peptide may share at least some activity. The TopPredII computer program predicts a potential transmembrane domain within the yk89_1 protein sequence centered around amino acid 250 of SEQ ID NO:186.

Clone "yl18_1"

A polynucleotide of the present invention has been identified as clone "yl18_1". yl18_1 was isolated from a human adult spleen cDNA library and was identified as encoding a secreted or transmembrane protein on the basis of computer analysis of the amino acid sequence of the encoded protein. yl18_1 is a full-length clone, including the entire coding sequence of a secreted protein (also referred to herein as "yl18_1 protein").

The nucleotide sequence of yl18_1 as presently determined is reported in SEQ ID NO:187, and includes a poly(A) tail. What applicants presently believe to be the proper reading frame and the predicted amino acid sequence of the yl18_1 protein corresponding to the foregoing nucleotide sequence is reported in SEQ ID NO:188. Amino acids 13 to of SEQ ID NO:188 are a predicted leader/signal sequence, with the predicted mature amino acid sequence beginning at amino acid 26. Due to the hydrophobic nature of the predicted leader/signal sequence, it is likely to act as a transmembrane domain should the predicted leader/signal sequence not be separated from the remainder of the yl18_1 protein.

The EcoRI/NotI restriction fragment obtainable from the deposit containing clone yl18_1 should be approximately 3116 bp.

The nucleotide sequence disclosed herein for yl18_1 was searched against the GenBank and GeneSeq nucleotide sequence databases using BLASTN/BLASTX and FASTA search protocols. yl18_1 demonstrated at least some similarity with sequences identified as AA156907 (zl20b04.r1 Soares pregnant uterus NbHPU *Homo sapiens* cDNA clone 502447 5', mRNA sequence). Based upon sequence similarity, yl18_1 proteins and each similar protein or peptide may share at least some activity. The TopPredII computer program predicts three additional potential transmembrane domains within the yl18_1 protein sequence, centered around amino acids 50, 105, and 115 of SEQ ID NO:188.

yl18_1 protein was expressed in a COS cell expression system, and an expressed protein band of approximately 27 kDa was detected in membrane fractions using SDS polyacrylamide gel electrophoresis.

Clone "yb325_1"

A polynucleotide of the present invention has been identified as clone "yb325_1". yb325_1 was isolated from a human fetal brain cDNA library and was identified as encoding a secreted or transmembrane protein on the basis of computer analysis of the amino acid sequence of the encoded protein. yb325_1 is a full-length clone, including the entire coding sequence of a secreted protein (also referred to herein as "yb325_1 protein").

The nucleotide sequence of yb325_1 as presently determined is reported in SEQ ID NO:189. What applicants presently believe to be the proper reading frame and the predicted amino acid sequence of the yb325_1 protein corresponding to the foregoing nucleotide sequence is reported in SEQ ID NO:190. Amino acids 3 to 15 of SEQ ID NO:190 are a predicted leader/signal sequence, with the predicted mature amino acid sequence beginning at amino acid 16. Due to the hydrophobic nature of the predicted leader/signal sequence, it is likely to act as a transmembrane domain should the predicted leader/signal sequence not be separated from the remainder of the yb325_1 protein.

The EcoRI/NotI restriction fragment obtainable from the deposit containing clone yb325_1 should be approximately 839 bp.

The nucleotide sequence disclosed herein for yb325_1 was searched against the GenBank and GeneSeq nucleotide sequence databases using BLASTN/BLASTX and FASTA search protocols. yb325_1 demonstrated at least some similarity with sequences identified as AA523268 (ni39g02.s1 NCI_CGAP_Lu1 *Homo sapiens* cDNA clone IMAGE: 979250, mRNA sequence). Based upon sequence similarity, yb235_1 proteins and each similar protein or peptide may share at least some activity. The TopPredII computer program predicts an additional potential transmembrane domain within the yb235_1 protein sequence, centered around amino acid 90 of SEQ ID NO:188.

Clone "yd261_1"

A polynucleotide of the present invention has been identified as clone "yd261_1". yd261_1 was isolated from a human adult brain cDNA library and was identified as encoding a secreted or transmembrane protein on the basis of computer analysis of the amino acid sequence of the encoded protein. yd261_1 is a full-length clone, including the entire coding sequence of a secreted protein (also referred to herein as "yd261_1 protein").

The nucleotide sequence of yd261_1 as presently determined is reported in SEQ ID NO:191, and includes a poly(A) tail. What applicants presently believe to be the proper reading frame and the predicted amino acid sequence of the yd261_1 protein corresponding to the foregoing nucleotide sequence is reported in SEQ ID NO:192. Amino acids 25 to 37 of SEQ ID NO:192 are a predicted leader/signal sequence, with the predicted mature amino acid sequence beginning at amino acid 38. Due to the hydrophobic nature of the predicted leader/signal sequence, it is likely to act as a transmembrane domain should the predicted leader/signal sequence not be separated from the remainder of the yd261_1 protein.

The EcoRI/NotI restriction fragment obtainable from the deposit containing clone yd261_1 should be approximately 491 bp.

The nucleotide sequence disclosed herein for yd261_1 was searched against the GenBank and GeneSeq nucleotide sequence databases using BLASTN/BLASTX and FASTA search protocols. yd261_1 demonstrated at least some similarity with sequences identified as Q61280 (Human brain Expressed Sequence Tag EST01297; standard; DNA) and T15557 (IB1543 Infant brain, Bento Soares *Homo sapiens* cDNA 3' end similar to EST01297 *H. sapiens* cDNA clone HHCPN24, mRNA sequence). Based upon sequence similarity, yd261_1 proteins and each similar protein or peptide may share at least some activity.

Clone "yh33_1"

A polynucleotide of the present invention has been identified as clone "yh33_1". yh33_1 was isolated from a human brain (fetal and adult) cDNA library and was identified as encoding a secreted or transmembrane protein on the basis of computer analysis of the amino acid sequence of the encoded protein. yh33_1 is a full-length clone, including the entire coding sequence of a secreted protein (also referred to herein as "yh33_1 protein").

The nucleotide sequence of yh33_1 as presently determined is reported in SEQ ID NO:193, and includes a poly(A) tail. What applicants presently believe to be the proper reading frame and the predicted amino acid sequence of the yh33_1 protein corresponding to the foregoing nucleotide sequence is reported in SEQ ID NO:194. Amino acids 80 to 92 of SEQ ID NO:194 are a possible leader/signal sequence, with the predicted mature amino acid sequence beginning at amino acid 93. Due to the hydrophobic nature of the predicted leader/signal sequence, it is likely to act as a transmembrane domain should the predicted leader/signal sequence not be separated from the remainder of the yh33_1 protein.

The EcoRI/NotI restriction fragment obtainable from the deposit containing clone yh33_1 should be approximately 2750 bp.

The nucleotide sequence disclosed herein for yh33_1 was searched against the GenBank and GeneSeq nucleotide sequence databases using BLASTN/BLASTX and FASTA search protocols. No significant hits were found in the database. The TopPredII computer program predicts three additional potential transmembrane domains within the yh33_1 protein sequence, centered around amino acids 124, 160, and 190 of SEQ ID NO:194, respectively. The nucleotide sequence of yh33_1 indicates that it may contain an Alu repetitive element.

Clone "yi16_1"

A polynucleotide of the present invention has been identified as clone "yi16_1". yi16_1 was isolated from a human adult brain cDNA library and was identified as encoding a secreted or transmembrane protein on the basis of computer analysis of the amino acid sequence of the encoded protein. yi16_1 is a full-length clone, including the entire coding sequence of a secreted protein (also referred to herein as "yi16_1 protein").

The nucleotide sequence of yi16_1 as presently determined is reported in SEQ ID NO:195, and includes a poly(A) tail. What applicants presently believe to be the proper reading frame and the predicted amino acid sequence of the yi16_1 protein corresponding to the foregoing nucleotide sequence is reported in SEQ ID NO:196. Amino acids 63 to 75 of SEQ ID NO:196 are a predicted leader/signal sequence, with the predicted mature amino acid sequence beginning at amino acid 76. Due to the hydrophobic nature of the predicted leader/signal sequence, it is likely to act as a transmembrane domain should the predicted leader/signal sequence not be separated from the remainder of the yi16_1 protein.

The EcoRI/NotI restriction fragment obtainable from the deposit containing clone yi16_1 should be approximately 3000 bp.

The nucleotide sequence disclosed herein for yi16_1 was searched against the GenBank and GeneSeq nucleotide sequence databases using BLASTN/BLASTX and FASTA search protocols. yi16_1 demonstrated at least some similarity with sequences identified as AI076775 (oz31f03.x1 Soares_total_fetus_Nb2HF8_9w *Homo sapiens* cDNA clone IMAGE 1676957 3', mRNA sequence), T19914 (Human gene signature HUMGS01041; standard; cDNA to mRNA), and U79267 (Human clone 23840 mRNA, partial cds). The predicted amino acid sequence disclosed herein for yi16_1 was searched against the GenPept and GeneSeq amino acid sequence databases using the BLASTX search protocol. The predicted yi16_1 protein demonstrated at least some similarity to the sequence identified as U79267 (unknown [*Homo sapiens*]). Based upon sequence similarity, yi16_1 proteins and each similar protein or peptide may share at least some activity.

Clone "yk46_1"

A polynucleotide of the present invention has been identified as clone "yk46_1". yk46_1 was isolated from a human adult thymus cDNA library and was identified as encoding a secreted or transmembrane protein on the basis of computer analysis of the amino acid sequence of the encoded protein. yk46_1 is a full-length clone, including the entire coding sequence of a secreted protein (also referred to herein as "yk46_1 protein").

The nucleotide sequence of yk46_1 as presently determined is reported in SEQ ID NO:197, and includes a poly(A) tail. What applicants presently believe to be the proper reading frame and the predicted amino acid sequence of the yk46_1 protein corresponding to the foregoing nucleotide sequence is reported in SEQ ID NO:198. Amino acids 28 to 40 of SEQ ID NO:198 are a possible leader/signal sequence, with the predicted mature amino acid sequence beginning at amino acid 41. Due to the hydrophobic nature of the predicted leader/signal sequence, it is likely to act as a transmembrane domain should the predicted leader/signal sequence not be separated from the remainder of the yk46_1 protein.

The EcoRI/NotI restriction fragment obtainable from the deposit containing clone yk46_1 should be approximately 1900 bp.

The nucleotide sequence disclosed herein for yk46_1 was searched against the GenBank and GeneSeq nucleotide sequence databases using BLASTN/BLASTX and FASTA search protocols. yk46_1 demonstrated at least some similarity with sequences identified as AA203346 (zx56h01.r1 Soares fetal liver spleen 1NFLS S1 *Homo sapiens* cDNA clone 446545 5', mRNA sequence). Based upon sequence similarity, yk46_1 proteins and each similar protein or peptide may share at least some activity. The TopPredII computer program predicts two additional potential transmembrane domains within the yk46_1 protein sequence, one centered around amino acid 20 and another around amino acid 57 of SEQ ID NO:198.

Clone "yk84_1"

A polynucleotide of the present invention has been identified as clone "yk84_1". yk84_1 was isolated from a human adult thymus cDNA library and was identified as encoding a secreted or transmembrane protein on the basis of computer analysis of the amino acid sequence of the encoded protein. yk84_1 is a full-length clone, including the entire coding sequence of a secreted protein (also referred to herein as "yk84_1 protein").

The nucleotide sequence of yk84_1 as presently determined is reported in SEQ ID NO:199, and includes a poly(A) tail. What applicants presently believe to be the proper reading frame and the predicted amino acid sequence of the yk84_1 protein corresponding to the foregoing nucleotide sequence is reported in SEQ ID NO:200. Amino acids 36 to 48 of SEQ ID NO:200 are a predicted leader/signal sequence, with the predicted mature amino acid sequence beginning at amino acid 49. Due to the hydrophobic nature of the predicted leader/signal sequence, it is likely to act as a transmembrane domain should the predicted leader/signal sequence not be separated from the remainder of the yk84_1 protein.

The EcoRI/NotI restriction fragment obtainable from the deposit containing clone yk84_1 should be approximately 2400 bp.

The nucleotide sequence disclosed herein for yk84_1 was searched against the GenBank and GeneSeq nucleotide sequence databases using BLASTN/BLASTX and FASTA search protocols. yk84_1 demonstrated at least some similarity with sequences identified as AC004052 (*Homo sapiens* chromosome 4 clone B209B10 map 4q25, complete sequence) and AQ0059417 (CIT-HSP-2348J2.TF CIT-HSP *Homo sapiens* genomic clone 2348J2, genomic survey sequence). Based upon sequence similarity, yk84_1 proteins and each similar protein or peptide may share at least some activity. The TopPredII computer program predicts a potential transmembrane domain within the yk84_1 protein sequence, centered around amino acid 49 of SEQ ID NO:200.

Clone "yk143_1"

A polynucleotide of the present invention has been identified as clone "yk143_1". yk143_1 was isolated from a human adult thymus cDNA library and was identified as encoding a secreted or transmembrane protein on the basis of computer analysis of the amino acid sequence of the encoded protein. yk143_1 is a full-length clone, including the entire coding sequence of a secreted protein (also referred to herein as "yk143_1 protein").

The nucleotide sequence of yk143_1 as presently determined is reported in SEQ ID NO:201, and includes a poly(A) tail. What applicants presently believe to be the proper reading frame and the predicted amino acid sequence of the yk143_1 protein corresponding to the foregoing nucleotide sequence is reported in SEQ ID NO:202. Amino acids 31 to 43 of SEQ ID NO:202 are a predicted leader/signal sequence, with the predicted mature amino acid sequence beginning at amino acid 44. Due to the hydrophobic nature of the predicted leader/signal sequence, it is likely to act as a transmembrane domain should the predicted leader/signal sequence not be separated from the remainder of the yk143_1 protein.

The EcoRI/NotI restriction fragment obtainable from the deposit containing clone yk143_1 should be approximately 1458 bp.

The nucleotide sequence disclosed herein for yk143_1 was searched against the GenBank and GeneSeq nucleotide sequence databases using BLASTN/BLASTX and FASTA search protocols. yk143_1 demonstrated at least some similarity with sequences identified as AA526186 (ni94h03.s1 NCI_CGAP_Pr21 *Homo sapiens* cDNA clone IMAGE:984533, mRNA sequence), AB006085 (*Danio rerio* mRNA for MINDIN2, complete cds), and T78360 (Human neuronal attachment factor-1 DNA; standard; DNA). The predicted amino acid sequence disclosed herein for yk143_1 was searched against the GenPept and GeneSeq amino acid sequence databases using the BLASTX search protocol. The predicted yk143_1 protein demonstrated at least some similarity to sequences identified as AB006085 (MINDIN2 [*Danio rerio*]) and W23663 (Human neuronal attachment factor-1). Human neuronal attachment factor-1 is thought to promote cell-cell interaction and cell adhesion. The predicted yk143_1 protein also demonstrated at least some similarity to the extracellular matrix proteins called F- and M-spodins. Based upon sequence similarity, yk143_1 proteins and each similar protein or peptide may share at least some activity. The TopPredII computer program predicts two additional potential transmembrane domains within the yk143_1 protein sequence, one centered around amino acid 204 and another around amino acid 280 of SEQ ID NO:202.

Clone "yk156_1"

A polynucleotide of the present invention has been identified as clone "yk156_1". yk156_1 was isolated from a human adult thymus cDNA library and was identified as encoding a secreted or transmembrane protein on the basis of computer analysis of the amino acid sequence of the encoded protein. yk156_1 is a full-length clone, including the entire coding sequence of a secreted protein (also referred to herein as "yk156_1 protein").

The nucleotide sequence of yk156_1 as presently determined is reported in SEQ ID NO:203, and includes a poly(A) tail. What applicants presently believe to be the proper reading frame and the predicted amino acid sequence of the yk156_1 protein corresponding to the foregoing nucleotide sequence is reported in SEQ ID NO:204. Amino acids 25 to 37 of SEQ ID NO:204 are a predicted leader/signal sequence, with the predicted mature amino acid sequence beginning at amino acid 38. Due to the hydrophobic nature of the predicted leader/signal sequence, it is likely to act as a transmembrane domain should the predicted leader/signal sequence not be separated from the remainder of the yk156_1 protein.

The EcoRI/NotI restriction fragment obtainable from the deposit containing clone yk156_1 should be approximately 1100 bp.

The nucleotide sequence disclosed herein for yk156_1 was searched against the GenBank and GeneSeq nucleotide sequence databases using BLASTN/BLASTX and FASTA search protocols. yk156_1 demonstrated at least some similarity with sequences identified as AC002550 (Human Chromosome 16 BAC clone CIT987SK-A-101F10, complete sequence) and N67878 (yz52b04.s1 *Homo sapiens* cDNA clone 286639 3' similar to gb M29610 GLYCOPHORIN E PRECURSOR (HUMAN)). Based upon sequence similarity, yk156_1 proteins and each similar protein or peptide may share at least some activity.

Clone "yk204_1"

A polynucleotide of the present invention has been identified as clone "yk204_1". yk204_1 was isolated from a human adult thymus cDNA library and was identified as encoding a secreted or transmembrane protein on the basis of computer analysis of the amino acid sequence of the encoded protein. yk204_1 is a full-length clone, including the entire coding sequence of a secreted protein (also referred to herein as "yk204_1 protein").

The nucleotide sequence of yk204_1 as presently determined is reported in SEQ ID NO:205, and includes a poly(A) tail. What applicants presently believe to be the proper reading frame and the predicted amino acid sequence of the yk204_1 protein corresponding to the foregoing nucleotide sequence is reported in SEQ ID NO:206. Amino acids 46 to 58 of SEQ ID NO:206 are a predicted leader/signal sequence, with the predicted mature amino acid sequence beginning at amino acid 59. Due to the hydrophobic nature of the predicted leader/signal sequence, it is likely to act as a transmembrane domain should the predicted leader/signal sequence not be separated from the remainder of the yk204_1 protein.

The EcoRI/NotI restriction fragment obtainable from the deposit containing clone yk204_1 should be approximately 1395 bp.

The nucleotide sequence disclosed herein for yk204_1 was searched against the GenBank and GeneSeq nucleotide sequence databases using BLASTN/BLASTX and FASTA search protocols. No significant hits were found in the database. The TopPredII computer program predicts two potential transmembrane domains within the yk204_1 protein sequence, one centered around amino acid 59 and another around amino acid 82 of SEQ ID NO:206. The nucleotide sequence of yk204_1 indicates that it may contain an Alu repetitive element.

Clone "yk224_1"

A polynucleotide of the present invention has been identified as clone "yk224_1". yk224_1 was isolated from a human adult thymus cDNA library and was identified as encoding a secreted or transmembrane protein on the basis of computer analysis of the amino acid sequence of the encoded protein. yk224_1 is a full-length clone, including the entire coding sequence of a secreted protein (also referred to herein as "yk224_1 protein").

The nucleotide sequence of yk224_1 as presently determined is reported in SEQ ID NO:207, and indudes a poly(A) tail. What applicants presently believe to be the proper reading frame and the predicted amino acid sequence of the yk224_1 protein corresponding to the foregoing nucleotide sequence is reported in SEQ ID NO:208. Amino acids 13 to 25 of SEQ ID NO:208 are a possible leader/signal sequence, with the predicted mature amino acid sequence beginning at amino acid 26. Due to the hydrophobic nature of the predicted leader/signal sequence, it is likely to act as a transmembrane domain should the predicted leader/signal sequence not be separated from the remainder of the yk224_1 protein.

The EcoRI/NotI restriction fragment obtainable from the deposit containing clone yk224_1 should be approximately 1600 bp.

The nucleotide sequence disclosed herein for yk224_1 was searched against the GenBank and GeneSeq nucleotide sequence databases using BLASTN/BLASTX and FASTA search protocols. yk224_1 demonstrated at least some similarity with sequences identified as AA789332 (aj28h05.s1 Soares testis NHT *Homo sapiens* cDNA clone 1391673 3' similar to WP:B0410.2 CE06708; mRNA sequence) and AF044208 (*Drosophila melanogaster* Strabismus (stbm) mRNA, complete cds). The predicted amino acid sequence disclosed herein for yk224_1 was searched against the GenPept and GeneSeq amino acid sequence databases using the BLASTX search protocol. The predicted yk224_1 protein demonstrated at least some similarity to the sequence identified as AF044208 (Strabismus [*Drosophila melanogaster*]). Strabismus is described as a protein "that regulates tissue polarity and cell fate decisions in Drosophila" (Wolff, T. and Rubin, G. M., 1998, *Development* 125(6): 1149–1159, which is incorporated by reference herein). Based upon sequence similarity, yk224_1 proteins and each similar protein or peptide may share at least some activity. The TopPredII computer program predicts four potential transmembrane domains within the yk224_1 protein sequence, centered around amino acids 26, 64, 98, and 134 of SEQ ID NO:208, respectively. The nucleotide sequence of yk224_1 indicates that it may contain an Alu repetitive element.

Clone "yk261_1"

A polynucleotide of the present invention has been identified as clone "yk261_1". yk261_1 was isolated from a human adult thymus cDNA library and was identified as encoding a secreted or transmembrane protein on the basis of computer analysis of the amino acid sequence of the encoded protein. yk261_1 is a full-length clone, including the entire coding sequence of a secreted protein (also referred to herein as "yk261_1 protein").

The nucleotide sequence of yk261_1 as presently determined is reported in SEQ ID NO:209, and includes a poly(A) tail. What applicants presently believe to be the proper reading frame and the predicted amino acid sequence of the yk261_1 protein corresponding to the foregoing nucleotide sequence is reported in SEQ ID NO:210. Amino acids 13 to 25 of SEQ ID NO:210 are a predicted leader/signal sequence, with the predicted mature amino acid sequence beginning at amino acid 26. Due to the hydrophobic nature of the predicted leader/signal sequence, it is likely to act as a transmembrane domain should the predicted leader/signal sequence not be separated from the remainder of the yk261_1 protein.

The EcoRI/NotI restriction fragment obtainable from the deposit containing clone yk261_1 should be approximately 2259 bp.

The nucleotide sequence disclosed herein for yk261_1 was searched against the GenBank and GeneSeq nucleotide sequence databases using BLASTN/BLASTX and FASTA search protocols. yk261_1 demonstrated at least some similarity with sequences identified as AI024733 (ov76e12.x1 Soares_testis_NHT *Homo sapiens* cDNA clone IMAGE:1643278 3', mRNA sequence). The predicted amino acid sequence disclosed herein for yk261_1 was searched against the GenPept and GeneSeq amino acid sequence databases using the BLASTX search protocol. The predicted yk261_1 protein demonstrated at least some similarity to sequences identified as AF040650 (contains similarity to sodium-potassium-chloride cotransport proteins [*Caenorhabditis elegans*]), AF051561 (similarity to sodium-potassium chloride cotransport proteins [rat]), U13174 (putative basolateral Na-K-2Cl cotransporter [*Mus musculus*]), U55054 (K-Cl cotransporter [*Homo sapiens*]), and Z36104 (similarity to sodium-potassium-chloride cotransport proteins [yeast]). Based upon sequence similarity, yk261_1 proteins and each similar protein or peptide may share at least some activity. The TopPredII computer program predicts two additional potential transmembrane domains within the yk261_1 protein sequence, one centered around amino acid 270 and another around amino acid 295 of SEQ ID NO:210.

Clone "ys3_1"

A polynucleotide of the present invention has been identified as clone "ys3_1". ys3_1 was isolated from a human adult thymus cDNA library and was identified as encoding a secreted or transmembrane protein on the basis of computer analysis of the amino acid sequence of the encoded protein. ys3_1 is a full-length clone, including the entire coding sequence of a secreted protein (also referred to herein as "ys3_1 protein").

The nucleotide sequence of ys3_1 as presently determined is reported in SEQ ID NO:211, and includes a poly(A) tail. What applicants presently believe to be the proper reading frame and the predicted amino acid sequence of the ys3_1 protein corresponding to the foregoing nucleotide sequence is reported in SEQ ID NO:212. Amino acids 112 to 124 of SEQ ID NO:212 are a possible leader/signal sequence, with the predicted mature amino acid sequence beginning at amino acid 125. Due to the hydrophobic nature of the predicted leader/signal sequence, it is likely to act as a transmembrane domain should the predicted leader/signal sequence not be separated from the remainder of the ys3_1 protein.

The EcoRI/NotI restriction fragment obtainable from the deposit containing clone ys3_1 should be approximately 1000 bp.

The nucleotide sequence disclosed herein for ys3_1 was searched against the GenBank and GeneSeq nucleotide sequence databases using BLASTN/BLASTX and FASTA search protocols. ys3_1 demonstrated at least some similarity with sequences identified as H93009 (yv07g03.s1 *Homo sapiens* cDNA clone 242068 3'). The predicted amino acid sequence disclosed herein for ys3_1 was searched against the GenPept and GeneSeq amino acid sequence databases using the BLASTX search protocol. The predicted ys3_1 protein demonstrated at least some similarity to sequences identified as L35848 (IgE receptor beta subunit

[*Homo sapiens*]) and R42337 (Human FceRI beta). Based upon sequence similarity, ys3_1 proteins and each similar protein or peptide may share at least some activity. The TopPredII computer program predicts five potential transmembrane domains within the ys3_1 protein sequence, centered around amino acids 60, 90, 125, 190, and 225 of SEQ ID NO:212, respectively.

ys3_1 protein was expressed in a COS cell expression system, and an expressed protein band of approximately 26 kDa was detected in membrane fractions using SDS polyacrylamide gel electrophoresis.

Clone "ys10_1"

A polynucleotide of the present invention has been identified as clone "ys10_1". ys10_1 was isolated from a human adult thymus cDNA library and was identified as encoding a secreted or transmembrane protein on the basis of computer analysis of the amino acid sequence of the encoded protein. ys10_1 is a full-length clone, including the entire coding sequence of a secreted protein (also referred to herein as "ys10_1 protein").

The nucleotide sequence of ys10_1 as presently determined is reported in SEQ ID NO:213, and includes a poly(A) tail. What applicants presently believe to be the proper reading frame and the predicted amino acid sequence of the ys10_1 protein corresponding to the foregoing nucleotide sequence is reported in SEQ ID NO:214. Amino acids 30 to 42 of SEQ ID NO:214 are a predicted leader/signal sequence, with the predicted mature amino acid sequence beginning at amino acid 43. Due to the hydrophobic nature of the predicted leader/signal sequence, it is likely to act as a transmembrane domain should the predicted leader/signal sequence not be separated from the remainder of the ys10_1 protein.

The EcoRI/NotI restriction fragment obtainable from the deposit containing clone ys10_1 should be approximately 1079 bp.

The nucleotide sequence disclosed herein for ys10_1 was searched against the GenBank and GeneSeq nucleotide sequence databases using BLASTN/BLASTX and FASTA search protocols. ys10_1 demonstrated at least some similarity with sequences identified as AA436002 (zu03b10.s1 Soares testis NHT *Homo sapiens* cDNA clone 730747 3', mRNA sequence) and T26591 (Human gene signature HUMGS08837; standard; cDNA to mRNA). Based upon sequence similarity, ys10_1 proteins and each similar protein or peptide may share at least some activity.

Deposit of Clones

Clones ya15_1, ya24_1, yb42_1, yc9_1, yc19_1, and yc20_1 were deposited on Feb. 11, 1998 with the American Type Culture Collection (10801 University Boulevard, Manassas, Va. 20110-2209 U.S.A.) as an original deposit under the Budapest Treaty and were given the accession number ATCC 98650, from which each clone comprising a particular polynucleotide is obtainable.

Clones ya9_1, ya11_1, ya28_1, yb81_1, and yc14_1 were deposited on Apr. 7, 1998 with the American Type Culture Collection (10801 University Boulevard, Manassas, Va. 20110-2209 U.S.A.) as an original deposit under the Budapest Treaty and were given the accession number ATCC 98724, from which each clone comprising a particular polynucleotide is obtainable.

Clones yc24_1, yc25_1, and ye2_1 were deposited on May 14, 1998 with the American Type Culture Collection (10801 University Boulevard, Manassas, Va. 20110-2209 U.S.A.) as an original deposit under the Budapest Treaty and were given the accession number ATCC 98755, from which each clone comprising a particular polynucleotide is obtainable.

Clones ya65_1, yb60_1, yb139_1, yc29_1, yc40_1, yd10_1, and yf5_1 were deposited on Aug. 11, 1998 with the American Type Culture Collection (10801 University Boulevard, Manassas, Va. 20110-2209 U.S.A.) as an original deposit under the Budapest Treaty and were given the accession number ATCC 98834, from which each clone comprising a particular polynucleotide is obtainable.

Clones ya67_1, ya70_1, yb51_1, yb101_1, yb124_1, yb125_1, yb179_1, yc48_1, ye21_1, and ye22_1 were deposited on Sep. 3, 1998 with the American Type Culture Collection (10801 University Boulevard, Manassas, Va. 20110-2209 U.S.A.) as an original deposit under the Budapest Treaty and were given the accession number ATCC 98864, from which each clone comprising a particular polynucleotide is obtainable.

Clones ye39_1, yf9_1, yh4_1, yi4_1, yj3_1, yj7_1, yj10_1, yj28_1, yj29_1, and yj32_1 were deposited on Sep. 2, 1998 with the American Type Culture Collection (10801 University Boulevard, Manassas, Va. 20110-2209 U.S.A.) as an original deposit under the Budapest Treaty and were given the accession number ATCC 98861, from which each clone comprising a particular polynucleotide is obtainable.

Clones yb186_1, yb226_1, yd50_1, yd51_1, yd73_1, ye43_1, yh71_1, yj100_1, yi3_1, yj23_1, and yl9_1 were deposited on Sep. 10, 1998 with the American Type Culture Collection (10801 University Boulevard, Manassas, Va. 20110-2209 U.S.A.) as an original deposit under the Budapest Treaty and were given the accession number ATCC 98872, from which each clone comprising a particular polynucleotide is obtainable.

Clones ya66_1, yb187_1, yb219_1, yb228_1, yc27_1, yc49_1, yd40_1, yd64_1, ye47_1, yh50_1, yh53_1, and yh98_1 were deposited on Sep. 23, 1998 with the American Type Culture Collection (10801 University Boulevard, Manassas, Va. 20110-2209 U.S.A.) as an original deposit under the Budapest Treaty and were given the accession number. ATCC 98887, from which each clone comprising a particular polynucleotide is obtainable.

Clones ya69_1, yd107_1, yd145_1, yh24_1, yi11_1, yi18_1, yk14_1, yk39_1, yk91_1, yk199_1, yl4_1, and yl14_1 were deposited on Oct. 6, 1998 with the American Type Culture Collection (10801 University Boulevard, Manassas, Va. 20110-2209 U.S.A.) as an original deposit under the Budapest Treaty and were given the accession number ATCC 98915, from which each clone comprising a particular polynucleotide is obtainable.

Clones ya80_1, yd61_1, yd88_1, yd109_1, yd141_1, yd153_1, yd165_1, yd178_1, and yd191_1 were deposited on Oct. 15, 1998 with the American Type Culture Collection (10801 University Boulevard, Manassas, Va. 20110-2209 U.S.A.) as an original deposit under the Budapest Treaty and were given the accession number ATCC 98925, from which each clone comprising a particular polynucleotide is obtainable.

Clones ye7_1, yf33_1, yi15_1, yi17_1, yk38_1, yk51_1, yk74_1, yk89_1, yk18_1 were deposited on Oct. 15, 1998 with the American Type Culture Collection (10801 University Boulevard, Manassas, Va. 20110-2209 U.S.A.) as an original deposit under the Budapest Treaty and were given the accession number ATCC 98924, from which each clone comprising a particular polynucleotide is obtainable.

Clones yb235_1, yd261_1, yh33_1, yi16_1, yk46_1, yk84_1, yk143_1, yk156_1, yk204_1, yk224_1, yk261_1, ys3_1, and ys10_1 were deposited on Oct. 27, 1998 with the American Type Culture Collection (10801 University Boulevard, Manassas, Va. 20110-2209 U.S.A.) as an original deposit under the Budapest Treaty and were given the accession number ATCC 98958, from which each clone comprising a particular polynucleotide is obtainable.

All restrictions on the availability to the public of the deposited material will be irrevocably removed upon the granting of the patent, except for the requirements specified in 37 C.F.R. § 1.808(b), and the term of the deposit will comply with 37 C.F.R. § 1.806.

Figure 1B:
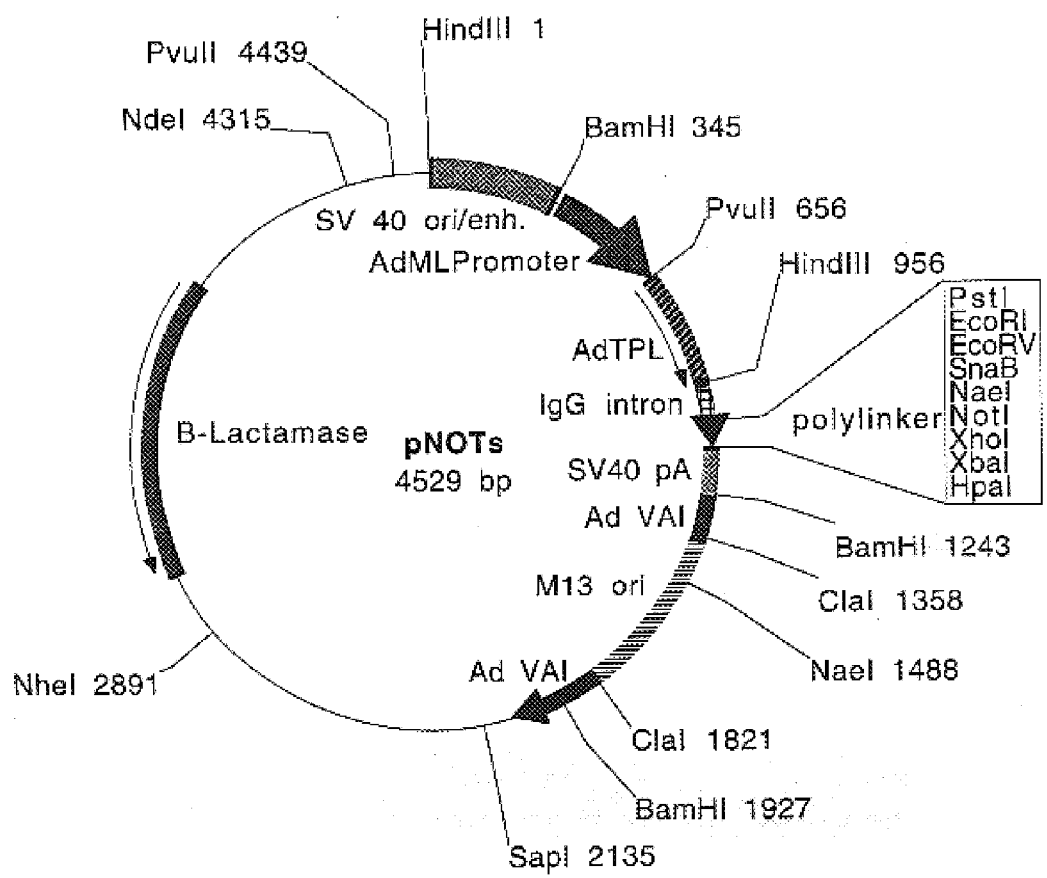

Each clone has been transfected into separate bacterial cells (*E. coli*) in these composite deposits. Each clone can be removed from the vector in which it was deposited by performing an EcoRI/NotI digestion (5' site, EcoRI; 3' site, NotI) to produce the appropriate fragment for such clone. Each clone was deposited in either the pED6 or pNOTs vector depicted in FIGS. 1A and 1B, respectively. The pED6dpc2 vector ("pED6") was derived from pED6dpc1 by insertion of a new polylinker to facilitate cDNA cloning (Kaufman et al., 1991, *Nucleic Acids Res.* 19: 4485–4490); the pNOTs vector was derived from pMT2 (Kaufman et al., 1989, *Mol. Cell. Biol.* 9: 946–958) by deletion of the DHFR sequences, insertion of a new polylinker, and insertion of the M13 origin of replication in the ClaI site. In some instances, the deposited clone can become "flipped" (i.e., in the reverse orientation) in the deposited isolate. In such instances, the cDNA insert can still be isolated by digestion with EcoRI and NotI. However, NotI will then produce the 5' site and EcoRI will produce the 3' site for placement of the cDNA in proper orientation for expression in a suitable vector. The cDNA may also be expressed from the vectors in which they were deposited.

Bacterial cells containing a particular clone can be obtained from the composite deposit as follows:

An oligonucleotide probe or probes should be designed to the sequence that is known for that particular clone. This sequence can be derived from the sequences provided herein, or from a combination of those sequences. The sequence of an oligonucleotide probe that was used to isolate or to sequence each full-length clone is identified below, and should be most reliable in isolating the clone of interest.

| Clone | Probe Sequence |
| --- | --- |
| ya15_1 | SEQ ID NO:215 |
| ya24_1 | SEQ ID NO:216 |
| yb42_1 | SEQ ID NO:217 |
| yc9_1 | SEQ ID NO:218 |
| yc19_1 | SEQ ID NO:219 |
| yc20_1 | SEQ ID NO:220 |
| ya9_1 | SEQ ID NO:221 |
| ya28_1 | SEQ ID NO:222 |
| yc14_1 | SEQ ID NO:223 |
| yc24_1 | SEQ ID NO:224 |
| yc25_1 | SEQ ID NO:225 |
| ye2_1 | SEQ ID NO:226 |
| yb60_1 | SEQ ID NO:227 |
| yc29_1 | SEQ ID NO:228 |
| yf5_1 | SEQ ID NO:229 |
| ya70_1 | SEQ ID NO:230 |
| yb51_1 | SEQ ID NO:231 |
| yb101_1 | SEQ ID NO:232 |
| yb124_1 | SEQ ID NO:233 |
| yb125_1 | SEQ ID NO:234 |
| yb179_1 | SEQ ID NO:235 |
| ye21_1 | SEQ ID NO:236 |
| ye22_1 | SEQ ID NO:237 |
| yf9_1 | SEQ ID NO:238 |
| yh71_1 | SEQ ID NO:239 |
| yh100_1 | SEQ ID NO:240 |
| yj23_1 | SEQ ID NO:241 |

-continued

| Clone | Probe Sequence |
| --- | --- |
| yb187_1 | SEQ ID NO:242 |
| yb219_1 | SEQ ID NO:243 |
| yd40_1 | SEQ ID NO:244 |
| ye47_1 | SEQ ID NO:245 |
| yh50_1 | SEQ ID NO:246 |
| yh53_1 | SEQ ID NO:247 |
| ya69_1 | SEQ ID NO:248 |
| yi11_1 | SEQ ID NO:249 |
| yl4_1 | SEQ ID NO:250 |
| ye7_1 | SEQ ID NO:251 |
| yf33_1 | SEQ ID NO:252 |
| yi15_1 | SEQ ID NO:253 |
| yi17_1 | SEQ ID NO:254 |
| yk38_1 | SEQ ID NO:255 |
| yk89_1 | SEQ ID NO:256 |
| yl18_1 | SEQ ID NO:257 |
| yh33_1 | SEQ ID NO:258 |
| yi16_1 | SEQ ID NO:259 |
| yk46_1 | SEQ ID NO:260 |
| yk84_1 | SEQ ID NO:261 |
| yk204_1 | SEQ ID NO:262 |
| yk224_1 | SEQ ID NO:263 |
| yk261_1 | SEQ ID NO:264 |

In the sequences listed above which include an N at position 2, that position is occupied in preferred probes/primers by a biotinylated phosphoaramidite residue rather than a nucleotide (such as, for example, that produced by use of biotin phosphoramidite (1-dimethoxytrityloxy-2-(N-biotinyl-4-aminobutyl)-propyl-3-O-(2-cyanoethyl)-(N,N-diisopropyl)-phosphoramadite) (Glen Research, cat; no. 10-1953)).

The design of the oligonucleotide probe should preferably follow these parameters:

(a) It should be designed to an area of the sequence which has the fewest ambiguous bases ("N's"), if any;

(b) It should be designed to have a $T_m$ of approx. 80° C. (assuming 2° for each A or T and 4 degrees for each G or C).

The oligonucleotide should preferably be labeled with $\gamma$-$^{32}$P ATP (specific activity 6000 Ci/mmole) and T4 polynucleotide kinase using commonly employed techniques for labeling oligonucleotides. Other labeling techniques can also be used. Unincorporated label should preferably be removed by gel filtration chromatography or other established methods. The amount of radioactivity incorporated into the probe should be quantitated by measurement in a scintillation counter. Preferably, specific activity of the resulting probe should be approximately 4e+6 dpm/pmole.

The bacterial culture containing the pool of full-length clones should preferably be thawed and 100 μl of the stock used to inoculate a sterile culture flask containing 25 ml of sterile L-broth containing ampicillin at 100 μg/ml. The culture should preferably be grown to saturation at 37° C., and the saturated culture should preferably be diluted in fresh L-broth. Aliquots of these dilutions should preferably be plated to determine the dilution and volume which will yield approximately 5000 distinct and well-separated colonies on solid bacteriological media containing L-broth containing ampicillin at 100 μg/ml and agar at 1.5% in a 150 mm petri dish when grown overnight at 37° C. Other known methods of obtaining distinct, well-separated colonies can also be employed.

Standard colony hybridization procedures should then be used to transfer the colonies to nitrocellulose filters and lyse, denature and bake them.

The filter is then preferably incubated at 65° C. for 1 hour with gentle agitation in 6×SSC (20×stock is 175.3 g NaCl/ liter, 88.2 g Na citrate/liter, adjusted to pH 7.0 with NaOH) containing 0.5% SDS, 100 μg/ml of yeast RNA, and 10 mM EDTA (approximately 10 mL per 150 mm filter). Preferably, the probe is then added to the hybridization mix at a concentration greater than or equal to 1e+6 dpm/mL. The filter is then preferably incubated at 65° C. with gentle agitation overnight. The filter is then preferably washed in 500 mL of 2×SSC/0.5% SDS at room temperature without agitation, preferably followed by 500 mL of 2×SSC/0.1% SDS at room temperature with gentle shaking for 15 minutes. A third wash with 0.1×SSC/0.5% SDS at 65° C. for 30 minutes to 1 hour is optional. The filter is then preferably dried and subjected to autoradiography for sufficient time to visualize the positives on the X-ray film. Other known hybridization methods can also be employed.

The positive colonies are picked, grown in culture, and plasmid DNA isolated using standard procedures. The clones can then be verified by restriction analysis, hybridization analysis, or DNA sequencing.

Fragments of the proteins of the present invention which are capable of exhibiting biological activity are also encompassed by the present invention. Fragments of the protein may be in linear form or they maybe cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of protein binding sites. For example, fragments of the protein may be fused through "linker" sequences to the Fc portion of an immunoglobulin. For a bivalent form of the protein, such a fusion could be to the Fc portion of an IgG molecule. Other immunoglobulin isotypes may also be used to generate such fusions. For example, a protein—IgM fusion would generate a decavalent form of the protein of the invention.

The present invention also provides both full-length and mature forms of the disclosed proteins. The full-length form of the such proteins is identified in the sequence listing by translation of the nucleotide sequence of each disclosed clone. The mature form(s) of such protein may be obtained by expression of the disclosed full-length polynucleotide (preferably those deposited with ATCC) in a suitable mammalian cell or other host cell. The sequence(s) of the mature form(s) of the protein may also be determinable from the amino acid sequence of the full-length form.

The present invention also provides genes corresponding to the polynucleotide sequences disclosed herein. "Corresponding genes" are the regions of the genome that are transcribed to produce the mRNAs from which cDNA polynucleotide sequences are derived and may include contiguous regions of the genome necessary for the regulated expression of such genes. Corresponding genes may therefore include but are not limited to coding sequences, 5' and 3' untranslated regions, alternatively spliced exons, introns, promoters, enhancers, and silencer or suppressor elements. The corresponding genes can be isolated in accordance with known methods using the sequence information disclosed herein. Such methods include the preparation of probes or primers from the disclosed sequence information for identification and/or amplification of genes in appropriate genomic libraries or other sources of genomic materials. An "isolated gene" is a gene that has been separated from the adjacent coding sequences, if any, present in the genome of the organism from which the gene was isolated.

The chromosomal location corresponding to the polynucleotide sequences disclosed herein may also be determined, for example by hybridizing appropriately labeled polynucleotides of the present invention to chromosomes in situ. It may also be possible to determine the corresponding chromosomal location for a disclosed polynucleotide by identifying significantly similar nucleotide sequences in public databases, such as expressed sequence tags (ESTs), that have already been mapped to particular chromosomal locations. For at least some of the polynucleotide sequences disclosed herein, public database sequences having at least some similarity to the polynucleotide of the present invention have been listed by database accession number. Searches using the GenBank accession numbers of these public database sequences can then be performed at an Internet site provided by the National Center for Biotechnology Information having the address http://www.ncbi.nlm.nih.gov/UniGene/, in order to identify "UniGene clusters" of overlapping sequences. Many of the "UniGene clusters" so identified will already have been mapped to particular chromosomal sites.

Organisms that have enhanced, reduced, or modified expression of the gene(s) corresponding to the polynucleotide sequences disclosed herein are provided. The desired change in gene expression can be achieved through the use of antisense polynucleotides or ribozymes that bind and/or cleave the mRNA transcribed from the gene (Albert and Morris, 1994, *Trends Pharmacol. Sci.* 15(7): 250–254; Lavarosky et al., 1997, *Biochem. Mol. Med.* 62(1): 11–22; and Hampel, 1998, *Prog. Nucleic Acid Res. Mol. Biol.* 58: 1–39; all of which are incorporated by reference herein). Transgenic animals that have multiple copies of the gene(s) corresponding to the polynucleotide sequences disclosed herein, preferably produced by transformation of cells with genetic constructs that are stably maintained within the transformed cells and their progeny, are provided.

Transgenic animals that have modified genetic control regions that increase or reduce gene expression levels, or that change temporal or spatial patterns of gene expression, are also provided (see European Patent No. 0 649 464 B1, incorporated by reference herein).

In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, preferably followed by imprecise excision, of transposable elements (Plasterk, 1992, *Bioessays* 14(9): 629–633; Zwaal et al., 1993, *Proc. Natl. Acad. Sci. USA* 90(16): 7431–7435; Clark et al., 1994, *Proc. Natl. Acad. Sci. USA* 91(2): 719–722; all of which are incorporated by reference herein), or through homologous recombination, preferably detected by positive/negative genetic selection strategies (Mansour et al., 1988, *Nature* 336: 348–352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are preferably eukaryotes and more preferably are mammals. Such organisms are useful for the development of non-human models for the study of disorders involving the corresponding gene(s), and for the development of assay systems for the identification of molecules that interact with the protein product(s) of the corresponding gene(s).

Where the protein of the present invention is membrane-bound (e.g., is a receptor), the present invention also provides for soluble forms of such protein. In such forms, part or all of the intracellular and transmembrane domains of the protein are deleted such that the protein is fully secreted from the cell in which it is expressed. The intracellular and transmembrane domains of proteins of the invention can be identified in accordance with known techniques for determination of such domains from sequence information. For example, the TopPredII computer program can be used to predict the location of transmembrane domains in an amino acid sequence, domains which are described by the location of the center of the transmsmbrane domain, with at least ten transmembrane amino acids on each side of the reported central residue(s).

Proteins and protein fragments of the present invention include proteins with amino acid sequence lengths that are at least 25%(more preferably at least 50%, and most preferably at least 75%) of the length of a disclosed protein and have at least 60% sequence identity (more preferably, at least 75% identity; most preferably at least 90% or 95% identity) with that disclosed protein, where sequence identity is determined by comparing the amino acid sequences of the proteins when aligned so as to maximize overlap and identity while minimizing sequence gaps. Also included in the present invention are proteins and protein fragments that contain a segment preferably comprising 8 or more (more preferably 20 or more, most preferably 30 or more) contiguous amino acids that shares at least 75% sequence identity (more preferably, at least 85% identity; most preferably at least 95% identity) with any such segment of any of the disclosed proteins.

In particular, sequence identity may be determined using WU-BLAST (Washington University BLAST) version 2.0 software, which builds upon WU-BLAST version 1.4, which in turn is based on the public domain NCBI-BLAST version 1.4 (Altschul and Gish, 1996, Local alignment statistics, Doolittle ed., *Methods in Enzymology* 266: 460–480; Altschul et al., 1990, Basic local alignment search tool, *Journal of Molecular Biology* 215: 403–410; Gish and States, 1993, Identification of protein coding regions by database similarity search, *Nature Genetics* 3: 266–272; Karlin and Altschul, 1993, Applications and statistics for multiple high-scoring segments in molecular sequences, *Proc. Natl. Acad. Sci. USA* 90: 5873–5877; all of which are incorporated by reference herein). WU-BLAST version 2.0 executable programs for several UNIX platforms can be downloaded from ftp://blast.wustl.edu/blast/executables. The complete suite of search programs (BLASTP, BLASTN, BLASTX, TBLASTN, and TBLASTX) is provided at that site, in addition to several support programs. WU-BLAST 2.0 is copyrighted and may not be sold or redistributed in any form or manner without the express written consent of the author; but the posted executables may otherwise be freely used for commercial, nonprofit, or academic purposes. In all search programs in the suite—BLASTP, BLASTN, BLASTX, TBLASTN and TBLASTX—the gapped alignment routines are integral to the database search itself, and thus yield much better sensitivity and selectivity while producing the more easily interpreted output. Gapping can optionally be turned off in all of these programs, if desired. The default penalty (Q) for a gap of length one is Q=9 for proteins and BLASTP, and Q=10 for BLASTN, but may be changed to any integer value including zero, one through eight, nine, ten, eleven, twelve through twenty, twenty-one through fifty, fifty-one through one hundred, etc. The default per-residue penalty for extending a gap (R) is R=2 for proteins and BLASTP, and R=10 for BLASTN, but may be changed to any integer value including zero, one, two, three, four, five, six, seven, eight, nine, ten, eleven, twelve through twenty, twenty-one through fifty, fifty-one through one hundred, etc. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Species homologues of the disclosed polynucleotides and proteins are also provided by the present invention. As used herein, a "species homologue" is a protein or polynucleotide with a different species of origin from that of a given protein or polynucleotide, but with significant sequence similarity to the given protein or polynucleotide. Preferably, polynucleotide species homologues have at least 60% sequence identity (more preferably, at least 75% identity; most preferably at least 90% identity) with the given polynucleotide, and protein species homologues have at least 30% sequence identity (more preferably, at least 45% identity; most preferably at least 60% identity) with the given protein, where sequence identity is determined by comparing the nucleotide sequences of the polynucleotides or the amino acid sequences of the proteins when aligned so as to maximize overlap and identity while minimizing sequence gaps. Species homologues may be isolated and identified by making suitable probes or primers from the sequences provided herein and screening a suitable nucleic acid source from the desired species. Preferably, species homologues are those isolated from mammalian species. Most preferably, species homologues are those isolated from certain mammalian species such as, for example, *Pan troglodytes, Gorilla gorilla, Pongo pygmaeus, Hylobates concolor, Macaca mulatta, Papio papio, Papio hamadryas, Cercopithecus aethiops, Cebus capucinus, Aotus trivirgatus, Sanguinus oedipus, Microcebus murinus, Mus musculus, Rattus norvegicus, Cricetulus griseus, Felis catus, Mustela vzison, Canis familiaris, Oryctolagus cuniculus, Bos taurus, Ovis aries, Sus scrofa,* and *Equus caballus,* for which genetic maps have been created allowing the identification of syntenic relationships between the genomic organization of genes in one species and the genomic organization of the related genes in another species (O'Brien and Seuanez, 1988, *Ann. Rev. Genet.* 22: 323–351; O'Brien et al., 1993, *Nature Genetics* 3:103–112; Johansson et al., 1995, *Genomics* 25: 682–690; Lyons et al., 1997, *Nature Genetics* 15:47–56; O'Brien et al., 1997, *Trends in Genetics* 13(10): 393–399; Carver and Stubbs, 1997, *Genome Research* 7:1123–1137; all of which are incorporated by reference herein).

The invention also encompasses allelic variants of the disclosed polynucleotides or proteins; that is, naturally-occurring alternative forms of the isolated polynucleotides which also encode proteins which are identical or have significantly similar sequences to those encoded by the disclosed polynucleotides. Preferably, allelic variants have at least 60% sequence identity (more preferably, at least 75% identity; most preferably at least 90% identity) with the given polynucleotide, where sequence identity is determined by comparing the nucleotide sequences of the polynucleotides when aligned so as to maximize overlap and identity while minimizing sequence gaps. Allelic variants may be isolated and identified by making suitable probes or primers from the sequences provided herein and screening a suitable nucleic acid source from individuals of the appropriate species.

The invention also includes polynucleotides with sequences complementary to those of the polynucleotides disclosed herein.

The present invention also includes polynucleotides that hybridize under reduced stringency conditions, more preferably stringent conditions, and most preferably highly stringent conditions, to polynucleotides described herein. Examples of stringency conditions are shown in the table below: highly stringent conditions are those that are at least as stringent as, for example, conditions A–F; stringent conditions are at least as stringent as, for example, conditions G–L; and reduced stringency conditions are at least as stringent as, for example, conditions M–R.

| Stringency Condition | Polynucleotide Hybrid | Hybrid Length (bp)‡ | Hybridization Temperature and Buffer† | Wash Temperature and Buffer† |
|---|---|---|---|---|
| A | DNA:DNA | ≥50 | 65° C.; 1 × SSC -or- 42° C.; 1 × SSC, 50% formamide | 65° C.; 0.3 × SSC |
| B | DNA:DNA | <50 | $T_B*$; 1 × SSC | $T_B*$; 1 × SSC |
| C | DNA:RNA | ≥50 | 67° C.; 1 × SSC -or- 45° C.; 1 × SSC, 50% formamide | 67° C.; 0.3 × SSC |
| D | DNA:RNA | <50 | $T_D*$; 1 × SSC | $T_D*$; 1 × SSC |
| E | RNA:RNA | ≥50 | 70° C.; 1 × SSC -or- 50° C.; 1 × SSC, 50% formamide | 70° C.; 0.3 × SSC |
| F | RNA:RNA | <50 | $T_F*$; 1 × SSC | $T_F*$; 1 × SSC |
| G | DNA:DNA | ≥50 | 65° C.; 4 × SSC -or- 42° C.; 4 × SSC, 50% formamide | 65° C.; 1 × SSC |
| H | DNA:DNA | <50 | $T_H*$; 4 × SSC | $T_H*$; 4 × SSC |
| I | DNA:RNA | ≥50 | 67° C.; 4 × SSC -or- 45° C.; 4 × SSC, 50% formamide | 67° C.; 1 × SSC |
| J | DNA:RNA | <50 | $T_J*$; 4 × SSC | $T_J*$; 4 × SSC |
| K | RNA:RNA | ≥50 | 70° C.; 4 × SSC -or- 50° C.; 4 × SSC, 50% formamide | 67° C.; 1 × SSC |
| L | RNA:RNA | <50 | $T_L*$; 2 × SSC | $T_L*$; 2 × SSC |
| M | DNA:DNA | ≥50 | 50° C.; 4 × SSC -or- 40° C.; 6 × SSC, 50% formamide | 50° C.; 2 × SSC |
| N | DNA:DNA | <50 | $T_N*$; 6 × SSC | $T_N*$; 6 × SSC |
| O | DNA:RNA | ≥50 | 55° C.; 4 × SSC -or- 42° C.; 6 × SSC, 50% formamide | 55° C.; 2 × SSC |
| P | DNA:RNA | <50 | $T_P*$; 6 × SSC | $T_P*$; 6 × SSC |
| Q | RNA:RNA | ≥50 | 60° C.; 4 × SSC -or- 45° C.; 6 × SSC, 50% formamide | 60° C.; 2 × SSC |
| R | RNA:RNA | <50 | $T_R*$; 4 × SSC | $T_R*$; 4 × SSC |

‡The hybrid length is that anticipated for the hybridized region(s) of the hybridizing polynucleotides. When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity.

†SSPE (1 × SSPE is 0.15M NaCl, 10 mM $NaH_2PO_4$, and 1.25 mM EDTA, pH 7.4) can be substituted for SSC (1 × SSC is 0.15M NaCl and 15 mM sodium citrate) in the hybridization and wash buffers; washes are performed for 15 minutes after hybridization is complete.

*$T_B$–$T_R$: The hybridization temperature for hybrids anticipated to be less than 50 base pairs in length should be 5–10° C. less than the melting temperature ($T_m$) of the hybrid, where $T_m$ is determined according to the following equations. For hybrids less than 18 base pairs in length, $T_m$(° C.) = 2(# of A + T bases) + 4(# of G + C bases). For hybrids between 18 and 49 base pairs in length, $T_m$(° C.) = 81.5 + 16.6($\log_{10}$[$Na^+$]) + 0.41(% G + C) − (600/N), where N is the number of bases in the hybrid, and [$Na^+$] is the concentration of sodium ions in the hybridization buffer ([$Na^+$] for 1 × SSC = 0.165M).

Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3–6.4, incorporated herein by reference.

Preferably, each such hybridizing polynucleotide has a length that is at least 25% (more preferably at least 50%, and most preferably at least 75%) of the length of the polynucleotide of the present invention to which it hybridizes, and has at least 60% sequence identity (more preferably, at least 75% identity; most preferably at least 90% or 95% identity) with the polynucleotide of the present invention to which it hybridizes, where sequence identity is determined by comparing the sequences of the hybridizing polynucleotides when aligned so as to maximize overlap and identity while minimizing sequence gaps.

The isolated polynucleotide endcoing the protein of the invention may be operably linked to an expression control sequence such as the pMT2 or pED expression vectors disclosed in Kaufman et al., Nucleic Acids Res. 19, 4485–4490 (1991), in order to produce the protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and an expression control sequence are situated within a vector or cell in such a way that the protein is expressed by a host cell which has been transformed (transfected) with the ligated polynucleotide/expression control sequence.

A number of types of cells may act as suitable host cells for expression of the protein. Mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

Alternatively, it may be possible to produce the protein in lower eukaryotes such as yeast or in prokaryotes such as bacteria. Potentially suitable yeast strains include *Saccharomyces cerevisiae, Schizosaccharomyces pombe*, Kluyveromyces strains, Candida, or any yeast strain capable of expressing heterologous proteins. Potentially suitable bacterial strains include *Escherichia coli, Bacillus subtilis, Salmonella typhimurium*, or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

The protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No. 1555* (1987) incorporated herein by reference. As used herein, an insect cell capable of expressing a polynucleotide of the present invention is "transformed."

The protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the protein of the invention may also be expressed in a form which will facilitate purification. For example, it may be expressed as a fusion protein, such as those of maltose binding protein (MBP), glutathione-S-transferase (GST) or thioredoxin (TRX). Kits for expression and purification of such fusion proteins are commercially available from New England BioLabs (Beverly, Mass.), Pharmacia (Piscataway, N.J.) and Invitrogen Corporation (Carlsbad, Calif.), respectively. The protein can also be tagged with an epitope and subsequently purified by using a specific antibody directed to such epitope. One such epitope ("Flag") is commercially available from the Eastman Kodak Company (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the protein. Some or all of the foregoing purification steps, in various combinations, can also be employed to provide a substantially homogeneous isolated recombinant protein. The protein thus purified is substantially free of other mammalian proteins and is defined in accordance with the present invention as an "isolated protein."

The protein of the invention may also be expressed as a product of transgenic animals, e.g., as a component of the milk of transgenic cows, goats, pigs, or sheep which are characterized by somatic or germ cells containing a nucleotide sequence encoding the protein.

The protein may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with proteins may possess biological properties in common therewith, including protein activity. Thus, they may be employed as biologically active or immunological substitutes for natural, purified proteins in screening of therapeutic compounds and in immunological processes for the development of antibodies.

The proteins provided herein also include proteins characterized by amino acid sequences similar to those of purified proteins but into which modification are naturally provided or deliberately engineered. For example, modifications in the peptide or DNA sequences can be made by those skilled in the art using known techniques. Modifications of interest in the protein sequences may include the alteration, substitution, replacement, insertion or deletion of a selected amino acid residue in the coding sequence. For example, one or more of the cysteine residues may be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein.

Other fragments and derivatives of the sequences of proteins which would be expected to retain protein activity in whole or in part and may thus be useful for screening or other immunological methodologies may also be easily made by those skilled in the art given the disclosures herein. Such modifications are believed to be encompassed by the present invention.

USES AND BIOLOGICAL ACTIVITY

The polynucleotides and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Research Uses and Utilities

The polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, those described in Gyuris et al., 1993, *Cell* 75: 791–803 and in Rossi et al., 1997, *Proc. Natl. Acad. Sci. USA* 94: 8405–8410, all of which are incorporated by reference herein) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor-dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol 1 pp. 3.12.1–3.12.14, John Wiley and Sons, Toronto. 1994; and Measurement of mouse and human Interferon γ, Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. USA 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to regulate immune responses in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci USA, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of. human autoimmune diseases. Examples include murine experimental autoimmune encephalitis, systemic lupus erythematosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of. tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I α chain protein and β$_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. USA 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolr et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In *Current Protocols in Immunology*. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. USA 88:7548–7551, 1991.

Hematopoiesis Regulating Activity

A protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify; among others, proteins that influence embryonic differentiation hematopoiesis) include, without limitation, those described in: Johansson et al. Cellular Biology 15:141–151, 1995; Keller et al., Molecular and Cellular Biology 13:473486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M. G. In *Culture of Hematopoietic Cells*. R. I. Freshney, et al. eds. Vol pp. 265–268, Wiley-Liss, Inc., New York, N.Y. 1994; Hirayama et al., Proc. Natl. Acad. Sci. USA 89:5907–5911, 1992; Primitive hematopoietic colony forming cells with high proliferative potential, McNiece, I. K. and Briddell, R. A. In *Culture of Hematopoietic Cells*. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In *Culture of Hematopoietic Cells*. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In *Culture of Hematopoietic Cells*. R. I. Freshney, et al. eds. Vol pp. 163–179, Wiley-Liss, Inc., New York, N.Y. 1994; Long term culture initiating cell assay, Sutherland, H. J. In *Culture of Hematopoietic Cells*. R. I. Freshney, et al. eds. Vol pp. 139–162, Wiley-Liss, Inc., New York, N.Y. 1994.

Tissue Growth Activity

A protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells -or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendinitis, carpal tunnel syndrome and other tendon or ligament defects. The compositions may also include an appropriate matrix and/or sequestering agent as a carrier as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, *Epidermal Wound Healing* pps. 71–112 (Maibach, H I and Rovee, D T, eds.), Year Book Medical Publishers, Inc., Chicago, as modified by Eaglstein and Mertz, J. Invest. Dermatol 71:382–84 (1978).

Activin/Inhibin Activity

A protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-β group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., Endocrinology 91:562–572, 1972; Ling et al., Nature 321:779–782, 1986; Vale et al., Nature 321:776–779, 1986; Mason et al., Nature 318:659–663, 1985; Forage et al., Proc. Natl. Acad. Sci. USA 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by the following methods:

Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 6.12, Measurement of alpha and beta Chemokines 6.12.1–6.12.28; Taub et al. J. Clin. Invest. 95:1370–1376, 1995; Lind et al. APMIS 103:140–146, 1995; Muller et al Eur. J. Immunol. 25: 1744_1748; Gruber et al. J. of Immunol. 152:5860–5867, 1994; Johnston et al. J. of Immunol. 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., J. Clin. Pharmacol. 26:131–140, 1986; Burdick et al., Thrombosis Res. 45:413–419, 1987; Humphrey et al., Fibrinolysis 5:71–79 (1991); Schaub, Prostaglandins 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell-cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in:Current Protocols in Immunology, Ed by J. E. Coligan, A. M. Kruisbeek, D. H. Margulies, E. M. Shevach, W. Strober, Pub. Greene Publishing Associates and Wiley-Interscience (Chapter 7.28, Measurement of Cellular Adhesion under static conditions 7.28.1–7.28.22), Takai et al., Proc. Natl. Acad. Sci. USA 84:6864–6868, 1987; Bierer et al., J. Exp. Med. 168:1145–1156, 1988; Rosenstein et al., J. Exp. Med. 169:149–160 1989; Stoltenborg et al., J. Immunol. Methods 175:59–68, 1994; Stitt et al., Cell 80:661–670, 1995.

Anti-inflammatory Activity

Proteins of the present invention may also exhibit anti-inflammatory activity. The anti-inflammatory activity may be achieved by providing a stimulus to cells involved in the inflammatory response, by inhibiting or promoting cell-cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Cadherin/Tumor Invasion Suppressor Activity

Cadherins are calcium-dependent adhesion molecules that appear to play major roles during development, particularly in defining specific cell types. Loss or alteration of normal cadherin expression can lead to changes in cell adhesion properties linked to tumor growth and metastasis. Cadherin malfunction is also implicated in other human diseases, such as pemphigus vulgaris and pemphigus foliaceus (autoimmune blistering skin diseases), Crohn's disease, and some developmental abnormalities.

The cadherin superfamily includes well over forty members, each with a distinct pattern of expression. All members of the superfamily have in common conserved extracellular repeats (cadherin domains), but structural differences are found in other parts of the molecule. The cadherin domains bind calcium to form their tertiary structure and thus calcium is required to mediate their adhesion. Only a few amino acids in the first cadherin domain provide the basis for homophilic adhesion; modification of this recognition site can change the specificity of a cadherin so that instead of recognizing only itself, the mutant molecule can now also bind to a different cadherin. In addition, some cadherins engage in heterophilic adhesion with other cadherins.

E-cadherin, one member of the cadherin superfamily, is expressed in epithelial cell types. Pathologically, if E-cadherin expression is lost in a tumor, the malignant cells become invasive and the cancer metastasizes. Transfection of cancer cell lines with polynucleotides expressing E-cadherin has reversed cancer-associated changes by returning altered cell shapes to normal, restoring cells' adhesiveness to each other and to their substrate, decreasing the cell growth rate, and drastically reducing anchorage-independent cell growth. Thus, reintroducing E-cadherin expression reverts carcinomas to a less advanced stage. It is likely that other cadherins have the same invasion suppressor role in carcinomas derived from other tissue types. Therefore, proteins of the present invention with cadherin activity, and polynucleotides of the present invention encoding such proteins, can be used to treat cancer. Introducing such proteins or polynucleotides into cancer cells can reduce or eliminate the cancerous changes observed in these cells by providing normal cadherin expression.

Cancer cells have also been shown to express cadherins of a different tissue type than their origin, thus allowing these cells to invade and metastasize in a different tissue in the body. Proteins of the present invention with cadherin activity, and polynucleotides of the present invention encoding such proteins, can be substituted in these cells for the inappropriately expressed cadherins, restoring normal cell adhesive properties and reducing or eliminating the tendency of the cells to metastasize.

Additionally, proteins of the present invention with cadherin activity, and polynucleotides of the present invention encoding such proteins, can used to generate antibodies recognizing and binding to cadherins. Such antibodies can be used to block the adhesion of inappropriately expressed tumor-cell cadherins, preventing the cells from forming a tumor elsewhere. Such an anti-cadherin antibody can also be used as a marker for the grade, pathological type, and prognosis of a cancer, i.e. the more progressed the cancer, the less cadherin expression there will be, and this decrease in cadherin expression can be detected by the use of a cadherin-binding antibody.

Fragments of proteins of the present invention with cadherin activity, preferably a polypeptide comprising a decapeptide of the cadherin recognition site, and polynucleotides of the present invention encoding such protein fragments, can also be used to block cadherin function by binding to cadherins and preventing them from binding in ways that produce undesirable effects. Additionally, fragments of proteins of the present invention with cadherin activity, preferably truncated soluble cadherin fragments which have been found to be stable in the circulation of cancer patients, and polynucleotides encoding such protein fragments, can be used to disturb proper cell-cell adhesion.

Assays for cadherin adhesive and invasive suppressor activity include, without limitation, those described in: Hortsch et al. J Biol Chem 270 (32): 18809–18817, 1995; Miyaki et al. Oncogene 11: 2547–2552, 1995; Ozawa et al. Cell 63: 1033–1038, 1990.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via antibody-dependent cell-mediated cytotoxicity (ADCC)). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or caricadic cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

ADMINISTRATION AND DOSING

A protein of the present invention (from whatever source derived, including without limitation from recombinant and non-recombinant sources) may be used in a pharmaceutical composition when combined with a pharmaceutically acceptable carrier.

Such a composition may also contain (in addition to protein and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IFN, TNF0, TNF1, TNF2, G-CSF, Meg-CSF, thrombopoietin, stem cell factor, and erythropoietin. The pharmaceutical composition may further contain other agents which either enhance the activity of the protein or compliment its activity or use in treatment. Such additional factors and/or agents may be included in the pharmaceutical composition to produce a synergistic effect with protein of the invention, or to minimize side effects. Conversely, protein of the present invention may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

A protein of the present invention may be active in multimers (e.g., heterodimers or homodimers) or complexes with itself or other proteins. As a result, pharmaceutical compositions of the invention may comprise a protein of the invention in such multimeric or complexed form.

The pharmaceutical composition of the invention may be in the form of a complex of the protein(s) of present invention along with protein or peptide antigens. The protein and/or peptide antigen will deliver a stimulatory signal to both B and T lymphocytes. B lymphocytes will respond to antigen through their surface immunoglobulin receptor. T lymphocytes will respond to antigen through the T cell receptor (TCR) following presentation of the antigen by MHC proteins. MHC and structurally related proteins including those encoded by class I and class II MHC genes on host cells will serve to present the peptide antigen(s) to T lymphocytes. The antigen components could also be supplied as purified MHC-peptide complexes alone or with co-stimulatory molecules that can directly signal T cells. Alternatively antibodies able to bind surface immunolgobulin and other molecules on B cells as well as antibodies able to bind the TCR and other molecules on T cells can be combined with the pharmaceutical composition of the invention.

The pharmaceutical composition of the invention may be in the form of a liposome in which protein of the present invention is combined, in addition to other pharmaceutically acceptable carriers, with amphipathic agents such as lipids which exist in aggregated form as micelies, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of protein of the present invention is administered to a mammal having a condition to be treated. Protein of the present invention may be administered in accordance with the method of the invention either alone or in combination with other therapies such as treatments employing cytokines, lymphokines or other hematopoietic factors. When co-administered with one or more cytokines, lymphokines or other hematopoietic factors, protein of the present invention may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering protein of the present invention in combination with cytokine(s), lymphokine(s), other hematopoietic factor(s), thrombolytic or anti-thrombotic factors.

Administration of protein of the present invention used in the pharmaceutical composition or to practice the method of the present invention can be carried out in a variety of conventional ways, such as oral ingestion, inhalation, topical application or cutaneous, subcutaneous, intraperitoneal, parenteral or intravenous injection. Intravenous administration to the patient is preferred.

When a therapeutically effective amount of protein of the present invention is administered orally, protein of the present invention will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% protein of the present invention, and preferably from about 25 to 90% protein of the present invention. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of protein of the present invention, and preferably from about 1 to 50% protein of the present invention.

When a therapeutically effective amount of protein of the present invention is administered by intravenous, cutaneous or subcutaneous injection, protein of the present invention will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to protein of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of protein of the present invention in the pharmaceutical composition of the present invention will depend upon the nature and severity of the condition being treated, and on the nature of prior treatments which the patient has undergone. Ultimately, the attending physician will decide the amount of protein of the present invention with which to treat each individual patient. Initially, the attending physician will administer low doses of protein of the present invention and observe the patient's response. Larger doses of protein of the present invention may be administered until the optimal therapeutic effect is obtained for the patient, and at that point the dosage is not increased further. It is contemplated that the various pharmaceutical compositions;used to practice the method of the present invention should contain about 0.01 μg to about 100 mg (preferably about 0.1 ng to about 10 mg, more preferably about 0.1 μg to about 1 mg) of protein of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the protein of the present invention will be in the range of 12 to 24 hours of continuous intravenous administration. Ultimately the attending physician will decide on the appropriate duration of intravenous therapy using the pharmaceutical composition of the present invention.

Protein of the invention may also be used to immunize animals to obtain polyclonal and monoclonal antibodies which specifically react with the protein. As used herein, the term "antibody" includes without limitation a polyclonal antibody, a monoclonal antibody, a chimeric antibody, a single-chain antibody, a CDR-grafted antibody, a humanized antibody, or fragments thereof which bind to the indicated protein. Such term also includes any other species derived from an antibody or antibody sequence which is capable of binding the indicated protein.

Antibodies to a particular protein can be produced by methods well known to those skilled in the art. For example, monoclonal antibodies can be produced by generation of antibody-producing hybridomas in accordance with known methods (see for example, Goding, 1983, Monoclonal antibodies: principles and practice, Academic Press Inc., New York; and Yokoyama, 1992, "Production of Monoclonal Antibodies" in Current Protocols in Immunology, Unit 2.5, Greene Publishing Assoc. and John Wiley & Sons). Polyclonal sera and antibodies can be produced by inoculation of a mammalian subject with the relevant protein or fragments thereof in accordance with known methods. Fragments of antibodies, receptors, or other reactive peptides can be produced from the corresponding antibodies by cleavage of and collection of the desired fragments in accordance with known methods (see for example, Goding, supra; and Andrew et al., 1992, "Fragmentation of Immunoglobulins" in Current Protocols in Immunology, Unit 2.8, Greene Publishing Assoc. and John Wiley & Sons). Chimeric antibodies and single chain antibodies can also be produced in accordance with known recombinant methods (see for example, U.S. Pat. Nos. 5,169,939, 5,194,594, and 5,576,184). Humanized antibodies can also be made from corresponding murine antibodies in accordance with well known methods (see for example, U.S. Pat. Nos. 5,530,101, 5,585,089, and 5,693,762). Additionally, human antibodies may be produced in non-human animals such as mice that have been genetically altered to express human antibody molecules (see for example Fishwild et al., 1996, *Nature Biotechnology* 14: 845–851; Mendez et al., 1997, *Nature Genetics* 15: 146–156 (erratum *Nature Genetics* 16: 410); and U.S. Pat. Nos. 5,877,397 and 5,625,126). Such antibodies may be obtained using either the entire protein or fragments thereof as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Monoclonal antibodies binding to the protein of the invention may be useful diagnostic agents for the immunodetection of the protein. Neutralizing monoclonal antibodies binding to the protein may also be useful therapeutics for both conditions associated with the protein and also in the treatment of some forms of cancer where abnormal expression of the protein is involved. In the case of cancerous cells or leukemic cells, neutralizing monoclonal antibodies against the protein may be useful in detecting and preventing the metastatic spread of the cancerous cells, which may be mediated by the protein.

For compositions of the present invention which are useful for bone, cartilage, tendon or ligament regeneration, the therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or tissue damage. Topical administration may be suitable for wound healing and tissue repair. Therapeutically useful agents other than a protein of the invention which may also optionally be included in the composition as described above, may alternatively or additionally, be administered simultaneously or sequentially with the composition in the methods of the invention. Preferably for bone and/or cartilage formation, the composition would include a matrix capable of delivering the protein-containing composition to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions will define the appropriate formulation. Potential matrices for the compositions may be biodegradable and chemically defined calcium sulfate, tricalciumphosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-luminate-phosphate and processing to alter pore size, particle size, particle shape, and biodegradability.

Presently preferred is a 50:50 (mole weight) copolymer of lactic acid and glycolic acid in the form of porous particles having diameters ranging from 150 to 800 microns. In some applications, it will be useful to utilize a sequestering agent, such as carboxymethyl cellulose or autologous blood clot, to prevent the protein compositions from disassociating from the matrix.

A preferred family of sequestering agents is cellulosic materials such as alkylcelluloses (including hydroxyalkylceluloses), including methylcellulose, ethylcellulose, hydroxyethylcellulose, hydroxypropylcellulose, hydroxypropylmethylcellulose, and carboxymethylcellulose, the most preferred being cationic salts of carboxymethylcellulose (CMC). Other preferred sequestering agents include hyaluronic acid, sodium alginate, poly(ethylene glycol), polyoxyethylene oxide, carboxyvinyl polymer and poly(vinyl alcohol). The amount of sequestering agent useful herein is 0.5–20 wt %, preferably 1–10 wt % based on total formulation weight, which represents the amount necessary to prevent desorbtion of the protein from the polymer matrix and to provide appropriate handling of the composition, yet not so much that the progenitor cells are prevented from infiltrating the matrix, thereby providing the protein the opportunity to assist the osteogenic activity of the progenitor cells.

In further compositions, proteins of the invention may be combined with other agents beneficial to the treatment of the bone and/or cartilage defect, wound, or tissue in question. These agents include various growth factors such as epidermal growth factor (EGF), platelet derived growth factor (PDGF), transforming growth factors (TGF-α and TGF-β), and insulin-like growth factor (IGF).

The therapeutic compositions are also presently valuable for veterinary applications. Particularly domestic animals and thoroughbred horses, in addition to humans, are desired patients for such treatment with proteins of the present invention.

The dosage regimen of a protein-containing pharmaceutical composition to be used in tissue regeneration will be determined by the attending physician considering various factors which modify the action of the proteins, e.g., amount of tissue weight desired to be formed, the site of damage, the condition of the damaged tissue, the size of a wound, type of damaged tissue (e.g., bone), the patient's age, sex, and diet, the severity of any infection, time of administration and other clinical factors. The dosage may vary with the type of matrix used in the reconstitution and with inclusion of other proteins in the pharmaceutical composition. For example, the addition of other known growth factors, such as IGF I (insulin like growth factor I), to the final composition, may also effect the dosage. Progress can be monitored by periodic assessment of tissue/bone growth and/or repair, for example, X-rays, histomorphometric determinations and tetracycline labeling.

Polynucleotides of the present invention can also be used for gene therapy. Such polynucleotides can be introduced either in vivo or ex vivo into cells for expression in a mammalian subject. Polynucleotides of the invention may also be administered by other known methods for introduction of nucleic acid into a cell or organism (including, without limitation, in the form of viral vectors or naked DNA).

Cells may also be cultured ex vivo in the presence of proteins of the present invention in order to proliferate or to produce a desired effect on or activity in such cells. Treated cells can then be introduced in vivo for therapeutic purposes.

Patent and literature references cited herein are incorporated by reference as if fully set forth.

What is claimed is:

1. An isolated polynucleotide which comprises the nucleotide sequence of SEQ ID NO: 9 from nucleotide 584 to nucleotide 823.

2. An isolated polynucleotide which comprises the nucleotide sequence of a mature coding sequence of clone yc19_1 deposited under accession number ATCC 98650.

3. An isolated polynucleotide which comprises the nucleotide sequence encoding a mature protein encoded by DNA insert of clone yc19_1 deposited under accession number ATCC 98650.

* * * * *

UNITED STATES PATENT AND TRADEMARK OFFICE
CERTIFICATE OF CORRECTION

PATENT NO. : 6,706,869 B1
DATED : March 16, 2004
INVENTOR(S) : Gordon G. Wong et al.

It is certified that error appears in the above-identified patent and that said Letters Patent is hereby corrected as shown below:

Title page,
Item [56], References Cited, OTHER PUBLICATIONS, "Hillier et al.," reference, "NOv. 1996.*" should read -- Nov. 1996.* --.

Column 16,
Line 31, "add" should read -- acid --.

Column 21,
Lines 49 and 51, "yb8111" should read -- yb81_1 --.

Column 22,
Line 26, "yb8111" should read -- yb81_1 --.

Column 54,
Lines 9 and 12, "add" should read -- acid --.

Column 56,
Line 39, "(e)" should read -- (f) --.

Column 70,
Line 62, "done" should read -- clone --.

Column 129,
Line 54, "; polynucleotide" should read -- polynucleotide --; and
Line 56, "NO:12" should read -- NO:121 --.

Column 130,
Line 25, "NO:22" should read -- NO:122 --; and
Line 27, "9" should read -- 91 --.

Column 206,
Line 56, "embodiments;" should read -- embodiments, --.

Column 220,
Line 25, "ATCC 98958;," should read -- ATCC 98958; --.

Column 239,
Line 55, (close up left margin).

UNITED STATES PATENT AND TRADEMARK OFFICE
CERTIFICATE OF CORRECTION

PATENT NO. : 6,706,869 B1
DATED : March 16, 2004
INVENTOR(S) : Gordon G. Wong et al.

It is certified that error appears in the above-identified patent and that said Letters Patent is hereby corrected as shown below:

Column 240,
Line 66, "contains" should be deleted and "element-" should read -- element; --; and
Line 67, ";contains" should read -- contains --.

Column 243,
Line 32, "contains" should be deleted.

Column 250,
Line 40, (close up right margin); and
Line 41, (close up left margin).

Column 253,
Line 17, "element. yj32_1" should read -- element.¶yj32_1 --.

Column 265,
Lines 33 and 36, "similar to" should be deleted.

Column 274,
Line 32, "mRNA" should read -- mRNA; --; and
Line 33, ";contains" should read -- contains --.

Column 275,
Line 8, "domains" should read -- domain --.

Column 283,
Line 27, "13 to" should read -- 13 to 25 --.

Column 295,
Line 23, "maybe" should read -- may be --.

Column 296,
Lines 34 and 39, (close up right margin).
Lines 35 and 40, (close up left margin).

Column 298,
Line 33, "vzison," should read -- vision, --.

UNITED STATES PATENT AND TRADEMARK OFFICE
CERTIFICATE OF CORRECTION

PATENT NO. : 6,706,869 B1
DATED : March 16, 2004
INVENTOR(S) : Gordon G. Wong et al.

It is certified that error appears in the above-identified patent and that said Letters Patent is hereby corrected as shown below:

Column 306,
Lines 10 and 45, "of." should read -- of --.

Column 308,
Line 62, "identify;" should read -- identify, --.

Column 309,
Line 44, "-or" should read -- or --.

Column 311,
Line 5, "and" should be deleted; and
Line 8, "a" should read -- α --.

Column 312,
Line 44, "in:Current" should read -- in: Current --.

Column 313,
Line 64, "can" should read -- can be --.

Column 315,
Line 16, (close up right margin);
Line 17, (close up left margin); and
Line 61, "micelies," should read -- micelles, --.

Column 317,
Line 25, "compositions; used" should read -- compositions used --.

Signed and Sealed this

Third Day of August, 2004

JON W. DUDAS
*Acting Director of the United States Patent and Trademark Office*